US011591381B2

(12) United States Patent
Sluch et al.

(10) Patent No.: US 11,591,381 B2
(45) Date of Patent: *Feb. 28, 2023

(54) GENE-EDITED NATURAL KILLER CELLS

(71) Applicant: CRISPR THERAPEUTICS AG, Zug (CH)

(72) Inventors: Valentin Sluch, Cambridge, MA (US); Alireza Rezania, Cambridge, MA (US); Jason Sagert, Cambridge, MA (US); Danielle Swain, Cambridge, MA (US)

(73) Assignee: CRISPR THERAPEUTICS AG, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/538,699

(22) Filed: Nov. 30, 2021

(65) Prior Publication Data

US 2022/0169988 A1 Jun. 2, 2022

Related U.S. Application Data

(60) Provisional application No. 63/119,512, filed on Nov. 30, 2020, provisional application No. 63/214,134, filed on Jun. 23, 2021, provisional application No. 63/250,048, filed on Sep. 29, 2021.

(51) Int. Cl.
| | |
|---|---|
| *A61K 35/17* | (2015.01) |
| *C07K 14/74* | (2006.01) |
| *C07K 14/54* | (2006.01) |
| *C07K 14/725* | (2006.01) |
| *C07K 14/715* | (2006.01) |
| *C07K 14/81* | (2006.01) |
| *C07K 16/28* | (2006.01) |
| *C12N 5/0783* | (2010.01) |
| *C12N 15/90* | (2006.01) |
| *C12N 5/0735* | (2010.01) |
| *C12N 5/074* | (2010.01) |
| *C12N 5/10* | (2006.01) |
| *C12N 15/66* | (2006.01) |

(52) U.S. Cl.
CPC ........ *C07K 14/70539* (2013.01); *A61K 35/17* (2013.01); *C07K 14/5443* (2013.01); *C07K 14/7051* (2013.01); *C07K 14/7155* (2013.01); *C07K 14/8121* (2013.01); *C07K 16/2878* (2013.01); *C12N 5/0606* (2013.01); *C12N 5/0646* (2013.01); *C12N 5/0696* (2013.01); *C12N 5/10* (2013.01); *C12N 15/66* (2013.01); *C12N 15/907* (2013.01); *C07K 2319/00* (2013.01); *C12N 2310/20* (2017.05); *C12N 2506/11* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 7,387,776 | B2 | 6/2008 | Keler et al. |
| 8,652,845 | B2 | 2/2014 | Niwa et al. |
| 9,121,011 | B2 | 9/2015 | Osafune et al. |
| 9,260,696 | B2 | 2/2016 | Kaumnan et al. |
| 9,629,877 | B2 | 4/2017 | Cooper et al. |
| 9,765,330 | B1 | 9/2017 | Niazi et al. |
| 9,834,754 | B2 | 12/2017 | Keller et al. |
| 9,890,357 | B2 | 2/2018 | Osafune et al. |
| 9,931,377 | B2 | 4/2018 | Pavlakis et al. |
| 9,938,499 | B2 | 4/2018 | Slukvin et al. |
| 10,150,805 | B2 | 12/2018 | Wong et al. |
| 10,166,255 | B2 | 1/2019 | Moriarity et al. |
| 10,196,652 | B2 | 2/2019 | Conway et al. |
| 10,287,606 | B2 | 5/2019 | Valamehr et al. |
| 10,370,452 | B2 | 8/2019 | Themeli et al. |
| 10,428,305 | B2 | 10/2019 | Campana et al. |
| 10,500,229 | B2 | 12/2019 | Lee et al. |
| 10,501,543 | B2 | 12/2019 | Bernett et al. |
| 10,626,372 | B1 | 4/2020 | Valamehr et al. |
| 10,738,279 | B2 | 8/2020 | Lee |
| 10,815,301 | B2 | 10/2020 | Kochenderfer |

(Continued)

FOREIGN PATENT DOCUMENTS

| | | |
|---|---|---|
| CN | 111235105 A | 6/2020 |
| EP | 2699593 B1 | 8/2017 |

(Continued)

OTHER PUBLICATIONS

Abel et al., "Natural Killer Cells: Development, Maturation, and Clinical Utilization", Frontiers in Immunology, Aug. 2018, pp. 1-23, vol. 9, No. 1869.
Bhardwaj et al., "Sonic hedgehog induces the proliferation of primitive human hematopoietic cells via BMP regulation", Nature Immunology, Feb. 2001, pp. 172-180, vol. 2, No. 2.
Bhatia et al., "Bone Morphogenetic Proteins Regulate the Developmental Program of Human Hematopoietic Stem Cells", Journal of Experimental Medicine, Apr. 5, 1999, pp. 1139-1147, vol. 189, No. 7.

(Continued)

*Primary Examiner* — Marcia S Noble
(74) *Attorney, Agent, or Firm* — Sheppard, Mullin, Richter & Hampton LLP

(57) ABSTRACT

The present invention relates to, inter alia, an engineered cell (e.g., iPSC, IPS-derived NK, or NK cell) comprising a disrupted B2M gene and an inserted polynucleotide encoding one or more of SERPINB9, a fusion of IL15 and IL15Rα, and/or HLA-E. The engineered cell can further comprise a disrupted CIITA gene and an inserted polynucleotide encoding a CAR, wherein the CAR can be an anti-BCMA CAR or an anti-CD30 CAR. The engineered cell may further comprise a disrupted ADAM17 gene, a disrupted FAS gene, a disrupted CISH gene, and/or a disrupted REGNASE-1 gene. Methods for producing the engineered cells are also provided, and therapeutic uses of the engineered cells are also described. Guide RNA sequences targeting described target sequences are also described.

27 Claims, 65 Drawing Sheets

Specification includes a Sequence Listing.

(56) References Cited

U.S. PATENT DOCUMENTS

| | | |
|---|---|---|
| 10,905,743 B2 | 2/2021 | Qu et al. |
| 10,927,346 B2 | 2/2021 | Valamehr et al. |
| 10,968,426 B2 | 4/2021 | Meissner et al. |
| 11,059,876 B2 | 7/2021 | Yeung et al. |
| 11,072,781 B2 | 7/2021 | Valamehr et al. |
| 2013/0287751 A1 | 10/2013 | Kaufman et al. |
| 2016/0097035 A1 | 4/2016 | Yonemitsu et al. |
| 2016/0120906 A1 | 5/2016 | Galetto et al. |
| 2018/0008637 A1 | 1/2018 | Murphy et al. |
| 2018/0021378 A1 | 1/2018 | Kang et al. |
| 2018/0044636 A1 | 2/2018 | Spanholtz et al. |
| 2018/0072992 A1 | 3/2018 | Valamehr et al. |
| 2018/0142034 A1 | 5/2018 | Chang |
| 2018/0298101 A1 | 10/2018 | Huntington et al. |
| 2018/0305664 A1 | 10/2018 | Vodyanyk et al. |
| 2018/0346877 A1 | 12/2018 | Zhang et al. |
| 2019/0048060 A1 | 2/2019 | Conway et al. |
| 2019/0054122 A1 | 2/2019 | Moriarity et al. |
| 2019/0060363 A1 | 2/2019 | Moriarity et al. |
| 2019/0060364 A1 | 2/2019 | Moriarity et al. |
| 2019/0062735 A1 | 2/2019 | Welstead et al. |
| 2019/0125795 A1 | 5/2019 | Rosen et al. |
| 2019/0134095 A1 | 5/2019 | Stassinopoulos et al. |
| 2019/0136261 A1 | 5/2019 | Conway et al. |
| 2019/0144828 A1 | 5/2019 | Ng et al. |
| 2019/0153389 A1 | 5/2019 | Ffischkoff et al. |
| 2019/0271005 A1 | 9/2019 | Valamehr et al. |
| 2019/0309259 A1 | 10/2019 | Meissner et al. |
| 2019/0330592 A1 | 10/2019 | Hariri et al. |
| 2019/0345491 A1 | 11/2019 | Zhao et al. |
| 2019/0365812 A1 | 12/2019 | Sutlu et al. |
| 2019/0365876 A1 | 12/2019 | Russell et al. |
| 2019/0376036 A1 | 12/2019 | Dipierro |
| 2019/0376045 A1 | 12/2019 | Schrepfer et al. |
| 2019/0381154 A1 | 12/2019 | Russell et al. |
| 2020/0024342 A9 | 1/2020 | Ma et al. |
| 2020/0069734 A1 | 3/2020 | Valamehr et al. |
| 2020/0078402 A1 | 3/2020 | Ostertag et al. |
| 2020/0080059 A1 | 3/2020 | Thomson et al. |
| 2020/0085872 A1 | 3/2020 | Rezvani et al. |
| 2020/0095543 A1 | 3/2020 | Bhattacharya et al. |
| 2020/0095544 A1 | 3/2020 | Boehm et al. |
| 2020/0095604 A1 | 3/2020 | Valamehr et al. |
| 2020/0123501 A1 | 4/2020 | Vodyanyk et al. |
| 2020/0131475 A1 | 4/2020 | Kimbrel et al. |
| 2020/0157503 A1 | 5/2020 | Lanza et al. |
| 2020/0163992 A1 | 5/2020 | Metelitsa et al. |
| 2020/0181573 A1 | 6/2020 | Rosen et al. |
| 2020/0208111 A1 | 7/2020 | Moriarity et al. |
| 2020/0255494 A1 | 8/2020 | Pule et al. |
| 2020/0263133 A1 | 8/2020 | Van Dijk et al. |
| 2020/0281977 A1 | 9/2020 | Mantovani et al. |
| 2020/0289564 A1 | 9/2020 | Patakas et al. |
| 2020/0306310 A1 | 10/2020 | Moriarity et al. |
| 2020/0309776 A1 | 10/2020 | Hantash |
| 2020/0332255 A1 | 10/2020 | Lee et al. |
| 2020/0354673 A1 | 11/2020 | Schrepfer et al. |
| 2020/0407458 A1 | 12/2020 | Chmielewski et al. |
| 2020/0407686 A1 | 12/2020 | Campana et al. |
| 2020/0407713 A1 | 12/2020 | Lim et al. |
| 2020/0407728 A1 | 12/2020 | Zhao et al. |
| 2021/0015859 A1 | 1/2021 | Valamehr et al. |
| 2021/0024884 A1 | 1/2021 | Chaplin et al. |
| 2021/0032664 A1 | 2/2021 | Bartsevich et al. |
| 2021/0040449 A1 | 2/2021 | Gschweng et al. |
| 2021/0062151 A1 | 3/2021 | Valamehr et al. |
| 2021/0087537 A1 | 3/2021 | Valamehr et al. |
| 2021/0106622 A1 | 4/2021 | Metelitsa et al. |
| 2021/0106655 A1 | 4/2021 | Qu et al. |
| 2021/0145883 A1 | 5/2021 | Kaufman et al. |
| 2021/0161971 A1 | 6/2021 | Nagy et al. |
| 2021/0163622 A1 | 6/2021 | Valamehr et al. |
| 2021/0180017 A1 | 6/2021 | Valamehr et al. |
| 2021/0187025 A1 | 6/2021 | Dipierro et al. |
| 2021/0198342 A1 | 7/2021 | Boissel et al. |
| 2021/0207100 A1 | 7/2021 | Mostoslavsky et al. |
| 2021/0220403 A1 | 7/2021 | Metelitsa et al. |
| 2021/0222126 A1 | 7/2021 | Valamehr et al. |
| 2021/0230243 A1 | 7/2021 | Desjarlais et al. |
| 2021/0230548 A1 | 7/2021 | Daher et al. |
| 2021/0260117 A1 | 8/2021 | Moriarity et al. |
| 2021/0268087 A1 | 9/2021 | Odunsi et al. |
| 2021/0292715 A1 | 9/2021 | Schrepfer et al. |
| 2021/0308183 A1 | 10/2021 | Schrepfer et al. |

FOREIGN PATENT DOCUMENTS

| | | |
|---|---|---|
| EP | 3692794 A1 | 8/2020 |
| EP | 3693384 A1 | 8/2020 |
| EP | 3699268 A1 | 8/2020 |
| EP | 3380117 B1 | 1/2021 |
| EP | 3783098 A1 | 2/2021 |
| EP | 3805371 A1 | 4/2021 |
| EP | 3712268 A4 | 3/2022 |
| WO | 2010/099539 A1 | 9/2010 |
| WO | 2016/183041 A2 | 11/2016 |
| WO | 2016/209021 A1 | 12/2016 |
| WO | 2017/078807 A1 | 5/2017 |
| WO | 2017/079673 A1 | 5/2017 |
| WO | 2017/100861 A1 | 6/2017 |
| WO | 2017/152015 A1 | 9/2017 |
| WO | 2017/193177 A1 | 11/2017 |
| WO | 2017/222593 A1 | 12/2017 |
| WO | 2018/227286 A1 | 12/2018 |
| WO | 2019/068099 A1 | 4/2019 |
| WO | 2019/112899 A2 | 6/2019 |
| WO | 2019/118516 A1 | 6/2019 |
| WO | 2019/143292 A1 | 7/2019 |
| WO | 2019/209991 A1 | 10/2019 |
| WO | 2019/213517 A1 | 11/2019 |
| WO | 2019/213610 A1 | 11/2019 |
| WO | 2019/217956 A1 | 11/2019 |
| WO | 2019/229109 A1 | 12/2019 |
| WO | 2020/007593 A1 | 1/2020 |
| WO | 2020/012033 A1 | 1/2020 |
| WO | 2020/018620 A1 | 1/2020 |
| WO | 2020/086889 A1 | 4/2020 |
| WO | 2020/096646 A1 | 5/2020 |
| WO | 2020/097164 A1 | 5/2020 |
| WO | 2020/097346 A1 | 5/2020 |
| WO | 2020/112870 A1 | 6/2020 |
| WO | 2020/113029 A2 | 6/2020 |
| WO | 2020/117526 A1 | 6/2020 |
| WO | 2020/118447 A1 | 6/2020 |
| WO | 2020/150534 A2 | 7/2020 |
| WO | 2020/154412 A1 | 7/2020 |
| WO | 2020/168300 A1 | 8/2020 |
| WO | 2020/168317 A2 | 8/2020 |
| WO | 2020/172555 A1 | 8/2020 |
| WO | 2020/198128 A1 | 10/2020 |
| WO | 2020/209759 A2 | 10/2020 |
| WO | 2020/228039 A1 | 11/2020 |
| WO | 2020/247392 A1 | 12/2020 |
| WO | 2020/252303 A1 | 12/2020 |
| WO | 2020/260563 A1 | 12/2020 |
| WO | 2021/011936 A2 | 1/2021 |
| WO | 2021/016606 A1 | 1/2021 |
| WO | 2021/016609 A1 | 1/2021 |
| WO | 2021/022223 A1 | 2/2021 |
| WO | 2021/027795 A1 | 2/2021 |
| WO | 2021/041316 A1 | 3/2021 |
| WO | 2021/055985 A1 | 3/2021 |
| WO | 2021/062227 A2 | 4/2021 |
| WO | 2021/062281 A2 | 4/2021 |
| WO | 2021/071962 A1 | 4/2021 |
| WO | 2021/072302 A1 | 4/2021 |
| WO | 2021/077117 A1 | 4/2021 |
| WO | 2021/092252 A1 | 5/2021 |
| WO | 2021/092581 A1 | 5/2021 |
| WO | 2021/097521 A1 | 5/2021 |
| WO | 2021/102324 A1 | 5/2021 |
| WO | 2021/113577 A1 | 6/2021 |

(56) References Cited

FOREIGN PATENT DOCUMENTS

| WO | 2021/127594 A1 | 6/2021 |
|---|---|---|
| WO | 2021/146719 A1 | 7/2021 |
| WO | 2021/222928 A1 | 11/2021 |

OTHER PUBLICATIONS

Cao et al., "Differentiation and Functional Comparison of Monocytes and Macrophages from hiPSCs with Peripheral Blood Derivatives", Stem Cell Reports, Jun. 11, 2019, pp. 1282-1297, vol. 12.

Ceccaldi et al., "Homologous recombination-deficient tumors are hyper-dependent on Polθ-mediated repair", Nature, Feb. 2015, pp. 258-262, vol. 518.

Chadwick et al., "Cytokines and BMP-4 promote hematopoietic differentiation of human embryonic stem cells", Blood, Aug. 1, 2003, pp. 906-915, vol. 102, No. 3.

Chang et al., "A Chimeric Receptor with NKG2D Specificity Enhances Natural Killer Cell Activation and Killing of Tumor Cells", Cancer Research, Mar. 15, 2013, pp. 1777-1786, vol. 73, No. 6.

Chen et al., "Small molecule-mediated disruption of Wnt-dependent signaling in tissue regeneration and cancer", Nat Chem Biol., Feb. 2009, pp. 100-107, vol. 5, No. 2.

Chen et al., "Pharmacological inhibition of porcupine induces regression of experimental skin fibrosis by targeting Wnt signalling", Ann Rheum Dis., Feb. 2017, pp. 773-778, vol. 76, No. 4.

Cho et al., "DNA repair: Familiar ends with alternative endings", Nature, Feb. 2015, pp. 174-176, vol. 518.

Cichocki et al., "iPSC-derived NK cells maintain high cytotoxicity and enhance in vivo tumor control in concert with T cells and anti-PD-1 therapy", Sci Transl Med., Nov. 2020, 30 pgs., vol. 12.

Cox et al., "Therapeutic Genome Editing: Prospects and Challenges", Nature Medicine, Feb. 2015, pp. 121-131, vol. 21, No. 2.

Davidson et al., "Turning Mesoderm into Blood: The Formation of Hematopoietic Stem Cells during Embryogenesis", Current Topics in Developmental Biology, 2000, pp. 45-60, vol. 50.

Delconte et al., "CIS is a potent checkpoint in NK cell-mediated tumor immunity", Nature Immunology, Jul. 2016, pp. 816-824, vol. 17, No. 7.

Deng et al., "Transcription Factor Foxo1 Is a Negative Regulator of Natural Killer Cell Maturation and Function", Immunity, Mar. 17, 2015, pp. 457-470, vol. 42.

Dodge et al., "Diverse Chemical Scaffolds Support Direct Inhibition of the Membrane-Bound O-Acyltransferase Porcupine", Journal of Biological Chemistry, Jun. 29, 2012, pp. 23246-23254, vol. 287, No. 27.

Drexler et al., "FLT3: Receptor and Ligand", Growth Factors, Jun. 2004, pp. 71-73, vol. 22, No. 2.

Duraiswamy et al., "Discovery and Optimization of a Porcupine Inhibitor", Journal of Medicinal Chemistry, 2015, 11 pgs., vol. 58.

Enblad et al., "CAR T-Cell Therapy: The Role of Physical Barriers and Immunosuppression in Lymphoma", Human Gene Therapy, 2015, pp. 498-505, vol. 26, No. 8.

Gornalusse et al., "HLA-E-expressing pluripotent stem cells escape allogeneic responses and lysis by NK cells", Nature Biotechnology, 2017, p. 765-773, vol. 35.

Guo et al., "Immunobiology of the IL-15/IL-15Rα complex as an antitumor and antiviral agent", Cytokine and Growth Factor Reviews, 2017, pp. 10-21, vol. 38.

Guo et al., "Structure-based rational design of a novel chimeric PD1-NKG2D receptor for natural killer cells", Molecular Immunology, 2019, pp. 108-113, vol. 114.

Hagn et al., "A Colorimetric Assay that Specifically Measures Granzyme B Proteolytic Activity: Hydrolysis of Boc-Ala-Ala-Asp-S-Bzl", Journal of Visualized Experiments, Nov. 2014, e52419, pp. 1-9, vol. 93.

Han et al., "Generation of hypoimmunogenic human pluripotent stem cells", PNAS, May 2019, pp. 10441-10446, vol. 116, No. 21.

Huber et al., "Cooperative Effects of Growth Factors Involved in the Induction of Hematopoietic Mesoderm", Blood, Dec. 1, 1998, pp. 4128-4137, vol. 92, No. 11.

Hurton et al., "Tethered IL-15 augments antitumor activity and promotes a stem-cell memory subset in tumor-specific T cells", PNAS, Nov. 14, 2016, pp. E7788-E7797, vol. 113, No. 48.

Mai et al., "Genetic modification of primary natural killer cells overcomes inhibitory signals and induces specific killing of leukemic cells", Blood, Jul. 2005, pp. 376-383, vol. 106, No. 1.

Jackson et al., "Differentiating Embryonic Stem Cells Pass through 'Temporal Windows' That Mark Responsiveness to Exogenous and Paracrine Mesendoderm Inducing Signals", PLoS ONE, May 2010, e10706, pp. 1-12, vol. 5, No. 5.

Jiang et al., "Inactivating mutations of RNF43 confer Wnt dependency in pancreatic ductal adenocarcinoma", PNAS, Jul. 2013, pp. 12649-12654, vol. 110, No. 31.

Kakarla et al., "CAR T cells for solid tumors: armed and ready to go?", Cancer Journal, 2014, pp. 151-155, vol. 20.

Kent et al., "Mechanism of Microhomology-Mediated End-Joining Promoted by Human DNA Polymerase θ", Nature Structural and Molecular Biology, Mar. 2015, pp. 230-237, vol. 22.

Kiselyov et al., "Structural Basis for a Direct Interaction between FGFR1 and NCAM and Evidence for a Regulatory Role of ATP", Structure, Jun. 2003, pp. 691-701, vol. 11.

Kitajima et al., "GSK3β inhibition activates the CDX/HOX pathway and promotes hemogenic endothelial progenitor differentiation from human pluripotent stem cells", Experimental Hematology, 2016, pp. 68-74, vol. 44.

Lin et al., "Synthetic peptide F2A4-K-NS mimics fibroblast growth factor-2 in vitro and is angiogenic in vivo", International Journal of Molecular Medicine, 2006, pp. 833-839, vol. 17.

Liu et al., "Targeting Wnt-driven cancer through the inhibition of Porcupine by LGK974", PNAS, Dec. 2013, pp. 20224-20229, vol. 110, No. 50.

Ludwig et al., "Derivation of human embryonic stem cells in defined conditions", Nature Biotechnology, Feb. 2006, pp. 185-187, vol. 24, No. 2.

Madan et al., "Wnt addiction of genetically defined cancers reversed by PORCN inhibition", Oncogene, 2016, pp. 2197-2207, vol. 35.

Marshall et al., "Polarized expression of bone morphogenetic protein-4 in the human aorta-gonad-mesonephros region", Blood, Aug. 2000, pp. 1591-1593, vol. 96, No. 4.

Mateos-Gomez et al., "Mammalian Polymerase θ Promotes Alternative-NHEJ and Suppresses Recombination", Nature, Feb. 2015, pp. 254-257, vol. 518.

Matsubara et al., "Induction of human pluripotent stem cell-derived natural killer cells for immunotherapy under chemically defined conditions", Biochemical and Biophysical Research Communications, 2019, pp. 1-8, vol. 515.

Maude et al., "CD19-targeted chimeric antigen receptor T-cell therapy for acute lymphoblastic leukemia", Blood, Jun. 2015, pp. 4017-4023, vol. 125, No. 26.

Mishra et al., "Anti-ADAM17 monoclonal antibody MEDI3622 increases IFNγ production by human NK cells in the presence of antibody-bound tumor cells", Cancer Immunol Immunother., Sep. 2018, pp. 1407-1416, vol. 67.

Ng et al., "A protocol describing the use of a recombinant protein-based, animal product-free medium (APEL) for human embryonic stem cell differentiation as spin embryoid bodies", Nature Protocols, 2008, pp. 768-776, vol. 3, No. 5.

Poulsen et al., "A Pharmacophore Model for Wnt/Porcupine Inhibitors and its Use for Drug Design", Journal of Chemical Information and Modeling, 2015, pp. 1-49, vol. 55.

Proffitt et al., "Pharmacological Inhibition of the Wnt Acyltransferase PORCN Prevents Growth of WNT-Driven Mammary Cancer", Cancer Research, Jan. 2013, pp. 502-507, vol. 73.

Ratajczak et al., "Effect of basic (FGF-2) and acidic (FGF-1) fibroblast growth factors on early haemopoietic cell development", British Journal of Haematology, 1996, pp. 772-782, vol. 93.

Rautela et al., "Therapeutic blockade of Activin-A improves NK cell function and anti-tumor immunity", Sci Signal., 2019, pp. 1-54, vol. 12.

(56) References Cited

OTHER PUBLICATIONS

Savoldo et al., "CD28 costimulation improves expansion and persistence of chimeric antigen receptor-modified T cells in lymphoma patients". The Journal of Clinical Investigation, May 2011, pp. 1822-1826, vol. 121, No. 5.

Uenishi et al., "Tenascin C Promotes Hematoendothelial Development and T Lymphoid Commitment from Human Pluripotent Stem Cells in Chemically Defined Conditions", Stem Cell Reports, Dec. 2014, pp. 1073-1084, vol. 3.

Van der Stegen et al., "The pharmacology of second-generation chimeric antigen receptors", Nature Reviews, Drug Discovery, Jul. 2015, pp. 499-509, vol. 14.

Wang et al., "The Development of Highly Potent Inhibitors for Porcupine", J Med Chem., Mar. 2013, pp. 2700-2704, vol. 56.

Wu et al., "Role of ADAM17 as a regulatory checkpoint of CD16A in NK cells and as a potential target for cancer mmunotherapy", Journal of Leukocyte Biology, 2019, pp. 1297-1303, vol. 105.

Xie et al., "CAR-NK cells: A promising cellular immunotherapy for cancer", EBioMedicine, 2020,102975, pp. 1-10, vol. 59.

Zhu et al., "An Improved Method to Produce Clinical-Scale Natural Killer Cells from Human Pluripotent Stem Cells", Methods in Molecular Biology, 2019, pp. 107-119, vol. 2048.

Zhu et al., "Metabolic reprograming via deletion of CISH in human iPSC-derived NK cells promotes in vivo persistence and enhances anti-tumor activity", Cell Stem Cell, Aug. 2020, pp. 224-237, vol. 27.

International Search Report and Written Opinion relating to International Application No. PCT/IB2021/061148, dated Feb. 22, 2022; 17 pgs.

International Search Report and Written Opinion relating to International Application No. PCT/IB2021/061150, dated Mar. 7, 2022; 17 pgs.

Harding et al., "Induction of long-term allogeneic cell acceptance and formation of immune privileged tissue in immunocompetent hosts", Jul. 30, 2019, pp. 1-34; XP055718117, DOI: 10.1101/716571. Retrieved from the Internet: URL:https://www.biorxiv.org/content/10.1101/716571v1.full.pdf (retrieved Jul. 27, 2020).

Lanza et al., "Engineering universal cells that evade immune detection", Nature Reviews/ Immunology, Dec. 2019, pp. 723-733, vol. 19.

Zhao et al., "Strategies for Genetically Engineering Hypoimmunogenic Universal Pluripotent Stem Cells", iScience, Jun. 2020, 101162, pp. 1-9, vol. 23.

US 11,591,381 B2

GENE-EDITED NATURAL KILLER CELLS

CROSS-REFERENCE TO RELATED APPLICATIONS

This application claims the benefit of U.S. Provisional Application No. 63/119,512, filed Nov. 30, 2020, U.S. Provisional Application No. 63/214,134, filed Jun. 23, 2021, and U.S. Provisional Application No. 63/250,048, filed Sep. 29, 2021, the disclosure of each is hereby incorporated by reference in its entirety.

INCORPORATION BY REFERENCE OF SEQUENCE LISTING

This application contains a Sequence Listing that has been submitted in ASCII format via EFS-Web and is hereby incorporated by reference in its entirety. The ASCII copy, created on Nov. 24, 2021, is named 100867-707586_CT150-US2_Sequence_Listing.txt, and is about 251,000 bytes in size.

FIELD OF THE INVENTION

The invention relates to the field of gene-edited iPSC and Natural Killer (NK) cells.

BACKGROUND

There is a need for adoptive cell therapy that does not rely on the use of cells obtained from patients or donors and does not induce allogeneic rejection. Natural Killer (NK) cells are potent anti-tumor effectors, making them attractive candidates for cancer immunotherapy. However, the use of NK cells, in particular NK cells expressing a chimeric antigen receptor (CAR), for adoptive cell therapy remains to be challenging. For example, there is a need to improve the efficacy, persistence, cytotoxic activity, immune evasion and tumor targeting of therapeutic NK cells. There is also a need for a uniform pool of therapeutic NK cells that can be manufactured in a consistent manner for use in any patients in need thereof.

SUMMARY OF THE INVENTION

In some aspects, the present disclosure provides engineered cells that have been edited using, for example, CRISPR/Cas9 gene editing technology, to prevent alloimmune responses, be immune evasive, have increased survival and persistence, increased activation, and/or specific cell targeting.

In some aspects, the present disclosure provides engineered cells comprising (a) a disrupted beta-2-microglobulin (B2M) gene, and (b) an insertion of a first polynucleotide and a second polynucleotide in the disrupted B2M gene, the first polynucleotide encoding a SERPINB9 protein and the second polynucleotide encoding a fusion protein of interleukin 15 (IL15) and interleukin 15 receptor subunit alpha (IL15Rα), wherein the cells express the SERPINB9 protein and the fusion protein of IL15 and IL15Rα, and the cells have disrupted expression of B2M. In some embodiments, the engineered cells comprise a disrupted Class II major histocompatibility complex transactivator (CIITA) gene, wherein the cells have disrupted expression of CIITA. In still other embodiments, the engineered cells further comprise an insertion of a third polynucleotide encoding a chimeric antigen receptor (CAR), wherein the cells express the CAR.

In additional embodiments, the engineered cells further comprise an insertion of a fourth polynucleotide encoding a human leukocyte antigen E (HLA-E) trimer, and the cells further express the HLA-E trimer. In other embodiments, the engineered cells further comprise a disrupted cytokine-inducible SH2-containing protein (CISH) gene, wherein the cells have disrupted expression of CISH. In still other embodiments, the engineered cells further comprise a disrupted Fas cell surface death receptor (FAS) gene, wherein the cells have disrupted expression of FAS.

In further aspects, the present disclosure provides an in vitro method for generating an engineered cell, the method comprising delivering to a cell: (a) a first RNA-guided nuclease and a first guide RNA (gRNA) targeting a target site in a B2M gene locus; (b) a first vector comprising a nucleic acid, the nucleic acid comprising: (i) nucleotide sequence encoding a SERPINB9 protein and a nucleotide sequence encoding a fusion protein of IL15 and IL15Rα; (ii) a nucleotide sequence having sequence homology with a genomic region located left of the target site in the B2M gene locus; and (iii) a nucleotide sequence having sequence homology with a genomic region located right of the target site in the B2M gene locus, wherein (i) is flanked by (ii) and (iii); wherein the B2M gene locus is cleaved at the target site and the nucleotide sequences encoding the SERPINB9 protein and the fusion protein of IL15 and IL15Rα are inserted into the B2M gene locus, thereby disrupting the B2M gene. In some embodiments, the method further comprising delivering to the cell: (c) a second RNA-guided nuclease and a second gRNA targeting a target site in a CIITA gene locus; and (d) a second vector comprising a nucleic acid, the nucleic acid comprising: (i) a nucleotide sequence encoding a chimeric antigen receptor (CAR); (ii) a nucleotide sequence having sequence homology with a genomic region located left of the target site in the CIITA gene locus; and (iii) a nucleotide sequence having sequence homology with a genomic region located right of the target site in the CIITA gene locus, wherein (i) is flanked by (ii) and (iii); and wherein the CIITA gene locus is cleaved at the target site and the nucleotide sequence encoding the CAR is inserted into the CIITA gene locus, thereby disrupting the CIITA gene. In some embodiments, the nucleotide sequence of (d)(i) further comprises a nucleotide sequence encoding an HLA-E trimer. In some embodiments, the method further comprises delivering to the cell a third RNA-guided nuclease and a third gRNA targeting a target site in a CISH gene locus; wherein the CISH gene locus is cleaved at the target site and at least one insertion-deletion mutation is introduced into the CISH gene, thereby disrupting the CISH gene. In some embodiments, the method further comprises delivering to the cell a fourth RNA-guided nuclease and a fourth gRNA targeting a target site in a FAS gene locus, wherein the FAS gene locus is cleaved at the target site and at least one insertion-deletion mutation is introduced into the FAS gene, thereby disrupting the FAS gene.

In further aspects, the present disclosure provides a plurality of any of the engineered cells described herein. The present disclosure also provides compositions comprising any of the engineered cells disclosed herein or cells derived from or obtained from any of the engineered cells disclosed herein, wherein any of the composition is used as a medicament. In some embodiments, any of the compositions disclosed herein is for use in treating cancer.

In some aspects, the present disclosure provides a method for treating of a subject in need thereof, the method comprising: (a) obtaining or having obtained the plurality of engineered cells described herein following differentiation into lineage-restricted progenitor cells or fully differentiated somatic cells; and (b) administering the lineage-restricted progenitor cells or fully differentiated somatic cells to the subject.

Other aspects and iterations of the present disclosure are detailed below.

BRIEF DESCRIPTION OF THE DRAWINGS

FIG. 10 provides an image of an agarose gel demonstrating B2M indels. Clones with a band at 573 bp demonstrate a WT, unedited or heterozygous genotype. Clones with no band demonstrate a clone with successful knock-in.

DETAILED DESCRIPTION OF THE INVENTION

Figure 1:
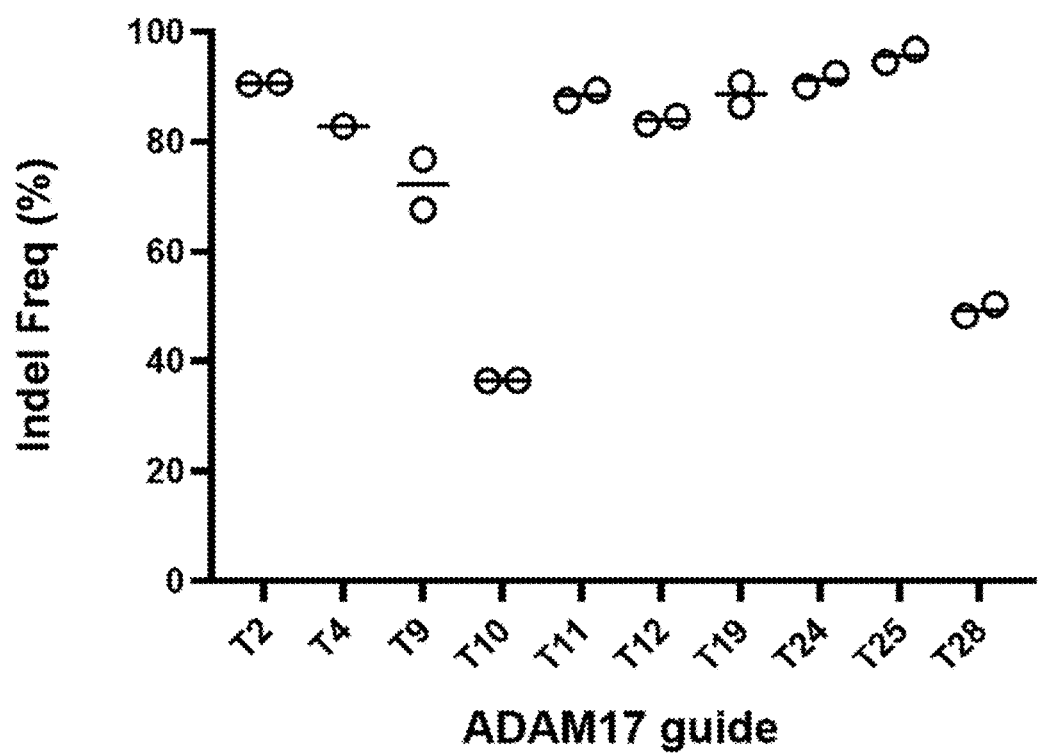
FIG. 1 provides a graph showing the cutting efficiency of 10 ADAM17 guides. Inducible pluripotent stem cells (iPSC) were electroporated with ADAM17 gRNA and sequenced to measured indel frequency.

The present disclosure provides compositions of engineered stem cells (e.g., iPSCs), and lineage-restricted progenitor cells or fully differentiated somatic cells derived therefrom (e.g., hematopoietic cells such as NK cells, in particular, human NK cells).

In certain embodiments, the engineered cells described herein evade immune response and/or survive following engraftment into a subject at higher success rates than an unmodified cell. In some embodiments, the engineered cells are hypoimmunogenic. In some embodiments, the engineered cells have improved persistency, (ii) improved immune evasiveness, (iii) improved cytotoxic activity, (iv) improved ADCC activity, and/or (v) improved anti-tumor activity as compared to a unmodified or wild-type cell, e.g., a wild-type iPSC or a wild-type NK cell.

In some embodiments, the engineered cells lack a functional major histocompatibility complex (MHC). In some embodiments, the engineered cells described herein are gene-edited to disrupt one or more of the genes of an MHC-I or MHC-II complex.

In some embodiments, the engineered cells have a disrupted B2M gene and have a reduced expression of B2M (e.g., express less than 30%, less than 25%, less than 20%, less than 10%, less than 5% of the level of an unmodified cell) or eliminated expression of B2M (e.g., do not express a detectable level of level of B2M).

In some embodiments, the engineered cells have a disrupted CIITA gene and have a reduced expression of CIITA (e.g., express less than 30%, less than 25%, less than 20%, less than 10%, less than 5% of the level of an unmodified cell) or eliminated expression of CIITA (e.g., do not express a detectable level of CIITA).

In some embodiments, the engineered cells have a disrupted ADAM17 gene and have a reduced expression of ADAM17 (e.g., express less than 30%, less than 25%, less than 20%, less than 10%, less than 5% of the level of an unmodified cell) or eliminated expression of ADAM17 (e.g., do not express a detectable level of ADAM17).

In some embodiments, the engineered cells have a disrupted FAS gene and have a reduced expression of FAS (e.g., express less than 30%, less than 25%, less than 20%, less than 10%, less than 5% of the level of an unmodified cell) or eliminated expression of FAS (e.g., do not express a detectable level of FAS).

In some embodiments, the engineered cells have a disrupted CISH gene and have a reduced expression of CISH (e.g., express less than 30%, less than 25%, less than 20%, less than 10%, less than 5% of the level of an unmodified cell) or eliminated expression of CISH (e.g., do not express a detectable level of CISH).

In some embodiments, the engineered cells have a disrupted REGNASE-1 gene and have a reduced expression of REGNASE-1 (e.g., express less than 30%, less than 25%, less than 20%, less than 10%, less than 5% of the level of an unmodified cell) or eliminated expression of REGNASE-1 (e.g., do not express a detectable level of REGNASE-1).

In some embodiments, the genome of the engineered cells has a disrupted B2M gene and one or more inserted polynucleotide(s) encoding one or all of: SERPINB9, IL15, IL15Rα, and HLA-E. In certain embodiments, the one or more inserted polynucleotide encodes a fusion protein of IL15 and IL15Rα ("IL15/IL15Rα") and an HLA-E trimer comprising a B2M signal peptide fused to an HLA-G presentation peptide fused to the B2M membrane protein fused to the HLA-E protein without a signal peptide. In certain embodiments, the one or more inserted polynucleotide encodes SERPINB9 and a fusion protein of IL15 and IL15Rα. The inserted polynucleotide(s) can be inserted in the disrupted B2M gene locus (e.g., in exon 1 of the B2M gene locus).

In some embodiments, the genome of the engineered cells has a disrupted CIITA gene and one or more inserted polynucleotide(s) encoding one or more CARs (e.g., a BCMA CAR or a CD30 CAR). The inserted polynucleotide(s) can be inserted in the disrupted CIITA gene locus (e.g., in exon 2 of the CIITA gene locus).

In some embodiments, the genome of the engineered cells has a disrupted CIITA gene and one or more inserted polynucleotide(s) encoding CAR and/or HLA-E trimer. In some embodiments, the one or more inserted polynucleotide(s) encodes a CAR (e.g., a CD30 CAR) and HLA-E trimer. The inserted polynucleotide(s) can be inserted in the disrupted CIITA gene locus (e.g., in exon 2 of the CIITA gene locus).

In some embodiments, the genome of the engineered cells has one or more disrupted genes encoding a component of a MHC-I or MHC-II complex, a disrupted ADAM17, and one or more inserted polynucleotide(s) encoding one or more CARs (e.g., a BCMA CAR or a CD30 CAR).

In some embodiments, the genome of the engineered cells has one, two, three, four or all of the following gene edits: (i) a disrupted B2M gene; (ii) one or more inserted polynucleotide(s) encoding one or all of: SERPINB9, IL15/IL15Rα, and HLA-E (e.g., a polynucleotide encoding a fusion protein of IL15 and IL15Rα and an HLA-E trimer comprising a B2M signal peptide fused to an HLA-G presentation peptide fused to the B2M membrane protein fused to the HLA-E protein without a signal peptide, or a polynucleotide encoding SERPINB9 and fusion protein of IL15 and IL15Rα); (iii) a disrupted CIITA gene; (iv) one or more inserted polynucleotide(s) encoding one or more CARs (e.g., a BCMA CAR or a CD30 CAR); and (v) a disrupted ADAM17 gene. In some embodiments, the engineered cell further comprises a disrupted FAS, CISH, and/or REGNASE-1 gene.

In some embodiments, the genome of the engineered cells comprises (a) a disrupted B2M gene; (b) an insertion of a first polynucleotide and a second polynucleotide in the disrupted B2M gene, the first polynucleotide encoding a SERPINB9 protein and the second polynucleotide encoding a fusion of IL15 and IL15Rα; (c) a disrupted CIITA gene; (d) an insertion of a third polynucleotide and a fourth polynucleotide in the disrupted CIITA gene, the third polynucleotide encoding a CAR and the fourth polynucleotide encoding an HLA-E trimer; (e) a disrupted CISH gene; and (f) a disrupted FAS gene.

In some embodiments, the engineered cells described herein are stem cells. In some embodiments, the engineered cells described herein are iPSCs. In some embodiments, the engineered cells described herein are mesodermal cells. In some embodiments, the engineered cells described herein are hemogenic endothelium (HE) cells (e.g., definitive hemogenic endothelium cells). In some embodiments, the engineered cells described herein are hematopoietic stem or progenitor cells (HSPCs) (e.g., definitive hematopoietic stem or progenitor cells). In some embodiments, the engineered cells described herein are common lymphoid progenitor (CLP) cells. In some embodiments, the engineered cells described herein are NK progenitor cells. In some embodiments, the engineered cells described herein are immature NK cells. In some embodiments, the engineered cells described herein are NK cells. In some embodiments, the engineered cells described herein are fully differentiated hematopoietic cells (e.g., NK cells). In some embodiments, stem cells (e.g., iPSCs) are gene-edited as described herein and then differentiated into one, two, three, four, five, six or more of the following cell types: mesodermal cells, HE cells, HSPCs, CLP cells, NK progenitor cells, immature NK cells and NK cells. In some embodiments, the differentiated cells maintain all edits made in the cells from which they were derived (e.g., NK cells maintain all edits of gene-edited stem cells (e.g., iPSC cells) from which they were derived. In some embodiments, the engineered cells described herein are CD34$^+$ cells. In some embodiments, the engineered cells described herein are multipotent progenitors (MPP). In some embodiments, the engineered cells described herein are common lymphoid progenitor cells. In some embodiments, the engineered cells described herein are T cell progenitors.

In some embodiments, a hematopoietic cell such as an NK cell (derived from an engineered stem cell) comprises the gene-edits described herein.

Definitions

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% compared to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or 1% about a reference quantity, level, value, number, frequency, percentage, dimension, size, amount, weight or length.

As used herein, the term "induced pluripotent stem cells" or, iPSCs, means that the stem cells are produced from differentiated adult, neonatal or fetal cells that have been induced or changed, i.e., reprogrammed into cells capable of differentiating into tissues of all three germ or dermal layers: mesoderm, endoderm, and ectoderm. The iPSCs produced do not refer to cells as they are found in nature.

The term "hematopoietic stem and progenitor cells," "hematopoietic stem cells," "hematopoietic progenitor cells," or "hematopoietic precursor cells" refers to cells which are committed to a hematopoietic lineage but are capable of further hematopoietic differentiation and include, multipotent hematopoietic stem cells (hematoblasts), myeloid progenitors, megakaryocyte progenitors, erythrocyte progenitors, and lymphoid progenitors. Hematopoietic stem and progenitor cells (HSCs) are multipotent stem cells that give rise to all the blood cell types including myeloid (monocytes and macrophages, neutrophils, basophils, eosinophils, erythrocytes, megakaryocytes/platelets, dendritic cells), and lymphoid lineages (T cells, B cells, NK cells). The term "definitive hematopoietic stem cell" as used herein, refers to CD34$^+$ hematopoietic cells capable of giving rise to both mature myeloid and lymphoid cell types including T cells, NK cells and B cells. Hematopoietic cells also include various subsets of primitive hematopoietic cells that give rise to primitive erythrocytes, megakarocytes and macrophages.

As used herein, the term "NK cell" or "Natural Killer cell" refer to a subset of peripheral blood lymphocytes defined by the expression of CD56 or CD16 and the absence of the T cell receptor (CD3). As used herein, the terms "adaptive NK cell" and "memory NK cell" are interchangeable and refer to a subset of NK cells that are phenotypically CD3- and CD56$^+$, expressing at least one of NKG2C and CD57, and optionally, CD16, but lack expression of one or more of the following: PLZF, SYK, FceRy, and EAT-2. In some embodiments, isolated subpopulations of CD56$^+$ NK cells comprise expression of CD16, NKG2C, CD57, NKG2D, NCR ligands, NKp30, NKp40, NKp46, activating and inhibitory KIRs, NKG2A and/or DNAM-1.

As used herein, the terms "disruption," "genetic modification" or "gene-edit" generally refer to a genetic modification wherein a site or region of genomic DNA is altered, e.g., by a deletion or insertion, by any molecular biology method, e.g., methods described herein, e.g., by delivering to a site of genomic DNA an endonuclease and at least one gRNA. Exemplary genetic modifications include insertions, deletions, duplications, inversions, and translocations, and combinations thereof. In some embodiments, a genetic modification is a deletion. In some embodiments, a genetic modification is an insertion. In other embodiments, a genetic modification is an insertion-deletion mutation (or indel), such that the reading frame of the target gene is shifted leading to an altered gene product or no gene product. As used herein, the term "engineered cell" refers to a cell with any disruption, genetic modification, or gene-edit.

As used herein, the term "deletion" which may be used interchangeably with the terms "genetic deletion", "knockout", or "KO", generally refers to a genetic modification wherein a site or region of genomic DNA is removed by any molecular biology method, e.g., methods described herein, e.g., by delivering to a site of genomic DNA an endonuclease and at least one gRNA. Any number of nucleotides can be deleted. In some embodiments, a deletion involves the removal of at least one, at least two, at least three, at least four, at least five, at least ten, at least fifteen, at least twenty, or at least 25 nucleotides. In some embodiments, a deletion involves the removal of 10-50, 25-75, 50-100, 50-200, or more than 100 nucleotides. In some embodiments, a deletion involves the removal of part of a target gene, e.g., all or part of a promoter and/or coding sequence of a B2M gene, a CIITA gene, a ADAM17 gene, a FAS gene, a CISH gene, and/or a REGNASE-1 gene. In some embodiments, a deletion involves the removal of an entire target gene, e.g., a B2M gene, a CIITA gene, a ADAM17 gene, a FAS gene, a CISH gene, and/or a REGNASE-1 gene. In some embodiments, a deletion involves the removal of a transcriptional regulator, e.g., a promoter region, of a target gene. In some embodiments, a deletion involves the removal of all or part of a coding region such that the product normally expressed by the coding region is no longer expressed, is expressed as a truncated form, or expressed at a reduced level. In some embodiments, a deletion leads to a decrease in expression of a gene relative to an unmodified cell. In some embodiments, the decrease in expression can be a reduced level of expression (e.g., express less than 30%, less than 25%, less than 20%, less than 10%, less than 5% of the level of an unmodified cell). In some embodiments, the decrease in expression can be eliminated expression (e.g., no expression or do not express a detectable level of RNA and/or protein). Expression can be measured using any standard RNA-based, protein-based, and/or antibody-based detection method (e.g., RT-PCR, ELISA, flow cytometry, immunocytochemistry, and the like). Detectable levels are defined as being higher that the limit of detection (LOD), which is the lowest concentration that can be measured (detected) with statistical significance by means of a given detection method.

As used herein, the term "endonuclease" generally refers to an enzyme that cleaves phosphodiester bonds within a polynucleotide. In some embodiments, an endonuclease specifically cleaves phosphodiester bonds within a DNA polynucleotide. In some embodiments, an endonuclease is a zinc finger nuclease (ZFN), transcription activator like effector nuclease (TALEN), homing endonuclease (HE), meganuclease, MegaTAL, or a CRISPR-associated endonuclease. In some embodiments, an endonuclease is a RNA-guided endonuclease. In certain aspects, the RNA-guided endonuclease is a CRISPR nuclease, e.g., a Type II CRISPR Cas9 endonuclease or a Type V CRISPR Cpf1 endonuclease. In some embodiments, an endonuclease is a Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease, or a homolog thereof, a recombination of the naturally occurring molecule thereof, a codon-optimized version thereof, or a modified version thereof, or combinations thereof. In some embodiments, an endonuclease may introduce one or more single-stranded breaks (SSBs) and/or one or more double-stranded breaks (DSBs).

As used herein, the term "guide RNA" or "gRNA" generally refers to short ribonucleic acid that can interact with, e.g., bind to, to an endonuclease and bind, or hybridize to a target genomic site or region. In some embodiments, a gRNA is a single-molecule guide RNA (sgRNA). In some embodiments, a gRNA may comprise a spacer extension region. In some embodiments, a gRNA may comprise a tracrRNA extension region. In some embodiments, a gRNA is single-stranded. In some embodiments, a gRNA comprises naturally occurring nucleotides. In some embodiments, a gRNA is a chemically modified gRNA. In some embodiments, a chemically modified gRNA is a gRNA that comprises at least one nucleotide with a chemical modification, e.g., a 2'-O-methyl sugar modification. In some embodiments, a chemically modified gRNA comprises a modified nucleic acid backbone. In some embodiments, a chemically modified gRNA comprises a 2'-O-methyl-phosphorothioate residue. In some embodiments, a gRNA may be pre-complexed with a DNA endonuclease.

As used herein, the term "insertion" which may be used interchangeably with the terms "genetic insertion" or "knock-in", generally refers to a genetic modification wherein a polynucleotide is introduced or added into a site or region of genomic DNA by any molecular biological method, e.g., methods described herein, e.g., by delivering to a site of genomic DNA an endonuclease and at least one gRNA. In some embodiments, an insertion may occur within or near a site of genomic DNA that has been the site of a prior genetic modification, e.g., a deletion or insertion-deletion mutation. In some embodiments, an insertion occurs at a site of genomic DNA that partially overlaps, completely overlaps, or is contained within a site of a prior genetic modification, e.g., a deletion or insertion-deletion mutation. In some embodiments, an insertion involves the introduction of a polynucleotide that encodes a protein of interest. In some embodiments, an insertion involves the introduction of a polynucleotide that encodes a tolerogenic factor (e.g., HLA-E), a CAR, a fusion protein of IL15 and ILRα, and/or SERPINB9. In some embodiments, an insertion involves the introduction of an exogenous promoter, e.g., a constitutive promoter, e.g., a CAG promoter. In some embodiments, an insertion involves the introduction of a polynucleotide that encodes a noncoding gene. In general, a polynucleotide to be inserted is flanked by sequences (e.g., homology arms) having substantial sequence homology with genomic DNA at or near the site of insertion.

As used herein, the terms "Major histocompatibility complex class I" or "MHC-I" generally refer to a class of biomolecules that are found on the cell surface of all nucleated cells in vertebrates, including mammals, e.g., humans; and function to display peptides of non-self or foreign antigens, e.g., proteins, from within the cell (i.e. cytosolic) to cytotoxic T cells, e.g., $CD8^+$ T cells, in order to stimulate an immune response. In some embodiments, a MHC-I biomolecule is a MHC-I gene or a MHC-I protein. Complexation of MHC-I proteins with beta-2 microglobulin (02M) protein is required for the cell surface expression of all MHC-I proteins. In some embodiments, decreasing the expression of a MHC-I human leukocyte antigen (HLA) relative to an unmodified cell involves a decrease (or reduction) in the expression of a MHC-I gene. In some embodiments, decreasing the expression of a MHC-I human leukocyte antigen (HLA) relative to an unmodified cell involves a decrease (or reduction) in the cell surface expression of a MHC-I protein. In some embodiments, a MHC-I biomolecule is HLA-A (NCBI Gene ID No: 3105), HLA-B (NCBI Gene ID No: 3106), HLA-C(NCBI Gene ID No: 3107), or B2M (NCBI Gene ID No: 567).

As used herein, the term "Major histocompatibility complex class II" or "MHC-II" generally refer to a class of biomolecules that are typically found on the cell surface of antigen-presenting cells in vertebrates, including mammals, e.g., humans; and function to display peptides of non-self or foreign antigens, e.g., proteins, from outside of the cell (extracellular) to cytotoxic T cells, e.g., $CD8^+$ T cells, in order to stimulate an immune response. In some embodiments, an antigen-presenting cell is a dendritic cell, macrophage, or a B cell. In some embodiments, a MHC-II biomolecule is a MHC-II gene or a MHC-II protein. In some embodiments, decreasing the expression of a MHC-II human leukocyte antigen (HLA) relative to an unmodified cell involves a decrease (or reduction) in the expression of a MHC-II gene. In some embodiments, decreasing the expression of a MHC-II human leukocyte antigen (HLA) relative to an unmodified cell involves a decrease (or reduction) in the cell surface expression of a MHC-II protein. In some embodiments, a MHC-II biomolecule is HLA-DPA (NCBI Gene ID No: 3113), HLA-DPB (NCBI Gene ID No: 3115), HLA-DMA (NCBI Gene ID No: 3108), HLA-DMB (NCBI Gene ID No: 3109), HLA-DOA (NCBI Gene ID No: 3111), HLA-DOB (NCBI Gene ID No: 3112), HLA-DQA (NCBI Gene ID No: 3117), HLA-DQB (NCBI Gene ID No: 3119), HLA-DRA (NCBI Gene ID No: 3122), or HLA-DRB (NCBI Gene ID No: 3123).

As used herein, the term "polynucleotide", which may be used interchangeably with the term "nucleic acid" generally refers to a biomolecule that comprises two or more nucleotides. In some embodiments, a polynucleotide comprises at least two, at least five at least ten, at least twenty, at least 30, at least 40, at least 50, at least 100, at least 200, at least 250, at least 500, or any number of nucleotides. A polynucleotide may be a DNA or RNA molecule or a hybrid DNA/RNA molecule. A polynucleotide may be single-stranded or double-stranded. In some embodiments, a polynucleotide is a site or region of genomic DNA. In some embodiments, a polynucleotide is an endogenous gene that is comprised within the genome of an unmodified cell or gene-edited iPSC. In some embodiments, a polynucleotide is an exogenous polynucleotide that is not integrated into genomic DNA. In some embodiments, a polynucleotide is an exogenous polynucleotide that is integrated into genomic DNA. In some embodiments, a polynucleotide is a plasmid or an adeno-associated viral vector. In some embodiments, a polynucleotide is a circular or linear molecule.

As used herein, the term "subject" refers to a mammal. In some embodiments, a subject is non-human primate or rodent. In some embodiments, a subject is a human. In some embodiments, a subject has, is suspected of having, or is at risk for, a disease or disorder. In some embodiments, a subject has one or more symptoms of a disease or disorder.

As used herein, the term "transcriptional regulator of MHC-I or MHC-II" generally refers to a biomolecule that modulates, e.g., increases or decreases, the expression of an MHC-I and/or MHC-II human leukocyte antigen. In some embodiments, a biomolecule is a polynucleotide, e.g., a gene, or a protein. In some embodiments, a transcriptional regulator of MHC-I or MHC-II will increase or decrease the cell surface expression of at least one MHC-I or MHC-II protein. In some embodiments, a transcriptional regulator of MHC-I or MHC-II will increase or decrease the expression of at least one MHC-I or MHC-II gene. In some embodiments, the transcriptional regulator is CIITA (NCBI Gene ID No: 4261) or NLRC5 (NCBI Gene ID No: 84166). In some embodiments, deletion or reduction of expression of CIITA or NLRC5 decreases expression of at least one MHC-I or MHC-II gene.

As used herein, the term "engineered cell" generally refers to a genetically modified cell that is less susceptible to allogeneic rejection during a cellular transplant and/or demonstrates increased survival after transplantation, relative to an unmodified cell. In some embodiments, a genetically modified cell as described herein is an engineered cell. In some embodiments, the engineered cell has increased immune evasion and/or cell survival compared to an unmodified cell. In some embodiments, the engineered cell has increased cell survival compared to an unmodified cell. In some embodiments, the engineered cell has improved persistency, (ii) improved immune evasiveness, (iii) improved cytotoxic activity, (iv) improved ADCC activity, and/or (v) improved anti-tumor activity compared to an unmodified cell. In some embodiments, an engineered cell may be a stem cell. In some embodiments, an engineered cell may be an embryonic stem cell (ESC), an adult stem cell (ASC), an induced pluripotent stem cell (iPSC), or a hematopoietic stem or progenitor cell (HSPC). In some embodiments, an engineered cell may be a differentiated cell. In some embodiments, an engineered cell may be a somatic cell (e.g., immune system cells). In some embodiments, an engineered cell is administered to a subject. In some embodiments, an engineered cell is administered to a subject who has, is suspected of having, or is at risk for a disease. In some embodiments, the engineered cell is capable of being differentiated into lineage-restricted progenitor cells or fully differentiated somatic cells. In some embodiments, the lineage-restricted progenitor cells are pancreatic endoderm progenitors, pancreatic endocrine progenitors, mesenchymal progenitor cells, muscle progenitor cells, blast cells, or neural progenitor cells. In some embodiments, the fully differentiated somatic cells are endocrine secretory cells such as pancreatic beta cells, epithelial cells, endodermal cells, macrophages, hepatocytes, adipocytes, kidney cells, blood cells, or immune system cells.

As used herein, the term "unmodified cell" refers to a cell that has not been subjected to a genetic modification involving a polynucleotide or gene that encodes any of the genes described herein. In some embodiments, an unmodified cell may be a stem cell. In some embodiments, an unmodified cell may be an embryonic stem cell (ESC), an adult stem cell (ASC), an induced pluripotent stem cell (iPSC), or a hematopoietic stem or progenitor cell (HSPC). In some embodiments, an unmodified cell may be a differentiated cell. In some embodiments, an unmodified cell may be selected from somatic cells (e.g., immune system cells, e.g., a T cell, e.g., a $CD8^+$ T cell). If a gene-edited iPSC or NK cell is compared "relative to an unmodified cell", the iPSC or NK cell and the unmodified cell are the same cell type or share a common parent cell line, e.g., a gene-edited NK cell is compared relative to an unmodified NK cell.

As used herein, the term "within or near a gene" refers to a site or region of genomic DNA that is an intronic or exonic component of a said gene or is located proximal to a said gene. In some embodiments, a site of genomic DNA is within a gene if it comprises at least a portion of an intron or exon of said gene. In some embodiments, a site of genomic DNA located near a gene may be at the 5' or 3' end of said gene (e.g., the 5' or 3' end of the coding region of said gene). In some embodiments, a site of genomic DNA located near a gene may be a promoter region or repressor region that modulates the expression of said gene. In some embodiments, a site of genomic DNA located near a gene may be on the same chromosome as said gene. In some embodiments, a site or region of genomic DNA is near a gene if it is within 50Kb, 40Kb, 30Kb, 20Kb, 10Kb, 5Kb, 1Kb, or closer to the 5' or 3' end of said gene (e.g., the 5' or 3' end of the coding region of said gene).

As used herein, the term "tolerogenic factor" generally refers to a protein (e.g., expressed by a polynucleotide as described herein) that, when increased or decreased in a cell, enables the cell, e.g., an engineered cell, to inhibit or evade immune rejection after transplantation or engraftment into a host subject at higher rates relative to an unmodified cell. In some embodiments, a tolerogenic factor is a human tolerogenic factor. In some embodiments, the genetic modification of at least one tolerogenic factor (e.g., the insertion or deletion of at least one tolerogenic factor) enables a cell, e.g., an engineered cell, to inhibit or evade immune rejection with rates at least 1.05, at least 1.1, at least 1.25, at least 1.5, at least 2, at least 3, at least 4, at least 5, at least 10, at least 20, or at least 50 times higher than an unmodified cell following engraftment. In some embodiments, a tolerogenic factor is HLA-E (NCBI Gene ID No: 3133), HLA-G (NCBI Gene ID No: 3135), CTLA-4 (NCBI Gene ID No: 1493), CD47 (NCBI Gene ID No: 961), or PD-L1 (NCBI Gene ID No: 29126). In some embodiments, a tolerogenic factor is inserted into a cell, e.g., an engineered cell. In some embodiments, a tolerogenic factor is deleted from a cell, e.g., an engineered cell. In some embodiments, an insertion of a polynucleotide that encodes HLA-E, HLA-G, CTLA-4, CD47, and/or PD-L1 enables a cell, e.g., an engineered cell, to inhibit or evade immune rejection after transplantation or engraftment into a host subject.

As used herein, the term "comprising" or "comprises" is inclusive or open-ended and does not exclude additional, unrecited elements, ingredients, or method steps; the phrase "consisting of" or "consists of" is closed and excludes any element, step, or ingredient not specified; and the phrase "consisting essentially of" or "consists essentially" means that specific further components can be present, namely those not materially affecting the essential characteristics of the compound, composition, or method. When used in the context of a sequence, the phrase "consisting essentially of" or "consists essentially" means that the sequence can comprise substitutions and/or additional sequences that do not change the essential function or properties of the sequence.

Gene Editing

Described herein are strategies to enable genetically modified cells to evade immune response and/or increase their survival, or viability following engraftment into a subject. In some embodiments, these strategies enable gene-edited cells to evade immune response and/or survive at higher success rates than an unmodified cell.

In certain embodiments, any cells described herein are gene-edited using any of the gene-editing methods described herein (e.g., using CRISPR/Cas gene editing to insert or delete one or more nucleotides). In some embodiments, a disrupted gene is a gene that does not encode functional protein. In some embodiments, a cell that comprises a disrupted gene does not express (e.g., at the cell surface) a detectable level (e.g. by antibody, e.g., by flow cytometry) of the protein encoded by the gene. A cell that does not express a detectable level of the protein may be referred to as a knockout cell.

In some embodiments, the cells described herein are gene-edited to disrupt one or more of the genes encoding an MHC-I or MHC-II human leukocyte antigen, a component of a MHC-I or MHC-II complex, or a transcriptional regulator of a MHC-I or MHC-II complex. In some embodiments, the cells described herein are gene-edited to disrupt one or more of the genes encoding an MHC-I or MHC-II human leukocyte antigen. In some embodiments, the cells described herein are gene-edited to disrupt one or more of the genes encoding one or more components of an MHC-I or MHC-II complex. In some embodiments, the cells described herein are gene-edited to disrupt one or more of the genes encoding one or more transcriptional regulator of an MHC-I or MHC-II complex.

In some embodiments, the cells described herein are gene-edited to disrupt one or more genes including but not limited to: B2M, CIITA, ADAM17, CISH, REGNASE1, FAS, TIGIT, PD-1, NKG2A, CD70 and/or ALK4, type I activin receptor (e.g., conditionally). In some embodiments, the cells described herein are gene-edited to disrupt B2M, CIITA, CISH, FAS, and/or ADAM17. In some embodiments, the cells described herein are gene-edited to disrupt B2M. In some embodiments, the cells described herein are gene-edited to disrupt CIITA. In some embodiments, the cells described herein are gene-edited to disrupt ADAM17.

In some embodiments, the cells described herein are gene-edited to disrupt CISH. In some embodiments, the cells described herein are gene-edited to disrupt REGNASE1. In some embodiments, the cells described herein are gene-edited to disrupt FAS. In some embodiments, the cells described herein are gene-edited to disrupt TIGIT. In some embodiments, the cells described herein are gene-edited to disrupt PD-1. In some embodiments, the cells described herein are gene-edited to disrupt NKG2A. In some embodiments, the cells described herein are gene-edited to disrupt CD70. In some embodiments, the cells described herein are gene-edited to disrupt ALK4, type I activin receptor (e.g., conditionally).

In some embodiments, the cells described herein are gene-edited to insert a polynucleotide encoding, without limitation, one or more of the following: a tolerogenic factor, IL15, IL15R& IL15/IL15Rα, HLA-E, a CAR, and SERPINB9. In some embodiments, the cells described herein are gene-edited to insert a polynucleotide encoding IL15. In some embodiments, the cells described herein are gene-edited to insert a polynucleotide encoding IL15Rα. In some embodiments, the cells described herein are gene-edited to insert a polynucleotide encoding a fusion protein of IL15 and IL15Rα. In some embodiments, the cells described herein are gene-edited to insert a polynucleotide encoding a tolerogenic factor, such as HLA-E (e.g., wherein the HLA-E is a trimer comprising a B2M signal peptide fused to an HLA-G presentation peptide fused to the B2M membrane protein fused to the HLA-E protein without a signal peptide). In some embodiments, the cells described herein are gene-edited to insert a polynucleotide encoding a CAR. In some embodiments, the cells described herein are gene-edited to insert a polynucleotide encoding an IL15/IL15Rα-P2A-HLA-E trimer construct. In some embodiments, the cells described herein are gene-edited to insert a polynucleotide encoding a SERPINB9-P2A-HLA-E trimer construct. In some embodiments, the cells described herein are gene-edited to insert a polynucleotide encoding a SERPINB9-P2A-IL15/IL15Rα construct. In some embodiments the cells described herein are gene-edited to insert a polynucleotide encoding a CAR-P2A-HLA-E trimer construct.

In some embodiments, the cells described herein are gene-edited to insert a polynucleotide encoding CD16 (e.g., a high affinity non-cleavable CD16). In some embodiments, the cells described herein are not gene-edited to insert a polynucleotide encoding CD16. In some embodiments, the cells described herein are not gene-edited to insert a polynucleotide encoding a high affinity non-cleavable CD16. In some embodiments, the cells described herein are gene-edited to insert a polynucleotide encoding, without limitation, one or more of the following: IL15, IL15R&, IL15/IL15R&, HLA-E and CD16 (e.g., a high affinity non-cleavable CD16), wherein the cell has a disrupted expression of B2M (e.g., the cell is gene-edited to disrupt B2M leading to, e.g., elimination of B2M expression). In some embodiments, the polynucleotide encoding IL15/IL15Rα, and HLA-E (e.g., HLA-E trimer comprising a B2M signal peptide fused to an HLA-G presentation peptide fused to the B2M membrane protein fused to the HLA-E protein without a signal peptide), or the polynucleotide encoding IL15/IL15Rα-P2A-HLA-E trimer is inserted in the B2M gene locus (e.g., in exon 1 of the B2M gene locus).

In some embodiments, the cells described herein are gene-edited to insert any of the polynucleotides described herein wherein the cell has a disrupted expression of CIITA (e.g., the cell is gene-edited to disrupt CIITA leading to, e.g., elimination of CIITA expression). In some embodiments, the cells described herein are gene-edited to insert any of the polynucleotides described herein in the disrupted CIITA gene locus (e.g., in exon 2 of the CIITA gene locus).

In some embodiments, the cells described herein are gene-edited to insert a polynucleotide encoding one or more chimeric antigen receptors (CARs). In some embodiments, and without limitation, the CAR is a BCMA (i.e., B cell maturation antigen) CAR, CD30 CAR, CD19 CAR, CD33 CAR, NKG2D (i.e., natural killer group 2D receptor) CAR (or a CAR or receptor comprising an NKG2D ectodomain), CD70 CAR, NKp30 (i.e., natural killer protein 30) CAR, CD73 CAR, GPR87 (i.e., G protein-coupled receptor 87) CAR, or SLC7A11 (i.e., solute carrier family 7 member 11, which is also called xCT) CAR. In some embodiments, the CAR is a BCMA CAR. In some embodiments, the polynucleotide encoding a CAR comprises or has the sequence of SEQ ID NO: 70. In some embodiments, the CAR is a CD33 CAR. In some embodiments, the CAR is a CD19 CAR. In some embodiments, the CAR is a CD33 CAR. In some embodiments, the CAR is a NKG2D CAR (or a CAR or receptor comprising an NKG2D ectodomain). In some embodiments, the CAR is a CD70 CAR. In some embodiments, the CAR is a NKp30 CAR. In some embodiments, the CAR is a CD73 CAR. In some embodiments, the CAR is a GPR87 CAR. In some embodiments, the CAR is a SLC7A11 (xCT) CAR.

In some embodiments, the cells described herein are gene-edited to insert a polynucleotide encoding a CAR, wherein the cell has a disrupted expression of CIITA (e.g., the cell is gene-edited to disrupt CIITA leading to, e.g., elimination of CIITA expression). In some embodiments, the polynucleotide encoding a CAR is inserted in the disrupted CIITA gene. In some embodiments, the polynucleotide encoding a CAR is inserted in exon 2 of the CIITA gene locus. In some embodiments, the cells described herein are gene-edited to insert a polynucleotide encoding a CAR-P2A-HLA-E trimer construct, wherein the cell has a disrupted expression of CIITA (e.g., the cell is gene-edited to disrupt CIITA leading to, e.g., elimination of CIITA expression). In some embodiments, the polynucleotide encoding a CAR-P2A-HLA-E trimer construct is inserted in the disrupted CIITA gene. In some embodiments, the polynucleotide encoding a CAR-P2A-HLA-E trimer construct is inserted in exon 2 of the CIITA gene locus.

In some embodiments, the cells described herein are gene-edited to insert a polynucleotide encoding a CAR, wherein the cell has a disrupted expression of B2M (e.g., the cell is gene-edited to disrupt B2M leading to, e.g., elimination of B2M expression). In some embodiments, the CAR is inserted in the disrupted B2M gene locus (e.g., in exon 1 of the B2M gene locus).

In some embodiments, the cells described herein are edited to disrupt (i) one or more of the genes encoding an MHC-I or MHC-II human leukocyte antigen, a component of a MHC-I or MHC-II complex, or a transcriptional regulator of a MHC-I or MHC-II complex, and (ii) ADAM17. In some embodiments, such cells are further gene-edited to insert a polynucleotide encoding one or more chimeric antigen receptors (CARs), such as any CARs described herein (e.g., a BCMA CAR). In some embodiments, such cells are hypoimmunogenic. In some embodiments, such cells are further gene-edited to disrupt one or more genes described herein, e.g., CIITA. In some embodiments, such cells are further gene-edited to insert any polynucleotide described herein, e.g., a polynucleotide encoding IL15, IL15Rα, IL15/IL15R&, HLA-E (e.g., HLA-E trimer comprising a B2M signal peptide fused to an HLA-G presentation peptide fused to the B2M membrane protein fused to the HLA-E protein without a signal peptide), or a polynucleotide encoding IL15/IL15Rα-P2A-HLA-E trimer.

In some embodiments, the present disclosure provides a method of generating genome-engineered stem cells (e.g., iPSCs), wherein the stem cells comprise at least one targeted genomic modification at one or more selected sites in genome, the method comprising genetically engineering a cell type as described herein by introducing into said cells one or more constructs to allow targeted modification at a selected site; introducing into said cells one or more double strand breaks at the selected sites using one or more endonuclease capable of selected site recognition; and culturing the edited cells to allow endogenous DNA repair to generate targeted insertions or deletions at the selected sites; thereby obtaining genome-modified stem cells. In some embodiments, the cell that is engineered (i.e., the starting cell) is a stem cell (e.g., an embryonic stem cell (ESC), an adult stem cell (ASC), an induced pluripotent stem cell (iPSC), or a hematopoietic stem or progenitor cell (HSPC)). The stem cells (e.g., iPSCs) generated or obtainable by this method will comprise at least one functional targeted genomic modification, and wherein the genome-modified cells, are then capable of being differentiated into progenitor cells or fully-differentiated cells (e.g., natural killer (NK) cells). In some embodiments, the differentiated cells (e.g., NK cells) maintain all of the gene-edits of the cells from which they were derived.

In some embodiments, a ribonucleoprotein particle (RNP) containing an RNA-guided nuclease (e.g., a Cas nuclease, such as a Cas9 nuclease) and a gRNA targeting the gene to be disrupted are delivered to any cell described herein (e.g., iPSC). A RNP is an RNA-guided nuclease (e.g., Cas9) pre-complexed/complexed with a gRNA. In other embodiments, the RNA-guided nuclease and gRNA are delivered separately to cells. In some embodiments, at least 50% of the engineered cells of a population of cells does not express a detectable level of the protein encoded by the disrupted gene. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered cells of a population do not express a detectable level of the disrupted gene product.

In some embodiments, at least 50% of the engineered cells of a population of cells expresses a detectable level of the protein encoded by the inserted polynucleotide. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered cells of a population express a detectable level of the protein encoded by the inserted polynucleotide.

MHC I and MHC II Edits

Major histocompatibility complex I and II (MHC I and MHC II respectively) are cell surface proteins which perform an essential role in the adaptive immune system. The genes that encode the major histocompatibility complex (MHC) are located on human Chr. 6p21. The resultant proteins coded by the MHC genes are a series of surface proteins that are essential in donor compatibility during cellular transplantation. MHC genes are divided into MHC class I (MHC-I) and MHC class II (MHC-II). MHC-I genes (HLA-A, HLA-B, and HLA-C) are expressed in almost all tissue cell types, presenting "non-self" antigen-processed peptides to $CD8^+$ T cells, thereby promoting their activation to cytolytic $CD8^+$ T cells. Transplanted or engrafted cells expressing "non-self" MHC-I molecules will cause a robust cellular immune response directed at these cells and ultimately resulting in their demise by activated cytolytic CD8+ T cells. MHC-I proteins are intimately associated with beta-2-microglobulin (B2M) in the endoplasmic reticulum, which is essential for forming functional MHC-I molecules on the cell surface. In addition, there are three non-classical MHC-II molecules (HLA-E, HLA-F, and HLA-G), which have immune regulatory functions. MHC-II biomolecule include HLA-DP, HLA-DM, HLA-DOA, HLA-DOB, HLA-DQ, and HLA-DR. Due to their primary function in the immune response, MHC-I and MHC-II biomolecules contribute to immune rejection following cellular engraftment of non-host cells, e.g., cellular engraftment for purposes of regenerative medicine.

In some embodiments, a cell comprises a genomic modification of one or more MHC-I or MHC-II genes. In some embodiments, a cell comprises a genomic modification of one or more polynucleotide sequences that regulates the expression of MHC-I and/or MHC-II. In some embodiments, a genetic modification of the disclosure is performed using any gene editing method including but not limited to those methods described herein.

In some embodiments, any of the cells described herein have MHC I and/or MHC II genetic modifications. In some embodiments, MHC I is disrupted. In some embodiments, MHC II is disrupted. In some embodiments, both MHC I and MHC II are disrupted. In some embodiments, an MHC I encoding gene is inserted. In some embodiments, an MHC II encoding gene is inserted. In some embodiments, any genetically modified cell described herein comprises the introduction of at least one genetic modification within or near at least one gene that decreases the expression of one or more MHC-I and MHC-II human leukocyte antigens relative to an unmodified cell; at least one genetic modification that increases the expression of at least one polynucleotide that encodes a tolerogenic factor relative to an unmodified cell. In some embodiments, genetically modified cells comprise the introduction of at least one genetic modification within or near at least one gene that decreases the expression of one or more MHC-I and MHC-II human leukocyte antigens relative to an unmodified cell; at least one genetic modification that increases the expression of at least one polynucleotide that encodes a tolerogenic factor relative to an unmodified cell. In other embodiments, genetically modified cells comprise at least one deletion or insertion-deletion mutation within or near at least one gene that alters the expression of one or more MHC-I and MHC-II human leukocyte antigens relative to an unmodified cell; and at least one insertion of a polynucleotide that encodes at least one tolerogenic factor at a site that partially overlaps, completely overlaps, or is contained within, the site of a deletion of a gene that alters the expression of one or more MHC-I and MHC-II HLAs.

In some embodiments, decreasing the expression of one or more MHC-I and MHC-II human leukocyte antigens relative to an unmodified cell is accomplished by targeting, e.g., for genetic deletion and/or insertion of at least one base pair, in a MHC-I and/or MHC-II gene directly. In some embodiments, decreasing the expression of one or more MHC-I and MHC-II human leukocyte antigens relative to an unmodified cell is accomplished by targeting, e.g., for genetic deletion, a CIITA gene. In some embodiments, decreasing the expression of one or more MHC-I and MHC-II human leukocyte antigens relative to an unmodified cell is accomplished by targeting, e.g., for genetic deletion, at least one transcriptional regulator of MHC-I or MHC-II.

In some embodiments, a transcriptional regulator of MHC-I or MHC-II is a NLRC5, or CIITA gene. In some embodiments, a transcriptional regulator of MHC-I or MHC-II is a RFX5, RFXAP, RFXANK, NFY-A, NFY-B, NFY-C, IRF-1, and/or TAP1 gene.

In some embodiments, the genome of a cell has been modified to delete the entirety or a portion of an HLA-A, HLA-B, and/or HLA-C gene. In some embodiments, the genome of a cell has been modified to delete the entirety or a portion of a promoter region of an HLA-A, HLA-B, and/or HLA-C gene. In some embodiments, the genome of a cell has been modified to delete the entirety or a portion of a gene that encodes a transcriptional regulator of MHC-I or MHC-II. In some embodiments, the genome of a cell has been modified to delete the entirety or a portion of a promoter region of a gene that encodes a transcriptional regulator of MHC-I or MHC-II.

MHC-I cell surface molecules are composed of MHC-encoded heavy chains (HLA-A, HLA-B, or HLA-C) and the invariant subunit beta-2-microglobulin (B2M). Thus, a reduction in the concentration of B2M within a cell allows for an effective method of reducing the cell surface expression of MHC-I cell surface molecules. In some embodiments, tolerogenic factors can be inserted or reinserted into genetically modified cells to create immune-privileged iPSC or NK cells. In some embodiments, the iPSC or NK cells disclosed herein have been further modified to express one or more tolerogenic factors. Exemplary tolerogenic factors include, without limitation, one or more of HLA-C, HLA-E, HLA-F, HLA-G, PD-L1, CTLA-4-Ig, CD47, CI-inhibitor, and IL-35. In some embodiments, the genetic modification, e.g., insertion, of at least one polynucleotide encoding at least one tolerogenic factor enables a gene-edited iPSC or NK cell to inhibit or evade immune rejection with rates at least 1.05, at least 1.1, at least 1.25, at least 1.5, at least 2, at least 3, at least 4, at least 5, at least 10, at least 20, or at least 50 times higher than an unmodified cell following engraftment. In some embodiments, an insertion of a polynucleotide that encodes HLA-E, HLA-G, CTLA-4, CD47, and/or PD-L1 enables a iPSC or NK cell to inhibit or evade immune rejection after transplantation or engraftment into a host subject.

The polynucleotide encoding the tolerogenic factor generally comprises left and right homology arms that flank the sequence encoding the tolerogenic factor. The homology arms have substantial sequence homology to genomic DNA at or near the targeted insertion site. For example, the left homology arm can be a nucleotide sequence homologous with a region located to the left or upstream of the target site or cut site and the right homology arm can be a nucleotide sequence homologous with a region located to the right or downstream of the target site or cut site. The proximal end of each homology arm can be homologous to genomic DNA sequence abutting the cut site. Alternatively, the proximal end of each homology arm can be homologous to genomic DNA sequence located up to about 10, 20, 30, 40, 50, 60, or 70 nucleobases away from the cut site. As such, the polynucleotide encoding the tolerogenic factor can be inserted into the targeted gene locus within about 10, 20, 30, 40, 50, 60, or 70 base pairs of the cut site, and additional genomic DNA bordering the cut site (and having no homology to a homolog arm) can be deleted. The homology arms can range in length from about 50 nucleotides to several of thousands of nucleotides. In some embodiments, the homology arms can range in length from about 500 nucleotides to about 1000 nucleotides. In some embodiments, the homology arms are 600 bp, 700 bp, 800 bp, or 900 bp. In some embodiments, the homology arms are 800 bp. In some embodiments, the substantial sequence homology between the homology arms and the genomic DNA is at least about 80%, at least about 85%, at least about 90%, at least about 95%, or at least about 99%. In some embodiments, the homology arms have 100% sequence identity with genomic DNA flanking the target site.

In some embodiments, the at least one polynucleotide encoding at least one tolerogenic factor is operably linked to an exogenous promoter. In some embodiments, the exogenous promoter can be a constitutive, inducible, temporal-, tissue-, or cell type-specific promoter. In some embodiments, the exogenous promoter is a CAGGS, CMV, EF1a, PGK, CAG, or UBC promoter.

In some embodiments, the at least one polynucleotide encoding at least one tolerogenic factor is inserted into a safe harbor locus, e.g., the AAVS 1 locus. In some embodiments, a safe harbor locus for inserting any gene described herein is selected from, but not limited to AAVS1 (PPP1 R12C), ALB, Angptl3, ApoC3, ASGR2, CCR5, FIX (F9), G6PC, Gys2, HGD, Lp(a), Pcsk9, Serpinal, TF, and TTR.

In some embodiments, the at least one polynucleotide encoding at least one tolerogenic factor is inserted into a site or region of genomic DNA that partially overlaps, completely overlaps, or is contained within (i.e., is within or near) a MHC-I gene, MHC-II gene, or a transcriptional regulator of MHC-I or MHC-II.

In some embodiments, the genome of a cell has been modified to decrease the expression of the NLR family, CARD domain containing 5 (NLRC5). NLRC5 is a critical regulator of MHC-I-mediated immune responses and, similar to CITA, NLRC5 is highly inducible by IFN-γ and can translocate into the nucleus. NLRC5 activates the promoters of MHC-I genes and induces the transcription of MHC-I as well as related genes involved in MHC-I antigen presentation.

In some embodiments, cells having no MHC-II expression and moderate expression of MHC-I are genetically modified to have no surface expression of MHC-I or MHC-II. In another embodiment, cells with no surface expression of MHC-I/II are further edited to have expression of programmed death ligand-1 (PD-L1), e.g., insertion of a polynucleotide encoding PD-L1. In yet another embodiment, cells with no surface expression of MHC-I/II are further edited to have expression of PD-L1, e.g., insertion of a polynucleotide encoding PD-L1.

In some embodiments, the cells further comprise increased or decreased expression, e.g., by a genetic modification, of one or more additional genes that are not necessarily implicated in either immune evasion or cell survival post-engraftment. In some embodiments, the cells further comprise increased expression of one or more safety switch proteins relative to an unmodified cell. In some embodiments, the cells comprise increased expression of one or more additional genes that encode a safety switch protein. In some embodiments, a safety switch is also a suicide gene. In some embodiments, a safety switch is herpes simplex virus-1 thymidine kinase (HSV-tk) or inducible caspase-9. In some embodiments, a polynucleotide that encodes at least one safety switch is inserted into a genome, e.g., into a safe harbor locus. In some other embodiments, the one or more additional genes that are genetically modified encode one or more of safety switch proteins; targeting modalities; receptors; signaling molecules; transcription factors; pharmaceutically active proteins or peptides; drug target candidates; and proteins promoting engraftment, trafficking, homing, viability, self-renewal, persistence, and/or survival thereof integrated with the construct.

B2M Gene Edits

In some embodiments, the genome of any cell described herein is modified to disrupt beta-2-microglobulin (B2M or β2M) gene (NCBI Gene ID: 567). B2M is a non-polymorphic gene that encodes a common protein subunit required for surface expression of all polymorphic MHC class I heavy chains. HLA-I proteins are intimately associated with B2M in the endoplasmic reticulum, which is essential for forming functional, cell-surface expressed HLA-I molecules. Disrupting its expression by gene editing will prevent host versus therapeutic cell responses leading to increased therapeutic cell persistence. In some embodiments, expression of the endogenous B2M gene is eliminated to prevent a host-versus-graft response. In some embodiments, the disrupted B2M can prevent allo-immune response due to MHC-I.

In some embodiments, any of the gene-editing methods described herein are used to disrupt the B2M gene. In some embodiments, any engineered cell described herein comprises a disrupted B2M gene. In some embodiments, an iPSC described herein comprises a disrupted B2M gene. In some embodiments, an NK cell described herein comprises a disrupted B2M gene.

In some embodiments, a ribonucleoprotein particle (RNP) containing an RNA-guided nuclease (e.g., a Cas nuclease, such as a Cas9 nuclease) and a gRNA targeting the B2M gene (or any other gene of interest) are delivered to any cell described herein (e.g., iPSC). A ribonucleoprotein particle (RNP) is an RNA-guided nuclease (e.g., Cas9) pre-complexed/complexed with a gRNA. In other embodiments, the RNA-guided nuclease and gRNA are delivered separately to cells. In some embodiments, the gRNA targets a site in the B2M gene. Non-limiting examples of modified and unmodified B2M gRNA sequences that may be used as provided herein to create a genomic disruption in the B2M gene include sequences corresponding to a sequence of SEQ ID NOs: 34, 78 and 79. In some embodiments, a gRNA is used to target the B2M site for gene-editing. Other gRNA sequences may be designed using the B2M gene sequence located on Chromosome 15 (GRCh38 coordinates: Chromosome 15: 44,711,477-44,718,877; Ensembl: ENSG00000166710). In some embodiments, any B2M RNP described herein is used in combination with a donor plasmid containing B2M homology arms for insertion of any polynucleotide described herein.

In some embodiments, the gRNA comprises a polynucleotide sequence corresponding to a sequence of any one of SEQ ID NO: 34, SEQ ID NO: 78, and SEQ ID NO: 79. In some embodiments, a gRNA/CRISPR nuclease complex targets and cleaves a target site in the B2M gene locus. In some embodiments, the B2M gRNA targets a sequence comprising SEQ ID NOS: 34, 78, or 79. Repair of a double-stranded break by NHEJ can result in a deletion of at least on nucleotide and/or an insertion of at least one nucleotide, thereby disrupting or eliminating expression of B2M. In some embodiments, the B2M gene locus is targeted by at least two CRISPR systems each comprising a different gRNA, such that cleavage at two sites in the B2M gene locus leads to a deletion of the sequence between the two cuts, thereby eliminating expression of B2M.

In some embodiments, the homology arms are used with B2M guides (e.g., gRNA comprising the nucleotide sequence of SEQ ID NO: 34). In some embodiments, the homology arms are designed to be used with any B2M guide that would eliminate the start site of the B2M gene. In some embodiments, the B2M homology arms comprise or consist essentially of a polynucleotides of the sequence of SEQ ID NOs: 36 and 54, or polynucleotides having at least 85%, 90%, 95%, or 99% sequence identity with that of SEQ ID NOs: 36 or 54. In some embodiments, the left B2M homology arm can comprise or consist essentially of SEQ ID NO: 36, or a polynucleotide sequence having at least 85%, 90%, 95%, or 99% sequence identity with that of SEQ ID NO: 36. In some embodiments, the right B2M homology arm can comprise or consist essentially of SEQ ID NO: 54, or a polynucleotide sequence having at least 85%, 90%, 95%, or 99% sequence identity with that of SEQ ID NO:54.

In some embodiments, gRNAs targeting the B2M genomic region create Indels in the B2M gene disrupting expression of the mRNA or protein.

In some embodiments, at least 50% of the engineered cells of a population of cells does not express a detectable level of B2M surface protein. For example, at least 55%, at least 60%, at least 70%, at least 75%, at least 80%, at least 85%, at least 90%, or at least 95% of the engineered cells of a population may not express a detectable level of B2M surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered cells of a population does not express a detectable level of B2M surface protein.

In some embodiments, less than 50% of the engineered cells of a population of cells express a detectable level of B2M surface protein. In some embodiments, less than 30% of the engineered cells of a population of cells express a detectable level of B2M surface protein. For example, less than 50%, less than 30%, less than 25%, less than 20%, less than 15%, less than 10%, or less than 5% of the engineered cells of a population of cells express a detectable level of B2M surface protein. In some embodiments, 40%-30%, 40%-20%, 40%-10%, 40%-5%, 30%-20%, 30%-10%, 30%-5%, 20%-10%, 20%-5%, or 10%-5% of the engineered cells of a population of cells express a detectable level of B2M surface protein.

CIITA Gene Edits

In some embodiments, the genome of any cell described herein is modified to disrupt Class II major histocompatibility complex transactivator (CIITA) gene (NCBI Gene ID: 4261). CIITA is a member of the LR or nucleotide binding domain (NBD) leucine-rich repeat (LRR) family of proteins and regulates the transcription of MHC-II by associating with the MHC enhanceosome. The expression of CIITA is induced in B cells and dendritic cells as a function of developmental stage and is inducible by IFN-7 in most cell types. In some embodiments, the disrupted CIITA gene locus can prevent allo-immune response due to MHC-II.

In some embodiments, any of the gene-editing methods described herein are used to disrupt the CIITA gene. In some embodiments, any engineered cell described herein comprises a disrupted CIITA gene. In some embodiments, an iPSC described herein comprises a disrupted CIITA gene. In some embodiments, an NK cell described herein comprises a disrupted CIITA gene.

In some embodiments, a ribonucleoprotein particle (RNP) containing an RNA-guided nuclease (e.g., a Cas nuclease, such as a Cas9 nuclease) and a gRNA targeting the CIITA gene (or any other gene of interest) are delivered to any cell described herein (e.g., iPSC). A ribonucleoprotein particle (RNP) is a RNA-guided nuclease (e.g., Cas9) pre-complexed/complexed with a gRNA. In other embodiments, the RNA-guided nuclease and gRNA are delivered separately to cells. Non-limiting examples of modified and unmodified CIITA gRNA sequences that may be used as provided herein to create a genomic disruption in the CIITA gene are listed in Table 15 (e.g., corresponding sequences of SEQ ID NOS: 13-17). In some embodiments, the gRNA targets a site within the CIITA gene. In some embodiments, the CIITA gRNA targets a sequence comprising SEQ ID NOS: 13-17. In some embodiments, the gRNA comprises a polynucleotide sequence corresponding to a sequence of SEQ ID NO: 13. In some embodiments, any CIITA RNP described herein is used in combination with a donor plasmid containing CIITA homology arms for insertion of any polynucleotide described herein.

In some embodiments, gRNAs targeting the CIITA genomic region create Indels in the CIITA gene disrupting expression of the mRNA or protein. In some embodiments, a gRNA/CRISPR nuclease complex targets and cleaves a target site in the CIITA gene locus. Repair of a double-stranded break by NHEJ can result in a deletion of at least on nucleotide and/or an insertion of at least one nucleotide, thereby disrupting or eliminating expression of CIITA. In some embodiments, the CIITA gene locus is targeted by at least two CRISPR systems each comprising a different gRNA, such that cleavage at two sites in the CIITA gene locus leads to a deletion of the sequence between the two cuts, thereby eliminating expression of CIITA.

In some embodiments, the homology arms are used with CIITA guides (e.g., gRNAs comprising a nucleotide sequence corresponding to a sequence of any one of SEQ ID NOs: 13-17). In some embodiments, the homology arms are designed to be used with any CIITA guide that would eliminate the start site of the CIITA gene. In some embodiments, the CIITA homology arms comprise or consist essentially of polynucleotides of SEQ ID NOs: 22 and 32, or polynucleotide sequences having at least 85%, 90%, 95%, or 99% sequence identity with that of SEQ ID NOs: 22 or 32. In some embodiments, the left CIITA homology arm can comprise or consist essentially of SEQ ID NO: 22, or a polynucleotide sequence having at least 85%, 90%, 95%, or 99% sequence identity with that of SEQ ID NO: 22. In some embodiments, the right CIITA homology arm can comprise or consist essentially of SEQ ID NO: 32, or a polynucleotide sequence having at least 85%, 90%, 95%, or 99% sequence identity with that of SEQ ID NO: 32.

In some embodiments, at least 50% of the engineered cells of a population of cells does not express a detectable level of CIITA protein. For example, at least 55%, at least 60%, at least 70%, at least 75%, at least 80%, at least 85%, at least 90%, or at least 95% of the engineered cells of a population may not express a detectable level of CIITA surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered cells of a population does not express a detectable level of CIITA protein.

In some embodiments, less than 50% of the engineered cells of a population of cells express a detectable level of CIITA protein. In some embodiments, less than 30% of the engineered cells of a population of cells express a detectable level of CIITA protein. For example, less than 50%, less than 30%, less than 25%, less than 20%, less than 15%, less than 10%, or less than 5% of the engineered cells of a population of cells express a detectable level of CIITA protein. In some embodiments, 40%-30%, 40%-20%, 40%-10%, 40%-5%, 30%-20%, 30%-10%, 30%-5%, 20%-10%, 20%-5%, or 10%-5% of the engineered cells of a population of cells express a detectable level of CIITA protein.

In some embodiments, any polynucleotide described herein is inserted into the CIITA gene locus such that 86 base pairs (bp) of the CIITA exon 2 are removed after homology directed repair.

HLA-E Gene Edits

In some embodiments, the genome of any cell described herein comprises an insertion of a polynucleotide encoding human leukocyte antigen E (HLA-E; also called major histocompatibility complex, class I, E). HLA-E is encoded by HLA-E gene (gene (NCBI Gene ID: 3133). HLA-E is a heterodimer class I molecule. HLA-E primarily functions as a ligand for the NK cell inhibitory receptor KLRD1-KLRC1. HLA-E enables NK cells to monitor other MHC class I molecule expression and to tolerate self-expression. In some embodiments, the insertion of the HLA-E can protect the iNK from PB-NK "missing self" response. In some embodiments, expression of HLA-E is increased in cells. In some embodiments, an iPSC comprises an inserted polynucleotide encoding in HLA-E (or HLA-E knock-in). In some embodiments, an NK cell comprises an inserted polynucleotide encoding in HLA-E (or HLA-E knock-in). In some embodiments, the HLA-E is an HLA-E trimer.

Non-limiting examples of modified and unmodified HLA-E cDNA sequences that may be used as provided herein to create a genomic knock-in of the HLA-E gene include SEQ ID NO: 51 (i.e., HLA-E CDS) and SEQ ID NO: 75 (e.g., HLA-E trimer, consisting of SEQ ID NOS: 46-51). In some embodiments, the HLA-E trimer polynucleotide has at least 90%, 91%, 92%, 93%, 94%, 95%, 96%, 97%, 98%, or 99% identity to SEQ ID NO: 75. In some embodiments, the HLA trimer has the amino acid sequence of SEQ ID NO: 142.

In some embodiments, at least 50% of the engineered cells of a population of cells express a detectable level of HLA-E surface protein. For example, at least 55%, at least 60%, at least 70%, at least 75%, at least 80%, at least 85%, at least 90%, or at least 95% of the engineered cells of a population express a detectable level of HLA-E surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered cells of a population express a detectable level of HLA-E surface protein.

In some embodiments, less than 50% of the engineered cells of a population of cells do not express a detectable level of HLA-E surface protein. In some embodiments, less than 30% of the engineered cells of a population of cells do not express a detectable level of HLA-E surface protein. For example, less than 50%, less than 30%, less than 25%, less than 20%, less than 15%, less than 10%, or less than 5% of the engineered cells of a population of cells do not express a detectable level of HLA-E surface protein. In some embodiments, 40%-30%, 40%-20%, 40%-10%, 40%-5%, 30%-20%, 30%-10%, 30%-5%, 20%-10%, 20%-5%, or 10%-5% of the engineered cells of a population of cells do not express a detectable level of HLA-E surface protein.

In some embodiments, any of the HLA-E polynucleotides described herein are inserted into any safe-harbor locus described herein. In some embodiments, any of the HLA-E polynucleotides described herein are inserted into any B2M gene locus described herein. In some embodiments, any of the HLA-E polynucleotides described herein are inserted into any CIITA gene locus described herein. In some embodiments, the HLA-E polynucleotide is an HLA-E trimer composed of a B2M signal peptide fused to an HLA-G presentation peptide fused to the B2M membrane protein fused to the HLA-E protein without its signal peptide. In some embodiments, the HLA-E trimer comprises or consists essentially of SEQ ID NO: 75. In some embodiments, the HLA-E polynucleotide has at least 90%, 91%, 92%, 93%, 94%, 95%, 96%, 97%, 98%, or 99% identity to SEQ ID NO: 75. In some embodiments, the trimer design is that described in Gornalusse et al. (2017) Nat. Biotechnol. 35(8): 765-772, which is incorporated herein in its entirety.

IL15 and IL15Rα Gene Edits

In some embodiments, the genome of any cell described herein comprises an insertion of polynucleotide encoding interleukin-15 (IL15), IL15Rα, and/or a fusion protein of IL15 and IL15Rα ("IL15/IL15Rα"). IL15 is a cytokine that functions in regulating NK cell proliferation and activation, and is encoded by IL15 gene (MCBI Gene ID: 3600). IL15Rα (also called IR15a) is the receptor that binds IL15, and is encoded by IL15Rα gene (MCBI Gene ID: 16169). In some embodiments, the insertion of the polynucleotide encoding IL15, IL15Rα, and/or fusion protein of IL15 and IL15Rα can lead to increased iNK persistence of the engineered cell.

In some embodiments, a cell has insertion of a polynucleotide encoding 115, and the polynucleotide comprises or consists of SEQ ID NO: 41. In some embodiments, a cell has insertion of a polynucleotide encoding IL15Rα, and the polynucleotide comprises or consists of SEQ ID NO: 43. In some embodiments, a cell has insertion of a polynucleotide encoding a fusion protein of IL15 and IL15Rα ("IL15/IL15Rα"). In some embodiments, the fusion sequence is as described in Hurton et al. (2016) Proc Natl Acad Sci USA; 113(48):E7788-E7797. doi: 10.1073/pnas.1610544113, which is incorporated herein in its entirety. In some embodiments, the polynucleotide encoding IL15/IL15Rα comprises or consists of SEQ ID NO: 76 (which consists of SEQ ID NOS: 40-44). In some embodiments, the IL15/IL15Rα polynucleotide has at least 90%, 91%, 92%, 93%, 94%, 95%, 96%, 97%, 98%, or 99% identity to SEQ ID NO: 76. In some embodiments, the IL15/IL15Rα fusion has the amino acid sequence of SEQ ID NO: 143.

In some embodiments, 115 and IL15Rα are co-expressed. In some embodiments, a self-cleaving peptide is used to co-express IL15 and IL15Rα. In some embodiments, the self-cleaving peptide is selected from, but not limited to, P2A (derived from porcine teschovirus-1 2A), E2A (derived from equine rhinitis A virus), F2A (derived from foot-and-mouth disease virus 18), and T2A (derived thosea asigna virus 2A). In some embodiments, the self-cleaving peptide is derived from P2A. In some embodiments, a cell has insertion of a polynucleotide encoding IL15, P2A, IL15Rα (IL15-P2A-IL15Rα). In some embodiments, an iPSC comprises a knock-in of the IL15-P2A-IL15Rα polynucleotide. In some embodiments, an NK cell comprises a knock-in of the IL15-P2A-IL15Rα polynucleotide.

In some embodiments, at least 50% of the engineered cells of a population of cells express a detectable level of any IL15, IL15Rα, and/or IL15/IL15Rα described herein. For example, at least 55%, at least 60%, at least 70%, at least 75%, at least 80%, at least 85%, at least 90%, or at least 95% of the engineered cells of a population express a detectable level of IL15, IL15Rα, and/or IL15/IL15Rα. In some embodiments, 50%-100%, 50%-90%, 50%-80%, 50%-70%, 50%-60%, 60%-100%, 60%-90%, 60%%-80%, 60%-70%, 70%-100%, 70%-90%, 70%-80%, 80%-100%, 80%-90%, or 90%-100% of the engineered cells of a population expresses a detectable level of IL15, IL15Rα, and/or IL15/IL15Rα.

In some embodiments, less than 50% of the engineered cells of a population of cells do not express a detectable level of IL15, IL15Rα, and/or IL15/IL15Rα. In some embodiments, less than 30% of the engineered cells of a population of cells do not express a detectable level of IL15, IL15Rα, and/or IL15/IL15Rα. For example, less than 50%, less than 30%, less than 25%, less than 20%, less than 15%, less than 10%, or less than 5% of the engineered cells of a population of cells do not express a detectable level of IL15, IL15Rα, and/or IL15/IL15Rα. In some embodiments, 40%-30%, 40%-20%, 40%-10%, 40%-5%, 30%-20%, 30%-10%, 30%-5%, 20%-10%, 20%-5%, or 10%-5% of the engineered cells of a population of cells do not express a detectable level of IL15, IL15Rα, and/or IL15/IL15Rα.

In some embodiments, any of the IL15, IL15Rα, and/or IL15/IL15Rα polynucleotides described herein are inserted into any safe-harbor locus described herein. In some embodiments, any of the IL15, IL15Rα, and/or IL15/IL15Rα polynucleotides described herein are inserted into any B2M gene locus described herein.

SERPINB9 Gene Edits

In some embodiments, the genome of any cell described herein comprises an insertion of a polynucleotide encoding SERPINB9. SERPINB9, which is encoded by SERPINB9 gene (NCBI Gene ID: 5272), is a member of a large family of apoptosis inhibitors that mainly function by targeting intermediate proteases (e.g., covalently bind a protease in 1:1 complex, thereby inhibiting the protease). As such, expression of SERPINB9 may increase survival of the engineered cells. For example, iNK cells engineered to express SERPINB9 can survive NK cell attack by inhibiting activity of the released granzymes. In some embodiments, expression of SERPINB9 is increased in cells. In some embodiments, an iPSC comprises an insertion of a polynucleotide encoding SERPINB9 (or a SERPINB9 knock-in). In some embodiments, an NK cell comprises an insertion of a polynucleotide encoding SERPINB9 (or a SERPINB9 knock-in).

An example of a SERPINB9 cDNA sequence that may be used as provided herein to create a genomic knock-in of the SERPINB9 gene is SEQ ID NO: 129. In some embodiments, the SERPINB9 polynucleotide has at least 90%, 91%, 92%, 93%, 94%, 95%, 96%, 97%, 98%, or 99% identity to SEQ ID NO: 129. In some embodiments, the SERPINB9 protein has the amino acid sequence of SEQ ID NO: 144.

In some embodiments, at least 50% of the engineered cells of a population of cells express a detectable level of SERPINB9 protein. For example, at least 55%, at least 60%, at least 70%, at least 75%, at least 80%, at least 85%, at least 90%, or at least 95% of the engineered cells of a population express a detectable level of SERPINB9 protein. In some embodiments, 50%-100%, 50%-90%, 50%-80%, 50%-70%, 50%-60%, 60%-100%, 60%/6-90%, 60%-80%, 60%-70%, 70%-100%, 70%-90%, 70%-80%, 80%-100%, 80%-90%, or 90%-100% of the engineered cells of a population express a detectable level of SERPINB9 protein.

In some embodiments, less than 50% of the engineered cells of a population of cells do not express a detectable level of SERPINB9. In some embodiments, less than 30% of the engineered cells of a population of cells do not express a detectable level of SERPINB9. For example, less than 50%, less than 30%, less than 25%, less than 20%, less than 15%, less than 10%, or less than 5% of the engineered cells of a population of cells do not express a detectable level of SERPINB9. In some embodiments, 40%-30%, 40%-20%, 40%-10%, 40%-5%, 30%-20%, 30%-10%, 30%-5%, 20%-10%, 20%-5%, or 10%-5% of the engineered cells of a population of cells do not express a detectable level of SERPINB9.

In some embodiments, any of the SERPINB9 polynucleotides described herein are inserted into any safe-harbor locus described herein. In some embodiments, any of the SERPINB9 polynucleotides described herein are inserted into any B2M gene locus described herein.

ADAM17 Gene Edits

In some embodiments, the genome of any cell described herein is modified to disrupt a disintegrin and metalloprotease domain 17 (ADAM17) gene (NCBI Gene ID: 6868). ADAM17 cleaves TNF-α precursor. ADAM17 is responsible for proteolytic cleavage of several surface proteins. In some embodiments, the disrupted ADAM17 can increase ADCC killing by preventing CD16 cleavage.

In some embodiments, any of the gene-editing methods described herein are used to disrupt the ADAM17 gene. In some embodiments, an iPSC comprises a disrupted ADAM17 gene. In some embodiments, an NK cell comprises a disrupted ADAM17 gene.

In some embodiments, a ribonucleoprotein particle (RNP) containing an RNA-guided nuclease (e.g., a Cas nuclease, such as a Cas9 nuclease) and a gRNA targeting the ADAM17 gene (or any other gene of interest) are delivered to any cell described herein (e.g., iPSC). A ribonucleoprotein particle (RNP) is RNA-guided nuclease (e.g., Cas9) pre-complexed/complexed with a gRNA. In other embodiments, the RNA-guided nuclease and gRNA are delivered separately to cells.

Non-limiting examples of modified and unmodified ADAM17 gRNA sequences that may be used as provided herein to create a genomic disruption in the ADAM17 gene include sequences corresponding to sequences of SEQ ID NOS: 1-10. In some embodiments, the ADAM17 gRNA targets a sequence comprising any one of SEQ ID NOS: 1-10.

In some embodiments, gRNAs targeting the ADAM17 genomic region create Indels in the ADAM17 gene disrupting expression of the mRNA or protein.

In some embodiments, at least 50% of the engineered cells of a population of cells does not express a detectable level of ADAM17 protein. For example, at least 55%, at least 60%, at least 70%, at least 75%, at least 80%, at least 85%, at least 90%, or at least 95% of the engineered cells of a population may not express a detectable level of ADAM17 surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%/90%, or 90%-100% of the engineered cells of a population does not express a detectable level of ADAM17 protein.

In some embodiments, less than 50% of the engineered cells of a population of cells express a detectable level of ADAM17 protein. In some embodiments, less than 30% of the engineered cells of a population of cells express a detectable level of ADAM17 protein. For example, less than 50%, less than 30%, less than 25%, less than 20%, less than 15%, less than 10%, or less than 5% of the engineered cells of a population of cells express a detectable level of ADAM17 protein. In some embodiments, 40%-30%, 40%-20%, 40%-10%, 40%-5%, 30%-20%, 30%-10%, 30%-5%, 20%-10%, 20%-5%, or 10%-5% of the engineered cells of a population of cells express a detectable level of ADAM17 protein.

CISH Gene Edits

In some embodiments, the genome of any cell described herein is modified to disrupt a cytokine inducible SH2 containing protein (CISH, also called CIS) gene (NCBI Gene ID: 1154). CISH is a transcriptional co-activator that controls expression of HLA class II genes. In some embodiments, the disrupted CISH can increase iNK sensitivity to cytokines, improve iNK persistence, and/or increase tumor killing. In some embodiments, an iPSC comprises a disrupted CISH gene. In some embodiments, an NK cell comprises a disrupted CISH gene.

In some embodiments, gRNAs targeting the CISH genomic region create Indels in the CISH gene disrupting expression of the mRNA or protein. In some embodiments, the gRNA targets a site within the CISH gene. In some embodiments, the CISH gRNA targets a sequence comprising SEQ ID NOS: 81-92. In some embodiments, a gRNA targeting the CISH gene comprises a spacer sequence corresponding to a sequence comprising any one of SEQ ID NOS: 81-92.

In some embodiments, at least 50% of the engineered cells of a population of cells does not express a detectable level of CISH protein. For example, at least 55%, at least 60%, at least 70%, at least 75%, at least 80%, at least 85%, at least 90%, or at least 95% of the engineered cells of a population may not express a detectable level of CISH surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%/90%, or 90%-100% of the engineered cells of a population does not express a detectable level of CISH protein.

In some embodiments, less than 50% of the engineered cells of a population of cells express a detectable level of CISH protein. In some embodiments, less than 30% of the engineered cells of a population of cells express a detectable level of CISH protein. For example, less than 50%, less than 30%, less than 25%, less than 20%, less than 15%, less than 10%, or less than 5% of the engineered cells of a population of cells express a detectable level of CISH surface protein. In some embodiments, 40%-30%, 40%-20%, 40%-10%, 40%-5%, 30%-20%, 30%-10%, 30%-5%, 20%-10%, 20%-5%, or 10%-5% of the engineered cells of a population of cells express a detectable level of CISH protein.

REGNASE-1 Gene Edits

In some embodiments, the genome of any cell described herein is modified to disrupt a REGNASE-1 gene encoding zinc finger CCCH-type containing 12A (NCBI Gene ID: 80149). REGNASE-1 is an endoribonuclease involved in mRNA decay. In some embodiments, the disrupted REGNASE-1 can increase iNK persistence and/or increase tumor killing. In some embodiments, an iPSC comprises a disrupted REGNASE-1 gene. In some embodiments, an NK cell comprises a disrupted REGNASE-1 gene.

In some embodiments, gRNAs targeting the REGNASE-1 genomic region create Indels in the REGNASE-1 gene disrupting expression of the mRNA or protein. In some embodiments, the gRNA targets a site within the REGNASE-1 gene. In some embodiments, the REGNASE-1 gRNA targets a sequence comprising SEQ ID NOS: 93-101. In some embodiments, a gRNA targeting the REGNASE-1 gene comprises a spacer sequence corresponding to a sequence comprising any one of SEQ ID NOS: 93-101.

In some embodiments, at least 50% of the engineered cells of a population of cells does not express a detectable level of REGNASE-1 protein. For example, at least 55%, at least 60%, at least 70%, at least 75%, at least 80%, at least 85%, at least 90%, or at least 95% of the engineered cells of a population may not express a detectable level of REGNASE-1 protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered cells of a population does not express a detectable level of REGNASE-1 protein.

In some embodiments, less than 50% of the engineered cells of a population of cells express a detectable level of REGNASE-1 protein. In some embodiments, less than 30% of the engineered cells of a population of cells express a detectable level of REGNASE-1 protein. For example, less than 50%, less than 30%, less than 25%, less than 20%, less than 15%, less than 10%, or less than 5% of the engineered cells of a population of cells express a detectable level of REGNASE-1 protein. In some embodiments, 40%-30%, 40%-20%, 40%-10%, 40%-5%, 30%-20%, 30%-10%, 30%-5%, 20%-10%, 20%-5%, or 10%-5% of the engineered cells of a population of cells express a detectable level of REGNASE-1 protein.

FAS Gene Edits

In some embodiments, the genome of any cell described herein is modified to disrupt a Fas cell surface death receptor (FAS) gene (NCBI Gene ID: 355). FAS is a member of the TNF-receptor superfamily and contributes to the regulation of programmed cell death. In some embodiments, the disrupted FAS can reduce activation-induced cell death (AICD), resist apoptosis, and/or increase tumor killing. In some embodiments, an iPSC comprises a disrupted FAS gene. In some embodiments, an NK cell comprises a disrupted FAS gene.

In some embodiments, gRNAs targeting the FAS genomic region create Indels in the FAS gene disrupting expression of the mRNA or protein. In some embodiments, the gRNA targets a site within the FAS gene. In some embodiments, the FAS gRNA targets a sequence comprising SEQ ID NOS: 35, 37, 38, 39, 53, 55, or 80. In some embodiments, a gRNA targeting the FAS gene comprises a spacer sequence corresponding to a sequence comprising any one of SEQ ID NOS: 35, 37, 38, 39, 53, 55, or 80.

In some embodiments, at least 50% of the engineered cells of a population of cells does not express a detectable level of FAS protein. For example, at least 55%, at least 60%, at least 70%, at least 75%, at least 80%, at least 85%, at least 90%, or at least 95% of the engineered cells of a population may not express a detectable level of FAS surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered cells of a population does not express a detectable level of FAS protein.

In some embodiments, less than 50% of the engineered cells of a population of cells express a detectable level of FAS protein. In some embodiments, less than 30% of the engineered cells of a population of cells express a detectable level of FAS protein. For example, less than 50%, less than 30%, less than 25%, less than 20%, less than 15%, less than 10%, or less than 5% of the engineered cells of a population of cells express a detectable level of FAS protein. In some embodiments, 40%-30%, 40%-20%, 40%-10%, 40%-5%, 30%-20%, 30%-10%, 30%-5%, 20%-10%, 20%-5%, or 10%-5% of the engineered cells of a population of cells express a detectable level of FAS protein.

Edits to Knock-In Chimeric Antigen Receptors

A chimeric antigen receptor (CAR) refers to an artificial immune cell receptor that is engineered to recognize and bind to an antigen expressed by tumor cells. CARs or nucleotides encoding a CAR can be inserted into any cells described herein. CARs are chimeras of a signaling domain of the T-cell receptor (TCR) complex and an antigen-recognizing domain (e.g., a single chain fragment (scFv) of an antibody or other antibody fragment) (Enblad et al., Human Gene Therapy. 2015; 26(8):498-505). CARs have the ability to redirect cell specificity and reactivity toward a selected target in a non-MHC-restricted manner. The non-MHC-restricted antigen recognition gives cells expressing CARs the ability to recognize an antigen independent of antigen processing, thus bypassing a major mechanism of tumor escape. CARs are often referenced to by the antigen they bind. For example, a "CD30 CAR", "CD19 CAR", a "CD70 CAR", a "CD33 CAR" and a "BCMA CAR" are CARs comprising antigen binding domains that specifically bind to CD30, CD19, CD70, CD33 or BCMA, respectively. Accordingly, such terms are interchangeable with anti-CD30 CAR, anti-CD19 CAR, anti-CD70 CAR, anti-CD33 CAR and anti-BCMA CAR. It will be understood by those of ordinary skill in the art that a CAR that specifically binds an antigen can be referred to with either terminology.

In some embodiments, any iPSC described herein expresses a CAR. In some embodiments, any NK cell described herein expresses a CAR. In some embodiments, any HSPC described herein expresses a CAR.

There are four generations of CARs, each of which contains different components. First generation CARs join an antibody-derived scFv to the CD3zeta ((or z) intracellular signaling domain of the T-cell receptor through hinge and transmembrane domains. Second generation CARs incorporate an additional domain, e.g., CD28, 4-1BB (41BB), or ICOS, to supply a costimulatory signal. Third-generation CARs contain two costimulatory domains fused with the TCR CD3ζ chain. Third-generation costimulatory domains may include, e.g., a combination of CD3ζ, CD27, CD28, 4-1BB, ICOS, or OX40. Fourth-generation CARs include immune stimulatory cytokines to improve cell persistence and expansion. Cytokines for fourth-generation CARS include individually or in combination any of IL-7, IL-12, IL-15, IL-18, or IL-23. CARs, in some embodiments, contain an ectodomain, commonly derived from a single chain variable fragment (scFv), a hinge, a transmembrane domain, and an endodomain with one (first generation), two (second generation), or three (third generation) signaling domains derived from CD3Z and/or co-stimulatory molecules (Maude et al., Blood. 2015; 125(26):4017-4023; Kakarla and Gottschalk, Cancer J. 2014; 20(2):151-155).

CARs typically differ in their functional properties. The CD3ζ signaling domain of the T-cell receptor, when engaged, will activate and induce proliferation of T-cells but can lead to anergy (a lack of reaction by the body's defense mechanisms, resulting in direct induction of peripheral lymphocyte tolerance). Lymphocytes are considered anergic when they fail to respond to a specific antigen. The addition of a costimulatory domain in second-generation CARs improved replicative capacity and persistence of modified T-cells. Similar antitumor effects are observed in vitro with CD28 or 4-1BB CARs, but preclinical in vivo studies suggest that 4-1BB CARs may produce superior proliferation and/or persistence. Clinical trials suggest that both of these second-generation CARs are capable of inducing substantial T-cell proliferation in vivo, but CARs containing the 4-1BB costimulatory domain appear to persist longer. Third generation CARs combine multiple signaling domains (costimulatory) to augment potency.

In some embodiments, a chimeric antigen receptor is a first-generation CAR. In other embodiments, a chimeric antigen receptor is a second-generation CAR. In yet other embodiments, a chimeric antigen receptor is a third-generation CAR. In some embodiments, a chimeric antigen receptor is a fourth-generation CAR.

A CAR, in some embodiments, comprises an extracellular (ecto) domain comprising an antigen binding domain (e.g., an antibody, such as an scFv), a transmembrane domain, and a cytoplasmic (endo) domain.

Ectodomain of CARs

The ectodomain is the region of the CAR that is exposed to the extracellular fluid and, in some embodiments, includes an antigen binding domain, and optionally a signal peptide, a spacer domain, and/or a hinge domain. In some embodiments, the antigen binding domain is a single-chain variable fragment (scFv) that includes the VL and VH of immunoglobulins connected with a short linker peptide. The linker, in some embodiments, includes hydrophilic residues with stretches of glycine and serine for flexibility as well as stretches of glutamate and lysine for added solubility. A single-chain variable fragment (scFv) is not actually a fragment of an antibody, but instead is a fusion protein of the variable regions of the heavy (VH) and light chains (VL) of immunoglobulins, connected with a short linker peptide of ten to about 25 amino acids. The linker is usually rich in glycine for flexibility, as well as serine or threonine for solubility, and can either connect the N-terminus of the VH with the C-terminus of the VL, or vice versa. This protein retains the specificity of the original immunoglobulin, despite removal of the constant regions and the introduction of the linker. In some embodiments, the scFv of the present disclosure is humanized. In other embodiments, the scFv is fully human. In yet other embodiments, the scFv is a chimera (e.g., of mouse and human sequence).

In some embodiments, the scFv is an anti-BCMA scFv (binds specifically to BCMA or B-cell maturation antigen). In some embodiments, the anti-BCA scFv comprises or consists of the nucleotide sequence of SEQ ID NO: 71. In some embodiments, the anti-BCA scFv polynucleotide has at least 90%, 91%, 92%, 93%, 94%, 95%, 96%, 97%, 98%, or 99% identity to SEQ ID NO: 71. In some embodiments, the anti-BCMA CAR comprises the amino acid sequence of SEQ ID NO: 74.

In some embodiments, the scFv is an anti-CD30 scFv (binds specifically to CD30, also called TNF receptor superfamily member 8 or TNFRSF8). In some embodiments, anti-CD30 scFv may comprise variable domains from mouse monoclonal AC10 (e.g., Brentuximab). In other embodiments, anti-CD30 scFv may comprise variable domains from human 5F11 antibody (U.S. Pat. No. 7,387, 776). In some embodiments the scFV of a CD30 CAR may comprise the nucleotide sequence of SEQ ID NO: 106, SEQ ID NO: 111, or SEQ ID NO: 115. In some embodiments, the anti-CD30 CAR coding sequence comprises SEQ ID NO: 108, SEQ ID NO: 112, or SEQ ID NO: 116. In some embodiments, the anti-CD30 CAR coding sequence polynucleotide has at least 90%, 91%, 92%, 93%, 94%, 95%, 96%, 97%, 98%, or 99% identity to SEQ ID NO: 108, SEQ ID NO: 112, or SEQ ID NO: 116. Non-limiting examples of a CD30 CAR that may be used as provided herein may include the amino acid sequence of SEQ ID NO: 109, SEQ ID NO: 113, or SEQ ID NO: 117.

In some embodiments, the scFv is an anti-CD19 scFv (binds specifically to CD19).

In some embodiments, the scFv is an anti-CD70 scFv (binds specifically to CD70).

In some embodiments, the scFv is an anti-CD33 scFv (binds specifically to CD33).

Other scFv proteins may be used.

The signal peptide can enhance the antigen specificity of CAR binding. Signal peptides can be derived from antibodies, such as, but not limited to, CD8, as well as epitope tags such as, but not limited to, GST or FLAG. Examples of signal peptides include MLLLVTSLLLCELPHPAFLLIP (SEQ ID NO: 68) and MALPVTALLLPLALLLHAARP (SEQ ID NO: 69). Other signal peptides may be used.

In some embodiments, a spacer domain or hinge domain is located between an extracellular domain (comprising the antigen binding domain) and a transmembrane domain of a CAR, or between a cytoplasmic domain and a transmembrane domain of the CAR. A spacer domain is any oligopeptide or polypeptide that functions to link the transmembrane domain to the extracellular domain and/or the cytoplasmic domain in the polypeptide chain. A hinge domain is any oligopeptide or polypeptide that functions to provide flexibility to the CAR, or domains thereof, or to prevent steric hindrance of the CAR, or domains thereof. In some embodiments, a spacer domain or a hinge domain may comprise up to 300 amino acids (e.g., 10 to 100 amino acids, or 5 to 20 amino acids). In some embodiments, one or more spacer domain(s) may be included in other regions of a CAR. In some embodiments, the hinge domain is a CD8 hinge domain. Other hinge domains may be used.

Transmembrane Domain of CARs

The transmembrane domain is a hydrophobic alpha helix that spans the membrane. The transmembrane domain provides stability of the CAR. In some embodiments, the transmembrane domain of a CAR as provided herein is a CD8 transmembrane domain. In other embodiments, the transmembrane domain is a CD28 transmembrane domain. In yet other embodiments, the transmembrane domain is a chimera of a CD8 and CD28 transmembrane domain. Other transmembrane domains may be used as provided herein. In some embodiments, the CD8a transmembrane domain is the nucleotide of SEQ ID NO: 28. In some embodiments, the transmembrane domain is a CD8a transmembrane domain: FVPVFLPAKPTTTPAPRPPTPAPTIASQPLSLRPEACR-PAAGGAVHTRGLDFACDIYIWAP LAGTCGVLLLSLVITLYCNHRNR (SEQ ID NO: 72). In some embodiments, the transmembrane domain is a CD8a transmembrane domain comprising the amino acid sequence: IYIWAPLAGTCGVLLLSLVITLY (SEQ ID NO: 73). In some embodiments, the transmembrane domain is a CD8 transmembrane domain comprising the amino acid sequence SAAAFVPVFLPAKPTTTPAPRPPTPAPTIA-SQPLSLRPEACRPAAGGAVHTRGLDFACDIY IWAPLAGTCGVLLLSLVITLYCNHRNR (SEQ ID NO: 122). Other transmembrane domains may be used.

In some embodiments, the transmembrane domain is selected from transmembrane domains of: NKG2D, FcYRIIIa, NKp44, NKp30, NKp46, actKIR, NKG2C, CD8a, and IL15Rb. In some embodiments, the transmembrane domain is an NKG2D transmembrane domain.

Endodomain of CARs

The endodomain is the functional end of the receptor. Following antigen recognition, receptors cluster and a signal is transmitted to the cell. The most commonly used endodomain component is CD3-zeta, which contains three (3) immunoreceptor tyrosine-based activation motif (ITAM)s. This transmits an activation signal to the T cell after the antigen is bound. In many cases, CD3-zeta may not provide a fully competent activation signal and, thus, a co-stimulatory signaling is used. For example, CD28 and/or 4-1BB may be used with CD3-zeta (CD3ζ) to transmit a proliferative/survival signal. Thus, in some embodiments, the co-stimulatory molecule of a CAR as provided herein is a CD28 co-stimulatory molecule. In other embodiments, the co-stimulatory molecule is a 4-1BB co-stimulatory molecule. In some embodiments, a CAR includes CD3-zeta and CD28. In other embodiments, a CAR includes CD3-zeta and 4-1BB. In still other embodiments, a CAR includes CD3ζ, CD28, and 4-1BB. Table A provides examples of signaling domains derived from CD28, 4-1BB, and CD3-zeta that may be used herein.

TABLE A

| Name | Sequence | SEQ ID NO: |
|---|---|---|
| CD28 | SKRSRLLHSDYMNMTPRRPGPTRKHYQPYAPPRDFAAY RS | 123 |
| 4-1BB | KRGRKKLLYIFKQPFMRPVQTTQEEDGCSCRFPEEEEGG CEL | 124 |
| CD3-zeta | RVKFSRSADAPAYQQGQNQLYNELNLGRREEYDVLDK RRGRDPEMGGKPRRKNPQEGLYNELQKDKMAEAYSEI GMKGERRRGKGHDGLYQGLSTATKDTYDALHMQALPP R | 125 |

In some embodiments, any of the CARs described herein have one, two or more intracellular signaling domains from, e.g., CD137/41 BB, DNAM-1, NKrdO, 2B4, NTBA, CRACC, CD2, CD27, one or more integrins (e.g., ITGB1, ITGB2, or ITGB3), IL-15R, IL-18R, IL-12R, IL-21 R, or IRE1a (e.g., any combination of signaling domains from two or more of these molecules).

Natural Killer cells express a number of transmembrane adapters providing them with signal enhancement. In some embodiments, the intracellular signaling domain of any CAR described herein comprises a transmembrane adapter. In some embodiments, the transmembrane adapter is a transmembrane adaptor from one or more of: FceR1 y, CD3ζ, DAP12, and DAP10.

In some embodiments, any CARs described herein have one of more co-stimulatory domains. In some embodiments, a 2B4 co-stimulatory domain is used. In some embodiments, a CD3ζ intracellular signaling domain is used. In some embodiments, a DAP10 or DAP12 co-stimulatory domains are used with a CD3ζ intracellular signaling domain. In some embodiments, a DAP10 co-stimulatory signaling domain is used with an NKG2D transmembrane domain. In some embodiments, the transmembrane domain is from NKG2D, and the endodomain is from DAP10 and CD3ζ (e.g., as described in Chang Y H et al. *Caner Res.* 2013. 73(6):1777-86). In some embodiments, the CAR comprises an NKG2D transmembrane domain fused to 4-1BB and DAP10 signaling and/or co-stimulatory domains (e.g., as described in Guo C. et al. *Mol Immunol.* 2019. 114:108-113). In some embodiments, the CAR comprises a co-stimulatory domain from 2B4. In some embodiments, the CAR comprises a CD8 transmembrane domain and 4-1BB-CD3ζ signaling domains (e.g., as in a construct as described by Imai C, et al. *Blood.* 2005, 106(1). 376-383).

In some embodiments, the CAR has a CD8 transmembrane domain, a 4-1BB intracellular domain, and a CD3ζ signaling domain. In some embodiments, the CAR has a CD28 transmembrane domain, a CD28 intracellular domain, and a CD3ζ signaling domain. In some embodiments, the CAR has a DAP12 transmembrane and intracellular domains. In some embodiments, the CAR has a 2B4 transmembrane and intracellular domains and a CD3ζ signaling domain. In some embodiments, the CAR has a CD8 transmembrane domain, a 2B4 intracellular domain, and a CD3ζ signaling domain. In some embodiments, the CAR has a CD28 transmembrane and intracellular domains, a 4-1BB intracellular domain, and a CD3ζ signaling domain. In some embodiments, the CAR has a CD16 transmembrane domain, a 2B4 intracellular domain, and a CD3ζ signaling domain. In some embodiments, the CAR has a NKp44 transmembrane domain, a DAP10 intracellular domain, and a CD3ζ signaling domain. In some embodiments, the CAR has a NKp46 transmembrane domain, a2B4 intracellular domain, and a CD3ζ signaling domain. In some embodiments, the CAR has a NKG2D transmembrane domain, a 4-1BB intracellular domain, and a CD3ζ signaling domain. In some embodiments, the CAR has a NKG2D transmembrane domain, a 4-1BB intracellular domain, and a CD3ζ signaling domain. In some embodiments, the CAR has an NKG2D transmembrane domain, a DAP12 intracellular domain, a 2B4 intracellular domain, and a CD3ζ signaling domain. In some embodiments, the CAR has an NKG2D transmembrane domain, a DAP10 intracellular domain, a 2B4 intracellular domain, and a CD3ζ signaling domain. In some embodiments, the CAR has an NKG2D transmembrane domain, a 4-1BB intracellular domain, a 2B4 intracellular domain, and a CD3ζ signaling domain. In some embodiments, the CAR has an NKG2D transmembrane domain and a CD3ζ signaling domain.

Multi-Gene Editing

In some embodiments, the engineered cells of the present disclosure include more than one gene edit, for example, in more than one gene. In some embodiments, two, three, four, five, six or more genes are edited. In some embodiments, the gene-edit is an insertion (KI). In some embodiments, the gene-edit is a disruption (KO). In some embodiments, the combination of two or more gene edits described herein is a combination of insertions (KI) and disruptions (KO). In some embodiments, the gene-edits are any combination of one, two, three, four, five, six or more of the gene-edits selected from: B2M KO, IL15 KI, IL15Rα KI, IL15/IL15Rα KI, HLA-E KI, SERPINB9 KI, CIITA KO, ADAM17 KO, BCMA CAR KI, CD30 CAR KI, CISH KO, REGNASE-1 KO, FAS KO, TIGIT KO, PD-1 KO, NKG2A KO, CD70 KO, ALK4 type I activin receptor KO (e.g., a conditional KO), CD16 KI, CD70 CAR KI, CD19 CAR KI, CD33 CAR KI, NKGD2 CAR KI, a CAR or receptor comprising NKG2D ectodomain KI, NKp30 CAR KI, CD73 CAR KI, GPR87 CAR KI, and SLC7A11(xCT) CAR KI. In some embodiments, the editing of two or more genes is simultaneous, such as in the same method step. For example, an engineered cell may comprise a disrupted CIITA gene, a disrupted B2M gene, or a combination thereof. In some embodiments, any iPSC cell described herein has a disrupted CIITA gene and a disrupted B2M gene. In some embodiments, any engineered NK cell described herein comprises a disrupted CIITA gene and a disrupted B2M gene.

In some embodiments, any of the inserted polynucleotides described herein are linked to a promoter. In some embodiments, any of the inserted polynucleotides described herein are linked to an exogenous promoter. In some embodiments, the promoter is selected from but not limited to CAG promoter (also known as CBA promoter or CAGGS promoter), CMV promoter (derived from cytomegalovirus), EF-1 alpha promoter (derived from alpha subunit of EF-1 gene), PGK promoter (derived from phosphoglycerate kinase gene), UBC promoter (derived from ubiquitin C gene), or other constitutive, inducible, temporal-, tissue-, or cell type-specific promoter.

In some embodiments, the genome-engineered cells comprise introduced or increased expression in at least one of HLA-E, IL15/IL15Rα, a CAR, and SERPINB9. In some embodiments, any genome-engineered cell is HLA class I and/or class II deficient. In some embodiments, the genome-engineered cells comprise integrated or non-integrated exogenous polynucleotide encoding one or more of HLA-E, IL15/IL15Rα, a CAR, and SERPINB9 proteins. In some embodiments, said introduced expression is an increased expression from either non-expressed or lowly expressed genes comprised in said cells. In some embodiments, the non-integrated exogenous polynucleotides are introduced using Sendai virus, AAV, episomal, or plasmid. In some embodiments, the cells are B2M null, with introduced expression of HLA-E. In some embodiments, the cells are HLA-A, HLA-B, and HLA-C null, with introduced expression of HLA-E. In some embodiments, the cells are B2M null, with introduced expression of one or more of HLA-E, IL15/IL15Rα, and SERPINB9. Methods of generating any of the genetically modified cells described herein are contemplated to be performed using but not limited to, any of the gene editing methods described herein.

In some embodiments, a polynucleotide encoding HLA-E is inserted at a site within or near a B2M gene locus in any cell described herein. In some embodiments, a polynucleotide encoding HLA-E is inserted at a site within or near a B2M gene locus concurrent with or following a deletion of all or part of a B2M gene or promoter. In some embodiments, the polynucleotide encoding HLA-E is operably linked to an exogenous promoter. In some embodiments, the polynucleotide encoding HLA-E is operably linked to the CAGGS promoter. In some embodiments, any cell described herein is gene edited to express a polynucleotide encoding HLA-E operably linked to the CAGGS promoter.

In some embodiments, a polynucleotide encoding IL15/IL15Rα fusion protein is inserted at a site within or near a B2M gene locus in any cell described herein. In some embodiments, a polynucleotide encoding IL15/IL15Rα fusion protein is inserted at a site within or near a B2M gene locus concurrent with or following a deletion of all or part of a B2M gene or promoter. In some embodiments, the polynucleotide encoding IL15/IL15Rα fusion protein is operably linked to an exogenous promoter. In some embodiments, the polynucleotide encoding IL15/IL15Rα fusion protein is operably linked to the CAGGS promoter. In some embodiments, any cell described herein is gene edited to express a polynucleotide encoding IL15/IL15Rα fusion protein operably linked to the CAGGS promoter.

In some embodiments, a polynucleotide encoding SERPINB9 is inserted at a site within or near a B2M gene locus in any cell described herein. In some embodiments, a polynucleotide encoding SERPINB9 is inserted at a site within or near a B2M gene locus concurrent with or following a deletion of all or part of a B2M gene or promoter. In some embodiments, the polynucleotide encoding SERPINB9 is operably linked to an exogenous promoter. In some embodiments, the polynucleotide encoding SERPINB9 is operably linked to the CAGGS promoter. In some embodiments, any cell described herein is gene edited to express a polynucleotide encoding SERPINB9 operably linked to the CAGGS promoter.

In some embodiments, the edited cells described herein express at least one chimeric antigen receptor (CAR). In some embodiments, the CAR is inserted at a specific gene locus. In some embodiments, the CAR is inserted at a specific locus to simultaneously disrupt expression of a target gene.

In some embodiments, a polynucleotide encoding any CAR described herein is inserted within or near a CIITA gene locus. In some embodiments, a polynucleotide encoding any CAR described herein is inserted within or near a CIITA gene locus concurrent with or following a deletion of CIITA. In some embodiments, a polynucleotide encoding a BCMA-CAR is inserted within the CIITA gene locus. In some embodiments, the polynucleotide of SEQ ID NO: 66 encoding a BCMA-CAR is inserted at a site within or near a CIITA gene locus. In some embodiments, a polynucleotide encoding BCMA-CAR is inserted at a site within or near a CIITA gene locus concurrent with or following a deletion of a CIITA gene or promoter. In some embodiments, the BCMA CAR is inserted into the CIITA gene locus wherein 86 base pairs (bp) of CIITA exon 2 are removed after homology directed repair. In some embodiments, the BCMA CAR is inserted in the CIITA gene locus using into a donor plasmid. In some embodiments, a BCMA CAR donor plasmid is electroporated into any cell described herein along with the ribonucleoprotein (RNP) complex made of up of any CIITA targeting gRNA and Cas9 protein. In some embodiments, the BCMA-CAR inserted into the CIITA gene locus is driven by any promoter described herein. In some embodiments, the BCMA-CAR inserted into the CIITA gene locus is driven by the CAG promoter. In some embodiments, any cell described herein is gene-edited to express a BCMA-CAR within the CIITA gene locus. In some embodiments, an iPSC is gene-edited to express a BCMA-CAR within the CIITA gene locus.

In some embodiments, the BCMA-CAR donor plasmid (SEQ ID NO: 66) is electroporated into any cell described herein along with the ribonucleoprotein (RNP) complex made of up of any CIITA targeting gRNA (corresponding to a sequence of any one of SEQ ID NOs: 13-17) and Cas9 protein to yield a CIITA null, BCMA-CAR expressing cell. In some embodiments, the BCMA CAR donor plasmid (SEQ ID NO: 66) is electroporated into any iPSC described herein along with the ribonucleoprotein (RNP) complex made of up of CIITA targeting gRNA (SEQ ID NO: 13) and Cas9 protein to yield a CIITA null, BCMA-CAR KI expressing cell.

In some embodiments, a polynucleotide encoding a CD30-CAR is inserted within the CIITA gene locus. In some embodiments, the polynucleotide of SEQ ID NO: 108, 112, or 116 encoding a CD30 CAR is inserted at a site within or near a CIITA gene locus. In some embodiments, the polynucleotide of SEQ ID NO: 119, 120, or 121 encoding a CD30 CAR-P2A-HLA-E trimer is inserted at a site within or near a CIITA gene locus. In some embodiments, a polynucleotide encoding CD30 CAR or CD30 CAR-P2A-HLA-E trimer is inserted at a site within or near a CIITA gene locus concurrent with or following a deletion of a CIITA gene or promoter. In some embodiments, the CD30 CAR or CD30 CAR-P2A-HLA-E trimer is inserted into the CIITA gene locus wherein 86 base pairs (bp) of CIITA exon 2 are removed after homology directed repair. In some embodiments, the CD30 CAR or CD30 CAR-P2A-HLA-E trimer is inserted into in the CIITA gene locus using a donor plasmid. In some embodiments, a CD30 CAR or CD30 CAR-P2A-HLA-E trimer donor plasmid is electroporated into any cell described herein along with the ribonucleoprotein (RNP) complex made of up of any CIITA targeting gRNA and Cas9 protein. In some embodiments, the CD30 CAR or CD30 CAR-P2A-HLA-E trimer inserted into the CIITA gene locus is driven by any promoter described herein. In some embodiments, the CD30 CAR or CD30 CAR-P2A-HLA-E trimer inserted into the CIITA gene locus is driven by the CAG promoter. In some embodiments, any cell described herein is gene-edited to express a CD30 CAR or CD30 CAR-P2A-HLA-E trimer within the CIITA gene locus. In some embodiments, an iPSC is gene-edited to express a CD30 CAR or CD30 CAR-P2A-HLA-E trimer within the CIITA gene locus.

In some embodiments, the CD30 CAR-P2A-HLA-E trimer donor plasmid (SEQ ID NO: 110, 114, or 118) is electroporated into any cell described herein along with the ribonucleoprotein (RNP) complex made of up of any CIITA targeting gRNA (corresponding to a sequence of any one of SEQ ID NOs: 13-17) and Cas9 protein to yield a CIITA null, CD30 CAR, HLA-E expressing cell. In some embodiments, the CD30 CAR-P2A-HLA-E trimer donor plasmid (SEQ ID NO: 110, 114, or 118) is electroporated into any iPSC described herein along with the ribonucleoprotein (RNP) complex made of up of CIITA targeting gRNA (SEQ ID NO: 13) and Cas9 protein to yield a CIITA null, CD30 CAR, HLA-E expressing cell.

In some embodiments, a cell described herein has an insertion of a polynucleotide encoding any one or more of IL15/IL15Rα, P2A, HLA-E trimer, and SERPINB9. In some embodiments, any cell described herein has an insertion of a polynucleotide encoding any one or more of IL15/IL15Rα, P2A, HLA-E trimer, and SERPINB9 into the B2M gene locus. In some embodiments, any cell described herein has insertion of a polynucleotide encoding IL15/IL15Rα fusion protein. In some embodiments, the IL15/IL15Rα fusion protein is designed as previously described in Hurton et al. (2016) Proc Natl Acad Sci USA; 113(48): E7788-E7797. doi: 10.1073/pnas.1610544113, or which is incorporated herein in its entirety.

In some embodiments, a cell described herein has insertion of a polynucleotide encoding an IL15/IL15Rα-P2A-HLA-E trimer. In some embodiments, a cell described herein has insertion of a polynucleotide encoding an IL15/IL15Rα-P2A-HLA-E trimer encoded by SEQ ID NO: 77. In some embodiments, a cell has insertion of a polynucleotide encoding IL15/IL15Rα-P2A-HLA-E trimer into the B2M gene locus. In some embodiments, the IL15/IL15Rα-P2A-HLA-E trimer coding sequence is driven by any promoter described herein. In some embodiments, the IL15/IL15Rα-P2A-HLA-E trimer coding sequence is driven by a CAGGS promoter. In some embodiments, a donor plasmid comprising IL15/IL15Rα-P2A-HLA-E trimer sequence driven by a CAGGS promoter comprises the nucleotide sequence of SEQ ID NO: 67. In some embodiments, any cell described herein is gene-edited to express an IL15/IL15Rα-P2A-HLA-E trimer. In some embodiments, an iPSC is gene-edited to express an IL15/IL15Rα-P2A-HLA-E trimer. In some embodiments, a NK cell is gene-edited to express an IL15/IL15Rα-P2A-HLA-E trimer.

In some embodiments, the IL15/IR15α-P2A-HLA-E trimer donor plasmid (SEQ ID NO: 67) is electroporated into any cell described herein along with the ribonucleoprotein (RNP) complex made of up of B2M targeting gRNA (corresponding to a sequence of SEQ ID NOs:34, 78, or 79) and Cas9 protein to yield a B2M null, IL15/IL15Rα-P2A-HLA-E trimer expressing cell. In some embodiments, the IL15/IR15α-P2A-HLA-E trimer donor plasmid (SEQ ID NO: 67) is electroporated into any iPSC described herein along with the ribonucleoprotein (RNP) complex made of up of B2M targeting gRNA (SEQ ID NO: 34) and Cas9 protein to yield a B2M null, IL15/IR15α-P2A-HLA-E trimer expressing cell.

In some embodiments, a cell described herein has insertion of a polynucleotide encoding SERPINB9-P2A-HLA-E trimer. In some embodiments, a cell described herein has insertion of a polynucleotide encoding a SERPINB9-P2A-HLA-E trimer, wherein the polynucleotide comprises the sequence of SEQ ID NO: 131. In some embodiments, a cell has insertion of a polynucleotide encoding SERPINB9-P2A-HLA-E trimer into the B2M gene locus. In some embodiments, the SERPINB9-P2A-HLA-E trimer sequence is driven by any promoter described herein. In some embodiments, the SERPINB9-P2A-HLA-E trimer sequence is driven by a CAGGS promoter. In some embodiments, a plasmid comprising the polynucleotide encoding SERPINB9-P2A-HLA-E trimer driven by a CAGGS promoter comprises SEQ ID NO: 130. In some embodiments, any cell described herein is gene-edited to express a SERPINB9-P2A-HLA-E trimer. In some embodiments, an iPSC is gene-edited to express a SERPINB9-P2A-HLA-E trimer. In some embodiments, a NK cell is gene-edited to express a SERPINB9-P2A-HLA-E trimer.

In some embodiments, the SERPINB9-P2A-HLA-E trimer donor plasmid (SEQ ID NO: 130) is electroporated into any cell described herein along with the ribonucleoprotein (RNP) complex made of up of B2M targeting gRNA (corresponding to a sequence of SEQ ID NOs:34, 78, or 79) and Cas9 protein to yield a B2M null, SERPINB9-P2A-HLA-E trimer expressing cell. In some embodiments, the SERPINB9-P2A-HLA-E trimer donor plasmid (SEQ ID NO: 130 is electroporated into any iPSC described herein along with the ribonucleoprotein (RNP) complex made of up of B2M targeting gRNA (SEQ ID NO: 34) and Cas9 protein to yield a B2M null, SERPINB9-P2A-HLA-E trimer expressing cell.

In some embodiments, a cell described herein has insertion of a polynucleotide encoding SERPINB9-P2A-IL15/IL15Rα. In some embodiments, a cell described herein has insertion of a polynucleotide encoding SERPINB9-P2A-IL15/IL15Rα, wherein the coding sequence comprises SEQ ID NO: 137. In some embodiments, a cell has insertion of a polynucleotide encoding SERPINB9-P2A-IL15/IL15Rα into the B2M gene locus. In some embodiments, the SERPINB9-P2A-IL15/IL15Rα sequence is driven by any promoter described herein. In some embodiments, the SERPINB9-P2A-IL15/IL15Rα sequence is driven by a CAGGS promoter. In some embodiments, a plasmid comprising the polynucleotide encoding SERPINB9-P2A-IL15/IL15Rα driven by a CAGGS promoter comprises SEQ ID NO: 148. In some embodiments, any cell described herein is gene-edited to express SERPINB9-P2A-IL15/IL15Rα. In some embodiments, an iPSC is gene-edited to express SERPINB9-P2A-IL15/IL15Rα. In some embodiments, a NK cell is gene-edited to express SERPINB9-P2A-IL15/IL15Rα.

In some embodiments, the SERPINB9-P2A-IL15/IL15Rα donor plasmid (SEQ ID NO: 148) is electroporated into any cell described herein along with the ribonucleoprotein (RNP) complex made of up of B2M targeting gRNA (corresponding to a sequence of SEQ ID NOs:34, 78, or 79) and Cas9 protein to yield a B2M null, SERPINB9-P2A-IL15/IL15Rα expressing cell. In some embodiments, the SERPINB9-P2A-IL15/IL15Rα donor plasmid (SEQ ID NO: 148 is electroporated into any iPSC described herein along with the ribonucleoprotein (RNP) complex made of up of B2M targeting gRNA (SEQ ID NO: 34) and Cas9 protein to yield a B2M null, SERPINB9-P2A-IL15/IL15Rα expressing cell.

In some embodiments, any B2M null, IL15/IR15α-P2A-HLA-E trimer KI cell described herein is electroporated with BCMA-CAR donor plasmid (SEQ ID NO: 66) along with the ribonucleoprotein (RNP) complex made of up of CIITA targeting gRNA (corresponding to a sequence of any one of SEQ ID NOs: 13-17) and Cas9 protein to yield a B2M null, IL15/IL15Rα-P2A-HLA-E trimer KI, BCMA-CAR KI, CIITA null expressing cell. In some embodiments, any B2M null, IL15/IR15α-P2A-HLA-E trimer KI iPSC described herein is electroporated with BCMA-CAR donor plasmid (SEQ ID NO: 66) along with the ribonucleoprotein (RNP) complex made of up of CIITA targeting gRNA (corresponding to a sequence of any one of SEQ ID NOs: 13-17) and Cas9 protein to yield a B2M null, IL15/IL15Rα-P2A-HLA-E trimer expressing, CIITA null BCMA-CAR expressing iPSC. The engineered iPSC may then be differentiated into an NK cell.

In some embodiments, any CIITA null, BCMA-CAR KI cell described herein is electroporated with IL15/IR15α-P2A-HLA-E trimer donor plasmid (SEQ ID NO: 67) along with the ribonucleoprotein (RNP) complex made of up of B2M targeting gRNA (corresponding to a sequence of SEQ ID NO: 34) and Cas9 protein to yield a B2M null, IL15/IL15Rα-P2A-HLA-E trimer KI, BCMA-CAR KI, CIITA null expressing cell. In some embodiments, any CIITA null, BCMA-CAR KI iPSC described herein is electroporated with IL15/IR15α-P2A-HLA-E trimer donor plasmid (SEQ ID NO: 67) along with the ribonucleoprotein (RNP) complex made of up of B2M targeting gRNA (corresponding to a sequence of SEQ ID NO: 34) and Cas9 protein to yield a B2M null, IL15/IL15Rα-P2A-HLA-E trimer expressing, CIITA null, BCMA-CAR expressing iPSC. The engineered iPSC may then be differentiated into an NK cell.

In some embodiments, any B2M null, SERPINB9-P2A-IL15/IR15a KI cell described herein is electroporated with a CAR-P2A-HLA-E donor plasmid (SEQ ID NOS: 110, 114, 118) along with the ribonucleoprotein (RNP) complex made of up of CIITA targeting gRNA (corresponding to a sequence of any one of SEQ ID NOs: 13-17) and Cas9 protein to yield a B2M null, SERPINB9-P2A-IL15/IR15a expressing, CIITA null, CD30 CAR-P2A-HLA-E trimer expressing cell.

In some embodiments, any CIITA null, CAR-P2A-HLA-E trimer KI cell described herein is electroporated with a SERPINB9-P2A-IL15/IR15a donor plasmid (SEQ ID NO: 148) along with the ribonucleoprotein (RNP) complex made of up of B2M targeting gRNA (corresponding to a sequence of SEQ ID NO: 34) and Cas9 protein to yield a B2M null, CAR-P2A-HLA-E trimer expressing, CIITA null, SERPINB9-P2A-IL15/IR15a expressing cell.

In some embodiments, any B2M null, SERPINB9-P2A-IL15/IR15a expressing, CIITA null, CAR-P2A-HLA-E trimer expressing cell further comprises FAS KO and CISH KO.

In some embodiments, any cell described herein has disruption of the ADAM17 gene.

In some embodiments, any B2M null, IL15/IR15α-P2A-HLA-E trimer KI, BCMA-CAR KI, CIITA null cell described herein is gene-edited to disrupt ADAM17. In some embodiments, a B2M null, IL15/IR15α-P2A-HLA-E trimer KI, BCMA-CAR KI, CIITA null iPSC is gene-edited to disrupt ADAM17. In some embodiments ADAM17 is knocked-out using an RNP with a gRNA corresponding to a sequence consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. In some embodiments, ADAM17 is knocked-out using an RNP with the gRNA corresponding to a sequence of SEQ ID NO: 1. In some embodiments, an iPSC described herein is a B2M null, IL15/IR15α-P2A-HLA-E trimer KI, BCMA-CAR KI, CIITA null, ADAM17 null. In some embodiments, a NK cell described herein is B2M null, IL15/IR15α-P2A-HLA-E trimer KI, BCMA-CAR KI, CIITA null, ADAM17 null. In some embodiments, the cell further comprises FAS KO, CISH KO, and/or REGNASE-I KO.

In some embodiments, a B2M null, IL15/IR15α-P2A-HLA-E trimer KI, BCMA-CAR KI, CIITA null iPSC is gene-edited to disrupt ADAM17 and then differentiated into an NK cell. In some embodiments, a B2M null, IL15/IR15α-P2A-HLA-E trimer KI, BCMA-CAR KI, CIITA null iPSC is gene-edited to disrupt ADAM17, FAS, CISH, REGNASE-1 and then differentiated into an NK cell.

Genome Editing Methods

Genome editing generally refers to the process of modifying the nucleotide sequence of a genome, preferably in a precise or pre-determined manner. In some embodiments, genome editing methods as described herein, e.g., the CRISPR-endonuclease system, are used to genetically modify a cell as described herein, e.g., to create a gene-edited iPSC cell. In some embodiments, genome editing methods as described herein, e.g., the CRISPR-endonuclease system, are used to genetically modify a cell as described herein, e.g., to introduce at least one genetic modification within or near at least one gene that increases the expression of one or more MHC-I and/or MHC-II human leukocyte antigens or other components of the MHC-I or MHC-II complex relative to an unmodified cell; to introduce at least one genetic modification that increases the expression of at least one polynucleotide that encodes a tolerogenic factor relative to an unmodified cell; and/or introduce at least one genetic modification that increases or decreases the expression of at least one gene that encodes a targeting factor that improves immunogenicity.

Examples of methods of genome editing described herein include methods of using site-directed nucleases to cut deoxyribonucleic acid (DNA) at precise target locations in the genome, thereby creating single-strand or double-strand DNA breaks at particular locations within the genome. Such breaks can be and regularly are repaired by natural, endogenous cellular processes, such as homology-directed repair (HDR) and non-homologous end joining (NHEJ), as described in Cox et al., "Therapeutic genome editing: prospects and challenges,", Nature Medicine, 2015, 21(2), 121-31. These two main DNA repair processes consist of a family of alternative pathways. NHEJ directly joins the DNA ends resulting from a double-strand break, sometimes with the loss or addition of nucleotide sequence, which may disrupt or enhance gene expression. HDR utilizes a homologous sequence, or donor sequence, as a template for inserting a defined DNA sequence at the break point. The homologous sequence can be in the endogenous genome, such as a sister chromatid. Alternatively, the donor sequence can be an exogenous polynucleotide, such as a plasmid, a single-strand oligonucleotide, a double-stranded oligonucleotide, a duplex oligonucleotide or a virus, that has regions (e.g., left and right homology arms) of high homology with the nuclease-cleaved locus, but which can also contain additional sequence or sequence changes including deletions that can be incorporated into the cleaved target locus. A third repair mechanism can be microhomology-mediated end joining (MMEJ), also referred to as "Alternative NHEJ," in which the genetic outcome is similar to NHEJ in that small deletions and insertions can occur at the cleavage site. MMEJ can make use of homologous sequences of a few base pairs flanking the DNA break site to drive a more favored DNA end joining repair outcome, and recent reports have further elucidated the molecular mechanism of this process; see, e.g., Cho and Greenberg, Nature, 2015, 518, 174-76; Kent et al., Nature Structural and Molecular Biology, 2015, 22(3):230-7; Mateos-Gomez et al., Nature, 2015, 518, 254-57; Ceccaldi et al., Nature, 2015, 528, 258-62. In some instances, it may be possible to predict likely repair outcomes based on analysis of potential microhomologies at the site of the DNA break.

Each of these genome editing mechanisms can be used to create desired genetic modifications. A step in the genome editing process can be to create one or two DNA breaks, the latter as double-strand breaks or as two single-stranded breaks, in the target locus as near the site of intended mutation. This can be achieved via the use of endonucleases, as described and illustrated herein.

In general, the genome editing methods described herein can be in vitro or ex vivo methods. In some embodiments, the genome editing methods disclosed herein are not methods for treatment of the human or animal body by therapy and/or are not processes for modifying the germ line genetic identity of human beings.

CRISPR Endonuclease System

The CRISPR-endonuclease system is a naturally occurring defense mechanism in prokaryotes that has been repurposed as an RNA-guided DNA-targeting platform used for gene editing. CRISPR systems include Types I, II, III, IV, V, and VI systems. In some aspects, the CRISPR system is a Type II CRISPR/Cas9 system. In other aspects, the CRISPR system is a Type V CRISPR/Cprf system. CRISPR systems rely on a DNA endonuclease, e.g., Cas9, and two noncoding RNAs—crisprRNA (crRNA) and trans-activating RNA (tracrRNA)—to target the cleavage of DNA.

The crRNA drives sequence recognition and specificity of the CRISPR-endonuclease complex through Watson-Crick base pairing, typically with a ~20 nucleotide (nt) sequence in the target DNA. Changing the sequence of the 5' 20 nt in the crRNA allows targeting of the CRISPR-endonuclease complex to specific loci. The CRISPR-endonuclease complex only binds DNA sequences that contain a sequence match to the first 20 nt of the single-guide RNA (sgRNA) if the target sequence is followed by a specific short DNA motif (with the sequence NGG) referred to as a protospacer adjacent motif (PAM).

TracrRNA hybridizes with the 3' end of crRNA to form an RNA-duplex structure that is bound by the endonuclease to form the catalytically active CRISPR-endonuclease complex, which can then cleave the target DNA.

Once the CRISPR-endonuclease complex is bound to DNA at a target site, two independent nuclease domains within the endonuclease each cleave one of the DNA strands three bases upstream of the PAM site, leaving a double-strand break (DSB) where both strands of the DNA terminate in a base pair (a blunt end).

In some embodiments, the endonuclease is a Cas9 (CRISPR associated protein 9). In some embodiments, the Cas9 endonuclease is from Streptococcus pyogenes, although other Cas9 homologs may be used, e.g., S. aureus Cas9, N. meningitidis Cas9, S. thermophilus CRISPR 1 Cas9, S. thermophilus CRISPR 3 Cas9, or T. denticola Cas9. In some embodiments, the CRISPR endonuclease is Cpf1, e.g., L. bacterium ND2006 Cpf1 or Acidaminococcus sp.

BV3L6 Cpf1. In some embodiments, the endonuclease is Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease. In some embodiments, wild-type variants may be used. In some embodiments, modified versions (e.g., a homolog thereof, a recombination of the naturally occurring molecule thereof, codon-optimized thereof, or modified versions thereof) of the preceding endonucleases may be used.

The CRISPR nuclease can be linked to at least one nuclear localization signal (NLS). The at least one NLS can be located at or within 50 amino acids of the amino-terminus of the CRISPR nuclease and/or at least one NLS can be located at or within 50 amino acids of the carboxy-terminus of the CRISPR nuclease.

Exemplary CRISPR/Cas polypeptides include the Cas9 polypeptides as published in Fonfara et al., "Phylogeny of Cas9 determines functional exchangeability of dual-RNA and Cas9 among orthologous type II CRISPR-Cas systems," Nucleic Acids Research, 2014, 42: 2577-2590. The CRISPR/Cas gene naming system has undergone extensive rewriting since the Cas genes were discovered. Fonfara et al. also provides PAM sequences for the Cas9 polypeptides from various species.

Zinc Finger Nucleases

Zinc finger nucleases (ZFNs) are modular proteins comprised of an engineered zinc finger DNA binding domain linked to the catalytic domain of the type II endonuclease FokI. Because FokI functions only as a dimer, a pair of ZFNs must be engineered to bind to cognate target "half-site" sequences on opposite DNA strands and with precise spacing between them to enable the catalytically active FokI dimer to form. Upon dimerization of the FokI domain, which itself has no sequence specificity per se, a DNA double-strand break is generated between the ZFN half-sites as the initiating step in genome editing.

The DNA binding domain of each ZFN is typically comprised of 3-6 zinc fingers of the abundant Cys2-His2 architecture, with each finger primarily recognizing a triplet of nucleotides on one strand of the target DNA sequence, although cross-strand interaction with a fourth nucleotide also can be important. Alteration of the amino acids of a finger in positions that make key contacts with the DNA alters the sequence specificity of a given finger. Thus, a four-finger zinc finger protein will selectively recognize a 12 bp target sequence, where the target sequence is a composite of the triplet preferences contributed by each finger, although triplet preference can be influenced to varying degrees by neighboring fingers. An important aspect of ZFNs is that they can be readily re-targeted to almost any genomic address simply by modifying individual fingers. In most applications of ZFNs, proteins of 4-6 fingers are used, recognizing 12-18 bp respectively. Hence, a pair of ZFNs will typically recognize a combined target sequence of 24-36 bp, not including the typical 5-7 bp spacer between half-sites. The binding sites can be separated further with larger spacers, including 15-17 bp. A target sequence of this length is likely to be unique in the human genome, assuming repetitive sequences or gene homologs are excluded during the design process. Nevertheless, the ZFN protein-DNA interactions are not absolute in their specificity so off-target binding and cleavage events do occur, either as a heterodimer between the two ZFNs, or as a homodimer of one or the other of the ZFNs. The latter possibility has been effectively eliminated by engineering the dimerization interface of the FokI domain to create "plus" and "minus" variants, also known as obligate heterodimer variants, which can only dimerize with each other, and not with themselves. Forcing the obligate heterodimer prevents formation of the homodimer. This has greatly enhanced specificity of ZFNs, as well as any other nuclease that adopts these FokI variants.

A variety of ZFN-based systems have been described in the art, modifications thereof are regularly reported, and numerous references describe rules and parameters that are used to guide the design of ZFNs; see, e.g., Segal et al., Proc Natl Acad Sci, 1999 96(6):2758-63; Dreier B et al., J Mol Biol., 2000, 303(4):489-502; Liu Q et al., J Biol Chem., 2002, 277(6):3850-6; Dreier et al., J Biol Chem., 2005, 280(42):35588-97; and Dreier et al., J Biol Chem. 2001, 276(31):29466-78.

Transcription Activator-Like Effector Nucleases (TALENs)

TALENs represent another format of modular nucleases whereby, as with ZFNs, an engineered DNA binding domain is linked to the FokI nuclease domain, and a pair of TALENs operate in tandem to achieve targeted DNA cleavage. The major difference from ZFNs is the nature of the DNA binding domain and the associated target DNA sequence recognition properties. The TALEN DNA binding domain derives from TALE proteins, which were originally described in the plant bacterial pathogen *Xanthomonas* sp. TALEs are comprised of tandem arrays of 33-35 amino acid repeats, with each repeat recognizing a single base pair in the target DNA sequence that is typically up to 20 bp in length, giving a total target sequence length of up to 40 bp. Nucleotide specificity of each repeat is determined by the repeat variable diresidue (RVD), which includes just two amino acids at positions 12 and 13. The bases guanine, adenine, cytosine and thymine are predominantly recognized by the four RVDs: Asn-Asn, Asn-Ile, His-Asp and Asn-Gly, respectively. This constitutes a much simpler recognition code than for zinc fingers, and thus represents an advantage over the latter for nuclease design. Nevertheless, as with ZFNs, the protein-DNA interactions of TALENs are not absolute in their specificity, and TALENs have also benefitted from the use of obligate heterodimer variants of the FokI domain to reduce off-target activity.

Additional variants of the FokI domain have been created that are deactivated in their catalytic function. If one half of either a TALEN or a ZFN pair contains an inactive FokI domain, then only single-strand DNA cleavage (nicking) will occur at the target site, rather than a DSB. The outcome is comparable to the use of CRISPR/Cas9 or CRISPR/Cpf1 "nickase" mutants in which one of the Cas9 cleavage domains has been deactivated. DNA nicks can be used to drive genome editing by HDR, but at lower efficiency than with a DSB. The main benefit is that off-target nicks are quickly and accurately repaired, unlike the DSB, which is prone to NHEJ-mediated mis-repair.

A variety of TALEN-based systems have been described in the art, and modifications thereof are regularly reported; see, e.g., Boch, Science, 2009 326(5959):1509-12; Mak et al., Science, 2012, 335(6069):716-9; and Moscou et al., Science, 2009, 326(5959):1501. The use of TALENs based on the "Golden Gate" platform, or cloning scheme, has been described by multiple groups; see, e.g., Cermak et al., Nucleic Acids Res., 2011, 39(12):e82; Li et al., Nucleic Acids Res., 2011, 39(14):6315-25; Weber et al., PLoS One, 2011, 6(2):e16765; Wang et al., J Genet Genomics, 2014, 41(6):339-47; and Cermak T et al., Methods Mol Biol., 2015 1239:133-59.

Homing Endonucleases

Homing endonucleases (HEs) are sequence-specific endonucleases that have long recognition sequences (14-44 base pairs) and cleave DNA with high specificity—often at sites unique in the genome. There are at least six known families of HEs as classified by their structure, including GIY-YIG, His-Cis box, H-N-H, PD–(D/E)×K, and Vsr-like that are derived from a broad range of hosts, including eukarya, protists, bacteria, archaea, cyanobacteria and phage. As with ZFNs and TALENs, HEs can be used to create a DSB at a target locus as the initial step in genome editing. In addition, some natural and engineered HEs cut only a single strand of DNA, thereby functioning as site-specific nickases. The large target sequence of HEs and the specificity that they offer have made them attractive candidates to create site-specific DSBs.

A variety of HE-based systems have been described in the art, and modifications thereof are regularly reported; see, e.g., the reviews by Steentoft et al., Glycobiology, 2014, 24(8):663-80; Belfort and Bonocora, Methods Mol Biol., 2014, 1123:1-26; and Hafez and Hausner, Genome, 2012, 55(8):553-69.

MegaTAL/Tev-mTALEN/MegaTev

As further examples of hybrid nucleases, the MegaTAL platform and Tev-mTALEN platform use a fusion of TALE DNA binding domains and catalytically active HEs, taking advantage of both the tunable DNA binding and specificity of the TALE, as well as the cleavage sequence specificity of the HE; see, e.g., Boissel et al., Nucleic Acids Res., 2014, 42: 2591-2601; Kleinstiver et al., G3, 2014, 4:1155-65; and Boissel and Scharenberg, Methods Mol. Biol., 2015, 1239: 171-96.

In a further variation, the MegaTev architecture is the fusion of a meganuclease (Mega) with the nuclease domain derived from the GIY-YIG homing endonuclease I-TevI (Tev). The two active sites are positioned ~30 bp apart on a DNA substrate and generate two DSBs with non-compatible cohesive ends; see, e.g., Wolfs et al., Nucleic Acids Res., 2014, 42, 8816-29. It is anticipated that other combinations of existing nuclease-based approaches will evolve and be useful in achieving the targeted genome modifications described herein.

dCas9-FokI or dCpf1-FokI and Other Nucleases

Combining the structural and functional properties of the nuclease platforms described above offers a further approach to genome editing that can potentially overcome some of the inherent deficiencies. As an example, the CRISPR genome editing system typically uses a single Cas9 endonuclease to create a DSB. The specificity of targeting is driven by a 20 or 24 nucleotide sequence in the guide RNA that undergoes Watson-Crick base-pairing with the target DNA (plus an additional 2 bases in the adjacent NAG or NGG PAM sequence in the case of Cas9 from *S. pyogenes*). Such a sequence is long enough to be unique in the human genome, however, the specificity of the RNA/DNA interaction is not absolute, with significant promiscuity sometimes tolerated, particularly in the 5' half of the target sequence, effectively reducing the number of bases that drive specificity. One solution to this has been to completely deactivate the Cas9 or Cpf1 catalytic function—retaining only the RNA-guided DNA binding function—and instead fusing a FokI domain to the deactivated Cas9; see, e.g., Tsai et al., Nature Biotech, 2014, 32: 569-76; and Guilinger et al., Nature Biotech., 2014, 32: 577-82. Because FokI must dimerize to become catalytically active, two guide RNAs are required to tether two FokI fusions in close proximity to form the dimer and cleave DNA. This essentially doubles the number of bases in the combined target sites, thereby increasing the stringency of targeting by CRISPR-based systems.

As further example, fusion of the TALE DNA binding domain to a catalytically active HE, such as I-TevI, takes advantage of both the tunable DNA binding and specificity of the TALE, as well as the cleavage sequence specificity of I-TevI, with the expectation that off-target cleavage can be further reduced.

Base Editing

In some embodiments, a gene is edited in a cell using base editing. Base Editing is a technique enabling the conversion of one nucleotide into another without double-stranded breaks in the DNA. Base editing allows for conversion of a C to T, G to A, or vice versa. An example editor for cytosine includes rAPOBEC1 which is fused to a catalytically inactive form of Cas9. The Cas9 helps to bind a site of interest and the rAPOBEC1 cytidine deaminase induces the point mutation. Conversion of adenine requires a mutant transfer RNA adenosine deaminase (TadA), a Cas9 nickase, and a sgRNA, as described herein. The construct is able to introduce the site-specific mutation without introducing a strand break. In some embodiments, Base Editing is used to introduce one or more mutations in a cell described herein.

RNA-Guided Endonucleases

The RNA-guided endonuclease systems as used herein can comprise an amino acid sequence having at least 10%, at least 15%, at least 20%, at least 30%, at least 40%, at least 50%, at least 60%, at least 70%, at least 75%, at least 80%, at least 85%, at least 90%, at least 95%, at least 99%, or 100% amino acid sequence identity to a wild-type exemplary endonuclease, e.g., Cas9 from *S. pyogenes*, US2014/0068797 Sequence ID No. 8 or Sapranauskas et al., Nucleic Acids Res, 39(21): 9275-9282 (2011). The endonuclease can comprise at least 70, 75, 80, 85, 90, 95, 97, 99, or 100% identity to a wild-type endonuclease (e.g., Cas9 from *S. pyogenes*, supra) over 10 contiguous amino acids. The endonuclease can comprise at most: 70, 75, 80, 85, 90, 95, 97, 99, or 100% identity to a wild-type endonuclease (e.g., Cas9 from *S. pyogenes*, supra) over 10 contiguous amino acids. The endonuclease can comprise at least: 70, 75, 80, 85, 90, 95, 97, 99, or 100% identity to a wild-type endonuclease (e.g., Cas9 from *S. pyogenes*, supra) over 10 contiguous amino acids in a HNH nuclease domain of the endonuclease. The endonuclease can comprise at most: 70, 75, 80, 85, 90, 95, 97, 99, or 100% identity to a wild-type endonuclease (e.g., Cas9 from *S. pyogenes*, supra) over 10 contiguous amino acids in a HNH nuclease domain of the endonuclease. The endonuclease can comprise at least: 70, 75, 80, 85, 90, 95, 97, 99, or 100% identity to a wild-type endonuclease (e.g., Cas9 from *S. pyogenes*, supra) over 10 contiguous amino acids in a RuvC nuclease domain of the endonuclease. The endonuclease can comprise at most: 70, 75, 80, 85, 90, 95, 97, 99, or 100% identity to a wild-type endonuclease (e.g., Cas9 from *S. pyogenes*, supra) over 10 contiguous amino acids in a RuvC nuclease domain of the endonuclease.

The endonuclease can comprise a modified form of a wild-type exemplary endonuclease. The modified form of the wild-type exemplary endonuclease can comprise a mutation that reduces the nucleic acid-cleaving activity of the endonuclease. The modified form of the wild-type exemplary endonuclease can have less than 90%, less than 80%, less than 70%, less than 60%, less than 50%, less than 40%, less than 30%, less than 20%, less than 10%, less than 5%, or less than 1% of the nucleic acid-cleaving activity of the wild-type exemplary endonuclease (e.g., Cas9 from *S. pyogenes*, supra). The modified form of the endonuclease can have no substantial nucleic acid-cleaving activity. When an endonuclease is a modified form that has no substantial nucleic acid-cleaving activity, it is referred to herein as "enzymatically inactive."

Mutations contemplated can include substitutions, additions, and deletions, or any combination thereof. The mutation converts the mutated amino acid to alanine. The mutation converts the mutated amino acid to another amino acid (e.g., glycine, serine, threonine, cysteine, valine, leucine, isoleucine, methionine, proline, phenylalanine, tyrosine, tryptophan, aspartic acid, glutamic acid, asparagine, glutamine, histidine, lysine, or arginine). The mutation converts the mutated amino acid to a non-natural amino acid (e.g., selenomethionine). The mutation converts the mutated amino acid to amino acid mimics (e.g., phosphomimics). The mutation can be a conservative mutation. For example, the mutation converts the mutated amino acid to amino acids that resemble the size, shape, charge, polarity, conformation, and/or rotamers of the mutated amino acids (e.g., cysteine/serine mutation, lysine/asparagine mutation, histidine/phenylalanine mutation). The mutation can cause a shift in reading frame and/or the creation of a premature stop codon. Mutations can cause changes to regulatory regions of genes or loci that affect expression of one or more genes.

Guide RNAs

The present disclosure provides a guide RNAs (gRNAs) that can direct the activities of an associated endonuclease to a specific target site within a polynucleotide. A guide RNA can comprise at least a spacer sequence that hybridizes to a target nucleic acid sequence of interest, and a CRISPR repeat sequence. In CRISPR Type II systems, the gRNA also comprises a second RNA called the tracrRNA sequence. In the CRISPR Type II guide RNA (gRNA), the CRISPR repeat sequence and tracrRNA sequence hybridize to each other to form a duplex. In CRISPR Type V systems, the gRNA comprises a crRNA that forms a duplex. In some embodiments, a gRNA can bind an endonuclease, such that the gRNA and endonuclease form a complex. The gRNA can provide target specificity to the complex by virtue of its association with the endonuclease. The genome-targeting nucleic acid thus can direct the activity of the endonuclease.

Exemplary guide RNAs include a spacer sequences that comprises 15-200 nucleotides wherein the gRNA targets a genome location based on the GRCh38 human genome assembly. As is understood by the person of ordinary skill in the art, each gRNA can be designed to include a spacer sequence complementary to its genomic target site or region. See Jinek et al., Science, 2012, 337, 816-821 and Deltcheva et al., Nature, 2011, 471, 602-607.

The gRNA can be a double-molecule guide RNA. The gRNA can be a single-molecule guide RNA.

A double-molecule guide RNA can comprise two strands of RNA. The first strand comprises in the 5' to 3' direction, an optional spacer extension sequence, a spacer sequence and a minimum CRISPR repeat sequence. The second strand can comprise a minimum tracrRNA sequence (complementary to the minimum CRISPR repeat sequence), a 3' tracrRNA sequence and an optional tracrRNA extension sequence.

A single-molecule guide RNA (sgRNA) can comprise, in the 5' to 3' direction, an optional spacer extension sequence, a spacer sequence, a minimum CRISPR repeat sequence, a single-molecule guide linker, a minimum tracrRNA sequence, a 3' tracrRNA sequence and an optional tracrRNA extension sequence. The optional tracrRNA extension can comprise elements that contribute additional functionality (e.g., stability) to the guide RNA. The single-molecule guide linker can link the minimum CRISPR repeat and the minimum tracrRNA sequence to form a hairpin structure. The optional tracrRNA extension can comprise one or more hairpins.

In some embodiments, a sgRNA comprises a 20 nucleotide spacer sequence at the 5' end of the sgRNA sequence. In some embodiments, a sgRNA comprises a less than a 20 nucleotide spacer sequence at the 5' end of the sgRNA sequence. In some embodiments, a sgRNA comprises a more than 20 nucleotide spacer sequence at the 5' end of the sgRNA sequence. In some embodiments, a sgRNA comprises a variable length spacer sequence with 17-30 nucleotides at the 5' end of the sgRNA sequence. In some embodiments, a sgRNA comprises a spacer extension sequence with a length of more than 1, 5, 10, 15, 20, 25, 30, 35, 40, 45, 50, 60, 70, 80, 90, 100, 120, 140, 160, 180, or 200 nucleotides. In some embodiments, a sgRNA comprises a spacer extension sequence with a length of less than 3, 5, 10, 15, 20, 25, 30, 35, 40, 45, 50, 60, 70, 80, 90, or 100 nucleotides.

In some embodiments, a sgRNA comprises a spacer extension sequence that comprises another moiety (e.g., a stability control sequence, an endoribonuclease binding sequence, or a ribozyme). The moiety can decrease or increase the stability of a nucleic acid targeting nucleic acid. The moiety can be a transcriptional terminator segment (i.e., a transcription termination sequence). The moiety can function in a eukaryotic cell. The moiety can function in a prokaryotic cell. The moiety can function in both eukaryotic and prokaryotic cells. Non-limiting examples of suitable moieties include: a 5' cap (e.g., a 7-methylguanylate cap (m7 G)), a riboswitch sequence (e.g., to allow for regulated stability and/or regulated accessibility by proteins and protein complexes), a sequence that forms a dsRNA duplex (i.e., a hairpin), a sequence that targets the RNA to a subcellular location (e.g., nucleus, mitochondria, chloroplasts, and the like), a modification or sequence that provides for tracking (e.g., direct conjugation to a fluorescent molecule, conjugation to a moiety that facilitates fluorescent detection, a sequence that allows for fluorescent detection, etc.), and/or a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like).

In some embodiments, a sgRNA comprises a spacer sequence that hybridizes to a sequence in a target polynucleotide. The spacer of a gRNA can interact with a target polynucleotide in a sequence-specific manner via hybridization (i.e., base pairing). The nucleotide sequence of the spacer can vary depending on the sequence of the target nucleic acid of interest.

In a CRISPR-endonuclease system, a spacer sequence can be designed to hybridize to a target polynucleotide that is located 5' of a PAM of the endonuclease used in the system. The spacer may perfectly match the target sequence or may have mismatches. Each endonuclease, e.g., Cas9 nuclease, has a particular PAM sequence that it recognizes in a target DNA. For example, S. pyogenes Cas9 recognizes a PAM that comprises the sequence 5'-NRG-3', where R comprises either A or G, where N is any nucleotide and N is immediately 3' of the target nucleic acid sequence targeted by the spacer sequence.

A target polynucleotide sequence can comprise 20 nucleotides. The target polynucleotide can comprise less than 20 nucleotides. The target polynucleotide can comprise more than 20 nucleotides. The target polynucleotide can comprise at least: 5, 10, 15, 16, 17, 18, 19, 20, 21, 22, 23, 24, 25, 30 or more nucleotides. The target polynucleotide can comprise at most: 5, 10, 15, 16, 17, 18, 19, 20, 21, 22, 23, 24, 25, 30 or more nucleotides. The target polynucleotide sequence can comprise 20 bases immediately 5' of the first nucleotide of the PAM.

A spacer sequence that hybridizes to a target polynucleotide can have a length of at least about 6 nucleotides (nt). The spacer sequence can be at least about 6 nt, at least about 10 nt, at least about 15 nt, at least about 18 nt, at least about 19 nt, at least about 20 nt, at least about 25 nt, at least about 30 nt, at least about 35 nt or at least about 40 nt, from about 6 nt to about 80 nt, from about 6 nt to about 50 nt, from about 6 nt to about 45 nt, from about 6 nt to about 40 nt, from about 6 nt to about 35 nt, from about 6 nt to about 30 nt, from about 6 nt to about 25 nt, from about 6 nt to about 20 nt, from about 6 nt to about 19 nt, from about 10 nt to about 50 nt, from about 10 nt to about 45 nt, from about 10 nt to about 40 nt, from about 10 nt to about 35 nt, from about 10 nt to about 30 nt, from about 10 nt to about 25 nt, from about 10 nt to about 20 nt, from about 10 nt to about 19 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt. In some examples, the spacer sequence can comprise 20 nucleotides. In some examples, the spacer can comprise 19 nucleotides. In some examples, the spacer can comprise 18 nucleotides. In some examples, the spacer can comprise 22 nucleotides.

In some examples, the percent complementarity between the spacer sequence and the target nucleic acid is at least about 30%, at least about 40%, at least about 50%, at least about 60%, at least about 65%, at least about 70%, at least about 75%, at least about 80%, at least about 85%, at least about 90%, at least about 95%, at least about 97%, at least about 98%, at least about 99%, or 100%. In some examples, the percent complementarity between the spacer sequence and the target nucleic acid is at most about 30%, at most about 40%, at most about 50%, at most about 60%, at most about 65%, at most about 70%, at most about 75%, at most about 80%, at most about 85%, at most about 90%, at most about 95%, at most about 97%, at most about 98%, at most about 99%, or 100%. In some examples, the percent complementarity between the spacer sequence and the target nucleic acid is 100% over the six contiguous 5'-most nucleotides of the target sequence of the complementary strand of the target nucleic acid. The percent complementarity between the spacer sequence and the target nucleic acid can be at least 60% over about 20 contiguous nucleotides. The length of the spacer sequence and the target nucleic acid can differ by 1 to 6 nucleotides, which may be thought of as a bulge or bulges.

A tracrRNA sequence can comprise nucleotides that hybridize to a minimum CRISPR repeat sequence in a cell. A minimum tracrRNA sequence and a minimum CRISPR repeat sequence may form a duplex, i.e. a base-paired double-stranded structure. Together, the minimum tracrRNA sequence and the minimum CRISPR repeat can bind to an RNA-guided endonuclease. At least a part of the minimum tracrRNA sequence can hybridize to the minimum CRISPR repeat sequence. The minimum tracrRNA sequence can be at least about 30%, about 40%, about 50%, about 60%, about 65%, about 70%, about 75%, about 80%, about 85%, about 90%, about 95%, or 100% complementary to the minimum CRISPR repeat sequence.

The minimum tracrRNA sequence can have a length from about 7 nucleotides to about 100 nucleotides. For example, the minimum tracrRNA sequence can be from about 7 nucleotides (nt) to about 50 nt, from about 7 nt to about 40 nt, from about 7 nt to about 30 nt, from about 7 nt to about 25 nt, from about 7 nt to about 20 nt, from about 7 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt or from about 15 nt to about 25 nt long. The minimum tracrRNA sequence can be approximately 9 nucleotides in length. The minimum tracrRNA sequence can be approximately 12 nucleotides. The minimum tracrRNA can consist of tracrRNA nt 23-48 described in Jinek et al., supra.

The minimum tracrRNA sequence can be at least about 60% identical to a reference minimum tracrRNA (e.g., wild-type, tracrRNA from *S. pyogenes*) sequence over a stretch of at least 6, 7, or 8 contiguous nucleotides. For example, the minimum tracrRNA sequence can be at least about 65% identical, about 70% identical, about 75% identical, about 80% identical, about 85% identical, about 90% identical, about 95% identical, about 98% identical, about 99% identical or 100% identical to a reference minimum tracrRNA sequence over a stretch of at least 6, 7, or 8 contiguous nucleotides.

The duplex between the minimum CRISPR RNA and the minimum tracrRNA can comprise a double helix. The duplex between the minimum CRISPR RNA and the minimum tracrRNA can comprise at least about 1, 2, 3, 4, 5, 6, 7, 8, 9, or 10 or more nucleotides. The duplex between the minimum CRISPR RNA and the minimum tracrRNA can comprise at most about 1, 2, 3, 4, 5, 6, 7, 8, 9, or 10 or more nucleotides.

The duplex can comprise a mismatch (i.e., the two strands of the duplex are not 100% complementary). The duplex can comprise at least about 1, 2, 3, 4, or 5 or mismatches. The duplex can comprise at most about 1, 2, 3, 4, or 5 or mismatches. The duplex can comprise no more than 2 mismatches.

In some embodiments, a tracrRNA may be a 3' tracrRNA. In some embodiments, a 3' tracrRNA sequence can comprise a sequence with at least about 30%, about 40%, about 50%, about 60%, about 65%, about 70%, about 75%, about 80%, about 85%, about 90%, about 95%, or 100% sequence identity to a reference tracrRNA sequence (e.g., a tracrRNA from *S. pyogenes*).

In some embodiments, a gRNA may comprise a tracrRNA extension sequence. A tracrRNA extension sequence can have a length from about 1 nucleotide to about 400 nucleotides. The tracrRNA extension sequence can have a length of more than 1, 5, 10, 15, 20, 25, 30, 35, 40, 45, 50, 60, 70, 80, 90, 100, 120, 140, 160, 180, or 200 nucleotides. The tracrRNA extension sequence can have a length from about 20 to about 5000 or more nucleotides. The tracrRNA extension sequence can have a length of less than 5, 10, 15, 20, 25, 30, 35, 40, 45, 50, 60, 70, 80, 90, or 100 nucleotides. The tracrRNA extension sequence can comprise less than 10 nucleotides in length. The tracrRNA extension sequence can be 10-30 nucleotides in length. The tracrRNA extension sequence can be 30-70 nucleotides in length.

The tracrRNA extension sequence can comprise a functional moiety (e.g., a stability control sequence, ribozyme, endoribonuclease binding sequence). The functional moiety can comprise a transcriptional terminator segment (i.e., a transcription termination sequence). The functional moiety can have a total length from about 10 nucleotides (nt) to about 100 nucleotides, from about 10 nt to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt, from about 15 nt to about 80 nt, from about 15 nt to about 50 nt, from about 15 nt to about 40 nt, from about 15 nt to about 30 nt, or from about 15 nt to about 25 nt.

In some embodiments, a sgRNA may comprise a linker sequence with a length from about 3 nucleotides to about 100 nucleotides. In Jinek et al., supra, for example, a simple 4 nucleotide "tetraloop" (-GAAA-) was used (Jinek et al., Science, 2012, 337(6096):816-821). An illustrative linker has a length from about 3 nucleotides (nt) to about 90 nt, from about 3 nt to about 80 nt, from about 3 nt to about 70 nt, from about 3 nt to about 60 nt, from about 3 nt to about 50 nt, from about 3 nt to about 40 nt, from about 3 nt to about 30 nt, from about 3 nt to about 20 nt, from about 3 nt to about 10 nt. For example, the linker can have a length from about 3 nt to about 5 nt, from about 5 nt to about 10 nt, from about 10 nt to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. The linker of a single-molecule guide nucleic acid can be between 4 and 40 nucleotides. The linker can be at least about 100, 500, 1000, 1500, 2000, 2500, 3000, 3500, 4000, 4500, 5000, 5500, 6000, 6500, or 7000 or more nucleotides. The linker can be at most about 100, 500, 1000, 1500, 2000, 2500, 3000, 3500, 4000, 4500, 5000, 5500, 6000, 6500, or 7000 or more nucleotides.

Linkers can comprise any of a variety of sequences, although in some examples the linker will not comprise sequences that have extensive regions of homology with other portions of the guide RNA, which might cause intramolecular binding that could interfere with other functional regions of the guide. In Jinek et al., supra, a simple 4 nucleotide sequence -GAAA- was used (Jinek et al., Science, 2012, 337(6096):816-821), but numerous other sequences, including longer sequences can likewise be used.

The linker sequence can comprise a functional moiety. For example, the linker sequence can comprise one or more features, including an aptamer, a ribozyme, a protein-interacting hairpin, a protein binding site, a CRISPR array, an intron, or an exon. The linker sequence can comprise at least about 1, 2, 3, 4, or 5 or more functional moieties. In some examples, the linker sequence can comprise at most about 1, 2, 3, 4, or 5 or more functional moieties.

In some embodiments, a sgRNA does not comprise a uracil, e.g., at the 3' end of the sgRNA sequence. In some embodiments, a sgRNA does comprise one or more uracils, e.g., at the 3' end of the sgRNA sequence. In some embodiments, a sgRNA comprises 1, 2, 3, 4, 5, 6, 7, 8, 9, or 10 uracils (U) at the 3' end of the sgRNA sequence.

A sgRNA may be chemically modified. In some embodiments, a chemically modified gRNA is a gRNA that comprises at least one nucleotide with a chemical modification, e.g., a 2'-O-methyl sugar modification. In some embodiments, a chemically modified gRNA comprises a modified nucleic acid backbone. In some embodiments, a chemically modified gRNA comprises a 2'-O-methyl-phosphorothioate residue. In some embodiments, chemical modifications enhance stability, reduce the likelihood or degree of innate immune response, and/or enhance other attributes, as described in the art.

In some embodiments, a modified gRNA may comprise a modified backbones, for example, phosphorothioates, phosphotriesters, morpholinos, methyl phosphonates, short chain alkyl or cycloalkyl intersugar linkages or short chain heteroatomic or heterocyclic intersugar linkages.

Morpholino-based compounds are described in Braasch and David Corey, Biochemistry, 2002, 41(14): 4503-4510; Genesis, 2001, Volume 30, Issue 3; Heasman, Dev. Biol., 2002, 243: 209-214; Nasevicius et al., Nat. Genet., 2000, 26:216-220; Lacerra et al., Proc. Natl. Acad. Sci., 2000, 97: 9591-9596; and U.S. Pat. No. 5,034,506, issued Jul. 23, 1991.

Cyclohexenyl nucleic acid oligonucleotide mimetics are described in Wang et al., J. Am. Chem. Soc., 2000, 122: 8595-8602.

In some embodiments, a modified gRNA may comprise one or more substituted sugar moieties, e.g., one of the following at the 2' position: OH, SH, $SCH_3$, F, OCN, $OCH_3$, $OCH_3$ $O(CH_2)_n$ $CH_3$, $O(CH_2)_n$ $NH_2$, or $O(CH_2)_n$ $CH_3$, where n is from 1 to about 10; C1 to C10 lower alkyl, alkoxyalkoxy, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2$ $CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; 2'-O-(2-methoxyethyl); 2'-methoxy (2'-O—$CH_3$); 2'-propoxy (2'-$OCH_2$ $CH_2CH_3$); and 2'-fluoro (2'-F). Similar modifications may also be made at other positions on the gRNA, particularly the 3' position of the sugar on the 3' terminal nucleotide and the 5' position of 5' terminal nucleotide. In some examples, both a sugar and an internucleoside linkage, i.e., the backbone, of the nucleotide units can be replaced with novel groups.

Guide RNAs can also include, additionally or alternatively, nucleobase (often referred to in the art simply as "base") modifications or substitutions. As used herein, "unmodified" or "natural" nucleobases include adenine (A), guanine (G), thymine (T), cytosine (C), and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine, and 2,6-diaminopurine. Kornberg, A., DNA Replication, W. H. Freeman & Co., San Francisco, pp 75-77, 1980; Gebeyehu et al., Nucl. Acids Res. 1997, 15:4513. A "universal" base known in the art, e.g., inosine, can also be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are aspects of base substitutions.

Modified nucleobases can comprise other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine, and 3-deazaguanine and 3-deazaadenine.

Complexes of a Genome-Targeting Nucleic Acid and an Endonuclease

A gRNA interacts with an endonuclease (e.g., a RNA-guided nuclease such as Cas9), thereby forming a complex. The gRNA guides the endonuclease to a target polynucleotide.

The endonuclease and gRNA can each be administered separately to a cell or a subject. In some embodiments, the endonuclease can be pre-complexed with one or more guide RNAs, or one or more crRNA together with a tracrRNA. The pre-complexed material can then be administered to a cell or a subject. Such pre-complexed material is known as a ribonucleoprotein particle (RNP). The endonuclease in the RNP can be, for example, a Cas9 endonuclease or a Cpf1 endonuclease. The endonuclease can be flanked at the N-terminus, the C-terminus, or both the N-terminus and C-terminus by one or more nuclear localization signals (NLSs). For example, a Cas9 endonuclease can be flanked by two NLSs, one NLS located at the N-terminus and the second NLS located at the C-terminus. The NLS can be any NLS known in the art, such as a SV40 NLS. The weight ratio of genome-targeting nucleic acid to endonuclease in the RNP can be 1:1. For example, the weight ratio of sgRNA to Cas9 endonuclease in the RNP can be 1:1.

Cells

Provided herein are any of the cells described herein having any of the gene-edits described herein. In some embodiments, a cell (and corresponding unmodified cell) is a mammalian cell. In some embodiments, a cell (and corresponding unmodified cell) is a human cell. In some embodiments, a cell (and corresponding unmodified cell) is a stem cell. In some embodiments, a cell (and corresponding unmodified cell) is a pluripotent stem cell (PSC). In some embodiments, a cell (and corresponding unmodified cell) is an embryonic stem cell (ESC), an adult stem cell (ASC), an induced pluripotent stem cell (iPSC), or a hematopoietic stem or progenitor cell (HSPC). In some embodiments, a cell is an iPSC. In some embodiments, a cell may be a differentiated cell. In some embodiments, a cell is a somatic cell, e.g., an immune system cell or a contractile cell, e.g., a skeletal muscle cell.

In some embodiments, the stem cells described herein (e.g., iPSCs) are gene-edited as described herein and then differentiated into a cell type of interest. In some embodiments, the differentiated cell retains the gene-edits of the cell from which it is derived.

The cells described herein may be differentiated into relevant cell types. In general, differentiation comprises maintaining the cells of interest for a period time and under conditions sufficient for the cells to differentiate into the differentiated cells of interest. For example, the engineered stem cells disclosed herein may be differentiated into mesenchymal progenitor cells (MPCs), hypoimmunogenic cardiomyocytes, muscle progenitor cells, blast cells, endothelial cells (ECs), macrophages, natural killer cells, hepatocytes, beta cells (e.g., pancreatic beta cells), pancreatic endoderm progenitors, pancreatic endocrine progenitors, or neural progenitor cells (NPCs). In some embodiments, any of the stem cells described herein are differentiated after gene-editing. In some embodiments, a cell is differentiated into a natural killer (NK) cell.

Stem cells are capable of both proliferation and giving rise to more progenitor cells, these in turn having the ability to generate a large number of mother cells that can in turn give rise to differentiated or differentiable daughter cells. The daughter cells themselves can be induced to proliferate and produce progeny that subsequently differentiate into one or more mature cell types, while also retaining one or more cells with parental developmental potential. The term "stem cell" refers then, to a cell with the capacity or potential, under particular circumstances, to differentiate to a more specialized or differentiated phenotype, and which retains the capacity, under certain circumstances, to proliferate without substantially differentiating. In one aspect, the term progenitor or stem cell refers to a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell that itself is derived from a multipotent cell, and so on. While each of these multipotent cells may be considered stem cells, the range of cell types that each can give rise to may vary considerably. Some differentiated cells also have the capacity to give rise to cells of greater developmental potential. Such capacity may be natural or may be induced artificially upon treatment with various factors. In many biological instances, stem cells can also be "multipotent" because they can produce progeny of more than one distinct cell type, but this is not required for "stem-ness."

A "differentiated cell" is a cell that has progressed further down the developmental pathway than the cell to which it is being compared. Thus, stem cells can differentiate into lineage-restricted precursor cells (such as a hematopoietic stem and progenitor cell (HSPC)), which in turn can differentiate into other types of precursor cells further down the pathway (such as a common lymphoid progenitor cell), and then to an end-stage differentiated cell, such as a natural killer cell, which plays a characteristic role in a certain tissue type, and may or may not retain the capacity to proliferate further.

In some embodiments, any of the gene-edited cells described herein have one of more of the following characteristics; increased persistency, immune evasiveness, lack of an alloimmune T cell response, increased cytotoxic activity, improved antibody-dependent cellular cytotoxicity (ADCC), or increased anti-tumor activity. In some embodiments, any of the gene-edited cells described herein have one of more of the following characteristics relative to an un-edited (wild-type) cell described herein; increased persistency, immune evasiveness, lack of an alloimmune T cell response, increased cytotoxic activity, improved antibody-dependent cellular cytotoxicity (ADCC), or increased anti-tumor activity. In some embodiments, any of the gene-edited cells described herein are capable of cell expansion in the absence of exogenous IL15.

Embryonic Stem Cells

The cells described herein may be embryonic stem cells (ESCs). ESCs are derived from blastocytes of mammalian embryos and are able differentiate into any cell type and propagate rapidly. ESCs are also believed to have a normal karyotype, maintaining high telomerase activity, and exhibiting remarkable long-term proliferative potential, making these cells excellent candidates for use as gene-edited stem cells. In some embodiments, ESCs with one, two, three, four, five, six or all of the following edits: B2M null, CIITA null, ADAM17 null, HLA-E knock-in, IL15/IL15Rα knock-in, BCMA CAR knock-in, CD30 CAR knock-in, SERPINB9 knock-in, FAS null, CISH null, and REGNASE-1 null, are differentiated into NK cells.

Adult Stem Cells

The cells described herein may be adult stem cells (ASCs). ASCs are undifferentiated cells that may be found in mammals, e.g., humans. ASCs are defined by their ability to self-renew, e.g., be passaged through several rounds of cell replication while maintaining their undifferentiated state, and ability to differentiate into several distinct cell types, e.g., glial cells. Adult stem cells are a broad class of stem cells that may encompass hematopoietic stem cells, mammary stem cells, intestinal stem cells, mesenchymal stem cells, endothelial stem cells, neural stem cells, olfactory adult stem cells, neural crest stem cells, and testicular cells. In some embodiments, ASCs with one, two, three, four, five, six or all of the following edits: B2M null, CIITA null, ADAM17 null, HLA-E knock-in, IL15/IL15Rα knock-in, BCMA CAR knock-in, CD30 CAR knock-in, SERPINB9 knock-in, FAS null, CISH null, and REGNASE-1 null, are differentiated into NK cells.

Induced Pluripotent Stem Cells

The cells described herein may be induced pluripotent stem cells (iPSCs). An iPSC may be generated directly from an adult human cell by introducing genes that encode critical transcription factors involved in pluripotency, e.g., Oct4, Sox2, cMyc, and Klf4. An iPSC may be derived from the same subject to which subsequent progenitor cells are to be administered. That is, a somatic cell can be obtained from a subject, reprogrammed to an induced pluripotent stem cell, and then re-differentiated into a progenitor cell to be administered to the subject (e.g., autologous cells). However, in the case of autologous cells, a risk of immune response and poor viability post-engraftment remain. In some embodiments, iPSC are generated from adult somatic cells using genetic reprogramming methods known in the art. In some embodiments, the iPSCs are derived from a commercial source. In some embodiments, the cells described herein are iPSCs or a derivative cell. In some embodiments, iPSC with one, two, three, four, five, six or all of the following edits: B2M null, CIITA null, ADAM17 null, HLA-E knock-in, IL15/IL15Rα knock-in, BCMA CAR knock-in, CD30 CAR knock-in, SERPINB9 knock-in, FAS null, CISH null, and REGNASE-1 null, are differentiated into NK cells.

Mesoderm

The cells described herein may be mesodermal cells. This cell type is one of the three germinal layers in embryonic development. The mesoderm eventually differentiates into, but is not limited to muscle, connective tissue, bone, red blood cells, white blood cells, and microglia. In some embodiments, the gene-edited cells described herein are mesodermal cells. In some embodiments, mesodermal cells are derived from any of the stem cells described herein. In some embodiments, mesodermal cells are derived from iPSC. In some embodiments, the mesodermal cells have any of the gene-edits described herein. In some embodiments, the mesodermal cells are differentiated into NK cells. In some embodiments, mesodermal cells with one, two, three, four, five, six or all of the following edits: B2M null, CIITA null, ADAM17 null, HLA-E knock-in, IL15/IL15Rα knock-in, BCMA CAR knock-in, CD30 CAR knock-in, SERPINB9 knock-in, FAS null, CISH null, and REGNASE-1 null, are differentiated into NK cells.

Hemogenic Endothelium

The cells described herein may be hemogenic endothelium (HE) cells. This cell type is an intermediate precursor of hematopoietic progenitors. In some embodiments, the cells described herein are hemogenic endothelium cells. In some embodiments, the gene-edited cells described herein are hemogenic endothelium cells. In some embodiments, hemogenic endothelium cells are derived from any of the stem cells described herein. In some embodiments, hemogenic endothelium cells are derived from iPSC. In some embodiments, the hemogenic endothelial cells have any of the gene-edits described herein. In some embodiments, the hemogenic endothelial cells are differentiated into NK cells. In some embodiments, HE cells with one, two, three, four, five, six or all of the following edits: B2M null, CIITA null, ADAM17 null, HLA-E knock-in, IL15/IL15Rα knock-in, BCMA CAR knock-in, CD30 CAR knock-in, SERPINB9 knock-in, FAS null, CISH null, and REGNASE-1 null, are differentiated into NK cells.

Human Hematopoietic Stem and Progenitor Cells

The cells described herein may be human hematopoietic stem and progenitor cells (hHSPCs). This stem cell lineage gives rise to all blood cell types, including erythroid (erythrocytes or red blood cells (RBCs)), myeloid (monocytes and macrophages, neutrophils, basophils, eosinophils, megakaryocytes/platelets, and dendritic cells), and lymphoid (T-cells, B-cells, NK-cells). Blood cells are produced by the proliferation and differentiation of a very small population of pluripotent hematopoietic stem cells (HSCs) that also have the ability to replenish themselves by self-renewal. During differentiation, the progeny of HSCs progress through various intermediate maturational stages, generating multi-potential and lineage-committed progenitor cells prior to reaching maturity. Bone marrow (BM) is the major site of hematopoiesis in humans and, under normal conditions, only small numbers of hematopoietic stem and progenitor cells (HSPCs) can be found in the peripheral blood (PB). Treatment with cytokines, some myelosuppressive drugs used in cancer treatment, and compounds that disrupt the interaction between hematopoietic and BM stromal cells can rapidly mobilize large numbers of stem and progenitors into the circulation. In some embodiments, HSPCs are derived from any of the stem cells described herein. In some embodiments, HSPCs are derived from iPSCs. In some embodiments, the HSPCs have any of the gene-edits described herein. In some embodiments, the HSPCs cells are differentiated into NK cells. In some embodiments, HSPCs with one, two, three, four, five, six or all of the following edits: B2M null, CIITA null, ADAM17 null, HLA-E knock-in, IL15/IL15Rα knock-in, BCMA CAR knock-in, CD30 CAR knock-in, SERPINB9 knock-in, FAS null, CISH null, and REGNASE-1 null, are differentiated into NK cells.

Common Lymphoid Progenitor

The cells described herein may be common lymphoid progenitor (CLP) cells. CLPs are descendants of HSPCs. These cells differentiate into the lymphoid lineage of blood cells. Further differentiation yields B-cell progenitor cells, Natural Killer cells, and Thymocytes. In some embodiments, the cells described herein are common lymphoid progenitors. In some embodiments, the gene-edited cells described herein are common lymphoid progenitors. In some embodiments, CLP cells are derived from iPSCs. In some embodiments, the CLP cells have any of the gene-edits described herein. In some embodiments, the CLP cells are differentiated into NK cells. In some embodiments, CLP cells with one, two, three, four, five, six or all of the following edits: B2M null, CIITA null, ADAM17 null, HLA-E knock-in, IL15/IL15Rα knock-in, BCMA CAR knock-in, CD30 CAR knock-in, SERPINB9 knock-in, FAS null, CISH null, and REGNASE-1 null, are differentiated into NK cells.

Differentiation of Cells into Other Cell Types

Another step of the methods of the present disclosure may comprise differentiating cells into differentiated cells. The differentiating step may be performed according to any method known in the art. For example, human iPSCs are differentiated into natural killer cells using methods known in the art. In some embodiments, the differentiating step may be performed according to Zhu and Kaufman, bioRxiv 2019; dx.doi.org/10.1101/614792. A differentiated cell may be any somatic cell of a mammal, e.g., a human. In some embodiments, a somatic cell may be an endocrine secretory epithelial cell (e.g., thyroid hormone secreting cells, adrenal cortical cells), an exocrine secretory epithelial cell (e.g., salivary gland mucous cell, prostate gland cell), a hormone-secreting cell (e.g., anterior pituitary cell, pancreatic islet cell), a keratinizing epithelial cell (e.g., epidermal keratinocyte), a wet stratified barrier epithelial cell, a sensory transducer cell (e.g., a photoreceptor), an autonomic neuron cells, a sense organ and peripheral neuron supporting cell (e.g., Schwann cell), a central nervous system neuron, a glial cell (e.g., astrocyte, oligodendrocyte), a lens cell, an adipocyte, a kidney cell, a barrier function cell (e.g., a duct cell), an extracellular matrix cell, a contractile cell (e.g., skeletal muscle cell, heart muscle cell, smooth muscle cell), a blood cell (e.g., erythrocyte), an immune system cell (e.g., megakaryocyte, microglial cell, neutrophil, mast cell, a T cell, a B cell, a Natural Killer cell), a germ cell (e.g., spermatid), a nurse cell, or an interstitial cell. In some embodiments, any of the stem cells described herein are differentiated into NK cells. In some embodiments, any of the derivative cell types described herein are differentiated into NK cells.

Provided herein, in some embodiments, are methods for generating Natural Killer (NK) cells from stem cells. The method includes: (a) culturing a population of stem cells in a first medium comprising a ROCK inhibitor under conditions sufficient to form aggregates; (b) culturing the aggregates in a second medium comprising BMP-4; (c) culturing the aggregates in a third medium comprising BMP-4, FGF2, a WNT pathway activator, and Activin A; (d) culturing the aggregates in a fourth medium comprising FGF2, VEGF, TPO, SCF, IL-3, FLT3L, WNT C-59 and an activin/nodal inhibitor to form a cell population comprising hematopoietic stem and progenitor cells (HSPCs); (e) culturing the cell population in a fifth medium comprising FGF2, VEGF, TPO, SCF, IL-3 and FLT3L; (f) culturing the cell population in a sixth medium comprising IL-3, IL-7, FLT3L, IL-15 and SCF; (g) culturing the cell population in a seventh medium comprising IL-7, FLT3L, IL-15 and SCF for a time sufficient to generate NK cells. In some embodiments, the method includes (a) culturing a population of stem cells in a first medium comprising a ROCK inhibitor under conditions sufficient to form aggregates; (b) culturing the aggregates in a second medium comprising BMP-4; (c) culturing the aggregates in a third medium comprising BMP-4, FGF2, a WNT pathway activator, and Activin A; (d) culturing the aggregates in a fourth medium comprising FGF2, VEGF, TPO, SCF, IL-3, FLT3L, and an activin/nodal inhibitor to form a cell population comprising hematopoietic stem and progenitor cells (HSPCs); (e) culturing the cell population in a fifth medium comprising FGF2, VEGF, TPO, SCF, IL-3 and FLT3L; (f) culturing the cell population in a sixth medium comprising IL-3, IL-7, FLT3L, IL-15 and SCF; (g) culturing the cell population in a seventh medium comprising IL-7, FLT3L, IL-15 and SCF and (h) culturing the cell population in an eighth medium comprising IL-7, FLT3L, IL-15, SCF and nicotinamide for a time sufficient to generate NK cells. In some embodiments, the method includes (a) culturing a population of stem cells in a first medium comprising a ROCK inhibitor under conditions sufficient to form aggregates; (b) culturing the aggregates in a second medium comprising BMP-4; (c) culturing the aggregates in a third medium comprising BMP-4, FGF2, a WNT pathway activator, and Activin A; (d) culturing the aggregates in a fourth medium comprising FGF2, VEGF, TPO, SCF, IL-3, FLT3L, and an activin/nodal inhibitor to form a cell population comprising hematopoietic stem and progenitor cells (HSPCs); (e) culturing the cell population in a fifth medium comprising FGF2, VEGF, TPO, SCF, IL-3 and FLT3L; (f) culturing the cell population in a sixth medium comprising IL-3, IL-7, FLT3L, IL-15 and SCF; (g) culturing the cell population in a seventh medium comprising IL-7, FLT3L, IL-15 and SCF and (h) culturing the cell population in an eighth medium comprising IL-7, FLT3L, IL-15, and SCF for a time sufficient to generate NK cells. In some embodiments, the second medium further includes a ROCK inhibitor. In some embodiments, the ROCK inhibitor is thiazovivin. In some embodiments, the ROCK inhibitor is Y27652. In some embodiments, the WNT pathway activator is CHIR-99021. In some embodiments, the activin/nodal inhibitor is SB-431542.

In some embodiments, steps (a)-(g) occurs between 20-35 days. In some embodiments, step (a) includes culturing for 12-48 hours. In some embodiments, step (b) includes culturing for up to 24 hours. In some embodiments, step (c) includes culturing for 1-3 days. In some embodiments, step (d) includes culturing for 1-3 days. In some embodiments, step (e) includes culturing for 1-3 days. In some embodiments, step (f) includes culturing for up to 7 days. In some embodiments, step (g) includes culturing for at least 6 days and up to 21-28 days total. In some embodiments, step (a) includes culturing for 16-20 hours; step (b) includes culturing for 6-10 hours; step (c) includes culturing for 2 days; step (d) includes culturing for 2 days; step (e) includes culturing for 2 days; step (f) includes culturing for 4 days; and/or step (g) includes culturing for 14-28 days.

In some embodiments, steps (a)-(h) occurs between 19 and 36 days. In some embodiments, steps (a)-(h) occurs between 19 and 33 days. In some embodiments, steps (a)-(h) occurs between 24 and 36 days. In some embodiments, step (a) includes culturing for 12-48 hours. In some embodiments, step (b) includes culturing for up to 24 hours. In some embodiments, step (c) includes culturing for 1-3 days. In some embodiments, step (d) includes culturing for 1-3 days. In some embodiments, step (e) includes culturing for 1-3 days. In some embodiments, step (f) includes culturing for up to 7 days. In some embodiments, step (g) includes culturing for up to 6 days. In some embodiments, step (h) includes culturing for at least 6 days and up to 10-16 days total. In some embodiments, step (a) includes culturing for 16-20 hours; step (b) includes culturing for 6-10 hours; step (c) includes culturing for 2 days; step (d) includes culturing for 2 days; step (e) includes culturing for 2 days; step (f)

includes culturing for 4 days; step (g) includes culturing for 6 days and/or step (h) includes culturing for 10-16 days.

In some embodiments, the method is carried out under suspension agitation. In some embodiments, the suspension agitation includes rotation. In some embodiments, the first media includes StemFlex or StemBrew medium. In some embodiments, the second, third, fourth and fifth media include APEL medium. In some embodiments, the sixth and seventh media can include DMEM/F12 medium. In some aspects, the sixth and seventh media comprise DMEM (high glucose)/F12 medium. In some embodiments, the sixth and seventh media include human serum (e.g., at the concentration of 10-20%), zinc sulfate (e.g., at a concentration of about 20-40 µM), ethanolamine (e.g., at a concentration of about 10-100 µM), β-mercaptoethanol (e.g., at a concentration of about 0.1-5 µM), glucose (e.g., at a total concentration of 2-40 mM), or any combination thereof. In some embodiments, the sixth and seventh media include human serum (e.g., at the concentration of 15%), zinc sulfate (e.g., at a concentration of about 36 or 37 µM), ethanolamine (e.g., at a concentration of about 50 µM), β-mercaptoethanol (e.g., at a concentration of about 1 µM), glucose (e.g., at a total concentration of 27 mM), or any combination thereof. In some embodiments, the sixth and seventh media include human serum (e.g., at a concentration of about 10-40%), zinc sulfate (e.g., at a concentration of about 20-40 µM), ethanolamine (e.g., at a concentration of about 10-100 µM), glucose (e.g., at a total concentration of about 2-40 mM), or any combination thereof. In some embodiments, the sixth and seventh media include human serum (e.g., at a concentration of about 20%), zinc sulfate (e.g., at a concentration of about 37 µM), ethanolamine (e.g., at a concentration of about 50 µM), glucose (e.g., at a total concentration of about 20 mM), or any combination thereof. In some embodiments, the eighth media includes human serum (e.g., at a concentration of about 2-15%), zinc sulfate (e.g., at a concentration of about 20-40 µM), ethanolamine (e.g., at a concentration of about 10-100 µM), glucose (e.g., at a total concentration of about 2-40 mM), or any combination thereof. In some embodiments, the eighth media can include DMEM/F12 medium. In some aspects, the eighth media comprises DMEM (high glucose)/F12 medium. In some embodiments, the eighth media includes human serum (e.g., at a concentration of about 10%), zinc sulfate (e.g., at a concentration of about 37 µM), ethanolamine (e.g., at a concentration of about 50 µM), glucose (e.g., at a total concentration of about 20 mM), or any combination thereof. In any of the sixth, seventh, and eighth media provided herein, the total glucose concentration comprises glucose from all sources including glucose present in the base media and any added glucose. In each of the sixth, seventh, and eighth media provided herein, additional glucose may be added to a glucose containing base media (e.g., DMEM, F12 or DMEM (high glucose)/F12 medium) to reach the "total" glucose concentration. In some embodiments, about 10.25 mM of glucose is added to the base media of the sixth or seventh media to reach the total glucose concentration of about 27 mM. In some embodiments, about 4.66 mM of glucose is added to the base media of the sixth or seventh media to reach the total glucose concentration of about 20 mM. In some embodiments, about 2.33 mM of glucose is added to the base media of the eighth media to reach the total glucose concentration of about 20 mM. In some embodiments, the first medium includes 10 µM of the ROCK inhibitor. In some embodiments, the second medium includes 30 ng/mL BMP-4. In some embodiments, the second medium includes 30 ng/mL BMP-4 and 10 µM of a ROCK inhibitor. In some embodiments, the third medium includes 30 ng/mL BMP-4, 100 ng/mL FGF2, 6 µM CHIR-99021, and 2.5-5 ng/mL Activin A. In some embodiments, the third medium includes 30 ng/mL BMP-4, 100 ng/mL FGF2, 7 µM CHIR-99021, and 2.5-5 ng/mL Activin A.

In some embodiments, half of the third medium is added to the stem cell aggregates. In some embodiments, the fourth and fifth media include 20 ng/mL FGF, 20 ng/mL VEGF, 20 ng/mL TPO, 100 ng/mL SCF, 40 ng/mL IL-3, and 10-20 ng/mL FLT3L. In some embodiments, the fourth medium further includes 2 µM WNT C-59 and 5 µM SB-431542. In some embodiments, the fourth medium further includes 5 µM SB-431542. In some embodiments, the fourth medium does not include WNT C-59. In some embodiments, the sixth and seventh media includes 20 ng/mL IL-7, 10-20 ng/mL FLT3L, 10-20 ng/mL IL-15, and 20 ng/mL SCF. In some embodiments, the sixth medium includes 5 ng/mL IL-3. In some embodiments, the eighth media includes IL-7, FLT3L, IL-15, SCF and nicotinamide. In various embodiments, the eighth medium includes 10-20 ng/mL IL-7, 5-20 ng/mL FLT3L, 10-30 ng/mL IL-15, 20-40 ng/mL SCF, and 1-15 mM nicotinamide. In various embodiments, the eighth medium includes 10 ng/mL IL-7, 7.5 ng/mL FLT3L, 15 ng/mL IL-15, 20 ng/mL SCF and 6.5 mM nicotinamide. In some embodiments, the eighth media includes IL-7, FLT3L, IL-15, and SCF. In various embodiments, the eighth medium includes 10-20 ng/mL IL-7, 5-20 ng/mL FLT3L, 10-30 ng/mL IL-15, and 20-40 ng/mL SCF. In various embodiments, the eighth medium includes 10 ng/mL IL-7, 7.5 ng/mL FLT3L, 15 ng/mL IL-15, and 20 ng/mL SCF. In some embodiments, the eighth medium does not comprise nicotinamide.

In some embodiments, the HSPCs of step (d) express CD34. In some embodiments, the NK cells express CD56. In some embodiments, the NK cells express at least one activating receptor. In some embodiments, the at least one activating receptor is selected from the group of NKp44, NKp46, CD16, KIR2DL4, and any combination thereof. In some embodiments, the NK cells express at least one inhibitory receptor. In some embodiments, the at least one inhibitory receptor is selected from the group of CD94, NKG2A, KIR3DL2, and any combination thereof.

In some embodiments, the NK cells include at least one function associated with endogenous NK cells. In some embodiments, the at least one function includes the ability to induce cell lysis and cell death of a target cell. In some embodiments, the at least one function includes degranulation. In some embodiments, the degranulation includes release of perforin and granzyme B. In some embodiments, the degranulation includes expression of CD107a on the cell surface of an NK cell.

In some embodiments, the population of stem cells is a population of engineered cells, such as the engineered cells generated or obtained by the methods disclosed herein. In some embodiments, the population of engineered cells is differentiated by the methods of generating Natural Killer (NK) cells from stem cells disclosed herein.

In some embodiments, a plurality of Natural Killer (NK) cells is generated or obtained by the method of generating Natural Killer (NK) cells from stem cells disclosed herein. Also disclosed herein is a plurality of NK cells is for use in treating a subject in need thereof. In some embodiments, the subject is a human who has, is suspected of having, or is at risk for a cancer. Also disclosed herein is a method comprising administering to a subject the plurality of NK cells.

Natural Killer Cells

Natural killer (NK) cells are a subpopulation of lymphocytes which play a critical role in the innate immune system. NK cells have cytotoxicity against a variety of cells including but not limited to tumor cells and virus-infected cells. In some embodiments, the stem cells described herein are differentiated to Natural Killer cells. In some embodiments, iPSCs are differentiated into NK cells. In some embodiments, the engineered NK cells (such as cells derived from gene-edited iPSCs by differentiation, i.e., iNK cells) have enhanced anti-tumor activity as compared to un-edited or wild-type NK cells. In some embodiments, anti-tumor activity of the engineered NK cells is increased by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, or at least 90% relative to control (e.g., un-edited or wild-type) NK cells.

In some embodiments, the engineered NK cells exhibit increased cellular lysis capability relative to control cells. In some embodiments, the engineered NK cells of the present disclosure exhibit at least 10% increase in cellular lysis capability (kill at least 10% more target cells), or at least 20% increase in cellular lysis capability (kill at least 20% more target cells), relative to control (e.g., un-edited or wild-type) cells. For example, the engineered NK cells of the present disclosure may exhibit an at least at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, or at least 90% increase in cellular lysis capability, relative to control (e.g., un-edited or wild-type) cells. In some embodiments, the engineered NK cells of the present disclosure exhibit a 20%-100%, 20%-90%, 20%-80%, 20%-70%, 20%-60%, 20%-50%, 30%-100%, 30%-90%, 30%-80%, 30%-70%, 30%-60%, 30%-50%, 40%-100%, 40%-90%, 40%-80%, 40%-70%, 40%-60%, 40%-50%, 50%-100%, 50%-90%, 50%-80%, 50%-70%, or 50%-60% increase in cellular lysis capability, relative to control (e.g., un-edited or wild-type) cells. In some embodiments, the target cells are T cells. In some embodiments, the target cells are cancer cells. In some embodiments, the target cells are leukemia cells. In some embodiments, this increase in cellular lysis capability is observed at E:T (effector:target cell) ratio of at or about 0.1:1. In some embodiments, this increase in cellular lysis capability is observed at E:T (effector:target cell) ratio of at or about 0.5:1. In some embodiments, this increase in cellular lysis capability is observed at E:T (effector:target cell) ratio of at or about 1:1. In some embodiments, this increase in cellular lysis capability is observed at E:T (effector:target cell) ratio of at or about 0.1:1, when the target cell is K562 and when the cells are co-cultured for, e.g., 24 hours. In some embodiments, this increase in cellular lysis capability is observed at E:T (effector:target cell) ratio of at or about 0.5:1, when the target cell is K562 and when the cells are co-cultured for, e.g., 24 hours. In some embodiments, this increase in cellular lysis capability is observed at E:T (effector:target cell) ratio of at or about 1:1, when the target cell is K562 and when the cells are co-cultured for, e.g., 24 hours. In some embodiments, this increase in cellular lysis capability is observed at E:T (effector:target cell) ratio of at or about 0.1:1, when the target cell is RPMI and when the cells are co-cultured for, e.g., 24 hours. In some embodiments, this increase in cellular lysis capability is observed at E:T (effector:target cell) ratio of at or about 0.5:1, when the target cell is RPMI and when the cells are co-cultured for, e.g., 24 hours. In some embodiments, this increase in cellular lysis capability is observed at E:T (effector:target cell) ratio of at or about 1:1, when the target cell is RPMI and when the cells are co-cultured for, e.g., 24 hours.

In some embodiments, the engineered NK cells express at least one, two, three, four, five, six, seven, eight or all of the following markers: CD45, CD56, CD94, NKG2A, CD16, NKp44, NKp46, KIR2DL4, and KIR3DL2, and optionally wherein the markers are expressed at least at 25%, 30%, 40%, 50%, 75%, 80%, 90%, 95% or 100% level or more relative to their expression in un-edited or wild-type NK cells. In some embodiments, the engineered NK cells expresses at least one, two, three, four, five or all of the following markers: CD56, NKp44, NKp46, CD94, NKG2A and KIR2DL4, and optionally wherein the markers are expressed at least at 25%, 30%, 40%, 50%, 75%, 80%, 90%, 95% or 100% level or more relative to their expression in un-edited or wild-type NK cells. In some embodiments, the engineered NK cells have at least 25%, at least 30%, at least 40%, at least 50%, at least 60%, at least 70%, at least 80%, at least 90%, at least 95% or at least 99% of the cell population expressing one, two, three, four, five, six, seven, eight or all of the following markers: CD45, CD56, CD94, NKG2A, CD16, NKp44, NKp46, KIR2DL4, and KIR3DL2. In some embodiments, the engineered NK cells have at least 25%, at least 30%, at least 40%, at least 50%, at least 60%, at least 70%, at least 80%, at least 90%, at least 95% or at least 99% of the cell population expressing one, two, three, four, five or all of the following markers: CD56, NKp44, NKp46, CD94, NKG2A and KIR2DL4.

In some embodiments, the engineered NK cells express at least one, two, three or all of the following markers: CD38, CD96, DNAM-1, and ICAM-1, and optionally wherein the markers are expressed at least at 25%, 30%, 40%, 50%, 75%, 80%, 90%, 95% or 100% level or more relative to their expression in un-edited or wild-type NK cells. In some embodiments, the engineered NK cells express at least one, two, three or all of the following markers: CD38, CD96, DNAM-1, and ICAM-1, and optionally wherein the markers are expressed at least at 25%, 30%, 40%, 50%, 75%, 80%, 90%, 95% or 100% level or more relative to their expression in un-edited or wild-type NK cells. In some embodiments, the engineered NK cells have at least 25%, at least 30%, at least 40%, at least 50%, at least 60%, at least 70%, at least 80%, at least 90%, at least 95% or at least 99% of the cell population expressing one, two, three or all of the following markers: CD38, CD96, DNAM-1, and ICAM-1. In some embodiments, the engineered NK cells have at least 25%, at least 30%, at least 40%, at least 50%, at least 60%, at least 70%, at least 80%, at least 90%, at least 95% or at least 99% of the cell population expressing one, two, three or all of the following markers: CD38, CD96, DNAM-1, and ICAM-1.

In some embodiments, the engineered NK cells express at least one, two, three or all of the following markers: NKG2D, TIM3, CD16, and CD25, and optionally wherein the markers are expressed at least at 25%, 30%, 40%, 50%, 75%, 80%, 90%, 95% or 100% level or more relative to their expression in un-edited or wild-type NK cells. In some embodiments, the engineered NK cells express at least one, two, three or all of the following markers: NKG2D, TIM3, CD16, and CD25, and optionally wherein the markers are expressed at least at 25%, 30%, 40%, 50%, 75%, 80%, 90%, 95% or 100% level or more relative to their expression in un-edited or wild-type NK cells. In some embodiments, the engineered NK cells have at least 10%, at least 15%, at least 20%, at least 25%, at least 30%, at least 40%, at least 50%, at least 60%, at least 70%, at least 80%, at least 90%, at least 95% or at least 99% of the cell population expressing one, two, three or all of the following markers: NKG2D, TIM3, CD16, and CD25. In some embodiments, the engineered NK cells have at least 10%, at least 15%, at least 20%, at least 25%, at least 30%, at least 40%, at least 50%, at least 60%, at least 70%, at least 80%, at least 90%, at least 95% or at least 99% of the cell population expressing one, two, three or all of the following markers: NKG2D, TIM3, CD16, and CD25.

In some embodiments, the engineered NK cells of the present disclosure exhibit an increased cytokine secretion relative to control (e.g., un-edited or wild-type) cells. In some embodiments, the engineered NK cells of the present disclosure exhibit about the same cytokine secretion level relative to control (e.g., un-edited or wild-type) cells. In some embodiments, the engineered NK cells of the present disclosure exhibit a reduced (e.g., reduced by less than 10%, less than 20%, less than 30%, less than 40%, or less than 50%) cytokine secretion level relative to control (e.g., un-edited or wild-type) cells. In some embodiments, the engineered NK cells of the present disclosure exhibit a reduced (e.g., reduced by more than 20%, more than 30%, more than 40%, more than 50%, or more than 75%) cytokine secretion level relative to control (e.g., un-edited or wild-type) cells. In some embodiments, the engineered NK cells of the present disclosure exhibit an increased (e.g., increased by at least 5%, at least 10%, at least 20%, at least 30%, at least 40%, at least 50%, or at least 75%) cytokine secretion level relative to control (e.g., un-edited or wild-type) cells. The cytokine(s) being measured can be, without limitation any one or more of: TNFα, IFNγ and IL-7. In some embodiments, the level of cytokines (e.g., TNFα, IFNγ and IL-7) secreted by the engineered NK cells is about the same as the level in control (e.g., un-edited or wild-type) cells, when cells are co-cultured with target cells at the E:T ratio of or about 0.1:1. In some embodiments, the level of cytokines (e.g., TNFα, IFNγ and IL-7) secreted by the engineered NK cells is reduced (by, e.g., at least 10%, 20%, 30%, 40%, 50%, 60% or 70%, and/or no more than 50%, 60%, 70%, 80%, or 90%) relative to the level in control (e.g., un-edited or wild-type) cells, when cells are co-cultured with target cells at the E:T ratio of or about 0.1:1. In some embodiments, the level of cytokines (e.g., TNFα, IFNγ and IL-7) secreted by the engineered NK cells is increased (by, e.g., at least 5%, 10%, 20%, 30%, 40%, 50%, 60% or 70%) relative to the level in control (e.g., un-edited or wild-type) cells, when cells are co-cultured with target cells at the E:T ratio of or about 0.1:1.

In some embodiments, the engineered NK cells of the present disclosure exhibit an increased expression or release of Granzyme B or perforin relative to control (e.g., un-edited or wild-type) cells. In some embodiments, the engineered NK cells of the present disclosure exhibit about the same expression or release level of Granzyme B or perforin relative to control (e.g., un-edited or wild-type) cells. In some embodiments, the engineered NK cells of the present disclosure exhibit a reduced (e.g., reduced by less than 10%, less than 20%, less than 30%, less than 40%, or less than 50%) Granzyme B or perforin expression or release level relative to control (e.g., un-edited or wild-type) cells. In some embodiments, the engineered NK cells of the present disclosure exhibit a reduced (e.g., reduced by more than 20%, more than 30%, more than 40%, more than 50%, or more than 75%) Granzyme B or perforin expression or release level relative to control (e.g., un-edited or wild-type) cells. In some embodiments, the engineered NK cells of the present disclosure exhibit an increased (e.g., increased by at least 5%, at least 10%, at least 20%, at least 30%, at least 40%, at least 50%, or at least 75%) Granzyme B or perforin expression or release level relative to control (e.g., un-edited or wild-type) cells. In some embodiments, the level of Granzyme B or perforin secreted by the engineered NK cells is about the same as the level in control (e.g., un-edited or wild-type) cells, when cells are co-cultured with target cells at the E:T ratio of or about 0.1:1. In some embodiments, the level of Granzyme B or perforin secreted by the engineered NK cells is reduced (by, e.g., at least 10%, 20%, 30%, 40%, 50%, 60% or 70%, and/or no more than 50%, 60%, 70%, 80%, or 90%) relative to the level in control (e.g., un-edited or wild-type) cells, when cells are co-cultured with target cells at the E:T ratio of or about 0.1:1. In some embodiments, the level of Granzyme B or perforin secreted by the engineered NK cells is increased (by, e.g., at least 5%, 10%, 20%, 30%, 40%, 50%, 60% or 70%) relative to the level in control (e.g., un-edited or wild-type) cells, when cells are co-cultured with target cells at the E:T ratio of or about 0.1:1.

In some embodiments, the engineered NK cells of the present disclosure exhibit an increased (e.g., increased by at least 5%, at least 10%, at least 20%, at least 30%, at least 40%, at least 50%, or at least 75%) expression level of CD107a relative to control (e.g., un-edited or wild-type) cells. In some embodiments, the engineered NK cells of the present disclosure exhibit about the same expression level of CD107a relative to control (e.g., un-edited or wild-type) cells. In some embodiments, engineered NK cells of the present disclosure exhibit a reduced (e.g., reduced by less than 10%, less than 20%, less than 30%, less than 40%, or less than 50%) CD107a expression level relative to control (e.g., un-edited or wild-type) cells. In some embodiments, the engineered NK cells of the present disclosure exhibit a reduced (e.g., reduced by more than 20%, more than 30%, more than 40%, more than 50%, or more than 75%) CD107a expression level relative to control (e.g., un-edited or wild-type) cells.

In some embodiments, the engineered NK cells have higher proliferative capacity as compared to un-edited or wild-type NK cells. In some embodiments, the engineered NK cells have approximately the same proliferative capacity compared to un-edited or wild-type NK cells.

In some embodiments, the engineered NK cells do not exhibit exhaustion or exhibit a low level of exhaustion (e.g., a level of exhaustion markers associated with a functional NK cell). In some embodiments, exhaustion is detected by detecting a reduced expression of IFNγ, granzyme B, perforin, CD107a, and/or TNFα in cells. In some embodiments, exhaustion is detected by detecting increased expression (e.g., on the surface of the cell) of an exhaustion marker, e.g., PD-1, LAG-3, TIGIT and/or TIM-3. In some embodiments, the engineered NK cells have normal or higher than normal expression of perforin, granzyme B, CD107a, IFNγ and/or TNFα (relative to un-edited or wild-type cells). In some embodiments, the engineered NK cells have lower than normal or no expression of PD-1, LAG-3, TIGIT and/or TIM-3 (relative to un-edited or wild-type cells). In some embodiments, engineered NK cells of the present disclosure exhibit reduced exhaustion, relative to control (e.g., un-edited cells or wild-type) NK cells.

In some embodiments, the engineered NK cells of the present disclosure exhibit about the same cellular viability as control (e.g., un-edited or wild-type) cells. In some embodiments, the engineered NK cells of the present disclosure exhibit increased cellular viability relative to control (e.g., un-edited or wild-type) cells. In some embodiments, the engineered NK cells of the present disclosure exhibit at least 10% or at least 20% increase in cellular viability, relative to control cells. For example, the engineered NK cells of the present disclosure may exhibit at least 25%, at least 30%, at least 35%, at least 40%, at least 45%, at least 50%, at least 55%, at least 60%, at least 65%, at least 70%, at least 75%, at least 80%, or at least 90% increase in cellular viability, relative to control cells. In some embodiments, the engineered NK cells of the present disclosure exhibit a 20%-100%, 20%-90%, 20%-80%, 20%-70%, 20%-60%, 20%-50%, 30%-100%, 30%-90%, 30%-80%, 30%-70%, 30%-60%, 30%-50%, 40%-100%, 40%-90%, 40%-80%, 40%-70%, 40%-60%, 40%-50%, 50%-100%, 50%-90%, 50%-80%, 50%-70%, or 50%-60% increase in cellular viability, relative to control cells. Methods of measuring cell viability are known to those of skill in the art and described herein.

In some embodiments, the engineered NK cells have higher expression of one or more cell cycle genes, one or more cell division genes, and/or one or more DNA replication genes, as compared to un-edited or wild-type NK cells. In some embodiments, the engineered NK cells have approximately the same expression of one or more cell cycle genes, one or more cell division genes, and/or one or more DNA replication genes, as compared to un-edited or wild-type NK cells.

In some embodiments, gene-edited iPSC cells are differentiated into NK cell having any of the characteristics described herein. In some embodiments, iPSC cells are gene-edited with one or more of the following, B2M null, CHTA null, ADAM17 null, HLA-E knock-in, IL15/IL15Rα knock-in, BCMA CAR knock-in, CD30 CAR knock-in, SERPINB9 knock-in, FAS null, CISH null, and REGNASE-1 null CAR, then differentiated into NK cells. In some embodiments, iPSC cells are edited with B2M null, IL15/IL15Rα KI, and HLA-E KI, then differentiated into NK cells. In some embodiments, iPSC cells are edited with B2M null, SERPINB9 KI, and HLA-E KI, then differentiated into NK cells. In some embodiments, iPSC cells are edited with B2M null, SERPINB9 KI, IL15/IL15Rα KI, then differentiated into NK cells. In some embodiments, B2M null, CIITA null, ADAM17 null, HLA-E knock-in, IL15/IL15Rα knock-in, CAR KI gene-edited iPSC cells are differentiated into NK cells. The CAR can be, without limitation, a BCMA CAR or a CD30 CAR. In some embodiments, B2M null, CIITA null, CISH null, FAS null, SERPINB9 knock-in, IL15/IL15Rα knock-in, CD30 CAR knock-in, HLA-E knock-in gene-edited iPSC cells are differentiated into NK cells.

In some embodiments, the engineered NK cells having any of the characteristics described herein have the following gene edits: B2M null, IL15/IL15Rα KI, and HLA-E KI (e.g., IL15/IL15Rα-P2A-HLA-E trimer KI, B2M KO). In some embodiments, the engineered NK cells having any of the characteristics described herein have the following gene edits: B2M null, CIITA null, ADAM17 null, HLA-E knock-in, IL15/IL15Rα knock-in, CAR KI. In some embodiments, the CAR is BCMA. In some embodiments, the engineered NK cells express a CAR specific for BCMA and the target cell (e.g., cancer cell) expresses BCMA. In some embodiments, the CAR is CD30. In some embodiments, the engineered NK cells express a CAR specific for CD30 and the target cell (e.g., cancer cell) expresses CD30.

In some embodiments, the engineered NK cells having any of the characteristics described herein have the following gene edits: B2M null, CIITA null, CISH null, FAS null, SERPINB9 knock-in, IL15/IL15Rα knock-in, CD30 CAR knock-in, HLA-E knock-in (e.g, SERPINB9-P2A-IL15/IL15Rα KI, CD30 CAR-P2A-HLA-E trimer KI, B2M KO, CIITA KO, CISH KO, FAS KO).

In some embodiments, any of the engineered NK cells described herein have one or more of the following characteristics relative to an un-edited (wild-type) NK cell described herein: increased persistency, increased immune evasiveness, lack of an alloimmune T cell response, increased cytotoxic activity, improved antibody-dependent cellular cytotoxicity (ADCC), or increased anti-tumor activity.

In some embodiments, the population of engineered cells of the present disclosure is engineered (e.g., by use of CRISPR-Cas9 gene-editing) to induce a site-specific disruption in a target gene sequence that eliminates the expression of an allogeneic antigen. In some embodiments, an allogeneic antigen is a major histocompatibility antigen. In some embodiments, a major histocompatibility antigen is a MHC I complex. In some embodiments, the target gene sequence is found in the B2M gene that encodes a protein component of the MHC I complex.

In some embodiments, persistence of the engineered cells is assessed by analyzing their presence and quantity in one or more tissue samples that are collected from a subject following administration of the engineered cells to the subject. In some embodiments, persistence is defined as the longest duration of time from administration to a time wherein a detectable level of the engineered cells is present in a given tissue type (e.g., peripheral blood). In some embodiments, persistence is defined as the continued absence of disease (e.g., complete response or partial response). Determination of the absence of disease and response to treatment are known to those of skill in the art and described herein.

Methods of appropriate tissue collection, preparation, and storage are known to one skilled in the art. In some embodiments, persistence of cells is assessed in one or more tissue samples from a group comprised of peripheral blood, cerebrospinal fluid, tumor, skin, bone, bone marrow, breast, kidney, liver, lung, lymph node, spleen, gastrointestinal tract, tonsils, thymus and prostate. In some embodiments, a quantity of cells is measured in a single type of tissue sample (e.g., peripheral blood). In some embodiments, a quantity of cells is measured in multiple tissue types (e.g., peripheral blood in addition to bone marrow and cerebrospinal fluid). By measuring quantity of cells in multiple tissue types, the distribution of cells throughout different tissues of the body can be determined. In some embodiments, a quantity of cells is measured in one or more tissue samples at a single time point following administration. In some embodiments, a quantity of cells is measured in one or more tissue samples at multiple time points following administration.

A detectable level of the engineered cells in a given tissue can be measured by known methodologies. Methods for assessing the presence or quantity of cells in a tissue of interest are known to those of skill in the art. Such methods include, but are not limited to, reverse transcription polymerase chain reaction (RT-PCR), competitive RT-PCR, real-time RT-PCR, RNase protection assay (RPA), quantitative immunofluorescence (QIF), flow cytometry, northern blotting, nucleic acid microarray using DNA, western blotting, enzyme-linked immunosorbent assay (ELISA), radioimmunoassay (RIA), tissue immunostaining, immunoprecipitation assay, complement fixation assay, fluorescence-activated cell sorting (FACS), mass spectrometry, magnetic bead-antibody immunoprecipitation, or protein chip.

As used herein, in some embodiments, persistence is the longest period from the time of administration to a time wherein a detectable level of the engineered cells is measured. In some embodiments, a detectable level of cells is defined in terms of the limit of detection of a method of analysis. The limit of detection can be defined as the lowest quantity of a component or substance that can be reliably and reproducibly measured by an analytical procedure when compared to a tissue sample expected to have no quantity of the component or substance of interest. A non-limiting exemplary method to determine a reproducible limit of detection is to measure the analytical signal for replicates of a zero calibrator relative to a blank sample (Armbruster, D. et al. (2008) Clin Biochem Rev. 29:S49-S52). A blank sample is known to be devoid of an analyte of interest. A zero calibrator is the highest dilution of a test sample of known concentration or quantity that gives analytical signal above that measured for the blank sample. By quantifying the analytical signal for at least 5, 6, 7, 8, 9, 10, 11, 12, 13, 14, 15, 16, 17, 18, 19, 20, 21, 22, 23, 24, 25, 26, 27, 28, 29, or 30 replicates of a zero calibrator, one can determine an average and standard deviation (SD) for the limit of detection of an analytical method of interest. Selection of a method with a suitable limit of detection for quantifying donor T cells in a given tissue can be ascertained by one skilled in the art. In some embodiments, a detectable level of cells is any quantity of cells in a tissue sample that gives an analytical signal above the limit of detection for a method of analysis. In some embodiments, a detectable level of cells is any quantity of cells in a tissue sample that gives an analytical signal that is at least 2 SDs, 3 SDs, 4 SDs, 5 SDs, 6 SDs, 7 SDs, 8 SDs, 9 SDs, or 10 SDs, above the limit of detection for the method of analysis.

It is known that CAR-expressing donor cells can undergo expansion following administration to a recipient. Expansion is a response to antigen recognition and signal activation (Savoldo, B. et al. (2011) J Clin Invest. 121:1822; van der Stegen, S. et al. (2015) Nat Rev Drug Discov. 14:499-509). In some embodiments, following expansion, CAR-expressing engineered cells undergo a contraction period, wherein a portion of the cell population that are short-lived effector cells are eliminated and what remains is a portion of the cell population that are long-lived memory cells. In some embodiments, persistence is a measure of the longevity of the engineered cell population following expansion and contraction. The duration of the expansion, contraction and persistence phases are evaluated using a pharmacokinetic profile. In some embodiments, a pharmacokinetic (PK) profile is a description of the cells measured in a given tissue over time and is readily ascertained by one skilled in the art by measuring the cells in a given tissue (e.g., peripheral blood) at multiple time points. In some embodiments, a measure of a PK profile provides a method of evaluating or monitoring the effectiveness of the engineered cell therapy in a subject (e.g., having cancer). In some embodiments, a measure of a PK profile provides a method of evaluating the persistence of the engineered cells in a subject. In some embodiments, a PK profile provides a method of evaluating the expansion of the engineered cells in a subject. In some embodiments, a measure of persistence of engineered cells in a subject is used to evaluate the effectiveness of engineered cell therapy in a subject. In some embodiments, a measure of expansion of engineered cells in a subject is used to evaluate the effectiveness of engineered cell therapy in a subject.

In some embodiments, a PK profile is prepared by measuring a quantity of engineered cells in a sample of a given tissue type (e.g., peripheral blood) collected from a recipient and repeating the assessment at different time points. In some embodiments, a baseline tissue sample is collected from a recipient no more than 1 day, 2 days, 3 days, 4 days, 5 days, 6 days, 7 days, 8 days, 9 days, 10 days, 12 days, 13 days, 14 days, or 15 days prior to administration. In some embodiments, tissue collection from a recipient is performed within 0.25-2 hours, within 1-3 hours, within 2-6 hours, within 3-11 hours, within 4-20 hours, within 5-48 hours of the time of administration of engineered cells. In some embodiments, tissue collection from a recipient is performed on a daily basis starting on day 1, day 2, day 3, or day 4 and continuing through at least day 5, day 6, day 7, day 8, day 9, day 10, day 11, day 12, day 13, day 14, day 15, day 16, day 17, day 18, day 19, or day 20. In some embodiments, tissue collection from a recipient is performed at least 1 time, 2 times, 3 times, 4 times, 5 times, or 6 times per week for up to 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, or 16 weeks following administration of cells. In some embodiments, tissue collection from a recipient is performed at least 1 time, 2 times, 3 times, 4 times, 5 times, or 6 times per month for up to 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, or 24 months following administration of cells. In some embodiments, tissue collection from a recipient is performed at least 1 time, 2 times, 3 times, 4 times, 5 times, or 6 times per year for up to 1 year, 2 years, 3 years, 4 years, 5 years, 6 year, 7 years, 8 years, 9 years, or 10 years following administration of cells.

In some embodiments, engineered cell persistence is defined as the duration of time from administration wherein a quantity of engineered cells is present that is at least 0.005-0.05%, 0.01-0.1%, 0.05-0.5%, 0.1-1%, 0.5%-5%, 1-10%, 5%-10%, or 10%-15% (e.g., at least 1%, 5%, 10%, or 15%) of the peak quantity of engineered cells. In some embodiments, a persistence of cells is determined by comparing the quantity of cells measured in a given tissue type (e.g., peripheral blood) to the peak quantity of cells that is measured in the same tissue type. In some embodiments, a persistence of cells is determined by comparing the quantity of cells measured in a given subject (e.g., peripheral blood) to the peak quantity of cells that is measured in the same subject. In some embodiments, a persistence of cells is determined by comparing the quantity of cells measured in a given subject (e.g., peripheral blood) to the peak quantity of cells that is measured in a different subject (i.e., a subject with partial response, a subject with complete response).

In some embodiments, a persistence of engineered cells is present in one or more tissue types (e.g. peripheral blood) following administration wherein engineered cells are administered on day 1. In some embodiments, a persistence of engineered cells is present in one or more tissue types (e.g. peripheral blood) up to 1 day, 2 days, 3 days, 4, days, 5 days, 6 days, 7 days, 8 days, 9 days, 10 days, 11 days, 12 days, 13 days, 14 days, 15 days, 16 days, 17 days, 18 days, 19 days, 21 days, 21 days, 22 days, 23 days, 24 days, 25 days, 26 days, 27 days, 28 days, 29 days, 30 days, 31 days, 32 days, 33 days, 34 days, or 35 days following administration wherein engineered cells are administered on day 1. In some embodiments, a persistence of engineered cells is present in one or more tissue types (e.g. peripheral blood) up to 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 21 months, 22 months, 23 months, or 24 months following administration of engineered cells). In some embodiments, a persistence of engineered cells is measured in one or more tissue types (e.g. peripheral blood) up to 1 year, 2 years, 3 years, 4 years, 5 years, 6 years, 7 years, 8 years, 9 years, and 10 years following administration of engineered cells. In some embodiments, a persistence of engineered cells that is at least 10-25 days, at least 25-50 days, at least 50-100 days, at least 100-364 days, at least one year, at least two years, at least three years, at least four years or at least five years from administration wherein engineered cells are administered on day 1 is indicative of a response in a recipient (e.g. complete response or partial response).

Isolation and Purification of Cells
Purfication

In some embodiments, the population of gene-edited cells (e.g., iPSC, iNK, or NK cells) described herein are activated and/or expanded before or after genome editing. In some embodiments, iPSC cells are differentiated after gene-editing. In some embodiments, cells are activated and expanded for about 1 day to about 4 days, about 1 day to about 3 days, about 1 day to about 2 days, about 2 days to about 3 days, about 2 days to about 4 days, about 3 days to about 4 days, or about 1 day, about 2 days, about 3 days, or about 4 days prior to genome editing.

In some embodiments, the disclosure provides a method for substantially isolating cells that express a detectable level of a surface protein (e.g., B2M) from a population of cells comprising any of the engineered NK cells disclosed herein (e.g., IL15/IL15Rα KI, HLA-E KI, B2M null, CIITA null, CAR KI, ADAM17 null cells or SERPINB9 KI, IL15/IL15Rα KI, HLA-E KI, CAR KI, B2M null, CIITA null, FAS null, CISH null cells).

In some embodiments, the disclosure provides a method for isolating a population of cells comprising any of the engineered CAR NK cells disclosed herein (e.g., comprising CAR KI and B2M KO, CIITA KO, ADAM17 KO, FAS KO, CISH KO. REGNASE-1 KO, IL15/IL15Rα KI, HLA-E KI, and/or SERPINB9 KI) comprising: providing the population of cells wherein the engineered CAR NK cells comprise a disrupted CIITA gene, a disrupted B2M gene, a disrupted ADAM17 gene, a disrupted FAS gene, a disrupted CISH gene, and/or a disrupted REGNASE-1 gene; and isolating the population of cells expressing a CAR (e.g. such that >99% of the population comprises the CAR expressing cells).

In some embodiments, the disclosure provides a population of cells comprising engineered NK cells described herein (e.g., B2M KO, CIITA KO, ADAM17KO, FAS KO, CISH KO. REGNASE-1 KO, IL15/IL15Rα KI, HLA-E KI, CAR KI, and/or SERPINB9 KI) wherein less than 0.5% of the cells in the population express a detectable level of ADAM17, B2M, CIITA, FAS, and/or CISH. In some embodiments, the disclosure provides a population of cells comprising engineered NK cells described herein, wherein less than 0.1%, less than 0.2%, less than 0.3%, less than 0.4%, less than 0.5%, less than 1%, less than 2%, less than 3%, less than 4%, less than 5% or less than 10% of the cells in the population express a detectable level of ADAM17, B2M, CIITA. FAS, CISH, and/or REGNASE-1.

Removal of a subset of cells from a population can be performed using conventional cell purification methods. Non-limiting examples of cell sorting methods include fluorescence-activated cell sorting, immunomagnetic separation, chromatography, and microfluidic cell sorting. In some embodiments, CAR-expressing cells are removed from a population of cells comprising engineered NK cells by immunomagnetic separation. In some embodiments, HLA-E-expressing cells are removed from a population of cells comprising engineered NK cells by immunomagnetic separation.

In some embodiments, genome edited cells are sorted into single cells. In some embodiments, single cell isolates of gene-edited cells are grown into single cell clonal populations. In some embodiments, multiple single-cell clones are generated. In some embodiments, an edited clone is expanded to generate a master cell bank (MCB).

Formulations and Administrations
Formulation and Delivery for Gene Editing

Guide RNAs, polynucleotides, e.g., polynucleotides that encode any protein described herein or polynucleotides that encode an endonuclease, and endonucleases as described herein may be formulated and delivered to cells in any manner known in the art.

Guide RNAs and/or polynucleotides may be formulated with pharmaceutically acceptable excipients such as carriers, solvents, stabilizers, adjuvants, diluents, etc., depending upon the particular mode of administration and dosage form. Guide RNAs and/or polynucleotides compositions can be formulated to achieve a physiologically compatible pH, and range from a pH of about 3 to a pH of about 11, about pH 3 to about pH 7, depending on the formulation and route of administration. In some cases, the pH can be adjusted to a range from about pH 5.0 to about pH 8. In some cases, the compositions can comprise a therapeutically effective amount of at least one compound as described herein, together with one or more pharmaceutically acceptable excipients. Optionally, the compositions can comprise a combination of the compounds described herein, or can include a second active ingredient useful in the treatment or prevention of bacterial growth (for example and without limitation, anti-bacterial or anti-microbial agents), or can include a combination of reagents of the present disclosure.

Suitable excipients include, for example, carrier molecules that include large, slowly metabolized macromolecules such as proteins, polysaccharides, polylactic acids, polyglycolic acids, polymeric amino acids, amino acid copolymers, and inactive virus particles. Other exemplary excipients can include antioxidants (for example and without limitation, ascorbic acid), chelating agents (for example and without limitation, EDTA), carbohydrates (for example and without limitation, dextrin, hydroxyalkylcellulose, and hydroxyalkylmethylcellulose), stearic acid, liquids (for example and without limitation, oils, water, saline, glycerol and ethanol), wetting or emulsifying agents, pH buffering substances, and the like.

Guide RNA polynucleotides (RNA or DNA) and/or endonuclease polynucleotide(s) (RNA or DNA) can be delivered by viral or non-viral delivery vehicles known in the art. Alternatively, endonuclease polypeptide(s) can be delivered by viral or non-viral delivery vehicles known in the art, such as electroporation or lipid nanoparticles. In further alternative aspects, the DNA endonuclease can be delivered as one or more polypeptides, either alone or pre-complexed with one or more guide RNAs, or one or more crRNA together with a tracrRNA.

Polynucleotides can be delivered by non-viral delivery vehicles including, but not limited to, nanoparticles, liposomes, ribonucleoproteins, positively charged peptides, small molecule RNA-conjugates, aptamer-RNA chimeras, and RNA-fusion protein complexes. Some exemplary non-viral delivery vehicles are described in Peer and Lieberman, Gene Therapy, 2011, 18: 1127-1133 (which focuses on non-viral delivery vehicles for siRNA that are also useful for delivery of other polynucleotides).

For polynucleotides of the disclosure, the formulation may be selected from any of those taught, for example, in International Application WO 2013090648.

Polynucleotides, such as guide RNA, sgRNA, and mRNA encoding an endonuclease, may be delivered to a cell or a subject by a lipid nanoparticle (LNP).

A LNP refers to any particle having a diameter of less than 1000 nm, 500 nm, 250 nm, 200 nm, 150 nm, 100 nm, 75 nm, 50 nm, or 25 nm. Alternatively, a nanoparticle may range in size from 1-1000 nm, 1-500 nm, 1-250 nm, 25-200 nm, 25-100 nm, 35-75 nm, or 25-60 nm.

LNPs may be made from cationic, anionic, or neutral lipids. Neutral lipids, such as the fusogenic phospholipid DOPE or the membrane component cholesterol, may be included in LNPs as 'helper lipids' to enhance transfection activity and nanoparticle stability. Limitations of cationic lipids include low efficacy owing to poor stability and rapid clearance, as well as the generation of inflammatory or anti-inflammatory responses.

LNPs may also be comprised of hydrophobic lipids, hydrophilic lipids, or both hydrophobic and hydrophilic lipids.

Any lipid or combination of lipids that are known in the art can be used to produce a LNP. Examples of lipids used to produce LNPs are: DOTMA, DOSPA, DOTAP, DMRIE, DC-cholesterol, DOTAP-cholesterol, GAP-DMORIE-DPyPE, and GL67A-DOPE-DMPE-polyethylene glycol (PEG). Examples of cationic lipids are: 98N12-5, C12-200, DLin-KC2-DMA (KC2), DLin-MC3-DMA (MC3), XTC, MD1, and 7C1. Examples of neutral lipids are: DPSC, DPPC, POPC, DOPE, and SM. Examples of PEG-modified lipids are: PEG-DMG, PEG-CerC14, and PEG-CerC20.

The lipids can be combined in any number of molar ratios to produce an LNP. In addition, the polynucleotide(s) can be combined with lipid(s) in a wide range of molar ratios to produce an LNP.

A recombinant adeno-associated virus (AAV) vector can be used for delivery. Techniques to produce rAAV particles, in which an AAV genome to be packaged that includes the polynucleotide to be delivered, rep and cap genes, and helper virus functions are provided to a cell are standard in the art. Production of rAAV typically requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived, and may be from a different AAV serotype than the rAAV genome ITRs, including, but not limited to, AAV serotypes described herein. Production of pseudotyped rAAV is disclosed in, for example, international patent application publication number WO 01/83692.

Formulation and Administration of Cells

Genetically modified cells, as described herein may be formulated and administered to a subject by any manner known in the art.

The terms "administering," "introducing", "implanting", "engrafting" and "transplanting" are used interchangeably in the context of the placement of cells, e.g., progenitor cells, into a subject, by a method or route that results in at least partial localization of the introduced cells at a desired site. The cells e.g., progenitor cells, or their differentiated progeny can be administered by any appropriate route that results in delivery to a desired location in the subject where at least a portion of the implanted cells or components of the cells remain viable. The period of viability of the cells after administration to a subject can be as short as a few hours, e.g., twenty-four hours, to a few days, to as long as several years, or even the lifetime of the subject, i.e., long-term engraftment.

In some embodiments, a genetically modified cell as described herein is viable after administration to a subject for a period that is longer than that of an unmodified cell.

In some embodiments, a composition comprising cells as described herein are administered by a suitable route, which may include intravenous administration, e.g., as a bolus or by continuous infusion over a period of time. In some embodiments, intravenous administration may be performed by intramuscular, intraperitoneal, intracerebrospinal, subcutaneous, intra-articular, intrasynovial, or intrathecal routes. In some embodiments, a composition may be in solid form, aqueous form, or a liquid form. In some embodiments, an aqueous or liquid form may be nebulized or lyophilized. In some embodiments, a nebulized or lyophilized form may be reconstituted with an aqueous or liquid solution.

A cell composition can also be emulsified or presented as a liposome composition, provided that the emulsification procedure does not adversely affect cell viability. The cells and any other active ingredient can be mixed with excipients that are pharmaceutically acceptable and compatible with the active ingredient, and in amounts suitable for use in the therapeutic methods described herein.

Additional agents included in a cell composition can include pharmaceutically acceptable salts of the components therein. Pharmaceutically acceptable salts include the acid addition salts (formed with the free amino groups of the polypeptide) that are formed with inorganic acids, such as, for example, hydrochloric or phosphoric acids, or such organic acids as acetic, tartaric, mandelic and the like. Salts formed with the free carboxyl groups can also be derived from inorganic bases, such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the cell compositions that is effective in the treatment of a particular disorder or condition can depend on the nature of the disorder or condition, and can be determined by standard clinical techniques.

In some embodiments, a composition comprising cells may be administered to a subject, e.g., a human subject, who has, is suspected of having, or is at risk for a disease. In some embodiments, a composition may be administered to a subject who does not have, is not suspected of having or is not at risk for a disease. In some embodiments, a subject is a healthy human. In some embodiments, a subject e.g., a human subject, who has, is suspected of having, or is at risk for a genetically inheritable disease. In some embodiments, the subject is suffering or is at risk of developing symptoms indicative of a disease.

Treatment Methods

Provided herein, in some embodiments, are methods for treating cancer (e.g., leukemias, e.g., acute myeloid leukemia) using any engineered cells described herein (or any population of cells described herein). Non-limiting examples of cancers that may be treated as provided herein include multiple myeloma, Hodgkin's lymphoma, lung cancer, leukemia, B-cell acute lymphoblastic leukemia (B-ALL), B-cell non-Hodgkin's lymphoma (B-NL), chronic lymphocytic leukemia (C-CLL), acute myeloid leukemia (AML), T cell lymphoma, T cell leukemia, clear cell renal cell carcinoma (ccRCC), thyroid cancer, nasopharyngeal cancer, non-small cell lung cancer (NSCLC), pancreatic cancer, melanoma, ovarian cancer, colon cancer, glioblastoma, and cervical cancer.

In some embodiments, leukemias that may be treated as provided herein include chronic lymphocytic leukemia (CLL), non-Hodgkin lymphomas (e.g., diffuse large B-cell lymphoma (DLBCL), high grade B-cell lymphoma, transformed follicular lymphoma (FL), grade 3B FL, and Richter's transformation of CLL, and acute lymphoblastic leukemia (ALL). In some embodiments, provided herein is a method of treating cancer in a subject (e.g., human) in need thereof, comprising administering any engineered cell described herein to the subject (e.g., wherein the subject has or has been diagnosed with cancer). In some embodiments, provided herein is a method of treating a non-Hodgkin lymphoma (e.g., diffuse large B-cell lymphoma (DLBCL), high grade B-cell lymphoma, transformed follicular lymphoma (FL), grade 3B FL, and Richter's transformation of CLL in a subject (e.g., human) in need thereof, comprising administering any engineered cell described herein to the subject (e.g., wherein the subject has or has been diagnosed with a non-Hodgkin lymphoma, or is at risk of a non-Hodgkin lymphoma). In some embodiments, the subject (e.g., a human) has (e.g., has been diagnosed with) a relapsed and/or refractory non-Hodgkin lymphoma. In some embodiments, the subject (e.g., a human) has (e.g., has been diagnosed with) a non-relapsed or early stage non-Hodgkin lymphoma. In some embodiments, provided herein is a method of treating chronic lymphocytic leukemia (CLL) or acute lymphoblastic leukemia (ALL) in a subject (e.g., human) in need thereof, comprising administering any engineered cell described herein to the subject (e.g., wherein the subject has or has been diagnosed with CLL or ALL). In some embodiments, the subject (e.g., a human) has (e.g., has been diagnosed with) a relapsed and/or refractory CLL or ALL. In some embodiments, the subject (e.g., a human) has (e.g., has been diagnosed with) a non-relapsed or early stage CLL or ALL. The engineered cell can be administered at any dose described herein, in particular, in a therapeutically effective amount. In some embodiments, a human being treated is an adult, e.g., a human over 18 years of age. In some embodiments, a human being treated is under 18 years of age. In some embodiments, the method is not a method for treatment of the human or animal body by therapy.

In some embodiments, the methods comprise delivering the engineered cells (e.g., anti-BCMA CAR NK cells) of the present disclosure to a subject having a cancer (e.g., leukemia), wherein cancer cells express BCMA. In some embodiments, the methods comprise delivering the engineered cells (e.g., anti-CD30 CAR NK cells) of the present disclosure to a subject having a cancer (e.g., leukemia), wherein cancer cells express CD30. In some embodiments where the disease being treated is a non-Hodgkin lymphoma, the cells used express a CD30 CAR (e.g., anti-CD30 CAR NK cells).

The step of administering may include the placement (e.g., transplantation) of cells, e.g., engineered NK cells, into a subject, by a method or route that results in at least partial localization of the introduced cells at a desired site, such as tumor, such that a desired effect(s) is produced. Engineered cells can be administered by any appropriate route that results in delivery to a desired location in the subject where at least a portion of the implanted cells or components of the cells remain viable. The period of viability of the cells after administration to a subject can be as short as a few hours, e.g., twenty-four hours, to a few days, to as long as several years, or even the life-time of the subject, i.e., long-term engraftment. For example, in some embodiments, an effective amount of engineered NK cell is administered via a systemic route of administration, such as an intraperitoneal or intravenous route.

A subject may be any subject for whom diagnosis, treatment, or therapy is desired. In some embodiments, the subject is a mammal. In some embodiments, the subject is a human.

In some embodiments, an engineered NK cell population being administered according to the methods described herein comprises gene edited hematopoietic cells (e.g., NK cells) differentiated from gene-edited stem cells (e.g., iPSC cells).

In some embodiments, an engineered cell population (e.g. NK cells) being administered according to the methods described herein does not induce toxicity in the subject, e.g., the engineered NK cells do not induce toxicity in non-cancer cells. In some embodiments, an engineered cell population (e.g., NK cells) being administered does not trigger complement mediated lysis, or does not stimulate antibody-dependent cell mediated cytotoxicity (ADCC).

In some embodiments, the subject being treated has no chronic immune suppression.

An effective amount refers to the amount of a population of engineered cells (e.g., NK cells) needed to prevent or alleviate at least one or more signs or symptoms of a medical condition (e.g., cancer), and relates to a sufficient amount of a composition to provide the desired effect, e.g., to treat a subject having a medical condition. An effective amount also includes an amount sufficient to prevent or delay the development of a symptom of the disease, alter the course of a symptom of the disease (for example but not limited to, slow the progression of a symptom of the disease), or reverse a symptom of the disease. It is understood that for any given case, an appropriate effective amount can be determined by one of ordinary skill in the art using routine experimentation.

In some embodiments, a subject is administered a population of cells comprising any of the engineered cells disclosed herein at a dose in the range of about $1 \times 10^7$ to $1 \times 10^9$ engineered cells. In some embodiments, a subject is administered a population of cells comprising any of the engineered cells disclosed herein at a dose in the range of about $1 \times 10^7$ to $3 \times 10^8$ engineered cells. In some embodiments, a subject is administered a population of cells comprising any of the engineered cells disclosed herein at a dose in the range of about $3 \times 10^7$ to $3 \times 10^8$ engineered cells.

In some embodiments, the cells are NK cells. In some embodiments, the cells are derived from iPSCs. In some embodiments, the cells are expanded in culture prior to administration to a subject in need thereof.

Modes of administration include but are not limited to injection and infusion. In some embodiments, injection includes, without limitation, intravenous, intrathecal, intraperitoneal, intraspinal, intracerebrospinal, and intrasternal infusion. In some embodiments, the route is intravenous. In some embodiments, cells described herein are administered as a bolus or by continuous infusion (e.g., intravenous infusion) over a period of time. In some embodiments, cells described herein are administered in several doses over a period of time (e.g., several infusions over a period of time). The cells described herein can be administered in a single dose or in 2, 3, 4, 5, 6 or more doses (or infusions). In some embodiments, the subject being treated is dosed (e.g., with an infusion) about every 1, 2, 3, 4, 5, 6, 7 or 8 weeks. In some embodiments, the subject being treated is dosed (e.g., with an infusion) every 2-4 weeks (e.g., every 2 weeks, 3 weeks or 4 weeks).

In some embodiments, engineered cells (e.g., NK cells) are administered systemically, which refers to the administration of a population of cells other than directly into a target site, tissue, or organ, such that it enters, instead, the subject's circulatory system and, thus, is subject to metabolism and other like processes.

The efficacy of a treatment comprising a composition for the treatment of a medical condition can be determined by the skilled clinician. A treatment is considered "effective treatment," if any one or all of the signs or symptoms of, as but one example, levels of functional target are altered in a beneficial manner (e.g., increased by at least 10%), or other clinically accepted symptoms or markers of disease (e.g., cancer) are improved or ameliorated. Efficacy can also be measured by failure of a subject to worsen as assessed by hospitalization or need for medical interventions (e.g., progression of the disease is halted or at least slowed). Methods of measuring these indicators are known to those of skill in the art and/or described herein. Treatment includes any treatment of a disease in subject and includes: (1) inhibiting the disease, e.g., arresting, or slowing the progression of symptoms; or (2) relieving the disease, e.g., causing regression of symptoms; and (3) preventing or reducing the likelihood of the development of symptoms.

In some embodiments, the disclosure provides methods for treating a non-Hodgkin lymphoma (NHL) in a human patient by administering an intravenous dose of about $1 \times 10^7$-$3 \times 10^8$ engineered NK cells expressing a detectable level of CAR described herein (e.g., anti-BCMA CAR or anti-CD30 CAR). In some embodiments, the disclosure provides methods for treating a non-Hodgkin lymphoma (NHL) in a human patient by administering an intravenous dose of about $3 \times 10^7$ engineered NK cells expressing a detectable level of CAR described herein (e.g., anti-BCMA CAR or anti-CD30 CAR). In some embodiments, the disclosure provides methods for treating a non-Hodgkin lymphoma (NHL) in a human patient by administering an intravenous dose of about $1 \times 10^8$ engineered NK cells expressing a detectable level of CAR described herein (e.g., anti-BCMA CAR or anti-CD30 CAR). In some embodiments, the disclosure provides methods for treating a non-Hodgkin lymphoma (NHL) in a human patient by administering an intravenous dose of about $3 \times 10^8$ engineered NK cells expressing a detectable level of CAR described herein (e.g., anti-BCMA CAR or anti-CD30 CAR).

In some embodiments, the disclosure provides methods for treating a non-Hodgkin lymphoma (NHL) in a human patient by intravenously administering NK cells at a dose of about $1 \times 10^7$-$3 \times 10^8$ engineered NK cells expressing a detectable level of anti-BCMA CAR or anti-CD30 CAR. In some embodiments, the disclosure provides methods for treating a non-Hodgkin lymphoma (NHL) in a human patient by intravenously administering NK cells at a dose of about $3 \times 10^7$ engineered NK cells expressing a detectable level of anti-BCMA CAR or anti-CD30 CAR. In some embodiments, the disclosure provides methods for treating a non-Hodgkin lymphoma (NHL) in a human patient by intravenously administering NK cells at a dose of about $1 \times 10^8$ engineered NK cells expressing a detectable level of anti-BCMA CAR or anti-CD30 CAR. In some embodiments, the disclosure provides methods for treating a non-Hodgkin lymphoma (NHL) in a human patient by intravenously administering NK cells at a dose of about $3 \times 10^8$ engineered NK cells expressing a detectable level of anti-BCMA CAR or anti-CD30 CAR.

Lymphodepletion Conditioning Therapy

In some embodiments, any engineered cells described herein (or any population of cells described herein) are administered to a subject (e.g., a human patient having a cancer, e.g., a non-Hodgkin lymphoma) after a subject has received a lymphodepleting regimen.

In some embodiments, the lymphodepleting regimen comprises administering at least one chemotherapeutic agent. In some embodiments, at least one chemotherapeutic agent is cyclophosphamide. In some embodiments, the lymphodepleting regimen comprises administering at least two chemotherapeutic agents. In some embodiments, at least two chemotherapeutic agents are cyclophosphamide and fludarabine.

In some embodiments, the first dose (e.g., infusion) of the engineered cells described herein is administered to a subject after lymphodepletion.

Specific Compositions and Methods of the Disclosure

Accordingly, the present disclosure relates, in particular, to the following non-limiting compositions and methods.

In a first composition, Composition 1, the present disclosure provides a composition comprising a engineered cell comprising: (a) a disrupted beta-2-microglobulin (B2M) gene, and (b) a first polynucleotide and a second polynucleotide inserted in the disrupted B2M gene, wherein i. the first polynucleotide encodes human leukocyte antigen E or HLA class I histocompatibility antigen, alpha chain E (HLA-E) and ii. the second polynucleotide encodes a fusion protein of Interleukin-15 (IL15) and Interleukin-15 receptor subunit alpha (IL15Rα), wherein the cell expresses HLA-E and the fusion protein of IL15 and IL15Rα and the cell has a disrupted expression of B2M.

In another composition, Composition 2, the present disclosure provides a composition, as provided in Composition 1, wherein disrupted expression of B2M comprises reduced or eliminated expression of B2M.

In another composition, Composition 3, the present disclosure provides a composition, as provided in Compositions 1 or 2, wherein the HLA-E is an HLA-E trimer comprising a B2M signal peptide fused to an HLA-G presentation peptide fused to the B2M membrane protein fused to the HLA-E protein without a signal peptide.

In another composition, Composition 4, the present disclosure provides a composition, as provided in Composition 3, wherein the first polynucleotide and second polynucleotide are inserted as a polynucleotide encoding a IL15/IL15Rα-P2A-HLA-E trimer construct, wherein the IL15/IL15Rα-P2A-HLA-E trimer construct comprises a fusion protein of IL15 and IL15Rα, a P2A peptide sequence, and the HLA-E trimer.

In another composition, Composition 5, the present disclosure provides a composition, as provided in Composition 4, wherein the polynucleotide encoding the IL15/IL15Rα-P2A-HLA-E trimer is inserted in exon 1 of the B2M gene locus.

In another composition, Composition 6, the present disclosure provides a composition, as provided in Compositions 1-5, further comprising a disrupted Class II Major Histocompatibility Complex Transactivator (CIITA) gene, wherein the cell has a disrupted expression of CIITA.

In another composition, Composition 7, the present disclosure provides a composition, as provided in Composition 6, wherein the disrupted expression of CIITA comprises reduced or eliminated expression of CIITA.

In another composition, Composition 8, the present disclosure provides a composition, as provided in Compositions 1-7, further comprising an insertion of a polynucleotide encoding a chimeric antigen receptor (CAR).

In another composition, Composition 9, the present disclosure provides a composition, as provided in Composition 8, wherein the CAR is inserted in the disrupted CIITA gene.

In another composition, Composition 10, the present disclosure provides a composition, as provided in Compositions 8 or 9, wherein the CAR is inserted in exon 2 of the CIITA gene locus.

In another composition, Composition 11, the present disclosure provides a composition, as provided in Compositions 1-10, further comprising a disrupted ADAM metallopeptidase domain 17 (ADAM17) gene, wherein the cell has a disrupted expression of ADAM17.

In another composition, Composition 12, the present disclosure provides a composition, as provided in Composition 11, wherein the disrupted expression of ADAM17 comprises reduced or eliminated expression of ADAM17.

In another composition, Composition 13, the present disclosure provides a composition comprising an engineered cell comprising: (a) a disrupted B2M gene, (b) a first polynucleotide and a second polynucleotide inserted in the disrupted B2M gene, wherein i. the first polynucleotide encodes HLA-E, and ii. the second polynucleotide encodes a fusion protein of IL15 and IL15Rα, (c) a disrupted CIITA gene, (d) an insertion of a polynucleotide encoding a CAR, optionally wherein the CAR is inserted in the disrupted CIITA gene, and (e) a disrupted ADAM17 gene, wherein the cell expresses HLA-E, the fusion protein of IL15 and IL15Rα, and the CAR, and the cell has a disrupted expression of B2M, CITA, and ADAM17.

In another composition, Composition 14, the present disclosure provides a composition, as provided in Composition 13, wherein the disrupted expression of B2M, CIITA, and/or ADAM17 comprises reduced or eliminated expression of B2M, CIITA, and/or ADAM17.

In another composition, Composition 15, the present disclosure provides a composition, as provided in Compositions 13 or 14, wherein the HLA-E is an HLA-E trimer comprising a B2M signal peptide fused to an HLA-G presentation peptide fused to the B2M membrane protein fused to the HLA-E protein without a signal peptide.

In another composition, Composition 16, the present disclosure provides a composition, as provided in Composition 15, wherein the first polynucleotide and second polynucleotide are inserted as a polynucleotide encoding a IL15/IL15Rα-P2A-HLA-E trimer construct, wherein the IL15/IL15Rα-P2A-HLA-E trimer construct comprises a fusion protein of IL15 and IL15Rα, a P2A peptide sequence, and the HLA-E trimer.

In another composition, Composition 17, the present disclosure provides a composition, as provided in Composition 16, wherein the polynucleotide encoding the IL15/IL15Rα-P2A-HLA-E trimer construct is inserted in exon 1 of the B2M gene locus.

In another composition, Composition 18, the present disclosure provides a composition, as provided in Compositions 13-17, wherein the CAR is inserted in exon 2 of the CIITA gene locus.

In another composition, Composition 19, the present disclosure provides a composition comprising an engineered cell comprising: (a) a disrupted ADAM17 gene, (b) a disrupted gene encoding an MHC-I or MHC-II human leukocyte antigen, or a component of, or a transcriptional regulator of, a MHC-I or MHC-II complex, and (c) an insertion of a polynucleotide encoding a CAR, wherein the cell expresses the CAR, has a disrupted expression of ADAM17, has a disrupted expression of the MHC-I or MHC-II human leukocyte antigen, or the component of, or the transcriptional regulator of, a MHC-I or MHC-II complex, and is hypoimmunogenic.

In another composition, Composition 20, the present disclosure provides a composition, as provided in Composition 19, wherein the disrupted expression of ADAM17 and/or the MHC-I or MHC-II human leukocyte antigen, or the component of, or the transcriptional regulator of, a MHC-I or MHC-II complex, comprises reduced or eliminated expression of the MHC-I or MHC-II human leukocyte antigen or the component of, or the transcriptional regulator of, a MHC-I or MHC-II complex.

In another composition, Composition 21, the present disclosure provides a composition, as provided in Compositions 19 or 20, wherein the disrupted gene encoding the MHC-I or MHC-II human leukocyte antigen or the component of, or the transcriptional regulator of, a MHC-I or MHC-II complex is a disrupted B2M gene.

In another composition, Composition 22, the present disclosure provides a composition, as provided in Composition 21, further comprising (d) an insertion of a first polynucleotide that encodes HLA-E, and (e) an insertion of a second polynucleotide that encodes a fusion protein of IL15 and IL15Rα, wherein the first polynucleotide and the second polynucleotide are inserted in the disrupted B2M gene, and wherein the cell expresses HLA-E and the fusion protein of IL15 and IL15Rα.

In another composition, Composition 23, the present disclosure provides a composition, as provided in Composition 22, wherein the HLA-E is an HLA-E trimer comprising a B2M signal peptide fused to an HLA-G presentation peptide fused to the B2M membrane protein fused to the HLA-E protein without a signal peptide.

In another composition, Composition 24, the present disclosure provides a composition, as provided in Composition 23, wherein the first polynucleotide and second polynucleotide are inserted as a polynucleotide encoding a IL15/IL15Rα-P2A-HLA-E trimer construct, wherein the IL15/IL15Rα-P2A-HLA-E trimer construct comprises a fusion protein of IL15 and IL15Rα, a P2A peptide sequence, and the HLA-E trimer.

In another composition, Composition 25, the present disclosure provides a composition, as provided in Composition 24, wherein the polynucleotide encoding the IL15/IL15Rα-P2A-HLA-E trimer is inserted in exon 1 of the B2M gene locus.

In another composition, Composition 26, the present disclosure provides a composition, as provided in Compositions 19-25, wherein the disrupted gene encoding the MHC-I or MHC-II human leukocyte antigen or the component of, or the transcriptional regulator of, a MHC-I or MHC-II complex is a disrupted CIITA gene.

In another composition, Composition 27, the present disclosure provides a composition, as provided in Compositions 19-26, wherein the CAR is inserted in the CIITA gene.

In another composition, Composition 28, the present disclosure provides a composition, as provided in Composition 27, wherein the CAR is inserted in exon 2 of the CIITA gene locus.

In another composition, Composition 29, the present disclosure provides a composition comprising an engineered cell comprising a disrupted CIITA gene and an insertion of a polynucleotide encoding a CAR in the disrupted CIITA gene, wherein the cell expresses the CAR and the cell has a disrupted expression of CIITA.

In another composition, Composition 30, the present disclosure provides a composition, as provided in Composition 29, wherein the disrupted expression of CIITA comprises reduced or eliminated expression of CIITA.

In another composition, Composition 31, the present disclosure provides a composition, as provided in Compositions 29 or 30, wherein the CAR is inserted in exon 2 of the CIITA gene locus.

In another composition, Composition 32, the present disclosure provides a composition, as provided in Compositions 29-31, further comprising a disrupted B2M gene, a first polynucleotide and a second polynucleotide inserted in the disrupted B2M gene, and optionally a disrupted ADAM17 gene, wherein the first polynucleotide encodes HLA-E and the second polynucleotide encodes a fusion protein of IL15 and IL5R&, and wherein the cell expresses HLA-E and the fusion protein of IL15 and IL15Rα and the cell has a disrupted expression of B2M and/or ADAM17.

In another composition, Composition 33, the present disclosure provides a composition, as provided in Composition 32, wherein the disrupted expression of B2M and/or ADAM17 comprises reduced or eliminated expression of ADAM17.

In another composition, Composition 34, the present disclosure provides a composition, as provided in Composition 32 or 33, wherein the HLA-E is an HLA-E trimer comprising a B2M signal peptide fused to an HLA-G presentation peptide fused to the B2M membrane protein fused to the HLA-E protein without a signal peptide.

In another composition, Composition 35, the present disclosure provides a composition, as provided in Composition 34, wherein the first polynucleotide and second polynucleotide are inserted as a polynucleotide encoding a IL15/IL15Rα-P2A-HLA-E trimer construct, wherein the IL15/IL15Rα-P2A-HLA-E trimer construct comprises a fusion protein of IL15 and IL15Rα, a P2A peptide sequence, and the HLA-E trimer.

In another composition, Composition 36, the present disclosure provides a composition, as provided in Composition 35, wherein the polynucleotide encoding the IL15/IL15Rα-P2A-HLA-E trimer is inserted in exon 1 of the B2M gene locus.

In another composition, Composition 37, the present disclosure provides a composition, as provided in Compositions 8-36, wherein the CAR comprises an ectodomain that binds anti-B cell maturation antigen.

In another composition, Composition 38, the present disclosure provides a composition, as provided in Composition 37, wherein the CAR comprises a polynucleotide sequence of SEQ ID NO: 70.

In another composition, Composition 39, the present disclosure provides a composition, as provided in Compositions 4-12, 16-18, 24-28, and 35-38, wherein the IL15/IL15Rα-P2A-HLA-E trimer construct comprises a polynucleotide sequence of SEQ ID NO: 77.

In another composition, Composition 40, the present disclosure provides a composition, as provided in Compositions 1-39, wherein the engineered cell does not comprise an insertion of a polynucleotide encoding CD16; optionally, wherein the genome of the cell does not comprise an insertion of a polynucleotide encoding a high affinity non-cleavable CD16 variant.

In another composition, Composition 41, the present disclosure provides a composition, as provided in Compositions 1-40, wherein the engineered cell is a stem cell.

In another composition, Composition 42, the present disclosure provides a composition, as provided in Composition 41, wherein the stem cell is an induced pluripotent stem cell (iPSC), a hematopoietic stem cell, an embryonic stem cell, or an adult stem cell.

In another composition, Composition 43, the present disclosure provides a composition, as provided in Compositions 1-40, wherein the engineered cell is a genome-edited iPSC.

In another composition, Composition 44, the present disclosure provides a composition, as provided in Compositions 1-40, wherein the engineered cell is a natural killer (NK) cell obtained from a genome-edited iPSC.

In another composition, Composition 45, the present disclosure provides a composition, as provided in Compositions 1-40, wherein the engineered cell is a differentiated cell or a somatic cell.

In another composition, Composition 46, the present disclosure provides a composition, as provided in Compositions 1-40, wherein the engineered cell is capable of being differentiated into lineage-restricted progenitor cells or fully differentiated somatic cells.

In another composition, Composition 47, the present disclosure provides a composition, as provided in Compositions 1-40, wherein the engineered cell is a natural killer (NK) cell.

In another composition, Composition 48, the present disclosure provides a composition, as provided in Composition 47, wherein the NK cell has been differentiated from a genome-edited iPSC, wherein the NK cell comprises the genome edits of the genome-edited iPSC, wherein the NK cell has not been genome-edited after the differentiation.

In another composition, Composition 49, the present disclosure provides a composition, as provided in Compositions 1-48, wherein the engineered cell expresses at least one, two, three, four or five of the following markers: CD56, NKp44, NKp46, CD94, NKG2A and KIR2DL4, and optionally wherein the markers are expressed at least at 25%, 30%, 40%, 50%, or 75% level relative to their expression in wild-type NK cells.

In another composition, Composition 50, the present disclosure provides a composition, as provided in Compositions 1-49, wherein the engineered cell has at least one of the following characteristics, or any combination thereof: (i) an alloimmune T cell reaction of less than 10% relative to an unmodified cell, and (ii) cytotoxic activity resulting in killing more than 50% of target cells when the engineered cells are mixed with the target cells at the ratio of 1:1; (iii) at least 50% increase in cellular viability relative to an unmodified cell.

In another composition, Composition 51, the present disclosure provides a composition, as provided in Compositions 1-49, wherein the engineered cell has at least one of the following characteristics, or any combination thereof: (i) improved persistency, (ii) improved immune evasiveness, (iii) improved cytotoxic activity, (iv) improved ADCC activity, and (v) improved anti-tumor activity; wherein the characteristics are improved relative to a wild-type cell, optionally, relative to a wild-type iPSC or a wild-type NK cell.

In another composition, Composition 52, the present disclosure provides a composition, as provided in Compositions 1-51, wherein the engineered cell is capable of cell expansion in the absence of exogenous IL15 in cell culture media.

In another composition, Composition 53, the present disclosure provides a composition comprising a plurality of engineered cells according to any one of Compositions 1 to 52.

In another composition, Composition 54, the present disclosure provides a composition, comprising a population of lineage-restricted progenitor cells or fully differentiated somatic cells derived from the plurality of engineered cells of Composition 53.

In another composition, Composition 55, the present disclosure provides a composition comprising the population of cells of Composition 54, wherein the lineage-restricted progenitor cells are hematopoietic progenitor cells, mesodermal cells, definitive hemogenic endothelium, definitive hematopoietic stem or progenitor cells, $CD34^+$ cells, multipotent progenitors (MPP), common lymphoid progenitor cells, T cell progenitors, NK cell progenitors, pancreatic endoderm progenitors, pancreatic endocrine progenitors, mesenchymal progenitor cells, muscle progenitor cells, blast cells, or neural progenitor cells, and the fully differentiated somatic cells are hematopoietic cells, pancreatic beta cells, epithelial cells, endodermal cells, macrophages, hepatocytes, adipocytes, kidney cells, blood cells, cardiomyocytes, or immune system cells.

In another composition, Composition 56, the present disclosure provides a composition, comprising the population of cells of Composition 55, wherein the hematopoietic cells are NK cells, T cells, B cells, or NKT cells.

In another composition, Composition 57, the present disclosure provides a composition comprising the population of cells of Composition 56, wherein the hematopoietic cells are human NK cells.

In another composition, Composition 58, the present disclosure provides a composition comprising the population of cells of any one of Compositions 54-57, wherein at least 25% or at least 50% of engineered cells of the population express the CAR, HLA-E, and/or the fusion protein of IL15 and IL15Rα.

In another composition, Composition 59, the present disclosure provides a composition comprising the population of cells of any one of Compositions 54-58, wherein at least 50% of engineered cells of the population do not express a detectable level of B2M protein, CIITA protein, and/or ADAM17 protein.

In another composition, Composition 60, the present disclosure provides a composition comprising the population of cells of any one of Compositions 57-59, wherein engineered human NK cells of the population, when co-cultured in vitro with a population of cancer cells, induce cell lysis of at least 70%, at least 80%, or at least 90% of the population of cancer cells.

In another composition, Composition 61, the present disclosure provides a composition comprising the population of cells of any one of Compositions 57-60, wherein engineered human NK cells of the population, when co-cultured in vitro with a population of cancer cells, secrete IFNγ.

In another composition, Composition 62, the present disclosure provides a composition comprising the population of cells of Compositions 60 or 61, wherein the ratio of engineered human NK cells to cancer cells is 0.1:1 to 2:1.

In another composition, Composition 63, the present disclosure provides a composition comprising the plurality of engineered cells of Composition 53 or the population of cells of Compositions 54-62.

In another composition, Composition 64, the present disclosure provides a composition, as provided in Composition 63 for use in treating a subject in need thereof.

In another composition, Composition 65, the present disclosure provides a composition, as provided in Composition 63 for use in treating cancer in a subject in need thereof.

In another composition, Composition 66, the present disclosure provides a composition, as provided in Composition 65, wherein the subject has multiple myeloma. Hodgkin's lymphoma, lung cancer, leukemia, B-cell acute lymphoblastic leukemia (B-ALL), B-cell non-Hodgkin's lymphoma (B-NL), Chronic lymphocytic leukemia (C-CLL), T cell lymphoma, T cell leukemia, clear cell renal cell carcinoma (ccRCC), thyroid cancer, nasopharyngeal cancer, non-small cell lung (NSCLC), pancreatic cancer, melanoma, ovarian cancer, glioblastoma, or cervical cancer.

In another composition, Composition 67, the present disclosure provides a composition, as provided in any one of Composition 64-66, wherein the subject is human.

In a first method, Method 1, the present disclosure provides a method of obtaining cells for administration to a subject in need thereof, the method comprising: (a) obtaining or having obtained the plurality of engineered cells of Composition 53, and (b) maintaining the plurality of engineered cells for a time and under conditions sufficient for the cells to differentiate into lineage-restricted progenitor cells or fully differentiated somatic cells.

In another method, Method 2, the present disclosure provides a method for treating of a subject in need thereof, the method comprising: (a) obtaining or having obtained the plurality of engineered cells of Composition 53 following differentiation into lineage-restricted progenitor cells or fully differentiated somatic cells; and (b) administering the lineage-restricted progenitor cells or fully differentiated somatic cells to the subject.

In another method, Method 3, the present disclosure provides a method as provided in Methods 1 or 2, wherein the lineage-restricted progenitor cells are hematopoietic progenitor cells, mesodermal cells, definitive hemogenic endothelium, definitive hematopoietic stem or progenitor cells, $CD34^+$ cells, multipotent progenitors (MPP), common lymphoid progenitor cells, T cell progenitors, NK cell progenitors, pancreatic endoderm progenitors, pancreatic endocrine progenitors, mesenchymal progenitor cells, muscle progenitor cells, blast cells, or neural progenitor cells, and the fully differentiated somatic cells are hematopoietic cells, pancreatic beta cells, epithelial cells, endodermal cells, macrophages, hepatocytes, adipocytes, kidney cells, blood cells, cardiomyocytes, or immune system cells.

In another method, Method 4, the present disclosure provides a method as provided in any one of Methods 1-3, wherein the subject has, is suspected of having, or is at risk for a cancer.

In another method, Method 5, the present disclosure provides a method as provided in any one of Methods 1-4, wherein the subject is human.

In another method, Method 6, the present disclosure provides an in vitro method for generating an engineered cell, the method comprising delivering to a cell: (a) a first ribonucleoprotein (RNP) complex comprising an RNA-guided nuclease and a guide RNA (gRNA) targeting a target site in a beta-2 microglobulin (B2M) gene locus; (b) a first vector comprising a nucleic acid, the nucleic acid comprising: (i) a nucleotide sequence encoding a IL15/IL15Rα-P2A-HLA-E trimer construct, wherein the IL15/IL15Rα-P2A-HLA-E trimer construct comprises a fusion protein of IL15 and IL15Rα, a P2A peptide sequence, and a HLA-E trimer; (ii) a nucleotide sequence having sequence homology with a genomic region located left of the target site in the B2M gene locus; and (iii) a nucleotide sequence having sequence homology with a genomic region located right of the target site in the B2M gene locus, wherein (i) is flanked by (ii) and (iii), wherein the B2M gene locus is cleaved at the target site and the nucleic acid comprising the nucleotide sequence encoding the IL15/IL15Rα-P2A-HLA-E trimer construct is inserted into the B2M gene locus, thereby disrupting the B2M gene.

In another method, Method 7, the present disclosure provides an in vitro method of Method 6, further comprising delivering to the cell: (c) a second RNP complex comprising an RNA-guided nuclease and a gRNA targeting a target site in a CIITA gene locus, (d) a second vector comprising a nucleic acid, the nucleic acid comprising: (i) a nucleotide sequence encoding a CAR; (ii) a nucleotide sequence having sequence homology with a genomic region located left of the target site in the CIITA gene locus, and (iii) a nucleotide sequence having sequence homology with a genomic region located right of the target site in the CIITA gene locus, wherein (i) is flanked by (ii) and (iii), and (e) a third RNP complex comprising an RNA-guided nuclease and a gRNA targeting a target site in a ADAM17 gene locus, wherein the CIITA gene locus is cleaved at the target site and the nucleic acid comprising the nucleotide sequence encoding the CAR is inserted into the CIITA gene locus, thereby disrupting the CIITA gene, and wherein the ADAM17 gene locus is cleaved at the target site and the ADAM17 gene is disrupted.

In another method, Method 8, the present disclosure provides an in vitro method for generating an engineered cell, the method comprising delivering to a cell: (a) a first ribonucleoprotein (RNP) complex comprising an RNA-guided nuclease and a guide RNA (gRNA) targeting a target site in a beta-2 microglobulin (B2M) gene locus, (b) a first vector comprising a nucleic acid, the nucleic acid comprising: (i) a nucleotide sequence encoding a IL15/IL15Rα-P2A-HLA-E trimer construct, wherein the IL15/IL15Rα-P2A-HLA-E trimer construct comprises a fusion protein of IL15 and IL15Rα, a P2A peptide sequence, and a HLA-E trimer; (ii) a nucleotide sequence having sequence homology with a genomic region located left of the target site in the B2M gene locus; and (iii) a nucleotide sequence having sequence homology with a genomic region located right of the target site in the B2M gene locus, wherein (i) is flanked by (ii) and (iii), (c) a second RNP complex comprising an RNA-guided nuclease and a gRNA targeting a target site in a CIITA gene locus, (d) a second vector comprising a nucleic acid, the nucleic acid comprising: (i) a nucleotide sequence encoding a CAR; (ii) a nucleotide sequence having sequence homology with a genomic region located left of the target site in the CIITA gene locus; and (iii) a nucleotide sequence having sequence homology with a genomic region located right of the target site in the CIITA gene locus, wherein (i) is flanked by (ii) and (iii); and (e) a third RNP complex comprising an RNA-guided nuclease and a gRNA targeting a target site in a ADAM17 gene locus, wherein the B2M gene locus is cleaved at the target site and the nucleic acid comprising the nucleotide sequence encoding the IL15/IL15Rα-P2A-HLA-E trimer construct is inserted into the B2M gene locus, thereby disrupting the B2M gene, wherein the CIITA gene locus is cleaved at the target site and the nucleic acid comprising the nucleotide sequence encoding the CAR is inserted into the CIITA gene locus, thereby disrupting the CIITA gene, and wherein the ADAM17 gene locus is cleaved at the target site and the ADAM17 gene is disrupted.

In another method, Method 9, the present disclosure provides in vitro method of any one of Methods 6-8, wherein the engineered cell has reduced or eliminated expression of B2M.

In another method, Method 10, the present disclosure provides in vitro method of any one of Methods 7-9, wherein the engineered cell has reduced or eliminated expression of CIITA.

In another method, Method 11, the present disclosure provides in vitro method of any one of Methods 7-10, wherein the engineered cell has reduced or eliminated expression of ADAM17.

In another method, Method 12, the present disclosure provides in vitro method of any one of Methods 6-11, wherein the gRNA of the first RNP complex comprises a spacer sequence corresponding to a sequence consisting of: SEQ ID NO:34, SEQ ID NO:78, or SEQ ID NO:79.

In another method, Method 13, the present disclosure provides in vitro method of any one of Methods 7-12, wherein the gRNA of the second RNP complex comprises a spacer sequence corresponding to a sequence consisting of SEQ ID NO: 13, SEQ ID NO: 14, SEQ ID NO: 15, SEQ ID NO: 16, or SEQ ID NO: 17 and the gRNA of the third RNP complex comprises a spacer sequence corresponding to a sequence consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10.

In another method, Method 14, the present disclosure provides in vitro method of any one of Methods 6-13, wherein the gRNA of the first RNP complex comprises a spacer sequence corresponding to a sequence consisting of SEQ ID NO: 34.

In another method, Method 15, the present disclosure provides in vitro method of any one of Methods 7-14, wherein the gRNA of the second RNP complex comprises a spacer sequence corresponding to a sequence consisting of SEQ ID NO: 13, SEQ ID NO: 14, SEQ ID NO: 15, SEQ ID NO: 16, or SEQ ID NO: 17, and the gRNA of the third RNP complex comprises a spacer sequence corresponding to a sequence consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10.

In another method, Method 16, the present disclosure provides in vitro method of any one of Methods 6-15, wherein the first vector is a plasmid vector.

In another method, Method 17, the present disclosure provides in vitro method of any one of Methods 7-16, wherein the second vector is a plasmid vector.

In another method, Method 18, the present disclosure provides in vitro method of any one of Methods 6-17, wherein the nucleotide sequence encoding the HLA-E trimer sequence consists essentially of SEQ ID NO: 75.

In another method, Method 19, the present disclosure provides in vitro method of any one of Methods 6-18, wherein the nucleotide sequence encoding the IL15/IL15Rα sequence consists essentially of SEQ ID NO: 76.

In another method, Method 20, the present disclosure provides in vitro method of any one of Methods 6-19, wherein the nucleotide sequence encoding the IL15/IL15Rα-P2A-HLA-E trimer construct consists essentially of SEQ ID NO: 77.

In another method, Method 21, the present disclosure provides in vitro method of any one of Methods 6-20, wherein the nucleotide sequence encoding the IL15/IL15Rα-P2A-HLA-E trimer construct is operably linked to an exogenous promoter.

In another method, Method 22, the present disclosure provides in vitro method of any one of Methods 7-21, wherein the nucleotide sequence encoding the CAR is operably linked to an exogenous promoter.

In another method, Method 23, the present disclosure provides in vitro method of any one of Methods 21 or 22, wherein the exogenous promoter is a CMV, EFla, PGK, CAG, or UBC promoter.

In another method, Method 24, the present disclosure provides in vitro method of any one of Methods 6-23, wherein of the first RNP complex comprises a molar ratio of RNA-guided nuclease to gRNA of 1:3.

In another method, Method 25, the present disclosure provides in vitro method of any one of Methods 7-24, wherein each of the second RNP complex and third RNP complex comprises a molar ratio of RNA-guided nuclease to gRNA of 1:3.

In another method, Method 26, the present disclosure provides in vitro method of any one of Methods 7-25, wherein the RNA-guided nuclease of the first RNP complex is a Cas9 nuclease.

In another method, Method 27, the present disclosure provides in vitro method of any one of Methods 7-26, wherein each of the RNA-guided nuclease of the second RNP complex and the third RNP complex is a Cas9 nuclease.

In another method, Method 28, the present disclosure provides in vitro method of Methods 26 or 27, wherein the Cas9 nuclease is linked to at least one nuclear localization signal.

In another method, Method 29, the present disclosure provides in vitro method of any one of Methods 6-28, wherein the cell is a stem cell.

In another method, Method 30, the present disclosure provides in vitro method of Method 29, wherein the stem cell is an embryonic stem cell, an adult stem cell, an induced pluripotent stem cell, or a hematopoietic stem cell.

In another method, Method 31, the present disclosure provides in vitro method of any one of Methods 29 or 30, wherein the stem cell is a human stem cell.

In another method, Method 32, the present disclosure provides in vitro method of any one of Methods 6-31, wherein the nucleotide sequence of (b)(ii) consists essentially of SEQ ID NO: 36, and the nucleotide sequence of (b)(iii) consists essentially of SEQ ID NO: 54.

In another method, Method 33, the present disclosure provides in vitro method of any one of Methods 6-32, wherein the nucleotide sequence of (d)(ii) consists essentially of SEQ ID NO: 22, and the nucleotide sequence of (d)(iii) consists essentially of SEQ ID NO: 32.

In another method, Method 34, the present disclosure provides in vitro method for generating an engineered cell, the method comprising delivering to a cell: (a) a first RNP complex comprising an RNA-guided nuclease and a gRNA targeting a target site in a CIITA gene locus, (b) a first vector comprising a nucleic acid, the nucleic acid comprising: (i) a nucleotide sequence encoding a CAR; (ii) a nucleotide sequence having sequence homology with a genomic region located left of the target site in the CIITA gene locus; and (iii) a nucleotide sequence having sequence homology with a genomic region located right of the target site in the CIITA gene locus, wherein (i) is flanked by (ii) and (iii); and wherein the CIITA gene locus is cleaved at the target site and the nucleic acid comprising the nucleotide sequence encoding the CAR is inserted into the CIITA gene locus, thereby disrupting the CIITA gene.

In another method, Method 35, the present disclosure provides in vitro method for generating an engineered cell, the method comprising delivering to a cell: (a) a first ribonucleoprotein (RNP) complex comprising an RNA-guided nuclease and a guide RNA (gRNA) targeting a target site in a ADAM17 gene locus, (b) a second RNP complex comprising an RNA-guided nuclease and a gRNA targeting a target site in a MHC-I or MHC-II human leukocyte antigen, or a component of, or a transcriptional regulator of, a MHC-I or MHC-II complex gene locus, (c) a first vector comprising a nucleic acid, the nucleic acid comprising: (i) a nucleotide sequence encoding a CAR; (ii) a nucleotide sequence having sequence homology with a genomic region located left of the target site in the MHC-I or MHC-II human leukocyte antigen or the component of, or the transcriptional regulator of, a MHC-I or MHC-II complex gene locus; and (iii) a nucleotide sequence having sequence homology with a genomic region located right of the target site in the MHC-I or MHC-II human leukocyte antigen, or the component of, or the transcriptional regulator of, a MHC-I or MHC-II complex gene locus, wherein (i) is flanked by (ii) and (iii), wherein the ADAM17 gene locus is cleaved at the target site and the ADAM17 gene is disrupted, and wherein the MHC-I or MHC-II human leukocyte antigen or a component or a transcriptional regulator of a MHC-I or MHC-II complex gene locus is cleaved at the target site and the nucleic acid comprising the nucleotide sequence encoding the CAR is inserted into the MHC-I or MHC-II human leukocyte antigen or the component of, or the transcriptional regulator of, a MHC-I or MHC-II complex gene locus, thereby disrupting the MHC-I or MHC-II human leukocyte antigen or the component of, or the transcriptional regulator of, a MHC-I or MHC-II complex gene.

In another composition, Composition 68, the present disclosure provides a plurality of engineered cells generated or obtainable by the method of any one of Methods 6-35.

In another composition, Composition 69, the present disclosure provides a plurality of engineered cells of Composition 68 maintained for a time and under conditions sufficient for the cells to undergo differentiation.

In another composition, Composition 70, the present disclosure provides a plurality of engineered cells of Compositions 69 or 70 for use in treating a subject in need thereof.

In another composition, Composition 71, the present disclosure provides a plurality of cells for use of Composition 70, wherein the subject is a human who has, is suspected of having, or is at risk for a cancer.

In another method, Method 36, the present disclosure provides a method comprising administering to a subject the plurality of engineered cells of Compositions 68 or 69.

In another method, Method 37, the present disclosure provides a method for treating of a subject in need thereof, the method comprising: (a) obtaining or having obtained the plurality of engineered cells of Composition 68 following differentiation into lineage-restricted progenitor cells or fully differentiated somatic cells, and (b) administering the lineage-restricted progenitor cells or fully differentiated somatic cells to the subject.

In another method, Method 38, the present disclosure provides a method of obtaining cells for administration to a subject in need thereof, the method comprising: (a) obtaining or having obtained the engineered cells of Composition 68, and (b) maintaining the engineered cells for a time and under conditions sufficient for the cells to differentiate into lineage-restricted progenitor cells or fully differentiated somatic cells.

In another method, Method 39, the present disclosure provides a method of Method 37 or 38, wherein the lineage-restricted progenitor cells are hematopoietic progenitor cells, mesodermal cells, definitive hemogenic endothelium, definitive hematopoietic stem or progenitor cells, CD34$^+$ cells, multipotent progenitors (MPP), common lymphoid progenitor cells, T cell progenitors, NK cell progenitors, pancreatic endoderm progenitors, pancreatic endocrine progenitors, mesenchymal progenitor cells, muscle progenitor cells, blast cells, or neural progenitor cells.

In another method, Method 40, the present disclosure provides the method of Methods 37 or 38, wherein the fully differentiated somatic cells are hematopoietic cells, pancreatic beta cells, epithelial cells, endodermal cells, macrophages, hepatocytes, adipocytes, kidney cells, blood cells, cardiomyocytes, or immune system cells.

In another method, Method 41, the present disclosure provides the method of any one of Methods 36-40, wherein the subject is a human who has, is suspected of having, or is at risk for cancer.

In another method, Method 42, the present disclosure provides the method of Methods 41, wherein the subject has multiple myeloma. Hodgkin's lymphoma, lung cancer, leukemia, B-cell acute lymphoblastic leukemia (B-ALL), B-cell non-Hodgkin's lymphoma (B-NL), Chronic lymphocytic leukemia (C-CLL), T cell lymphoma, T cell leukemia, clear cell renal cell carcinoma (ccRCC), thyroid cancer, nasopharyngeal cancer, non-small cell lung (NSCLC), pancreatic cancer, melanoma, ovarian cancer, glioblastoma, or cervical cancer.

In another composition, Composition 72, the present disclosure provides a guide RNA comprising a spacer sequence corresponding to a sequence consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10.

In another composition, Composition 73, the present disclosure provides a guide RNA comprising a spacer sequence corresponding to a sequence consisting of SEQ ID NO: 1.

In another method, Method 43, the present disclosure provides a method for generating Natural Killer (NK) cells from stem cells, the method comprising: (a) culturing a population of stem cells in a first medium comprising a ROCK inhibitor under conditions sufficient to form aggregates, (b) culturing the aggregates in a second medium comprising BMP-4, (c) culturing the aggregates in a third medium comprising BMP-4, FGF2, a WNT pathway activator, and Activin A, (d) culturing the aggregates in a fourth medium comprising FGF2, VEGF, TPO, SCF, IL-3, FLT3L, WNT C-59 and an activin/nodal inhibitor to form a cell population comprising hematopoietic stem and progenitor cells (HSPCs), (e) culturing the cell population in a fifth medium comprising FGF2, VEGF, TPO, SCF, IL-3 and FLT3L, (f) culturing the cell population in a sixth medium comprising IL-3, IL-7, FLT3L, IL-15 and SCF, (g) culturing the cell population in a seventh medium comprising IL-7, FLT3L, IL-15 and SCF; and, optionally (h) culturing the cell population in an eighth medium comprising IL-7, FLT3L, IL-15, SCF and nicotinamide for a time sufficient to generate NK cells.

In another method, Method 44, the present disclosure provides the method of Method 43, wherein the second medium further comprises a ROCK inhibitor.

In another method, Method 45, the present disclosure provides the method of Method 43 or Method 44, wherein the ROCK inhibitor is thiazovivin or Y27632.

In another method, Method 46, the present disclosure provides the method of any one of Methods 43-45, wherein the WNT pathway activator is CHIR-99021.

In another method, Method 47, the present disclosure provides the method of any one of Methods 43-46, wherein the activin/nodal inhibitor is SB-431542.

In another method, Method 48, the present disclosure provides the method of any one of Methods 43-47, wherein steps (a)-(g) occurs between 20-35 days or steps (a)-(h) occurs between 24-36 days.

In another method, Method 49, the present disclosure provides the method of any one of Methods 43-48, wherein (a) comprises culturing for 12-48 hours.

In another method, Method 50, the present disclosure provides the method of any one of Methods 43-49, wherein (b) comprises culturing for up to 24 hours.

In another method, Method 51, the present disclosure provides the method of any one of Methods 43-50, wherein (c) comprises culturing for 1-3 days.

In another method, Method 52, the present disclosure provides the method of any one of Methods 43-51, wherein (d) comprises culturing for 1-3 days.

In another method, Method 53, the present disclosure provides the method of any one of Methods 43-52, wherein (e) comprises culturing for 1-3 days.

In another method, Method 54, the present disclosure provides the method of any one of Methods 43-53, wherein (f) comprises culturing for up to 7 days.

In another method, Method 55, the present disclosure provides the method of any one of Methods 43-54, wherein (g) comprises culturing for at least 6 days and up to 21-28 days total; or wherein (g) comprises culturing for up to 6 days and (h) comprises culturing for at least 6 days and up to 10-16 days total.

In another method, Method 56, the present disclosure provides the method of any one of Methods 43-56, wherein: (a) comprises culturing for 16-20 hours, (b) comprises culturing for 6-10 hours, (c) comprises culturing for 2 days, (d) comprises culturing for 2 days, (e) comprises culturing for 2 days, (f) comprises culturing for 4 days, (g) comprises culturing for 14-28 days or (a) comprises culturing for 16-20 hours, (b) comprises culturing for 6-10 hours, (c) comprises culturing for 2 days, (d) comprises culturing for 2 days, (e) comprises culturing for 2 days, (f) comprises culturing for 4 days, (g) comprises culturing for 6 days, and (h) comprises culturing for 10-16 days.

In another method, Method 57, the present disclosure provides the method of any one of Methods 43-56, wherein the method is carried out under suspension agitation.

In another method, Method 58, the present disclosure provides the method of any one of Methods 57, wherein suspension agitation comprises rotation.

In another method, Method 59, the present disclosure provides the method of any one of Methods 43-58, wherein the first media comprises StemFlex or StemBrew medium.

In another method, Method 60, the present disclosure provides the method of any one of Methods 43-59, wherein the second, third, fourth and fifth media comprise APEL medium.

In another method, Method 61, the present disclosure provides the method of any one of Methods 43-60, wherein the sixth and seventh media comprising DMEM/F12 medium.

In another method, Method 62, the present disclosure provides the method of any one of Methods 43-61, wherein the sixth and seventh media comprise (a) human serum, zinc sulfate, ethanolamine, β-mercaptoethanol, glucose, or any combination thereof or (b) human serum, zinc sulfate, ethanolamine, glucose, or any combination thereof, and/or the eighth medium comprises human serum, zinc sulfate, ethanolamine, glucose, or any combination thereof.

In another method, Method 63, the present disclosure provides the method of any one of Method 62, wherein the concentration of human serum is 10-20%, 10%, 15% or 20%.

In another method, Method 64, the present disclosure provides the method of any one of Methods 43-63, wherein the first medium comprises 10 µM of the ROCK inhibitor.

In another method, Method 65, the present disclosure provides the method of any one of Methods 43-64, wherein the second medium comprises 30 ng/mL BMP-4 and, optionally, 10 µM of a ROCK inhibitor.

In another method, Method 66, the present disclosure provides the method of any one of Methods 43-65, wherein the third medium comprises 30 ng/mL BMP-4, 100 ng/mL FGF2, 6 µM or 7 µM CHIR-99021, and 2.5-5 ng/mL Activin A.

In another method, Method 67, the present disclosure provides the method of any one of Method 66, wherein half of the third medium is added to the stem cell aggregates.

In another method, Method 68, the present disclosure provides the method of any one of Methods 43-66, wherein the fourth and fifth media comprise 20 ng/mL FGF, 20 ng/mL VEGF, 20 ng/mL TPO, 100 ng/mL SCF, 40 ng/mL IL-3, and 10-20 ng/mL FLT3L.

In another method, Method 69, the present disclosure provides the method of any one of Methods 43-68, wherein the fourth medium further comprises 5 µM SB-431542 and, optionally, 2 µM WNT C-59.

In another method, Method 70, the present disclosure provides the method of any one of Methods 43-69, wherein the sixth and seventh media comprises 20 ng/mL IL-7, 10-20 ng/mL FLT3L, 10-20 ng/mL IL-15, and 20 ng/mL SCF.

In another method, Method 71, the present disclosure provides the method of any one of Methods 43-70, wherein the sixth medium comprises 5 ng/mL IL-3.

In another method, Method 72, the present disclosure provides the method of any one of Methods 43-71, wherein the HSPCs of (d) express CD34.

In another method, Method 73, the present disclosure provides the method of any one of Methods 43-72, wherein the NK cells express CD56.

In another method, Method 74, the present disclosure provides the method of any one of Methods 43-73, wherein the NK cells express at least one activating receptor.

In another method, Method 75, the present disclosure provides the method of any one of Method 74, wherein the at least one activating receptor is selected from the group of NKp44, NKp46, CD16, KIR2DL4, and any combination thereof.

In another method, Method 76, the present disclosure provides the method of any one of Methods 43-75, wherein the NK cells express at least one inhibitory receptor.

In another method, Method 77, the present disclosure provides the method of any one of Method 76, wherein the at least one inhibitory receptor is selected from the group of CD94, NKG2A, KIR3DL2, and any combination thereof.

In another method, Method 78, the present disclosure provides the method of any one of Methods 43-77, wherein the NK cells comprise at least one function associated with endogenous NK cells.

In another method, Method 79, the present disclosure provides the method of any one of Method 78, wherein the at least one function comprises the ability to induce cell lysis and cell death of a target cell.

In another method, Method 80, the present disclosure provides the method of any one of Methods 78 or 79, wherein the at least one function comprises degranulation.

In another method, Method 81, the present disclosure provides the method of any one of Method 80, wherein degranulation comprises release of perforin and granzyme B.

In another method, Method 82, the present disclosure provides the method of any one of Methods 80 or 81, wherein degranulation comprises expression of CD107a on the cell surface of an NK cell.

In another method, Method 83, the present disclosure provides the method of any one of Methods 43-82, wherein the population of stem cells is a population of engineered cells.

In another composition, Composition 74, the present disclosure provides a population of engineered cells generated or obtainable by the method of any one of Methods 6-35.

In another composition, Composition 75, the present disclosure provides a population of engineered cells is differentiated by the method of any one of Methods 43-82.

In another composition, Composition 76, the present disclosure provides the method of any one of Methods 43-82, wherein the population of stem cells is a population of engineered cells of Composition 75.

In another composition, Composition 77, the present disclosure provides a plurality of Natural Killer (NK) cells generated or obtainable by the method of any one of Methods 43-83.

In another composition, Composition 78, the present disclosure provides the plurality of engineered cells of Composition 77 for use in treating a subject in need thereof.

In another composition, Composition 79, the present disclosure provides the plurality of cells for use of Composition 78, wherein the subject is a human who has, is suspected of having, or is at risk for a cancer.

In another composition, Composition 80, the present disclosure provides a method comprising administering to a subject the plurality of NK cells of Composition 77.

In another composition, Composition 81, the present disclosure provides an engineered cell comprising: (a) a disrupted B2M gene, and (b) a first polynucleotide and a second polynucleotide inserted in the disrupted B2M gene, wherein (i) the first polynucleotide encodes SERPINB9 and (ii) the second polynucleotide encodes a fusion protein of Interleukin-15 (IL15) and Interleukin-15 receptor subunit alpha (IL15Rα), wherein the cell expresses SERPINB9 and the fusion protein of IL15 and IL15Rα and the cell has a disrupted expression of B2M.

In another composition, Composition 82, the present disclosure provides the engineered cell of Composition 81, wherein the disrupted expression of B2M comprises reduced or eliminated expression of B2M.

In another composition, Composition 83, the present disclosure provides the engineered cell of Compositions 81 or 82, wherein the first polynucleotide and second polynucleotide are inserted as a polynucleotide encoding a SERPINB9-P2A-IL15/IL15Rα construct, wherein the polynucleotide encoding the SERPINB9 is linked to the polynucleotide encoding the IL15/IL15Rα fusion by a 2A peptide coding sequence.

In another composition, Composition 84, the present disclosure provides the engineered cell of Composition 83, wherein the polynucleotide encoding the SERPINB9-P2A-IL15/IL15Rα is inserted in exon 1 of the B2M gene locus.

In another composition, Composition 85, the present disclosure provides the engineered cell of any one of Compositions 81-84, further comprising a disrupted CIITA gene, wherein the cell has a disrupted expression of CIITA.

In another composition, Composition 86, the present disclosure provides the engineered cell of Composition 85, wherein the disrupted expression of CIITA comprises reduced or eliminated expression of CIITA.

In another composition, Composition 87, the present disclosure provides 170. The engineered cell of any one of Compositions 81-86, further comprising an insertion of a polynucleotide encoding a chimeric antigen receptor (CAR), wherein the cell expresses the CAR.

In another composition, Composition 88, the present disclosure provides the engineered cell of Composition 87, wherein the CAR is inserted in the disrupted CIITA gene.

In another composition, Composition 89, the present disclosure provides the engineered cell of Compositions 87 or 88, wherein the CAR is inserted in exon 2 of the CIITA gene locus.

In another composition, Composition 90, the present disclosure provides the engineered cell of any one of Compositions 87-89, wherein the polynucleotide encoding the CAR is linked to a polynucleotide encoding HLA-E by a 2A peptide coding sequence (CAR-P2A-HLA-E), and wherein the cell expresses the CAR and HLA-E.

In another composition, Composition 91, the present disclosure provides the engineered cell of any one of Compositions 81-90, further comprising a disrupted CISH gene, wherein the cell has a disrupted expression of CISH.

In another composition, Composition 92, the present disclosure provides the engineered cell of Composition 91, wherein the disrupted expression of CISH comprises reduced or eliminated expression of CISH.

In another composition, Composition 93, the present disclosure provides the engineered cell of any one of Compositions 81-92, further comprising a disrupted FAS gene, wherein the cell has a disrupted expression of FAS.

In another composition, Composition 94, the present disclosure provides the engineered cell of Composition 93, wherein the disrupted expression of FAS comprises reduced or eliminated expression of FAS.

In another composition, Composition 95, the present disclosure provides an engineered cell comprising: (a) a disrupted B2M gene, and (b) an insertion of a first polynucleotide and a second polynucleotide, optionally wherein the first polynucleotide and the second polynucleotide are inserted in the disrupted B2M gene, wherein (i) the first polynucleotide encodes SERPINB9 and (ii) the second polynucleotide encodes a fusion protein of Interleukin-15 (1115) and Interleukin-15 receptor subunit alpha (IL15Rα), (c) a disrupted CIITA gene, (d) an insertion of a third polynucleotide encoding a CAR and a fourth polynucleotide encoding HLA-E, optionally wherein the CAR and HLA-E are inserted in the disrupted CIITA gene, (e) a disrupted CISH gene, and (f) a disrupted FAS gene, wherein the cell expresses SERPINB9, the fusion protein of IL15 and IL15Rα, HLA-E, and the CAR, and the cell has a disrupted expression of B2M, CIITA, CISH, and FAS.

In another composition, Composition 96, the present disclosure provides the engineered cell of Composition 95, wherein the disrupted expression of B2M, CIITA, CISH, and FAS comprises reduced or eliminated expression of B2M, CIITA, CISH, and FAS.

In another composition, Composition 97, the present disclosure provides the engineered cell of Compositions 95 or 96, wherein the first polynucleotide and second polynucleotide are inserted as a polynucleotide encoding a SERPINB9-P2A-IL15/IL15Rα construct, wherein the polynucleotide encoding the SERPINB9 is linked to the polynucleotide encoding the IL15/IL15Rα fusion by a 2A peptide coding sequence.

In another composition, Composition 98, the present disclosure provides the engineered cell of Composition 97, wherein the polynucleotide encoding the SERPINB9-P2A-IL15/IL15Rα construct is inserted in exon 1 of the B2M gene locus.

In another composition, Composition 99, the present disclosure provides the engineered cell of any one of Compositions 83-94, 97, and 98, wherein the polynucleotide encoding the SERPINB9-P2A-IL15/IL15Rα construct comprises a polynucleotide sequence of SEQ ID NO: 137.

In another composition, Composition 100, the present disclosure provides the engineered cell of any one of Compositions 83-94 and 97-99, wherein SERPINB9-P2A-IL15/IL15Rα is operably linked to an exogenous promoter.

In another composition, Composition 101, the present disclosure provides the engineered cell of Composition 100, wherein the exogenous promoter is a CAG, CMV, EF1α, PGK, or UBC promoter.

In another composition, Composition 102, the present disclosure provides the engineered cell of Compositions 100 or 101, wherein the exogenous promoter is CAG and CAG-SERPINB9-P2A-IL15/IL15Rα consists essentially of SEQ ID NO: 138.

In another composition, Composition 103, the present disclosure provides the engineered cell of any one of Compositions 95-102, wherein the third polynucleotide and fourth polynucleotide are inserted as a polynucleotide encoding a CAR-P2A-HLA-E construct, wherein the polynucleotide encoding the CAR is linked to the polynucleotide encoding the HLA-E by a 2A peptide coding sequence In another composition, Composition 104, the present disclosure provides the engineered cell of Composition 103 wherein the CAR-P2A-HLA-E construct is inserted in exon 2 of the CIITA gene locus.

In another composition, Composition 105, the present disclosure provides the engineered cell of any one of Composition 90-104, wherein the HLA-E is an HLA-E trimer comprising a B2M signal peptide fused to an HLA-G presentation peptide fused to the B2M membrane protein fused to the HLA-E protein without a signal peptide.

In another composition, Composition 106, the present disclosure provides the engineered cell of any one of Compositions 87-105 wherein the CAR is a CD30 CAR, a BCMA CAR, a GPC3 CAR, a CD19 CAR, a CD33 CAR, a NKG2D CAR, a CD70 CAR, an NKp30 CAR, a CD73 CAR, a GPR87 CAR, a L1V1A CAR, a A33 CAR, a EGFR CAR, a CD20 CAR, or a SLC7AI1 CAR.

In another composition, Composition 107, the present disclosure provides the engineered cell of any one of Compositions 87-106, wherein the CAR comprises an ectodomain that binds to CD30.

In another composition, Composition 108, the present disclosure provides the engineered cell of Composition 107, wherein the ectodomain that binds CD30 comprises a polynucleotide sequence of SEQ ID NO: 106, SEQ ID NO: 111, or SEQ ID NO: 115.

In another composition, Composition 109, the present disclosure provides the engineered cell of Compositions 107 or 108, wherein the polynucleotide encoding CAR-P2A-HLA-E comprises a polynucleotide sequence of SEQ ID NO: 119, SEQ ID NO: 120, or SEQ ID NO: 121.

In another composition, Composition 110, the present disclosure provides the engineered cell of any one of Compositions 90-94 and 103-109, wherein CAR-P2A-HLA-E is operably linked to an exogenous promoter.

In another composition, Composition 111, the present disclosure provides the engineered cell of Compositions 110, wherein the exogenous promoter is a CAG, CMV, EF1α, PGK, or UBC promoter.

In another composition, Composition 112, the present disclosure provides the engineered cell of Compositions 110 or 111, wherein the exogenous promoter is CAG and CAG-CAR-P2A-HLA-E consists essentially of SEQ ID NO: 139, SEQ ID NO: 140, or SEQ ID NO: 141.

In another composition, Composition 113, the present disclosure provides the engineered cell of any one of Compositions 81-112, wherein the engineered cell is a stem cell.

In another composition, Composition 114, the present disclosure provides the engineered cell of Compositions 113, wherein the stem cell is an induced pluripotent stem cell (iPSC), a hematopoietic stem cell, an embryonic stem cell, or an adult stem cell.

In another composition, Composition 115, the present disclosure provides the engineered cell of any one of Compositions 81-114, wherein the engineered cell is a genome-edited iPSC.

In another composition, Composition 116, the present disclosure provides the engineered cell of any one of Compositions 81-112, wherein the engineered cell is a natural killer (NK) cell obtained from a genome-edited iPSC.

In another composition, Composition 117, the present disclosure provides the engineered cell of any one of Compositions 81-112, wherein the engineered cell is a differentiated cell or a somatic cell.

In another composition, Composition 118, the present disclosure provides the engineered cell of any one of Compositions 81-112, wherein the engineered cell is capable of being differentiated into lineage-restricted progenitor cells or fully differentiated somatic cells.

In another composition, Composition 119, the present disclosure provides the engineered cell of any one of Compositions 81-118, wherein the engineered cell is a natural killer (NK) cell.

In another composition, Composition 120, the present disclosure provides the engineered cell of Composition 119, wherein the NK cell has been differentiated from a genome-edited iPSC, wherein the NK cell comprises the genome edits of the genome-edited iPSC, wherein the NK cell has not been genome-edited after the differentiation.

In another composition, Composition 121, the present disclosure provides the engineered cell of any one of Compositions 81-120, wherein the engineered cell expresses at least one, two, three, four or five of the following markers: CD56, NKp44, NKp46, CD94, NKG2A and KIR2DL4, and optionally wherein the markers are expressed at least at 25%, 30%, 40%, 50%, or 75% level relative to their expression in wild-type NK cells.

In another composition, Composition 122, the present disclosure provides the engineered cell of any one of Compositions 81-121, wherein the engineered cell has at least one of the following characteristics, or any combination thereof: (i) an alloimmune T cell reaction of less than 10% relative to an unmodified cell, and (ii) cytotoxic activity resulting in killing more than 50% of target cells when the engineered cells are mixed with the target cells at the ratio of 1:1; (iii) at least 50% increase in cellular viability relative to an unmodified cell.

In another composition, Composition 123, the present disclosure provides the engineered cell of any one of Composition 81-122, wherein the engineered cell has at least one of the following characteristics, or any combination thereof: (i) improved persistency, (ii) improved immune evasiveness, (iii) improved cytotoxic activity, (iv) improved ADCC activity, and (v) improved anti-tumor activity; wherein the characteristics are improved relative to a wild-type cell, optionally, relative to a wild-type iPSC or a wild-type NK cell.

In another composition, Composition 124, the present disclosure provides the engineered cell of any one of Compositions 81-123, wherein the engineered cell is capable of cell expansion in the absence of exogenous IL15 in cell culture media.

In another composition, Composition 125, the present disclosure provides a plurality of engineered cells according to any one of Compositions 81 to 124.

In another composition, Composition 126, the present disclosure provides a population of lineage-restricted progenitor cells or fully differentiated somatic cells derived from the plurality of engineered cells of Composition 125.

In another composition, Composition 127, the present disclosure provides the population of cells of Composition 126, wherein the lineage-restricted progenitor cells are hematopoietic progenitor cells, mesodermal cells, definitive hemogenic endothelium, definitive hematopoietic stem or progenitor cells, CD34$^+$ cells, multipotent progenitors (MPP), common lymphoid progenitor cells, T cell progenitors, NK cell progenitors, pancreatic endoderm progenitors, pancreatic endocrine progenitors, mesenchymal progenitor cells, muscle progenitor cells, blast cells, or neural progenitor cells, and the fully differentiated somatic cells are hematopoietic cells, pancreatic beta cells, epithelial cells, endodermal cells, macrophages, hepatocytes, adipocytes, kidney cells, blood cells, cardiomyocytes, or immune system cells.

In another composition, Composition 128, the present disclosure provides the population of cells of Composition 127, wherein the hematopoietic cells are NK cells, T cells, B cells, or NKT cells.

In another composition, Composition 129, the present disclosure provides the population of cells of Composition 128, wherein the hematopoietic cells are human NK cells.

In another composition, Composition 130, the present disclosure provides the population of cells of any one of Compositions 126-129, wherein at least 25% or at least 50% of engineered cells of the population express the CAR, HLA-E, and/or the fusion protein of IL15 and IL15Rα.

In another composition, Composition 131, the present disclosure provides the population of cells of any one of Compositions 126-130, wherein at least 50% of engineered cells of the population do not express a detectable level of B2M protein, CIITA protein, and/or ADAM17 protein.

In another composition, Composition 132, the present disclosure provides the population of cells of any one of Composition 129-131, wherein engineered human NK cells of the population, when co-cultured in vitro with a population of cancer cells, induce cell lysis of at least 70%, at least 80%, or at least 90% of the population of cancer cells.

In another composition, Composition 133, the present disclosure provides the population of cells of any one of Compositions 129-132, wherein engineered human NK cells of the population, when co-cultured in vitro with a population of cancer cells, secrete IFNγ.

In another composition, Composition 134, the present disclosure provides the population of cells of Compositions 132 or 133, wherein the ratio of engineered human NK cells to cancer cells is 0.1:1 to 2:1.

In another composition, Composition 135, the present disclosure provides a composition comprising the plurality of engineered cells of Composition 125 or the population of cells of any one of Composition 126-134.

In another composition, Composition 136, the present disclosure provides the composition of Composition 135 for use in treating a subject in need thereof.

In another composition, Composition 137, the present disclosure provides the composition of Composition 135 for use in treating cancer in a subject in need thereof.

In another composition, Composition 138, the present disclosure provides the composition or Composition 137, wherein the subject has multiple myeloma. Hodgkin's lymphoma, lung cancer, leukemia, B-cell acute lymphoblastic leukemia (B-ALL), B-cell non-Hodgkin's lymphoma (B-NL), Chronic lymphocytic leukemia (C-CLL), T cell lymphoma, T cell leukemia, clear cell renal cell carcinoma (ccRCC), thyroid cancer, nasopharyngeal cancer, non-small cell lung (NSCLC), pancreatic cancer, melanoma, ovarian cancer, glioblastoma, or cervical cancer.

In another composition, Composition 139, the present disclosure provides the composition of any one of Compositions 136-138, wherein the subject is human.

In another method, Method 84, the present disclosure provides a method of obtaining cells for administration to a subject in need thereof, the method comprising: (a) obtaining or having obtained the plurality of engineered cells of Composition 125, and (b) maintaining the plurality of engineered cells for a time and under conditions sufficient for the cells to differentiate into lineage-restricted progenitor cells or fully differentiated somatic cells.

In another method, Method 85, the present disclosure provides a method for treating of a subject in need thereof, the method comprising: (a) obtaining or having obtained the plurality of engineered cells of Composition 125 following differentiation into lineage-restricted progenitor cells or fully differentiated somatic cells; and (b) administering the lineage-restricted progenitor cells or fully differentiated somatic cells to the subject.

In another method, Method 86, the present disclosure provides the method of Methods 84 or 85, wherein the lineage-restricted progenitor cells are hematopoietic progenitor cells, mesodermal cells, definitive hemogenic endothelium, definitive hematopoietic stem or progenitor cells, CD34+ cells, multipotent progenitors (MPP), common lymphoid progenitor cells, T cell progenitors, NK cell progenitors, pancreatic endoderm progenitors, pancreatic endocrine progenitors, mesenchymal progenitor cells, muscle progenitor cells, blast cells, or neural progenitor cells, and the fully differentiated somatic cells are hematopoietic cells, pancreatic beta cells, epithelial cells, endodermal cells, macrophages, hepatocytes, adipocytes, kidney cells, blood cells, cardiomyocytes, or immune system cells.

In another method, Method 87, the present disclosure provides the method the method of any one of Methods 84-86, wherein the subject has, is suspected of having, or is at risk for a cancer.

In another method, Method 88, the present disclosure provides the method the method of any one of Methods 84-87, wherein the subject is human.

In another method, Method 89, the present disclosure provides an in vitro method for generating an engineered cell, the method comprising delivering to a cell: (a) a first RNP complex comprising an RNA-guided nuclease and a gRNA targeting a target site in a B2M gene locus; and (b) a first vector comprising a nucleic acid, the nucleic acid comprising: (i) nucleotide sequence encoding a SERPINB9 and a nucleotide sequence encoding an IL15/IL15Rα fusion; (ii) a nucleotide sequence having sequence homology with a genomic region located left of the target site in the B2M gene locus; and (iii) a nucleotide sequence having sequence homology with a genomic region located right of the target site in the B2M gene locus, wherein (i) is flanked by (ii) and (iii); wherein the B2M gene locus is cleaved at the target site and the nucleotide sequences encoding the SERPINB9 and the IL15/IL15Rα fusion are inserted into the B2M gene locus, thereby disrupting the B2M gene.

In another method, Method 90, the present disclosure provides the method 229 the in vitro method of Method 89, wherein the gRNA of the first RNP complex comprises a spacer sequence corresponding to a sequence consisting of: SEQ ID NO: 34, SEQ ID NO: 78, or SEQ ID NO: 79, optionally a spacer sequence corresponding to a sequence consisting of SEQ ID NO: 34.

In another method, Method 91, the present disclosure provides the in vitro method of 89 or 90, wherein the engineered cell has reduced or eliminated expression of B2M.

In another method, Method 92, the present disclosure provides the method the in vitro method of any one of Methods 89 to 91, wherein the nucleotide sequence of (b)(i) comprises the nucleotide sequence encoding the SERPINB9 linked to a nucleotide sequence encoding a P2A peptide sequence linked to the nucleotide sequence encoding the IL15/IL15Rα fusion (SERPINB9-P2A-IL15/IL15Rα).

In another method, Method 93, the present disclosure provides the in vitro method of Method 92, wherein SERPINB9-P2A-IL15/IL15Rα consists essentially of SEQ ID NO: 137.

In another method, Method 94, the present disclosure provides the in vitro method of Methods 92 or 93, wherein SERPINB9-P2A-IL15/IL15Rα is operably linked to an exogenous promoter.

In another method, Method 95, the present disclosure provides the in vitro method of Method 94, wherein the exogenous promoter is CAG (CAG-SERPINB9-P2A-IL15/IL15Rα), and CAG-SERPINB9-P2A-IL15/IL15Rα consists essentially of SEQ ID NO: 138.

In another method, Method 96, the present disclosure provides the in vitro method of any one of Methods 89 to 94, wherein the nucleotide sequence of (b)(ii) consists essentially of SEQ ID NO: 36, and the nucleotide sequence of (b)(iii) consists essentially of SEQ ID NO: 54.

In another method, Method 97, the present disclosure provides the in vitro method of any one of Methods 89 to 96, wherein the first vector consists essentially of SEQ ID NO: 148.

In another method, Method 98, the present disclosure provides the in vitro method of any one of Methods 89 to 97, further comprising delivering to the cell: (c) a second RNP complex comprising an RNA-guided nuclease and a gRNA targeting a target site in a CIITA gene locus, (d) a second vector comprising a nucleic acid, the nucleic acid comprising: (i) a nucleotide sequence encoding a CAR and a nucleotide sequence encoding a HLA-E trimer; (ii) a nucleotide sequence having sequence homology with a genomic region located left of the target site in the CIITA gene locus; and (iii) a nucleotide sequence having sequence homology with a genomic region located right of the target site in the CIITA gene locus, wherein (i) is flanked by (ii) and (iii), and wherein the CIITA gene locus is cleaved at the target site and the nucleotide sequences encoding the CAR and the HLA-E trimer are inserted into the CIITA gene locus, thereby disrupting the CIITA gene.

In another method, Method 99, the present disclosure provides the in vitro method of Method 98, wherein the gRNA of the second RNP complex comprises a spacer sequence corresponding to a sequence consisting of any one of SEQ ID NOS: 13-17, optionally a spacer sequence corresponding to a sequence consisting of SEQ ID NO: 13.

In another method, Method 100, the present disclosure provides the in vitro method of Methods 98 or 99, wherein the engineered cell has reduced or eliminated expression of CIITA.

In another method, Method 101, the present disclosure provides the in vitro method of any one of Methods 98 to 100, wherein the nucleotide sequence of (d)(i) comprises the nucleotide sequence encoding the CAR linked to a nucleotide sequence encoding a P2A peptide sequence linked to the nucleotide sequence encoding the HLA-E trimer.

In another method, Method 102, the present disclosure provides the in vitro method of any one of Methods 98 to 101, wherein the nucleotide sequence of (d)(ii) consists essentially of SEQ ID NO: 22, and the nucleotide sequence of (d)(iii) consists essentially of SEQ ID NO: 32.

In another method, Method 103, the present disclosure provides the in vitro method of any one of Methods 89 to 102, further comprising delivering to the cell a third RNP complex comprising an RNA-guided nuclease and a gRNA targeting a target site in a CISH gene locus.

In another method, Method 104, the present disclosure provides the in vitro method of Method 103, wherein the gRNA of the third RNP complex comprises a spacer sequence corresponding to a sequence consisting of SEQ ID NOS: 81-92, optionally a spacer sequence corresponding to a sequence consisting of SEQ ID NO: 82.

In another method, Method 105, the present disclosure provides the in vitro method of Methods 103 or 104, wherein the engineered cell has reduced or eliminated expression of CISH.

In another method, Method 106, the present disclosure provides the in vitro method of any one of Methods 89 to 105, further comprising delivering to the cell a fourth RNP complex comprising an RNA-guided nuclease and a gRNA targeting a target site in a FAS gene locus.

In another method, Method 107, the present disclosure provides the in vitro method of Method 106, wherein the gRNA of the fourth RNP complex comprises a spacer sequence corresponding to a sequence consisting of any one of SEQ ID NOS: 35, 37, 38, 39, 53, 55, and 80, optionally a spacer sequence corresponding to a sequence consisting of SEQ ID NO: 37.

In another method, Method 108, the present disclosure provides the in vitro method of Methods 106 or 107, wherein the engineered cell has reduced or eliminated expression of FAS.

In another method, Method 109, the present disclosure provides an in vitro method for generating an engineered cell, the method comprising delivering to a cell: (a) a first RNP complex comprising an RNA-guided nuclease and a gRNA targeting a target site in a B2M gene locus, (b) a first vector comprising a nucleic acid, the nucleic acid comprising: (i) nucleotide sequence encoding a SERPINB9 and a nucleotide sequence encoding an IL15/IL15Rα fusion; (ii) a nucleotide sequence having sequence homology with a genomic region located left of the target site in the B2M gene locus; and (iii) a nucleotide sequence having sequence homology with a genomic region located right of the target site in the B2M gene locus, wherein (i) is flanked by (ii) and (iii), (c) a second RNP complex comprising an RNA-guided nuclease and a gRNA targeting a target site in a CIITA gene locus; and (d) a second vector comprising a nucleic acid, the nucleic acid comprising: (i) a nucleotide sequence encoding a CAR and a nucleotide sequence encoding a HLA-E trimer; (ii) a nucleotide sequence having sequence homology with a genomic region located left of the target site in the CIITA gene locus; and (iii) a nucleotide sequence having sequence homology with a genomic region located right of the target site in the CIITA gene locus, wherein (i) is flanked by (ii) and (iii), (e) a third RNP complex comprising an RNA-guided nuclease and a gRNA targeting a target site in a CISH gene locus, and (f) a fourth RNP complex comprising an RNA-guided nuclease and a gRNA targeting a target site in a FAS gene locus, wherein the B2M gene locus is cleaved at the target site and the nucleotide sequences encoding the SERPINB9 and the IL15/IL15Rα fusion are inserted into the B2M gene locus, thereby disrupting the B2M gene, wherein the CIITA gene locus is cleaved at the target site and the nucleotide sequences encoding the CAR and the HLA-E trimer are inserted into the CIITA gene locus, thereby disrupting the CIITA gene, wherein the CISH gene locus is cleaved at the target site, thereby disrupting the CISH gene and wherein the FAS gene locus is cleaved at the target sire, thereby disrupting the FAS gene.

In another method, Method 110, the present disclosure provides the in vitro method of Method 109, wherein the gRNA of the first RNP complex comprises a spacer sequence corresponding to a sequence consisting of: SEQ ID NO: 34, SEQ ID NO: 78, or SEQ ID NO: 79, optionally a spacer sequence corresponding to a sequence consisting of SEQ ID NO: 34.

In another method, Method 111, the present disclosure provides the in vitro method of Methods 109 or 110, wherein the engineered cell has reduced or eliminated expression of B2M.

In another method, Method 112, the present disclosure provides the in vitro method of any one of Methods 109-111, wherein the nucleotide sequence of (b)(i) comprises the nucleotide sequence encoding the SERPINB9 linked to a nucleotide sequence encoding a P2A peptide sequence linked to the nucleotide sequence encoding the IL15/IL15Rα fusion (SERPINB9-P2A-IL15/IL15Rα).

In another method, Method 113, the present disclosure provides the method the in vitro method of Method 112, wherein SERPINB9-P2A-IL15/IL15Rα consists essentially of SEQ ID NO: 137.

In another method, Method 114, the present disclosure provides the in vitro method of Methods 112 or 113, wherein SERPINB9-P2A-IL15/IL15Rα is operably linked to an exogenous promoter.

In another method, Method 115, the present disclosure provides the in vitro method of Method 114, wherein the exogenous promoter is CAG (CAG-SERPINB9-P2A-IL15/IL15Rα), and CAG-SERPINB9-P2A-IL15/IL15Rα consists essentially of SEQ ID NO: 138.

In another method, Method 116, the present disclosure provides the in vitro method of any one of Methods 109 to 115, wherein the nucleotide sequence of (b)(ii) consists essentially of SEQ ID NO: 36, and the nucleotide sequence of (b)(iii) consists essentially of SEQ ID NO: 54.

In another method, Method 117, the present disclosure provides the in vitro method of any one of Methods 109 to 116, wherein the first vector consists essentially of SEQ ID NO: 148.

In another method, Method 118, the present disclosure provides the in vitro method of any one of Methods 109 to 117, wherein the gRNA of the second RNP complex comprises a spacer sequence corresponding to a sequence consisting of any one of SEQ ID NOS: 13-17, optionally a spacer sequence corresponding to a sequence consisting of SEQ ID NO: 13.

In another method, Method 119, the present disclosure provides the in vitro method of Method 118, wherein the engineered cell has reduced or eliminated expression of CIITA.

In another method, Method 120, the present disclosure provides the in vitro method of any one of Methods 109 to 119, wherein the nucleotide sequence of (d)(i) comprises the nucleotide sequence encoding the CAR linked to a nucleotide sequence encoding a P2A peptide sequence linked to the nucleotide sequence encoding the HLA-E trimer.

In another method, Method 121, the present disclosure provides the in vitro method of any one of Methods 109 to 120, wherein the nucleotide sequence of (d)(ii) consists essentially of SEQ ID NO: 22, and the nucleotide sequence of (d)(iii) consists essentially of SEQ ID NO: 32.

In another method, Method 122, the present disclosure provides the in vitro method of any one of Methods 98-121, wherein the HLA-E is an HLA-E trimer comprising a B2M signal peptide fused to an HLA-G presentation peptide fused to the B2M membrane protein fused to the HLA-E protein without a signal peptide.

In another method, Method 123, the present disclosure provides the in vitro method of any one of Methods 98-122, wherein the CAR is a CD30 CAR, a BCMA CAR, a GPC3 CAR, a CD19 CAR, a CD33 CAR, a NKG2D CAR, a CD70 CAR, an NKp30 CAR, a CD73 CAR, a GPR87 CAR, a L1V1A CAR, a A33 CAR, a EGFR CAR, a CD20 CAR, or a SLC7A11 CAR.

In another method, Method 124, the present disclosure provides the in vitro method of any one of Methods 98-123, wherein the CAR comprises an ectodomain that binds to CD30.

In another method, Method 125, the present disclosure provides the in vitro method of Method 124, wherein the ectodomain that binds CD30 comprises a polynucleotide sequence of SEQ ID NO: 106, SEQ ID NO: 111, or SEQ ID NO: 115.

In another method, Method 126, the present disclosure provides the in vitro method of Methods 124 or 125, wherein the polynucleotide encoding CAR-P2A-HLA-E comprises a polynucleotide sequence of SEQ ID NO: 119, SEQ ID NO: 120, or SEQ ID NO: 121.

In another method, Method 127, the present disclosure provides the in vitro method of any one of Methods 101-108 and 120-126, wherein CAR-P2A-HLA-E is operably linked to an exogenous promoter.

In another method, Method 128, the present disclosure provides the in vitro method of Method 127, wherein the exogenous promoter is a CAG, CMV, EF1α, PGK, or UBC promoter.

In another method, Method 129, the present disclosure provides the in vitro method of any one of Methods 109-128, wherein the gRNA of the third RNP complex comprises a spacer sequence corresponding to a sequence consisting of any one of SEQ ID NOS: 81-92, optionally a spacer sequence corresponding to a sequence consisting of SEQ ID NO: 82.

In another method, Method 130, the present disclosure provides the in vitro method of Method 129, wherein the engineered cell has reduced or eliminated expression of CISH.

In another method, Method 131, the present disclosure provides the in vitro method of any one of Methods 109-130, wherein the gRNA of the fourth RNP complex comprises a spacer sequence corresponding to a sequence consisting of any one of SEQ ID NOS: 35, 37, 38, 39, 53, 55, and 80, optionally a spacer sequence corresponding to a sequence consisting of SEQ ID NO: 37.

In another method, Method 132, the present disclosure provides the in vitro method of Method 131, wherein the engineered cell has reduced or eliminated expression of FAS.

In another method, Method 133, the present disclosure provides the in vitro method of any one of Methods 98-132, wherein the first vector is a plasmid vector, wherein the first vector consists essentially of SEQ ID NO: 148.

In another method, Method 134, the present disclosure provides the in vitro method of any one of Methods 98-133, wherein the second vector is a plasmid vector, wherein the second vector consists essentially of SEQ ID NO: 110, SEQ ID NO: 114, or SEQ ID NO: 118.

In another method, Method 135, the present disclosure provides the in vitro method of any one of Methods 89 to 135, wherein the RNA-guided nuclease is a Cas9 nuclease.

In another method, Method 136, the present disclosure provides the in vitro method of Method 135, wherein the Cas9 nuclease is linked to at least one nuclear localization signal.

In another method, Method 137, the present disclosure provides the in vitro method of any one of Methods 89 to 136, wherein the cell is a stem cell.

In another method, Method 138, the present disclosure provides the in vitro method of Method 137, wherein the stem cell is an embryonic stem cell, an adult stem cell, an induced pluripotent stem cell, or a hematopoietic stem cell.

In another method, Method 139, the present disclosure provides the in vitro method of Methods 137 or 138, wherein the stem cell is a human stem cell.

In another composition, Composition 140, the present disclosure provides a plurality of engineered cells generated or obtainable by the method of any one of Methods 89 to 139.

In another composition, Composition 141, the present disclosure provides the plurality of engineered cells of Composition 140 maintained for a time and under conditions sufficient for the cells to undergo differentiation.

In another composition, Composition 142, the present disclosure provides the plurality of engineered cells of Compositions 140 or 141 for use in treating a subject in need thereof.

In another composition, Composition 143, the present disclosure provides the plurality of cells for use of Composition 142, wherein the subject is a human who has, is suspected of having, or is at risk for a cancer.

In another method, Method 140, the present disclosure provides a method comprising administering to a subject the plurality of engineered cells of Compositions 140 or 141.

In another method, Method 141, the present disclosure provides a method for treating of a subject in need thereof, the method comprising: (a) obtaining or having obtained the plurality of engineered cells of Composition 140 following differentiation into lineage-restricted progenitor cells or fully differentiated somatic cells, and (b) administering the lineage-restricted progenitor cells or fully differentiated somatic cells to the subject.

In another method, Method 142, the present disclosure provides a method of obtaining cells for administration to a subject in need thereof, the method comprising: (a) obtaining or having obtained the engineered cells of Composition 140, and (b) maintaining the engineered cells for a time and under conditions sufficient for the cells to differentiate into lineage-restricted progenitor cells or fully differentiated somatic cells.

In another method, Method 143, the present disclosure provides the method of Methods 141 or 142, wherein the lineage-restricted progenitor cells are hematopoietic progenitor cells, mesodermal cells, definitive hemogenic endothelium, definitive hematopoietic stem or progenitor cells, CD34$^+$ cells, multipotent progenitors (MPP), common lymphoid progenitor cells, T cell progenitors, NK cell progenitors, definitive endoderm, hepatoblasts, pancreatic endoderm progenitors, pancreatic endocrine progenitors, mesenchymal progenitor cells, muscle progenitor cells, blast cells, or neural progenitor cells, and the fully differentiated somatic cells are hematopoietic cells, hepatocytes, pancreatic beta cells, epithelial cells, endodermal cells, macrophages, hepatocytes, adipocytes, kidney cells, blood cells, cardiomyocytes, or immune system cells.

In another method, Method 144, the present disclosure provides the method of any one of Methods 139 to 143, wherein the subject is a human who has, is suspected of having, or is at risk for a cancer.

In another method, Method 145, the present disclosure provides the method of Method 143, wherein the subject has multiple myeloma. Hodgkin's lymphoma, lung cancer, leukemia, B-cell acute lymphoblastic leukemia (B-ALL), B-cell non-Hodgkin's lymphoma (B-NL), Chronic lymphocytic leukemia (C-CLL), T cell lymphoma, T cell leukemia, clear cell renal cell carcinoma (ccRCC), thyroid cancer, nasopharyngeal cancer, non-small cell lung (NSCLC), pancreatic cancer, liver cancer, melanoma, ovarian cancer, glioblastoma, or cervical cancer.

In another composition, Composition 144, the present disclosure provides a gRNA comprising a spacer sequence corresponding to a sequence consisting of any one of SEQ ID NOS: 35, 37, 38, 39, 53, 55, and 80.

In another composition, Composition 145, the present disclosure provides a gRNA comprising a spacer sequence corresponding to a sequence consisting of any one of SEQ ID NOS: 81-92.

In another composition, Composition 146, the present disclosure provides a gRNA comprising a spacer sequence corresponding to a sequence consisting of any one of SEQ ID NOS: 93-101.

EXAMPLES

Example 1: Cell Maintenance and Expansion

Maintenance of hiPSCs. Cells of human induced pluripotent stem cell (hiPSC) line were maintained in STEMFLEX™ Complete media (Life Technologies, A3349401) with single cell passaging using ACCUTASE® (Stemcell Technologies 07920 or equivalent) on BIOLAMININ 521 LN (LN521), BIOLAMININ 511 LN (LN511), or Recombinant Laminin iMatrix-511 E8 (AMSBIO, AMS.892 011). For passaging, 1% REVITACELL™ Supplement (100×) was added.

Single cell cloning of hPSCs. For single cell cloning, hiPSCs were fed with STEMFLEX™ Complete media (Life Technologies, A3349401) with 1% REVITACELL™ Supplement (100×) (ThermoFisher Cat #A2644501). Following dissociation with ACCUTASE®, the cells were sorted as a single cell per well of a pre-coated plate. The 96 well plates were pre-coated with a 1:10 or a 1:20 dilution of BIOLAMININ 521 LN (LN521) in DPBS, calcium, magnesium (Life Technologies, 14040133) for 2 hours at 37° C. The WOLF FACS-sorter (Nanocellect) was used to sort single cells into the wells. The plates were pre-filled with 100-200 µL of STEMFLEX™ Complete with REVITACELL™ Supplement (100×) and 4 µL/mL of Recombinant Laminin iMatrix-511 E8 (AMSBIO, AMS.892 011). Three days post cell seeding, the cells were fed with fresh STEMFLEX™ and continued to be fed every other day with 100-200 µL of media. After 10 days of growth, the cells were fed daily with STEMFLEX™ until day 12-16. At this time, the plates were dissociated with ACCUTASE® and the collected cell suspensions were split 1:2 with half going into a new 96 well plate for maintenance and half going into a DNA extraction solution QuickExtract™ DNA Extraction Solution (Lucigen). Following DNA extraction, PCR was performed to assess presence or absence of desired gene edits at the targeted DNA locus. Sanger sequencing was used to verify desired knock-out (KO) edits.

Expansion of single cell derived hiPSCs clones. Successfully targeted clones were passaged from 96-well plates to 24-well plates using STEMFLEX™ and BIOLAMININ 521 or Recombinant Laminin iMatrix-511 E8 and 1% REVITACELL™ Supplement (100×). Following expansion in 24-well plates, the cells were passaged onto 6-well plates and then T25 and larger flask formats.

Example 2: Differentiating Stem Cells into Natural Killer Cells—Protocol 1

Protocol 1 was utilized to differentiate stem cells, such as wild-type and/or edited induced pluripotent stem (iPS) cells, into hematopoietic stem and progenitor cells (HSPCs) and then into natural killer (NK) cells. Prior to differentiation, frozen iPS cells were thawed and re-suspended in NK-MED-001 medium (Table 1). Flasks pre-coated with laminin-521 were used for cell culturing. Medium was changed daily using NK-MED-002 (Table 2) medium until cells were used for differentiation.

NK Cell Differentiation. iPS cells were differentiated using the following steps:

Day-1 (afternoon), iPSC aggregation: NK-MED-002 (Table 2) medium was aspirated from flasks containing iPSC and the cells were washed with DPBS (no calcium, no magnesium) (Thermo Fisher Scientific, 14190250). DPBS was aspirated and 2 mL ACCUTASE® (Innovative Cell Technologies, AT-104) was added per T25 flask (or 80 μL of ACCUTASE® per 1 $cm^2$). Cells were incubated at 37° C. for 3-5 min or until all the colonies detached. Accutase digested cells were diluted with NK-MED-002 medium to a ratio of at least 3:1 (NK-MED-002:ACCUTASE®). Cells were gently resuspended and transferred to a conical tube. Enough NK-MED-002 medium was added to cells to dilute the ACCUTASE® to a ratio of 4:1 (NK-MED-002:ACCUTASE®). Cells were pelleted and re-suspended in 10 ml of NK-MED-003 medium (Table 3). Cells were counted and the cell concentration was diluted to $1 \times 10^6$/mL. $6 \times 10^6$ cells were transferred to another tube and resuspended in a total of 6 mL of NK-MED-003 medium. The cells were transferred to 1 well of ultra-low adhesion 6-well plate (Corning, 3471) and the plate was placed on a platform shaker and rotated at 98 RPM for 18+/−2 hours (overnight).

2. At day 0, morning, at 18+/−2 hours after iPSC aggregation: The plate was rotated in a circular motion to move aggregates towards center of the well and aggregates were collected in a conical tube. Alternatively, all the aggregate solution mix was collected. Aggregates were allowed to settle for 15+/−5 minutes. Cells were resuspended in NK-MED-004 medium (Table 4). The cell number in aggregates was counted. The seeding density was adjusted as needed to resuspend $3 \times 10^5$ cells in aggregates in 2 mL NK-MED-004 medium and plated in one well of a 6-well low adhesion plate. Alternatively, for scale up, an appropriate number of cells was resuspended and transferred to a PBS spinner vessel (PBS Biotech). Seeding density tested for PBS seeding vessel was approximately $1\text{-}1.2 \times 10^5$ cells per mL per final media volume (day 0+8 hrs). The plate was placed on a platform shaker and rotated at 98 RPM for 8 hours or the PBS spinner vessel were placed on a PBS base (PBS-MINI MagDrive Base Unit; PBS Biotech), in $CO_2$ incubator with a rotation speed of RPM 38 to 39.

3. At day 0, afternoon, at 8 hours after NK-MED-004 medium addition: 2 mL per well of NK-MED-005 medium (Table 5) was added or scaled up for PBS spinner vessels. The plate was returned to platform shaker or PBS spinner vessel to its base in the $CO_2$ incubator and left undisturbed until day 2. NK-MED-005 medium components were 2× of their final concentration, therefore it was added to cells in NK-MED-004 at a 1:1 volume ratio.

4. At day 2: NK-MED-005 medium was replaced with NK-MED-006 medium (Table 6).

5. At day 4: NK-MED-006 medium was replaced with NK-MED-007 medium (Table 7).

6. At day 6: Starting at day 6, medium with all aggregates and single cells was transferred into an appropriate volume centrifuge conical tube. Cells were centrifuged and resuspended in NK-MED-008 medium (Table 8) and placed back into original wells and onto platform shaker, or into original vessels and onto base, and returned for continued culture.

7. At day 10: Half media change was made with NK-MED-008 medium.

8. At day 14: Full media change was made with NK-MED-009 medium (Table 9).

9. From day 17 onwards: Starting at day 17 (and at day 20, and every 2 to 3 days from day 20 onwards), single cell density was estimated from cell culture. If cell density exceeded $3 \times 10^6$, cells were diluted to $1\text{-}2 \times 10^6$ either by topping up cultures with fresh NK-MED-009 medium or by a complete medium change if medium color has completely turned yellow. Representative culture samples were harvested at day 6, day 10, day 14, day 17, day 20, and day 28 for FACS and TruSeq analysis to monitor differentiation of the cells.

In the tables below, the volumes are approximate to get the desired concentration.

TABLE 1

Medium composition for NK-MED-001

| Component | Working Conc. | Volume | Stock Conc. |
|---|---|---|---|
| STEMFLEX ™ Basal (Thermo Fisher, A3349401) | 90% | 900 mL | 100% |
| STEMFLEX ™ Supplement (Thermo Fisher, A3349401) | 1 X | 100 mL | 10 X |
| Thiazovivin (Biological Industry, 1226056-71-8) | 2 μM | 200 μL | 10 mM |

TABLE 2

Medium composition for NK-MED-002

| Component | Working Conc. | Volume | Stock Conc. |
|---|---|---|---|
| STEMFLEX ™ Basal (Thermo Fisher, A3349401) | 90% | 900 mL | 100% |
| STEMFLEX ™ Supplement (Thermo Fisher, A3349401) | 1 X | 100 mL | 10 X |

TABLE 3

Medium composition for NK-MED-003

| Component | Working Conc. | Volume | Stock Conc. |
|---|---|---|---|
| STEMFLEX ™ Basal (Thermo Fisher, A3349401) | 90% | 899 mL | 100% |
| STEMFLEX ™ Supplement (Thermo Fisher, A3349401) | 1 X | 100 mL | 10 X |
| Thiazovivin (Biological Industry, 1226056-71-8) | 10 μM | 1000 μL | 10 mM |

TABLE 4

Medium composition for NK-MED-004

| Component | Working Conc. | Volume | Stock Conc. |
|---|---|---|---|
| STEMdiff APEL 2 Medium (STEMCELL Technologies, 05275) | 100% | 999 mL | 100% |
| rh BMP-4 (Peprotech, 120-05ET) | 30 ng/mL | 300 μL | 100 μg/mL |
| Thiazovivin (Biological Industry, 1226056-71-8) | 10 μM | 1000 μL | 10 mM |

TABLE 5

Medium composition for NK-MED-005

| Component | Working Conc. | Volume | Stock Conc. |
|---|---|---|---|
| STEMdiff APEL 2 Medium (STEMCELL Technologies, 05275) | 100% | 998 mL | 100% |
| rh BMP-4 (Peprotech, 120-05ET) | 30 ng/mL | 300 μL | 100 μg/mL |
| rh FGF2 (Peprotech, 100-18C-1MG) | 100 ng/mL | 1000 μL | 100 μg/mL |
| CHIR 99021 (Selleckchem, S1263) | 6 μM | 600 μL | 10 mM |
| Activin-A (R&D Systems, 338-AC-01M/CF) | 5 ng/mL | 100 μL | 50 μg/mL |

TABLE 6

Medium composition for NK-MED-006

| Component | Working Conc. | Volume | Stock Conc. |
|---|---|---|---|
| STEMdiff APEL 2 Medium (STEMCELL Technologies, 05275) | 100% | 997 mL | 100% |
| rh FGF2 (Peprotech, 100-18C-1MG) | 20 ng/mL | 200 μL | 100 μg/mL |
| rh VEGF165 (Peprotech, 100-20-1MG) | 20 ng/mL | 200 μL | 100 μg/mL |
| rh TPO (Peprotech, 300-18) | 20 ng/mL | 200 μL | 100 μg/mL |
| rh SCF (Peprotech, 300-07) | 100 ng/mL | 1000 μL | 100 μg/mL |
| rh IL-3 (Peprotech, 200-03-100UG) | 40 ng/mL | 400 μL | 100 μg/mL |
| rh Flt3L (Peprotech, 300-19) | 20 ng/mL | 200 μL | 100 μg/mL |
| WNT C-59 (Selleckchem, S7037) | 2 μM | 200 μL | 10 mM |
| SB431542 (Selleckchem, S1067) | 5 μM | 500 μL | 10 mM |

TABLE 7

Medium composition for NK-MED-007

| Component | Working Conc. | Volume | Stock Conc. |
|---|---|---|---|
| STEMdiff APEL 2 Medium (STEMCELL Technologies, 05275) | 100% | 998 mL | 100% |
| rh FGF2 (Peprotech, 100-18C-1MG) | 20 ng/mL | 200 μL | 100 μg/mL |
| rh VEGF165 (Peprotech, 100-20-1MG) | 20 ng/mL | 200 μL | 100 μg/mL |
| rh TPO (Peprotech, 300-18) | 20 ng/mL | 200 μL | 100 μg/mL |
| rh SCF (Peprotech, 300-07) | 100 ng/mL | 1000 μL | 100 μg/mL |
| rh IL-3 (Peprotech, 200-03-100UG) | 40 ng/mL | 400 μL | 100 μg/mL |
| rh Flt3L (Peprotech, 300-19) | 20 ng/mL | 200 μL | 100 μg/mL |

TABLE 8

Medium composition for NK-MED-008

| Component | Working Conc. | Volume | Stock Conc. |
|---|---|---|---|
| DMEM (high glucose, GlutaMAX) (Thermo Fisher, 10566016) | 55.47% | 555 mL | 100% |
| F-12 with GlutaMAX (Thermo Fisher, 31765035) | 27.74% | 277 mL | 100% |
| GlutaMAX (Thermo Fisher, 35050079) | 1 X | 10 mL | 100 X |
| Glucose* | 10.25 mM | 4.1 mL | 2500 mM |
| Human AB serum (Valley Biomedical Inc, HP1022) | 15% | 150 mL | 100% |
| Zinc sulfate (Millipore Sigma, Z0251) | 37 μM | 978 μL | 37 mM |
| Ethanolamine (Millipore Sigma, E0135) | 50 μM | 3 μL | 16.6 M |
| Ascorbic acid (Fisher Scientific, NC0762606) | 20 μg/mL | 2000 μL | 10 mg/mL |
| Sodium selenite (Millipore Sigma, S9133-1MG) | 5 ng/mL | 50 μL | 100 μg/mL |
| β-mercaptoethanol (Thermo Fisher, 21985-023) | 1 μM | 18 μL | 55 mM |
| rh IL-3 (Peprotech, 200-03-100UG) | 5 ng/mL | 50 μL | 100 μg/mL |
| rh IL-7 (Peprotech, 200-07) | 20 ng/mL | 200 μL | 100 μg/mL |
| rh Flt3L (Peprotech, 300-19) | 15 ng/mL | 150 μL | 100 μg/mL |
| rh IL-15 (Peprotech, 200-15) | 15 ng/mL | 150 μL | 100 μg/mL |
| rh SCF (Peprotech, 300-07) | 20 ng/mL | 200 μL | 100 μg/mL |

*Total glucose concentration in medium is 27 mM (accounting for glucose in DMEM medium, F12 supplement and added glucose provided here).

TABLE 9

Medium composition for NK-MED-009

| Component | Working Conc. | Volume | Stock Conc. |
|---|---|---|---|
| DMEM (high glucose, GlutaMAX) (Thermo Fisher, 10566016) | 55.47% | 555 mL | 100% |
| F-12 with GlutaMAX (Thermo Fisher, 31765035) | 27.74% | 277 mL | 100% |
| GlutaMAX (Thermo Fisher, 35050079) | 1 X | 10 mL | 100 X |
| Glucose* | 10.25 mM | 4.1 mL | 2500 mM |
| Human AB serum (Valley Biomedical Inc, HP1022) | 15% | 150 mL | 100% |
| Zinc sulfate (Millipore Sigma, Z0251) | 37 μM | 978 μL | 37 mM |
| Ethanolamine (Millipore Sigma, E0135) | 50 μM | 3 μL | 16.6 M |
| Ascorbic acid (Fisher Scientific, NC0762606) | 20 μg/mL | 2000 μL | 10 mg/mL |
| Sodium selenite (Millipore Sigma, S9133-1MG) | 5 ng/mL | 50 μL | 100 μg/mL |
| β-mercaptoethanol (Thermo Fisher, 21985-023) | 1 μM | 18 μL | 55 mM |
| rh IL-7 (Peprotech, 200-07) | 20 ng/mL | 200 μL | 100 μg/mL |
| rh Flt3L (Peprotech, 300-19) | 15 ng/mL | 150 μL | 100 μg/mL |
| rh IL-15 (Peprotech, 200-15) | 15 ng/mL | 150 μL | 100 μg/mL |
| rh SCF (Peprotech, 300-07) | 20 ng/mL | 200 μL | 100 μg/mL |

*Total glucose concentration in medium is 27 mM (accounting for glucose in DMEM medium, F12 supplement and added glucose provided here).

Example 3: Differentiating Stem Cells into Natural Killer Cells—Protocol 1.5

Protocol 1.5 was utilized to differentiate stem cells, such as wild-type and/or edited iPS cells, into hematopoietic stem and progenitor cells (HSPCs) and then into natural killer (NK) cells. iPS cells were cultured in STEMFLEX™ (SF) (Thermo Fisher, A3349401) media prior to beginning differentiation. iPS cells were differentiated using the following steps. Media used throughout is shown in Tables 10-11:

Day-1 (afternoon): STEMFLEX™ media (SF) was aspirated and cells were washed with DPBS (no calcium, no magnesium) (Thermo Fisher Scientific, 14190250). DPBS was aspirated and 2 mL pre-warmed ACCUTASE® (Innovative Cell Technologies, AT-104) was added per flask (scale up if needed: 80 µL of ACCUTASE® per 1 $cm^2$). Cells were incubated at 37° C. for 3-5 minutes or until all the colonies detached. Accutase digested cells were diluted with SF for a ratio of 3:1 (SF:ACCUTASE®). Cells were gently pipetted 2-3 times with a serological pipet until cells detached. Cells were transferred to a conical tube and the plate was rinsed with SF, the rinse was added to the same tube. Enough SF was added to cells to dilute the ACCUTASE® to a ratio of 4:1 (SF:ACCUTASE®). Cells were spun for 5 minutes at 300 g. Supernatant was aspirated and cells were re-suspended in SF. Cells were counted. The cell concentration was adjusted to $1\times10^6$/mL by transferring $6\times10^6$ cells to another tube, resuspended in total 6 mL of NK-MED-003 medium. Cells were transferred to 1 well of ultra-low adhesion 6-well plate (Corning, 3471). The plate was placed on a horizontal orbital shaker.

2. Day 0 (morning): 16 hours later: Start differentiation: The plate was rotated in a circular motion to move aggregates towards center of the well, and aggregates were collected and transferred to a conical tube. The aggregates were allowed to settle. Aggregates were resuspended in NK-MED-004 medium (2 mL per aggregated well). Cell number in aggregates was counted. The cells in aggregates density was adjusted by resuspending $3\times10^5$ cells in aggregates in 2 mL APEL-B media and plated in 1 well of a 6-well low adhesion plate. The plate was placed on a horizontal orbital shaker and rotated for 8 hours.

3. Day 0 (afternoon, following 8 hours of pre-incubation): 2 mL per well of NK-MED-005 medium was added per well. The plate was returned to the orbital shaker and left untouched until day 2.

4. Day 2: NK-MED-006 was replaced with A-FVTSIF-SW media.

5. Day 4: NK-MED-007 media was replaced with A-FVTSIF media.

6. Day 6: Using this method, single cells (HSPCs) started emerging at day 5-6. Media with all embryoid bodies (EBs) and single cells were transferred into an appropriate volume centrifuge conical tube and centrifuged. For 6-well plates: EBs from each well were resuspended in 3 mL of DF-NK+IL3 media (Table 10) and transferred into their original wells. The plate was returned to the orbital shaker.

7. Day 10: 6-well plates: 3 mL of DF-NK+IL3 media was added to each well on top of the original media and then returned to orbital shaker.

8. Day 14: Full media change. Transfer cells to DF-NK media (Table 11), no IL3 was added from this point. Media with all EBs and single cells was transferred into a centrifuge conical tube and centrifuged. Supernatant was removed. 6-well plates: EBs from each well were resuspended in 3 mL of DF-NK media and transferred into their original wells.

9. Days 14-28: Every 3-4 days media was topped off with 3 mL of fresh DF-NK media, then 3-4 days later spent media was replaced with 3 mL of fresh DF-NK media by collecting the cells in a conical tube and centrifuging. Representative culture samples were harvested at days 6, 10, 14, 21, 28 and 35 for FACS and TruSeq analysis to monitor differentiation of the cells.

TABLE 10

DF-NK + IL3 Media

| Component | Working Conc. | Volume | Stock Conc. | Vendor | Item# |
|---|---|---|---|---|---|
| DMEM (high glucose, GlutaMAX) | Ratio 2 to F12 | 558 | 100% | Thermo Fisher Scientific | 10566016 |
| F-12 with GlutaMAX | Ratio 1 to DMEM | 279 | 100% | Thermo Fisher Scientific | 31765035 |
| GlutaMAX | 1X | 10 mL | 100X | | |
| Human AB serum | 15% | 150 mL | 100% | Valley Biomedical Inc | HP1022 |
| Ascorbic acid | 20 µg/mL | 2000 µL | 10 mg/mL | MilliporeSigma | |
| Sodium selenite | 5 ng/mL | 50 µL | 100 µg/mL | MilliporeSigma | |
| rh IL-3 | 5 ng/mL | 50 µL | 100 µg/mL | PeproTech | 200-03 |
| rh IL-7 | 20 ng/mL | 200 µL | 100 µg/mL | PeproTech | 200-07 |
| rh Flt3L | 15 ng/mL | 150 µL | 100 µg/mL | PeproTech | 300-19 |
| rh IL-15 | 15 ng/mL | 150 µL | 100 µg/mL | PeproTech | 200-15 |
| rh SCF | 20 ng/mL | 200 µL | 100 µg/mL | PeproTech | 300-07 |

TABLE 11

DF-NK Media

| Component | Working Conc. | Volume | Stock Conc. | Vendor | Item# |
|---|---|---|---|---|---|
| DMEM (high glucose, GlutaMAX) | Ratio 2 to F12 | 558 | 100% | Thermo Fisher Scientific | 10566016 |
| F-12 with GlutaMAX | Ratio 1 to DMEM | 279 | 100% | Thermo Fisher Scientific | 31765035 |
| GlutaMAX | 1X | 10 mL | 100X | | |

TABLE 11-continued

DF-NK Media

| Component | Working Conc. | Volume | Stock Conc. | Vendor | Item# |
|---|---|---|---|---|---|
| Human AB serum | 15% | 150 mL | 100% | Valley Biomedical Inc | HP1022 |
| Ascorbic acid | 20 µg/mL | 2000 µL | 10 mg/mL | MilliporeSigma | |
| Sodium selenite | 5 ng/mL | 50 µL | 100 µg/mL | MilliporeSigma | |
| rh IL-3 | | | | | |
| rh IL-7 | 20 ng/mL | 200 µL | 100 µg/mL | PeproTech | 200-07 |
| rh Flt3L | 15 ng/mL | 150 µL | 100 µg/mL | PeproTech | 300-19 |
| rh IL-15 | 15 ng/mL | 150 µL | 100 µg/mL | PeproTech | 200-15 |
| rh SCF | 20 ng/mL | 200 µL | 100 µg/mL | PeproTech | 300-07 |

Example 4: Generation of ADAM17-Null Human Pluripotent Stem Cells (hPSCs)

Guide RNA (gRNA) Selection for ADAM17 in hPSCs.

Ten ADAM17 targeting gRNAs were designed for targeting exon 1 of the ADAM17 coding sequence. These gRNAs had predicted low off-target scores based on sequence homology prediction using gRNA design software. The target sequences of the gRNAs with the corresponding PAMs are presented in Table 12. In some embodiments, the gRNA comprises RNA sequence corresponding to the target DNA sequence.

TABLE 12

ADAM17 gRNA Target Sequences

| Name | Target Sequence (5'-3') | SEQ ID NO: | PAM |
|---|---|---|---|
| ADAM17 Ex1_T2 | GGTCGCGGCGCCAGCACGAA | 1 | AGG |
| ADAM17 Ex1_T4 | CCGAAGCCCGGGTCATCCGG | 2 | AGG |
| ADAM17 Ex1_T9 | CCGCGACCTCCGGATGACCC | 3 | GGG |
| ADAM17 Ex1_T10 | CGTGCTGGCGCCGCGACCTC | 4 | CGG |
| ADAM17 Ex1_T11 | CGAAAGGAACCACGCTGGTC | 5 | AGG |
| ADAM17 Ex1_T12 | CAGCGTGGTTCCTTTCGTGC | 6 | TGG |
| ADAM17 Ex1_T19 | GCCGCGACCTCCGGATGACC | 7 | CGG |
| ADAM17 Ex1_T24 | GAACCACGCTGGTCAGGAAT | 8 | AGG |
| ADAM17 Ex1_T25 | CAGCACGAAAGGAACCACGC | 9 | TGG |
| ADAM17 Ex1_T28 | GTAGCGGGGCCGGGAACATG | 10 | AGG |

To assess their cutting efficiency in hPSCs, iPS cells were electroporated using the Neon Electroporator (Neon Transfection Kit ThermoFisher Cat #MPK5000) with a ribonucleoprotein (RNP) mixture of Cas9 protein (Biomay) and guide RNA (IDT) (See Table 12 for gRNA sequences) at a molar ratio of 5:1 (gRNA:Cas9) with absolute values of 125 pmol Cas9 and 625 pmol gRNA. To form the RNP complex, gRNA and Cas9 were combined in one vessel with R-buffer (Neon Transfection Kit) to a total volume of 25 µL and incubated for 15 min at RT. Cells were dissociated using ACCUTASE®, then resuspended in STEMFLEX™ media (Gibco, cat #11320033), counted using an NC-200 (ChemoMetec) and centrifuged. A total of $1 \times 10^6$ cells were resuspended with the RNP complex and R-buffer was added to a total volume of 125 µL. This mixture was then electroporated with 1 pulse for 20 ms at 1500 V and 1 pulse for 100 ms at 500 V. Following electroporation, the cells were pipetted out into an Eppendorf tube filled with STEMFLEX™ media with REVITACELL™ Supplement (100×). This cell suspension was then plated into tissue culture dishes pre-coated with BIOLAMININ 521 CTG at 1:20 dilution. Cells were cultured in a normoxia incubator (37° C., 8% $CO_2$) for 48 hours. After 48 hours, genomic DNA was harvested from the cells using QuickExtract (Lucigen, Middleton, Wis.; Cat #QE09050).

PCR for the target ADAM17 sequence was performed and the resulting amplified DNA was assessed for cutting efficiency by TIDE analysis. PCR for relevant regions was performed using Platinum Taq Supermix (Invitrogen, cat #125320176 and Cat #11495017). The sequences of the PCR primers are presented in Table 13; and the cycling conditions are provided in Table 14.

TABLE 13

ADAM17 TIDE/Indel Primers

| Name | Type | Sequence (5'-3') | SEQ ID NO: |
|---|---|---|---|
| ADAM17 F2 | forward | AGAATCTTCCCAGTAGGCGG | 11 |
| ADAM17 R2 | reverse | CTCAGGCGCTCAGTCACTAC | 12 |

TABLE 14

ADAM17 PCR/Indel PCR Cycling Parameters

| Step | Temperature | Time | Cycles |
|---|---|---|---|
| Denaturation | 94° C. | 2 min | 1 |
| Denaturation | 94° C. | 15 sec | 34 |
| Annealing | 57° C. | 30 sec | |
| Extension | 68° C. | 45 sec | |
| Elongation | 68° C. | 5 min | 1 |
| Hold | 4° C. | hold | |

The resulting amplicons were submitted for PCR cleanup and Sanger sequencing. Sanger sequencing results were input into Tsunami software along with the guide sequence. Indel percentages and identities were calculated by the software. Particular gRNAs were then selected based on their indel frequency in hPSCs. FIG. 1 shows the cutting efficiency of 10 ADAM17 guides. ADAM17 Ex1_T2 was chosen for further clone generation due to its high on-target activity.

ADAM17 KO hPSC Clone Generation and Characterization.

Using ADAM17 T2 gRNA, iPSCs were electroporated and single-cell sorted 3 days post electroporation using the WOLF FACS-sorter (Nanocellect) into BIOLAMININ 521 CTG coated 96-well plates with STEMFLEX™ and REVITACELL™ Supplement (100×). Plated single cells were grown in a normoxia incubator (37° C., 8% $CO_2$) with every other day media changes until colonies were large enough to be re-seeded as single cells. When confluent, samples were split for maintenance and genomic DNA extraction.

The ADAM17 KO state of clones was confirmed via PCR and Sanger sequencing, as described above. The resulting DNA sequences of the target ADAM17 region were aligned in Snapgene software to determine indel identity and homo- or heterozygosity. Karyotypic status of clones was evaluated through Cell Line Genetics service (Madison, Wis.) and normal karyotype was reported.

Example 5: Generation and Selection of CIITA gRNA

Guide RNA (gRNA) Selection for CIITA in hPSCs.

5 CIITA targeting gRNAs were designed for targeting exons 2 and 3 of the CIITA coding sequence. These gRNAs had predicted low off-target scores based on sequence homology prediction using gRNA design software. The target sequences of the gRNAs are presented in Table 15. In some embodiments, the gRNA comprises RNA sequence corresponding to the target DNA sequence.

TABLE 15

CIITA gRNA Target Sequences

| Name | Target Sequence (5'-3') | SEQ ID NO: | PAM |
|---|---|---|---|
| CIITA Ex3_T6 | GGTCCATCTGGTCATAGAAG | 13 | TGG |
| CIITA Ex3_T16 | GCTCCAGGTAGCCACCTTCT | 14 | AGG |
| CIITA Ex3_T20 | TAGGGGCCCCAACTCCATGG | 15 | TGG |
| CIITA Ex4_T1 | GGCTTATGCCAATATCGGTG | 16 | AGG |
| CIITA Ex4_T25 | AGGTGATGAAGAGACCAGGG | 17 | AGG |

To assess their cutting efficiency in hPSCs, human embryonic stem cells were electroporated using the Neon Electroporator (Neon Transfection Kit ThermoFisher Cat #MPK5000) with a ribonucleoprotein (RNP) mixture of Cas9 protein (Biomay) and guide RNA (Agilent) (See Table 15 for gRNA sequences) at a molar ratio of 5:1 (gRNA: Cas9) with absolute values of 125 pmol Cas9 and 625 pmol gRNA. To form the RNP complex, gRNA and Cas9 were combined in one vessel with R-buffer (Neon Transfection Kit) to a total volume of 25 μL and incubated for 15 min at RT. Cells were dissociated using ACCUTASE®, then resuspended in STEMFLEX™ media (Gibco, cat #11320033), counted using an NC-200 (ChemoMetec) and centrifuged. A total of $1\times10^6$ cells were resuspended with the RNP complex and R-buffer was added to a total volume of 125 μL. This mixture was then electroporated with 3 pulses for 30 ms at 1100 V. Following electroporation, the cells were pipetted out into an Eppendorf tube filled with STEMFLEX™ media with RevitaCell™. This cell suspension was then plated into tissue culture dishes pre-coated with BIOLAMININ 521 CTG at 1:20 dilution. Cells were cultured in a normoxia incubator (37° C., 8% $CO_2$) for 48 hours. After 48 hours, genomic DNA was harvested from the cells using QuickExtract (Lucigen, Middleton, Wis.; Cat #QE09050).

PCR for the target CIITA sequence was performed and the resulting amplified DNA was assessed for cutting efficiency by TIDE analysis. PCR for relevant regions was performed using Platinum Taq Supermix (Invitrogen, cat #125320176 and Cat #11495017). The sequences of the PCR primers are presented in Table 16; and the cycling conditions provided in Table 17.

TABLE 16

CIITA TIDE/Indel Primers

| Name | Type | Sequence (5'-3') | SEQ ID NO: |
|---|---|---|---|
| CIITA F5 | forward | TCCTGACTCTCTGGTGTGAGAT | 18 |
| CIITA R5 | reverse | CAGAGAGCGTCCCACAGAC | 19 |

TABLE 17

CIITA PCR/Indel PCR Cycling Parameters

| Step | Temperature | Time | Cycles |
|---|---|---|---|
| Denaturation | 94° C. | 2 min | 1 |
| Denaturation | 94° C. | 15 sec | 34 |
| Annealing | 57° C. | 30 sec | |
| Extension | 68° C. | 45 sec | |
| Elongation | 68° C. | 5 min | 1 |
| Hold | 4° C. | hold | |

Figure 2:
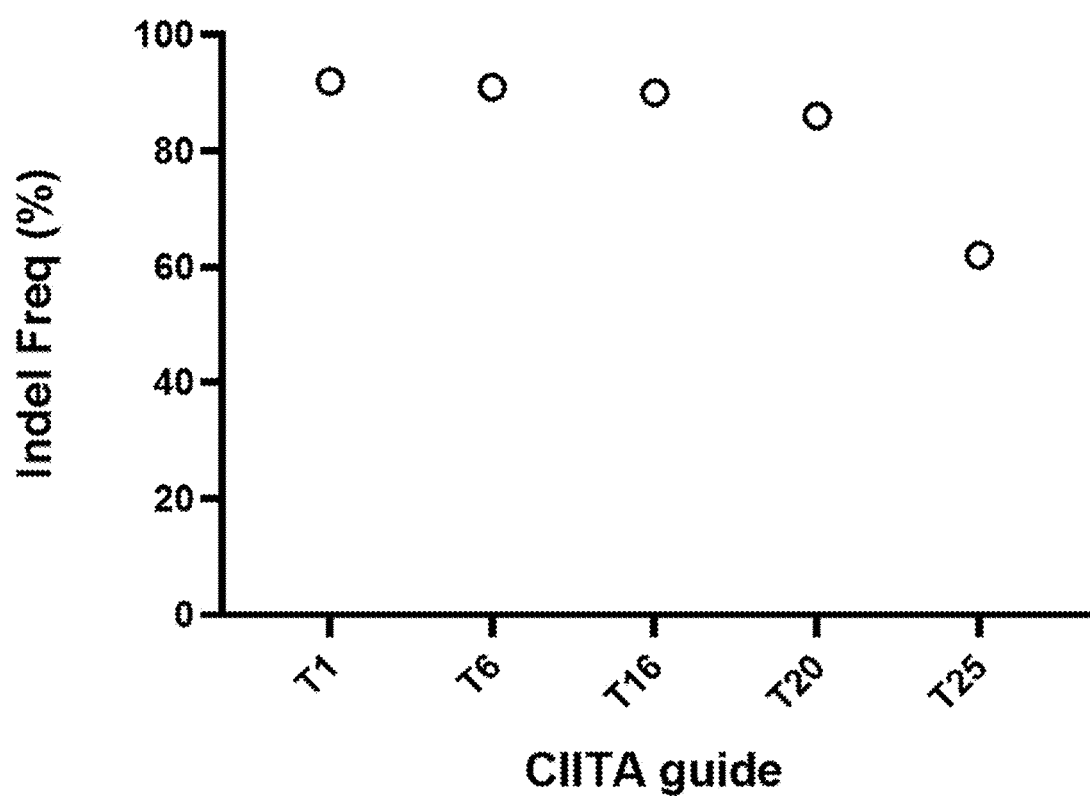
FIG. 2 provides a graph showing the cutting efficiency of 5 CIITA guides. Human embryonic stem cells were electroporated with CIITA gRNA and sequenced to measured indel frequency.

The resulting amplicons were submitted for PCR cleanup and Sanger sequencing. Sanger sequencing results were input into Tsunami software along with the guide sequence. Indel percentages and identities were calculated by the software. Particular gRNAs were then selected based on their indel frequency in hPSCs. FIG. 2 shows the cutting efficiency of 5 CIITA guides.

Off-targets of the selected gRNAs were assessed in the stem cell-derived DNA using hybrid capture analysis of the sequence similarity predicted sites. CIITA Ex3_T6 and CIITA Ex4_T1 guides did not show detectable off-target effects. CIITA T6 gRNA was chosen for further clone generation due to its high on-target activity and undetectable off-target activity.

Example 6: Generation of CAR Knock-In, CIITA Null Human Pluripotent Stem Cells (hPSCs)

Design of CIITA KO, CAR KI Strategy.

Figure 3:
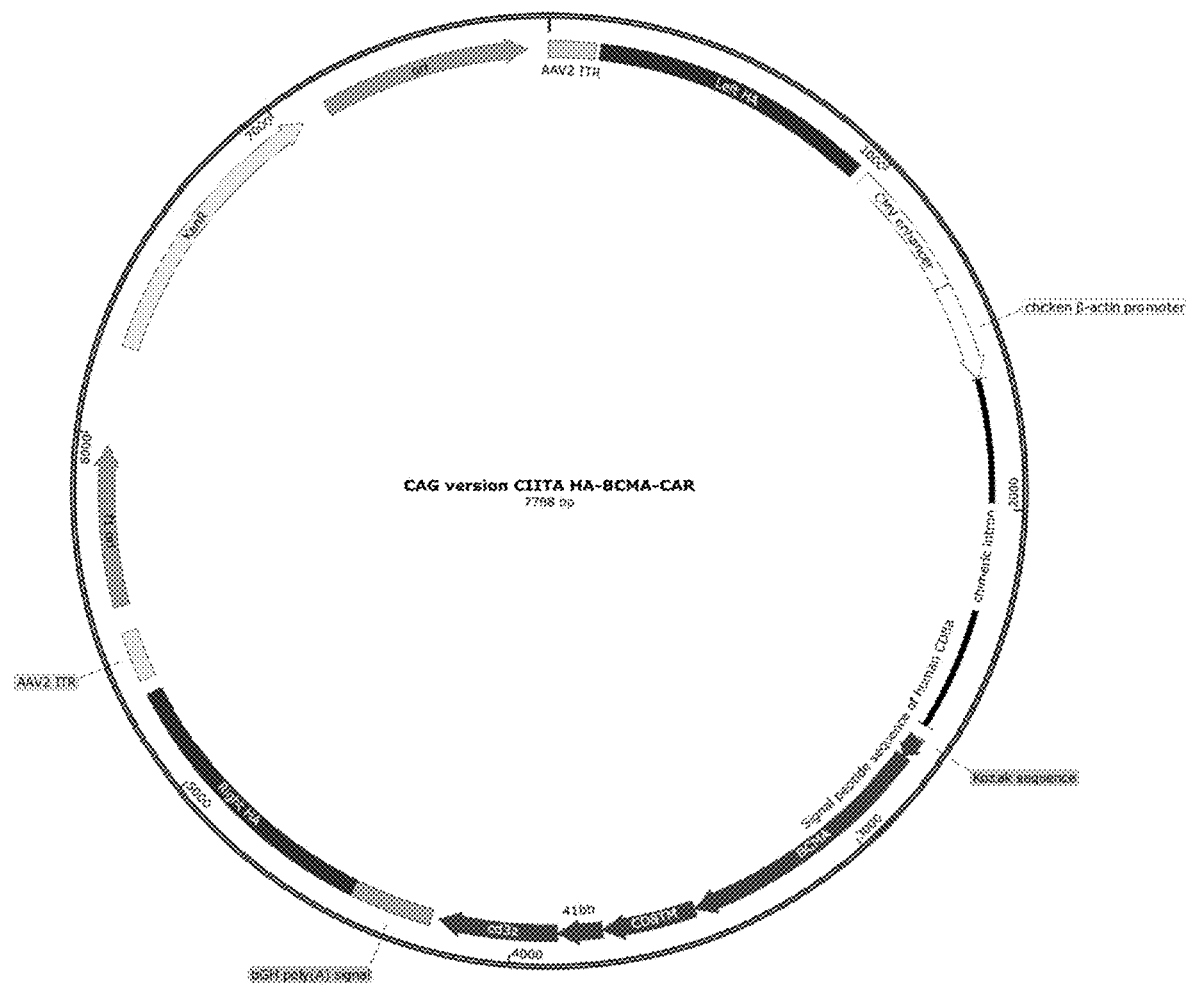
FIG. 3 provides the plasmid map of BCMA CAR knock-in, and CIITA knock-out.

Plasmid design to insert a CAR sequence, such as a BCMA CAR sequence, into the CIITA gene locus was made such that 86 base pairs (bp) of the CIITA exon 2 (GCCACCATGGAGTTGGGGCCCCTAGAAGGTGGCTACCTGAGCTTCTTAACAGCGATGCTGACCCCCTGTGCCTCTACCACTTCTA (SEQ ID NO: 20)) would be removed after undergoing homology directed repair (HDR). The removal of this portion of CIITA would result in a frame shift of the CIITA coding sequence (CDS) nullifying the expression of functional CIITA protein. Successful HDR would also result in the insertion of the CAR sequence into the genome. The donor plasmid contained a CAGGS promoter driven cDNA of a CAR sequence flanked by 800 base pair homology arms with identical sequence to the CIITA gene locus around exon 2. FIG. 3 presents a schematic of an example BCMA CAR encoding plasmid (SEQ ID NO: 66) and Table 18 identifies the elements and locations therein.

TABLE 18

Elements of BCMA CAR Donor Plasmid

| Element | Location (size in bp) | SEQ ID NO: |
|---|---|---|
| Left ITR | 1-130 (130) | 21 |
| LHA-CIITA | 145-944 (800) | 22 |
| CMV enhancer | 973-1352 (380) | 23 |
| chicken β-actin promoter | 1355-1630 (276) | 24 |
| chimeric intron | 1631-2639 (1009) | 25 |
| CD8a signal peptide | 2684-2746 (63) | 26 |
| BCMA targeting fragment | 2747-3481 (735) | 27 |
| CD8TM | 3482-3745 (264) | 28 |
| 41BB co-stim domain | 3746-3871 (126) | 29 |
| CD3Z domain | 3872-4207 (336) | 30 |
| bGH poly(A) signal | 4229-4453 (225) | 31 |
| RHA-CIITA | 4460-5259 (800) | 32 |
| Right ITR | 5301-5441 (141) | 33 |

The CIITA-T6 gRNA (Table 19) was used to facilitate insertion of the BCMA CAR transgene at the targeted CIITA gene locus. The target sequence of CIITA-T6 is not present in the donor plasmid and thus the donor plasmid itself would not be targeted by this gRNA. CIITA-T6 induced CRISPR cutting in the human genome at exon 2 of CIITA would lead to a frameshift and loss of CIITA protein. The BCMA CAR donor plasmid was introduced along with the ribonucleoprotein (RNP) complex made up of the CIITA targeting gRNA and Cas9 protein. Per 1 million of human embryonic stem cells, 4 μg of plasmid DNA was delivered along with the RNP via electroporation. Electroporation was carried out in hiPSC cells using the Neon Electroporator (Neon Transfection Kit ThermoFisher Cat #MPK5000) with the RNP mixture of Cas9 protein (Biomay) and guide RNA (Synthego) at a molar ratio of 5:1 (gRNA:Cas9) with absolute values of 125 pmol Cas9 and 625 pmol gRNA per 1 million cells. To form the RNP complex, gRNA and Cas9 were combined in one vessel with R-buffer (Neon Transfection Kit) to a total volume of 25-50 μL and incubated for 15 min at room temperature (RT). Cells were dissociated using ACCUTASE®, then resuspended in STEMFLEX™ media, counted using an NC-200 (ChemoMetec) and centrifuged. A total of 2×10⁶ cells were resuspended with the RNP complex and R-buffer was added to a total volume of 115 μL. This mixture was then electroporated with 1 pulse for 20 ms at 1500 V followed by 1 pulse for 100 ms at 500 V. Following electroporation, the cells were pipetted out into a well of a 6 well plate filled with STEMFLEX™ media with REVITACELL™ Supplement (100×) and laminin 511. The plates were pre-coated with BIOLAMININ 521 CTG at 1:10 dilution. Cells were cultured in a normoxia incubator (37° C., 8% $CO_2$).

Seven to ten days post electroporation, the cells were enriched for BCMA CAR expressing cells using an antibody against BCMA CAR (15C04-APC or 15C04-PE) via magnetic assisted cell sorting (MACS) using anti-mouse IgG Dynabeads (ThermoFisher, CELLection™ Pan Mouse IgG Kit, 11531D). These enriched cells represent a bulk KI population of BCMA-CAR positive cells.

TABLE 19 gRNA Target Sequences

| Name | Target Sequence (5'-3') | SEQ ID NO: | PAM |
|---|---|---|---|
| CIITA Ex3_T6 gRNA | GGTCCATCTGGTCATAGAAG | 13 | TGG |
| B2M-2 gRNA (Exon 1_T2) | GGCCGAGATGTCTCGCTCCG | 34 | TGG |
| ADAM17 Ex1_T2 gRNA | GGTCGCGGCGCCAGCACGAA | 1 | AGG |

Example 7: Generation of IL15/IR15α-P2A-HLA-E Trimer Knock-In, BCMA CAR Knock-In, CIITA Null, B2M Null Human Pluripotent Stem Cells (hPSCs)

Design of B2M KO, IL15/IR15α-P2A-HLA-E Trimer KI Strategy.

Figure 4:
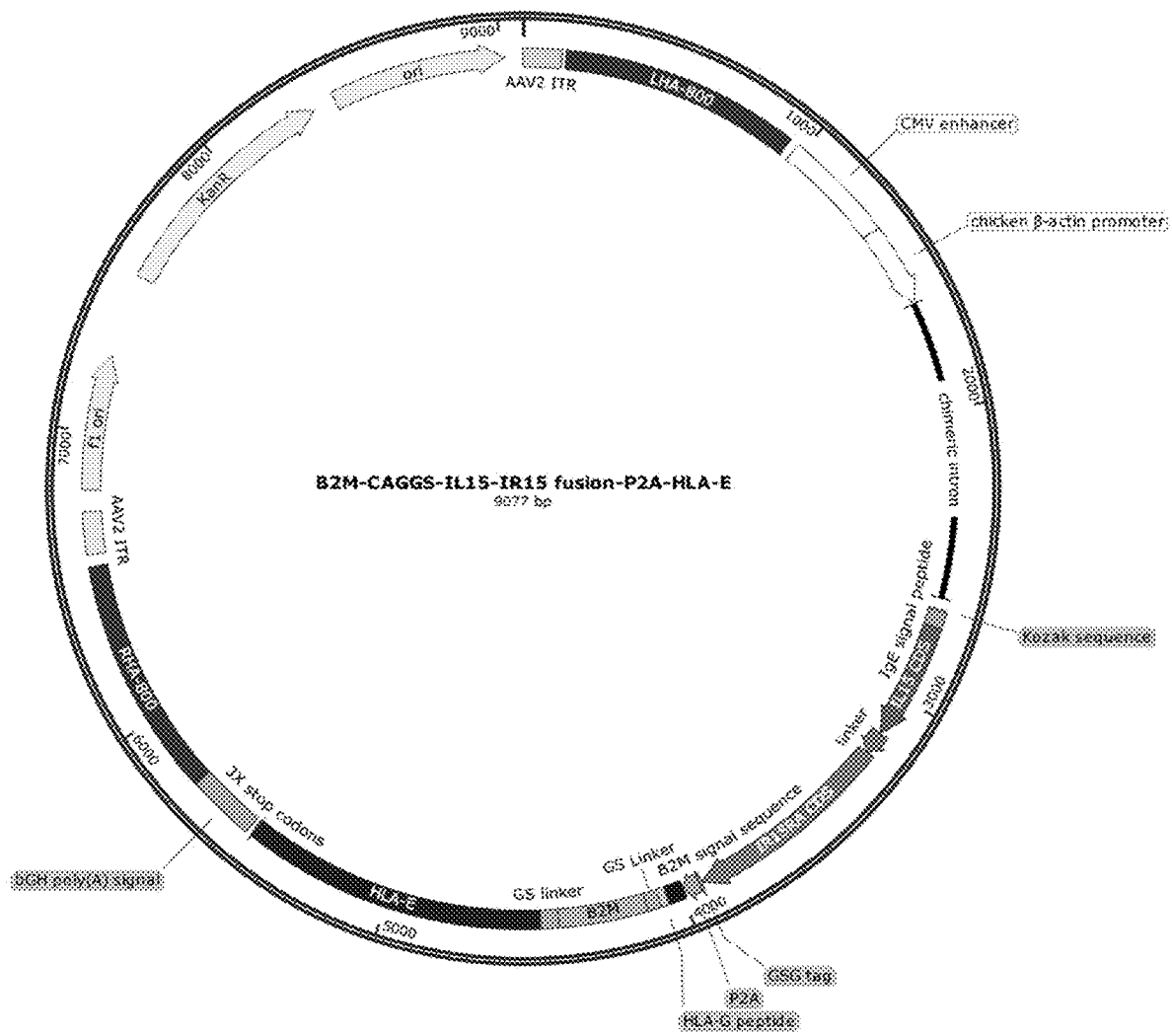
FIG. 4 provides the plasmid map of B2M-CAGGS-IL15-IR15 fusion-P2A-HLA-E. The IL15/IR15α-P2A-HLA-E trimer was inserted near exon 1 of the B2M gene locus to generate a B2M knock-out (KO)/IL15/IR15α-P2A-HLA-E knock-in (KI) plasmid.

Plasmid design to insert IL15/IR15α-P2A-HLA-E trimer into the B2M gene locus was made such that the starting codon of B2M was removed after undergoing homology directed repair (HDR) to insert IL15/IR15α-P2A-HLA-E trimer, nullifying any chance of partial B2M expression. FIG. 4 presents a schematic of the plasmid SEQ ID NO: 67 and Table 20 identifies the elements and locations therein. The donor plasmid contained a CAGGS promoter driven cDNA of IL15/IR15α-P2A-HLA-E trimer flanked by 800 base pair homology arms with identical sequence to the B2M gene locus around exon 1.

The IL15/IR15a fusion sequence was designed as previously published (Hurton et al. (2016) Proc Natl Acad Sci USA; 113(48):E7788-E7797. doi: 10.1073/pnas.1610544113.) The IL15/IR15a fusion coding sequence (including linkers) is SEQ ID NO: 76 (i.e., SEQ ID NOs: 40, 41, 42, 43, and 44).

The HLA-E trimer cDNA was composed of a B2M signal peptide fused to an HLA-G presentation peptide fused to the B2M membrane protein fused to the HLA-E protein without its signal peptide. The HLA-E trimer coding sequence (including linkers) is SEQ ID NO: 75 (i.e., SEQ ID NOs: 46, 47, 48, 49, 50, and 51). This trimer design has been previously published (Gornalusse et al. (2017) Nat. Biotechnol. 35(8): 765-772).

The P2A peptide sequence (derived from porcine teschovirus-1 2A) connecting IL15/IR15a fusion and the HLA-E trimer allows for the separate expression of both proteins from a single mRNA.

TABLE 20

Elements of IL15/IR15α-P2A-HLA-E Trimer Donor Plasmid

| Element | Location (size in bp) | SEQ ID NO: |
|---|---|---|
| Left ITR | 1-130 (130) | 21 |
| LHA-B2M | 145-944 (800) | 36 |
| CMV enhancer | 973-1352 (380) | 23 |
| chicken β-actin promoter | 1355-1630 (276) | 24 |
| chimeric intron | 1631-2639 (1009) | 25 |
| IgE signal peptide | 2684-2737 (54) | 40 |
| IL15 CDS | 2738-3136 (399) | 41 |
| linker | 3137-3214 (78) | 42 |
| IL15Rα CDS | 3215-3925 (711) | 43 |
| GSG tag | 3926-3934 (9) | 44 |
| P2A | 3935-3991 (57) | 45 |
| B2M signal sequence | 3992-4051 (60) | 46 |

TABLE 20-continued

Elements of IL15/IR15α-P2A-HLA-E Trimer Donor Plasmid

| Element | Location (size in bp) | SEQ ID NO: |
|---|---|---|
| HLA-G peptide | 4052-4078 (27) | 47 |
| GS linker | 4079-4123 (45) | 48 |
| B2M | 4124-4420 (297) | 49 |
| GS linker | 4421-4480 (60) | 50 |
| HLA-E | 4481-5491 (1011) | 51 |
| 3X Stop codons | 5492-5500 (9) | 52 |
| bGH poly(A) signal | 5518-5742 (225) | 31 |
| RHA-B2M | 5749-6548 (800) | 54 |
| Right ITR | 6590-6730 (141) | 33 |

To insert the IL15/IR15α-P2A-HLA-E trimer sequence into hiPSCs, BCMA CAR-enriched hiPSCs were produced, as described in Example 6. This population was first electroporated with donor plasmid only (without CRISPR editing reagents) one day prior to a second electroporation. In the first electroporation, the Neon Electroporator was used to deliver 1 μg of donor plasmid DNA per 1 million of hiPSCs. The cells were dissociated using ACCUTASE®, then resuspended in STEMFLEX™ media, counted using an NC-200 (ChemoMetec) and centrifuged. A total of 24×10$^6$ cells were resuspended with R-buffer and donor plasmid DNA to a total volume of ~600 μL. This mixture was then electroporated with 1 pulse for 20 ms at 1500 V followed by 1 pulse for 100 ms at 500 V. A total of 6 electroporations were performed and the cells were pipetted out into a 6 well plate filled with STEMFLEX™ media with REVITA-CELL™ Supplement (100×) and laminin 511. Cells were cultured in a normoxia incubator (37° C., 8% CO$_2$).

The following day, these cells were dissociated from the plate and electroporated again using additional reagents. The B2M-2 gRNA (Table 19) was used to facilitate the insertion of the IL15/IR15α-P2A-HLA-E trimer transgene at the targeted B2M gene locus. The IL15/IR15α-P2A-HLA-E trimer donor plasmid was introduced along with the ribonucleoprotein (RNP) complex made up of the B2M targeting gRNA and Cas9 protein. Per 1 million of hiPSC cells, 2 μg of plasmid DNA was delivered along with the RNP via electroporation. Electroporation was carried out in hiPSC cells using the Neon Electroporator with the RNP mixture of Cas9 protein (Biomay) and guide RNA (Biospring) at a molar ratio of 5:1 (gRNA:Cas9) with absolute values of 62.5 pmol Cas9 and 312.5 pmol gRNA per 1 million cells. To form the RNP complex, gRNA and Cas9 were combined in one vessel with R-buffer (Neon Transfection Kit) to a total volume of 25-50 μL and incubated for 15 min at room temperature (RT). Cells were dissociated using ACCUTASE®, then resuspended in STEMFLEX™ media, counted using an NC-200 (ChemoMetec) and centrifuged. A total of 7×10$^6$ cells were resuspended with the RNP complex and R-buffer was added to a total volume of ~300 μL. This mixture was then electroporated with 1 pulse for 20 ms at 1500 V followed by 1 pulse for 100 ms at 500 V. A total of 3 electroporations were performed. Following electroporation, the cells were pipetted out into 2 wells of a 6 well plate filled with STEMFLEX™ media with REVITACELL™ Supplement (100×) and laminin 511. Cells were cultured in a normoxia incubator (37° C., 8% CO$_2$).

Seven to ten days post electroporation, the cells were enriched for HLA-E trimer expressing cells using an antibody against HLA-E (see Table 21) via magnetic assisted cell sorting (MACS) using anti-mouse IgG Dynabeads (ThermoFisher, CELLection™ Pan Mouse IgG Kit, 11531D). These enriched cells represent a bulk KI population of IL15/IR15α-P2A-HLA-E trimer positive cells.

TABLE 21

Antibodies for Flow Cytometry

| Antigen | Clone | Fluorophore | Manufacturer | Catalog # |
|---|---|---|---|---|
| BCMA CAR | 15C04 | PE or APC | CRISPRtx | Custom |
| IL15 | 34559 | PE | ThermoFisher | MA5-23561 |
| B2M | 2M2 | PE | Biolegend | 316305 |
| HLA-ABC | W6/32 | Alexa 488 | Biolegend | 311415 |
| mIgG1 kappa | N/A | PE | BD Bioscience | 555749 |
| PD-L1 | B7-H1 | Alexa-488 | ThermoFisher | 53-5983-42 |
| HLA-E | 3D12 | PE | ThermoFisher | 12-9953-42 |
| HLA-E | 3D12 | APC | ThermoFisher | 17-9953-42 |

Example 8: Generation and Characterization of IL15/IR15α-P2A-HLA-E Trimer Knock-In, B2M Null Human Pluripotent Stem Cells (hPSCs)

The IL15/IR15α-P2A-HLA-E trimer sequence, as described in Example 7, was inserted into a hiPSC line. B2M-2 gRNA (Table 19) was used to facilitate the insertion of the IL15/IR15α-P2A-HLA-E trimer transgene at the targeted B2M gene locus. The IL15/IR15α-P2A-HLA-E trimer donor plasmid was introduced along with the ribonucleoprotein (RNP) complex made up of the B2M targeting gRNA and Cas9 protein. Per 1 million of hiPSC cells, 2 μg of plasmid DNA was delivered along with the RNP via electroporation. Electroporation was carried out in hiPSC cells using the Neon Electroporator with the RNP mixture of Cas9 protein (Biomay) and guide RNA (Biospring) at a molar ratio of 10:1 (gRNA:Cas9) with absolute values of 62.5 pmol Cas9 and 625 pmol gRNA per 1 million cells. To form the RNP complex, gRNA and Cas9 were combined in one vessel with R-buffer (Neon Transfection Kit) to a total volume of 25-50 μL and incubated for 15 min at room temperature (RT). Cells were dissociated using ACCUTASE®, then resuspended in STEMFLEX™ media, counted using an NC-200 (ChemoMetec) and centrifuged. A total of 2×10$^6$ cells were resuspended with the RNP complex and R-buffer was added to a total volume of ~115 μL. This mixture was then electroporated with 1 pulse for 20 ms at 1500 V followed by 1 pulse for 100 ms at 500 V. One electroporation was performed. Following electroporation, the cells were pipetted out into a well of a 6 well plate filled with STEMFLEX™ media with REVITACELL™ Supplement (100×) and laminin 511. The plates were pre-coated with BIOLAMININ 521 CTG at 1:10 dilution. Cells were cultured in a normoxia incubator (37° C., 8% CO$_2$).

Figure 5A:
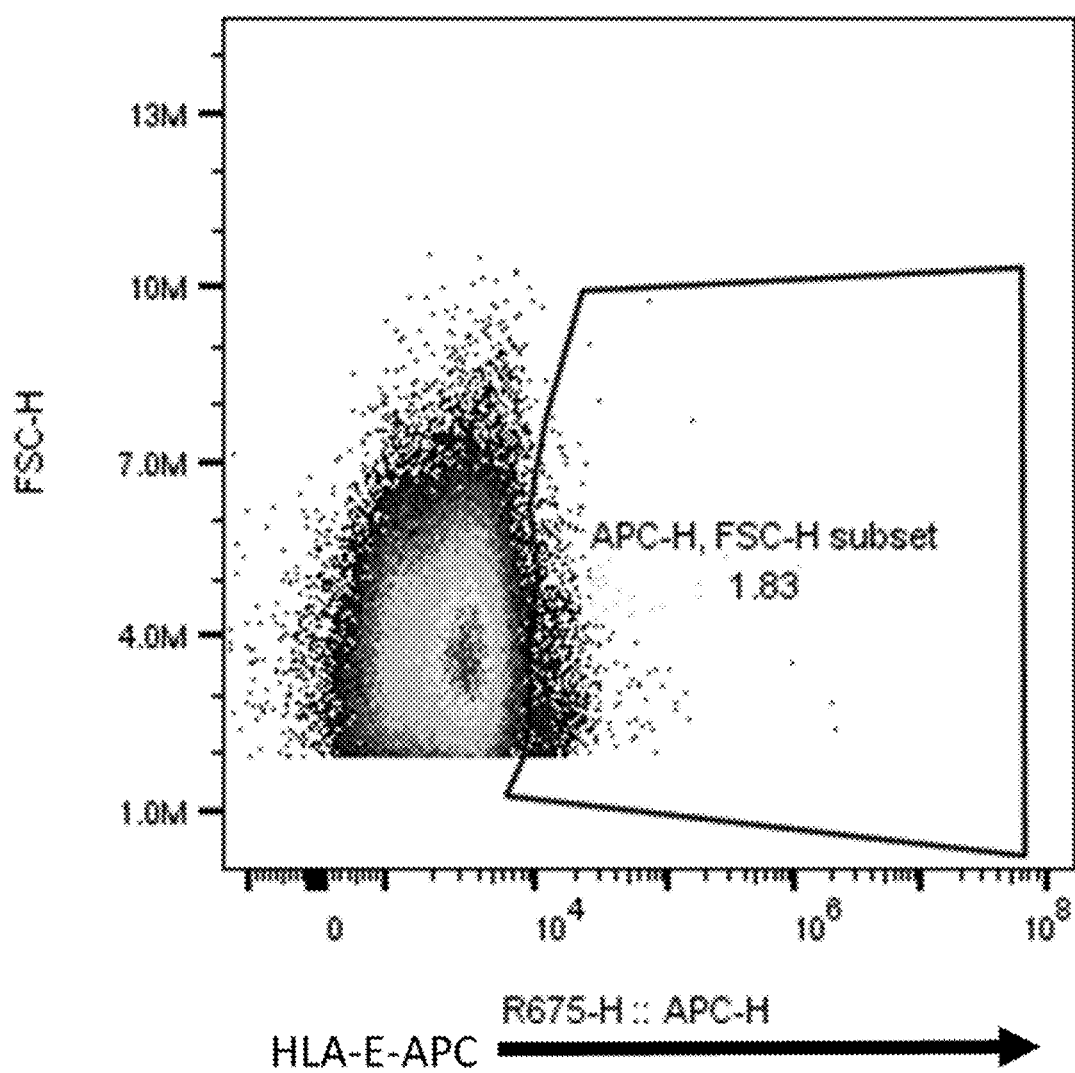
FIGS. 5A and 5B provide graphs of the flow cytometry analysis of HLA-E in IL15/IR15α-P2A-HLA-E trimer knock-in, B2M Null Human Pluripotent Stem Cells (hPSCs). Wild-type inducible pluripotent stem cells (iPSC) (FIG. 5A) and HLA-E edited iPSC (FIG. 5B) were analyzed using anti-HLA-E APC.
Figure 5B:
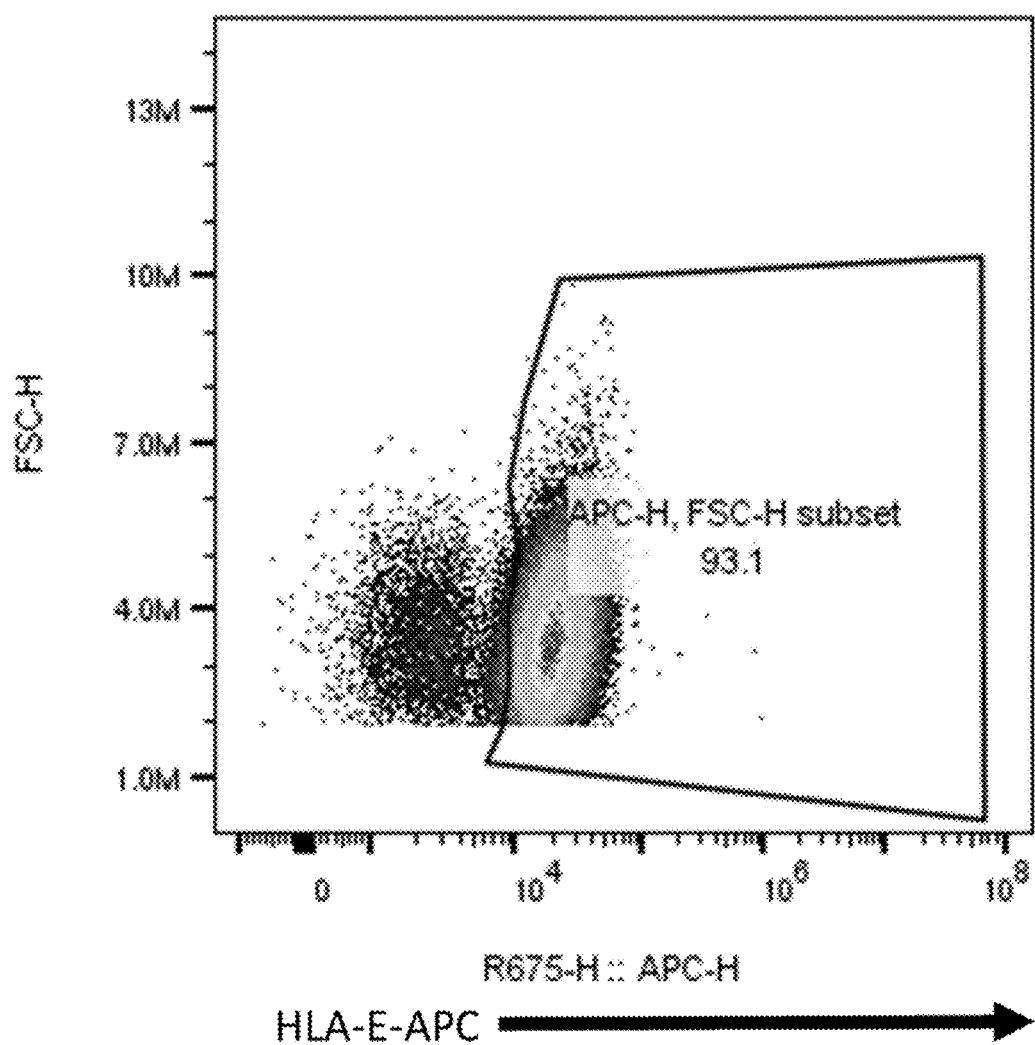

Seven to ten days post electroporation, the cells were enriched for HLA-E trimer expressing cells using an antibody against HLA-E (see Table 21) via magnetic assisted cell sorting (MACS) using anti-mouse IgG Dynabeads (ThermoFisher, CELLection™ Pan Mouse IgG Kit, 11531D). These enriched cells represent a bulk KI population of IL15/IR15α-P2A-HLA-E trimer positive cells. This population was assessed for HLA-E expression by flow cytometry, showing >90% HLA-E expression (FIG. 5B). WT iPSC cells were a negative control (FIG. 5A).

Figure 6:
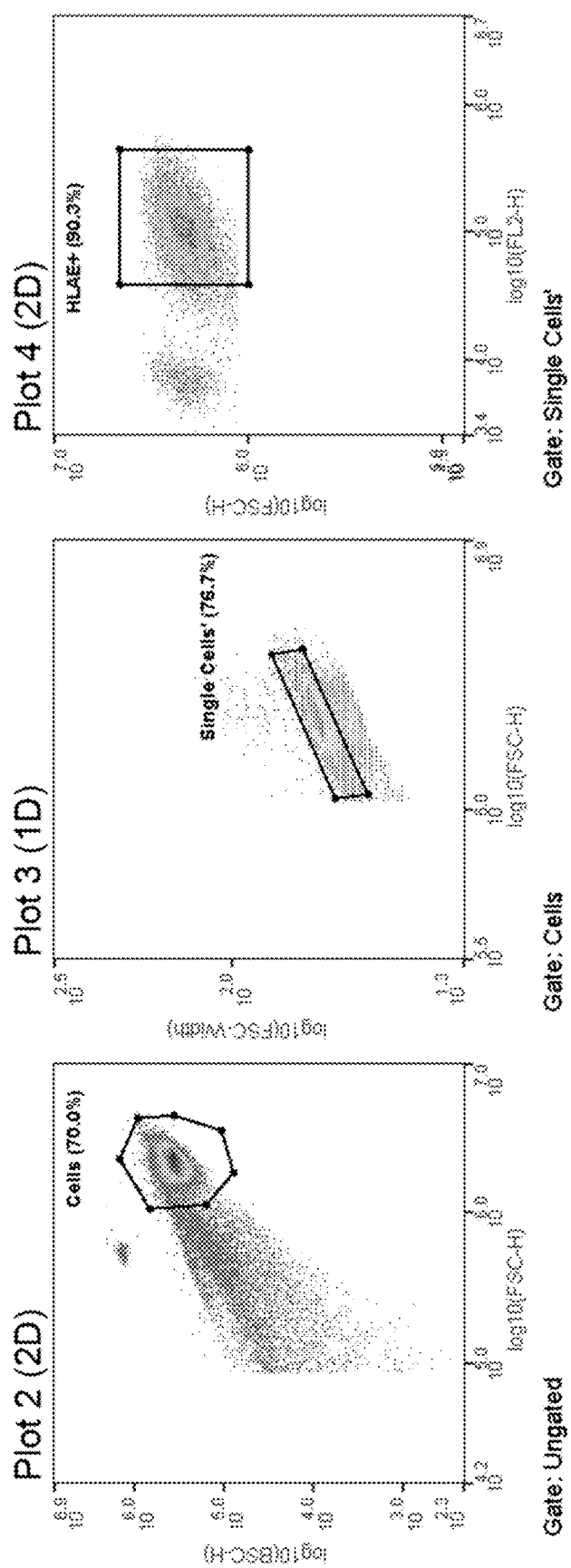
FIG. 6 demonstrates gating strategy for single-cell sorting of IL15/IR15α-P2A-HLA-E trimer knock-in, B2M Null hPSCs using an anti-HLA-E-PE antibody. FACS was used to sort single cells into 96-well plates.

Following MACS-enrichment, the cells were single-cell sorted as described in Example 1. The anti-HLA-E-PE antibody (see Table 21) was used for FACS-sorting into 96-well plates (FIG. 6). For FACS-sorting, unedited cells served as a negative control. After sorting, the cells were expanded as described in Example 1 and when confluent, samples were split for maintenance and genomic DNA extraction.

Figure 7A:
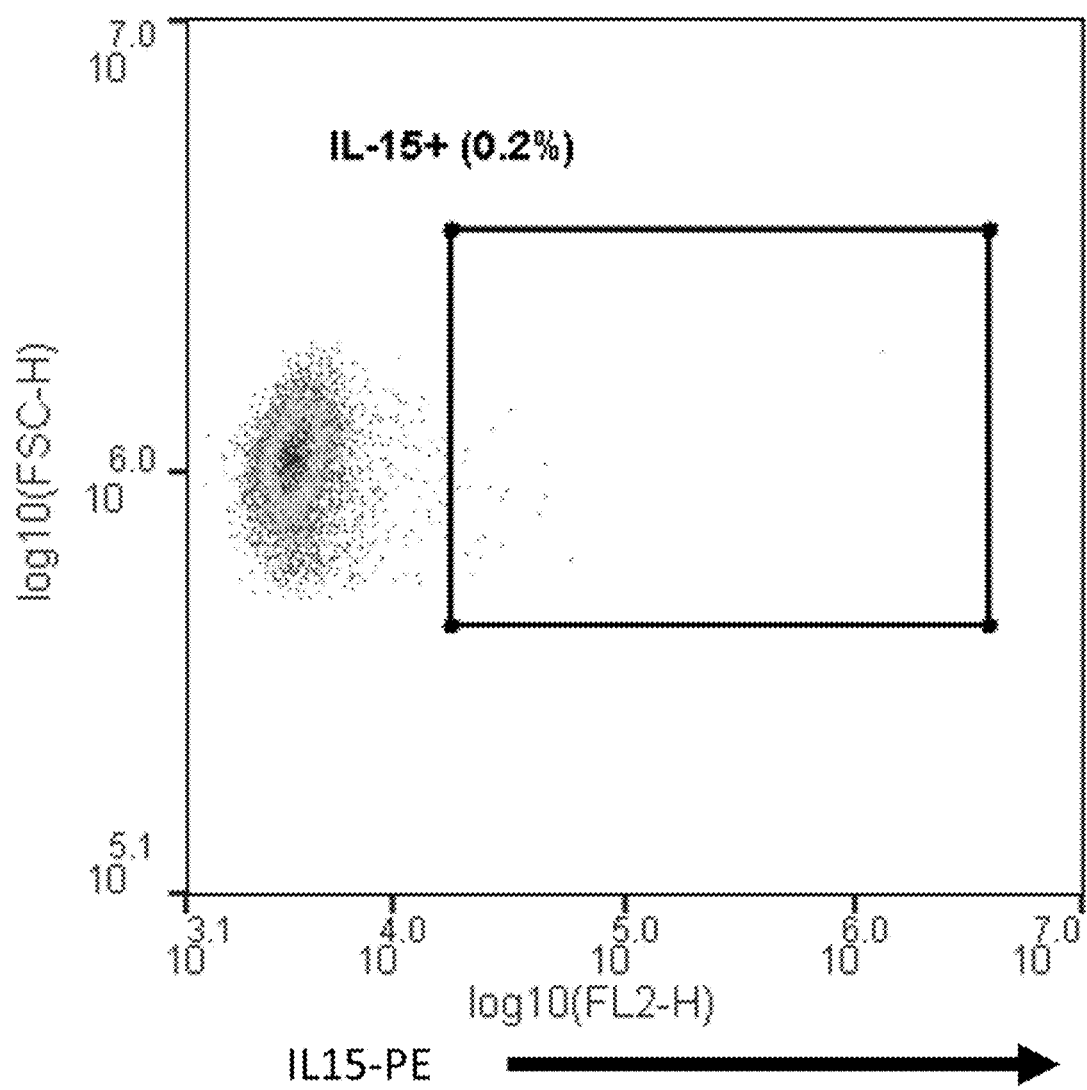
FIGS. 7A and 7B provide graphs of the flow cytometry analysis of IL-15 in single-cell "Clone 3" (IL15/IR15α-P2A-HLA-E trimer knock-in, B2M Null hPSCs). Wild-type inducible pluripotent stem cells (iPSC) (FIG. 7A) and Clone 3 IL-15 edited iPSC (FIG. 7B) were analyzed using anti-IL-15 PE.
Figure 7B:
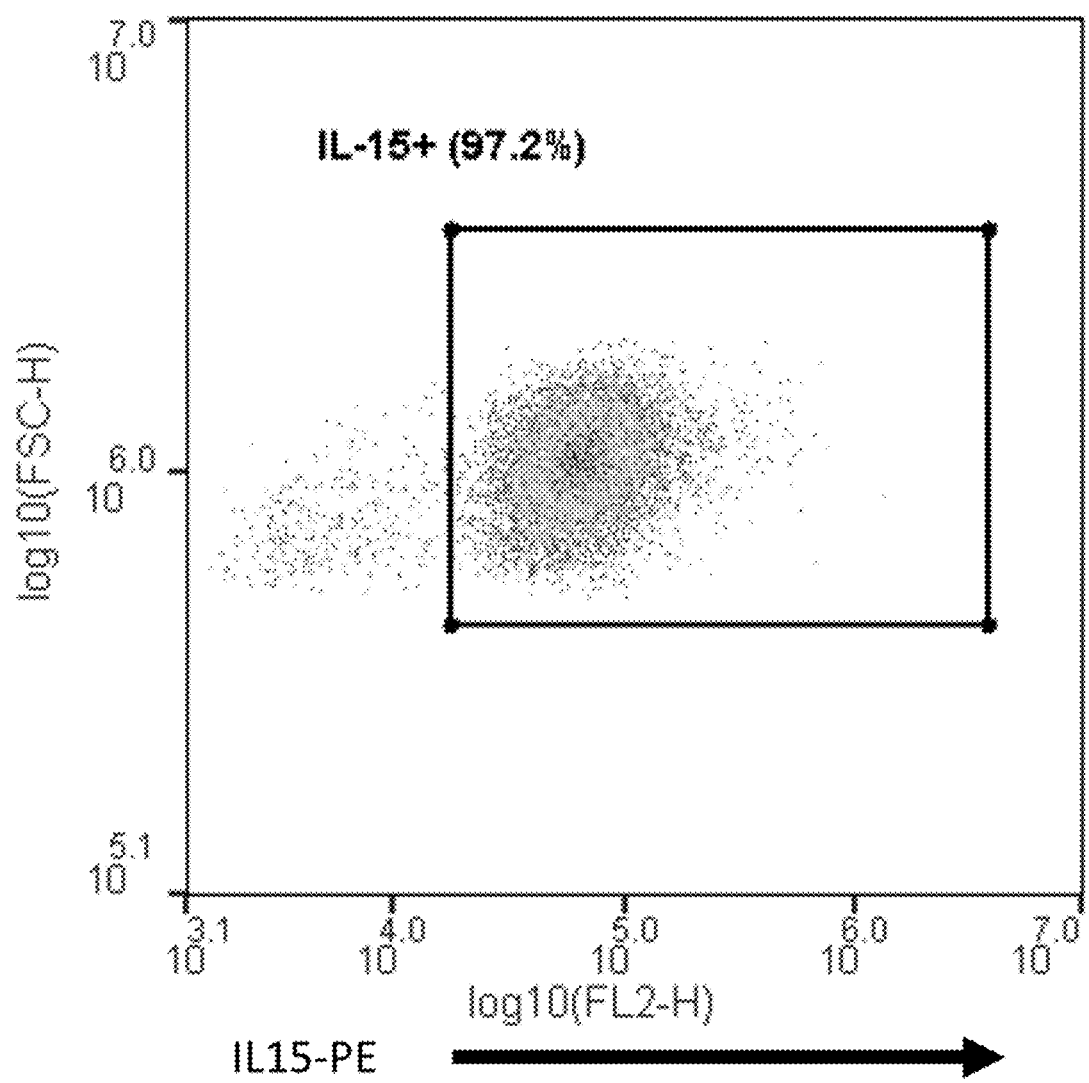

The single cell derived clones demonstrated IL15-PE expression post expansion confirming fidelity of the edit. The IL-15-PE expression in a clone named "Clone 3" (FIG. 7B) and WT iPSC control (FIG. 7A) was determined.

Figure 8:
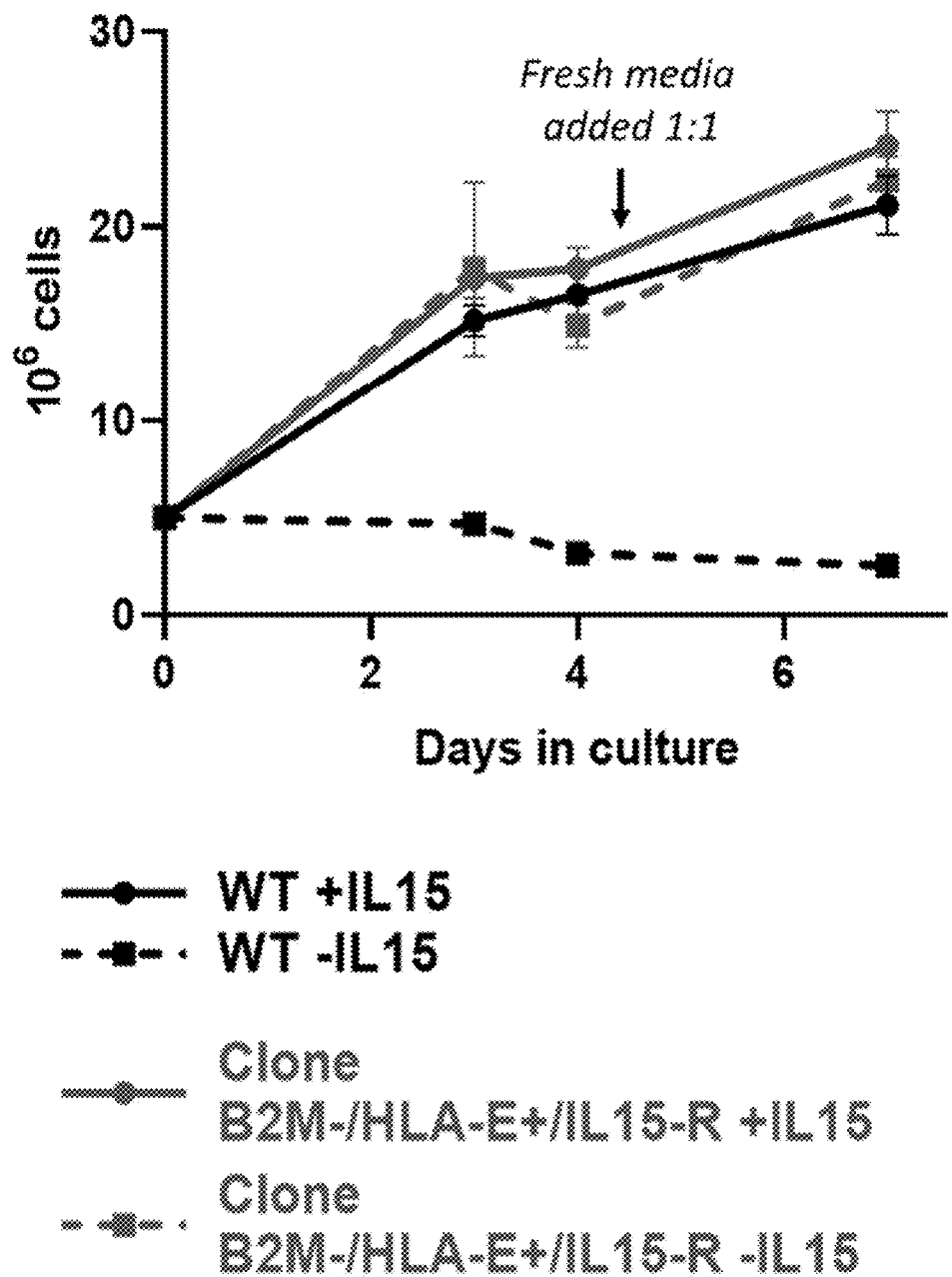
FIG. 8 provides a line graph demonstrating cell growth in wild-type (WT) and Clone 3 (IL15/IR15α-P2A-HLA-E trimer knock-in, B2M Null hPSC) derived iNK cells when administered exogenous IL15 or not administered exogenous IL 15. Cells were administered 20 ng/mL of IL-15 in addition to SCF (20 ng/mL), Flt3L (15 ng/mL), IL-7 (20 ng/mL) on day 0 and day 4.

Clone 3, an hiPSC gene edited clone containing the edits IL15/IR15α-P2A-HLA-E trimer knock-in, B2M Null, was differentiated to iNK cells using Protocol 2, as described in Example 3, using PBS spinner vessels. Day 20 iNK cells differentiated from WT or Clone 3 (IL15/IR15α-P2A-HLA-E trimer knock-in, B2M Null hPSC) were plated at $5 \times 10^6$ cells/well and grown with or without exogenous IL15 (20 ng/mL). In addition, all cells were administered SCF (20 ng/mL), Flt3L (15 ng/mL), IL-7 (20 ng/mL) on day 0 and day 4. Clone 3 (IL15/IR15α-P2A-HLA-E trimer knock-in, B2M Null hPSC) derived iNK expanded similarly in the presence or absence of exogenous IL15 in the culture media. FIG. 8 shows that the clone 3 cells persisted and expanded in the absence of exogenous IL15 while the WT iNK cell number declined in the absence of exogenous IL15.

The cytotoxicity of the day 36 Clone 3 derived iNK cells towards K562 cells was determined using a 24-hour killing assay. K562-GFP cells (50,000 cells per vial) were incubated with iNK effector cell lines at different ratios as indicated for 24 hours. After incubation, the cells were spun, and resuspended in 175 μl media containing SyTox Blue at a 1:1000 concentration. 25 μL of countbright beads per well were added. The plate was read using the Flow cytometer 100 μL volume per well was collected for analysis. GFP-positive, SyTox Blue-negative target cells (live cancer cells) and countbright beads were selected and measured absolute events count. Total live cells were calculated as follows:

[Total Cells=((No of live cells)/(Bead count for that sample))/(Bead count per 50 μL/2).

Figure 9:
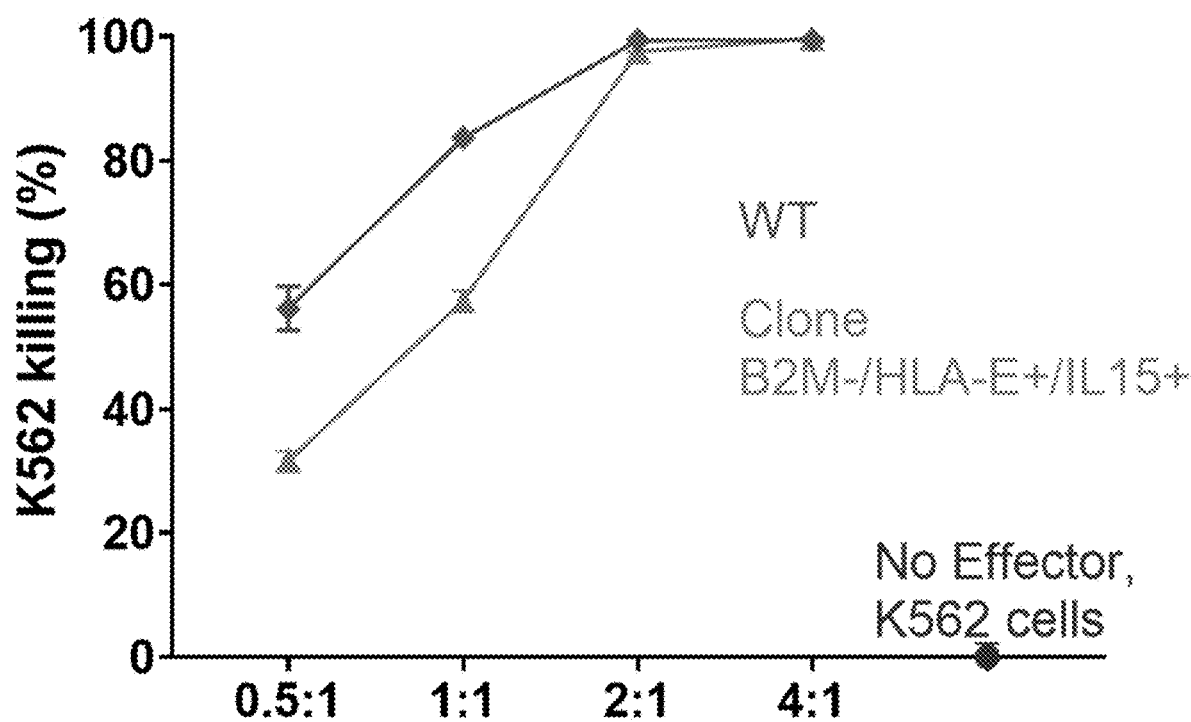
FIG. 9 provides a graph demonstrating K562 cell killing by WT and Clone 3 (IL15/IR15α-P2A-HLA-E trimer knock-in, B2M Null hPSC) derived iNK cells. Effector and K562 cells were plated at different effector:target (E:T) ratios for 24-hours. A no effector, K562 only cell, negative control was used.

The % of cell lysis was calculated using following formula: % Cell lysis=(1−((Total Number of target Cells in Test Sample)/(Total Number of Target Cells in Control Sample))×100. The WT and edited lines displayed effective cytotoxicity against K562 (FIG. 9).

Example 9: Generation of IL15/IR15α-P2A-HLA-E Trimer Knock-In, BCMA CAR Knock-In, CIITA Null, B2M Null, ADAM17 Null Human Pluripotent Stem Cells (hPSCs)

Design of ADAM17 KO.

The ADAM17-T2 gRNA (Table 19) was used to knock-out the ADAM17 protein by causing a frameshift mutation in the ADAM17 gene exon 1. BCMA CAR and IL15/IR15α-P2A-HLA-E trimer enriched hiPSCs were generated as described in Examples 6 and 7. Electroporation was carried out in these enriched hiPSC cells using the Neon Electroporator with the RNP mixture of Cas9 protein (Biomay) and guide RNA (IDT) at a molar ratio of 5:1 (gRNA:Cas9) with absolute values of 125 pmol Cas9 and 625 pmol gRNA per 1 million cells. To form the RNP complex, gRNA and Cas9 were combined in one vessel with R-buffer (Neon Transfection Kit) to a total volume of 25-50 μL and incubated for 15 min at room temperature (RT). This mixture was then combined with the cells to a total volume of ~115 μL using R-buffer. This mixture was then electroporated with 1 pulse for 20 ms at 1500 V followed by 1 pulse for 100 ms at 500 V. Following electroporation, the cells were pipetted out into a 6 well plate filled with STEMFLEX™ media with REVI-TACELL™ Supplement (100×) and laminin 511. Cells were cultured in a normoxia incubator (37° C., 8% $CO_2$).

Three to five days post electroporation, the cells were single-cell sorted as described in Example 1. The anti-BCMA CAR antibody (see Table 21) was used for FACS-sorting into 96-well plates. For FACS-sorting, unedited cells served as a negative control. After sorting, the cells were expanded as described in Example 1 and when confluent, samples were split for maintenance and genomic DNA extraction.

PCR for the genotyping of the edited clones (IL15/IR15α-P2A-HLA-E trimer knock-in, BCMA CAR knock-in, CIITA Null, B2M Null, ADAM17 Null Human Pluripotent Stem Cells (hPSCs)) was performed and the resulting amplified DNA was assessed for cutting efficiency by TIDE analysis.

For determining indels in the target B2M sequence, PCR for relevant regions was performed using Platinum Taq Supermix (Invitrogen, cat #125320176 and Cat #11495017). The sequences of the PCR primers are presented in Table 22; and the cycling conditions provided in Table 23.

TABLE 22

B2M Indel Primers

| Name | Type | Sequence (5'-3') | SEQ ID NO: |
|------|------|------------------|------------|
| B2MF2 | Forward | CAGACAGCAAACTCACCCAG | 56 |
| B2MR2 | Reverse | AAACTTTGTCCCGACCCTCC | 57 |

TABLE 23

B2M Indel PCR Cycling Parameters

| Step | Temperature | Time | Cycles |
|------|-------------|------|--------|
| Denaturation | 94° C. | 2 min | 1 |
| Denaturation | 94° C. | 15 sec | 30 |
| Annealing | 56° C. | 30 sec | |
| Extension | 68° C. | 45 sec | |
| Elongation | 68° C. | 5 min | 1 |
| Hold | 4° C. | hold | |

Figure 10:
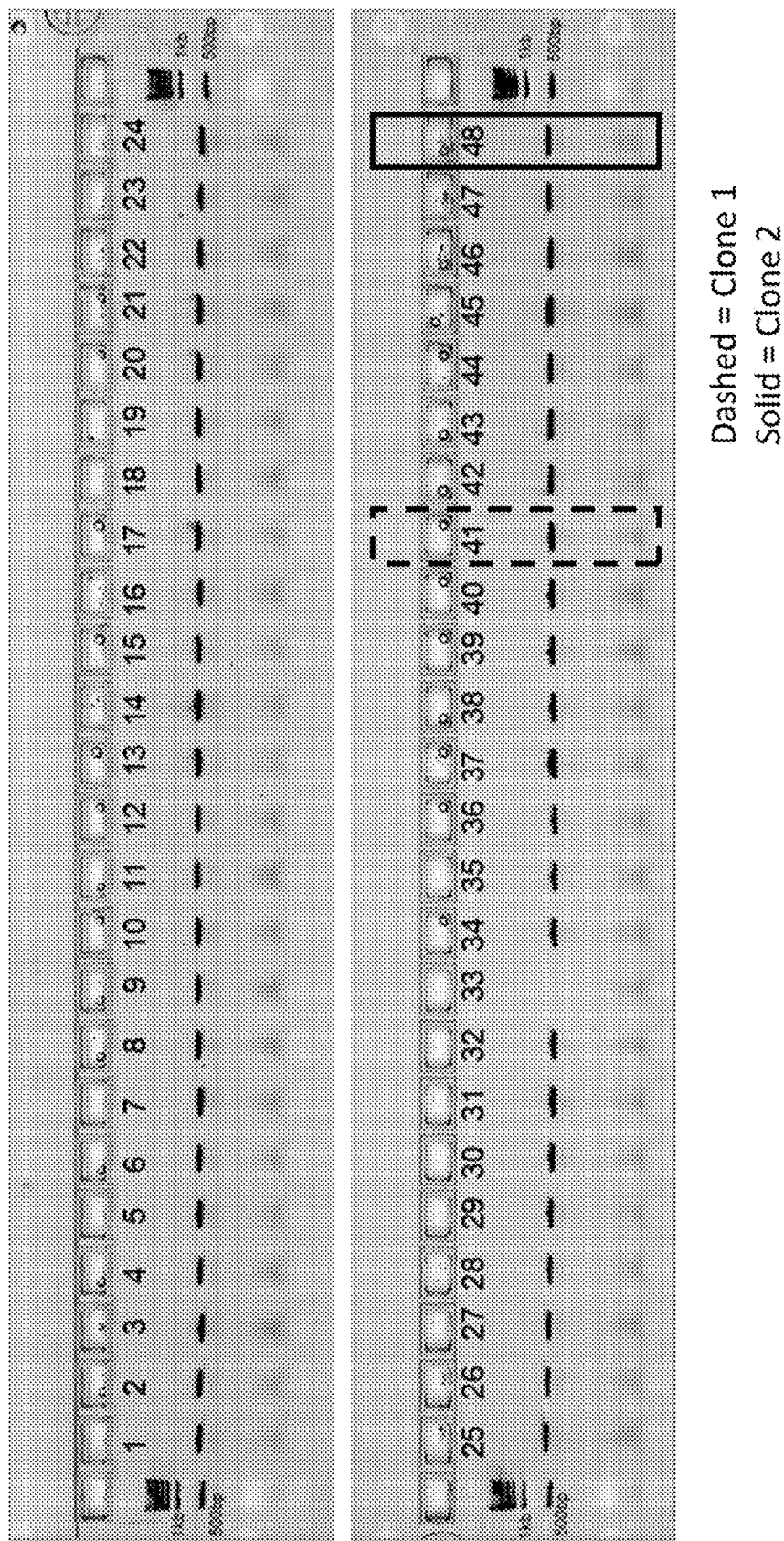

FIG. 10 shows the 2M indel results for various edited clones. The presence of a 573 bp band indicated a WT genotype which would be found in clones that are unedited or are heterozygous for the KI construct, as homozygous clones will not have a band. For determining B2M zygosity, PCR for relevant regions was performed using Platinum Taq Supermix (Invitrogen, cat #125320176 and Cat #11495017). The sequence of the PCR primers are presented in Table 24; and the cycling conditions provided in Table 25.

TABLE 24

B2M Zygosity Primers

| Name | Type | Sequence (5'-3') | SEQ ID NO: |
|------|------|------------------|------------|
| B2M-geno-F1 | forward | AAAAGATCTGTGGACTCCACCACCACGAAA TGGCGGCACCTTATTTATGGTC | 58 |
| B2M-geno-R1 | reverse | GCTCTGGAGAATCTCACGCAGAAGGCAGGC GTTTTTCTTAAAAAAAAATGCACGAATTA | 59 |

TABLE 25

B2M Zygosity PCR Cycling Parameters

| Step | Temperature | Time | Cycles |
|---|---|---|---|
| Denaturation | 94° C. | 2 min | 1 |
| Denaturation | 98° C. | 10 sec | 30 |
| Annealing | 65° C. | 30 sec | |
| Extension | 68° C. | 6 min 30 sec | |
| Elongation | 68° C. | 5 min | 1 |
| Hold | 4° C. | hold | |

Figure 11:
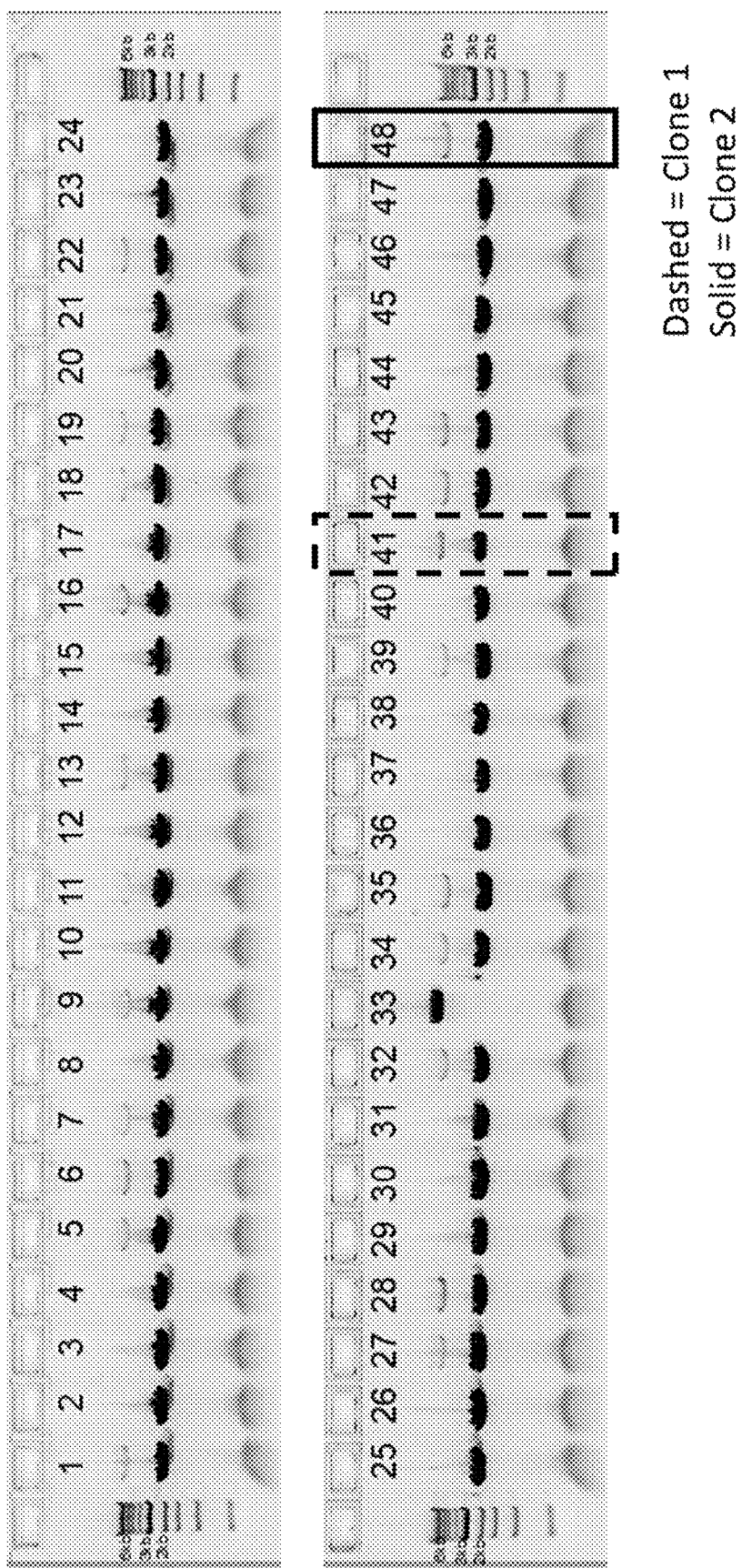
FIG. 11 provides an image of an agarose gel demonstrating B2M zygosity results. A 2.5 kb band indicates a WT unedited clone. Clones with a 6.6 kb band indicate successful integration of the IL15/IR15α-P2A-HLA-E trimer.

FIG. 11 shows the B2M zygosity results for various edited clones. The presence of a ~2.5 kb band indicated a WT genotype while the presence of a 6.6 kb band indicated successful integration of the KI construct into the B2M gene locus. Unedited clones would only have the WT band, clone heterozygous for the KI would have both bands, and homozygous clones would only have the KI band. The resulting amplicons were submitted for PCR cleanup and Sanger sequencing. Sanger sequencing results were input into Tsunami software along with the guide sequence. The resulting DNA sequences of the target 32M region were aligned in Snapgene software to determine indel identity and homo- or heterozygosity. For determining IL15/IR15α-P2A-HLA-E trimer knock-in genotyping in the target 32M sequence, PCR for relevant regions was performed using Platinum Taq Supermix (Invitrogen, cat #125320176 and Cat #11495017). The sequence of the PCR primers are presented in Table 26; and the cycling conditions provided in Table 27.

TABLE 26

B2M KI Primers

| Name | Type | Sequence (5'-3') | SEQ ID NO: |
|---|---|---|---|
| Poly-A-F | forward | AGGATTGGGAAGACAATAGCAGGCATGCTGGGGATGCGGTGG | 60 |
| B2M-geno-R1 | reverse | GCTCTGGAGAATCTCACGCAGAAGGCAGGCGTTTTTCTTAAAAAAAAATGCACGAATTA | 61 |

TABLE 27

B2M KI PCR Cycling Parameters

| Step | Temperature | Time | Cycles |
|---|---|---|---|
| Denaturation | 98° C. | 30 sec | 1 |
| Denaturation | 98° C. | 10 sec | 30 |
| Annealing | 65° C. | 30 sec | |
| Extension | 72° C. | 1 min 30 sec | |
| Elongation | 72° C. | 5 min | 1 |
| Hold | 4° C. | hold | |

Figure 12:
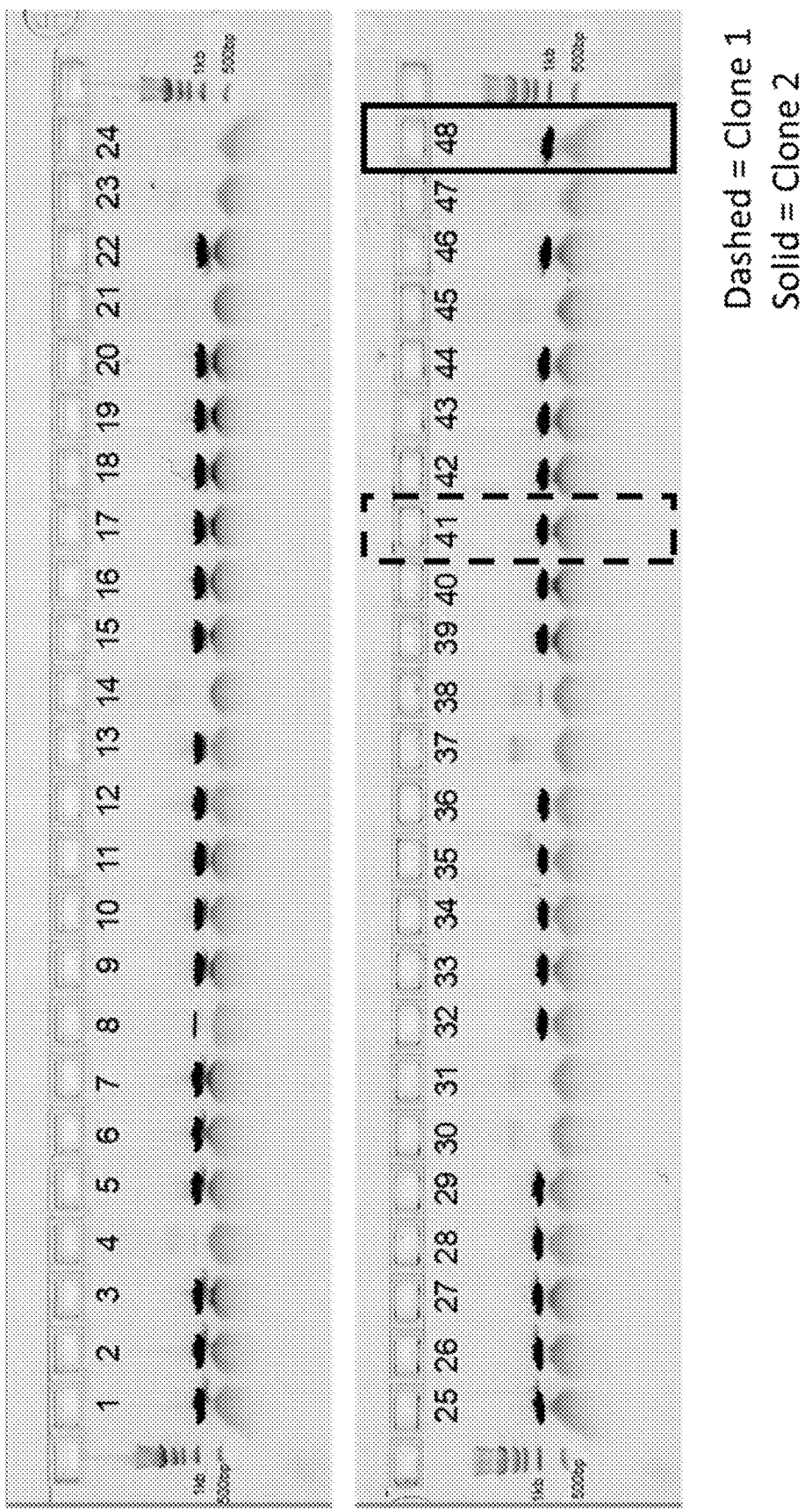
FIG. 12 provides an image of an agarose gel demonstrating B2M knock-in genotyping results. No band indicates a WT unedited clone. A 1.1 kb band indicates successful integration of the IL15/IR15α-P2A-HLA-E trimer.
Figure 13:
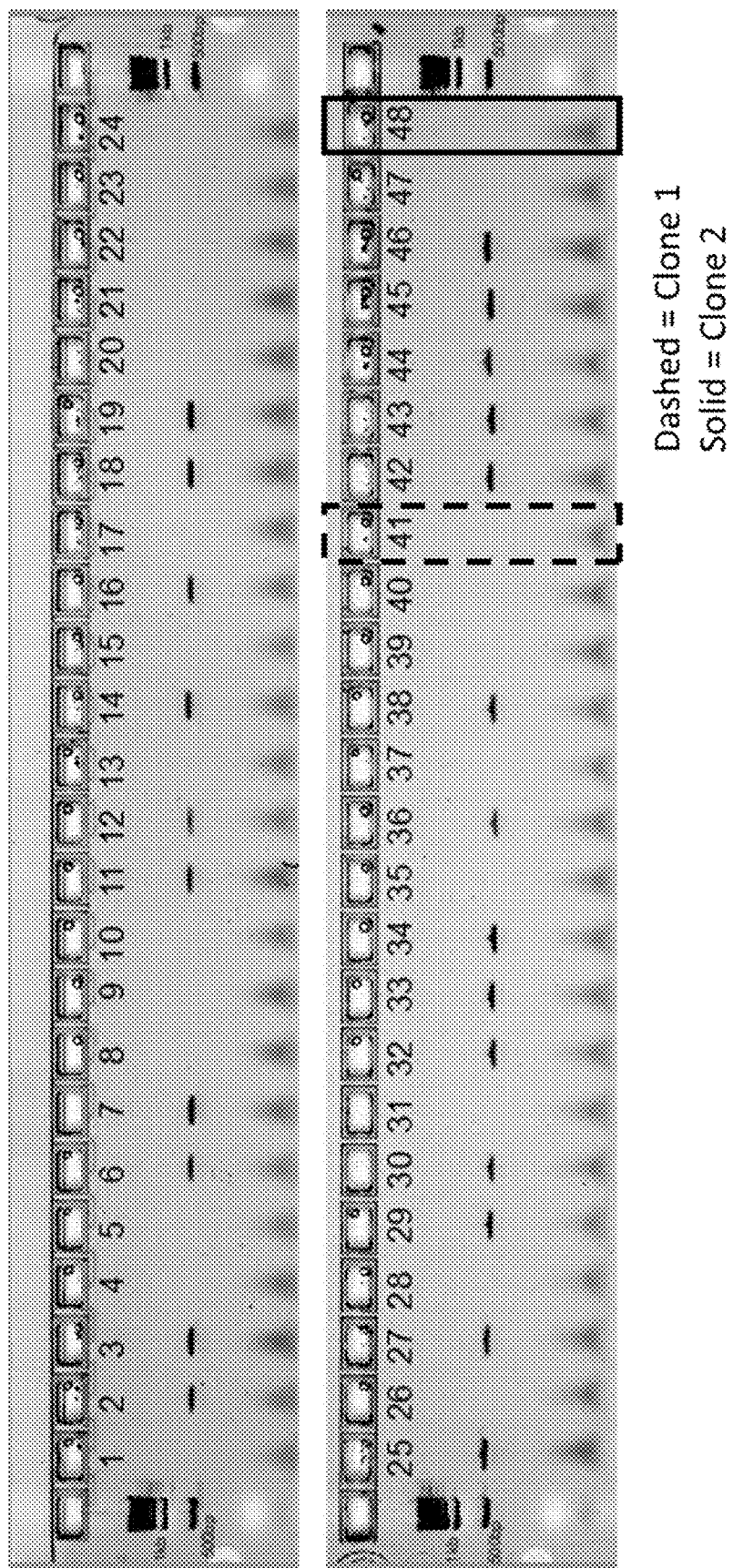
FIG. 13 provides an image of an agarose gel demonstrating CIITA genotyping results. A 557 bp indicates a WT unedited clone. Edited constructs do not have a band.

FIG. 12 shows the B2M KI genotyping results for various edited clones. The presence of a 1.1 kb band indicated successful integration of the KI construct into the B2M gene locus, while the absence of a band indicated a WT genotype. For determining indels in the target CIITA sequence, PCR for relevant regions was performed using Platinum Taq Supermix (Invitrogen, cat #125320176 and Cat #11495017). The sequence of the PCR primers are presented in Table 16; and the cycling conditions provided in Table 17. FIG. 13 shows the CIITA indel results for various edited clones. The presence of a 557 bp band indicated a WT genotype which would be found in clones that are unedited or are heterozygous for the KI construct, as homozygous clones will not have a band.

For determining CIITA zygosity, PCR for relevant regions was performed using Platinum Taq Supermix (Invitrogen, cat #125320176 and Cat #11495017). The sequences of the PCR primers are presented in Table 28; and the cycling conditions provided in Table 29

TABLE 28

CIITA Zygosity Primers

| Name | Type | Sequence (5'-3') | SEQ ID NO: |
|---|---|---|---|
| CIITA-OUT-F | forward | GCCCCACCCCTCCTACTTTATGTCTCCATGGATTTGCCTGTTTTGGTCATTTCA | 62 |
| CIITA-OUT-R | reverse | CTCTAATGCAAACTTGGGTAGGTCGTTTCACCTCTCTAAACCTCAATTTCCTCATTTG | 63 |

TABLE 29

CIITA Zygosity PCR Cycling Parameters

| Step | Temperature | Time | Cycles |
|---|---|---|---|
| Denaturation | 94° C. | 2 min | 1 |
| Denaturation | 98° C. | 10 sec | 30 |
| Annealing | 65° C. | 30 sec | |
| Extension | 68° C. | 5 min 30 sec | |
| Elongation | 68° C. | 5 min | 1 |
| Hold | 4° C. | hold | |

Figure 14:
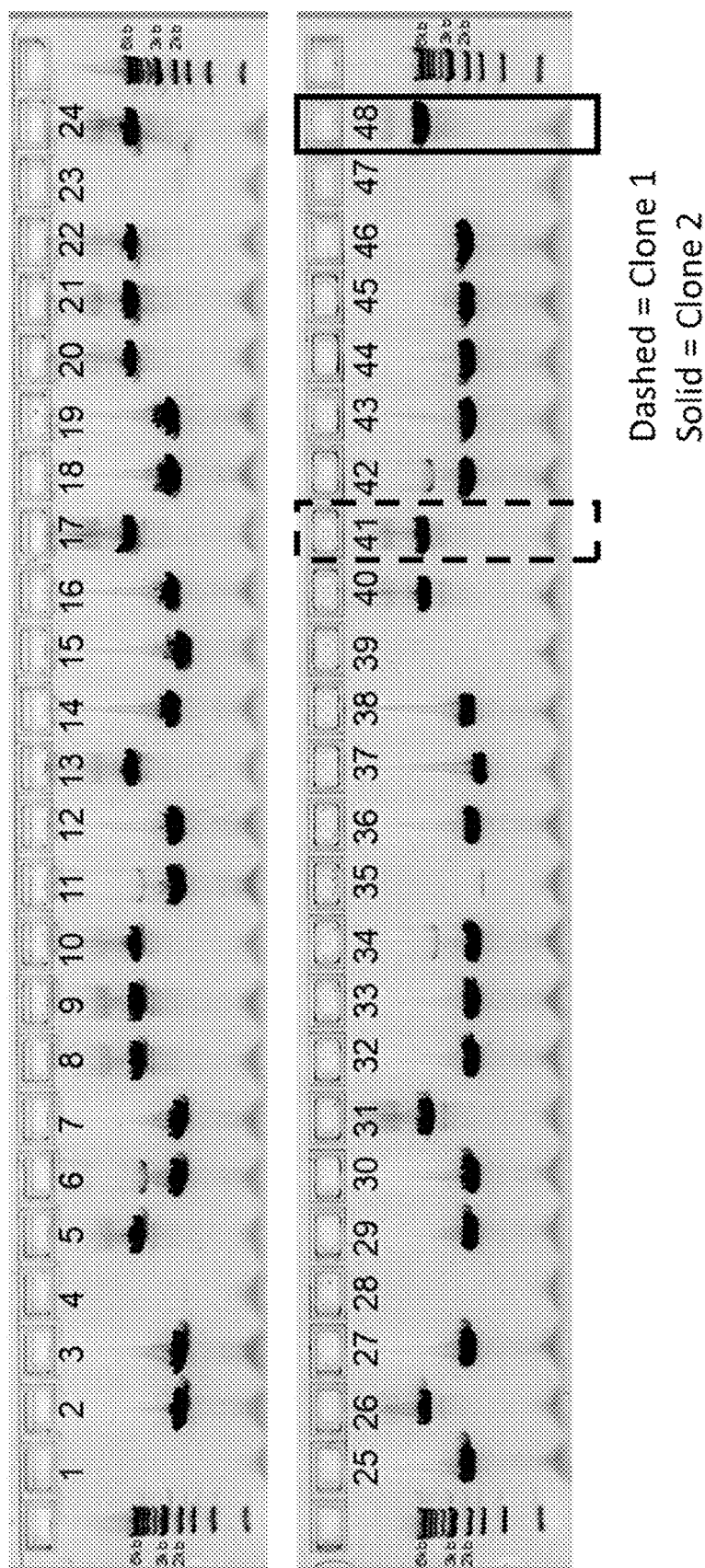
FIG. 14 provides an image of an agarose gel demonstrating CIITA zygosity results. results. A 2.5 kb band indicates a WT unedited clone. A 5.6 kb band indicates successful integration of the BCMA-CAR into the CIITA gene locus.

FIG. 14 shows the CIITA zygosity results for various edited clones. The presence of a ~2.5 kb band indicated a WT genotype while the presence of a 5.6 kb band indicated successful integration of the KI construct into the CIITA gene locus. Unedited clones would only have the WT band, clone heterozygous for the KI would have both bands, and homozygous clones would only have the KI band. The resulting amplicons were submitted for PCR cleanup and Sanger sequencing. Sanger sequencing results were input into Tsunami software along with the guide sequence. The resulting DNA sequences of the target CIITA region were aligned in Snapgene software to determine indel identity and homo- or heterozygosity.

For determining BCMA CAR knock-in genotyping in the target CIITA sequence, PCR for relevant regions was performed using Platinum Taq Supermix (Invitrogen, cat #125320176 and Cat #11495017). The sequences of the PCR primers are presented in Table 30; and the cycling conditions provided in Table 31.

TABLE 30

CIITA KI Primer

| Name | Type | Sequence (5'-3') | SEQ ID NO: |
|---|---|---|---|
| CD3Z-seq-F1 | forward | GAGTGAAGTTTTCCCGAAGCGCAGACGCTCCGGCATATCAGCAAGGACAG | 64 |
| CIITA-OUT-R | reverse | CTCTAATGCAAACTTGGGTAGGTCGTTTCACCTCTCTAAACCTCAATTTCCTCATTTG | 65 |

TABLE 31

CIITA KI PCR Cycling Parameters

| Step | Temperature | Time | Cycles |
|---|---|---|---|
| Denaturation | 98° C. | 30 sec | 1 |
| Denaturation | 98° C. | 10 sec | 30 |
| Annealing | 65° C. | 30 sec | |
| Extension | 72° C. | 1 min 30 sec | |
| Elongation | 72° C. | 5 min | 1 |
| Hold | 4° C. | hold | |

Figure 15:
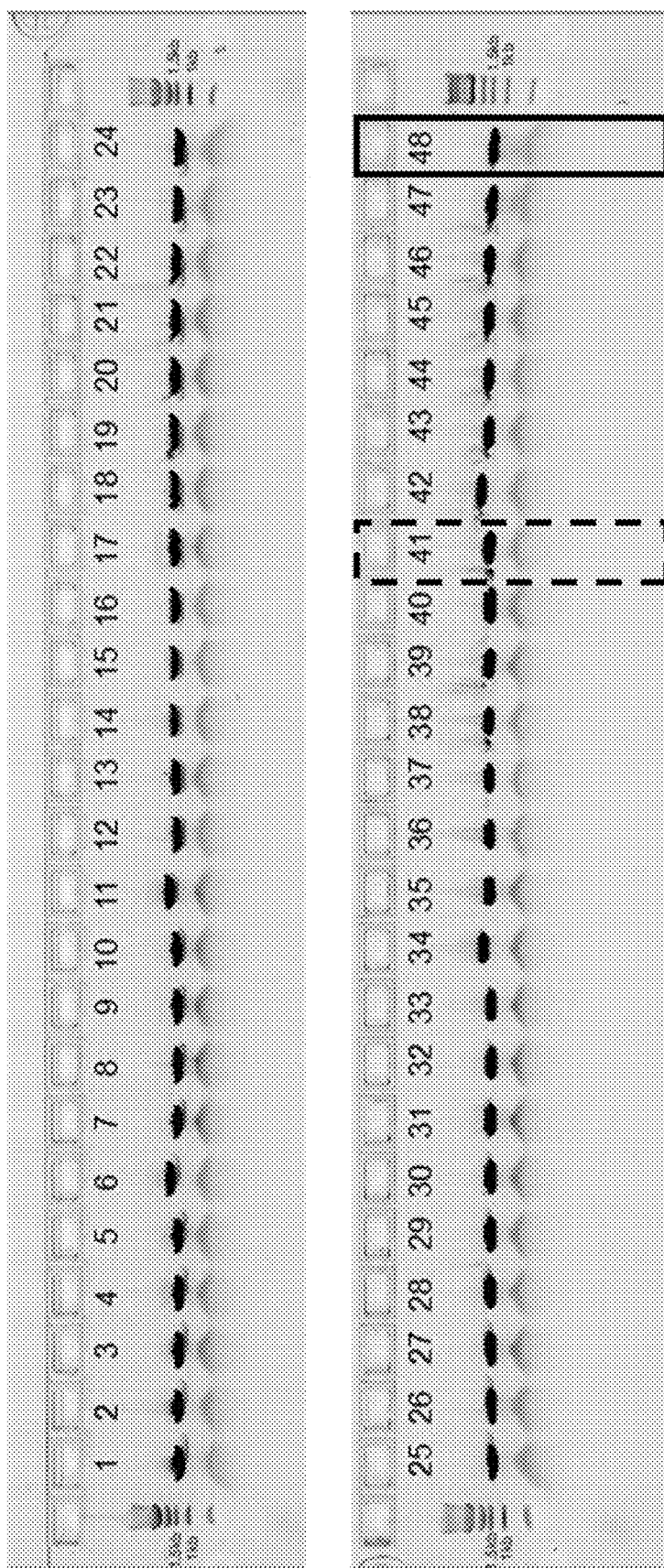
FIG. 15 provides an image of an agarose gel demonstrating CIITA genotyping results. The presence of a 1.5 kb band indicates successful integration of the KI construct into the CIITA gene locus, while the absence of a band indicates a WT genotype.

FIG. 15 shows the CIITA KI genotyping results for various edited clones. The presence of a 1.5 kb band indicated successful integration of the KI construct into the CIITA gene locus, while the absence of a band indicated a WT genotype. For determining indels in the target ADAM17 sequence, PCR for relevant regions was performed using Platinum Taq Supermix (Invitrogen, cat #125320176 and Cat #11495017). The sequence of the PCR primers are presented in Table 13; and the cycling conditions provided in Table 14. The resulting amplicons were submitted for PCR cleanup and Sanger sequencing. Sanger sequencing results were input into Tsunami software along with the guide sequence. The resulting DNA sequences of the target ADAM17 region were aligned in Snapgene software to determine indel identity and homo- or heterozygosity.

Based on the PCR and Sanger sequencing analysis of the edited clones, the clone shown in lane 41 in FIGS. 10-15 was chosen as "clone 1" and the clone shown in lane 48 was chosen as "clone 2," which were shown to have the BCMA CAR KI and the IL15/ILRa-P2A-HLA-E KI, while the sequencing data confirmed that B2M, CIITA, and ADAM17 were completely knocked-out. Clone 1 was heterozygous for the B2M KI and had an indel of +1T in the B2M WT band (Table 32). Clone 1 was homozygous for the CIITA KI and contained a homozygous +1G indel in the ADAM17 WT band (Table 33).

TABLE 32

KI genotypes of IL15/IR15α-P2A-HLA-E trimer knock-in, BCMA CAR knock-in, CIITA Null, B2M Null, ADAM17 Null Human Pluripotent Stem Cells Clones

| Clone | IL-15/IR-15 fusion-P2A-HLA-E into B2M | BCMA CAR into CIITA |
|---|---|---|
| 1 | Heterozygous KI | Homozygous KI |
| 2 | Heterozygous KI | Homozygous KI |

TABLE 33

KO genotypes of IL15/IR15α-P2A-HLA-E trimer knock-in, BCMA CAR knock-in, CIITA Null, B2M Null, ADAM17 Null Human Pluripotent Stem Cells Clones

| Clone | B2M indel | CIITA indel | ADAM17 indel |
|---|---|---|---|
| 1 | KI/+1 T | KI/KI | +1 G/+1 G |
| 2 | KI/+1 T | KI/KI | −20/large insertion |

Confirmation of KI gene expression and KO status at the hiPSC stage. To detect the BCMA CAR, HLA-E, and IL15 surface expression, fluorescent antibodies were used (see Table 21). Undifferentiated clone 1, the hiPSC clone containing all the edits (IL15/IR15α-P2A-HLA-E trimer knock-in, BCMA CAR knock-in, CIITA Null, B2M Null, ADAM17 Null) was assessed by flow cytometry with unedited WT cells as a negative control (Table 34). The gene edited clone 1 showed >99% BCMA CAR expression, >99% HLA-E expression, and >99% IL15 expression. To confirm KO status, fluorescent antibodies for HLA-ABC were used (see Table 21) with unedited WT iNK cells as a negative control (Table 34).

TABLE 34

| | WT iPSC | Clone 1 iPSC |
|---|---|---|
| CAR$^+$ | 1.06% | 99.7% |
| HLA-E$^+$ | 0.22% | 100% |
| IL-15$^+$ | 0.03% | 99.2% |
| HLA-A, B, C (MHC-I)$^-$ | 97.3% | 0.74% |

Figure 16:
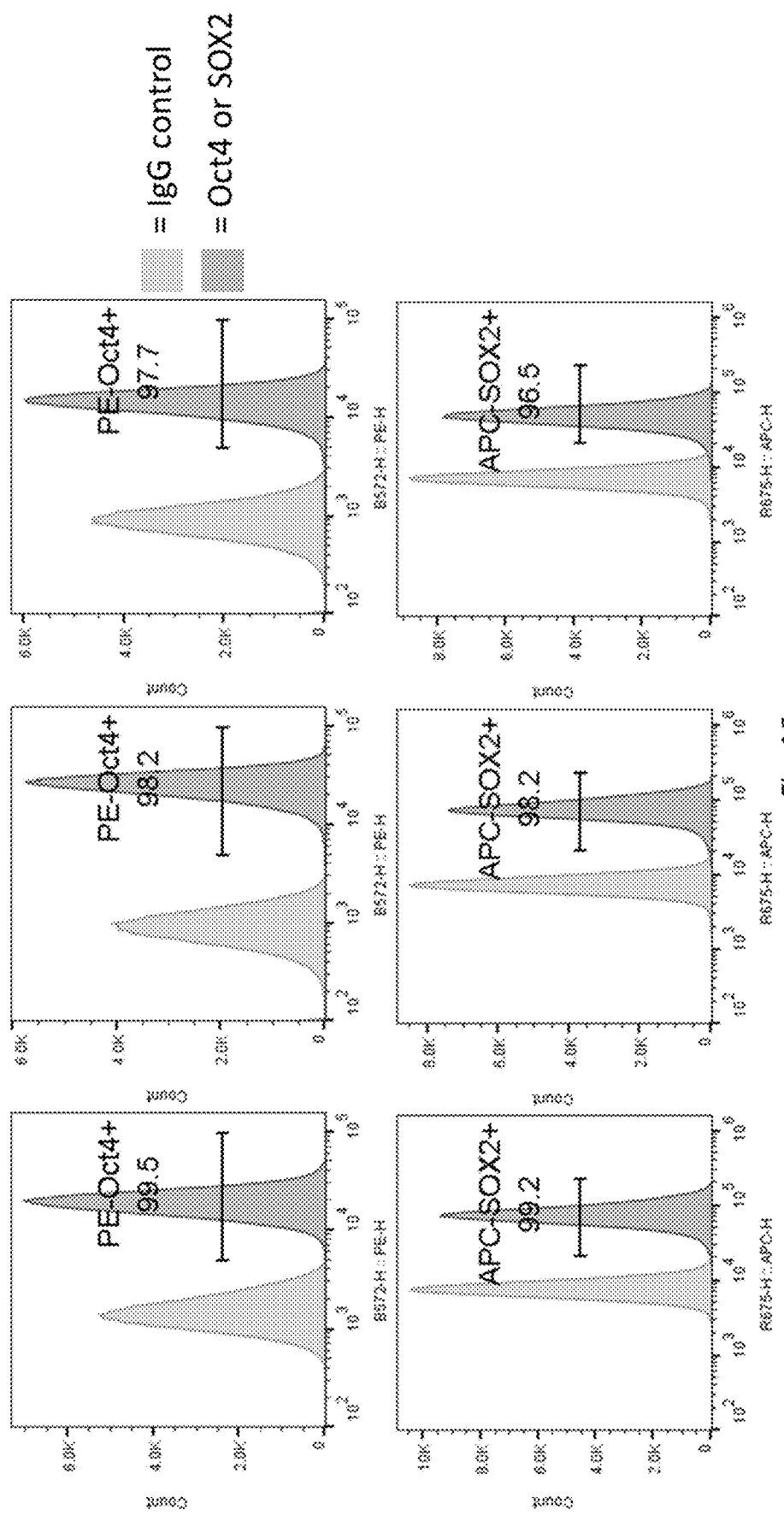
FIG. 16 provides histograms demonstrating pluripotency in hiPSC after genome editing. WT, Clone 1, and Clone 2 were stained for Oct4 and Sox2 and analyzed by flow cytometry.

Confirmation of hiPSC pluripotency after genome editing. To detect the Oct4 and Sox 2 intracellular expression fluorescent antibodies were used. iPS cells: WT and undifferentiated clones 1 and 2, containing all the edits (IL15/IR15α-P2A-HLA-E trimer knock-in, BCMA CAR knock-in, CIITA Null, B2M Null, ADAM17 Null) were assessed by flow cytometry. IgG-labeled cells served as a negative control (FIG. 16). Oct4 expression was 99.5% in WT, 98.2% in the gene edited clone 1 and 97.7% in the gene edited clone 2 (FIG. 16). There were the following percentages of Sox2-positive cells in iPSC populations: WT iPSC had >99%, edited clones 1 and 2 had >98 and >96% positive correspondently (FIG. 16). Edited clones retained high level of pluripotency.

Figure 17:
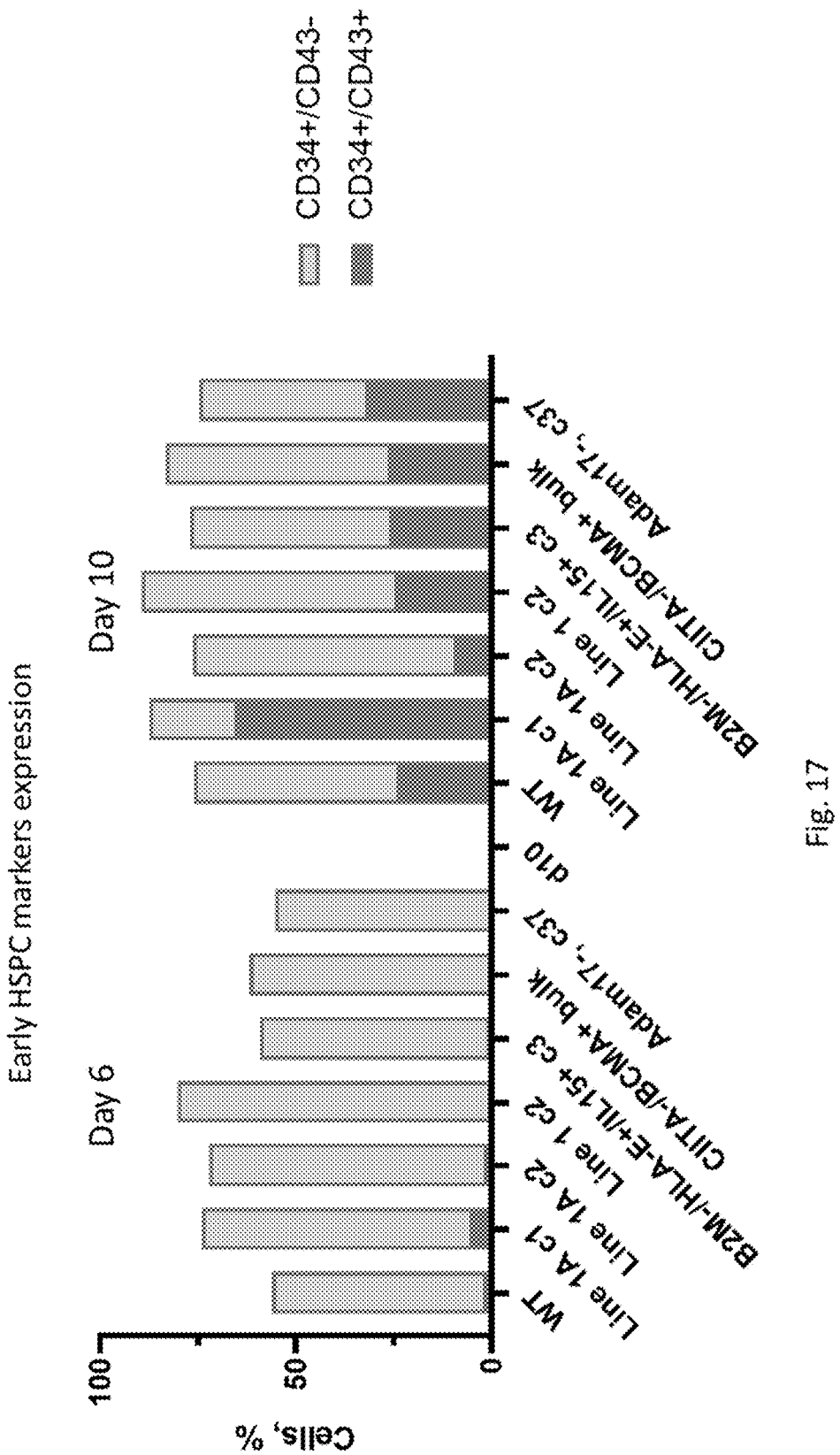
FIG. 17 provides a graph demonstrating CD34/CD43 expression in Clone 1 (Line 1A c1), Clone 2 (Line 1A c2), Clone 3 (B2M$^-$/HLA-E$^+$/IL15$^+$), a Line 1 clone, a CIITA$^-$/BCMA CAR$^+$ bulk population, and a ADAM17 KO clone ("Adam17$^-$, c37") cells compared to WT at Day 6 and Day 10 of differentiation from iPSC to iNK cells. Cells were analyzed by flow cytometry for CD34 and CD43 expression.
Figure 18:
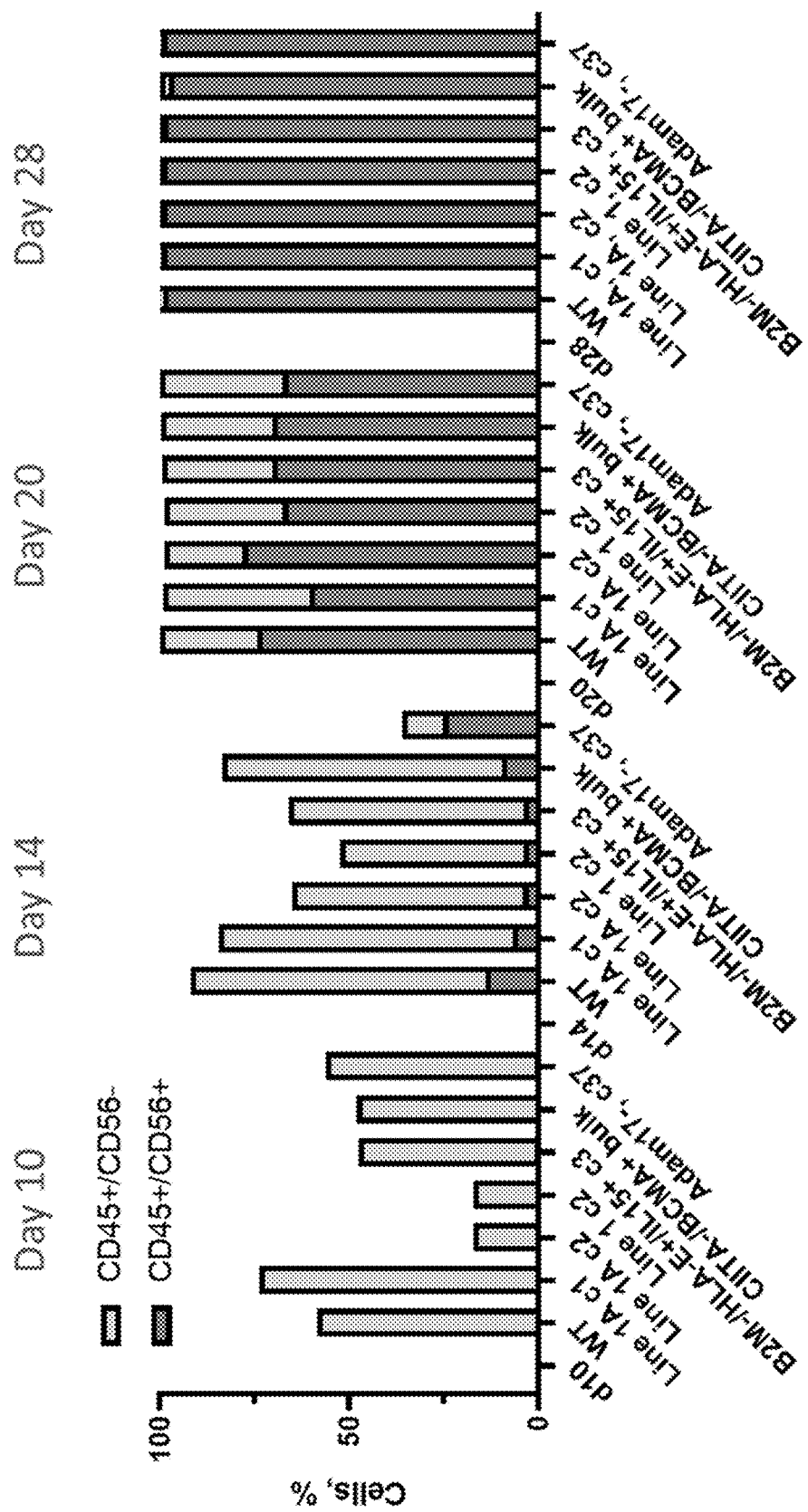
FIG. 18 provides a graph demonstrating CD45/CD56 expression in Clone 1 (Line 1A c1), Clone 2 (Line 1A c2), Clone 3 (B2M$^-$/HLA-E$^+$/IL15$^+$), a Line 1 clone 2, a CIITA$^-$/BCMA CAR$^+$ bulk population, and a ADAM17 KO clone ("Adam17$^-$, c37") cells compared to WT at Day 10 and Day 14, Day 20, and Day 28 of differentiation from iPSC to iNK cells. Cells were analyzed by flow cytometry for CD45 and CD56 expression.

Example 10: Differentiation and Characterization of IL15/IR15α-P2A-HLA-E Trimer Knock-In, BCMA CAR Knock-In, CIITA Null, B2M Null, ADAM17 Null hPSC WT, Clones 1 and 2 ("Line1A c1 and c2"; hiPSC gene edited clones containing the edits IL15/IR15α-P2A-HLA-E trimer knock-in, BCMA CAR knock-in, CIITA Null, B2M Null, ADAM17 Null), Clone 3 ("B2M$^-$/HLA-E$^+$/IL15$^+$ c3"); hiPSC gene edited clone containing the edits IL15/IR15α-P2A-HLA-E trimer knock-in, B2M Null), Line 1 clone 2 ("Line 1c2"; hiPSC gene edited clone containing the edits IL15/IR15α-P2A-HLA-E trimer knock-in, BCMA CAR knock-in, CIITA Null, B2M Null), a CIITA-BCMA CAR$^+$ bulk population, and a ADAM17 KO clone 37 ("Adam17$^-$, c37") were differentiated to iNK cells using Protocol 1, as described in Example 2. Flow cytometry of differentiated cells at Days 6 and 10 showed that all of the edited clones and bulk populations, including both edited iPSC clones 1 and 2, differentiated efficiently to HPSC (CD34$^+$/CD43-) cell population as compared with WT (FIG. 17). Edited iPSC clone 1 expressed CD43 earlier but that did not influence its overall differentiation into iNK and cytotoxicity. Throughout the differentiation process, cells were analyzed for CD45 and CD56 expression by flow cytometry (FIG. 18), showing efficient differentiation for all of the edited clones which was comparable to WT. By day 28, >99% of cells are CD56$^+$.

Figure 19A:
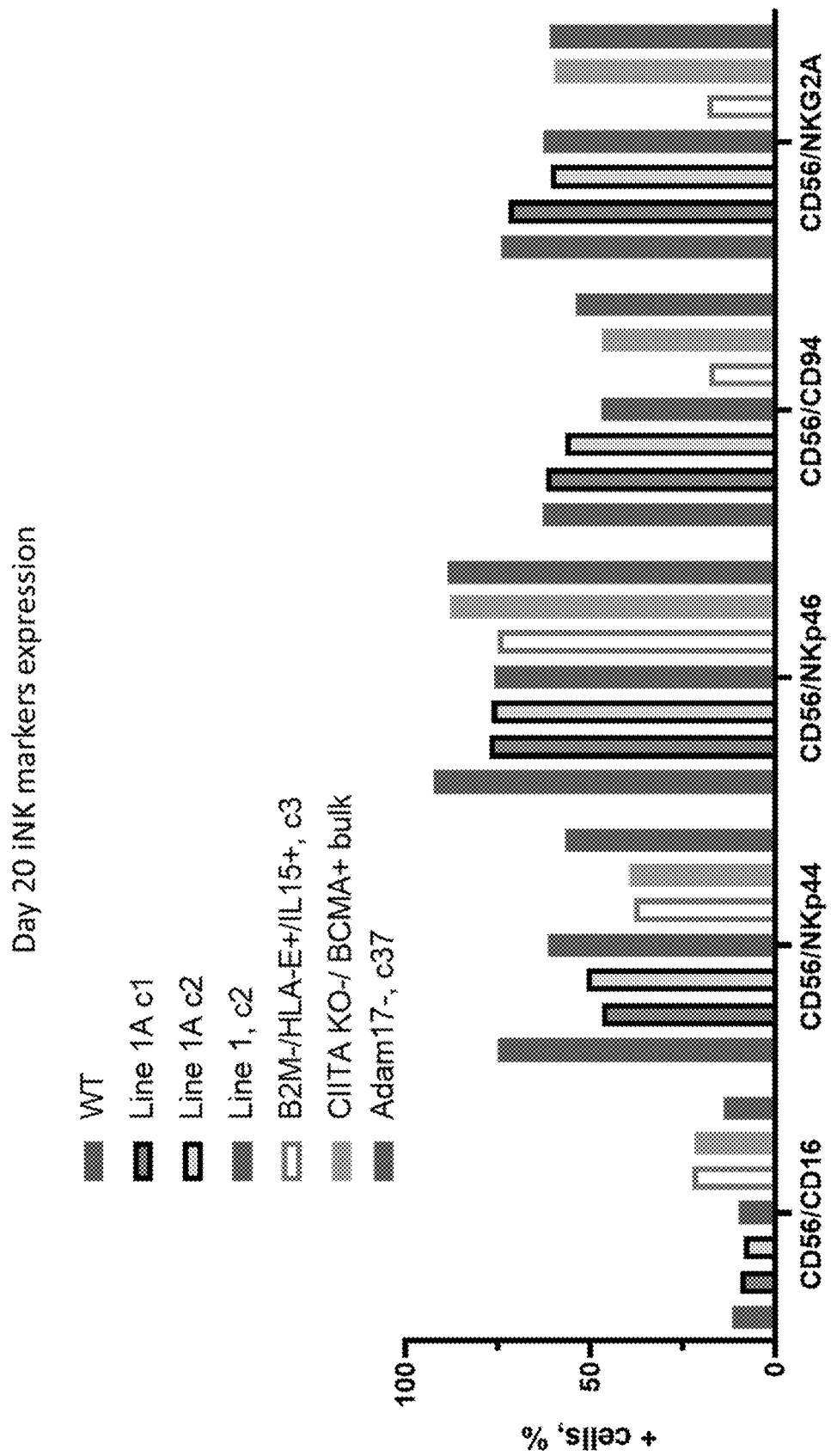
FIG. 19A provides a graph demonstrating expression of differentiation markers in Clone 1 (Line 1A c1), Clone 2 (Line 1A c2), Clone 3 (B2M$^-$/HLA-E$^+$/IL15$^+$), a Line 1 clone 2, a CIITA$^-$/BCMA CAR$^+$ bulk population, and a ADAM17 KO clone ("Adam17$^-$, c37") cells compared to WT at Day 20 of differentiation from iPSC to iNK cells. Cells were analyzed by flow cytometry for CD56$^+$/CD16$^+$, CD56$^+$/NKp44$^+$, CD56$^+$/NKp46$^+$, CD56$^+$/CD94$^+$, and CD56$^+$/NKG2A$^+$ expression.
Figure 19B:
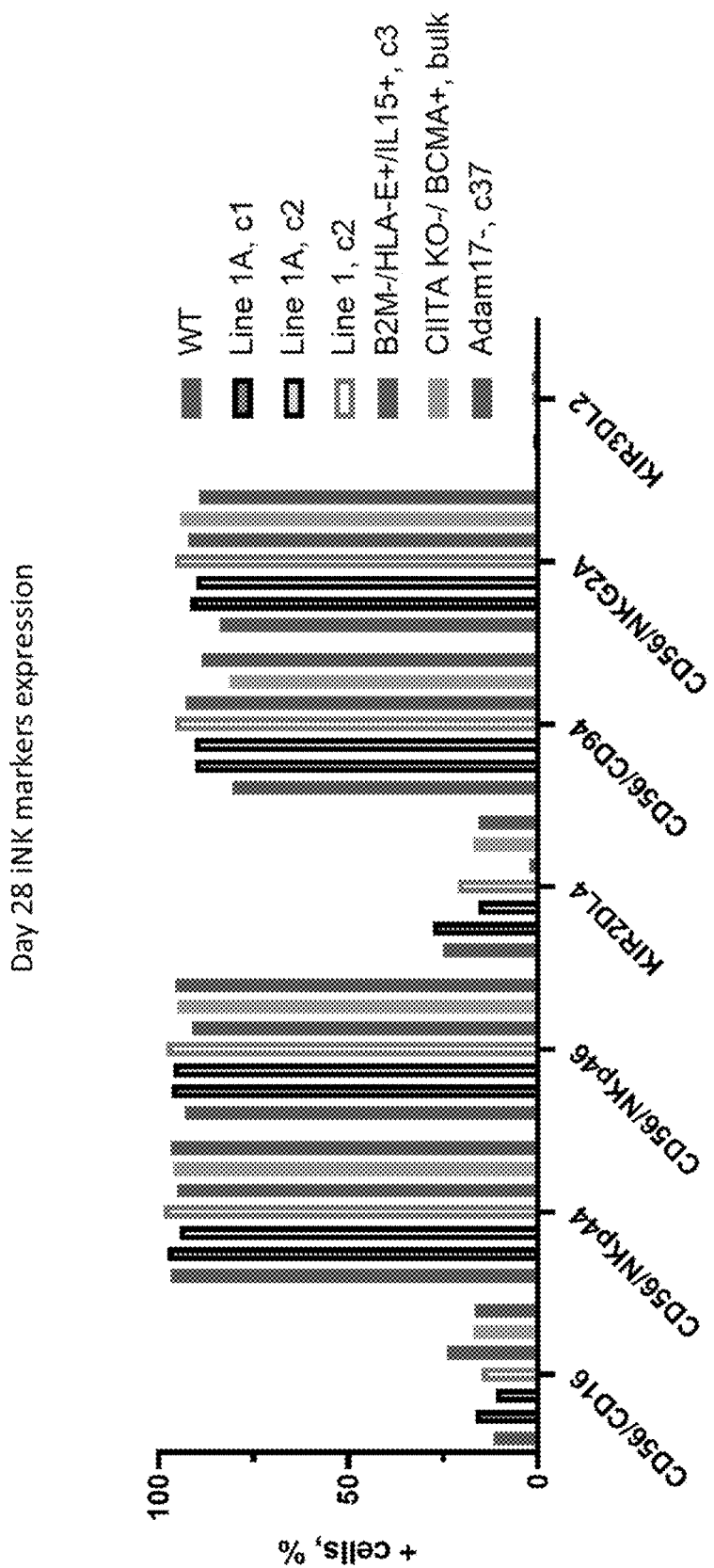
FIGS. 19B and 19C provide graphs demonstrating expression of differentiation markers in Clone 1 (Line 1A c1), Clone 2 (Line 1A c2), Clone 3 (B2M$^-$/HLA-E$^+$/IL15$^+$), a Line 1 clone 2, a CIITA$^-$/BCMA CAR$^+$ bulk population, and a ADAM17 KO clone ("Adam17$^-$, c37") cells compared to WT at Day 28 (FIG. 19B) and Day 35 (FIG. 19C) of differentiation from iPSC to iNK cells. Cells were analyzed by flow cytometry for CD56$^+$/CD16$^+$, CD56$^+$/NKp44$^+$, CD56$^+$/NKp46$^+$, CD56$^+$/CD94$^+$, CD56$^+$/NKG2A$^+$, KIR2DL4, and KIR3DL2 expression.
Figure 19C:
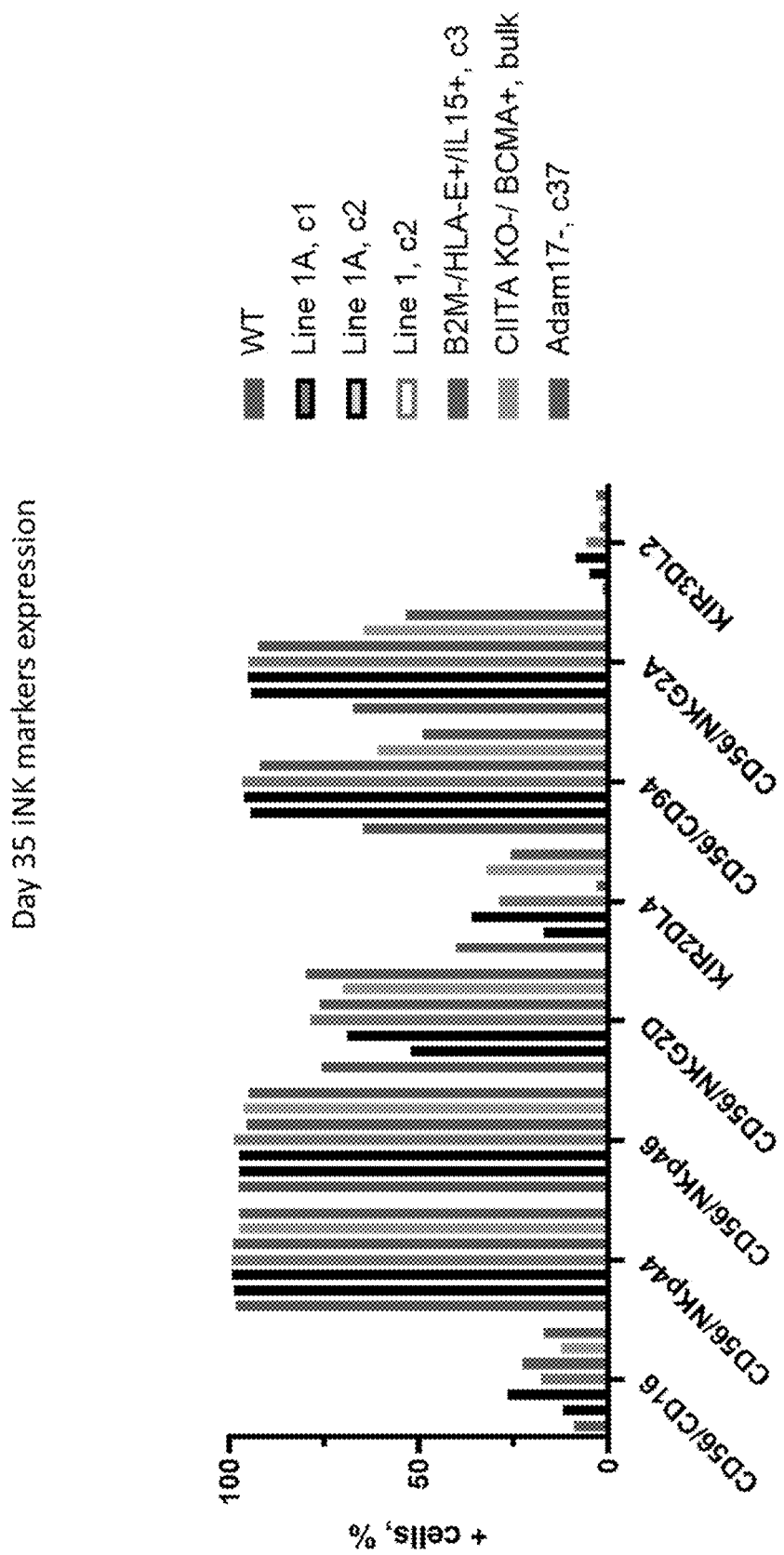
Figure 19D:
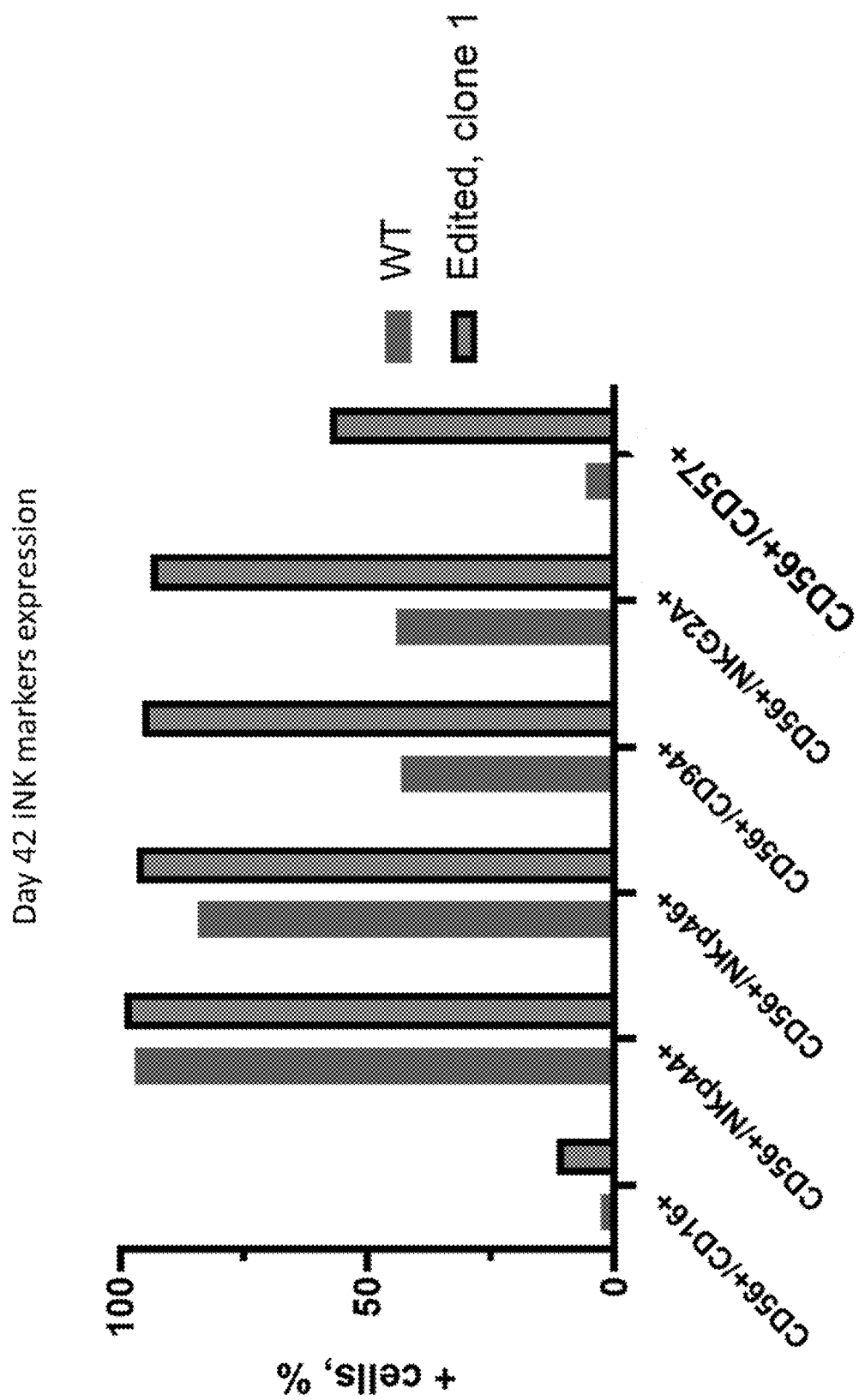
FIG. 19D provides a graph demonstrating expression of differentiation markers in Clone 1 compared to WT at Day 42 of differentiation from iPSC to iNK cells. Cells were analyzed by flow cytometry for CD56$^+$/CD16$^+$, CD56$^+$/NKp44$^+$, CD56$^+$/NKp46$^+$, CD56$^+$/CD94$^+$, CD56$^+$/NKG2A$^+$, and CD56$^+$/CD57$^+$ expression.

Flow cytometry was performed on digested cells aggregates on days 6, 10, and 14; and on single cells on days 20 (FIG. 19A), 28 (FIG. 19B), 35 (FIG. 19C), and 42 (FIG. 19D). Live cells were collected, washed with 1% BSA in PBS, and incubated with appropriate antibody cocktails in 5% BSA in PBS for 30 min on ice. The cells were washed and resuspended in 1% BSA in PBS containing 1:1000

SyTOX Blue cells viability dye followed by loading the plate on the Flow cytometer for analysis (see Table 35 for antibodies used). The differentiated Line 1A, clone 1 and 2, as well as edited IL15/IR15α-P2A-HLA-E trimer knock-in into B2M null, clone 3 iNK cells expressed a majority of maturation markers. On day 20 of differentiation all three edited lines displayed NK markers expression that was somewhat lower than WT. However the same markers were expressed at comparable or even higher than WT levels only a week later (at day 28).

TABLE 35

| antigen | fluorophore | company | catalog # | Dilution |
|---|---|---|---|---|
| CD16 | PE-Cy7 | BioLegend | 360708 | 1:50 |
| CD235a/ Glycophorin A | APC | BioLegend | 349114 | 1:10 |
| CD34 | FITC | Miltenyi | 130-113-178 | 1:25 |
| CD34 | PE | BD | 555822 | 1:10 |
| CD43 | BB515 | BD | 564542 | 1:500 |
| CD45 | PE-Cy7 | BD | 557748 | 1:100 |
| CD45 | BB515 | BD | 564585 | 1:100 |
| CD56 | PE | Miltenyi | 130-113-307 | 1:500 |
| CD56 | BB515 | BD | 564488 | 1:25 |
| CD56/NCAM1 | APC | BD | 555518 | 1:10 |
| CD57 | PE-Cy7 | BioLegend | 359624 | 1:10 |
| CD94/KLRD1 | APC | Miltenyi | 130-098-976 | 1:5 |
| CD95/Fas1 | FITC | BD | 555673 | 1:10 |
| HLA-ABC | FITC | eBioscience | 11-9983-42 | 1:10 |
| HLA-DR, DP, DQ | 647 | BioLegend | 361703 | 1:10 |
| HLA-E | APC | BioLegened | 342605 | 1:10 |
| hTACE/ADAM17 | PE | R&D | FAB9301P | 1:10 |
| IL-15 | APC | Invitrogen | MA5-23627 | 1:10 |
| IL-15 | PE | Invitrogen | MA5-23561 | 1:10 |
| IL-15 | FITC | Invitrogen | MA5-23664 | 1:10 |
| KIR2DL4/CD158d | APC | Miltenyi | 130-112-466 | 1:25 |
| KIR3DL2/CD158e/k | PE-Vio770 | Miltenyi | 130-116-180 | 1:100 |
| NKG2A/CD159a | APC | Miltenyi | 130-113-563 | 1:5 |
| NKG2D | BB515 | BD | 564566 | 1:2.5 |
| NKp44/CD336 | PE | BD | 558563 | 1:5 |
| NKp46/CD335 | PE-Cy7 | BD | 562101 | 1:5 |
| Oct3/4 | PE | BD Bioscience | 560186 | 1:10 |
| PD1/CD279 | APC | BioLegend | 621610 | 1:10 |
| PDL1/CD274 | PE-Cy7 | BD | 558017 | 1:10 |
| SOX2 | Alexa 647 | BD Bioscience | 562139 | 1:10 |
| Perforin, Clone delta G9, | PE | Miltenyi | 130-123-726 | 1:25 |
| Granzyme B Clone REA226, | APC | Miltenyi | 130-120-773 | 1:25 |

Confirmation of KI gene expression and KO status of edited cells differentiated to the WK stage. Using these differentiated Line 1A clone 1 cells, flow cytometry was repeated to assess KI gene expression and KO status. To detect the BCMA CAR, HLA-E, and 9%5 surface expression, fluorescent antibodies were used (see Table 21) with unedited WT iNK cells as a negative control (Table 36). The Line 1A clone 1-derived iNK cells showed >99% BCMA CAR expression, >90% HLA-E expression, and >99% 1115 expression. To confirm KO status, fluorescent antibodies for HLA-ABC were used (see Table 21) with unedited WT iNK cells as a negative control (Table 36).

TABLE 36

|  | WT iNK | Clone 1 iNK |
|---|---|---|
| CAR+ | 0.75% | 99.9% |
| HLA-E+ | 5.65% | 91% |
| IL-15+ | 0.33% | 99.1% |
| HLA-A, B, C (MHC-I)− | 99.8% | 0.8% |

Figure 20:
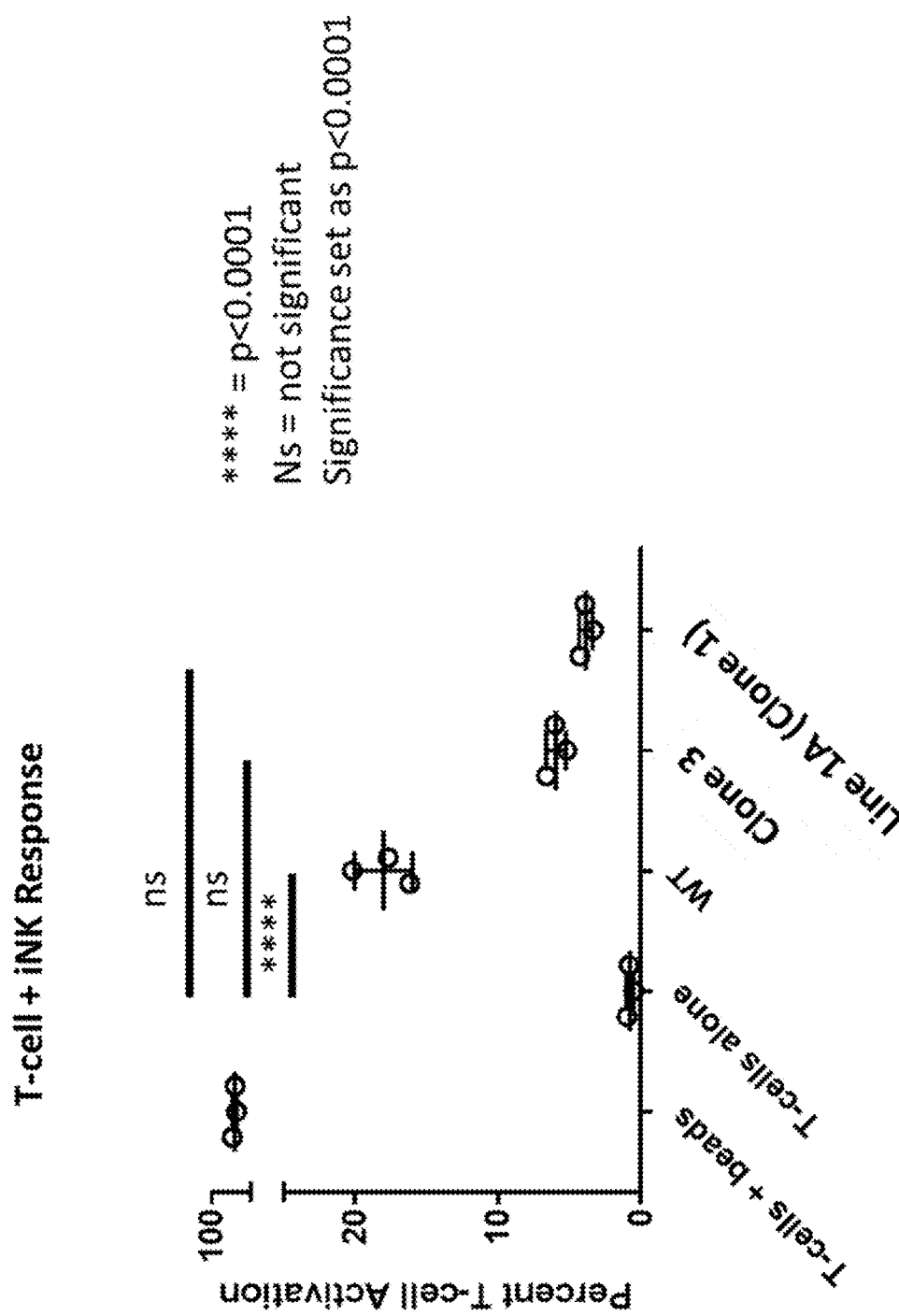
FIG. 20 provides a graph representing T-cell activation by differentiated iNK cells. Line 1A clone 1, Clone 3, and WT cells T cell activation was measured by carboxyfluorescein succinimidyl ester (CFSE) assay.

Immune phenotype of edited iNK cells. At the iNK stage, differentiated cells of clone 1 (an hiPSC gene edited clone containing all the edits (IL15/IR15α-P2A-HLA-E trimer knock-in, BCMA CAR knock-in, CIITA Null, B2M Null, ADAM17 Null) of Example 9 and clone 3 (an hiPSC gene edited clone containing B2M KO (IL15/IR15α-P2A-HLA-E trimer knock-in, B2M Null) of Example 8 and differentiated wild-type iPSC cells were co-cultured with donor derived T-cells that were labeled with CFSE. After 5 days of co-culture, the cells were analyzed for flow cytometry and the degree of CFSE loss was assessed. WT iNK cells induced a loss of CFSE signal in the T-cells, suggesting an allogeneic immune reaction had occurred. iNK cells derived from clone 1 or clone 3 did not produce CFSE loss in the T-cells, suggesting that these cells were immune-evasive (FIG. 20).

Figure 21A:
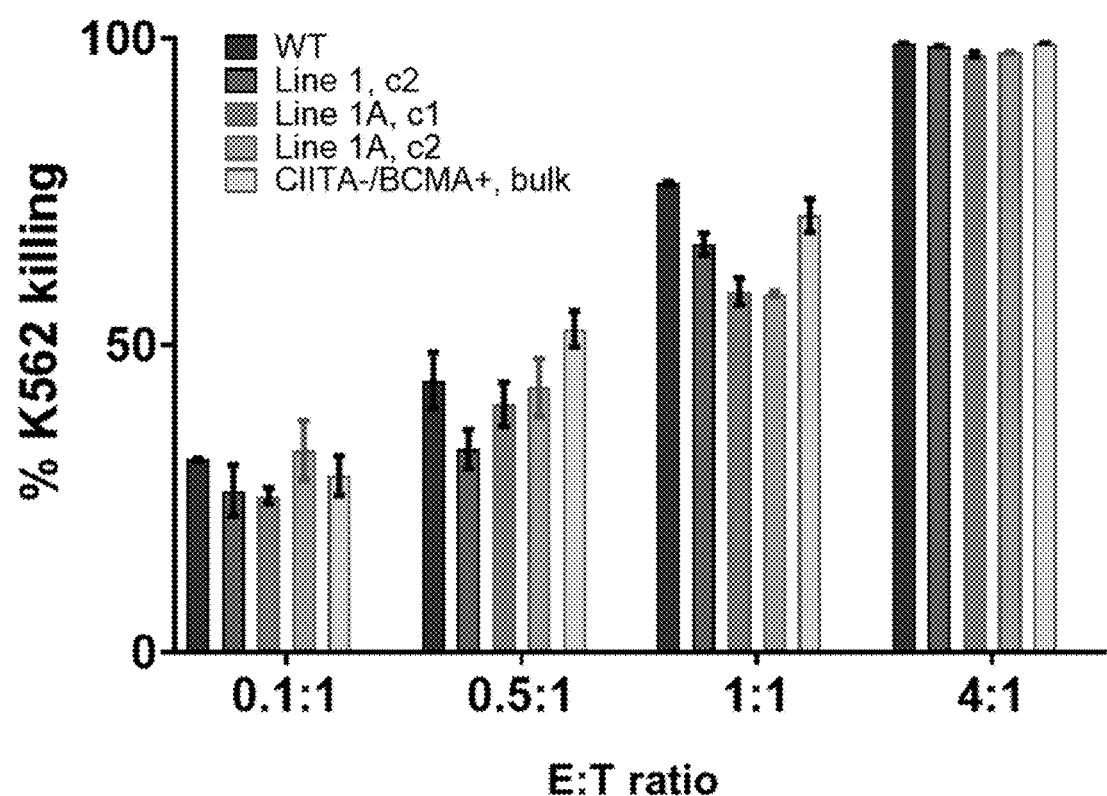
FIGS. 21A and 21B provide graphs measuring K562 (FIG. 21A) and RPMI (FIG. 21B) cell killing by the indicated iNK cell line. WT, Line 1 clone 2, Line 1A Clone 1, Line 1A Clone 2, and CIITA$^-$/BCMA CAR*("CIITA/BCMA*") bulk cells were cultured at different E:T ratios with K562 or RPMI cells for 24 hours.
Figure 21B:
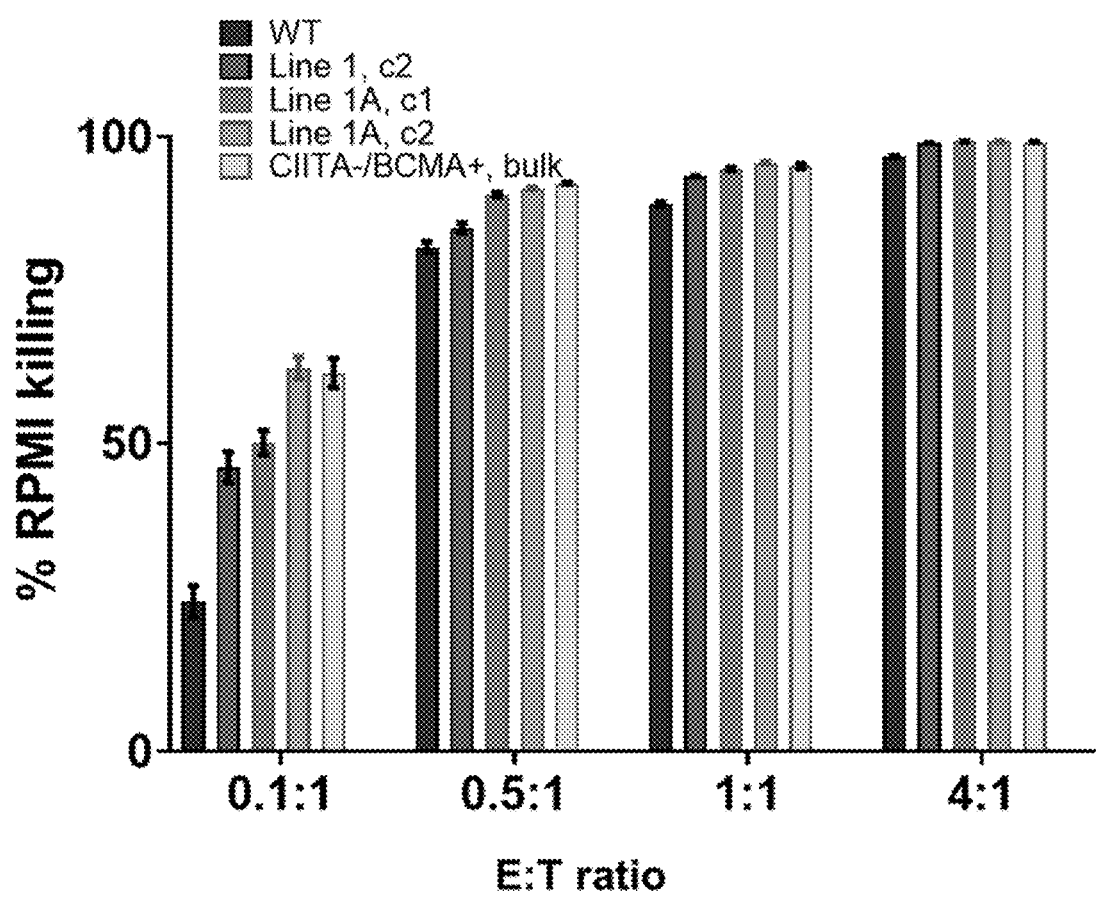

The cytotoxicity of the day 21 Line 1A clones 1 and 2, and Line 1 clone 2 (IL15/IR15α-P2A-HLA-E trimer knock-in, BCMA CAR knock-in, CIITA Null, B2M Null) cells towards K562 and RPMI cells was determined using a 24-hour killing assay, as described in Example 8. The WT and clones 1 and 2 line displayed effective cytotoxicity against K562 (FIG. 21A), while clones 1 and 2 also displayed greater cytotoxicity against BCMA+ expressing RPMI cancer cell line especially at lowest Effector to target cells ratio, 0.1:1 (FIG. 21B).

Figure 22:
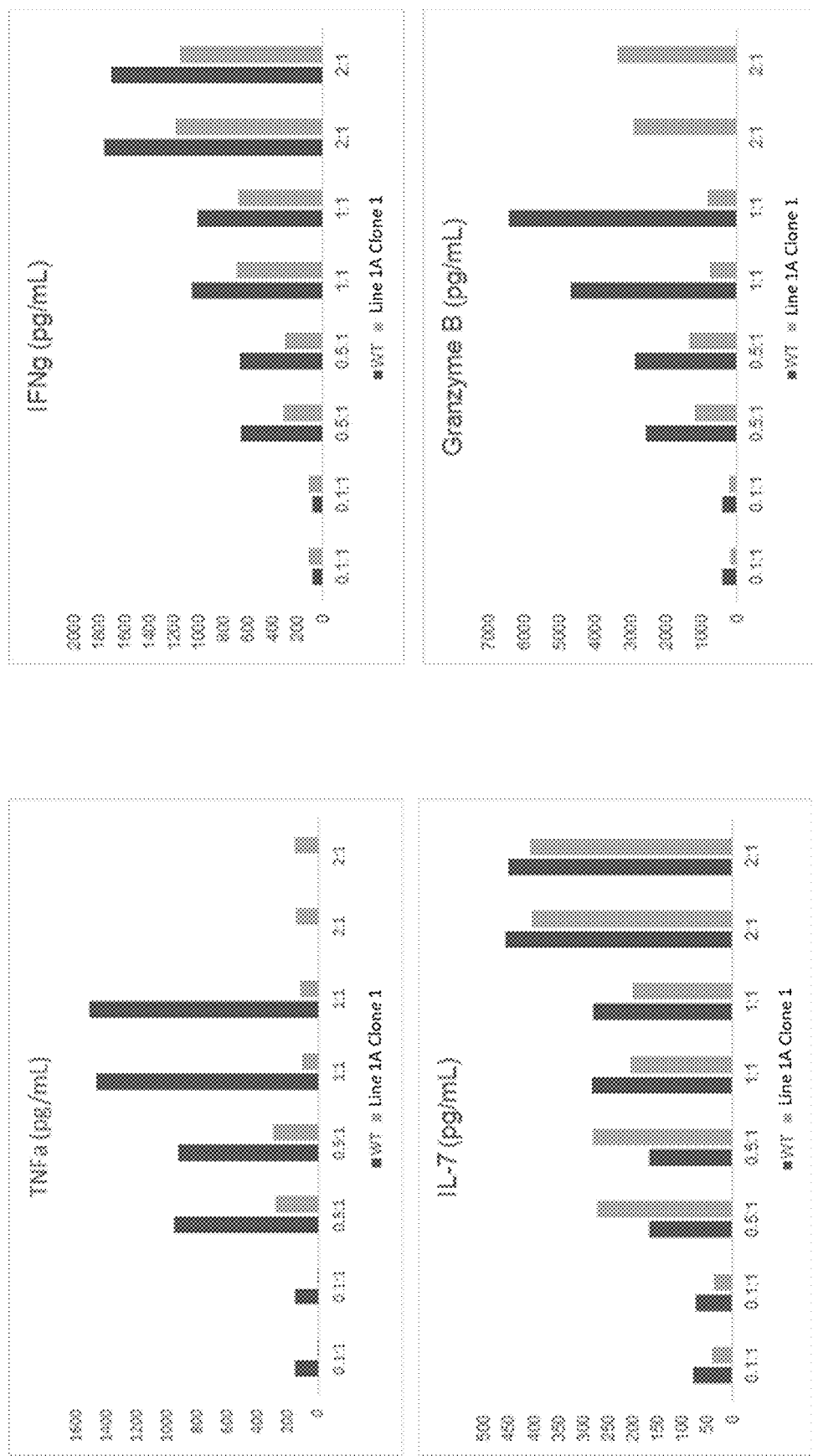
FIG. 22 provides graphs measuring TNFα, IFNg, IL-7, and Granzyme B levels in WT and Line 1A clone 1 cells co-cultured at different E:T ratios with RPMI cells.

Cytokines (IFNg, TNFa) were measured using the ProteinSimple Ella system, according to the manufacturer's instructions, with the software version v.3.5.2.20 of the Simple Plex Runner software, and Simple Plex Explorer software. Custom 8-plex Ella cartridges (32×8 Multiplex) were provided by ProteinSimple, along with dilution buffer which was used to dilute each sample (WT and Line 1A clone 1) at a 1:2 ratio prior to loading 40 μL sample per channel. As shown in FIG. 22, the IFNg levels in media correlated with an increased E:T ratio, being higher than WT in low E:T ratios (0.1:1). At higher E:T ratios, IFNg is somewhat lower in edited cells than WT, which might be the result of drastic decrease of target cells due to their efficient lysis over 24 hours. TNFα was higher in WT than in edited clone 1. This effect may be explained by lack of Adam17, a protease that cleaves TNFa.

Figure 23:
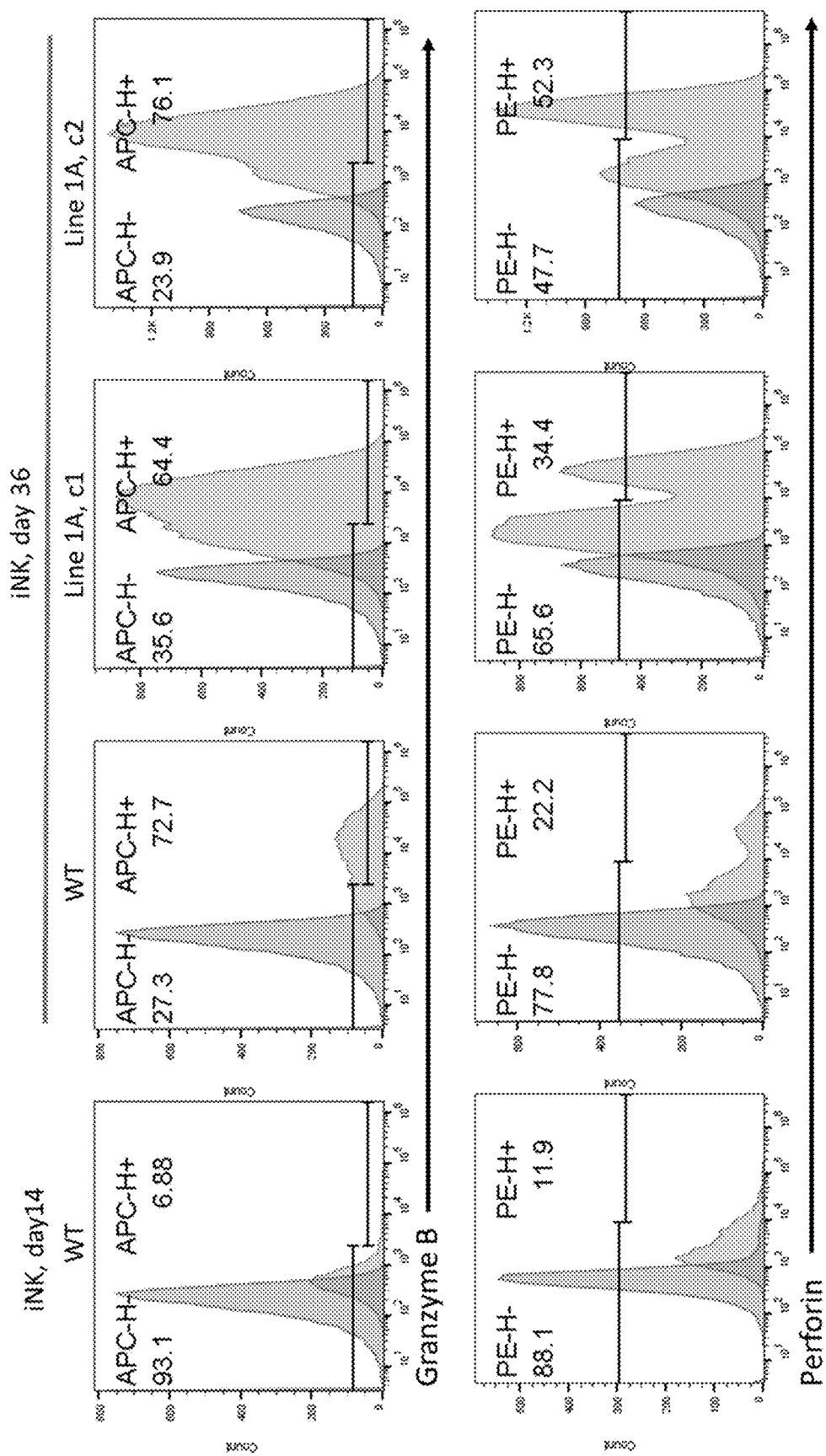
FIG. 23 provides flow cytometry graphs measuring Granzyme B and Perforin expressing cells at Day 14 (WT) and Day 36 (WT and Line 1A clones 1 and 2) of differentiation.

Perforin and granzyme-B expression in cells were measured by flow cytometry at day 14 and Day 36 of differentiation using commercially available antibodies. FIG. 23 shows that WT cells at day 14 of differentiation had little to no expression of perforin or granzyme-B but had higher expression at day 36. Line 1A clone 1 had similar expression patterns as WT.

Figure 24:
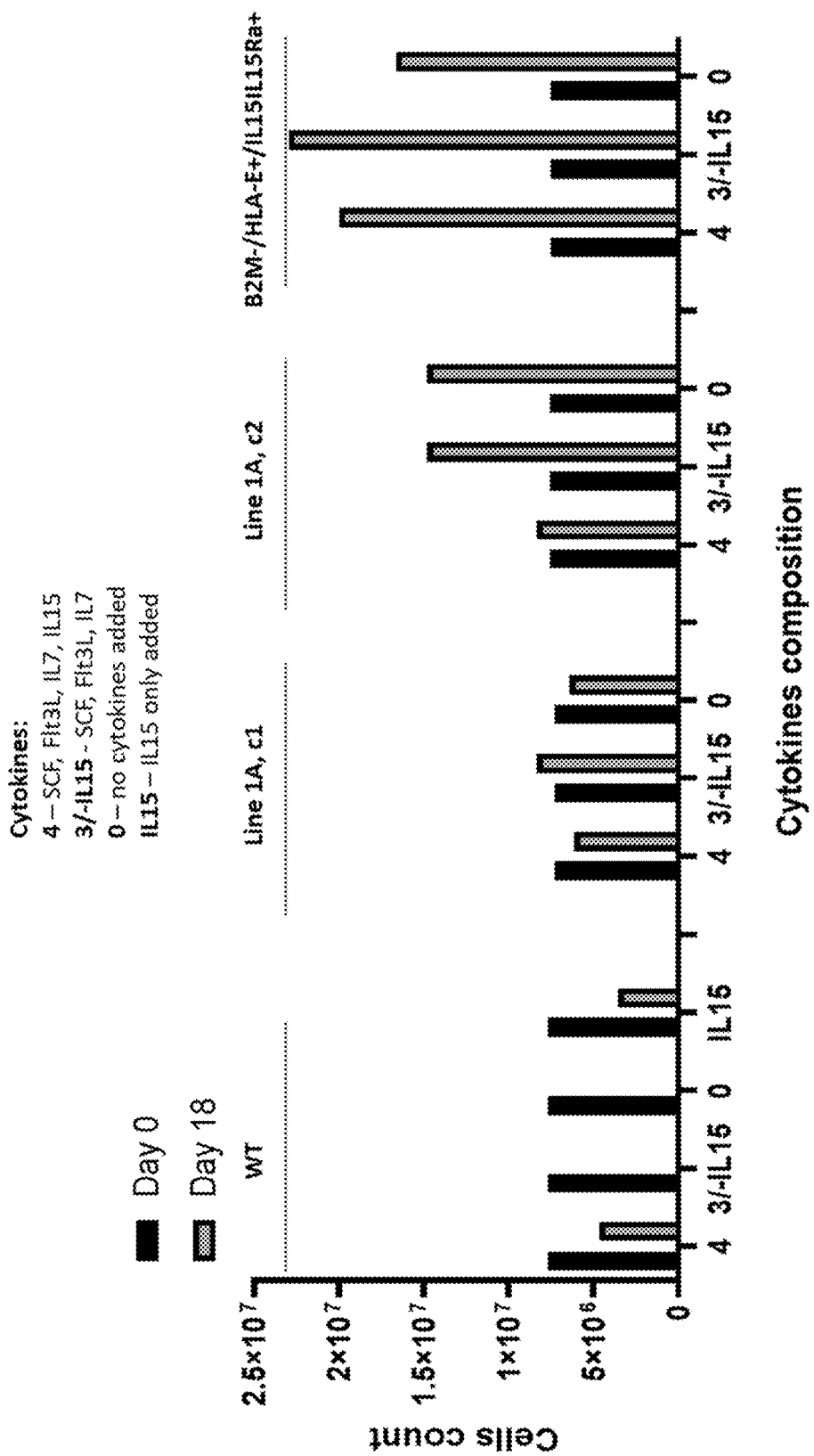
FIG. 24 provides graphs demonstrating cell count in wild-type (WT), Line 1A clone 1 ("Line 1A, c1"), Line 1A clone 2 ("Line 1A, c2"), and Clone 3 ("B2M$^-$/HLA-E$^+$/IL15/IL15Rα$^+$"; IL15/IR15α-P2A-HLA-E trimer knock-in, B2M Null hPSC) derived iNK cells when administered exogenous IL15 or not administered exogenous IL 15. Cells were administered SCF, Flt3L, IL7, and IL15 ("4"), SCF, Flt3L, and IL7 ("3/–IL15–"), no cytokines ("0"); or only IL15 ("IL15") on day 0 and day 9.

Day 20 iNKs differentiated from wild-type (WT), Line 1A clone 1 ("Line 1A, c1"), Line 1A clone 2 ("Line 1A, c2"), and Clone 3 ("B2M−/HILA-E+/IL15IL15Rα+"; IL15/IR15α-P2A-HLA-E trimer knock-in, B2M Null hPSC) derived iNK cells were plated at 5×10$^6$ cells/well and grown with or without exogenous cytokines. Cells were administered SCF (20 ng/mL), Flt3L (15 ng/mL), IL-7 (20 ng/mL), and IL-15 (15 ng/mL) ("4"), SCF, Flt3L, and IL-7 ("3/−IL15-"), no cytokines ("0"); or only IL-15 ("IL15") on day 0 and day 9 (FIG. 24). The edited clones persisted and expanded in the absence of exogenous IL15 while the WT iNK cell number declined in the absence of exogenous IL15.

Example 11: Generation and Selection of FAS gRNA, CISH gRNA, and REGNASE-1 gRNA

Targeting gRNAs were designed for targeting exons 1, 2, and 3 of the FAS coding sequence, exons 1, 2, and 3 of the CISH coding sequence, exons 2 and 4 of the REGNASE-1 coding sequence. The target sequences of the gRNAs are presented in Tables 37, 38, and 39, respectively. Each gRNA comprises an RNA spacer sequence corresponding to the target DNA sequence. These gRNAs had predicted low off-target scores based on sequence homology prediction using gRNA design software.

TABLE 37

FAS Target Sequences

| Name | Target Sequence (5'-3') | SEQ ID NO: | PAM |
|---|---|---|---|
| FAS Ex1 T7 | GGATTGCTCAACAACCATGC | 35 | TGG |
| FAS Ex1 T9 | GATTGCTCAACAACCATGCT | 37 | GGG |
| FAS Ex2 T1 | GTGACTGACATCAACTCCAA | 38 | GGG |
| FAS Ex2 T2 | CACTTGGGCATTAACACTTT | 39 | TGG |
| FAS Ex2 T3 | TTGGAAGGCCTGCATCATGA | 53 | TGG |
| FAS Ex2 T7 | ACTCCAAGGGATTGGAATTG | 55 | AGG |
| FAS Ex3 T1 | CTAGGGACTGCACAGTCAAT | 80 | GGG |

TABLE 38

CISH Target Sequences

| Name | Target Sequence (5'-3') | SEQ ID NO: | PAM |
|---|---|---|---|
| CISH Ex1 T2 | TCGCCGCTGCCGCGGGGACA | 81 | TGG |
| CISH Ex1 T18 | GACATGGTCCTCTGCGTTCA | 82 | GGG |
| CISH Ex2 T1 | GTCCGCTCCACAGCCAGCAA | 83 | AGG |
| CISH Ex2 T2 | GTTCCAGGGACGGGGCCCAC | 84 | AGG |
| CISH Ex3 T1 | TCGGGCCTCGCTGGCCGTAA | 85 | TGG |
| CISH Ex3 T2 | CGTACTAAGAACGTGCCTTC | 86 | TGG |
| CISH Ex3 T3 | GGGTTCCATTACGGCCAGCG | 87 | AGG |
| CISH Ex3 T5 | CAGGTGTTGTCGGGCCTCGC | 88 | TGG |
| CISH Ex3 T6 | TACTCAATGCGTACATTGGT | 89 | GGG |
| CISH Ex3 T9 | AAGGCTGACCACATCCGGAA | 90 | AGG |
| CISH Ex3 T11 | TACATTGGTGGGGCCACGAG | 91 | TGG |
| CISH Ex3 T14 | CTGTCAGTGAAAACCACTCG | 92 | TGG |

TABLE 39

REGNASE-1 Target Sequences

| Name | Target Sequence (5'-3') | SEQ ID NO: | PAM |
|---|---|---|---|
| REGNASE-1 Ex2 T1 | GGTCATCGATGGGAGCAACG | 93 | TGG |
| REGNASE-1 Ex2 T2 | CACCACCCCGCGGGACTAGA | 94 | GGG |
| ZC3H12A_Segment 2 T3 | GGTCTGGCGCTCCCGCTCGG | 95 | TGG |
| REGNASE-1 Ex2 T4 | CCACCACCCCGCGGGACTAG | 96 | AGG |
| REGNASE-1 Ex2 T5 | TTAGGGGTGCCACCACCCCG | 97 | CGG |

TABLE 39-continued

REGNASE-1 Target Sequences

| Name | Target Sequence (5'-3') | SEQ ID NO: | PAM |
|---|---|---|---|
| REGNASE-1 Ex4 T1 | TTCACACCATCACGACGCGT | 98 | GGG |
| ZC3H12A_Segment 4 T2 | ACACCATCACGACGCGTGGG | 99 | TGG |
| ZC3H12A_Segment 4 T3 | CTACGAGTCTGACGGGATCG | 100 | TGG |
| ZC3H12A_Segment 4 T7 | ACGACGCGTGGGTGGCAAGC | 101 | GGG |

To assess their cutting efficiency in hPSCs, iPS cells were electroporated using the Neon Electroporator (Neon Transfection Kit ThermoFisher Cat #MPK5000) with a ribonucleoprotein (RNP) mixture of Cas9 protein and guide RNA at a molar ratio of 5:1 (gRNA:Cas9) with absolute values of 125 pmol Cas9 and 625 pmol gRNA. To form the RNP complex, gRNA and Cas9 were combined in one vessel with R-buffer (Neon Transfection Kit) to a total volume of 25 µL and incubated for 15 min at RT. Cells were dissociated using ACCUTASE®, then resuspended in STEMFLEX™ media (Gibco, cat #11320033), counted using an NC-200 (ChemoMetec) and centrifuged. A total of 1×10$^6$ cells were resuspended with the RNP complex and R-buffer was added to a total volume of 125 µL. This mixture was then electroporated with 1 pulse for 20 ms at 1500 V and 1 pulse for 100 ms at 500 V. Following electroporation, the cells were pipetted out into an Eppendorf tube filled with STEMFLEX™ media with REVITACELL™ Supplement (100×). This cell suspension was then plated into tissue culture dishes pre-coated with BIOLAMININ 521 CTG at 1:10 dilution. Cells were cultured in a normoxia incubator (37° C., 8% CO$_2$) for 48 hours. After 48 hours, genomic DNA was harvested from the cells using QuickExtract (Lucigen, Middleton, Wis.; Cat #QE09050).

PCR for the target sequences was performed and the resulting amplified DNA was assessed for cutting efficiency by TIDE analysis. PCR for relevant regions was performed using Platinum Taq Supermix (Invitrogen, cat #125320176 and Cat #11495017). The resulting amplicons were submitted for PCR cleanup and Sanger sequencing. Sanger sequencing results were input into Tsunami software along with the guide sequence. Indel percentages and identities were calculated by the software. Particular gRNAs were then selected based on their indel frequency in hPSCs. FAS Ex1 T9 (SEQ ID NO; 37), CISH Ex1 T18 (SEQ ID NO: 82), and REGNASE-1 Ex2-T2 (SEQ ID NO: 94) were chosen for further clone generation due to their high on-target activity.

Example 12: Generation of IL15/IR15α-P2A-HLA-E Trimer Knock-In, BCMA CAR Knock-In, CIITA Null, B2M Null, ADAM17 Null, FAS Null, CISH Null, and REGNASE-1 Null hPSCs FAS Ex1 T9 (SEQ ID NO: 37), CISH Ex1 T18 (SEQ ID NO: 82), and REGNASE-1 Ex2 T2 (SEQ ID NO: 94) gRNAs were used to knock-out the FAS, CISH, and REGNASE-1 genes, respectively. IL15/IR15α-P2A-HLA-E trimer KI, BCMA CAR KI, CIITA Null, B2M Null, ADAM17 Null cells as described in Examples 9 and 10 were electroporated using the Neon Electroporator with RNP mixtures of Cas9 protein and guide RNA at a molar ratio of 5:1 (gRNA:Cas9) with absolute values of 125 pmol Cas9 and 625 pmol gRNA per 1 million cells. To form the RNP complexes, gRNA and Cas9 were combined in one vessel with R-buffer (Neon Transfection Kit) to a total volume of 25-50 μL and incubated for 15 min at room temperature (RT). This mixture was then combined with the cells to a total volume of ~115 μL using R-buffer. This mixture was then electroporated with 1 pulse for 20 ms at 1500 V followed by 1 pulse for 100 ms at 500 V. Following electroporation, the cells were pipetted out into a 6 well plate filled with STEMFLEX™ media with REVITACELL™ Supplement (100×) and laminin 511. Cells were cultured in a normoxia incubator (37° C., 8% CO$_2$).

Three to five days post electroporation, the cells were single-cell sorted as described in Example 1. The anti-BCMA CAR antibody (see Table 21) was used for FACS-sorting into 96-well plates. For FACS-sorting, unedited cells served as a negative control. After sorting, the cells were expanded as described in Example 1 and when confluent, samples were split for maintenance and genomic DNA extraction.

For determining indels in the target FAS, CISH, and REGNASE-1 sequences, PCR for relevant regions was performed using Platinum Taq Supermix (Invitrogen, Cat #125320176 and Cat #11495017). The resulting amplicons were submitted for PCR cleanup and Sanger sequencing. Sanger sequencing results were input into Tsunami software along with the guide sequence. The resulting DNA sequences of the target FAS, CISH, and REGNASE-1 regions were aligned in Snapgene software to determine indel identity and homo- or heterozygosity.

Figure 25A:
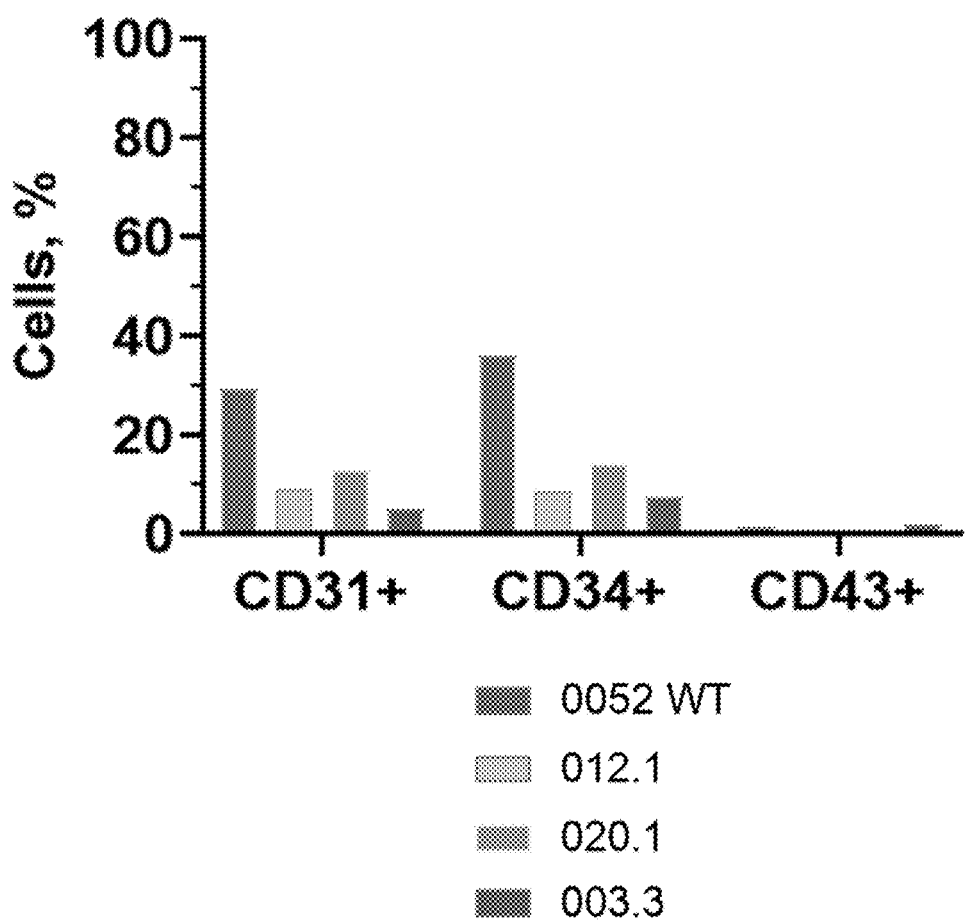
FIGS. 25A and 25B show CD31/CD34/CD45 expression profiles in aggregates after 10 days (FIG. 25A) or 14 days (FIG. 25B) of differentiation. Cell were differentiated from WT cells, IL15/IR15α-P2A-HLA-E trimer KI, BCMA CAR KI, CIITA Null, B2M Null, ADAM17 Null cells ("012.1") cells, IL15/IR15α-P2A-HLA-E trimer KI, BCMA CAR KI, CIITA Null, B2M Null, ADAM17 Null, FAS Null, CISH Null, REGNASE-1 Null cells ("020.1") cells, and IL15/IR15α-P2A-HLA-E KI, B2M null ("003.3") cells.
Figure 25B:
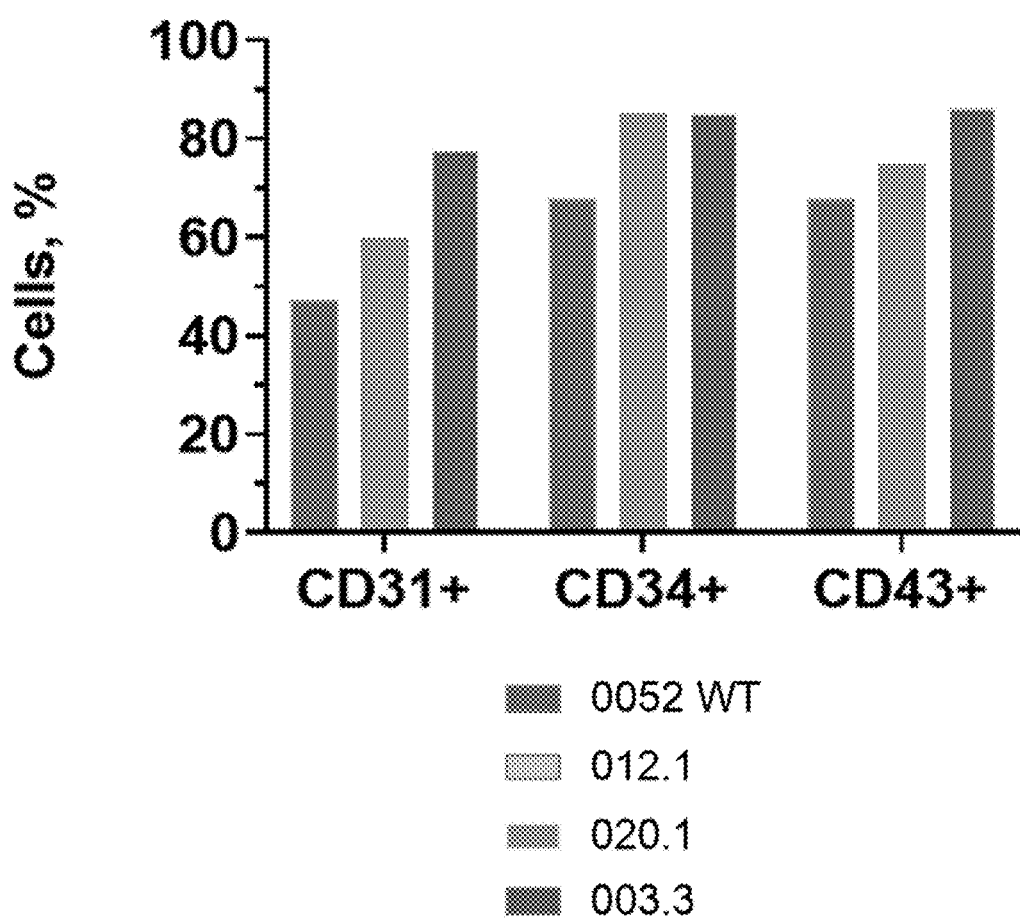
Figure 26:
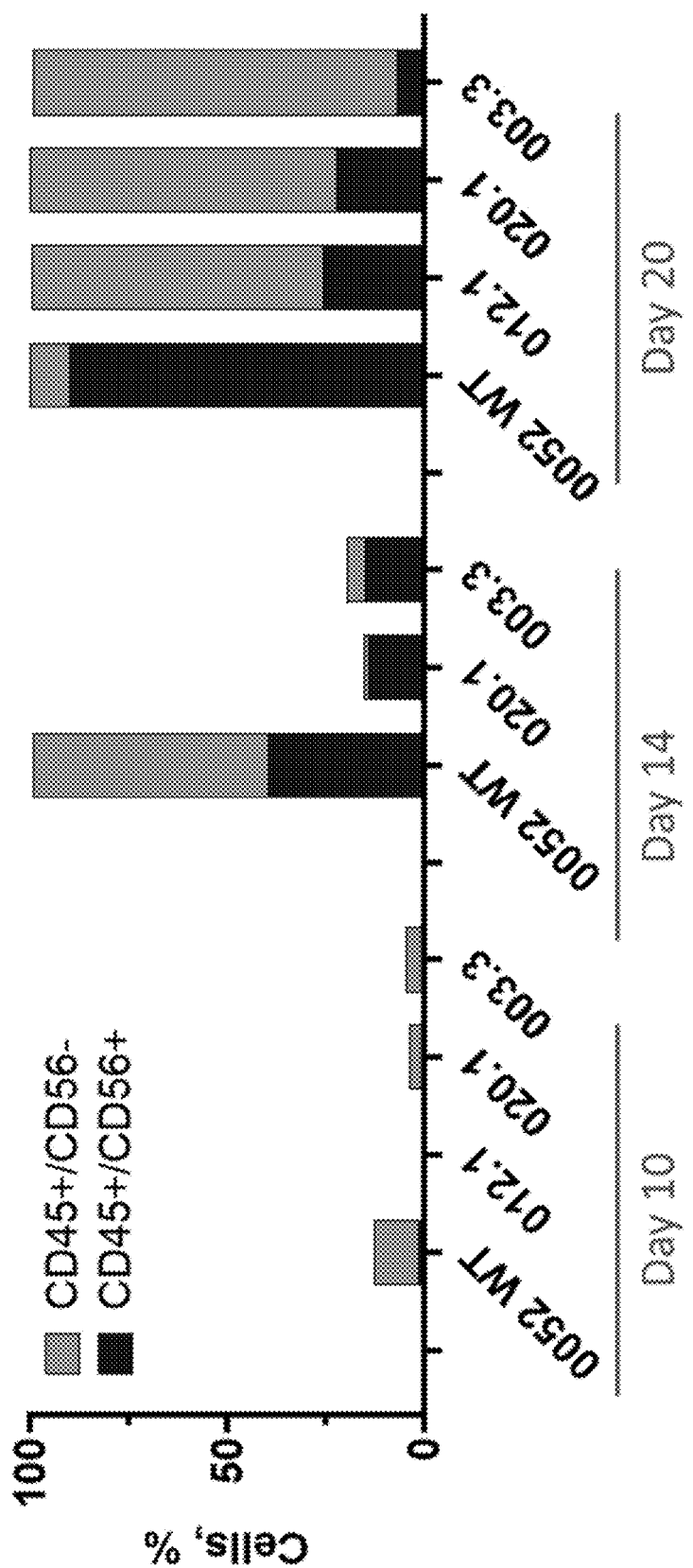
FIG. 26 present CD45/CD56 expression profiles in aggregates after 10 days, 14 days, or 20 days of differentiation. Cell were differentiated from WT cells, IL15/IR15α-P2A-HLA-E trimer KI, BCMA CAR KI, CIITA Null, B2M Null, ADAM17 Null cells ("012.1") cells, IL15/IR15α-P2A-HLA-E trimer KI, BCMA CAR KI, CIITA Null, B2M Null, ADAM17 Null, FAS Null, CISH Null, REGNASE-1 Null cells ("020.1") cells, and IL15/IR15α-P2A-HLA-E KI, B2M null ("003.3") cells.

Continued expression of BCMA CAR, HLA-E, and IL15 surface proteins was confirmed using fluorescent antibodies as described above in Example 9. Pluripotency of the edited cells was confirmed by detecting OCT4 and SOX2 expression as described above in Example 9. Clone 1 (020 clone 1), homozygous at FAS, CISH, and REGNASE-1 loci, was chosen for further analysis, Example 13: Characterization of NK Cells Differentiated from IL15/IR15α-P2A-HLA-E TrimerKknock-In, BCMA CARKknock-In, CIITA Null, B2M Null, ADAM17 Null, FAS Null, CISH Null, and REGNASE-1 Null hPSCs The "020 clone 1" hPSCs (IL15/IR15α-P2A-HLA-E trimer knock-in, BCMA CAR knock-in, CIITA Null, B2M Null, ADAM17 Null, FAS Null, CISH Null, and REGNASE-1 Null), as well as "012 clone 1" hPSCs (IL15/IR15α-P2A-HLA-E KI, BCMA CAR KI, CIITA Null, B2M Null, ADAM17 Null), "003 clone 3" hPSCS (IL15/IR15α-P2A-HLA-E KI, B2M Null), and wild-type (WT) were differentiated to iNK cells using Protocol 1, as described in Example 2. Flow cytometry of differentiated cells at Days 10 and 14 showed that the "020 clone 1" differentiated cells had similar patterns if CD31, CD34, and CD43 expression as WT and those differentiated from "012 clone 1" and "003 clone 3" (FIGS. 25A-25B). Throughout the differentiation process, cells were analyzed for CD45 and CD56 expression by flow cytometry, showing efficient differentiation for all of the edited clones as compared to WT. By day 20, similar levels of the edited clones were CD56$^+$ (FIG. 26). By day 35, more than 99% of the edited clones were CD45$^+$/CD56$^+$.

Figure 27A:
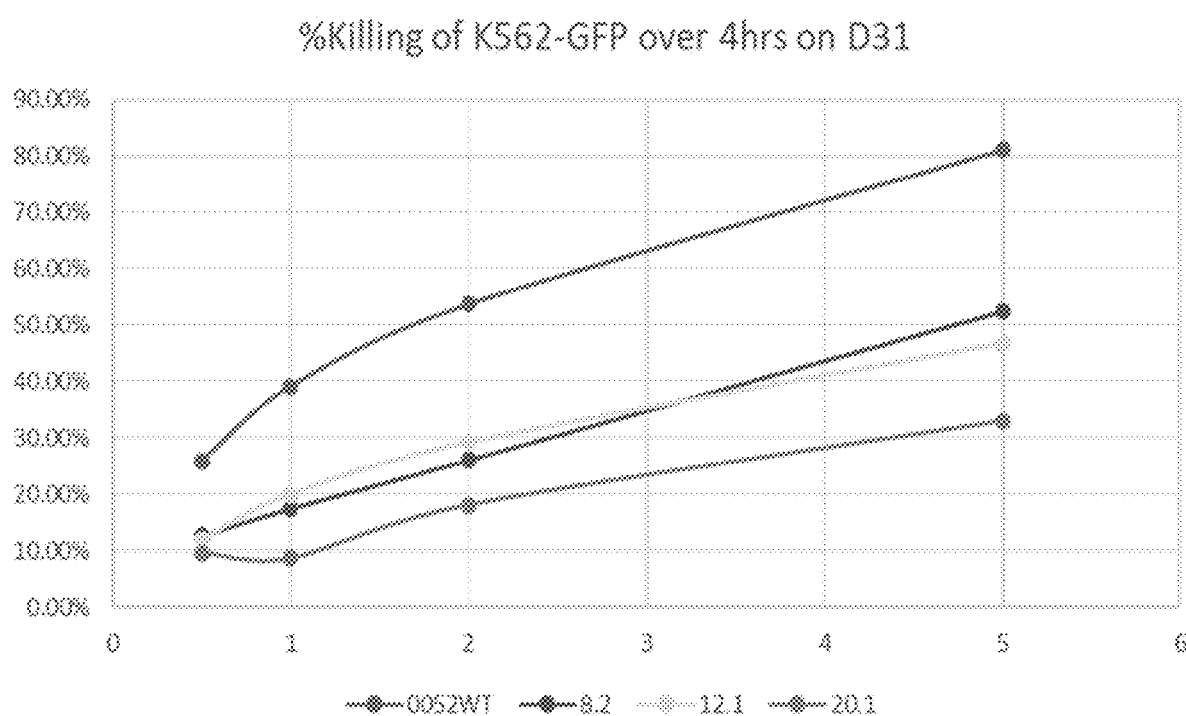
FIG. 27A shows the percent of killing of K562-GFP cells over 4 hours on Day 31 and FIG. 27B presents live NK cell ratios in NoTarget vs. 1:1 Killing in cells differentiated from WT cells, IL15/IR15a fusion-P2A-HLA-E KI into B2M and BCMA CAR into CIITA ("8.2") cells, IL15/IR15a fusion-P2A-HLA-E KI into B2M, BCMA CAR into CIITA, and ADAM17 KO ("12.1") cells, and IL15/IR15a fusion-P2A-HLA-E KI into B2M, BCMA CAR into CIITA, ADAM17 KO, FAS KO, CISH KO, and REGNASE-KO ("20.1") cells.
Figure 27B:
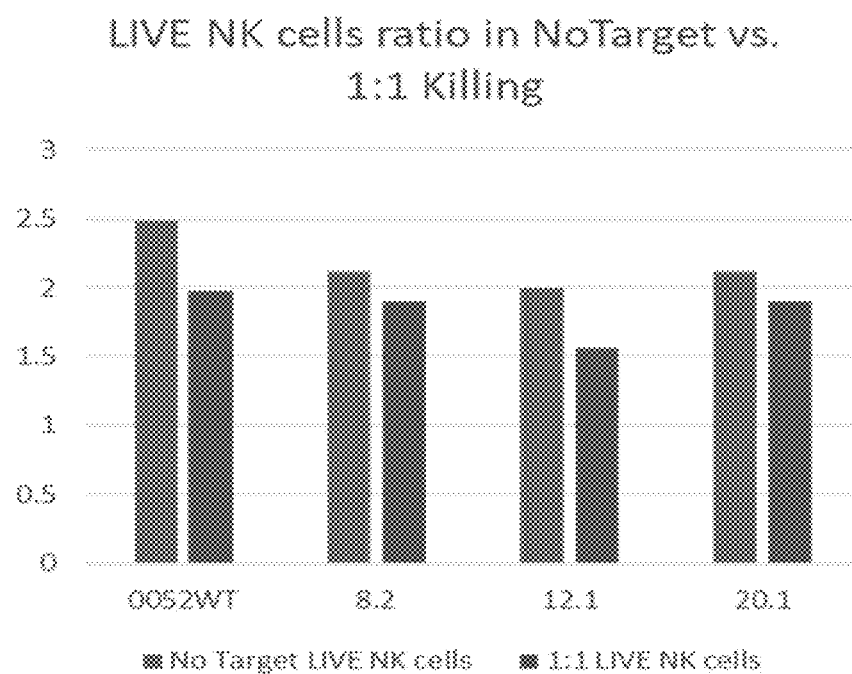
Figure 28A:
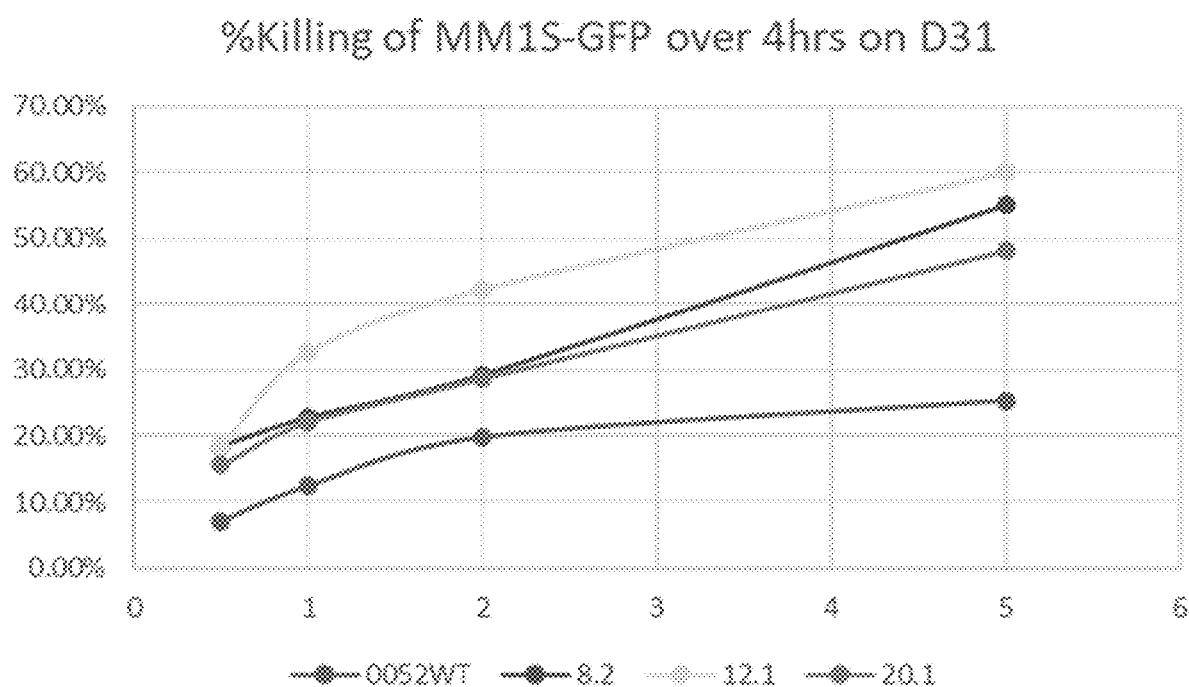
FIG. 28A shows the percent of killing of MM1S-GFP cells over 4 hours on Day 31 and FIG. 28B presents live NK cell ratios in NoTarget vs. 1:1 Killing in cells differentiated from WT cells, IL15/IR15a fusion-P2A-HLA-E KI into B2M and BCMA CAR into CIITA ("8.2") cells, IL15/IR15a fusion-P2A-HLA-E KI into B2M, BCMA CAR into CIITA, and ADAM17 KO ("12.1") cells, and IL15/IR15a fusion-P2A-HLA-E KI into B2M, BCMA CAR into CIITA, ADAM17 KO, FAS KO, CISH KO, and REGNASE-1 KO ("20.1") cells.
Figure 28B:
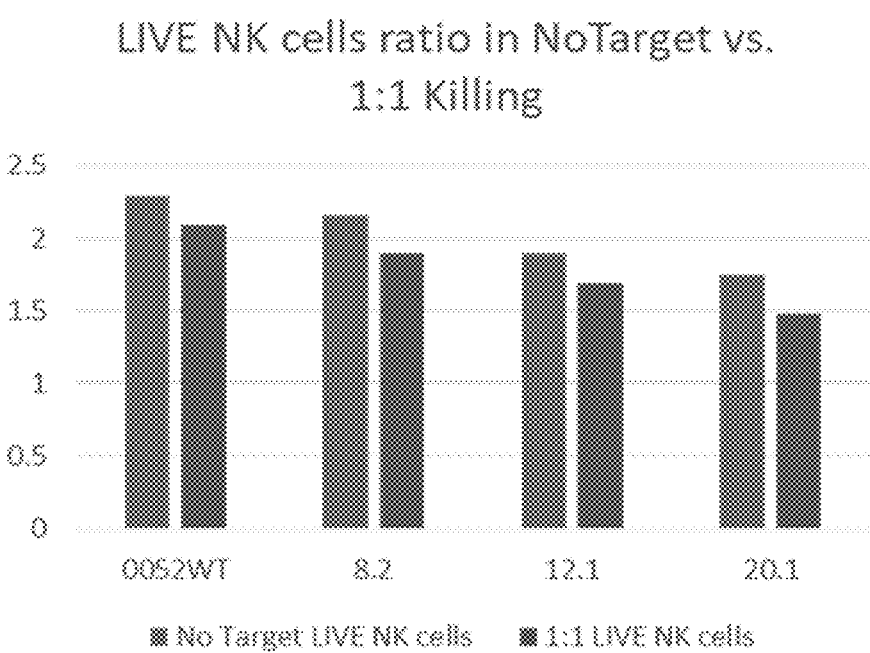

The cytotoxicity of day 31 "020 clone 1" (IL15/IR15α-P2A-HLA-E trimer knock-in, BCMA CAR knock-in, CIITA Null, B2M Null, ADAM17 Null, FAS Null, CISH Null, and REGNASE-1 Null), "012 clone 1" (IL15/IR15α-P2A-HLA-E KI, BCMA CAR KI, CIITA Null, B2M Null, ADAM17 Null), "008 clone 2" (IL15/IR15α-P2A-HLA-E KI, BCMA CAR KI, CIITA Null, B2M Null), and WT iNK cells towards K562 and MM1S cancer cells was determined using a GFP-based killing assay. The cancer cells were labeled with GFP and killing was monitored over 4 hours. WT cells displayed more effective cytotoxicity against K562 cells than the edited cells (FIGS. 27A, 27B). The "012 clone 1" cells displayed greater cytotoxicity against the BCMA$^+$ expressing MM1S cancer cell line than the WT and other edited cells (FIGS. 28A, 28B).

Example 14: Anti-CD30 CAR Development and Selection

Several CD30 CARS were constructed that included variable light and heavy domains from a mouse monoclonal (SEQ ID NOs: 102 and 103, respectively) or a human anti-CD30 antibody (SEQ ID NOs: 104 and 105, respectively), a CD8 transmembrane domain (SEQ ID NO: 122), a CD28 (SEQ ID NO: 123) or 41BB domain (SEQ ID NO: 124), and a CD3Z domain (SEQ ID NO: 125). Table 40 details anti-CD30 CARs.

TABLE 40

| Anti-CD30 CARS | |
|---|---|
| CAR | Name |
| 1 | Brent_vL_vH_CD28 |
| 2 | 5F11_vH_vL-CD28 |
| 3 | Brent_vL_vH_41BB |
| 4 | Brent_vH-vL_CD28 |
| 5 | 5F11_vH_vL_41BB |
| 6 | 5F11_vL_vH-41BB |
| 7 | Brent_vH_vL_41BB |

Figure 29A:
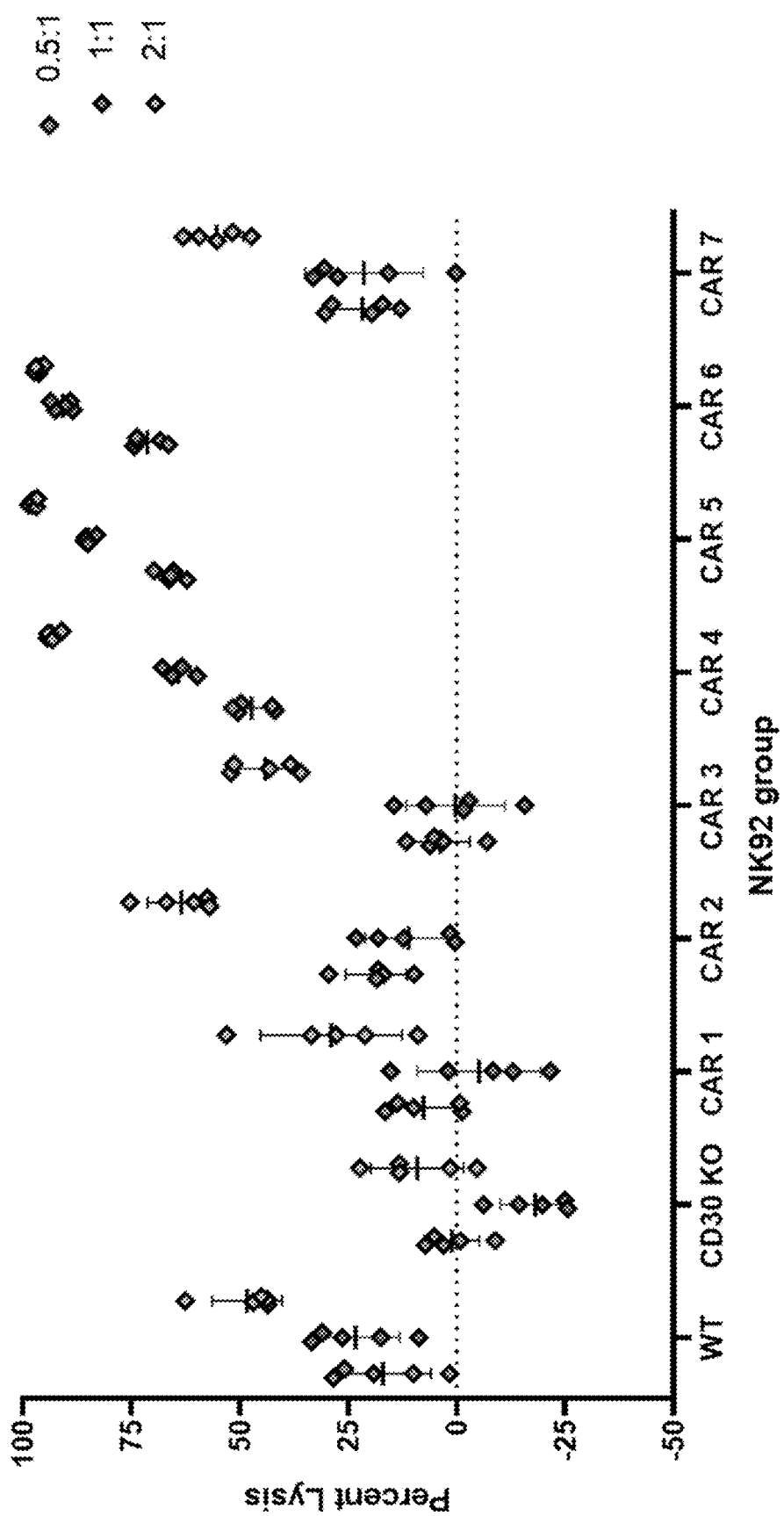
FIG. 29A shows killing of L428 cells after 4 hours and FIG. 29B shows killing of L428 cells after 24 hours by the indicated NK92 cells.
Figure 29B:
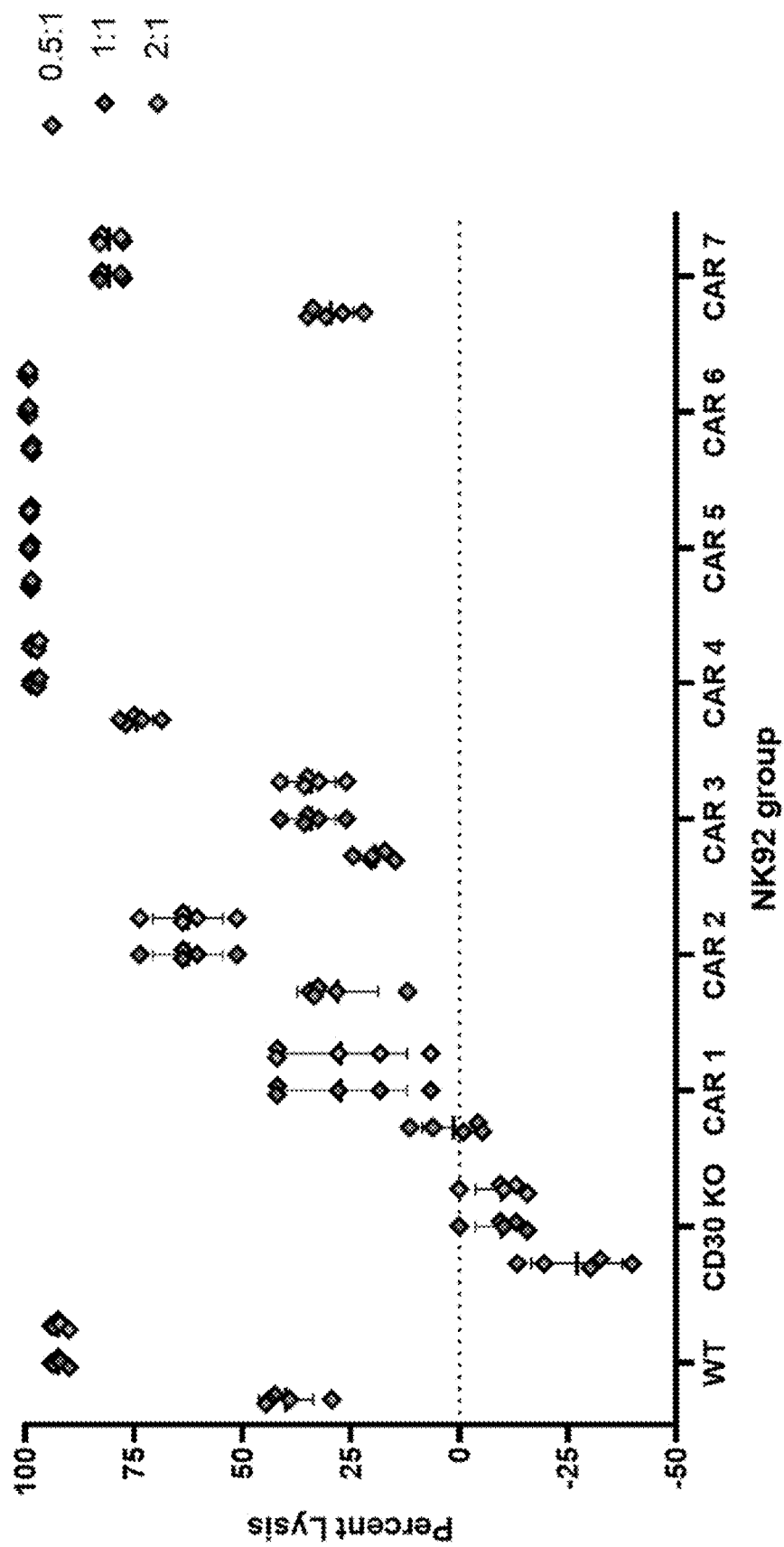
Figure 30A:
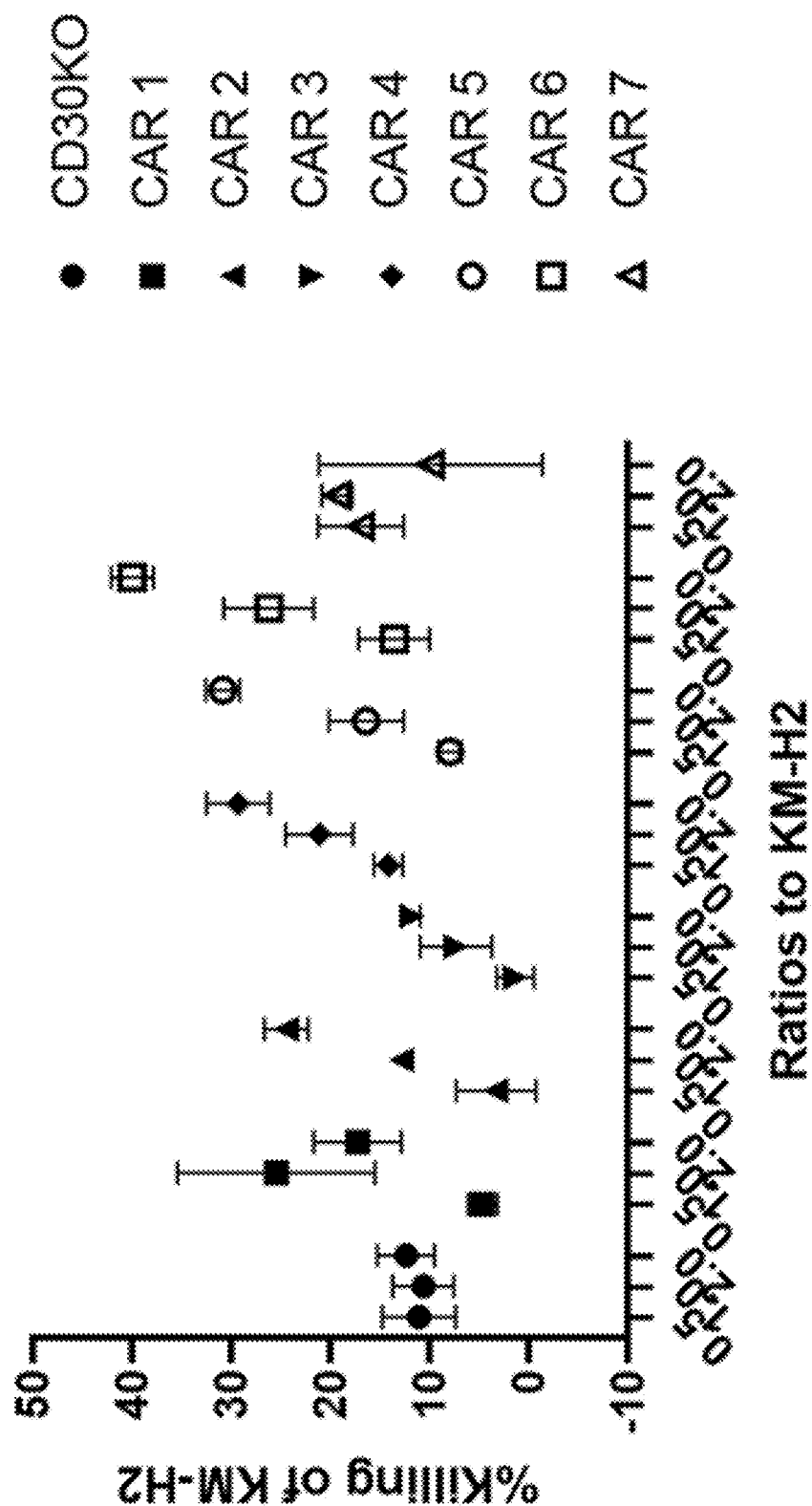
FIG. 30A shows killing of KM-H2 cells after 4 hours and FIG. 30B shows killing of KM-H2 cells after 24 hours by the indicated NK92 cells.
Figure 30B:
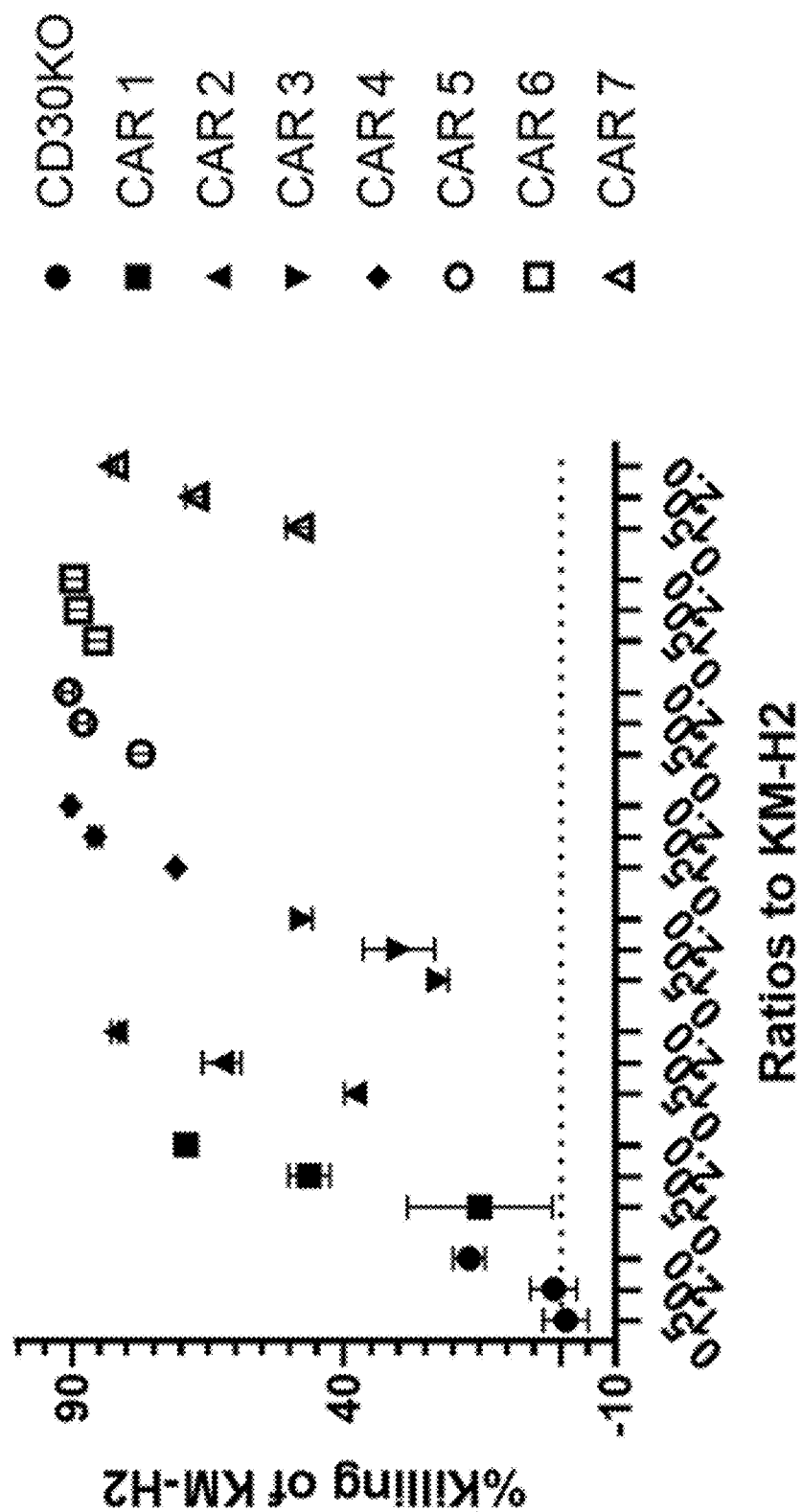

The anti-CD30 CARS were delivered to WT NK92 cells via lentiviral vectors. After selection, cytotoxicity against L428 cancer cell line was determined using a luciferase killing assay. FIG. 29A shows the NK92 anti-CD30 CAR killing results after 4 hours, wherein CARs 4, 5, and 6 outperformed WT at every ratio, with CARs 5 and 6 exhibiting the best killing. CD30 KO strongly reduced NK92 killing ability. FIG. 29B presents the results after 24 hours. CARs 4, 5, and 6 outperformed WT at 0.5:1, with CARs 5 and 6 showing nearly 100% killing for all ratios. Cytotoxicity was also tested against another cancer cell line, KM-H2. FIG. 30A present results at 4 hours and FIG. 30B shows killing at 24 hours. CARs 4, 5, and 6 showed the best killing. CARs 4, 5, and 6 were chosen for KI into the CIITA gene locus of iPSCs.

Example 15: Generation of Anti-CD30 CAR-P2A-HLA-E Trimer Knock-In, CIITA Null Human Pluripotent Stem Cells Plasmids were designed to insert an anti-CD30 CAR-P2A-HLA-E trimer into the CIITA gene locus essentially as described above in Example 6 (i.e., 86 bp of the CIITA exon 2 would be removed after undergoing HDR). Each donor plasmid contained a CAGGS promoter operably linked to a cDNA of an anti-CD30 CAR-P2A-HLA-E trimer flanked by 800 base pair homology arms with identical sequence to the CIITA gene locus around exon 2. The HLA-E trimer cDNA was composed of a B2M signal peptide fused to an HLA-G presentation peptide fused to the B2M membrane protein fused to the HLA-E protein without its signal peptide. The HLA-E trimer coding sequence (including linkers) is SEQ ID NO: 75 (i.e., SEQ ID NOs: 46, 47, 48, 49, 50, and 51). The P2A peptide sequence (SEQ ID NO: 45) connecting the anti-CD30 CAR and the HLA-E trimer allows for the separate expression of both proteins from the single mRNA. Each donor plasmid also contained a PD-L1 coding sequence (SEQ ID NO: 146) operably linked to an EF-1 alpha promoter (SEQ ID NO: 149) downstream of the right homology arm sequence (SEQ ID NO: 32) such that PD-L1 would be expressed if the plasmid integrated into the genome. Probes spanning the plasmid backbone can be used to detect plasmid integration using ddPCR. FACS with an anti-PD-L1 antibody can be used to remove PD-L1 positive cells.

Figure 31:
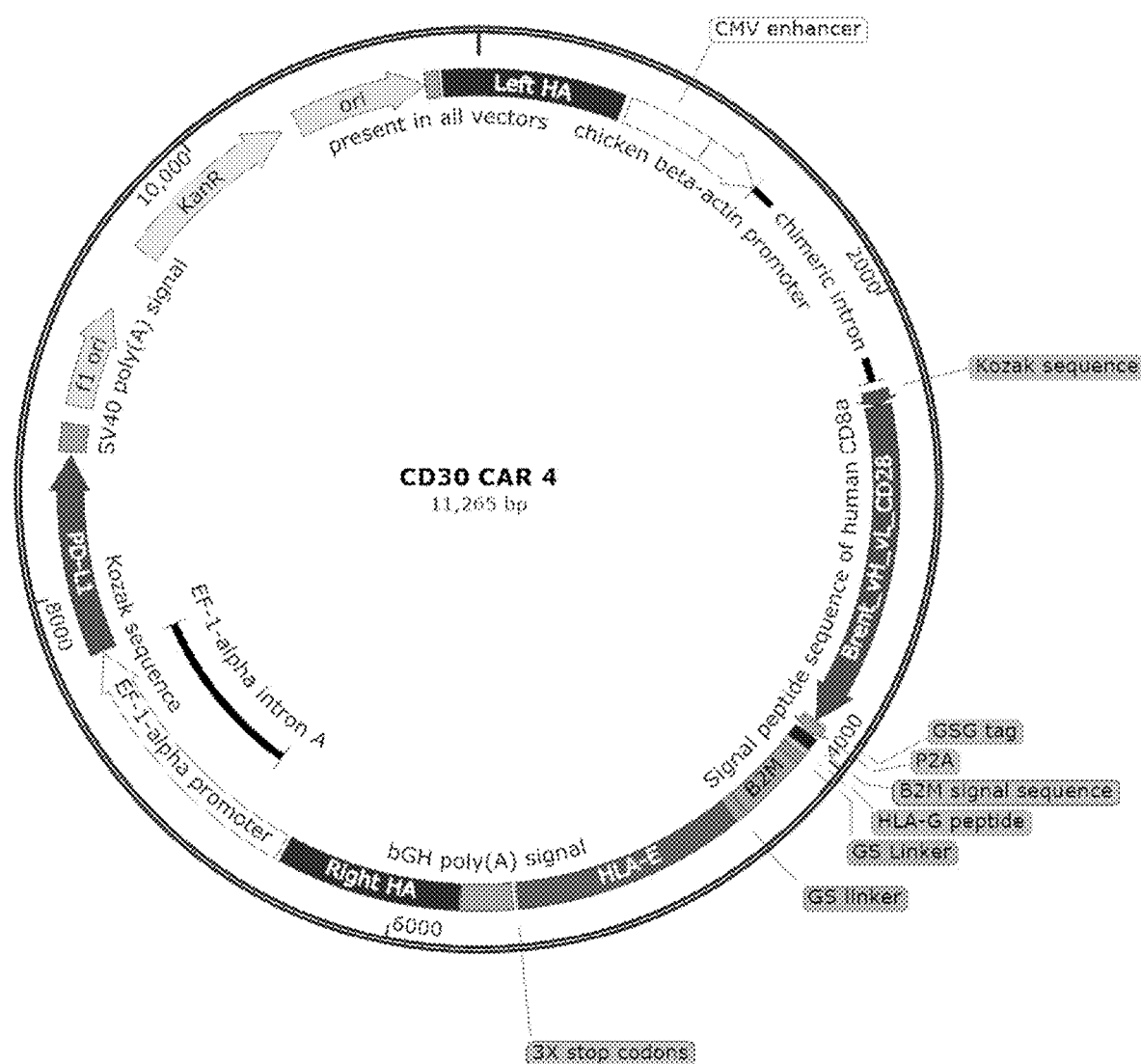
FIG. 31 presents the plasmid map of CD30 CAR 4-P2A-HLA-E trimer knock-in and CIITA knock-out.

FIG. 31 presents a schematic of an anti-CD30 CAR 4-P2A-HLA-E encoding plasmid (SEQ ID NO: 110) and Table 41 identifies the elements and locations therein. The anti-CD30 CAR 4 coding sequence is SEQ ID NO: 108 (i.e., SEQ ID NOS: 26, 106, 126, 107, and 128) and the anti-CD30 CAR 4 amino acid sequence is SEQ ID NO: 109. The anti-CD30 CAR 4-P2A-HLA-E coding sequence is SEQ ID NO: 119 (i.e., SEQ ID NOS: 26, 106, 126, 107, 128, and 44-51).

Figure 32:
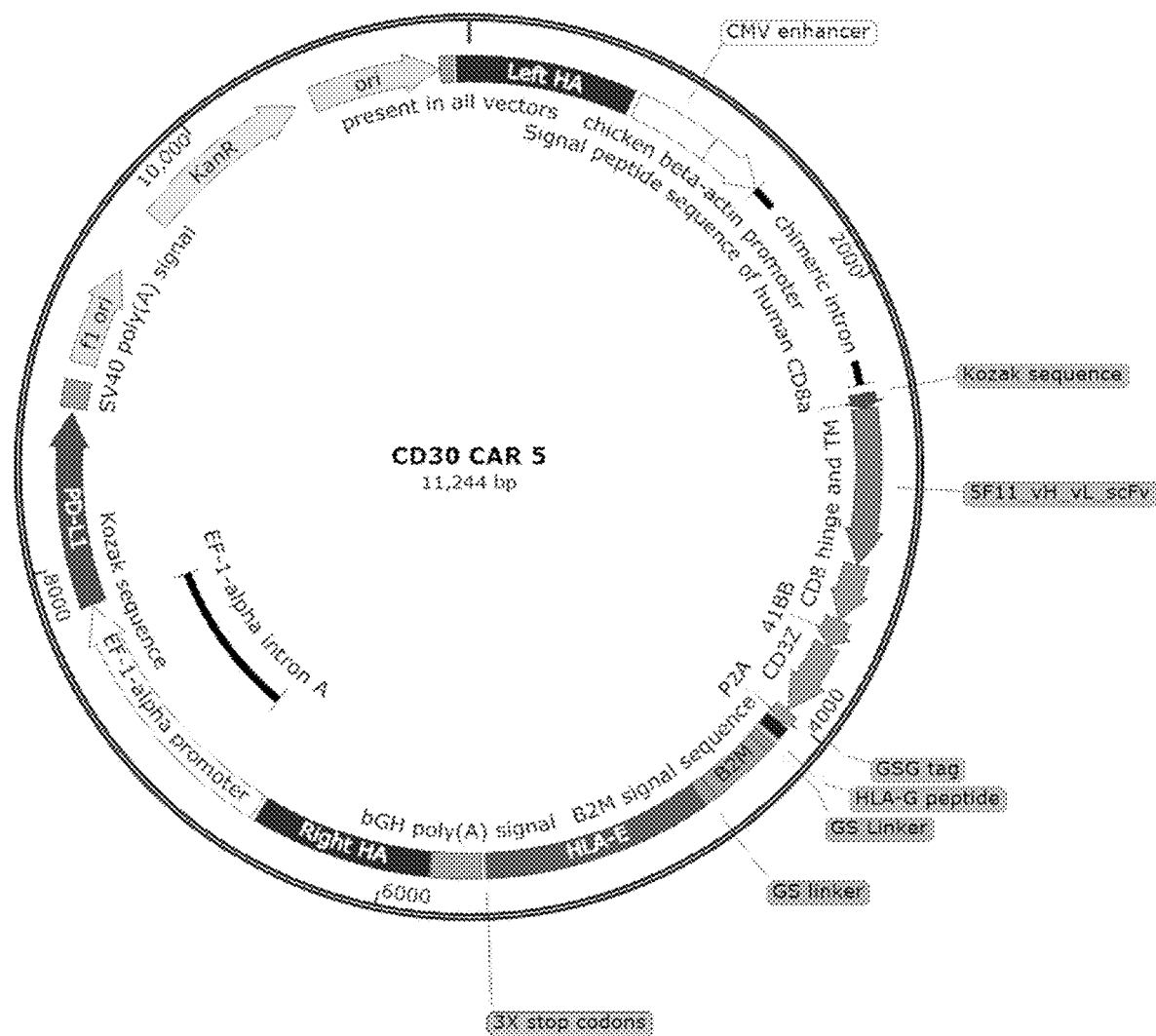
FIG. 32 presents the plasmid map of CD30 CAR 5-P2A-HLA-E trimer knock-in and CIITA knock-out.

FIG. 32 presents a schematic of an anti-CD30 CAR 5-P2A-HLA-E encoding plasmid (SEQ ID NO: 114) and Table 42 identifies the elements and locations therein. The anti-CD30 CAR 5 coding sequence is SEQ ID NO: 112 (i.e., SEQ ID NOS: 26, 111, 126, 127, and 128) and the anti-CD30 CAR 4 amino acid sequence is SEQ ID NO: 113. The anti-CD30 CAR 5-P2A-HLA-E coding sequence is SEQ ID NO: 120 (i.e., SEQ ID NOS: 26, 111, 126, 127, 128, and 44-51).

Figure 33:
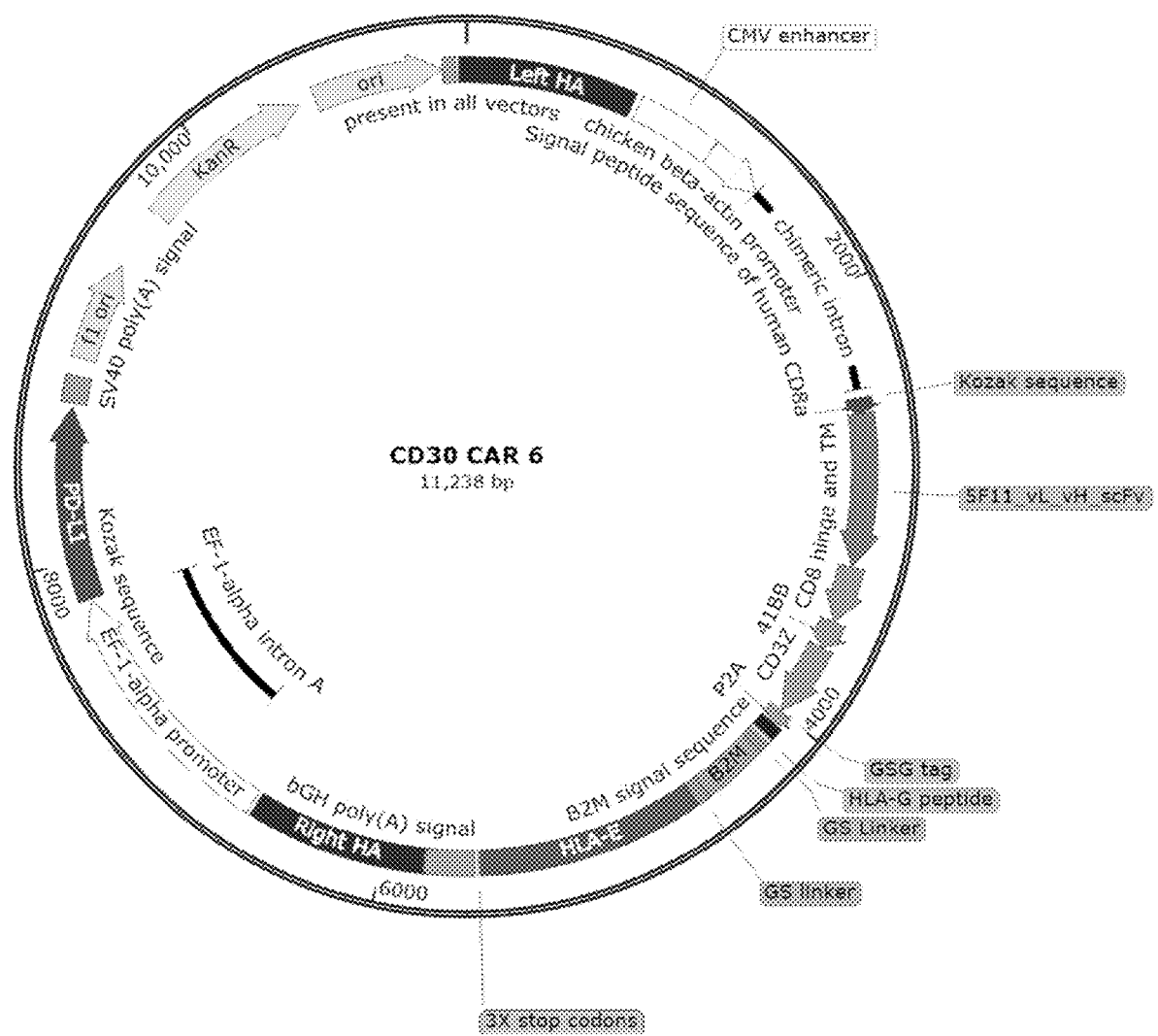
FIG. 33 presents the plasmid map of CD30 CAR 6-P2A-HLA-E trimer knock-in and CIITA knock-out.

FIG. 33 presents a schematic of an anti-CD30 CAR 6-P2A-HLA-E encoding plasmid (SEQ ID NO: 118) and Table 43 identifies the elements and locations therein. The anti-CD30 CAR 6 coding sequence is SEQ ID NO: 116 (i.e., SEQ ID NOS: 26, 115, 126, 127, and 128) and the anti-CD30 CAR 4 amino acid sequence is SEQ ID NO: 117. The anti-CD30 CAR 6-P2A-HLA-E coding sequence is SEQ ID NO: 121 (i.e., SEQ ID NOS: 26, 115, 126, 127, 128, and 44-51).

TABLE 41

Elements of anti-CD30 CAR 4-P2A-HLA-E Donor Plasmid

| Element | Location (size in bp) | SEQ ID NO: |
|---|---|---|
| LHA-CIITA | 11,107-641 (800) | 22 |
| CMV enhancer | 670-1049 (380) | 23 |
| chicken β-actin promoter | 1052-1327 (276) | 24 |
| chimeric intron | 1328-2336 (1009) | 25 |
| CD8a signal peptide | 2381-2443 (63) | 26 |
| Brent_vH_vL | 2444-3172 (729) | 106 |
| CD8TM | 3173-3436 (264) | 126 |
| CD28 domain | 3437-3556 (120) | 107 |
| CD3Z domain | 3557-3892 (336) | 128 |
| GSG tag | 3893-3901 (9) | 44 |
| P2A | 3902-3958 (57) | 45 |
| B2M signal sequence | 3959-4018 (60) | 46 |
| HLA-G peptide | 4019-4045 (27) | 47 |
| GS linker | 4046-4090 (45) | 48 |
| B2M | 4091-4387 (297) | 49 |
| GS linker | 4388-4447 (60) | 50 |
| HLA-E | 4448-5458 (1011) | 51 |
| 3X Stop codons | 5459-5467 (9) | 52 |
| bGH poly(A) signal | 5485-5709 (225) | 31 |
| RHA-CIITA | 5716-6515 (800) | 32 |
| EF-1 alpha promoter | 6535-7712 (1178) | 149 |
| PD-L1 CDS | 7728-8600 (873) | 146 |
| SV40 poly(A) sequence | 8618-8739 (122) | 147 |
| Total plasmid | 11,265 bp | 110 |

TABLE 42

Elements of anti-CD30 CAR 5-P2A-HLA-E Donor Plasmid

| Element | Location (size in bp) | SEQ ID NO: |
|---|---|---|
| LHA-CIITA | 11,205-766 (800) | 22 |
| CMV enhancer | 774-1153 (380) | 23 |
| chicken β-actin promoter | 1156-1431 (276) | 24 |
| chimeric intron | 1432-2440 (1009) | 25 |
| CD8a signal peptide | 2485-2547 (63) | 26 |
| 5F11_vH_vL | 2548-3249 (702) | 111 |
| CD8TM | 3250-3513 (264) | 126 |
| 41BB co-stim domain | 3514-3639 (126) | 127 |
| CD3Z domain | 3640-3975 (336) | 128 |
| GSG tag | 3976-3984 (9) | 44 |
| P2A | 3985-4041 (57) | 45 |
| B2M signal sequence | 4042-4101 (60) | 46 |
| HLA-G peptide | 4102-4128 (27) | 47 |
| GS linker | 4129-4173 (45) | 48 |
| B2M | 4174-4470 (297) | 49 |
| GS linker | 4471-4530 (60) | 50 |
| HLA-E | 4531-5541 (1011) | 51 |
| 3X Stop codons | 5542-5550 (9) | 52 |
| bGH poly(A) signal | 5568-5792 (225) | 31 |
| RIIA-CIITA | 5799-6598 (800) | 32 |
| EF-1 alpha promoter | 6618-7795 (1178) | 149 |
| PD-L1 CDS | 7811-8683 (873) | 146 |
| SV40 poly(A) sequence | 8701-8822 (122) | 147 |
| Total plasmid | 12,224 | 114 |

TABLE 43

Elements of anti-CD30 CAR 6-P2A-HLA-E Donor Plasmid

| Element | Location (size in bp) | SEQ ID NO: |
|---|---|---|
| LHA-CIITA | 11,205-766 (800) | 22 |
| CMV enhancer | 795-1174 (380) | 23 |
| chicken β-actin promoter | 1177-1452 (276) | 24 |
| chimeric intron | 1453-2461 (1009) | 25 |
| CD8a signal peptide | 2500-2568 (63) | 26 |
| 5F11_vL_vH | 2569-3270 (700) | 115 |
| CD8TM | 3271-3528 (264) | 126 |
| 41BB co-stim domain | 3529-3654 (126) | 127 |
| CD3Z domain | 3655-3990 (336) | 128 |
| GSG tag | 3991-3999 (9) | 44 |
| P2A | 4000-4056 (57) | 45 |
| B2M signal sequence | 4057-4116 (60) | 46 |
| HLA-G peptide | 4117-4143 (27) | 47 |
| GS linker | 4144-4188 (45) | 48 |
| B2M | 4189-4485 (297) | 49 |
| GS linker | 4486-4545 (60) | 50 |
| HLA-E | 4546-5556 (1011) | 51 |
| 3X Stop codons | 5557-5565 (9) | 52 |
| bGH poly(A) signal | 5583-5807 (225) | 31 |
| RIIA-CIITA | 5814-6613 (800) | 32 |
| EF-1 alpha promoter | 6633-7810 (1178) | 149 |
| PD-L1 CDS | 7826-8698 (873) | 146 |
| SV40 poly(A) signal | 8716-8837 (122) | 147 |
| Total plasmid | 11,238 bp | 118 |

The CIITA-T6 gRNA (Table 19) was used to facilitate insertion of the anti-CD30 CAR transgenes at the targeted CIITA gene locus. The target sequence of CIITA-T6 is not present in the donor plasmid and thus the donor plasmid itself would not be targeted by this gRNA. CIITA-T6 induced CRISPR cutting in the human genome at exon 2 of CIITA would lead to a frameshift and loss of CIITA protein. Each CD30 CAR donor plasmid was introduced along with a RNP complex made up of the CIITA targeting gRNA and Cas9 protein. Per 1 million of human embryonic stem cells, 2 μg of plasmid DNA was delivered along with the RNP via electroporation. Electroporation was carried out using the Neon Electroporator with the RNP mixture of Cas9 protein and guide RNA at a molar ratio of 1:5 with absolute values of 125 pmol Cas9 and 625 pmol gRNA per 2 million cells. To form the RNP complex, gRNA and Cas9 were combined in one vessel with R-buffer (Neon Transfection Kit) to a total volume of 25-50 µL and incubated for 15 min at room temperature (RT). Cells were dissociated using ACCUTASE®, then resuspended in STEMFLEX™ media, counted using an NC-200 (ChemoMetec) and centrifuged. A total of $2\times10^6$ cells were resuspended with the RNP complex and R-buffer was added to a total volume of 115 µL. This mixture was then electroporated with 3 pulses for 30 ms at 1000 V. Following electroporation, the cells were pipetted out into a well of a 6 well plate filled with STEMFLEX™ media with REVITACELL™ Supplement (100x) and BIO-LAMININ 521 CTG at 1:10 dilution. Cells were cultured in a normoxia incubator (37° C., 8% $CO_2$).

At 2 days post electroporation, the cells were enriched for transfection via fluorescence activated cell sorting (FACS) using an antibody against HLA-E (see Table 21). Plasmid integration analysis revealed that 1/46 cell clones was free of integrated plasmid. However, if PD-L1 positive cells were removed prior to the cell sorting, 24/82 cell clones were plasmid free. Thus, FACS was performed using PD-L1 negative cells. Seven to ten days post electroporation, the cells were again enriched for HLA-E trimer knock in cells using FACS. These enriched cells represent bulk KI population of anti-CD30 CAR-P2A-HLA-E trimer positive cells. PCR for the genotyping of the edited clones was performed and the resulting amplified DNA was assessed for cutting efficiency by TIDE analysis.

Example 16: Differentiating Stem Cells into Natural Killer Cells—Protocol 2

It was discovered that some induced pluripotent stem cells did not differentiate efficiently with Protocol 1 described above in Example 1. Thus, Protocol 2 (also called Aligned Process 2.0 or AP2.0) was developed to differentiate these iPSCs into hematopoietic stem and progenitor cells (HSPCs) and then into natural killer (NK) cells. Prior to differentiation, frozen iPSCs were thawed and re-suspended in NK-MED-001a medium (Table 44). Flasks pre-coated with laminin-521 were used for cell culturing. Medium was changed daily using NK-MED-002a (Table 45) medium until cells were used for differentiation.

NK Cell Differentiation. iPS cells were differentiated using the following steps:

1. Day-1 (afternoon), iPSC aggregation: NK-MED-002a medium was aspirated from flasks containing iPSC and the cells were washed with DPBS (no calcium, no magnesium) (Thermo Fisher Scientific, 14190250). DPBS was aspirated and 2 mL ACCUTASE® (Innovative Cell Technologies, AT-104) was added per T25 flask (or 80 µL of ACCUTASE® per 1 $cm^2$). Cells were incubated at 37° C. for 3-5 min (not more than 7 minutes). Accutase digested cells were diluted with cold NK-MED-002a medium to a ratio of at least 3:1 (NK-MED-002:ACCUTASE®). Cells were gently resuspended and transferred to a conical tube. Optionally, enough NK-MED-002a medium was added to cells to dilute the ACCUTASE® to a ratio of at least 1:1 and up to 4:1 (NK-MED-002a:ACCUTASE®). Cells were pelleted by spinning at 20-300 g for 4 to 5 minutes and re-suspended in 10 mL of NK-MED-003a medium (Table 46). Cells were counted and the cell concentration was diluted to $1\times10^6$/mL. $6\times10^6$ cells were transferred to another tube and resuspended in a total of 6 mL of NK-MED-003a medium. The cells were transferred to 1 well of ultra-low adhesion 6-well plate (Corning, 3471) and the plate was placed on a platform shaker and rotated at 98 RPM for 18+/−2 hours (overnight).

2. At day 0, morning, at 18+/−2 hours after iPSC aggregation: The plate was rotated in a circular motion to move aggregates towards center of the well and aggregates were collected in a conical tube. Alternatively, all the aggregate solution mix was collected. Aggregates were allowed to settle for 15+/−5 minutes. Cells were resuspended in NK-MED-004 medium (Table 47). The cell number in aggregates was counted. The seeding density was adjusted as needed to resuspend $3\times10^5$ cells in aggregates in 2 mL NK-MED-004 medium and plated in one well of a 6-well low adhesion plate. Alternatively, for scale up, an appropriate number of cells was resuspended and transferred to a PBS spinner vessel (PBS Biotech). Seeding density tested for PBS seeding vessel was approximately $1\times10^3$ cells per mL per final media volume (day 0+8 hrs). The plate was placed on a platform shaker and rotated at 98 RPM for 8 hours or the PBS spinner vessel were placed on a PBS base (PBS-MINI MagDrive Base Unit; PBS Biotech), in $CO_2$ incubator with a rotation speed of RPM 38 to 39.

3. At day 0, afternoon, at 8 hours after NK-MED-004 medium addition: 50 mL or 250 mL per well or spinner vessel, respectively, of NK-MED-005c medium (Table 48) was added. The plate was returned to platform shaker or PBS spinner vessel to its base in the $CO_2$ incubator and left undisturbed until day 2. NK-MED-005c medium components were 2x of their final concentration, therefore it was added to cells in NK-MED-004 at a 1:1 volume ratio.

4. At day 2: NK-MED-005c medium was replaced with NK-MED-006b medium (Table 49).

5. At day 4: NK-MED-006b medium was replaced with NK-MED-007 medium (Table 50).

6. At day 6: NK-MED-007 medium was replaced with NK-MED-008b medium (Table 51), or alternatively: starting at day 6, medium with all aggregates and single cells was transferred into an appropriate volume centrifuge conical tube. Cells were centrifuged and resuspended in NK-MED-008b medium and placed back into original wells and onto platform shaker, or into original vessels and onto base, and returned for continued culture.

7. At day 10: Half or full media change was made with NK-MED-008b medium.

8. At day 14: Full media change was made with NK-MED-009b medium (Table 52).

9. At day 17: One-third media change was made NK-MED-009b medium and then a full media change was made with NK-MED-009b medium.

From day 20 onwards: Starting at day 20, single cell density was estimated from cell culture. A full media change was made with NK-MED-010 medium (Table 53) and cell density adjusted to within 0.8 to $1.5\times10^6$ cells/mL. A full media change with NK-MED-010 medium and adjustment of cell density to $0.8$-$1.5\times10^6$ cells/mL was performed every 2-3 days from day 20 to 30.

In the tables below, the volumes are approximate to get the desired concentrations.

TABLE 44

Medium composition for NK-MED-001a

| Component | Working Conc. | Volume | Stock Conc. |
| --- | --- | --- | --- |
| StemBrew Basal Media | 90% | 980 mL | 100% |
| StemBrew Supplement | 1X | 20 mL | 50X |

TABLE 44-continued

Medium composition for NK-MED-001a

| Component | Working Conc. | Volume | Stock Conc. |
|---|---|---|---|
| Thiazovivin (Biological Industry, 1226056-71-8) | 2 µM | 200 µL | 10 mM |

TABLE 45

Medium composition for NK-MED-002a

| Component | Working Conc. | Volume | Stock Conc. |
|---|---|---|---|
| StemBrew Basal Media | 90% | 980 mL | 100% |
| StemBrew Supplement | 1 X | 20 mL | 50 X |

TABLE 46

Medium composition for NK-MED-003a

| Component | Working Conc. | Volume | Stock Conc. |
|---|---|---|---|
| StemBrew Basal | 90% | 979 mL | 100% |
| StemBrew Supplement | 1X | 20 mL | 50X |
| Thiazovivin (Biological Industry, 1226056-71-8) | 10 µM | 1000 µL | 10 mM |

TABLE 47

Medium composition for NK-MED-004

| Component | Working Conc. | Volume | Stock Conc. |
|---|---|---|---|
| STEMdiff APEL 2 Medium (STEMCELL Technologies, 05275) | 100% | 999 mL | 100% |
| rh BMP-4 (Peprotech, 120-05ET) | 30 ng/mL | 300 µL | 100 µg/mL |
| Thiazovivin (Biological Industry, 1226056-71-8) | 10 µM | 1000 µL | 10 mM |

TABLE 48

Medium composition for NK-MED-005c

| Component | Working Conc. | Volume | Stock Conc. |
|---|---|---|---|
| STEMdiff APEL 2 Medium (STEMCELL Technologies, 05275) | 100% | 998 mL | 100% |
| rh BMP-4 (Peprotech, 120-05ET) | 30 ng/mL | 300 µL | 100 µg/mL |
| rh FGF2 (Peprotech, 100-18C-1MG) | 100 ng/mL | 1000 µL | 100 µg/mL |
| CHIR-99021 (Selleckchem, S1263) | 7 µM | 700 µL | 10 mM |
| Activin-A (R&D Systems, 338-AC-01M/CF) | 5 ng/mL | 100 µL | 50 µg/mL |

TABLE 49

Medium composition for NK-MED-006b

| Component | Working Conc. | Volume | Stock Conc. |
|---|---|---|---|
| STEMdiff APEL 2 Medium (STEMCELL Technologies, 05275) | 100% | 997 mL | 100% |
| rh FGF2 (Peprotech, 100-18C-1MG) | 20 ng/mL | 200 µL | 100 µg/mL |
| rh VEGF165 (Peprotech, 100-20-1MG) | 20 ng/mL | 200 µL | 100 µg/mL |
| rh TPO (Peprotech, 300-18) | 20 ng/mL | 200 µL | 100 µg/mL |
| rh SCF (Peprotech, 300-07) | 100 ng/mL | 1000 µL | 100 µg/mL |
| rh IL-3 (Peprotech, 200-03-100UG) | 40 ng/mL | 400 µL | 100 µg/mL |
| rh Flt3L (Peprotech, 300-19) | 20 ng/mL | 200 µL | 100 µg/mL |
| SB431542 (Selleckchem, S1067) | 5 µM | 500 µL | 10 mM |

TABLE 50

Medium composition for NK-MED-007

| Component | Working Conc. | Volume | Stock Conc. |
|---|---|---|---|
| STEMdiff APEL 2 Medium (STEMCELL Technologies, 05275) | 100% | 998 mL | 100% |
| rh FGF2 (Peprotech, 100-18C-1MG | 20 ng/mL | 200 µL | 100 µg/mL |
| rh VEGF165 (Peprotech, 100-20-1MG) | 20 ng/mL | 200 µL | 100 µg/mL |
| rh TPO (Peprotech, 300-18) | 20 ng/mL | 200 µL | 100 µg/mL |
| rh SCF (Peprotech, 300-07) | 100 ng/mL | 1000 µL | 100 µg/mL |
| rh IL-3 (Peprotech, 200-03-100UG) | 40 ng/mL | 400 µL | 100 µg/mL |
| rh Flt3L (Peprotech, 300-19) | 20 ng/mL | 200 µL | 100 µg/mL |

TABLE 51

Medium composition for NK-MED-008b

| Component | Working Conc. | Volume | Stock Conc. |
|---|---|---|---|
| DMEM (high glucose, GlutaMAX) (Thermo Fisher, 10566016) | 50.3% | 503 mL | 100% |
| F-12 with GlutaMAX (Thermo Fisher, 31765035) | 28% | 280 mL | 100% |
| GlutaMAX (Thermo Fisher, 35050079) | 1x | 10 mL | 100X |
| Glucose* | 4.66 mM | 4.2 mL | 1110 mM |
| Human AB serum (Valley Biomedical Inc, HP1022) | 20% | 20 mL | 100% |
| Zinc sulfate (Millipore Sigma, Z0251) | 36.2 µM | 978 µL | 37 mM |
| Ethanolamine (Millipore Sigma, E0135) | 50 µM | 3 µL | 16.6M |
| Ascorbic acid (Fisher Scientific, NC0762606) | 15 µg/mL | 15 µL | 10 mg/mL |
| Sodium selenite (Millipore Sigma, S9133-1MG) | 5 ng/mL | 50 µL | 100 µg/mL |
| rh IL-3 (Peprotech, 200-03-100UG) | 5 ng/mL | 50 µL | 100 µg/mL |
| rh IL-7 (Peprotech, 200-07) | 20 ng/mL | 200 µL | 100 µg/mL |

TABLE 51-continued

Medium composition for NK-MED-008b

| Component | Working Conc. | Volume | Stock Conc. |
|---|---|---|---|
| rh Flt3L (Peprotech, 300-19) | 15 ng/mL | 150 μL | 100 μg/mL |
| rh IL-15 (Peprotech, 200-15) | 15 ng/mL | 150 μL | 100 μg/mL |
| rh SCF (Peprotech, 300-07) | 20 ng/mL | 200 μL | 100 μg/mL |

*Total glucose concentration in medium is 20 mM (accounting for glucose in DMEM medium, F12 supplement and added glucose provided here).

TABLE 52

Medium composition for NK-MED-009b

| Component | Working Conc. | Volume | Stock Conc. |
|---|---|---|---|
| DMEM (high glucose, GlutaMAX) (Thermo Fisher, 10566016) | 50.3% | 503 mL | 100% |
| F-12 with GlutaMAX (Thermo Fisher, 31765035) | 28% | 280 mL | 100% |
| GlutaMAX (Thermo Fisher, 35050079) | 1X | 10 mL | 100X |
| Glucose* | 4.66 mM | 4.2 mL | 1110 mM |
| Human AB serum (Valley Biomedical Inc, HP1022) | 20% | 20 mL | 100% |
| Zinc sulfate (Millipore Sigma, Z0251) | 37 μM | 978 μL | 37 mM |
| Ethanolamine (Millipore Sigma, E0135) | 50 μM | 3 μL | 16.6M |
| Ascorbic acid (Fisher Scientific, NC0762606) | 15 μg/mL | 1500 μL | 10 mg/mL |
| Sodium selenite (Millipore Sigma, S9133-1MG) | 5 ng/mL | 50 μL | 100 μg/mL |
| rh IL-7 (Peprotech, 200-07) | 20 ng/mL | 200 μL | 100 μg/mL |
| rh Flt3L (Peprotech, 300-19) | 15 ng/mL | 150 μL | 100 μg/mL |
| rh IL-15 (Peprotech, 200-15) | 15 ng/mL | 150 μL | 100 μg/mL |
| rh SCF (Peprotech, 300-07) | 20 ng/mL | 200 μL | 100 μg/mL |

*Total glucose concentration in medium is 20 mM (accounting for glucose in DMEM medium, F12 supplement and added glucose provided here).

TABLE 53

Medium composition for NK-MED-010

| Component | Working Conc. | Volume | Stock Conc. |
|---|---|---|---|
| DMEM (high glucose, GlutaMAX) | 60.5% | 605 mL | 100% |
| F-12 with GlutaMAX | 28% | 280 mL | 100% |
| GlutaMAX | 1x | 10 mL | 100X |
| Glucose* | 2.33 mM | 2.1 mL | 1110 mM |
| Human AB serum | 10% | 100 mL | 100% |
| Zinc sulfate | 37 μM | 978 μL | 37 mM |
| Ethanolamine | 50 μM | 3 μL | 16.6M |
| Ascorbic acid | 15 μg/mL | 1500 μL | 10 mg/mL |
| Sodium selenite | 5 ng/mL | 50 μL | 100 μg/mL |
| Nicotinamide | 6.5 mM | 6.5 mL | 1000 mM |
| rh IL-7 | 10 ng/mL | 100 μL | 100 μg/mL |
| rh Flt3L | 7.5 ng/mL | 75 μL | 100 μg/mL |
| rh IL-15 | 15 ng/mL | 150 μL | 100 μg/mL |
| rh SCF | 20 ng/mL | 200 μL | 100 μg/mL |

*Total glucose concentration in medium is 20 mM (accounting for glucose in DMEM medium, F12 supplement and added glucose provided here).

Example 17: Generation of Human Pluripotent Stem Cells with SERPINB9-P2A-HLA-E Trimer Knock-In and B2M Knock-Out The SERPINB9-P2A-HLA-E trimer sequence was inserted into a human iPSCs cell line. B2M-2 gRNA (SEQ ID NO: 34; Table 19) was used to facilitate the insertion of the SERPINB9-P2A-HLA-E trimer transgene at the targeted B2M gene locus.

Figure 34:
FIG. 34 presents a map of the B2M-CAGGS-SERPINB9-P2A-HLA-E donor plasmid.

A donor plasmid was designed to insert the SERPINB9-P2A-HLA-E trimer transgene into the B2M gene locus such that the starting codon of B2M was removed after undergoing homology directed repair (HDR) to insert the transgene, nullifying any chance of partial B2M expression. The SERPINB9 and HLA-E trimer sequences were linked by P2A peptide sequences to allow for expression of two separate proteins encoded from a single transcript. FIG. 34 presents a schematic of the donor plasmid (SEQ ID NO: 130) and Table 54 identifies the elements and locations therein. The donor plasmid comprises the SERPINB9-P2A-HLA-E trimer transgene (SEQ ID NO: 131) operably linked to a CAGGS promoter (comprising a CMV enhancer, a chicken β-actin promoter, and a chimeric intron) flanked by 800 base pair homology arms with sequence identity to the B2M gene locus around the target site in exon 1. The HLA-E trimer cDNA was composed of a B2M signal peptide fused to an HLA-G presentation peptide fused to the B2M membrane protein fused to the HLA-E protein without its signal peptide. The HLA-E trimer coding sequence (including linkers) is SEQ ID NO: 75 (i.e., SEQ ID NOs: 46, 4, 48, 49, 50, and 51). This HLA-E trimer design has been previously published (Gornalusse et al. (2017) Nat. Biotechnol. 35(8): 765-772).

TABLE 54

Elements of (B2M) SERPINB9-P2A-HLA-E Trimer Donor Plasmid

| Element | Location (size in bp) | SEQ ID NO: |
|---|---|---|
| Left ITR | 1-130 (130) | 21 |
| LHA-B2M | 145-944 (800) | 36 |
| CMV enhancer | 973-1352 (380) | 23 |
| chicken β-actin promoter | 1355-1630 (276) | 24 |
| chimeric intron | 1631-2639 (1009) | 25 |
| SERPINB9 CDS | 2684-3811 (1128) | 129 |
| GSG tag | 3812-3820 (9) | 44 |
| P2A | 3821-3877 (57) | 45 |
| B2M signal sequence | 3878-3937 (60) | 46 |
| HLA-G peptide | 3938-3964 (27) | 47 |
| GS linker 1 | 3965-4009 (45) | 48 |
| B2M membrane protein | 4010-4306 (297) | 49 |
| GS linker 2 | 4307-4366 (60) | 50 |
| HLA-E CDS | 4367-5377 (1011) | 51 |
| 3X Stop codons | 5378-5386 (9) | 52 |
| bGH poly(A) signal | 5404-5628 (225) | 31 |
| RHA-B2M | 5635-6434 (800) | 54 |
| Right ITR | 6476-6616 (141) | 33 |
| Entire plasmid | (8963) | 130 |

The SERPINB9-P2A-HLA-E trimer donor plasmid was introduced along with a ribonucleoprotein (RNP) complex made up of the B2M targeting gRNA and Cas9 protein. Per 1 million of hiPSC cells, 4 μg of plasmid DNA was delivered along with the RNP via electroporation. Electroporation was carried out in hiPSC cells using the Neon Electroporator with the RNP mixture of Cas9 protein (Biomay) and guide RNA (Biospring) at a molar ratio of 5:1 (gRNA:Cas9) with absolute values of 125 pmol Cas9 and 625 pmol gRNA per 1 million cells. To form the RNP complex, gRNA and Cas9 were combined in one vessel with R-buffer (Neon Transfection Kit) to a total volume of 25-50 μL and incubated for 15 min at room temperature (RT). Cells were dissociated using ACCUTASE®, then resuspended in StemFlex media, counted using an NC-200 (Chemometec) and centrifuged. A total of 2×10$^6$ cells were resuspended with the RNP complex and R-buffer was added to a total volume of ~115 μL. This mixture was then electroporated with 3 pulses for 30 ms at 1100 V. Two electroporations was performed. Following electroporation, the cells were pipetted out into a well of a 6 well plate filled with StemFlex media with RevitaCell and laminin 511. The plates were pre-coated with BIOLAMININ 521 CTG at 1:10 dilution. Cells were cultured in a normoxia incubator (37° C., 8% $CO_2$).

Figure 35:
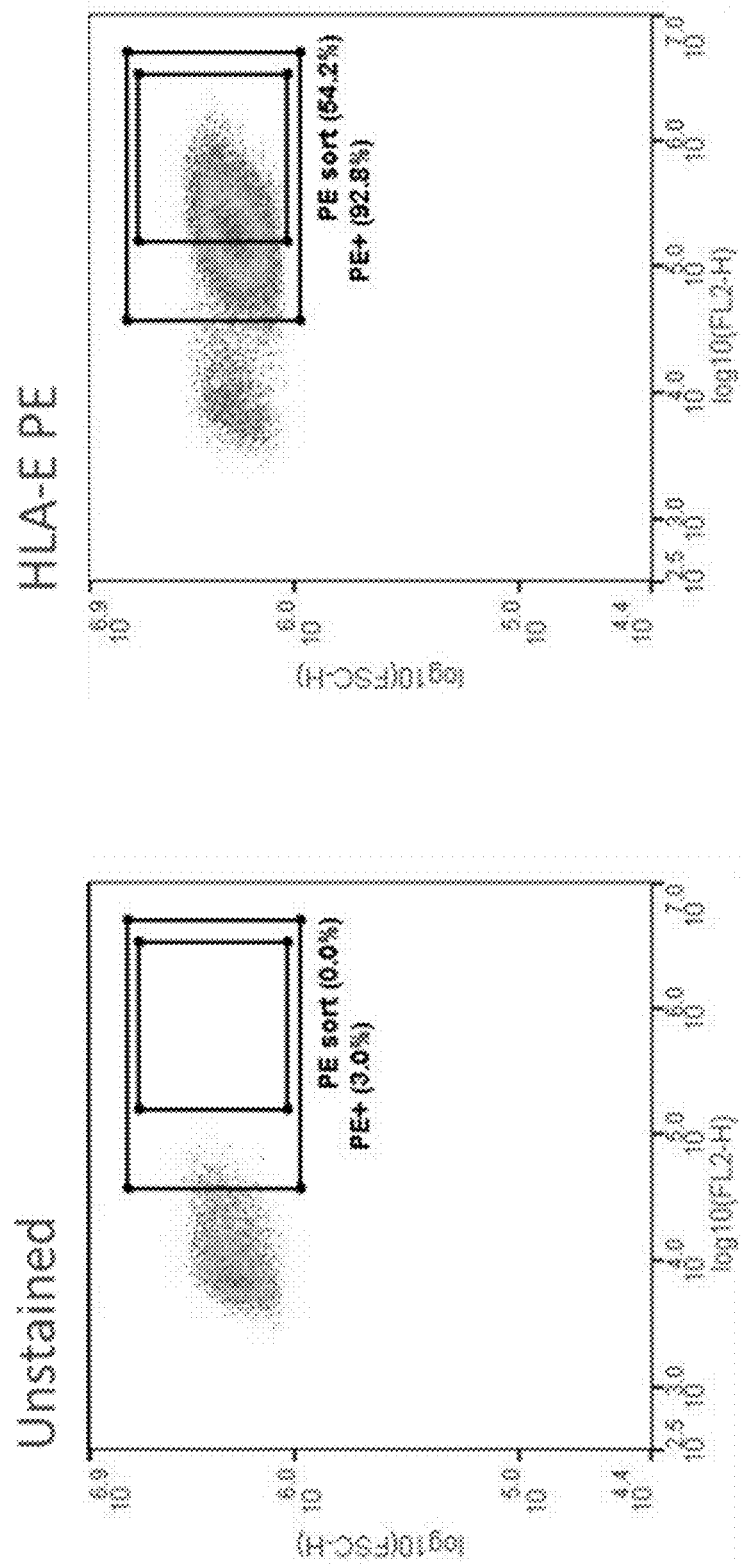
FIG. 35 shows FACS plots generated during the single cell sorting of the B2M-SERPINB-P2A-HLA-E bulk population previously enriched by MACS.

Seven to ten days post electroporation, the cells were enriched for HLA-E trimer expressing cells using an antibody against HLA-E (Table 21) via magnetic assisted cell sorting (MACS) using anti-mouse IgG Dynabeads (ThermoFisher, CELLection™ Pan Mouse IgG Kit, 11531D). These enriched cells represent a bulk KI population of SERPINB9-P2A-HLA-E trimer positive cells. This population was assessed for HLA-E expression by flow cytometry, showing >90% HLA-E expression (FIG. 35).

Following MACS-enrichment, the cells were single-cell sorted as described in Example 1. The anti-HLA-E-PE antibody (Table 21) was used for FACS-sorting into 96-well plates. For FACS-sorting, unedited cells served as a negative control. After sorting, the cells were expanded as described in Example 1 and when confluent, samples were split for maintenance and genomic DNA extraction.

PCR for the genotyping of the edited clones (SERPINB9-P2A-HLA-E trimer knock-in, B2M Null Human Pluripotent Stem Cells (hPSCs)) was performed and the resulting amplified DNA was assessed for cutting efficiency by TIDE analysis.

For determining SERPMN9-P2A-HLA-E trimer knock-in genotyping in the target B2M sequence, PCR for relevant regions was performed using a 2-step protocol with Platinum Taq Supermix (Invitrogen, cat #125320176 and Cat #11495017). The sequences of the PCR primers are presented above in Table 26; and the cycling conditions are provided in Table 27.

Figure 36:
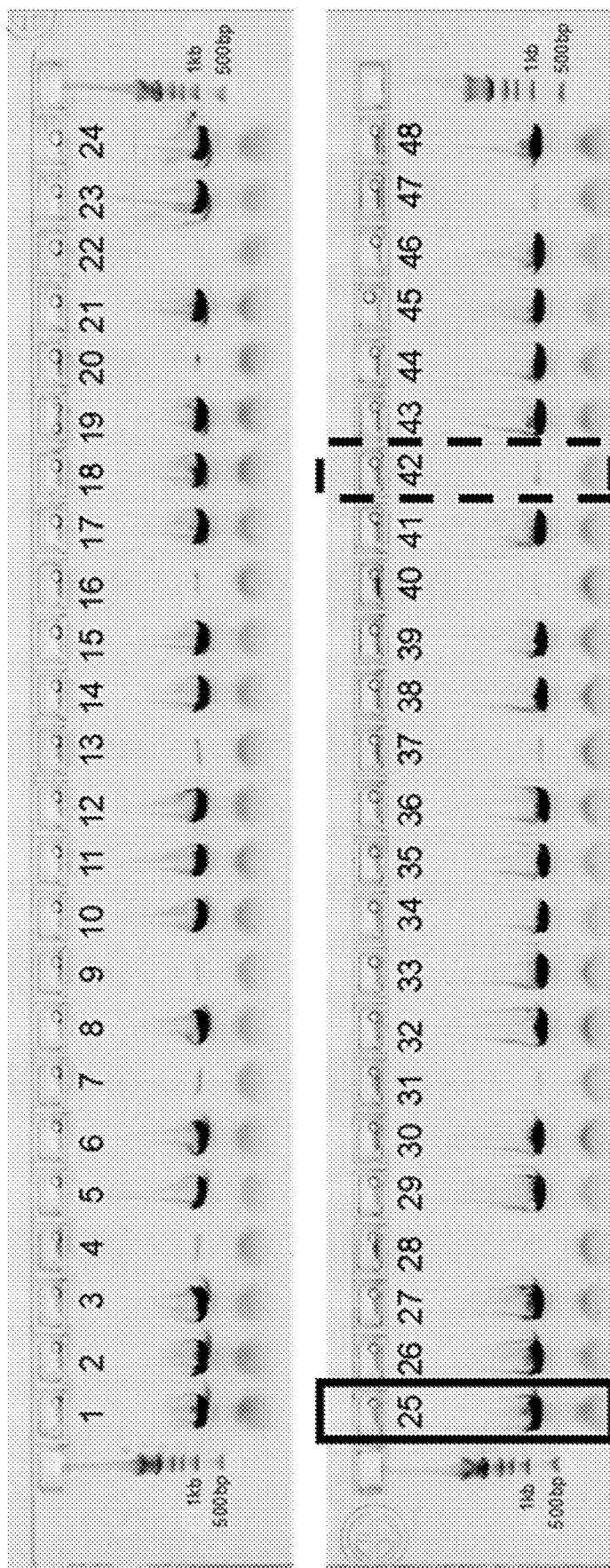
FIG. 36 presents PCR analysis of SERPINB9/HLA-E KI at the B2M gene locus. The gel shows PCR amplification of B2M region of the genome with the 3' primer stationed outside the knock-in (KI) site (not present in the plasmid donor) and the 5' primer stationed inside the KI-only region. Presence of a 1.1 kilo base (kb) band indicates successful integration of the KI construct into the B2M gene locus, the absence of a band indicates a WT genotype.

FIG. 36 shows genotyping results of the transgene KI into B2M gene locus for various edited clones. The presence of a 1.1 kb band indicated successful integration of the KI construct into the B2M gene locus, while the absence of a band indicated a WT genotype.

For determining the presence of any unwanted bacterial plasmid elements from the KI plasmid, two PCRs were performed using Platinum Taq Supermix (Invitrogen, cat #125320176 and Cat #11495017). The sequences of the PCR primers are presented in Tables 55 and 57; and the cycling conditions are provided in Tables 56 and 58.

TABLE 55

Plasmid #1 Primers

| Name | Type | Sequence (5'-3') | SEQ ID NO: |
|---|---|---|---|
| Ori-F2 | forward | CCCTTAACGTGAGTTTTCGTTCCACTGAGC GTCAGACCCCGTAGAAAAGATCAAAGG | 132 |
| Ori-R | reverse | GTCCAACCCGGTAAGACACGACTTATCGC CACTGGCAGCAGCCACTGGTAACAG | 133 |

TABLE 56

Plasmid #1 PCR Cycling Parameters

| Step | Temperature | Time | Cycles |
|---|---|---|---|
| Denaturation | 98° C. | 30 sec | 1 |
| Denaturation | 98° C. | 10 sec | 30 |
| Extension | 72° C. | 10 sec | |
| Elongation | 72° C. | 1 min | 1 |
| Hold | 4° C. | hold | |

TABLE 57

Plasmid #2 Primers

| Name | Type | Sequence (5'-3'') | SEQ ID NO: |
|---|---|---|---|
| F1-Ori-F | forward | CACTTGCCAGCGCCCTAGCGCCCGCTCCTT TCGCTTTCTTCCCTTCCTTTCTC | 134 |
| F1-Ori-R2 | reverse | GGGCGCGTCAGCGGGTGTTGGCGGGTGTC GGGG | 135 |

TABLE 58

Plasmid #2 PCR Cycling Parameters

| Step | Temperature | Time | Cycles |
|---|---|---|---|
| Denaturation | 98° C. | 30 sec | 1 |
| Denaturation | 98° C. | 10 sec | 30 |
| Extension | 72° C. | 10 sec | |
| Elongation | 72° C. | 1 min | 1 |
| Hold | 4 | hold | |

Figure 37:
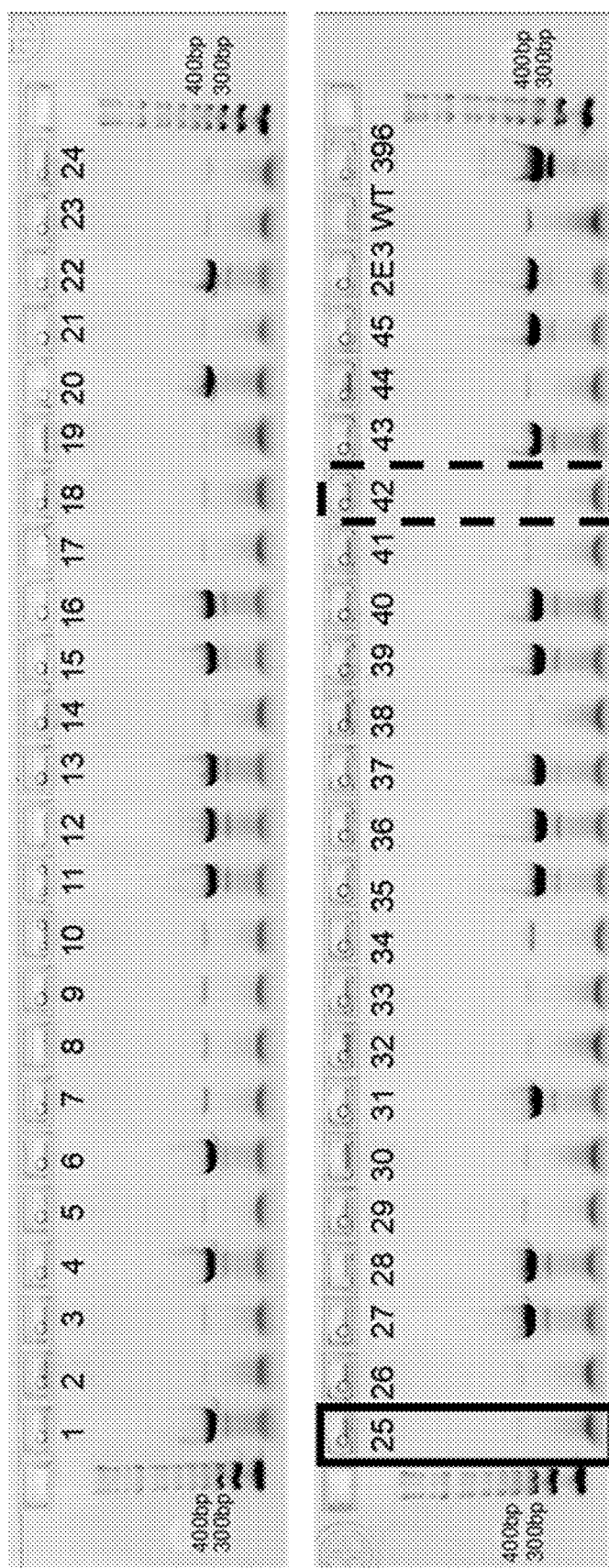
FIG. 37 shows PCR 1 analysis of random plasmid insertions during knock-in of SERPINB9/HLA-E in the B2M gene locus. PCR was performed with 5' and 3' primers that bind outside of the homology arms within the KI plasmid. Presence of a 340 base pair (bp) band indicates that there is random integration of the plasmid backbone within the genome, clones without bands do not have random plasmid insertion.

FIG. 37 shows the first PCR amplifying the bacterial plasmid elements that are not supposed to integrate into the genome by HDR because they are outside the homology arms. Both the 5' and 3' primers bind outside of the homology arms within the KI plasmid. The presence of a 340 bp band indicates that there is random integration of the plasmid backbone within the genome, clones without bands do not have plasmid insertion.

Figure 38:
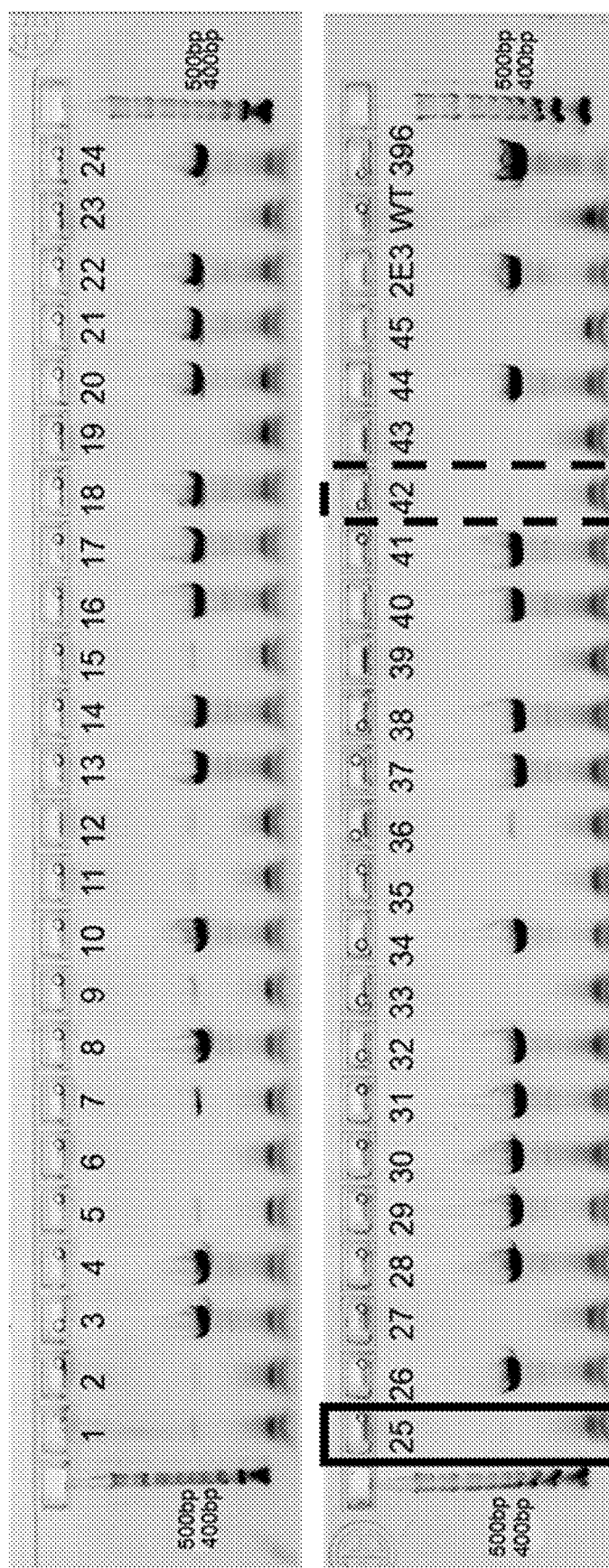
FIG. 38 shows PCR 2 analysis of random plasmid insertions during knock-in of SERPINB9/HLA-E in the B2M gene locus. PCR was performed with 5' and 3' primers that bind outside of the homology arms within the KI plasmid. Presence of a 476 bp band indicates that there is random integration of the plasmid backbone within the genome, clones without bands do not have random plasmid insertion.

FIG. 38 shows the second PCR amplifying the bacterial plasmid elements outside of the homology arms. The presence of a 476 bp band indicates that there is random integration of the plasmid backbone within the genome, clones without bands do not have plasmid insertion.

For determining indels in the target B2M sequence, PCR for relevant regions was performed using Platinum Taq Supermix (Invitrogen, cat #125320176 and Cat #11495017). The sequences of the PCR primers are presented above in Table 22; and the cycling conditions are provided in Table 23.

Figure 39:
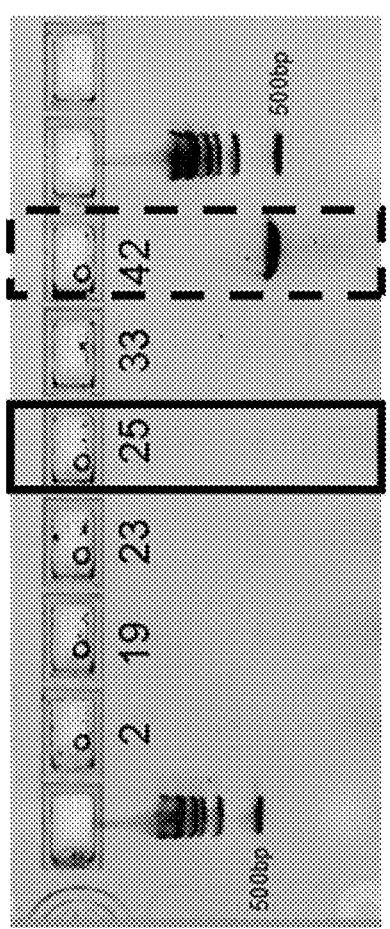
FIG. 39 shows zygosity at the B2M gene locus following knock-in of SERPINB9/HLA-E. Gel shows PCR products after amplification using primers spanning the gRNA cut site. Presence of a 573 bp band indicates a wild-type (WT) genotype which will be found in clones that are unedited or are heterozygous for the KI construct, a clone with a homozygous KI would not produce a band in this PCR because the KI size would be too large for the elongation time of this reaction.

FIG. 39 shows the B2M indel results for various edited clones. The presence of a 573 bp band indicated a WT genotype which would be found in clones that are unedited or are heterozygous for the KI construct, as homozygous clones will not have a band. The B2M KO state of clones was confirmed via PCR and Sanger sequencing. The resulting DNA sequences of the target B2M region were aligned in Snapgene software to determine indel identity and homo- or heterozygosity.

Based on the PCR and Sanger sequencing analysis of the edited clones, the clone shown in lane 25 in FIGS. 36-39 was chosen as "clone 1" and the clone shown in lane 42 was chosen as "clone 2," which were shown to have the SER-PINB9-P2A-HLA-E KI and no bacterial plasmid elements, while the sequencing data confirmed that B2M was completely knocked-out. Clone 1 was homozygous for the KI into B2M while clone 2 was heterozygous for the KI and had an indel of +1T in the B2M WT band. Clones in lanes 2, 19, 23, and 33 were also chosen as "clones 3-6," respectively, and were confirmed homozygous for the SERPINB9-P2A-HLA-E KI into B2M.

Example 18: Differentiation of Stem Cells into Natural Killer Cells

Figure 40:
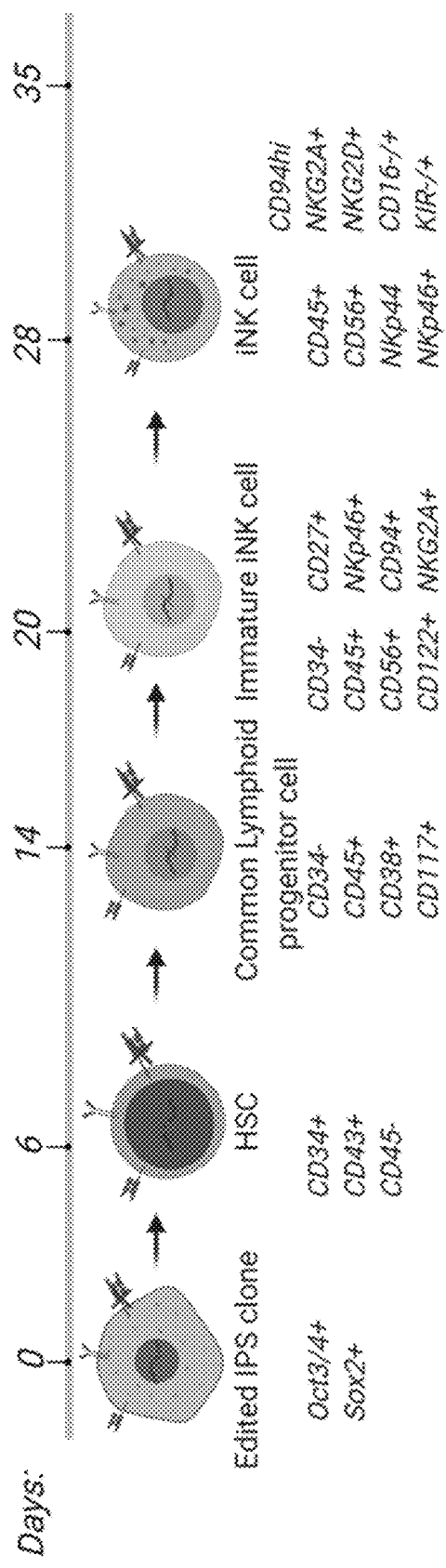
FIG. 40 presents a time course of NK cell differentiation.
Figure 41:
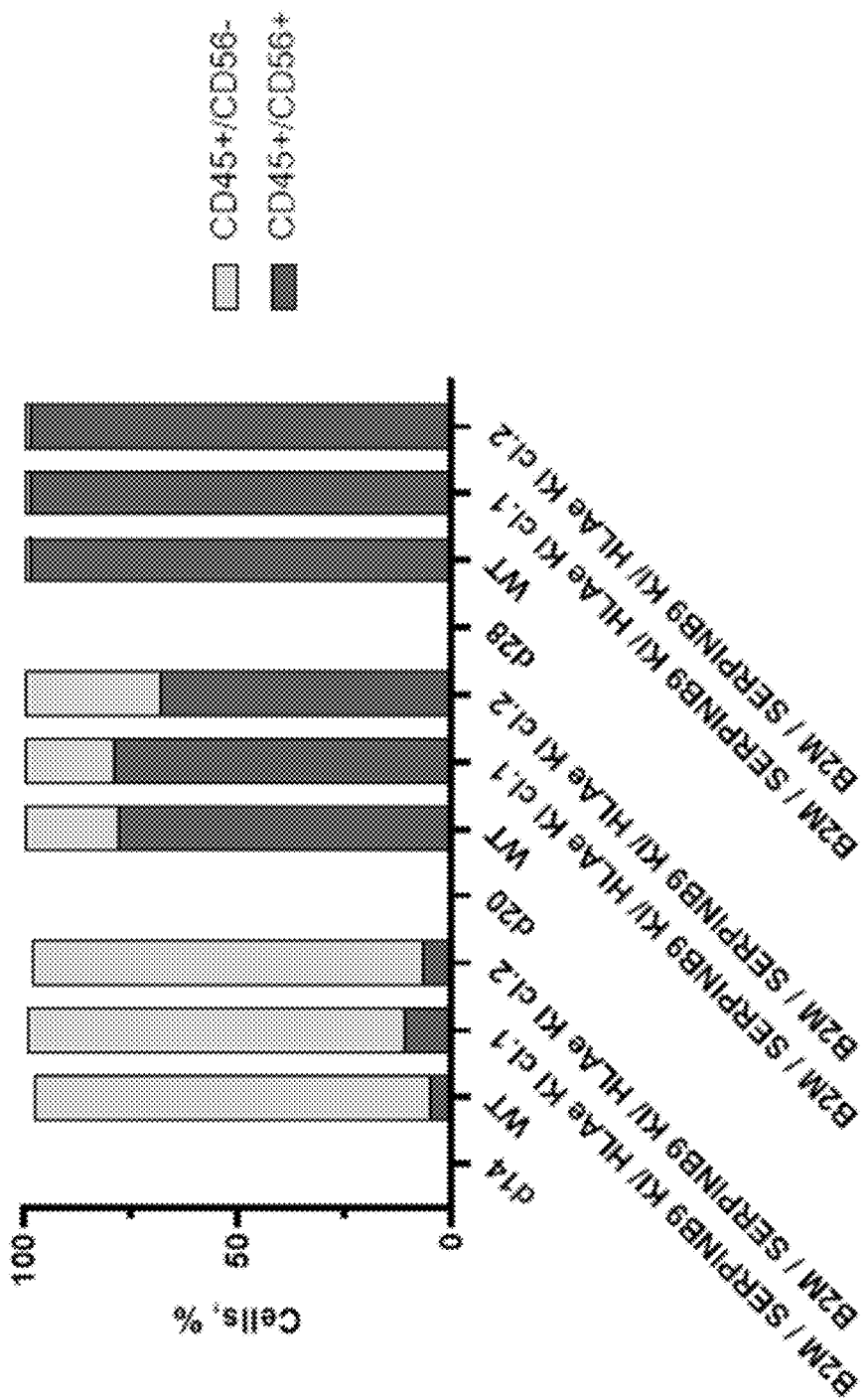
FIG. 41 shows the development of CD45$^+$/CD56$^+$ iNK over the differentiation time course, derived from WT or SERPINB9 KI/HLA-E KI/B2M KO clonal iPSCs.

The SERPINB9 KI/HLA-E KI/B2M KO stem cells (clones 1-4) prepared in Example 17, were differentiated into natural killer (NK) cells (iNK cells). FIG. 40 provides a schematic timeline and cell stages of iNK differentiation, as well as the characteristic cell markers at each stage. The iNK differentiation protocol was developed and based on published protocols (see e.g., Ng et al., Nat Protocols 3:768:776 (2008) and U.S. Pat. No. 9,260,696). The iNK cells expressed NK cell markers. FIG. 41 presents an example of $CD45^+/CD56^+$ iNK cells development during IPSC WT and SERPINB9 KI/HLA-E KI/B2M KO lines differentiation to iNK using the iNK differentiation protocol. Listed edits introduced into IPSC did not affect iNK differentiation.

Example 19: SERPINB9 Protects Differentiated Cells from NK Cell Killing

The ability of cells differentiated from the SERPINB9 KI stem cells to survive attack from peripheral blood NK (PB-NK) cells was determined using a luminescent cell viability assay (CellTiter-Glo®, Promega). This assay determines the number of viable cells based on quantitation of the ATP present, which signals the presence of metabolically active cells. After incubation with effector cells, the CellTiter-Glo reagent was added to the target cells and luminescence was measured. The light intensity is linearly related to ATP concentration.

Figure 42A:
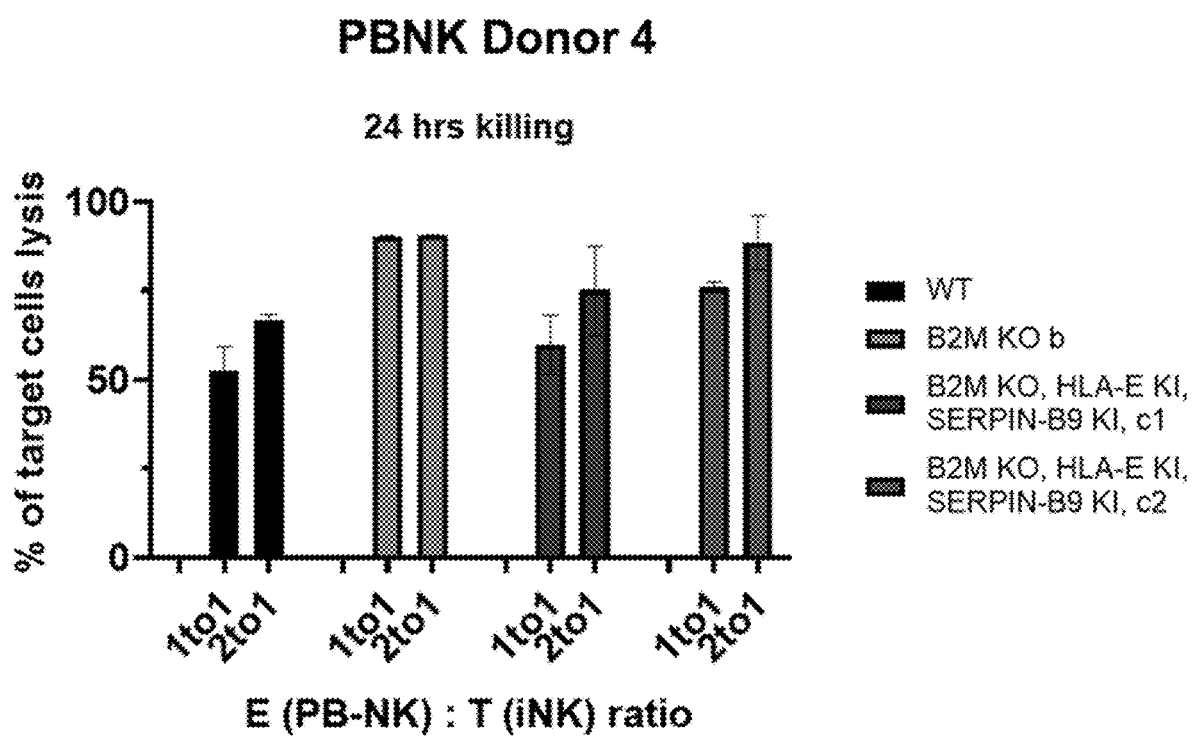
FIG. 42A presents a plot of the percentage of target (iNK) cells killed by peripheral blood NK (PB-NK) cells from PBNK donor 4. Various iNK cells were incubated with PB-NK cells at various E:T ratios for 24 hours.
Figure 42B:
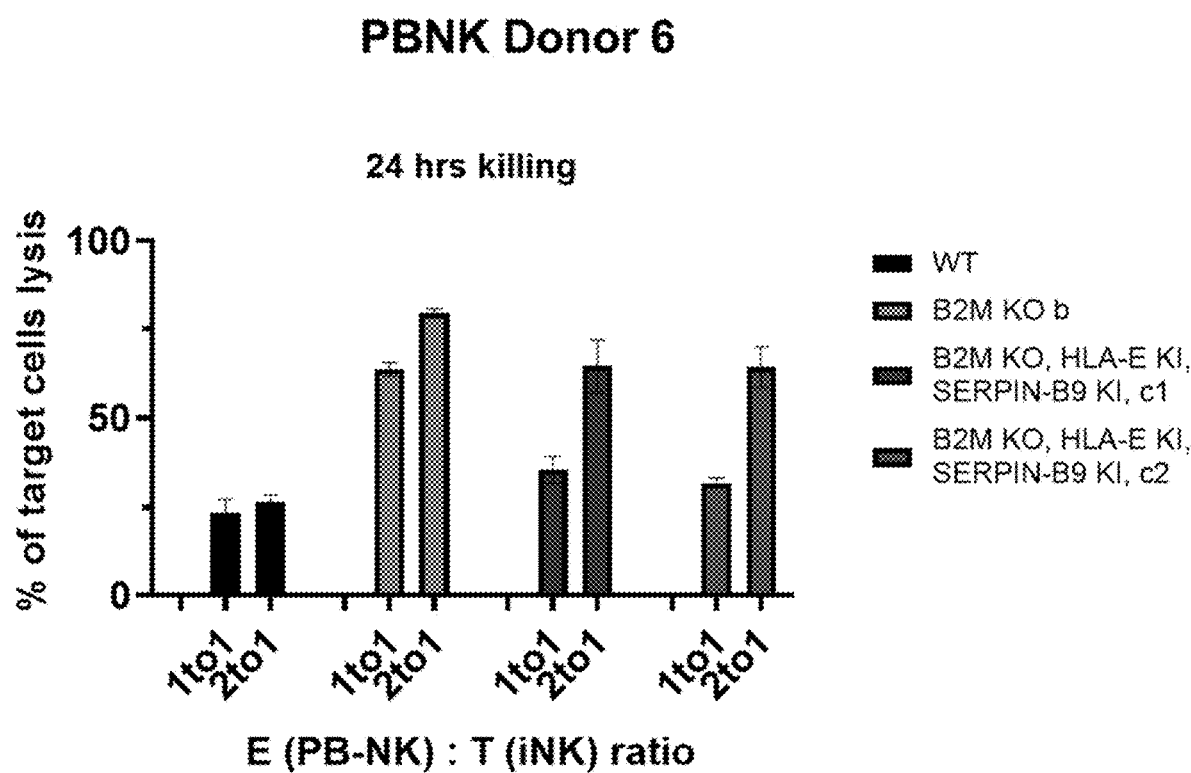
FIG. 42B shows a plot of the percentage of target iNK cells killed by PB-NK cells from PBNK donor 6. Various iNK cells were incubated with PB-NK cells at various E:T ratios for 24 hours.
Figure 42C:
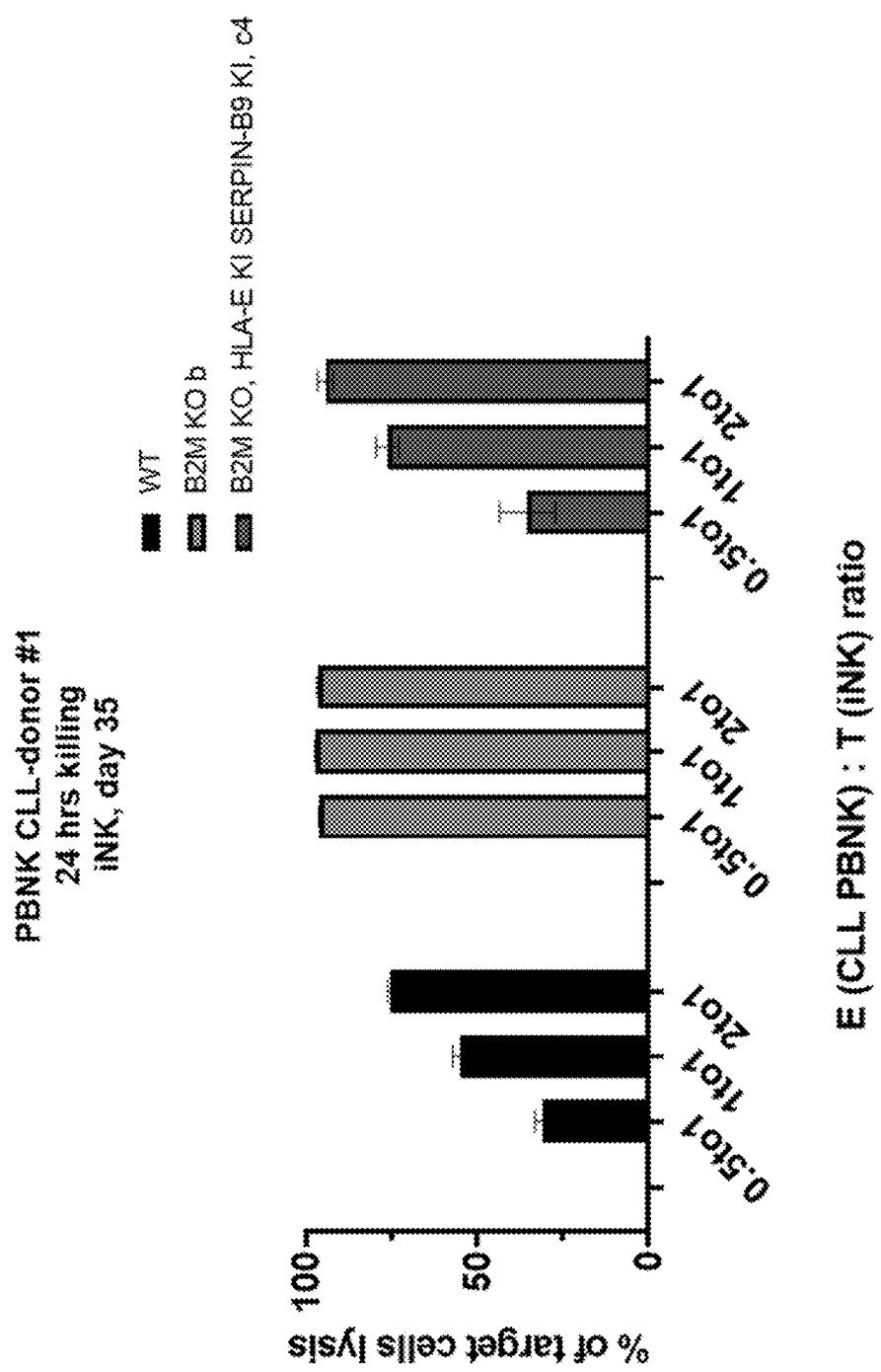
FIG. 42C shows a plot of the percentage of target iNK cells killed by PB-NK cells from PBNK-CLL donor 1. Various iNK cells were incubated with PB-NK cells at various E:T ratios for 24 hours.
Figure 42D:
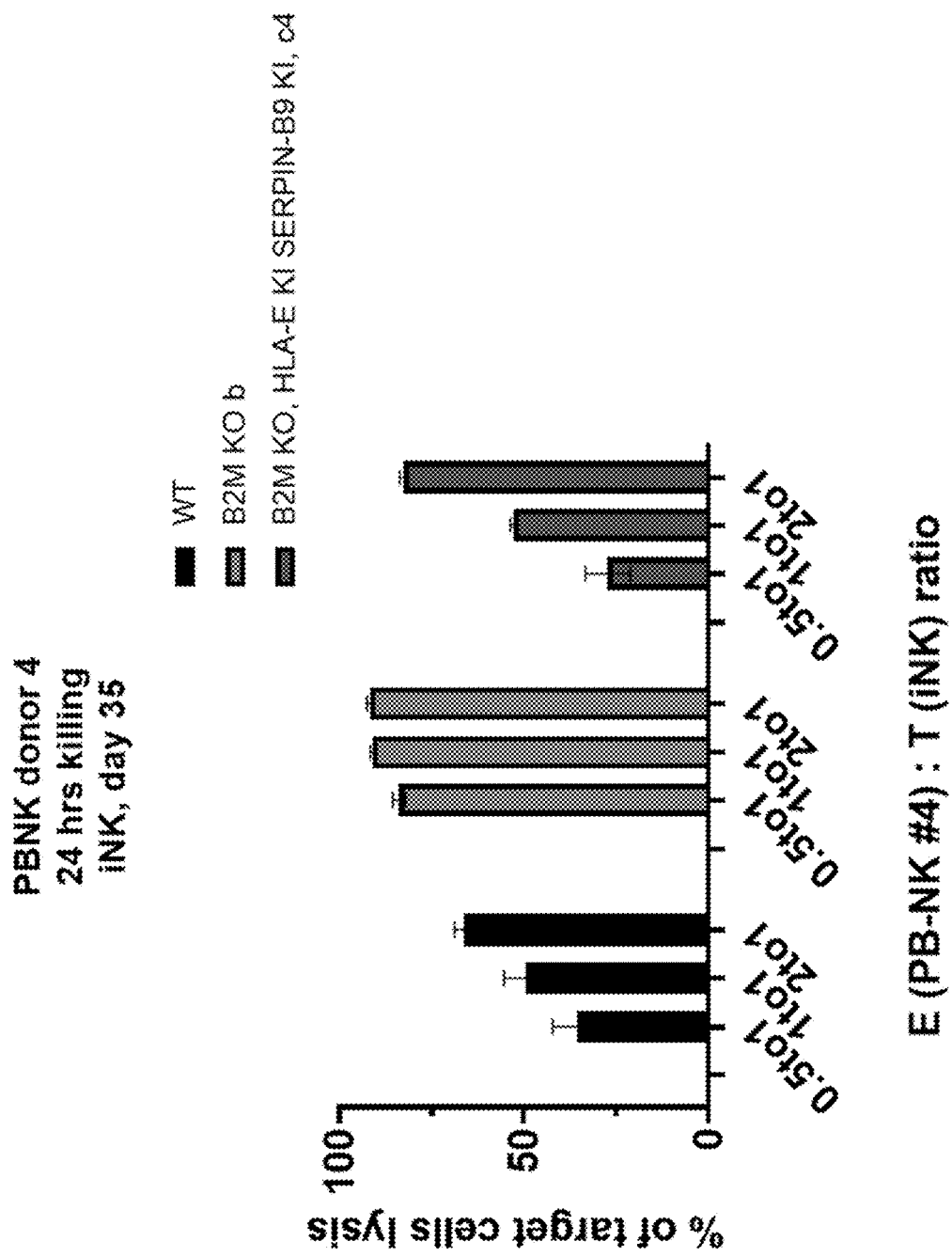
FIG. 42D shows a plot of the percentage of target iNK cells killed by PB-NK cells from PBNK donor 4. Various iNK cells were incubated with PB-NK cells at various E:T ratios for 24 hours.
Figure 42E:
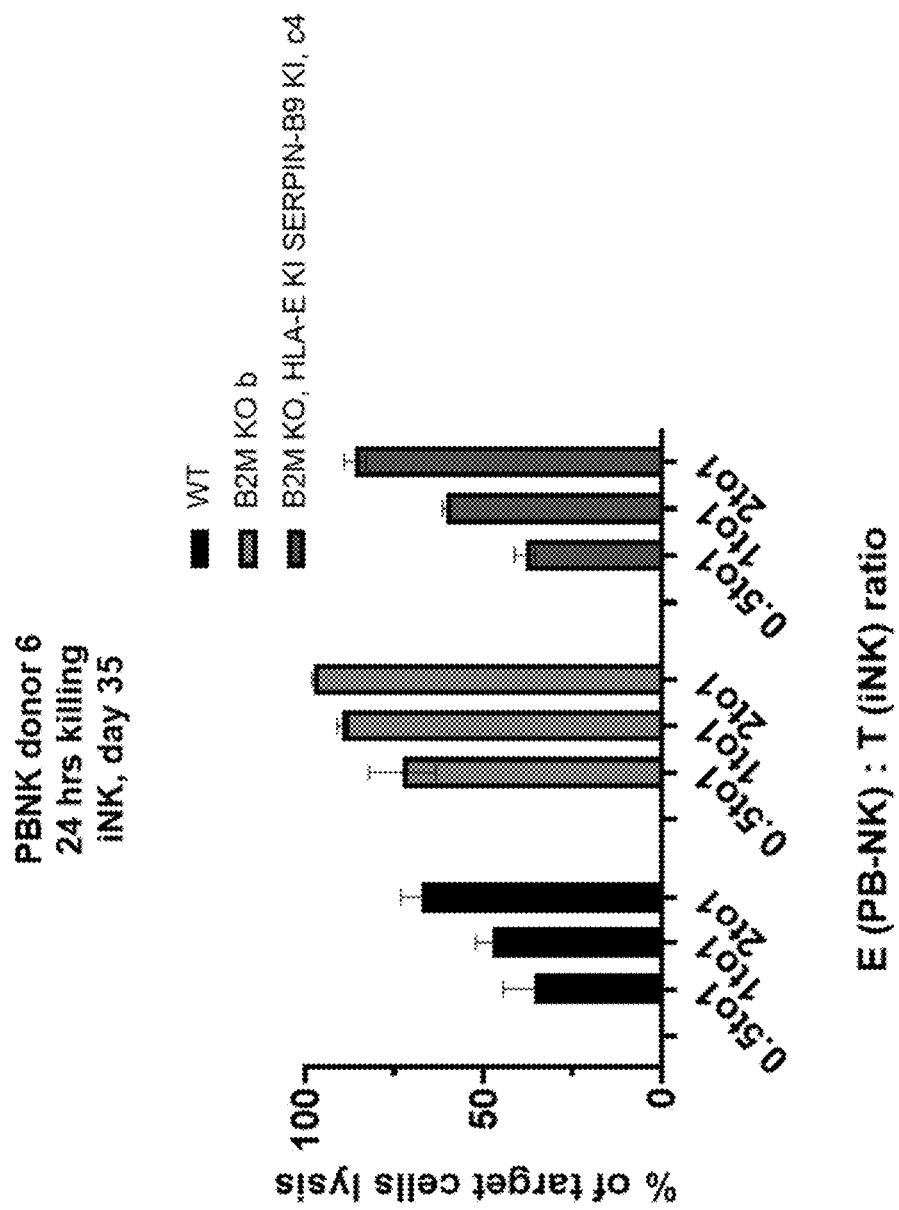
FIG. 42E shows a plot of the percentage of target iNK cells killed by PB-NK cells from PBNK donor 6. Various iNK cells were incubated with PB-NK cells at various E:T ratios for 24 hours.

The cytotoxicity of PB-NK cells toward iNK cells differentiated from edited iPSCs was examined. PB-NK effector cells derived from several donors were incubated with day 31 iNK target cells (derived from clones 1 and 2) prepared above in Example 18 at E:T ratios of 1:1 or 2:1 for 18-24 hour. Control target cells included iNK derived from wild-type iPSC cells and B2M KO iPSC cells. FIG. 42A and FIG. 42B present the percent of target cell lysis in the presence of PB-NK cells from two different donors, PBNK donor 4 (FIG. 42A) and PBNK donor 6 (FIG. 42B), respectively. The B2M KO/SERPINB9 KI/HLA-E KI provided protection from NK killing as compared to B2M KO alone. FIGS. 42C-42E show the percent of target cell lysis (i.e., day 35 iNK target cells (derived from clone 4) prepared above in Example 3) in the presence of PB-NK cells from 3 different donors, PBNK-CLL-donor #1 (FIG. 42C), PBNK donor 4 (FIG. 42D), and PBNK donor 6 (FIG. 42E), respectively, at E:T ratios of 0.5:1, 1:1 or 2:1 for 24 hours.

Figure 43:
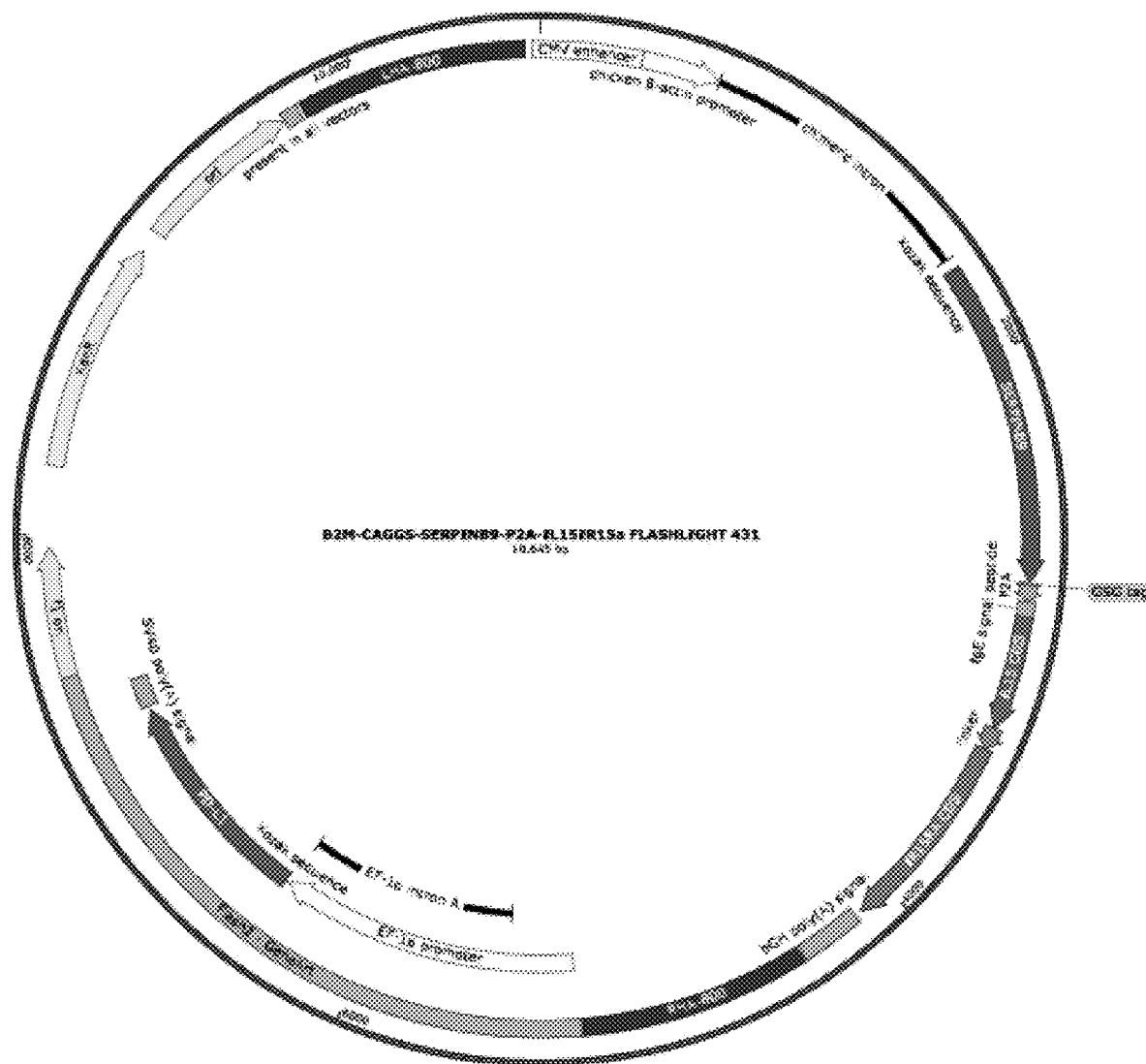
FIG. 43 presents a map the B2M-CAGGS-SERPINB9-P2A-IL15/IL15Rα fusion donor plasmid.

Example 20: Generation Off Human Pluripotent Stem Cells with SERPINB9-P2A-IL15/IL15Rα Fusion Knock-In and B2M Knock-Out A transgene comprising SERPINB9-P2A-IL15/IL15Rα fusion was inserted in the B2M gene locus of human iPSCs. The B2M-2 gRNA (SEQ ID NO: 34) shown in Table 19 was used. The donor plasmid was designed such that the starting codon of B2M was removed after undergoing homology directed repair to insert the SERPINB9-P2A-IL15/IL15Rα sequence, nullifying any chance of partial B2M expression. FIG. 43 presents a schematic of the plasmid (SEQ ID NO: 148) and Table 59 identifies the elements and locations therein. The donor plasmid contained a CAGGS promoter driven SERPINB9-P2A-IL15/IL15Rα cDNA sequence flanked by 800 base pair homology arms with identical sequence to the B2M gene locus around exon 1. The IL15/IR15a fusion sequence was designed as previously published (Hurton et al. (2016) Proc Natl Acad Sci USA; 113(48):E7788-E7797. doi: 10.1073/pnas.1610544113). The IL15/IR15a fusion coding sequence (including linkers) is SEQ ID NO: 76 (i.e., SEQ ID NOs: 40, 41, 42, and 43). The SERPINB9-P2A-IL15/IL15Rα coding sequence is SEQ ID NO: 137 (i.e., SEQ ID NOS: 129, 44, 45, and 40-43). The donor plasmid (SEQ ID NO: 148) also contained sequence encoding PD-L1 (SEQ ID NO: 146) driven by an EF-1 alpha promoter (SEQ ID NO: 145) downstream of the right homology arm for screening and removing cell clones in which the donor plasmid erroneously integrated into the genome.

TABLE 59

Elements of (B2M) SERPINB9-P2A-IL15/IL15Rα Donor Plasmid

| Element | Location (size in bp) | SEQ ID NO: |
| --- | --- | --- |
| LHA-B2M | 9791-10590 (800) | 36 |
| CMV enhancer | 10619-353 (380) | 23 |
| chicken β-actin promoter | 356-631 (276) | 24 |
| chimeric intron | 632-1640 (1009) | 25 |
| SERPINB9 CDS | 1685-2812(1128) | 129 |
| GSG tag | 2813-2821(9) | 44 |
| P2A | 2822-2878 (57) | 45 |
| IgE signal peptide | 2879-2932 (54) | 40 |
| IL-15 CDS | 2933-3331 (399) | 41 |
| linker | 3332-3409 (78) | 42 |
| IL15Rα CDS | 3410-4120(711) | 43 |
| bGH poly(A) signal | 4144-4368 (225) | 31 |
| RHA-B2M | 4375-5174 (800) | 54 |
| EF-1α promoter | 5194-6396 (1203) | 145 |
| PD-L1 | 6412-7284 (873) | 146 |
| SV40 poly(A) signal | 7302-7423 (122) | 147 |
| Entire plasmid | 10,645 bp | 148 |

Figure 44:
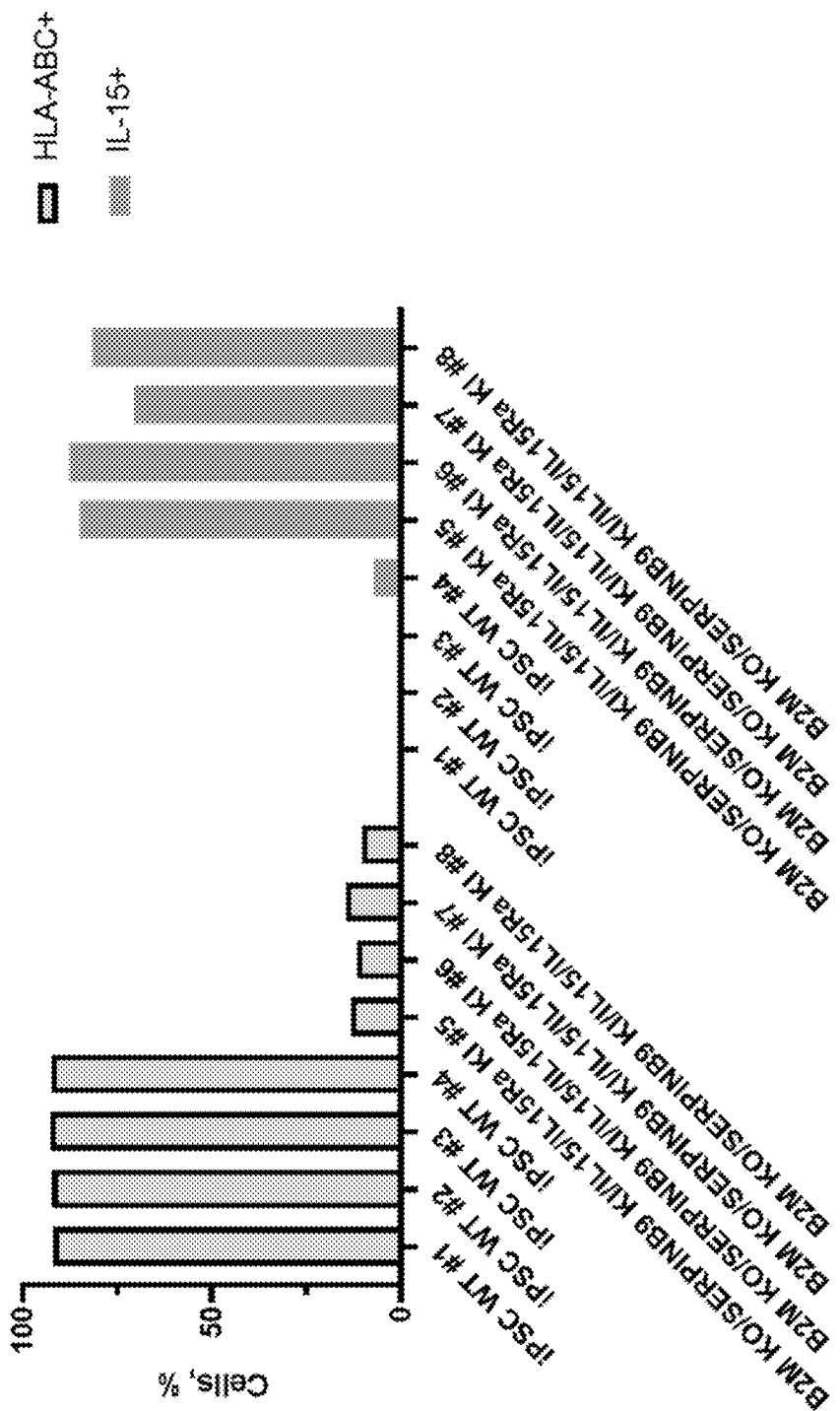
FIG. 44 shows percentage of cells in a bulk population that had HLA-ABC$^+$ expression or IL15 surface expression. Cells were analyzed by flow cytometry.
Figure 45A:
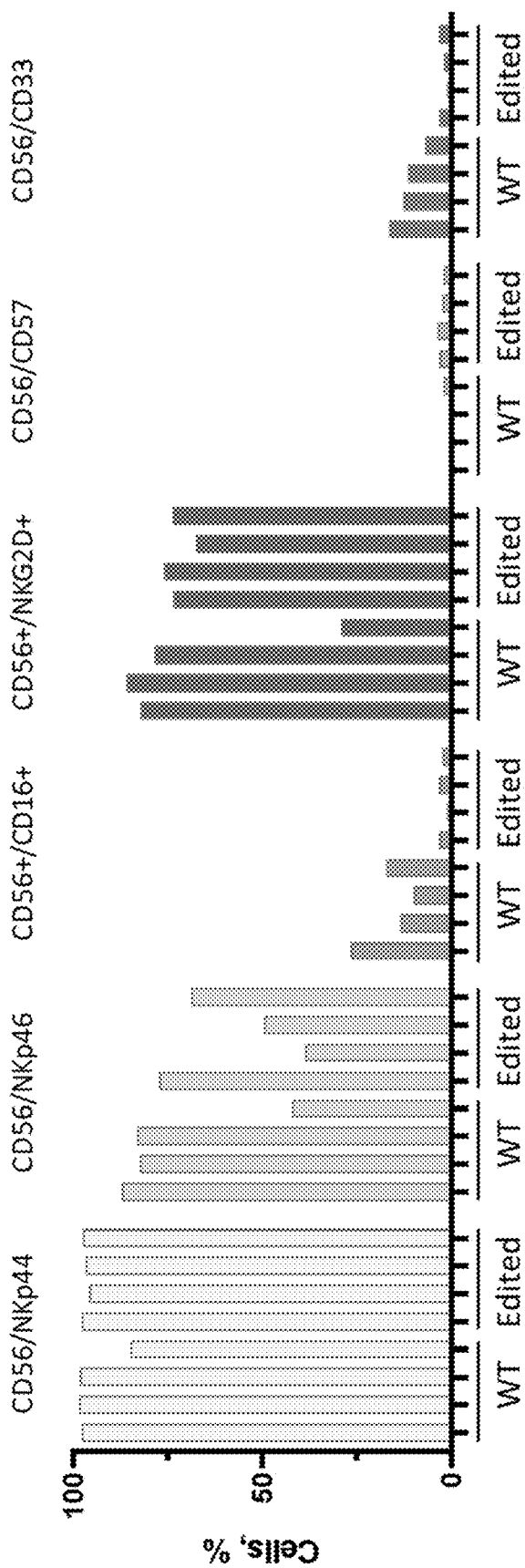
FIGS. 45A and 45B provide graphs demonstrating expression of differentiation markers in iPSC WT derived iNK cells and base edited iPSC derived iNK cells (B2M KO, SERPINB9 KI, IL15/IL15Rα KI). Cells were analyzed by flow cytometry for CD56+/NKp44+, CD56+/NKp46+, CD56+/CD16+, CD56+ NKG2D+, CD56+/CD57+, and CD56+/CD33+ (FIG. 45A) and CD56+/NKG2A+, CD56+/FAS+, CD56+/FAS-L+, CD56+/KIR+, and PD1+/TIGIT− (FIG. 45B).
Figure 45B:
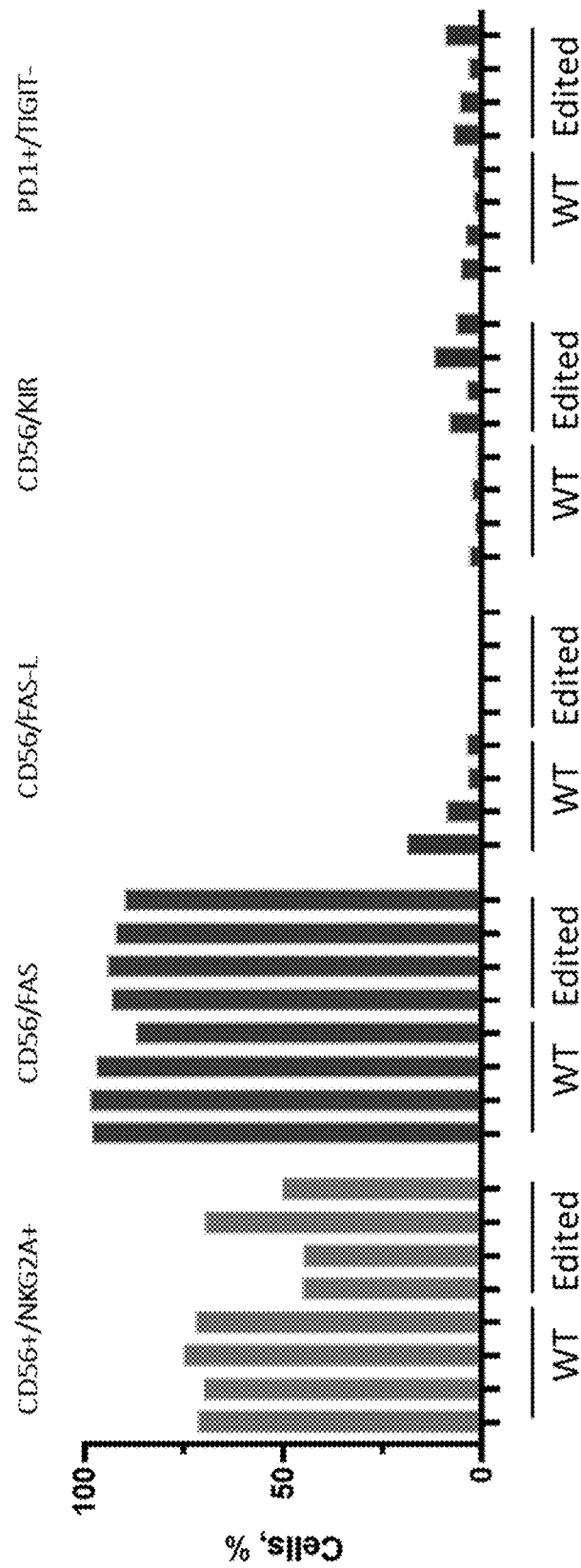

The cells were electroporated with an RNP comprising Cas9 and B2M-2 gRNA and the donor plasmid, cultured, and characterized essentially as described above in Examples 15 and 17. For example, PD-L1 negative cells were cell sorted for 1115 positive cells by FACS on day 2 post electroporation. 1115 positive cells were again cell sorted by FACS post day. 7. FIG. 44 shows that the edited cells were effectively edited and maintained in bulk populations. The bulk population of edited cells were differentiated, essentially as described in Example 16. iNK biomarkers were measured on Day 28 (FIGS. 45A and 45B). In a cell killing assay, day 28 and 35 iNK cells had high level of cytotoxicity against K562 cells (4 hr incubation).

After confirmation of the transgene KI and B2M KO, the cells with the base edits (SERPINB9 KI, IL15/IL15Rα KO, B2M KO) were further edited to have CISH KO (CISH Ex1 T18; SEQ ID NO: 82) and FAS KO (FAS Ex 1 T9; SEQ ID NO: 37) (i.e., prototype edits) and differentiated essentially as described above in Example 18.

Example 21: Generation of Human Pluripotent Stem Cells with SERPINB9-P2A-IL15/IL15Rα Fusion Knock-In and B2M Knock-Out, Anti-CD30 CAR-P2A-HLA-E Trimer Knock-In and CIITA Knock-Out, CISH Knock-Out, and Fas Knock-Out iPSC cells were generated to have SERPINB9-P2A-IL15/IR15a KI and B2M KO, anti-CD30 CAR-P2A-HLA-E KI and CIITA KO, as well as CISH KO and FAS KO, generally as described in Examples 15 and 20, with modifications.

First, SERPINB9-P2A-IL15/IR15a was knocked into the cells using the SERPINB9-P2A-IL15/IR15a plasmid (SEQ ID NO: 148) and the B2M-T2 gRNA. The iPSCs were passaged the day before electroporation and seeded as 10 million cells per T75 flask. On day of electroporation, the cells were split again and electroporated using the Neon Electroporator with the RNP mixture of Cas9 protein (Biomay) and guide RNA (IDT) at a molar ratio of 5:1 (gRNA:Cas9) with absolute values of 625 pmol gRNA and 125 pmol Cas9 per 2 million cells. To form the RNP complex, gRNA and Cas9 were combined in one vessel with R-buffer (Neon Transfection Kit) to a total volume of 25-50 µL and incubated for 15 min at room temperature (RT). This mixture was then combined with the cells to a total volume of ~115 µL using R-buffer. This mixture was then electroporated with 3 pulses for 30 ms at 1000 V. Following electroporation, the cells were pipetted out into a 6 well plate filled with STEMFLEX™ media with REVITACELL™ Supplement (100×) and BIOLAMININ 521 CTG at 1:10 dilution. Cells were cultured in a normoxia incubator (37° C., 8% $CO_2$).

On day 2 post electroporation, the PD-L1 negative cells were FACS-sorted (FACS #1) for IL15 positive cells to enrich for transfected cells. At 7 to 10 days post electroporation, the cells were FACS-sorted (FACS #2) again for IL15$^+$ cells to enrich for knock in positive cells (e.g., L5V018B cells). The cells were allowed to expand, and then FAS was knocked out using the FAS Ex1 T9 gRNA (SEQ ID NO: 37). The knockout edits were performed using an RNP of 5:1 (gRNA:Cas9) with absolute values of 625 pmol gRNA and 125 pmol Cas9 per 1 million cells. This mixture was then electroporated with 1 pulse for 20 ms at 1500 V followed by 1 pulse for 100 ms at 500 V. The cells were electroporated with RNP targeting FAS twice 3 days apart to ensure near 100% knockout. Following knockout of FAS, the cells were treated with RNP targeting CISH (CISH Ex1 T18 gRNA (SEQ ID NO: 82)) and were also electroporated twice 3 days apart to ensure near 100% knockout of CISH. After this targeting, the bulk population represents an enriched population of SERPINB9-P2A-IL15/IR15a KI cells with knockouts of B2M, FAS, and CISH (e.g., BL5V019B cells).

This population was expanded and the cells were electroporated with a plasmid encoding anti-CD30 CAR-P2A-HLA-E trimer (e.g., SEQ ID NO: 110, 114, or 118 encoding anti-CD30 CAR 4, 5, or 6, respectively) and RNP targeting CIITA. This electroporation for KI was done the same way as the electroporation for KI of SERPINB9-P2A-IL15/IR15a above. At 2 days post electroporation, the cells were enriched for transfection by performing FACS (FACS #3) for HLA-E. At 7 to 10 days post electroporation, the cells were FACS (FACS #4) sorted again for HLA-E to enrich for HLA-E knock in positive cells. After FACS #4, the cells were bulk sorted to remove residual PD-L1 positive cells. This population represents an enriched bulk of SERPINB9-P2A-IL15/IR15a KI and anti-CD30 CAR-P2A-HLA-E KI double positive cells with a knockout of B2M, FAS, CISH, and CIITA (e.g., termed L5V024B (anti-CD30 CAR4), L5V025B (anti-CD30 CAR5), or L5V026B (anti-CD30 CAR6) cells). The cells were differentiated essentially as described in Example 18 and characterized. Some of the cells from the bulk population cells were single cell sorted for EIL15 and HLA-E double positive cells and plated on 96 well plates for the generation of single cell clones.

Figure 46:
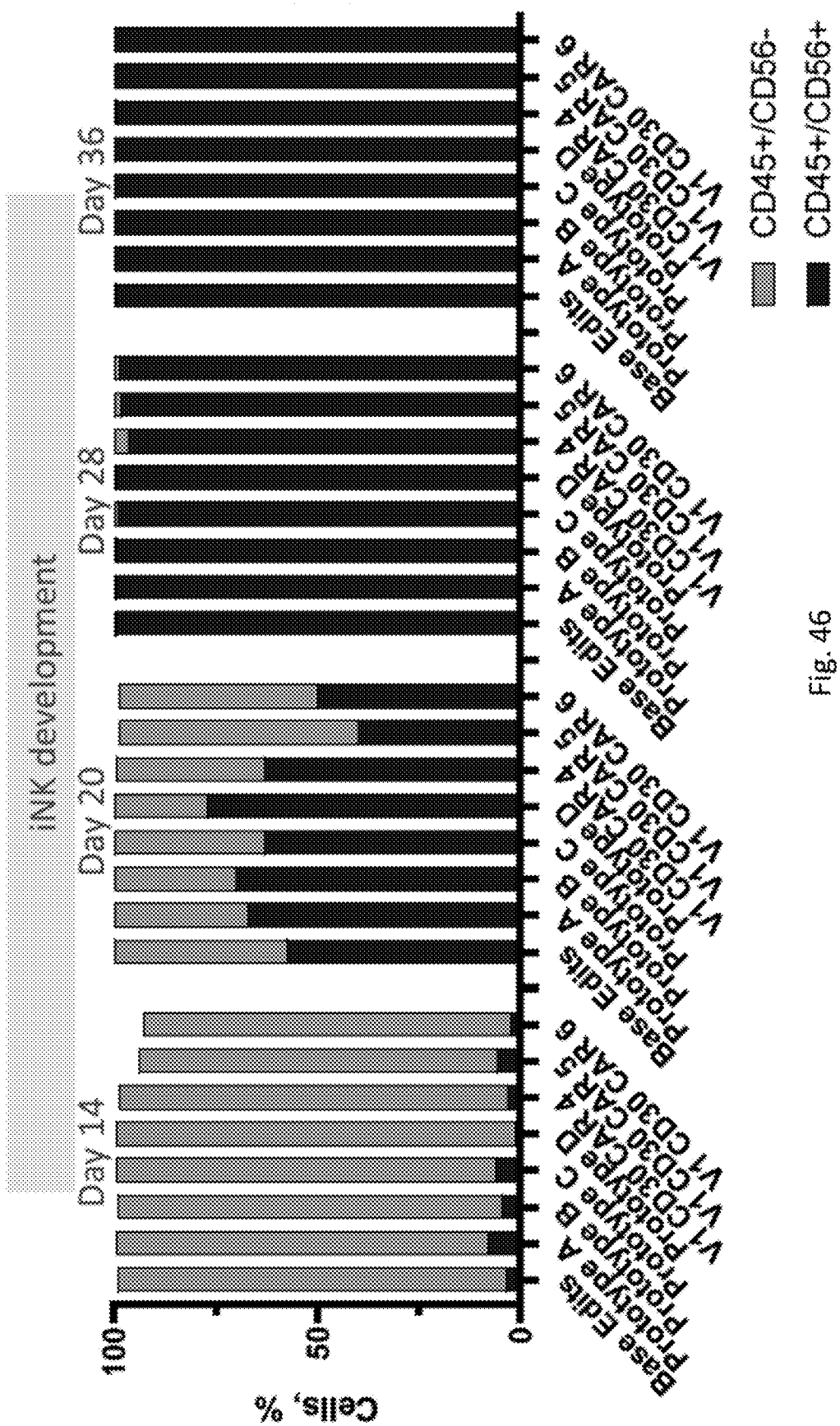
FIG. 46 presents the percentage of cells expressing of CD45 and/or CD56 at days 14, 20, 28, and 36 during differentiation of iNK cells from iPSCs with base edits (B2M KO, SERPINB9 KI, IL15/IL15Rα KI), prototype (B2M KO, SERPINB9 KI, IL15/IL15Rα KI, CISH KO. FAS KO), and prototype+CD30 CAR (4, 5, or 6) KI and HLA-E KI.
Figure 47A:
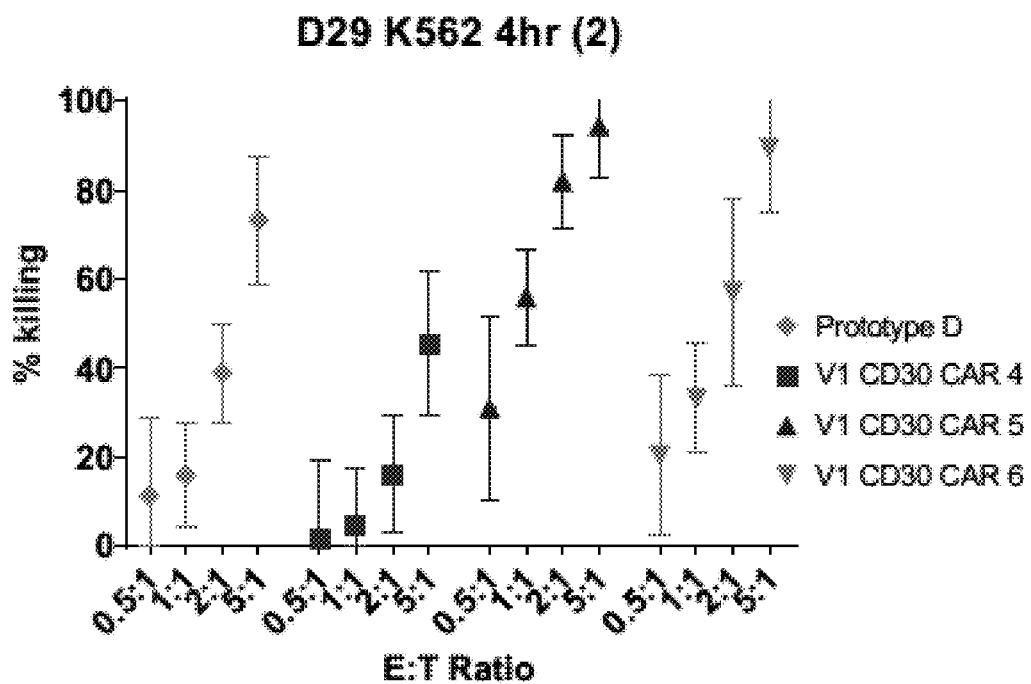
FIG. 47A-D present percent of killing by day 29 iNK cells differentiated from cells with base edits (B2M KO, SERPINB9 KI, IL15/IL15Rα KI), prototype (B2M KO, SERPINB9 KI, IL15/IL15Rα KI, CISH KO. FAS KO), and prototype+CD30 CAR (4, 5, or 6) KI and HLA-E KI of K562 cancer cells (FIG. 47A), KMH2 cancer cells (FIG. 47B), L428 cancer cells (FIG. 47C), or L540 cancer cells (FIG. 47D).
Figure 47B:
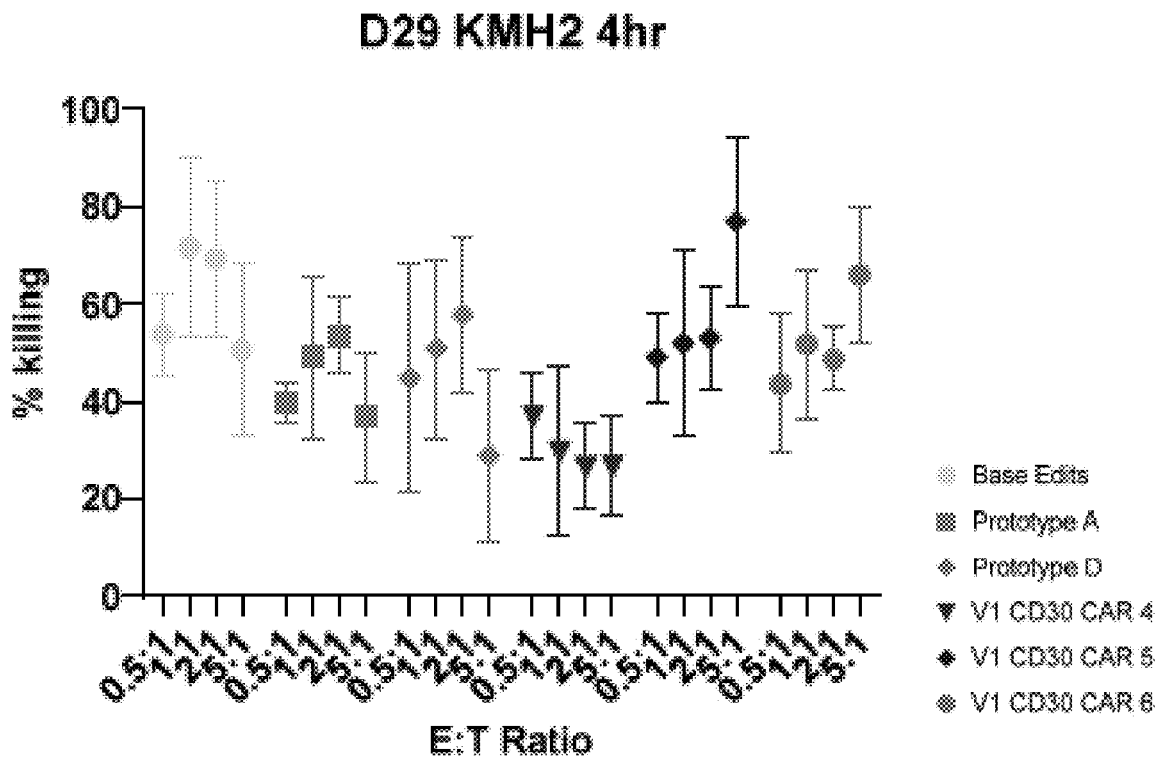
Figure 47C:
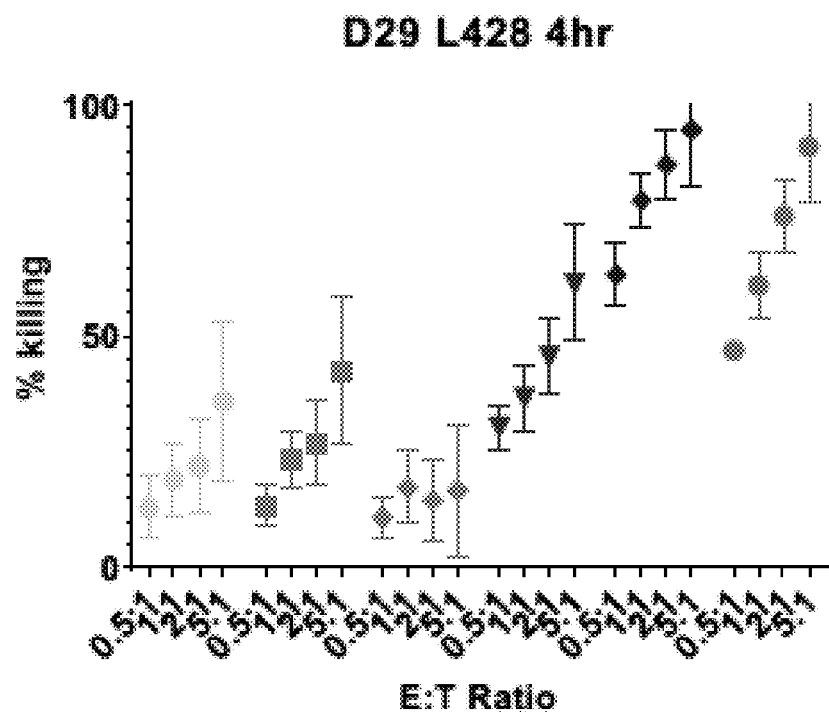
Figure 47D:
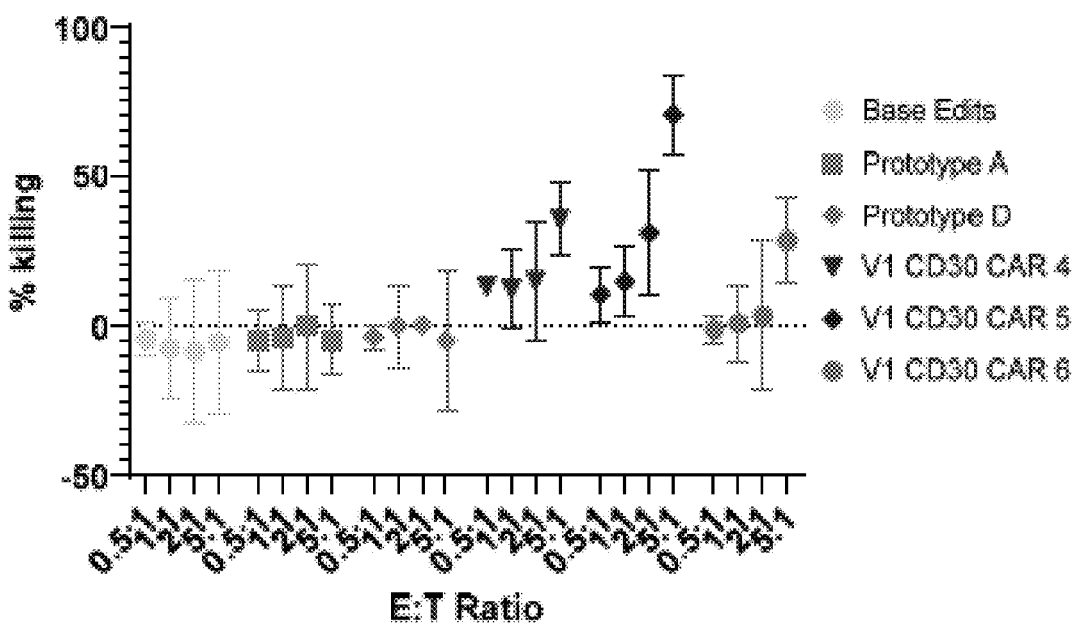

Example 22: Characterization of iNK Cells Derived from SERPINB9 KI, IL15/IL15Rα KI, Anti-CD30 CAR KI, HLA-E KI, B2M KO, CIITA KO, CISH KO, FAS KO Cells FIG. 46 presents expression patterns of CD45 and CD56 during iNK differentiation of the cells with base edits (e.g., SERPINB9-P2A-IL15/IR15a KI, B2M KO), prototype edits (e.g., SERPINB9-P2A-IL15/IR15a KI, B2M KO, CISH KO, FAS KO), and the CAR inserts (e.g., SERPINB9-P2A-IL15/IR15a KI, anti-CD30 CAR-P2A-HLA-E KI, B2M KO, FAS KO, CISH KO, and CIITA KO). By day 36, more than 99% of all the cell lines were CD45$^+$/CD56$^+$, indicating efficient iNK differentiation.

Co-incubation of day 29 iNK cells with various CD30$^+$ cancer cells revealed that the cells with the anti-CD30 CARS were more effective killers than the cells with base edits or prototype edits (see FIGS. 47A-D). Some of the anti-CD30 CAR cells had more than 90% killing after 4 hrs at the highest effector-target ratio (5:1). In general, CAR5 outperformed CAR4 and CAR6 in the CD30 cancer cell cytotoxicity assay.

Figure 48:
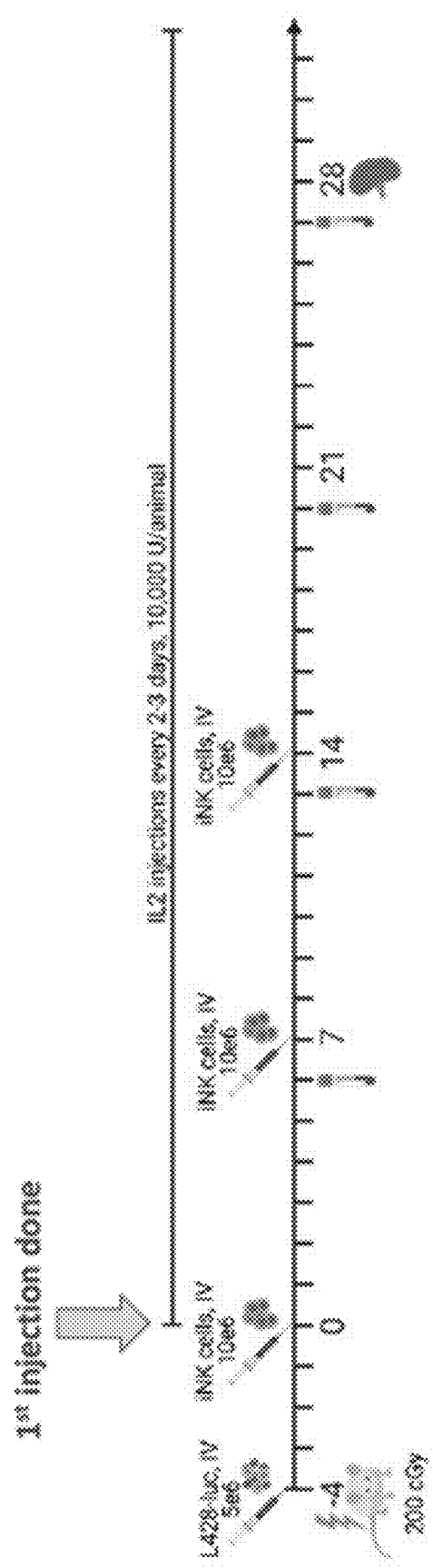
FIG. 48 present a schematic for an in vivo protocol to test the cytotoxicity of iNK cells comprising B2M KO, SERPINB9 KI, IL15/IL15Rα KI, CISH KO. FAS KO, CD30 CAR KI, HLA-E KI, and CIITA KO.

Example 23: In Vivo Testing of iNK Cells Derived from SERPINB9 KI, IL15/IL15Rα KI, Anti-CD30 CAR KI, HLA-E KI, B2M KO, CIITA KO, CISH KO, FAS KO Cells Mice were intravenously injected with $5\times10^6$ L428 cancer cells labeled with luciferase. Four days later (day 0), $10\times10^6$ iNK cells comprising CAR5 (2:1 E:T ratio) were intravenously injected into the mice. Two more intravenous injections of 10 million iNK cells at days 7 and 14 of iNK cells will be given, and the organs will be harvested at day 28 for cancer cell localization. FIG. 48 presents a schematic of the protocol.

Example 24: Alternatives to Differentiating Stem Cells into Natural Killer Cells—Protocol 2.5

The differentiation protocol according to Example 16 was repeated with the following alterations, alone or in combination:

1. During the NK Cell differentiation stage, iPS cells were cultured and aggregated using a "scaled up" approach. Specifically, the NK cell differentiation, Step 1 (Day-1 (afternoon), iPSC aggregation) step was performed as follows. iPSCs were grown in T175, T225, 1-cells stack or 2-cell stack and digested with Accutase as previously described. Accutase digested cells were diluted 1:1 with cold NK-MED-002 medium. Cells were gently resuspended and transferred to a conical tube. Cells were pelleted by spinning at 20-300 g for 4 to 5 minutes and re-suspended in 10 mL of NK-MED-003 medium. Cells were counted and the cell concentration was diluted to $1\times10^6$/mL. $60\text{-}100\times10^6$ cells were transferred to PBS100 and resuspended in a total of 60-100 mL of NK-MED-003 medium correspondingly. PBS vessels were placed onto PBS base and rotated overnight at 45 RPM.

2. ROCK Inhibitor: The ROCK inhibitor used in NK-MED-003 in the previous step, was Y-27652 (10 µM) instead of thiazovivin.

3. Nicotinamide: Nicotinamide was omitted from NK-MED-010 (used at day 20 onwards).

Cells were differentiated and characterized as described in previous examples.

INCORPORATION BY REFERENCE

Various references such as patents, patent applications, and publications, are cited herein, the disclosures of which are hereby incorporated by reference herein in their entireties.

What is claimed is:

1. An in vitro method for generating an engineered cell, the method comprising delivering to a cell:
   (a) a first CRISPR associated RNA-guided endonuclease and a first gRNA targeting a target site in a beta-2-microglobulin (B2M) gene locus; and
   (b) a first vector comprising a nucleic acid, the nucleic acid comprising: (i) a nucleotide sequence encoding a SERPINB9 protein and a nucleotide sequence encoding a fusion protein of interleukin 15 (IL15) and interleukin 15 receptor subunit alpha (IL15Rα); (ii) a nucleotide sequence having sequence homology with a genomic region located left of the target site in the B2M gene locus; and (iii) a nucleotide sequence having sequence homology with a genomic region located right of the target site in the B2M gene locus, wherein (i) is flanked by (ii) and (iii);
   wherein the B2M gene locus is cleaved at the target site and the nucleotide sequence encoding the SERPINB9 protein and the nucleotide sequence encoding the fusion protein of IL15 and IL15Rα are inserted into the B2M gene locus, thereby disrupting the B2M gene.

2. The in vitro method of claim 1, wherein the first CRISPR associated RNA-guided endonuclease is a Cas9 nuclease and the first gRNA comprises a spacer sequence corresponding to a target sequence consisting of SEQ ID NO: 34, SEQ ID NO: 78, or SEQ ID NO: 79.

3. The in vitro method of claim 1, wherein the engineered cell has reduced or eliminated expression of B2M.

4. The in vitro method of claim 1, wherein the nucleotide sequence of (b)(i) comprises a SERPINB9-P2A-IL15/IL15Rα construct in which the nucleotide sequence encoding the SERPINB9 protein is linked to the nucleotide sequence encoding the fusion protein of IL15 and IL15Rα by a P2A peptide sequence.

5. The in vitro method of claim 4, wherein the SERPINB9-P2A-IL15/IL15Rα construct comprises a nucleotide sequence consisting essentially of SEQ ID NO: 137.

6. The in vitro method of claim 4, wherein the SERPINB9-P2A-IL15/IL15Rα construct is operably linked to an exogenous promoter chosen from a CAG, a CMV, an EF1α, a PGK, or a UBC promoter.

7. The in vitro method of claim 1, wherein the nucleotide sequence of (b)(ii) consists essentially of SEQ ID NO: 36, and the nucleotide sequence of (b)(iii) consists essentially of SEQ ID NO: 54.

8. The in vitro method of claim 1, wherein the first vector comprises a nucleotide sequence consisting essentially of SEQ ID NO: 148.

9. The in vitro method of claim 1, further comprising delivering to the cell:
   (c) a second CRISPR associated RNA-guided endonuclease and a second gRNA targeting a target site in a Class II major histocompatibility complex transactivator (CIITA) gene locus;
   (d) a second vector comprising a nucleic acid, the nucleic acid comprising: (i) a nucleotide sequence encoding a chimeric antigen receptor (CAR) and a nucleotide sequence encoding a human leukocyte antigen E (HLA-E) trimer; (ii) a nucleotide sequence having sequence homology with a genomic region located left of the target site in the CIITA gene locus; and (iii) a nucleotide sequence having sequence homology with a genomic region located right of the target site in the CIITA gene locus, wherein (i) is flanked by (ii) and (iii); and
   wherein the CIITA gene locus is cleaved at the target site and the nucleotide sequence encoding the CAR and the nucleotide sequence encoding the HLA-E trimer are inserted into the CITTA gene locus, thereby disrupting the CIITA gene.

10. The in vitro method of claim 9, wherein the second CRISPR associated RNA-guided endonuclease is a Cas9 nuclease and the second gRNA comprises a spacer sequence corresponding to a target sequence consisting of SEQ ID NO: 13, SEQ ID NO: 14, SEQ ID NO: 15, SEQ ID NO: 16, or SEQ ID NO: 17.

11. The in vitro method of claim 9, wherein the engineered cell has reduced or eliminated expression of CIITA.

12. The in vitro method of claim 9, wherein the CAR is an anti-CD30 CAR.

13. The in vitro method of claim 9, wherein the polynucleotide encoding the CAR comprises a polynucleotide sequence consisting essentially of SEQ ID NO: 108, SEQ ID NO: 112, or SEQ ID NO: 116.

14. The in vitro method of claim 9, wherein the HLA-E trimer comprises a B2M signal peptide fused to an HLA-G presentation peptide fused to the B2M membrane protein fused to the HLA-E protein without a signal peptide.

15. The in vitro method of claim 9, wherein the nucleotide sequence of (d)(i) comprises a CAR-P2A-HLA-E construct in which the nucleotide sequence encoding the CAR is linked to the nucleotide sequence encoding the HLA-E trimer by a P2A peptide sequence.

16. The in vitro method of claim 15, wherein the CAR-P2A-HLA-E construct has a nucleotide sequence consisting essentially of SEQ ID NO: 119, SEQ ID NO: 120, or SEQ ID NO: 121.

17. The in vitro method of claim 9, wherein the nucleotide sequence of (d)(ii) consists essentially of SEQ ID NO: 22, and the nucleotide sequence of (d)(iii) consists essentially of SEQ ID NO: 32.

18. The in vitro method of claim 9, wherein the second vector comprises a nucleotide sequence consisting essentially of SEQ ID NO: 110, SEQ ID NO: 114, or SEQ ID NO: 118.

19. The in vitro method of claim 1, further comprising delivering to the cell a third CRISPR associated RNA-guided endonuclease and a third gRNA targeting a target site in a cytokine-inducible SH2-containing protein (CISH) gene locus; wherein the CISH gene locus is cleaved at the target site and at least one insertion-deletion mutation is introduced into the CISH gene, thereby disrupting the CISH gene.

20. The in vitro method of claim 19, wherein the third CRISPR associated RNA-guided endonuclease is a Cas9 nuclease and the third gRNA comprises a spacer sequence corresponding to a target sequence consisting of SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, or SEQ ID NO: 92.

21. The in vitro method of claim 19, wherein the engineered cell has reduced or eliminated expression of CISH.

22. The in vitro method of claim 1, further comprising delivering to the cell a fourth CRISPR associated RNA-guided endonuclease and a fourth gRNA targeting a target site in a Fas cell surface death receptor (FAS) gene locus, wherein the FAS gene locus is cleaved at the target site and at least one insertion-deletion mutation is introduced into the FAS gene, thereby disrupting the FAS gene.

23. The in vitro method of claim 22, wherein the fourth CRISPR associated RNA-guided endonuclease is a Cas9 nuclease and the fourth gRNA comprises a spacer sequence corresponding to a target sequence consisting of SEQ ID NOS: 35, SEQ ID NO: 37, SEQ ID NO; 38, SEQ ID NO: 39, SEQ ID NO: 53, SEQ ID NO: 55, or SEQ ID NO: 80.

24. The in vitro method of claim 22, wherein the engineered cell has reduced or eliminated expression of FAS.

25. The in vitro method of claim 1, wherein the engineered cell is an induced pluripotent stem cell (iPSC), a hematopoietic stem cell, an embryonic stem cell, or an adult stem cell.

26. The in vitro method of claim 1, wherein the engineered cell is capable of being differentiated into lineage-restricted progenitor cells or fully differentiated somatic cells.

27. The in vitro method of claim 1, wherein the engineered cell is a natural killer (NK) cell.

* * * * *

SEQUENCE LISTING

<160> NUMBER OF SEQ ID NOS: 149

<210> SEQ ID NO 1
<211> LENGTH: 20
<212> TYPE: DNA
<213> ORGANISM: Homo sapiens

<400> SEQUENCE: 1
ggtcgcggcg ccagcacgaa                                                   20

<210> SEQ ID NO 2
<211> LENGTH: 20
<212> TYPE: DNA
<213> ORGANISM: Homo sapiens

<400> SEQUENCE: 2
ccgaagcccg ggtcatccgg                                                   20

<210> SEQ ID NO 3
<211> LENGTH: 20
<212> TYPE: DNA
<213> ORGANISM: Homo sapiens

<400> SEQUENCE: 3
ccgcgacctc cggatgaccc                                                   20

<210> SEQ ID NO 4
<211> LENGTH: 20
<212> TYPE: DNA
<213> ORGANISM: Homo sapiens

<400> SEQUENCE: 4
cgtgctggcg ccgcgacctc                                                   20

<210> SEQ ID NO 5
<211> LENGTH: 20
<212> TYPE: DNA
<213> ORGANISM: Homo sapiens

<400> SEQUENCE: 5
cgaaaggaac cacgctggtc                                                   20

<210> SEQ ID NO 6
<211> LENGTH: 20
<212> TYPE: DNA
<213> ORGANISM: Homo sapiens

<400> SEQUENCE: 6
cagcgtggtt cctttcgtgc                                                   20

```
<210> SEQ ID NO 7
<211> LENGTH: 20
<212> TYPE: DNA
<213> ORGANISM: Homo sapiens

<400> SEQUENCE: 7
gccgcgacct ccggatgacc                                               20

<210> SEQ ID NO 8
<211> LENGTH: 20
<212> TYPE: DNA
<213> ORGANISM: Homo sapiens

<400> SEQUENCE: 8
gaaccacgct ggtcaggaat                                               20

<210> SEQ ID NO 9
<211> LENGTH: 20
<212> TYPE: DNA
<213> ORGANISM: Homo sapiens

<400> SEQUENCE: 9
cagcacgaaa ggaaccacgc                                               20

<210> SEQ ID NO 10
<211> LENGTH: 20
<212> TYPE: DNA
<213> ORGANISM: Homo sapiens

<400> SEQUENCE: 10
gtagcggggc cgggaacatg                                               20

<210> SEQ ID NO 11
<211> LENGTH: 20
<212> TYPE: DNA
<213> ORGANISM: Homo sapiens

<400> SEQUENCE: 11
agaatcttcc cagtaggcgg                                               20

<210> SEQ ID NO 12
<211> LENGTH: 20
<212> TYPE: DNA
<213> ORGANISM: Homo sapiens

<400> SEQUENCE: 12
ctcaggcgct cagtcactac                                               20

<210> SEQ ID NO 13
<211> LENGTH: 20
<212> TYPE: DNA
<213> ORGANISM: Homo sapiens

<400> SEQUENCE: 13
ggtccatctg gtcatagaag                                               20

<210> SEQ ID NO 14
<211> LENGTH: 20
<212> TYPE: DNA
<213> ORGANISM: Homo sapiens

<400> SEQUENCE: 14
gctccaggta gccaccttct                                               20
```

<210> SEQ ID NO 15
<211> LENGTH: 20
<212> TYPE: DNA
<213> ORGANISM: Homo sapiens

<400> SEQUENCE: 15
tagggccccc aactccatgg                                                    20

<210> SEQ ID NO 16
<211> LENGTH: 20
<212> TYPE: DNA
<213> ORGANISM: Homo sapiens

<400> SEQUENCE: 16
ggcttatgcc aatatcggtg                                                    20

<210> SEQ ID NO 17
<211> LENGTH: 20
<212> TYPE: DNA
<213> ORGANISM: Homo sapiens

<400> SEQUENCE: 17
aggtgatgaa gagaccaggg                                                    20

<210> SEQ ID NO 18
<211> LENGTH: 22
<212> TYPE: DNA
<213> ORGANISM: Homo sapiens

<400> SEQUENCE: 18
tcctgactct ctggtgtgag at                                                 22

<210> SEQ ID NO 19
<211> LENGTH: 19
<212> TYPE: DNA
<213> ORGANISM: Homo sapiens

<400> SEQUENCE: 19
cagagagcgt cccacagac                                                     19

<210> SEQ ID NO 20
<211> LENGTH: 86
<212> TYPE: DNA
<213> ORGANISM: Homo sapiens

<400> SEQUENCE: 20
gccaccatgg agttggggcc cctagaaggt ggctacctgg agcttcttaa cagcgatgct        60
gaccccctgt gcctctacca cttcta                                             86

<210> SEQ ID NO 21
<211> LENGTH: 130
<212> TYPE: DNA
<213> ORGANISM: Artificial Sequence
<220> FEATURE:
<223> OTHER INFORMATION: Synthetic

<400> SEQUENCE: 21
cctgcaggca gctgcgcgct cgctcgctca ctgaggccgc ccgggcgtcg ggcgaccttt        60
ggtcgcccgg cctcagtgag cgagcgagcg cgcagagagg gagtggccaa ctccatcact       120
aggggttcct                                                              130

<210> SEQ ID NO 22
<211> LENGTH: 800
<212> TYPE: DNA
<213> ORGANISM: Homo sapiens

<400> SEQUENCE: 22

```
catatttatg gggtatatgt gaatatttat tacatgcata gaaggtataa tgatcatgtc    60
aggatatttg aggtatccac atttgggatt gtttaaagat taaatgaaat agtgttaaaa   120
gtatttaata tgcccttcaa caaatgatga ggaaatctta gaatctgctc agactccttc   180
agtttacata ttaggaaact gaggcacaga aaggagcaga gacttgctca agtccaccca   240
aagcagtaga gcattgtggt taaatgcagg acttcagtca gactgtctgg gttcaaatcc   300
tggttccact tggacatggg tttccttaca taaatcactt cacctctctg agcctcagtt   360
ttctcatatg caaagtgagg ataataataa taccttcctt acatggttac tgatatgagt   420
attaaatgtg ccagctcatg tgcctggcgt ataggaggtg ctttataaac cttagctgtt   480
accactcatg gcattgccaa atgtgggacg ggtctcctga ctctctggtg tgagattgat   540
ggaatccaca ctttccagtt ccctttctca cctcctgggt atcttctcat atggttgtaa   600
gttccttgga ggaagggaat gtggcttgct ctctccacca cgctgagcat ataagaggtg   660
ctgaatgagc gcttttattc actcctctca tccccagccc tcaccagctg ggagttgttg   720
taggtgtcaa ttttctgcct cttttccaaca ccctgtgagg tgactgagca ttgtcttccc   780
tcccaggcag ctcacagtgt                                                800
```

<210> SEQ ID NO 23
<211> LENGTH: 380
<212> TYPE: DNA
<213> ORGANISM: Artificial Sequence
<220> FEATURE:
<223> OTHER INFORMATION: Synthetic - Cytomegalovirus

<400> SEQUENCE: 23

```
gacattgatt attgactagt tattaatagt aatcaattac ggggtcatta gttcatagcc    60
catatatgga gttccgcgtt acataactta cggtaaatgg cccgcctggc tgaccgccca   120
acgacccccg cccattgacg tcaataatga cgtatgttcc catagtaacg ccaataggga   180
ctttccattg acgtcaatgg gtggactatt tacggtaaac tgcccacttg gcagtacatc   240
aagtgtatca tatgccaagt acgccccta ttgacgtcaa tgacggtaaa tggcccgcct   300
ggcattatgc ccagtacatg acctatggg actttcctac ttggcagtac atctacgtat   360
tagtcatcgc tattaccatg                                                380
```

<210> SEQ ID NO 24
<211> LENGTH: 276
<212> TYPE: DNA
<213> ORGANISM: Gallus gallus

<400> SEQUENCE: 24

```
tcgaggtgag ccccacgttc tgcttcactc tccccatctc ccccccctcc ccacccccaa    60
ttttgtattt atttatttt taattatttt gtgcagcgat gggggcgggg gggggggggg   120
cgcgcgccag gcggggcggg gcggggcgag gggcggggcg gggcgaggcg gagaggtgcg   180
gcggcagcca atcagagcgg cgcgctccga aagtttcctt ttatggcgag gcggcggcgg   240
cggcggccct ataaaaagcg aagcgcgcgg cgggcg                             276
```

<210> SEQ ID NO 25
<211> LENGTH: 1009
<212> TYPE: DNA
<213> ORGANISM: Artificial Sequence
<220> FEATURE:
<223> OTHER INFORMATION: Synthetic

<400> SEQUENCE: 25

| | | | | | |
|---|---|---|---|---|---|
| ggagtcgctg | cgttgccttc | gccccgtgcc | ccgctccgcg | ccgcctcgcg | ccgcccgccc | 60 |
| cggctctgac | tgaccgcgtt | actcccacag | gtgagcgggc | gggacggccc | ttctcctccg | 120 |
| ggctgtaatt | agcgcttggt | ttaatgacgg | ctcgtttctt | ttctgtggct | gcgtgaaagc | 180 |
| cttaaagggc | tccgggaggg | ccctttgtgc | ggggggagc | ggctcggggg | gtgcgtgcgt | 240 |
| gtgtgtgtgc | gtggggagcg | ccgcgtgcgg | cccgcgctgc | ccggcggctg | tgagcgctgc | 300 |
| gggcgcggcg | cggggctttg | tgcgctccgc | gtgtgcgcga | ggggagcgcg | gccggggcg | 360 |
| gtgccccgcg | gtgcgggggg | gctgcgaggg | gaacaaaggc | tgcgtgcggg | gtgtgtgcgt | 420 |
| gggggggtga | gcaggggtg | tgggcgcggc | ggtcgggctg | taaccccccc | ctgcaccccc | 480 |
| ctccccgagt | tgctgagcac | ggcccggctt | cgggtgcggg | gctccgtgcg | gggcgtggcg | 540 |
| cggggctcgc | cgtgccgggc | gggggtggc | ggcaggtggg | ggtgccgggc | ggggcggggc | 600 |
| cgcctcgggc | cgggagggc | tcgggggagg | ggcgcggcgg | ccccggagcg | ccggcggctg | 660 |
| tcgaggcgcg | gcgagccgca | gccattgcct | tttatggtaa | tcgtgcgaga | gggcgcaggg | 720 |
| acttcctttg | tcccaaatct | ggcggagccg | aaatctggga | ggcgccgccg | caccccctct | 780 |
| agcgggcgcg | ggcgaagcgg | tgcggcgccg | gcaggaagga | aatgggcggg | gagggccttc | 840 |
| gtgcgtcgcc | gcgccgccgt | cccttctcc | atctccagcc | tcggggctgc | cgcagggga | 900 |
| cggctgcctt | cggggggac | ggggcaggc | ggggttcggc | ttctggcgtg | tgaccggcgg | 960 |
| ctctagagcc | tctgctaacc | atgttcatgc | cttcttcttt | ttcctacag | | 1009 |

<210> SEQ ID NO 26
<211> LENGTH: 63
<212> TYPE: DNA
<213> ORGANISM: Homo sapiens

<400> SEQUENCE: 26

| | | | | | |
|---|---|---|---|---|---|
| atggcgcttc | cggtgacagc | actgctcctc | cccttggcgc | tgttgctcca | cgcagcaagg | 60 |
| ccg | | | | | | 63 |

<210> SEQ ID NO 27
<211> LENGTH: 735
<212> TYPE: DNA
<213> ORGANISM: Artificial Sequence
<220> FEATURE:
<223> OTHER INFORMATION: Synthetic

<400> SEQUENCE: 27

| | | | | | |
|---|---|---|---|---|---|
| caggtgcagc | tggtgcagag | cggagccgag | ctcaagaagc | ccggagcctc | cgtgaaggtg | 60 |
| agctgcaagg | ccagcggcaa | caccctgacc | aactacgtga | tccactgggt | gagacaagcc | 120 |
| cccggccaaa | ggctggagtg | gatgggctac | atcctgccct | acaacgacct | gaccaagtac | 180 |
| agccagaagt | tccagggcag | ggtgaccatc | accaggata | agagcgcctc | caccgcctat | 240 |
| atggagctga | gcagcctgag | gagcgaggac | accgctgtgt | actactgtac | aaggtgggac | 300 |
| tgggacggct | tctttgaccc | ctggggccag | ggcacaacag | tgaccgtcag | cagcggcggc | 360 |
| ggaggcagcg | gcggcggcgg | cagcggcgga | ggcggaagcg | aaatcgtgat | gacccagagc | 420 |

```
cccgccacac tgagcgtgag ccctggcgag agggccagca tctcctgcag ggctagccaa    480
agcctggtgc acagcaacgg caacacccac ctgcactggt accagcagag acccggacag    540
gctcccaggc tgctgatcta cagcgtgagc aacaggttct ccgaggtgcc tgccaggttt    600
agcggcagcg gaagcggcac cgactttacc ctgaccatca gcagcgtgga gtccgaggac    660
ttcgccgtgt attactgcag ccagaccagc cacatccctt acaccttcgg cggcggcacc    720
aagctggaga tcaaa                                                    735

<210> SEQ ID NO 28
<211> LENGTH: 264
<212> TYPE: DNA
<213> ORGANISM: Homo sapiens

<400> SEQUENCE: 28
agtgctgctg cctttgtccc ggtatttctc ccagccaaac cgaccacgac tcccgccccg     60
cgccctccga cacccgctcc caccatcgcc tctcaacctc ttagtcttcg ccccgaggca    120
tgccgacccg ccgccggggg tgctgttcat acgaggggct tggacttcgc ttgtgatatt    180
tacatttggg ctccgttggc gggtacgtgc ggcgtccttt tgttgtcact cgttattact    240
ttgtattgta atcacaggaa tcgc                                          264

<210> SEQ ID NO 29
<211> LENGTH: 126
<212> TYPE: DNA
<213> ORGANISM: Homo sapiens

<400> SEQUENCE: 29
aaacggggca gaaagaaact cctgtatata ttcaaacaac catttatgag accagtacaa     60
actactcaag aggaagatgg ctgtagctgc cgatttccag aagaagaaga aggaggatgt    120
gaactg                                                              126

<210> SEQ ID NO 30
<211> LENGTH: 336
<212> TYPE: DNA
<213> ORGANISM: Homo sapiens

<400> SEQUENCE: 30
cgagtgaagt tttcccgaag cgcagacgct ccggcatatc agcaaggaca gaatcagctg     60
tataacgaac tgaatttggg acgccgcgag gagtatgacg tgcttgataa acgccggggg    120
agagacccgg aaatgggggg taaacccgga agaaagaatc cccaagaagg actctacaat    180
gaactccaga aggataagat ggcggaggcc tactcagaaa taggtatgaa gggcgaacga    240
cgacggggaa aaggtcacga tggcctctac caagggttga gtacggcaac caaagatacg    300
tacgatgcac tgcatatgca ggccctgcct cccaga                             336

<210> SEQ ID NO 31
<211> LENGTH: 225
<212> TYPE: DNA
<213> ORGANISM: Bos taurus

<400> SEQUENCE: 31
ctgtgccttc tagttgccag ccatctgttg tttgcccctc ccccgtgcct tccttgaccc     60
tggaaggtgc cactcccact gtcctttcct aataaaatga ggaaattgca tcgcattgtc    120
tgagtaggtg tcattctatt ctgggggggtg ggtggggca ggcagcaag ggggaggatt    180 gggaagacaa tagcaggcat gctggggatg cggtgggctc tatgg                   225
```

```
<210> SEQ ID NO 32
<211> LENGTH: 795
<212> TYPE: DNA
<213> ORGANISM: Homo sapiens

<400> SEQUENCE: 32
tgaccagatg gacctggctg gagaagaaga gattgagctc tactcaggtg ggccctcctc      60
cctctggtct cttccggtat ccccaccccc tcagcttgct gtagagacgg caatcagggg     120
aaattctggt ccctgccctc ccgtcagcac cacggacagc tcccacgtct gtgggacgct     180
ctctgcagat ggggatgatc tcccagccct gccccgcctc tccctcgttc cccaccagcc     240
ctctttccag aaatttcctt cttcatccaa gggactttc ctcccagaac ccgacacaga      300
caccatcaac tgcgaccagt tcagcaggct gttgtgtgac atggaaggtg atgaagagac     360
cagggaggct tatgccaata tcggtgagga agcacctgag cccagaaaag gacaatcaag     420
ggcaagagtt ctttgctgcc acttgtcaat atcacccatt catcatgagc cacgtcagtc     480
ccctcccaca gaaatcattg caaggggggat gcggagcaat ggctggagga acggagactc    540
cagggaagag aggggagatg gaggccagtg ggggaaatag gccccttcac taatgaccac     600
caagaaaaca aaatctcatg tttacatcct ccacctccat ttctatacgc atttctgctt     660
cttgctcttc tgtccatcct ttctacaaag cccataccat acacccttt cccttttcct      720 cccagctcct tagccaagct actctagtat ttgtaataac tagcatttac tggatactca     780
tagtatgctc attgc                                                       795

<210> SEQ ID NO 33
<211> LENGTH: 141
<212> TYPE: DNA
<213> ORGANISM: Artificial Sequence
<220> FEATURE:
<223> OTHER INFORMATION: Synthetic

<400> SEQUENCE: 33
aggaacccct agtgatggag ttggccactc cctctctgcg cgctcgctcg ctcactgagg      60
ccgggcgacc aaaggtcgcc cgacgcccgg gctttgcccg ggcggcctca gtgagcgagc     120
gagcgcgcag ctgcctgcag g                                               141

<210> SEQ ID NO 34
<211> LENGTH: 20
<212> TYPE: DNA
<213> ORGANISM: Homo sapiens

<400> SEQUENCE: 34
ggccgagatg tctcgctccg                                                  20

<210> SEQ ID NO 35
<211> LENGTH: 20
<212> TYPE: DNA
<213> ORGANISM: Homo sapiens

<400> SEQUENCE: 35
ggattgctca acaaccatgc                                                  20

<210> SEQ ID NO 36
<211> LENGTH: 800
<212> TYPE: DNA
<213> ORGANISM: Homo sapiens
```

-continued

<400> SEQUENCE: 36

```
gttctagggt ggaaactaag agaatgatgt acctagaggg cgctggaagc tctaaagccc    60
tagcagttac tgcttttact attagtggtc gttttttct cccccccgcc ccccgacaaa    120
tcaacagaac aaagaaaatt acctaaacag caaggacata gggaggaact tcttggcaca   180
gaactttcca acacttttt cctgaaggga tacaagaagc aagaaaggta ctctttcact    240
aggaccttct ctgagctgtc ctcaggatgc ttttgggact attttttctta cccagagaat   300
ggagaaaccc tgcagggaat tcccaagctg tagttataaa cagaagttct ccttctgcta   360
ggtagcattc aaagatctta atcttctggg tttccgtttt ctcgaatgaa aaatgcaggt   420
ccgagcagtt aactggctgg ggcaccatta gcaagtcact tagcatctct ggggccagtc   480
tgcaaagcga gggggcagcc ttaatgtgcc tccagcctga agtcctagaa tgagcgcccg   540
gtgtcccaag ctggggcgcg cacccccagat cggagggcgc cgatgtacag acagcaaact   600
cacccagtct agtgcatgcc ttcttaaaca tcacgagact ctaagaaaag gaaactgaaa   660
acgggaaagt ccctctctct aacctggcac tgcgtcgctg gcttggagac aggtgacggt   720
ccctgcgggc cttgtcctga ttggctgggc acgcgtttaa tataagtgga ggcgtcgcgc   780
tggcgggcat tcctgaagct                                              800
```

<210> SEQ ID NO 37
<211> LENGTH: 20
<212> TYPE: DNA
<213> ORGANISM: Homo sapiens

<400> SEQUENCE: 37

```
gattgctcaa caaccatgct                                              20
```

<210> SEQ ID NO 38
<211> LENGTH: 20
<212> TYPE: DNA
<213> ORGANISM: Homo sapiens

<400> SEQUENCE: 38

```
gtgactgaca tcaactccaa                                              20
```

<210> SEQ ID NO 39
<211> LENGTH: 20
<212> TYPE: DNA
<213> ORGANISM: Homo sapiens

<400> SEQUENCE: 39

```
cacttgggca ttaacacttt                                              20
```

<210> SEQ ID NO 40
<211> LENGTH: 54
<212> TYPE: DNA
<213> ORGANISM: Artificial Sequence
<220> FEATURE:
<223> OTHER INFORMATION: Synthetic

<400> SEQUENCE: 40

```
atggactgga cctggatcct gttcctggtg gccgccgcca ccagggtgca cagc          54
```

<210> SEQ ID NO 41
<211> LENGTH: 399
<212> TYPE: DNA
<213> ORGANISM: Homo sapiens

<400> SEQUENCE: 41

```
ggcattcatg tcttcatttt gggctgtttc agtgcagggc ttcctaaaac agaagccaac        60
tgggtgaatg taataagtga tttgaaaaaa attgaagatc ttattcaatc tatgcatatt       120
gatgctactt tatatacgga aagtgatgtt caccccagtt gcaaagtaac agcaatgaag       180
tgctttctct tggagttaca agttatttca cttgagtccg gagatgcaag tattcatgat       240
acagtagaaa atctgatcat cctagcaaac aacagtttgt cttctaatgg gaatgtaaca       300
gaatctggat gcaaagaatg tgaggaactg gaggaaaaaa atattaaaga attttttgcag      360 agttttgtac atattgtcca aatgttcatc aacacttct                              399
```

<210> SEQ ID NO 42
<211> LENGTH: 78
<212> TYPE: DNA
<213> ORGANISM: Artificial Sequence
<220> FEATURE:
<223> OTHER INFORMATION: Synthetic

<400> SEQUENCE: 42

```
agcggcggcg gcagcggcgg cggcggcagc ggcggcggcg gcagcggcgg cggcggcagc        60
ggcggcggca gcctgcag                                                     78
```

<210> SEQ ID NO 43
<211> LENGTH: 711
<212> TYPE: DNA
<213> ORGANISM: Homo sapiens

<400> SEQUENCE: 43

```
atcacgtgcc ctccccccat gtccgtggaa cacgcagaca tctgggtcaa gagctacagc        60
ttgtactcca gggagcggta catttgtaac tctggtttca gcgtaaagc cggcacgtcc        120 agcctgacgg agtgcgtgtt gaacaaggcc acgaatgtcg cccactggac aaccccagt        180 ctcaaatgca ttagagaccc tgccctggtt caccaaaggc cagcgccacc ctccacagta       240
acgacggcag gggtgacccc acagccagag agcctctccc cttctggaaa agagcccgca       300
gcttcatctc ccagctcaaa caacacagcg cccacaacag cagctattgt cccgggctcc       360
cagctgatgc cttcaaaatc accttccaca ggaaccacag agataagcag tcatgagtcc       420
tcccacggca cccctctca gacaacagcc aagaactggg aactcacagc atccgcctcc       480
caccagccgc caggtgtgta tccacagggc cacagcgaca ccactgtggc tatctccacg       540
tccactgtcc tgctgtgtgg gctgagcgct gtgtctctcc tggcatgcta cctcaagtca       600
aggcaaactc ccccgctggc cagcgttgaa atggaagcca tggaggctct gccggtgact       660
tgggggacca gcagcagaga tgaagacttg gaaaactgct ctcaccacct a                711
```

<210> SEQ ID NO 44
<211> LENGTH: 9
<212> TYPE: DNA
<213> ORGANISM: Artificial Sequence
<220> FEATURE:
<223> OTHER INFORMATION: Synthetic

<400> SEQUENCE: 44

```
ggaagcgga                                                                9
```

<210> SEQ ID NO 45
<211> LENGTH: 57
<212> TYPE: DNA

```
<213> ORGANISM: Artificial Sequence
<220> FEATURE:
<223> OTHER INFORMATION: Synthetic

<400> SEQUENCE: 45
gctactaact tcagcctgct gaagcaggct ggagacgtgg aggagaaccc tggacct        57

<210> SEQ ID NO 46
<211> LENGTH: 60
<212> TYPE: DNA
<213> ORGANISM: Artificial Sequence
<220> FEATURE:
<223> OTHER INFORMATION: Synthetic

<400> SEQUENCE: 46
atgtctcgct ccgttgcctt agctgtgctc gcgctactct ctctttctgg attagaggct    60

<210> SEQ ID NO 47
<211> LENGTH: 27
<212> TYPE: DNA
<213> ORGANISM: Homo sapiens

<400> SEQUENCE: 47
gtcatggcgc cccgaaccct cttcctg                                         27

<210> SEQ ID NO 48
<211> LENGTH: 45
<212> TYPE: DNA
<213> ORGANISM: Artificial Sequence
<220> FEATURE:
<223> OTHER INFORMATION: Synthetic

<400> SEQUENCE: 48
ggtggaggcg gttcaggcgg aggtggctct ggcggtggcg gatcg                     45

<210> SEQ ID NO 49
<211> LENGTH: 297
<212> TYPE: DNA
<213> ORGANISM: Homo sapiens

<400> SEQUENCE: 49
atccagcgta ctccaaagat tcaggtttac tcacgtcatc cagcagagaa tggaaagtca    60
aatttcctga attgctatgt gtctgggttt catccatccg acattgaagt tgacttactg   120
aagaatggag agagaattga aaagtggag cattcagact tgtctttcag caaggactgg    180
tctttctatc tcttgtacta cactgaattc accccactg aaaaagatga gtatgcctgc    240
cgtgtgaacc atgtgacttt gtcacagccc aagatagtta gtgggatcg agacatg       297

<210> SEQ ID NO 50
<211> LENGTH: 60
<212> TYPE: DNA
<213> ORGANISM: Artificial Sequence
<220> FEATURE:
<223> OTHER INFORMATION: Synthetic

<400> SEQUENCE: 50
ggtggtggtg gttctggtgg tgtggttct ggcggcggcg gctccggtgg tggtggatcc    60

<210> SEQ ID NO 51
<211> LENGTH: 1011
<212> TYPE: DNA
<213> ORGANISM: Homo sapiens
```

<400> SEQUENCE: 51

```
ggctcccact ccttgaagta tttccacact tccgtgtccc ggcccggccg cggggagccc      60
cgcttcatct ctgtgggcta cgtggacgac acccagttcg tgcgcttcga caacgacgcc     120
gcgagtccga ggatggtgcc gcgggcgccg tggatggagc aggagggtc agagtattgg      180
gaccgggaga cacggagcgc caggacacc gcacagattt ccgagtgaa tctgcggacg      240
ctgcgcggct actacaatca gagcgaggcc gggtctcaca ccctgcagtg gatgcatggc      300
tgcgagctgg ggcccgacgg gcgcttcctc cgcgggtatg aacagttcgc ctacgacggc      360
aaggattatc tcaccctgaa tgaggacctg cgctcctgga ccgcggtgga cacggcggct      420
cagatctccg agcaaaagtc aaatgatgcc tctgaggcgg agcaccagag agcctacctg      480
gaagacacat gcgtggagtg gctccacaaa tacctggaga aggggaagga gacgctgctt      540
cacctggagc ccccaaagac acacgtgact caccacccca tctctgacca tgaggccacc      600
ctgaggtgct gggcccctggg cttctaccct gcggagatca cactgacctg gcagcaggat      660
ggggagggcc atacccagga cacggagctc gtggagacca ggcctgcagg ggatggaacc      720
ttccagaagt gggcagctgt ggtggtgcct tctggagagg agcagagata cacgtgccat      780
gtgcagcatg aggggctacc cgagcccgtc accctgagat ggaagccggc ttcccagccc      840
accatcccca tcgtgggcat cattgctggc ctggttctcc ttggatctgt ggtctctgga      900
gctgtggttg ctgctgtgat atggaggaag aagagctcag gtggaaaagg agggagctac      960
tctaaggctg agtggagcga cagtgcccag gggtctgagt ctcacagctt g             1011
```

<210> SEQ ID NO 52
<211> LENGTH: 9
<212> TYPE: DNA
<213> ORGANISM: Artificial Sequence
<220> FEATURE:
<223> OTHER INFORMATION: Synthetic

<400> SEQUENCE: 52

```
taatgatag                                                               9
```

<210> SEQ ID NO 53
<211> LENGTH: 20
<212> TYPE: DNA
<213> ORGANISM: Homo sapiens

<400> SEQUENCE: 53

```
ttggaaggcc tgcatcatga                                                  20
```

<210> SEQ ID NO 54
<211> LENGTH: 800
<212> TYPE: DNA
<213> ORGANISM: Homo sapiens

<400> SEQUENCE: 54

```
ccagcgtgag tctctcctac cctcccgctc tggtccttcc tctcccgctc tgcaccctct      60
gtggccctcg ctgtgctctc tcgctccgtg acttcccttc tccaagttct ccttggtggc     120
cgccgtggg gctagtccag ggctggatct cggggaagcg gcggggtggc ctgggagtgg      180
ggaaggggt gcgcacccgg gacgcgcgct acttgcccct tcggcgggg agcaggggag      240
acctttggcc tacggcgacg ggagggtcgg gacaaagttt agggcgtcga taagcgtcag      300
agcgccgagg ttgggggagg gttctcttcc gctctttcg cggggcctct ggctccccca      360
```

```
gcgcagctgg agtgggggac gggtaggctc gtcccaaagg cgcggcgctg aggtttgtga      420
acgcgtggag gggcgcttgg ggtctggggg aggcgtcgcc cgggtaagcc tgtctgctgc      480
ggctctgctt cccttagact ggagagctgt ggacttcgtc taggcgcccg ctaagttcgc      540
atgtcctagc acctctgggt ctatgtgggg ccacaccgtg gggaggaaac agcacgcgac      600
gtttgtagaa tgcttggctg tgatacaaag cggtttcgaa taattaactt atttgttccc      660
atcacatgtc acttttaaaa aattataaga actacccgtt attgacatct ttctgtgtgc      720
caaggacttt atgtgctttg cgtcatttaa ttttgaaaac agttatcttc cgccatagat      780
aactactatg gttatcttct                                                   800
```

<210> SEQ ID NO 55
<211> LENGTH: 20
<212> TYPE: DNA
<213> ORGANISM: Homo sapiens

<400> SEQUENCE: 55

```
actccaaggg attggaattg                                                   20
```

<210> SEQ ID NO 56
<211> LENGTH: 20
<212> TYPE: DNA
<213> ORGANISM: Homo sapiens

<400> SEQUENCE: 56

```
cagacagcaa actcacccag                                                   20
```

<210> SEQ ID NO 57
<211> LENGTH: 20
<212> TYPE: DNA
<213> ORGANISM: Homo sapiens

<400> SEQUENCE: 57

```
aaactttgtc ccgaccctcc                                                   20
```

<210> SEQ ID NO 58
<211> LENGTH: 52
<212> TYPE: DNA
<213> ORGANISM: Homo sapiens

<400> SEQUENCE: 58

```
aaaagatctg tggactccac caccacgaaa tggcggcacc ttatttatgg tc              52
```

<210> SEQ ID NO 59
<211> LENGTH: 59
<212> TYPE: DNA
<213> ORGANISM: Homo sapiens

<400> SEQUENCE: 59

```
gctctggaga atctcacgca gaaggcaggc gttttctta aaaaaaatg cacgaatta          59
```

<210> SEQ ID NO 60
<211> LENGTH: 42
<212> TYPE: DNA
<213> ORGANISM: Homo sapiens

<400> SEQUENCE: 60

```
aggattggga agacaatagc aggcatgctg gggatgcggt gg                          42
```

<210> SEQ ID NO 61
<211> LENGTH: 59

```
<212> TYPE: DNA
<213> ORGANISM: Homo sapiens

<400> SEQUENCE: 61
gctctggaga atctcacgca gaaggcaggc gttttctta aaaaaaatg cacgaatta        59

<210> SEQ ID NO 62
<211> LENGTH: 54
<212> TYPE: DNA
<213> ORGANISM: Homo sapiens

<400> SEQUENCE: 62
gccccacccc tcctacttta tgtctccatg gatttgcctg ttttggtcat ttca           54

<210> SEQ ID NO 63
<211> LENGTH: 58
<212> TYPE: DNA
<213> ORGANISM: Homo sapiens

<400> SEQUENCE: 63
ctctaatgca aacttgggta ggtcgtttca cctctctaaa cctcaatttc ctcatttg       58

<210> SEQ ID NO 64
<211> LENGTH: 50
<212> TYPE: DNA
<213> ORGANISM: Homo sapiens

<400> SEQUENCE: 64
gagtgaagtt ttcccgaagc gcagacgctc cggcatatca gcaaggacag                50

<210> SEQ ID NO 65
<211> LENGTH: 58
<212> TYPE: DNA
<213> ORGANISM: Homo sapiens

<400> SEQUENCE: 65
ctctaatgca aacttgggta ggtcgtttca cctctctaaa cctcaatttc ctcatttg       58

<210> SEQ ID NO 66
<211> LENGTH: 7788
<212> TYPE: DNA
<213> ORGANISM: Artificial Sequence
<220> FEATURE:
<223> OTHER INFORMATION: Synthetic

<400> SEQUENCE: 66
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact   120
aggggttcct gcggccgcac gcgtcatatt tatgggtat atgtgaatat ttattacatg    180
catagaaggt ataatgatca tgtcaggata tttgaggtat ccacatttgg gattgtttaa   240
agattaaatg aaatagtgtt aaaagtattt aatatgccct tcaacaaatg atgaggaaat   300
cttagaatct gctcagactc cttcagttta catattagga aactgaggca cagaaaggag   360
cagagacttg ctcaagtcca cccaaaagcag tagagcattg tggttaaatg caggacttca   420
gtcagactgt ctgggttcaa atcctggttc cacttggaca tgggtttcct tacataaatc   480
acttcacctc tctgagcctc agttttctca tatgcaaagt gaggataata ataataccttt 540 ccttacatgg ttactgatat gagtattaaa tgtgccagct catgtgcctg cgtatagga    600 ggtgctttat aaaccttagc tgttaccact catggcattg ccaaatgtgg gacgggtctc   660
```

| | |
|---|---|
| ctgactctct ggtgtgagat tgatggaatc cacactttcc agttcccttt tctacctcct | 720 |
| gggtatcttc tcatatggtt gtaagttcct tggaggaagg gaatgtggct tgctctctcc | 780 |
| accacgctga gcatataaga ggtgctgaat gagcgctttt attcactcct ctcatcccca | 840 |
| gccctcacca gctgggagtt gttgtaggtg tcaattttct gcctctttcc aacaccctgt | 900 |
| gaggtgactg agcattgtct tccctcccag gcagctcaca gtgtaagctt gtggacgata | 960 |
| tcgaattcgc acgacattga ttattgacta gttattaata gtaatcaatt acggggtcat | 1020 |
| tagttcatag cccatatatg gagttccgcg ttacataact tacggtaaat ggcccgcctg | 1080 |
| gctgaccgcc caacgacccc cgcccattga cgtcaataat gacgtatgtt cccatagtaa | 1140 |
| cgccaatagg gactttccat tgacgtcaat gggtggacta tttacggtaa actgcccact | 1200 |
| tggcagtaca tcaagtgtat catatgccaa gtacgccccc tattgacgtc aatgacggta | 1260 |
| aatggcccgc ctggcattat gcccagtaca tgaccttatg ggactttcct acttggcagt | 1320 |
| acatctacgt attagtcatc gctattacca tgggtcgagg tgagcccac gttctgcttc | 1380 |
| actctcccca tctccccccc ctcccacccc caattttgt atttatttat tttttaatta | 1440 |
| ttttgtgcag cgatggggc ggggggggg gggcgcgcg ccaggcgggg cggggcgggg | 1500 |
| cgaggggcg ggcggggcga ggcggagagg tgcggcggca gccaatcaga gcggcgcgct | 1560 |
| ccgaaagttt ccttttatgg cgaggcggcg gcggcggcgg ccctataaaa agcgaagcgc | 1620 |
| gcggcgggcg ggagtcgctg cgttgccttc gccccgtgcc ccgctccgcg ccgcctcgcg | 1680 |
| ccgcccgccc cggctctgac tgaccgcgtt actcccacag gtgagcgggc gggacggccc | 1740 |
| ttctcctccg ggctgtaatt agcgcttggt ttaatgacgg ctcgtttctt ttctgtggct | 1800 |
| gcgtgaaagc cttaaagggc tccggagggc ccctttgtgc gggggggagc ggctcggggg | 1860 |
| gtgcgtgcgt gtgtgtgtgc gtggggagcg ccgcgtgcgg cccgcgctgc ccggcggctg | 1920 |
| tgagcgctgc gggcgcggcg cggggctttg tgcgctccgc gtgtgcgcga ggggagcgcg | 1980 |
| gccggggcg gtgccccgcg gtgcggggg gctgcgaggg gaacaaaggc tgcgtgcggg | 2040 |
| gtgtgtgcgt gggggggtga gcaggggggtg tgggcgcggc ggtcgggctg taacccccc | 2100 |
| ctgcaccccc ctccccgagt tgctgagcac ggcccggctt cgggtgcggg gctccgtgcg | 2160 |
| gggcgtggcg cggggctcgc cgtgccgggc gggggtggc ggcaggtggg ggtgccgggc | 2220 |
| ggggcgggc cgcctcgggc cggggaggc tcggggagg ggcgcggcgg ccccggagcg | 2280 |
| ccggcggctg tcgaggcgcg gcgagccgca gccattgcct tttatggtaa tcgtgcgaga | 2340 |
| gggcgcaggg acttcctttg tcccaaatct ggcggagccg aaatctggga ggcgccgccg | 2400 |
| cacccctct agcgggcgcg ggcgaagcgg tgcggcgccg gcaggaagga aatgggcggg | 2460 |
| gagggccttc gtgcgtcgcc gcgccgccgt cccttctcc atctccagcc tcggggctgc | 2520 |
| cgcagggga cggctgcctt cgggggggac ggggcaggc ggggttcggc ttctggcgtg | 2580 |
| tgaccggcgg ctctagagcc tctgctaacc atgttcatgc cttcttcttt ttcctacagg | 2640 |
| ggggatccgt ttatctgcag aattcgccct tgacgtcgcc accatggcgc ttccggtgac | 2700 |
| agcactgctc ctcccttgg cgctgttgct ccacgcagca aggccgcagg tgcagctggt | 2760 |
| gcagagcgga gccgagctca agaagccgg agcctccgtg aaggtgagct gcaaggccag | 2820 |
| cggcaacacc ctgaccaact acgtgatcca ctgggtgaga caagccccg ccaaaggct | 2880 |
| ggagtggatg ggctacatcc tgccctacaa cgacctgacc aagtacagcc agaagttcca | 2940 |
| gggcagggtg accatcacca gggataagag cgcctccacc gcctatatgg agctgagcag | 3000 |
| cctgaggagc gaggacaccg ctgtgtacta ctgtacaagg tgggactggg acggcttctt | 3060 |

```
tgaccoctgg ggccagggca caacagtgac cgtcagcagc ggcggcggag gcagcggcgg    3120
cggcggcagc ggcggaggcg gaagcgaaat cgtgatgacc cagagcccg ccacactgag     3180 cgtgagccct ggcgagaggg ccagcatctc ctgcagggct agccaaagcc tggtgcacag    3240
caacggcaac acccacctgc actggtacca gcagagaccc ggacaggctc ccaggctgct    3300
gatctacagc gtgagcaaca ggttctccga ggtgcctgcc aggtttagcg gcagcggaag    3360
cggcaccgac tttaccctga ccatcagcag cgtggagtcc gaggacttcg ccgtgtatta    3420
ctgcagccag accagccaca tcccttacac cttcggcggc ggcaccaagc tggagatcaa    3480
aagtgctgct gcctttgtcc cggtatttct cccagccaaa ccgaccacga ctccccgcccc   3540 gcgccctccg acacccgctc ccaccatcgc ctctcaacct cttagtcttc gccccgaggc    3600
atgccgaccc gccgccgggg gtgctgttca tacgaggggc ttggacttcg cttgtgatat    3660
ttacatttgg gctccgttgg cgggtacgtg cggcgtcctt tgttgtcac tcgttattac     3720 tttgtattgt aatcacagga atcgcaaacg gggcagaaag aaactcctgt atatattcaa    3780
acaaccattt atgagaccag tacaaactac tcaagaggaa gatggctgta gctgccgatt    3840
tccagaagaa gaagaaggag gatgtgaact gcgagtgaag ttttcccgaa gcgcagacgc    3900
tccggcatat cagcaaggac agaatcagct gtataacgaa ctgaatttgg gacgccgcga    3960
ggagtatgac gtgcttgata aacgccgggg gagagacccg gaaatggggg gtaaaccccg    4020
aagaaagaat ccccaagaag gactctacaa tgaactccag aaggataaga tggcggaggc    4080
ctactcagaa ataggtatga agggcgaacg acgacgggga aaaggtcacg atggcctcta    4140
ccaagggttg agtacggcaa ccaaagatac gtacgatgca ctgcatatgc aggccctgcc    4200
tcccagataa tccgctgatc agcctcgact gtgccttcta gttgccagcc atctgttgtt    4260 tgccctccc ccgtgccttc cttgaccctg gaaggtgcca ctcccactgt cctttcctaa     4320
taaaatgagg aaattgcatc gcattgtctg agtaggtgtc attctattct ggggggtggg    4380
gtggggcagg acagcaaggg ggaggattgg gaagacaata gcaggcatgc tggggatgcg    4440
gtgggctcta tgggtcgact gaccagatgg acctggctgg agaagaagag attgagctct    4500
actcaggtgg gccctcctcc ctctggtctc ttccggtatc ccccaccct cagcttgctg     4560 tagagacggc aatcagggga aattctggtc cctgccctcc cgtcagcacc acggacagct    4620
cccacgtctg tgggacgctc tctgcagatg gggatgatct cccagccctg ccccgcctct   4680 cctcgttcc ccaccagccc tctttccaga aattccttc ttcatccaag ggactttcc      4740 tcccagaacc cgacacagac accatcaact gcgaccagtt cagcaggctg ttgtgtgaca    4800
tggaaggtga tgaagagacc agggaggctt atgccaatat cggtgaggaa gcacctgagc    4860
ccagaaaagg acaatcaagg gcaagagttc tttgctgcca cttgtcaata tcacccattc    4920
atcatgagcc acgtcagtcc cctcccacag aaatcattgc aaggggggatg cggagcaatg   4980 gctggaggaa cggagactcc agggaagaga ggggagatgg aggccagtgg gggaaatagg    5040
ccccttcact aatgaccacc aagaaaacaa atctcatgt ttacatcctc cacctccatt     5100
tctatacgca tttctgcttc ttgctcttct gtccatcctt tctacaaagc ccataccata    5160
cacccctttc cctttttcctc ccagctcctt agccaagcta ctctagtatt tgtaataact   5220
agcatttact ggatactcat agtatgctca ttgctgtccg gtaaccacgt gcggaccgag    5280
gctgcagcgt cgtcctcct aggaacccct agtgatggag ttggccactc cctctctgcg    5340
cgctcgctcg ctcactgagg ccgggcgacc aaaggtcgcc cgacgcccgg gctttgcccg    5400
```

```
ggcggcctca gtgagcgagc gagcgcgcag ctgcctgcag gggcgcctga tgcggtattt    5460
tctccttacg catctgtgcg gtatttcaca ccgcatacgt caaagcaacc atagtacgcg    5520
ccctgtagcg gcgcattaag cgcggcgggt gtggtggtta cgcgcagcgt gaccgctaca    5580
cttgccagcg ccctagcgcc cgctcctttc gctttcttcc cttcctttct cgccacgttc    5640
gccggctttc cccgtcaagc tctaaatcgg gggctcccctt tagggttccg atttagtgct   5700
ttacggcacc tcgaccccaa aaaacttgat ttgggtgatg gttcacgtag tgggccatcg    5760
ccctgataga cggttttttcg cccttttgacg ttggagtcca cgttctttaa tagtggactc   5820
ttgttccaaa ctggaacaac actcaaccct atctcgggct attcttttga tttataaggg    5880
attttgccga tttcggccta ttggttaaaa aatgagctga tttaacaaaa atttaacgcg    5940
aattttaaca aaatattaac gtttacaatt ttatggtgca ctctcagtac aatctgctct    6000
gatgccgcat agttaagcca gccccgacac ccgccaacac ccgctgacgc gccctgacgg    6060
gcttgtctgc tcccggcatc cgcttacaga caagctgtga ccgtctccgg gagctgcatg    6120
tgtcagaggt tttcaccgtc atcaccgaaa cgcgcgagac gaaagggcct cgtgatacgc    6180 ctattttttat aggttaatgt catgaacaat aaaactgtct gcttacataa acagtaatac    6240
aaggggtgtt atgagccata ttcaacggga aacgtcgagg ccgcgattaa attccaacat    6300
ggatgctgat ttatatgggt ataaatgggc tcgcgataat gtcgggcaat caggtgcgac    6360
aatctatcgc ttgtatggga agcccgatgc gccagagttg tttctgaaac atggcaaagg    6420
tagcgttgcc aatgatgtta cagatgagat ggtcagacta aactggctga cggaatttat    6480
gcctcttccg accatcaagc attttatccg tactcctgat gatgcatggt tactcaccac    6540
tgcgatcccc ggaaaaacag cattccaggt attagaagaa tatcctgatt caggtgaaaa    6600
tattgttgat gcgctggcag tgttcctgcg ccggttgcat tcgattcctg tttgtaattg    6660
tccttttaac agcgatcgcg tatttcgtct cgctcaggcg caatcacgaa tgaataacgg    6720
tttggttgat gcgagtgatt ttgatgacga gcgtaatggc tggcctgttg aacaagtctg    6780
gaaagaaatg cataaacttt tgccattctc accggattca gtcgtcactc atggtgattt    6840
ctcacttgat aaccttattt ttgacgaggg gaaattaata ggttgtattg atgttggacg    6900
agtcggaatc gcagaccgat accaggatct tgccatccta tggaactgcc tcggtgagtt    6960
ttctccttca ttacagaaac ggcttttttca aaaatatggt attgataatc ctgatatgaa    7020
taaattgcag tttcatttga tgctcgatga gttttttctaa tctcatgacc aaaatccctt    7080
aacgtgagtt ttcgttccac tgagcgtcag acccccgtaga aaagatcaaa ggatcttctt    7140
gagatccttt ttttctgcgc gtaatctgct gcttgcaaac aaaaaaacca ccgctaccag    7200
cggtggtttg tttgccggat caagagctac caactctttt tccgaaggta actggcttca    7260
gcagagcgca gataccaaat actgtccttc tagtgtagcc gtagttaggc caccacttca    7320
agaactctgt agcaccgcct acatacctcg ctctgctaat cctgttacca gtggctgctg    7380
ccagtggcga taagtcgtgt cttaccgggt tggactcaag acgatagtta ccggataagg    7440
cgcagcggtc gggctgaacg gggggttcgt gcacacagcc cagcttggag cgaacgacct    7500
acaccgaact gagatacccta cagcgtgagc tatgagaaag cgccacgctt cccgaaggga    7560
gaaaggcgga caggtatccg gtaagcggca gggtcggaac aggagagcgc acgagggagc    7620
ttccaggggg aaacgcctgg tatctttata gtcctgtcgg gtttcgccac ctctgacttg    7680
agcgtcgatt tttgtgatgc tcgtcagggg ggcggagcct atggaaaaac gccagcaacg    7740 cggcctttttt acggttcctg gccttttgct ggccttttgc tcacatgt              7788
```

<210> SEQ ID NO 67
<211> LENGTH: 9077
<212> TYPE: DNA
<213> ORGANISM: Artificial Sequence
<220> FEATURE:
<223> OTHER INFORMATION: Synthetic

<400> SEQUENCE: 67

| | | | | | |
|---|---|---|---|---|---|
| cctgcaggca | gctgcgcgct | cgctcgctca | ctgaggccgc | ccgggcgtcg | ggcgaccttt | 60 |
| ggtcgcccgg | cctcagtgag | cgagcgagcg | cgcagagagg | gagtggccaa | ctccatcact | 120 |
| aggggttcct | gcggccgcac | gcgtgttcta | gggtggaaac | taagagaatg | atgtacctag | 180 |
| agggcgctgg | aagctctaaa | gccctagcag | ttactgcttt | tactattagt | ggtcgttttt | 240 |
| ttctcccccc | cgcccccga | caaatcaaca | gaacaaagaa | aattacctaa | acagcaagga | 300 |
| catagggagg | aacttcttgg | cacagaactt | tccaaacact | ttttcctgaa | gggatacaag | 360 |
| aagcaagaaa | ggtactcttt | cactaggacc | ttctctgagc | tgtcctcagg | atgcttttgg | 420 |
| gactattttt | cttacccaga | gaatggagaa | accctgcagg | gaattcccaa | gctgtagtta | 480 |
| taaacagaag | ttctccttct | gctaggtagc | attcaaagat | cttaatcttc | tgggtttccg | 540 |
| ttttctcgaa | tgaaaaatgc | aggtccgagc | agttaactgg | ctggggcacc | attagcaagt | 600 |
| cacttagcat | ctctggggcc | agtctgcaaa | gcgagggggc | agccttaatg | tgcctccagc | 660 |
| ctgaagtcct | agaatgagcg | cccggtgtcc | caagctgggg | cgcgcacccc | agatcggagg | 720 |
| gcgccgatgt | acagacagca | aactcaccca | gtcagtgca | tgccttctta | aacatcacga | 780 |
| gactctaaga | aaggaaact | gaaacggga | aagtccctct | ctctaacctg | gcactgcgtc | 840 |
| gctggcttgg | agacaggtga | cggtccctgc | gggccttgtc | ctgattggct | gggcacgcgt | 900 |
| ttaatataag | tggaggcgtc | gcgctggcgg | gcattcctga | agctaagctt | gtggacgata | 960 |
| tcgaattcgc | acgacattga | ttattgacta | gttattaata | gtaatcaatt | acggggtcat | 1020 |
| tagttcatag | cccatatatg | gagttccgcg | ttacataact | tacggtaaat | ggcccgcctg | 1080 |
| gctgaccgcc | caacgacccc | cgcccattga | cgtcaataat | gacgtatgtt | cccatagtaa | 1140 |
| cgccaatagg | gactttccat | tgacgtcaat | gggtggacta | tttacggtaa | actgcccact | 1200 |
| tggcagtaca | tcaagtgtat | catatgccaa | gtacgccccc | tattgacgtc | aatgacggta | 1260 |
| aatggcccgc | ctggcattat | gcccagtaca | tgaccttatg | ggactttcct | acttggcagt | 1320 |
| acatctacgt | attagtcatc | gctattacca | tgggtcgagg | tgagcccac | gttctgcttc | 1380 |
| actctcccca | tctcccccc | ctccccaccc | ccaattttgt | atttatttat | tttttaatta | 1440 |
| ttttgtgcag | cgatggggc | ggggggggg | gggcgcgcg | ccaggcgggg | cggggcgggg | 1500 |
| cgaggggcg | ggcggggcga | ggcggagagg | tgcggcggca | gccaatcaga | gcggcgcgct | 1560 |
| ccgaaagttt | cctttatgg | cgaggcggcg | gcggcggcgg | ccctataaaa | agcgaagcgc | 1620 |
| gcggcgggcg | ggagtcgctg | cgttgccttc | gccccgtgcc | ccgctccgcg | ccgcctcgcg | 1680 |
| ccgcccgccc | cggctctgac | tgaccgcgtt | actcccacag | gtgagcgggc | gggacggccc | 1740 |
| ttctcctccg | gctgtaatt | agcgcttggt | ttaatgacgg | ctcgtttctt | ttctgtggct | 1800 |
| gcgtgaaagc | cttaaagggc | tccggagggg | ccctttgtgc | gggggggagc | ggctcggggg | 1860 |
| gtgcgtgcgt | gtgtgtgtgc | gtggggagcg | ccgcgtgcgg | cccgcgctgc | ccggcggctg | 1920 |
| tgagcgctgc | gggcgcggcg | cggggctttg | tgcgctccgc | gtgtgcgcga | ggggagcgcg | 1980 |
| gccggggcg | gtgccccgcg | gtgcggggg | gctgcgaggg | gaacaaaggc | tgcgtgcggg | 2040 |

```
gtgtgtgcgt ggggggtga gcaggggtg tgggcgcggc ggtcgggctg taacccccc    2100 ctgcaccccc ctccccgagt tgctgagcac ggcccggctt cgggtgcggg gctccgtgcg    2160
gggcgtggcg cggggctcgc cgtgccgggc ggggggtggc ggcaggtggg ggtgccgggc    2220
ggggcggggc cgcctcgggc cggggagggc tcggggagg ggcgcggcgg ccccggagcg    2280
ccggcggctg tcgaggcgcg gcgagccgca gccattgcct tttatggtaa tcgtgcgaga    2340
gggcgcaggg acttcctttg tcccaaatct ggcggagccg aaatctggga ggcgccgccg    2400 cacccctct agcgggcgcg ggcgaagcgg tgcggcgccg gcaggaagga aatgggcggg    2460
gagggccttc gtgcgtcgcc gcgccgccgt cccttctcc atctccagcc tcggggctgc    2520 cgcagggga cggctgcctt cggggggac ggggcaggc ggggttcggc ttctggcgtg    2580
tgaccggcgg ctctagagcc tctgctaacc atgttcatgc cttcttcttt ttcctacagg    2640
ggggatccgt ttatctgcag aattcgccct tgacgtcgcc accatggact ggacctggat    2700
cctgttcctg gtggccgccg ccaccagggt gcacagcggc attcatgtct tcatttgg    2760 ctgtttcagt gcagggcttc ctaaaacaga agccaactgg gtgaatgtaa taagtgattt    2820 gaaaaaatt gaagatctta ttcaatctat gcatattgat gctactttat atacggaaag    2880
tgatgttcac cccagttgca aagtaacagc aatgaagtgc tttctcttgg agttacaagt    2940
tatttcactt gagtccgag atgcaagtat tcatgataca gtagaaaatc tgatcatcct    3000
agcaaacaac agtttgtctt ctaatgggaa tgtaacagaa tctggatgca aagaatgtga    3060
ggaactggag gaaaaaata ttaaagaatt tttgcagagt tttgtacata ttgtccaaat    3120
gttcatcaac acttctagcg gcggcggcag cggcggcggc ggcagcggcg gcggcggcag    3180
cggcggcggc ggcagcggcg gcggcagcct gcagatcacg tgcctcccc ccatgtccgt    3240 ggaacacgca gacatctggg tcaagagcta cagcttgtac tccagggagc ggtacatttg    3300
taactctggt ttcaagcgta aagccggcac gtccagcctg acggagtgcg tgttgaacaa    3360
ggccacgaat gtcgcccact ggacaacccc cagtctcaaa tgcattagag accctgccct    3420
ggttcaccaa aggccagcgc caccctccac agtaacgacg gcaggggtga ccccacagcc    3480
agagagcctc tccccttctg gaaaagagcc cgcagcttca tctcccagct caaacaacac    3540
agcggccaca acagcagcta ttgtcccggg ctcccagctg atgccttcaa aatcaccttc    3600
cacaggaacc acagagataa gcagtcatga gtcctccac ggcacccct ctcagacaac    3660 agccaagaac tgggaactca cagcatccgc ctcccaccag ccgccaggtg tgtatccaca    3720
gggccacagc gacaccactg tggctatctc cacgtccact gtcctgctgt gtgggctgag    3780
cgctgtgtct ctcctggcat gctacctcaa gtcaaggcaa actccccgc tggccagcgt    3840 tgaaatggaa gccatggagg ctctgccggt gacttggggg accagcagca gagatgaaga    3900
cttggaaaac tgctctcacc acctaggaag cggagctact aacttcagcc tgctgaagca    3960
ggctggagac gtgaggaga accctggacc tatgtctcgc tccgttgcct tagctgtgct    4020
cgcgctactc tctctttctg gattagaggc tgtcatggcg ccccgaaccc tcttcctggg    4080 tggaggcgt tcaggcggag gtggctctgg cggtggcgga tcgatccagc gtactccaaa    4140
gattcaggtt tactcacgtc atccagcaga gaatggaaag tcaaatttcc tgaattgcta    4200
tgtgtctggg tttcatccat ccgacattga agttgactta ctgaagaatg gagagagaat    4260
tgaaaaagtg gagcattcag acttgtcttt cagcaaggac tggtctttct atctcttgta    4320
ctacactgaa ttcaccccca ctgaaaaaga tgagtatgcc tgccgtgtga accatgtgac    4380
tttgtcacag cccaagatag ttaagtggga tcgagacatg ggtggtggtg gttctggtgg    4440
```

```
tggtggttct ggcggcggcg gctccggtgg tggtggatcc ggctcccact ccttgaagta   4500
tttccacact tccgtgtccc ggcccggccg cggggagccc cgcttcatct ctgtgggcta   4560
cgtggacgac acccagttcg tgcgcttcga caacgacgcc gcgagtccga ggatggtgcc   4620
gcgggcgccg tggatggagc aggaggggtc agagtattgg gaccgggaga cacggagcgc   4680
cagggacacc gcacagattt tccgagtgaa tctgcggacg ctgcgcggct actacaatca   4740
gagcgaggcc gggtctcaca ccctgcagtg gatgcatggc tgcgagctgg ggcccgacgg   4800
gcgcttcctc cgcgggtatg aacagttcgc ctacgacggc aaggattatc tcaccctgaa   4860
tgaggacctg cgctcctgga ccgcggtgga cacggcggct cagatctccg agcaaaagtc   4920
aaatgatgcc tctgaggcgg agcaccagag agcctacctg gaagacacat gcgtggagtg   4980
gctccacaaa tacctggaga aggggaagga gacgctgctt cacctggagc ccccaaagac   5040
acacgtgact caccacccca tctctgacca tgaggccacc ctgaggtgct gggccctggg   5100
cttctaccct gcggagatca cactgacctg gcagcaggat ggggagggcc atacccagga   5160
cacggagctc gtggagacca ggcctgcagg ggatggaacc ttccagaagt gggcagctgt   5220
ggtggtgcct tctggagagg agcagagata cacgtgccat gtgcagcatg aggggctacc   5280
cgagcccgtc accctgagat ggaagccggc ttcccagccc accatcccca tcgtgggcat   5340
cattgctggc ctggttctcc ttggatctgt ggtctctgga gctgtggttg ctgctgtgat   5400
atggaggaag aagagctcag gtggaaaagg agggagctac tctaaggctg agtggagcga   5460
cagtgcccag gggtctgagt ctcacagctt gtaatgatag ccgctgatca gcctcgactg   5520
tgccttctag ttgccagcca tctgttgttt gcccctcccc cgtgccttcc ttgaccctgg   5580
aaggtgccac tcccactgtc ctttcctaat aaaatgagga aattgcatcg cattgtctga   5640
gtaggtgtca ttctattctg gggggtgggg tggggcagga cagcaagggg gaggattggg   5700
aagacaatag caggcatgct ggggatgcgg tgggctctat gggtcgaccc agcgtgagtc   5760
tctcctaccc tcccgctctg gtccttcctc tcccgctctg caccctctgt ggccctcgct   5820
gtgctctctc gctccgtgac ttcccttctc caagttctcc ttggtggccc gccgtggggc   5880
tagtccaggg ctggatctcg gggaagcggc ggggtggcct gggagtgggg aaggggggtgc   5940
gcacccggga cgcgcgctac ttgccccttt cggcggggag caggggagac ctttggccta   6000
cggcgacggg agggtcggga caaagtttag ggcgtcgata agcgtcagag cgccgaggtt   6060
gggggagggt ttctcttccg ctctttcgcg ggcctctgg ctcccccagc gcagctggag   6120
tgggggacgg gtaggctcgt cccaaaggcg cggcgctgag gtttgtgaac gcgtggaggg   6180
gcgcttgggg tctgggggag gcgtcgcccg ggtaagcctg tctgctgcgg ctctgcttcc   6240
cttagactgg agagctgtgg acttcgtcta ggcgcccgct aagttcgcat gtcctagcac   6300
ctctgggtct atgtggggcc acaccgtggg gaggaaacag cacgcgacgt ttgtagaatg   6360
cttggctgtg atacaaagcg gtttcgaata attaacttat ttgttcccat cacatgtcac   6420
ttttaaaaaa ttataagaac tacccgttat tgacatcttt ctgtgtgcca aggactttat   6480
gtgctttgcg tcatttaatt ttgaaaacag ttatcttccg ccatagataa ctactatggt   6540
tatcttctgg taaccacgtg cggaccgagg ctgcagcgtc gtcctcccta ggaaccccta   6600
gtgatggagt tggccactcc ctctctgcgc gctcgctcgc tcactgaggc cgggcgacca   6660
aaggtcgccc gacgcccggg ctttgcccgg gcggcctcag tgagcgagcg agcgcgcagc   6720
tgcctgcagg ggcgcctgat gcggtatttt ctccttacgc atctgtgcgg tatttcacac   6780
```

```
cgcatacgtc aaagcaacca tagtacgcgc cctgtagcgg cgcattaagc gcggcgggtg    6840
tggtggttac gcgcagcgtg accgctacac ttgccagcgc cctagcgccc gctcctttcg    6900
ctttcttccc ttcctttctc gccacgttcg ccggctttcc ccgtcaagct ctaaatcggg    6960
ggctcccttt aggggtccga tttagtgctt tacggcacct cgaccccaaa aaacttgatt    7020
tgggtgatgg ttcacgtagt gggccatcgc cctgatagac ggttttttcgc cctttgacgt    7080 tggagtccac gttctttaat agtggactct tgttccaaac tggaacaaca ctcaaccccta    7140 tctcgggcta ttcttttgat ttataaggga ttttgccgat ttcggcctat tggttaaaaa    7200
atgagctgat ttaacaaaaa tttaacgcga atttttaacaa aatattaacg tttacaattt    7260
tatggtgcac tctcagtaca atctgctctg atgccgcata gttaagccag ccccgacacc    7320
cgccaacacc cgctgacgcg ccctgacggg cttgtctgct cccggcatcc gcttacagac    7380
aagctgtgac cgtctccggg agctgcatgt gtcagaggtt ttcaccgtca tcaccgaaac    7440
gcgcgagacg aaagggcctc gtgatacgcc tatttttata ggttaatgtc atgaacaata    7500
aaactgtctg cttacataaa cagtaataca agggtgtta tgagccatat tcaacgggaa    7560
acgtcgaggc cgcgattaaa ttccaacatg gatgctgatt tatatgggta taatgggct    7620 cgcgataatg tcgggcaatc aggtgcgaca atctatcgct tgtatgggaa gcccgatgcg    7680
ccagagttgt ttctgaaaca tggcaaaggt agcgttgcca atgatgttac agatgagatg    7740
gtcagactaa actggctgac ggaatttatg cctcttccga ccatcaagca ttttatccgt    7800
actcctgatg atgcatggtt actcaccact gcgatccccg gaaaaacagc attccaggta    7860
ttagaagaat atcctgattc aggtgaaaat attgttgatg cgctggcagt gttcctgcgc    7920
cggttgcatt cgattcctgt ttgtaattgt ccttttaaca gcgatcgcgt atttcgtctc    7980
gctcaggcgc aatcacgaat gaataacggt ttggttgatg cgagtgattt tgatgacgag    8040
cgtaatggct ggcctgttga acaagtctgg aaagaaatgc ataaactttt gccattctca    8100
ccggattcag tcgtcactca tggtgatttc tcacttgata accttatttt tgacgagggg    8160
aaattaatag gttgtattga tgttggacga gtcggaatcg cagaccgata ccaggatctt    8220
gccatcctat ggaactgcct cggtgagttt tctccttcat tacagaaacg cttttttcaa    8280
aaatatggta ttgataatcc tgatatgaat aaattgcagt ttcatttgat gctcgatgag    8340
tttttctaat ctcatgacca aaatcccttta acgtgagttt tcgttccact gagcgtcaga    8400
ccccgtagaa aagatcaaag gatcttcttg agatcctttt tttctgcgcg taatctgctg    8460
cttgcaaaca aaaaaaccac cgctaccagc ggtggtttgt ttgccggatc aagagctacc    8520
aactcttttt ccgaaggtaa ctggcttcag cagagcgcag ataccaaata ctgtccttct    8580
agtgtagccg tagttaggcc accacttcaa gaactctgta gcaccgccta catacctcgc    8640
tctgctaatc ctgttaccag tggctgctgc cagtggcgat aagtcgtgtc ttaccgggtt    8700
ggactcaaga cgatagttac cggataaggc gcagcggtcg ggctgaacgg ggggttcgtg    8760
cacacagccc agcttggagc gaacgaccta caccgaactg agatacctac agcgtgagct    8820
atgagaaagc gccacgcttc ccgaagggag aaaggcggac aggtatccgg taagcggcag    8880
ggtcggaaca ggagagcgca cgagggagct tccaggggga aacgcctggt atctttatag    8940
tcctgtcggg tttcgccacc tctgacttga gcgtcgattt ttgtgatgct cgtcaggggg    9000
gcggagccta tggaaaaacg ccagcaacgc ggcctttta cggttcctgg ccttttgctg    9060
gccttttgct cacatgt                                                   9077
```

```
<210> SEQ ID NO 68
<211> LENGTH: 22
<212> TYPE: PRT
<213> ORGANISM: Homo sapiens

<400> SEQUENCE: 68

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 69
<211> LENGTH: 21
<212> TYPE: PRT
<213> ORGANISM: Homo sapiens

<400> SEQUENCE: 69

Met Ala Leu Pro Val Thr Ala Leu Leu Leu Pro Leu Ala Leu Leu Leu
1               5                   10                  15

His Ala Ala Arg Pro
            20

<210> SEQ ID NO 70
<211> LENGTH: 1524
<212> TYPE: DNA
<213> ORGANISM: Artificial Sequence
<220> FEATURE:
<223> OTHER INFORMATION: Synthetic

<400> SEQUENCE: 70
```

| | | | | | |
|---|---|---|---|---|---|
| atggcgcttc | cggtgacagc | actgctcctc | cccttggcgc | tgttgctcca | cgcagcaagg    60 |
| ccgcaggtgc | agctggtgca | gagcggagcc | gagctcaaga | agcccggagc | ctccgtgaag   120 |
| gtgagctgca | aggccagcgg | caacaccctg | accaactacg | tgatccactg | ggtgagacaa   180 |
| gccccggcc | aaaggctgga | gtggatgggc | tacatcctgc | cctacaacga | cctgaccaag   240 |
| tacagccaga | agttccaggg | cagggtgacc | atcaccaggg | ataagagcgc | ctccaccgcc   300 |
| tatatggagc | tgagcagcct | gaggagcgag | gacaccgctg | tgtactactg | tacaaggtgg   360 |
| gactgggacg | gcttctttga | ccccgggggc | cagggcacaa | cagtgaccgt | cagcagcggc   420 |
| ggcggaggca | gcggcggcgg | cggcagcggc | ggaggcggaa | gcgaaatcgt | gatgacccag   480 |
| agccccgcca | cactgagcgt | gagccctggc | gagagggcca | gcatctcctg | cagggctagc   540 |
| caaagcctgg | tgcacagcaa | cggcaacacc | cacctgcact | ggtaccagca | gagacccgga   600 |
| caggctccca | ggctgctgat | ctacagcgtg | agcaacaggt | tctccgaggt | gcctgccagg   660 |
| tttagcggca | gcggaagcgg | caccgacttt | accctgacca | tcagcagcgt | ggagtccgag   720 |
| gacttcgccg | tgtattactg | cagccagacc | agccacatcc | cttacacctt | cggcggcggc   780 |
| accaagctgg | agatcaaaag | tgctgctgcc | tttgtcccgg | tatttctccc | agccaaaccg   840 |
| accacgactc | ccgcccgcg | ccctccgaca | cccgctccca | ccatcgcctc | tcaacctctt   900 |
| agtcttcgcc | ccgaggcatg | ccgacccgcc | gccgggggtg | ctgttcatac | gaggggcttg   960 |
| gacttcgctt | gtgatattta | catttgggct | ccgttggcgg | gtacgtgcgg | cgtcctttg  1020 |
| ttgtcactcg | ttattacttt | gtattgtaat | cacaggaatc | gcaaacgggg | cagaaagaaa  1080 |
| ctcctgtata | tattcaaaca | accatttatg | agaccagtac | aaactactca | agaggaagat  1140 |
| ggctgtagct | gccgatttcc | agaagaagaa | gaggaggat | gtgaactgcg | agtgaagttt  1200 |
| tcccgaagcg | cagacgctcc | ggcatatcag | caaggacaga | tcagctgta | taacgaactg  1260 |

```
aatttgggac gccgcgagga gtatgacgtg cttgataaac gccggggag agacccggaa      1320 atgggggta accccgaag aaagaatccc caagaaggac tctacaatga actccagaag       1380
gataagatgg cggaggccta ctcagaaata ggtatgaagg gcgaacgacg acggggaaaa     1440
ggtcacgatg gcctctacca agggttgagt acggcaacca agatacgta cgatgcactg      1500 catatgcagg ccctgcctcc caga                                           1524
```

<210> SEQ ID NO 71
<211> LENGTH: 735
<212> TYPE: DNA
<213> ORGANISM: Artificial Sequence
<220> FEATURE:
<223> OTHER INFORMATION: Synthetic

<400> SEQUENCE: 71

```
caggtgcagc tggtgcagag cggagccgag ctcaagaagc ccggagcctc cgtgaaggtg       60
agctgcaagg ccagcggcaa caccctgacc aactacgtga tccactgggt gagacaagcc      120
cccggccaaa ggctggagtg gatgggctac atcctgccct acaacgacct gaccaagtac      180
agccagaagt tccagggcag ggtgaccatc accaggata gagcgcctc caccgcctat        240 atggagctga gcagcctgag gagcgaggac accgctgtgt actactgtac aaggtgggac      300
tgggacggct tcttgaccc ctggggccag ggcacaacag tgaccgtcag cagcggcggc       360
ggaggcagcg gcggcggcgg cagcggcgga ggcggaagcg aaatcgtgat gacccagagc      420
cccgccacac tgagcgtgag ccctggcgag agggccagca tctcctgcag gctagccaa      480 agcctggtgc acagcaacgg caacacccac ctgcactggt accagcagag acccggacag      540
gctcccaggc tgctgatcta cagcgtgagc aacaggttct ccgaggtgcc tgccaggttt     600
agcggcagcg gaagcggcac cgactttacc ctgaccatca gcagcgtgga gtccgaggac      660
ttcgccgtgt attactgcag ccagaccagc cacatccctt acaccttcgg cggcggcacc     720
aagctggaga tcaaa                                                    735
```

<210> SEQ ID NO 72
<211> LENGTH: 84
<212> TYPE: PRT
<213> ORGANISM: Homo sapiens

<400> SEQUENCE: 72

```
Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp Ile Tyr Ile Trp Ala Pro Leu Ala Gly
    50                  55                  60

Thr Cys Gly Val Leu Leu Leu Ser Leu Val Ile Thr Leu Tyr Cys Asn
65                  70                  75                  80

His Arg Asn Arg
```

<210> SEQ ID NO 73
<211> LENGTH: 23
<212> TYPE: PRT
<213> ORGANISM: Homo sapiens

<400> SEQUENCE: 73

```
Ile Tyr Ile Trp Ala Pro Leu Ala Gly Thr Cys Gly Val Leu Leu
1               5                   10                  15

Ser Leu Val Ile Thr Leu Tyr
            20
```

<210> SEQ ID NO 74
<211> LENGTH: 508
<212> TYPE: PRT
<213> ORGANISM: Artificial Sequence
<220> FEATURE:
<223> OTHER INFORMATION: Synthetic

<400> SEQUENCE: 74

```
Met Ala Leu Pro Val Thr Ala Leu Leu Leu Pro Leu Ala Leu Leu
1               5                   10                  15

His Ala Ala Arg Pro Gln Val Gln Leu Val Gln Ser Gly Ala Glu Leu
                20                  25                  30

Lys Lys Pro Gly Ala Ser Val Lys Val Ser Cys Lys Ala Ser Gly Asn
            35                  40                  45

Thr Leu Thr Asn Tyr Val Ile His Trp Val Arg Gln Ala Pro Gly Gln
50                  55                  60

Arg Leu Glu Trp Met Gly Tyr Ile Leu Pro Tyr Asn Asp Leu Thr Lys
65                  70                  75                  80

Tyr Ser Gln Lys Phe Gln Gly Arg Val Thr Ile Thr Arg Asp Lys Ser
                85                  90                  95

Ala Ser Thr Ala Tyr Met Glu Leu Ser Ser Leu Arg Ser Glu Asp Thr
            100                 105                 110

Ala Val Tyr Tyr Cys Thr Arg Trp Asp Trp Asp Gly Phe Phe Asp Pro
        115                 120                 125

Trp Gly Gln Gly Thr Thr Val Thr Val Ser Ser Gly Gly Gly Gly Ser
130                 135                 140

Gly Gly Gly Gly Ser Gly Gly Gly Ser Glu Ile Val Met Thr Gln
145                 150                 155                 160

Ser Pro Ala Thr Leu Ser Val Ser Pro Gly Glu Arg Ala Ser Ile Ser
                165                 170                 175

Cys Arg Ala Ser Gln Ser Leu Val His Ser Asn Gly Asn Thr His Leu
            180                 185                 190

His Trp Tyr Gln Gln Arg Pro Gly Gln Ala Pro Arg Leu Leu Ile Tyr
        195                 200                 205

Ser Val Ser Asn Arg Phe Ser Glu Val Pro Ala Arg Phe Ser Gly Ser
        210                 215                 220

Gly Ser Gly Thr Asp Phe Thr Leu Thr Ile Ser Ser Val Glu Ser Glu
225                 230                 235                 240

Asp Phe Ala Val Tyr Tyr Cys Ser Gln Thr Ser His Ile Pro Tyr Thr
                245                 250                 255

Phe Gly Gly Gly Thr Lys Leu Glu Ile Lys Ser Ala Ala Ala Phe Val
            260                 265                 270

Pro Val Phe Leu Pro Ala Lys Pro Thr Thr Thr Pro Ala Pro Arg Pro
        275                 280                 285

Pro Thr Pro Ala Pro Thr Ile Ala Ser Gln Pro Leu Ser Leu Arg Pro
    290                 295                 300

Glu Ala Cys Arg Pro Ala Ala Gly Gly Ala Val His Thr Arg Gly Leu
305                 310                 315                 320
```

Asp Phe Ala Cys Asp Ile Tyr Ile Trp Ala Pro Leu Ala Gly Thr Cys
                325                 330                 335

Gly Val Leu Leu Leu Ser Leu Val Ile Thr Leu Tyr Cys Asn His Arg
            340                 345                 350

Asn Arg Lys Arg Gly Arg Lys Lys Leu Leu Tyr Ile Phe Lys Gln Pro
        355                 360                 365

Phe Met Arg Pro Val Gln Thr Thr Gln Glu Glu Asp Gly Cys Ser Cys
    370                 375                 380

Arg Phe Pro Glu Glu Glu Glu Gly Gly Cys Glu Leu Arg Val Lys Phe
385                 390                 395                 400

Ser Arg Ser Ala Asp Ala Pro Ala Tyr Gln Gln Gly Gln Asn Gln Leu
                405                 410                 415

Tyr Asn Glu Leu Asn Leu Gly Arg Arg Glu Glu Tyr Asp Val Leu Asp
            420                 425                 430

Lys Arg Arg Gly Arg Asp Pro Glu Met Gly Gly Lys Pro Arg Arg Lys
        435                 440                 445

Asn Pro Gln Glu Gly Leu Tyr Asn Glu Leu Gln Lys Asp Lys Met Ala
    450                 455                 460

Glu Ala Tyr Ser Glu Ile Gly Met Lys Gly Glu Arg Arg Arg Gly Lys
465                 470                 475                 480

Gly His Asp Gly Leu Tyr Gln Gly Leu Ser Thr Ala Thr Lys Asp Thr
                485                 490                 495

Tyr Asp Ala Leu His Met Gln Ala Leu Pro Pro Arg
            500                 505

<210> SEQ ID NO 75
<211> LENGTH: 1500
<212> TYPE: DNA
<213> ORGANISM: Artificial Sequence
<220> FEATURE:
<223> OTHER INFORMATION: Synthetic

<400> SEQUENCE: 75
atgtctcgct ccgttgcctt agctgtgctc gcgctactct ctctttctgg attagaggct      60
gtcatggcgc cccgaaccct cttcctgggt ggaggcggtt caggcggagg tggctctggc     120
ggtggcggat cgatccagcg tactccaaag attcaggttt actcacgtca tccagcagag     180 aatgaaagt caaatttcct gaattgctat gtgtctgggt tcatccatc cgacattgaa       240 gttgacttac tgaagaatgg agagagaatt gaaaaagtgg agcattcaga cttgtctttc     300
agcaaggact ggtctttcta tctcttgtac tacactgaat tcacccccac tgaaaaagat     360
gagtatgcct gccgtgtgaa ccatgtgact tgtcacagc caagatagt taagtgggat       420 cgagacatgg gtggtggtgg ttctggtggt ggtggttctg gcggcggcgg ctccggtggt     480
ggtggatccg gctcccactc cttgaagtat tccacactt ccgtgtcccg gcccggccgc     540
ggggagcccc gcttcatctc tgtgggctac gtggacgaca cccagttcgt gcgcttcgac     600
aacgacgccg cgagtccgag gatggtgccg cgggcgccgt ggatgagca gagggggtca     660 gagtattggg accgggagac acggagcgcc aggacaccg cacagatttt ccgagtgaat     720
ctgcggacgc tgcgcggcta ctacaatcag agcgaggcc ggtctcacac cctgcagtgg     780
atgcatggct gcgagctggg gcccgacggg cgcttcctcc gcgggtatga acagttcgcc     840
tacgacggca aggattatct cacccctgaat gaggacctgc gctcctggac gcgggtggac     900
acggcggctc agatctccga gcaaaagtca aatgatgcct ctgaggcgga gcaccagaga     960
gcctacctgg aagacacatg cgtggagtgg ctccacaaat acctggagaa ggggaaggag    1020

```
acgctgcttc acctggagcc cccaaagaca cacgtgactc accacccat ctctgaccat    1080 gaggccaccc tgaggtgctg ggccctgggc ttctaccctg cggagatcac actgacctgg    1140
cagcaggatg gggagggcca tacccaggac acggagctcg tggagaccag gcctgcaggg    1200
gatggaacct tccagaagtg ggcagctgtg gtggtgcctt ctggagagga gcagagatac    1260
acgtgccatg tgcagcatga ggggctaccc gagcccgtca ccctgagatg aagccggct    1320 tcccagccca ccatccccat cgtgggcatc attgctggcc tggttctcct tggatctgtg    1380
gtctctggag ctgtggttgc tgctgtgata tggaggaaga agagctcagg tggaaaagga    1440
gggagctact ctaaggctga gtggagcgac agtgcccagg ggtctgagtc tcacagcttg    1500
```

<210> SEQ ID NO 76
<211> LENGTH: 1251
<212> TYPE: DNA
<213> ORGANISM: Artificial Sequence
<220> FEATURE:
<223> OTHER INFORMATION: Synthetic

<400> SEQUENCE: 76

```
atggactgga cctggatcct gttcctggtg gccgccgcca ccagggtgca cagcggcatt      60
catgtcttca ttttgggctg tttcagtgca gggcttccta aaacagaagc caactgggtg     120
aatgtaataa gtgatttgaa aaaaattgaa gatcttattc aatctatgca tattgatgct     180
actttatata cggaaagtga tgttcacccc agttgcaaag taacagcaat gaagtgcttt     240
ctcttggagt tacaagttat ttcacttgag tccggagatg caagtattca tgatacagta     300
gaaaatctga tcatcctagc aaacaacagt ttgtcttcta atgggaatgt aacagaatct     360
ggatgcaaag aatgtgagga actggaggaa aaaaatatta agaatttttt gcagagtttt     420
gtacatattg tccaaatgtt catcaacact tctagcggcg gcggcagcgg cggcggcggc     480
agcggcggcg gcggcagcgg cggcggcggc agcggcggcg gcagcctgca gatcacgtgc     540
cctcccccca tgtccgtgga acacgcagac atctgggtca agagctacag cttgtactcc     600
agggagcggt acatttgtaa ctctggtttc aagcgtaaag ccggcacgtc cagcctgacg     660
gagtgcgtgt tgaacaaggc cacgaatgtc gcccactgga caaccccag tctcaaatgc     720 attagagacc ctgccctggt tcaccaaagg ccagcgccac cctccacagt aacgacggca     780
ggggtgaccc cacagccaga gagcctctcc ccttctggaa aagagcccgc agcttcatct     840
cccagctcaa caacacagc ggccacaaca gcagctattg tcccgggctc ccagctgatg     900
ccttcaaaat caccttccac aggaaccaca gagataagca gtcatgagtc ctcccacggc     960
accccctctc agacaacagc caagaactgg gaactcacag catccgcctc ccaccagccg    1020
ccaggtgtgt atccaggg ccacagcgac accactgtgg ctatctccac gtccactgtc    1080
ctgctgtgtg ggctgagcgc tgtgtctctc ctggcatgct acctcaagtc aaggcaaact    1140
cccccgctgg ccagcgttga aatggaagcc atggaggctc tgccggtgac ttgggggacc    1200
agcagcagag atgaagactt ggaaaactgc tctcaccacc taggaagcgg a              1251
```

<210> SEQ ID NO 77
<211> LENGTH: 2808
<212> TYPE: DNA
<213> ORGANISM: Artificial Sequence
<220> FEATURE:
<223> OTHER INFORMATION: Synthetic

<400> SEQUENCE: 77

```
atggactgga cctggatcct gttcctggtg gccgccgcca ccagggtgca cagcggcatt      60
catgtcttca ttttgggctg tttcagtgca gggcttccta aaacagaagc caactgggtg     120
aatgtaataa gtgatttgaa aaaaattgaa gatcttattc aatctatgca tattgatgct     180
actttatata cggaaagtga tgttcacccc agttgcaaag taacagcaat gaagtgcttt     240
ctcttggagt tacaagttat ttcacttgag tccggagatg caagtattca tgatacagta     300
gaaaatctga tcatcctagc aaacaacagt ttgtcttcta atgggaatgt aacagaatct     360
ggatgcaaag aatgtgagga actggaggaa aaaatatta aagaattttt gcagagtttt     420
gtacatattg tccaaatgtt catcaacact tctagcggcg gcggcagcgg cggcggcggc     480
agcggcggcg gcggcagcgg cggcggcggc agcggcggcg gcagcctgca gatcacgtgc     540
cctccccca tgtccgtgga acacgcagac atctgggtca agagctacag cttgtactcc     600
agggagcggt acatttgtaa ctctggtttc aagcgtaaag ccggcacgtc cagcctgacg     660
gagtgcgtgt tgaacaaggc cacgaatgtc gcccactgga caacccccag tctcaaatgc     720
attagagacc ctgccctggt tcaccaaagg ccagcgccac cctccacagt aacgacggca     780
ggggtgaccc cacagccaga gagcctctcc ccttctggaa aagagcccgc agcttcatct     840
cccagctcaa caacacagc ggccacaaca gcagctattg tccgggctc ccagctgatg     900
ccttcaaaat caccttccac aggaaccaca gagataagca gtcatgagtc ctcccacggc     960
accccctctc agacaacagc caagaactgg gaactcacag catccgcctc ccaccagccg    1020
ccaggtgtgt atccacaggg ccacagcgac accactgtgg ctatctccac gtccactgtc    1080
ctgctgtgtg ggctgagcgc tgtgtctctc ctggcatgct acctcaagtc aaggcaaact    1140
ccccgctgg ccagcgttga atggaagcc atggaggctc tgccggtgac ttggggacc    1200
agcagcagag atgaagactt ggaaaactgc tctcaccacc taggaagcgg agctactaac    1260
ttcagcctgc tgaagcaggc tggagacgtg gaggagaacc ctggacctat gtctcgctcc    1320
gttgccttag ctgtgctcgc gctactctct ctttctggat tagaggctgt catggcgccc    1380
cgaacctct tcctgggtgg aggcggttca ggcgaggtg ctctggcgg tggcggatcg    1440
atccagcgta ctccaaagat tcaggtttac tcacgtcatc cagcagagaa tggaaagtca    1500
aatttcctga attgctatgt gtctgggttt catccatccg acattgaagt tgacttactg    1560
aagaatggag agagaattga aaaagtggag cattcagact tgtctttcag caaggactgg    1620
tctttctatc tcttgtacta cactgaattc acccccactg aaaaagatga gtatgcctgc    1680
cgtgtgaacc atgtgacttt gtcacagccc aagatagtta agtgggatcg agacatgggt    1740
ggtggtggtt ctggtggtgg tggttctggc ggcggcggct ccgtggtgg tggatccggc    1800
tcccactcct tgaagtattt ccacactttcc gtgtcccggc ccggccgcgg ggagccccgc    1860
ttcatctctg tgggctacgt ggacgacacc cagttcgtgc gcttcgacaa cgacgccgcg    1920
agtccgagga tggtgccgcg ggcgccgtgg atggagcagg aggggtcaga gtattgggac    1980
cgggagacac ggagcgccag ggacaccgca cagattttcc gagtgaatct gcggacgctg    2040
cgcggctact acaatcagag cgaggccggg tctcacaccc tgcagtggat gcatggctgc    2100
gagctggggc ccgacgggcg cttcctccgc gggtatgaac agttcgccta cgacggcaag    2160
gattatctca ccctgaatga ggacctgcgc tcctggaccg cggtgacac ggcggctcag    2220
atctccgagc aaaagtcaaa tgatgcctct gaggcggagc accagagagc ctacctggaa    2280
```

```
gacacatgcg tggagtggct ccacaaatac ctggagaagg ggaaggagac gctgcttcac    2340
ctggagcccc caaagacaca cgtgactcac caccccatct ctgaccatga ggccaccctg    2400
aggtgctggg ccctgggctt ctaccctgcg gagatcacac tgacctggca gcaggatggg    2460
gagggccata cccaggacac ggagctcgtg gagaccaggc ctgcagggga tggaaccttc    2520
cagaagtggg cagctgtggt ggtgccttct ggagaggagc agagatacac gtgccatgtg    2580
cagcatgagg ggctacccga gcccgtcacc ctgagatgga agccggcttc ccagcccacc    2640
atccccatcg tgggcatcat tgctggcctg gttctccttg gatctgtggt ctctggagct    2700
gtggttgctg ctgtgatatg gaggaagaag agctcaggtg gaaaaggagg gagctactct    2760
aaggctgagt ggagcgacag tgcccagggg tctgagtctc acagcttg               2808
```

<210> SEQ ID NO 78
<211> LENGTH: 20
<212> TYPE: DNA
<213> ORGANISM: Homo sapiens

<400> SEQUENCE: 78
gctactctct ctttctggcc                                                20

<210> SEQ ID NO 79
<211> LENGTH: 20
<212> TYPE: DNA
<213> ORGANISM: Homo sapiens

<400> SEQUENCE: 79
cgcgagcaca gctaaggcca                                                20

<210> SEQ ID NO 80
<211> LENGTH: 20
<212> TYPE: DNA
<213> ORGANISM: Homo sapiens

<400> SEQUENCE: 80
ctagggactg cacagtcaat                                                20

<210> SEQ ID NO 81
<211> LENGTH: 20
<212> TYPE: DNA
<213> ORGANISM: Homo sapiens

<400> SEQUENCE: 81
tcgccgctgc cgcggggaca                                                20

<210> SEQ ID NO 82
<211> LENGTH: 20
<212> TYPE: DNA
<213> ORGANISM: Homo sapiens

<400> SEQUENCE: 82
gtccgctcca cagccagcaa                                                20

<210> SEQ ID NO 83
<211> LENGTH: 20
<212> TYPE: DNA
<213> ORGANISM: Homo sapiens

<400> SEQUENCE: 83
gtccgctcca cagccagcaa                                                20

```
<210> SEQ ID NO 84
<211> LENGTH: 20
<212> TYPE: DNA
<213> ORGANISM: Homo sapiens

<400> SEQUENCE: 84
gttccaggga cggggcccac                                                   20

<210> SEQ ID NO 85
<211> LENGTH: 20
<212> TYPE: DNA
<213> ORGANISM: Homo sapiens

<400> SEQUENCE: 85
tcgggcctcg ctggccgtaa                                                   20

<210> SEQ ID NO 86
<211> LENGTH: 20
<212> TYPE: DNA
<213> ORGANISM: Homo sapiens

<400> SEQUENCE: 86
cgtactaaga acgtgccttc                                                   20

<210> SEQ ID NO 87
<211> LENGTH: 20
<212> TYPE: DNA
<213> ORGANISM: Homo sapiens

<400> SEQUENCE: 87
gggttccatt acggccagcg                                                   20

<210> SEQ ID NO 88
<211> LENGTH: 20
<212> TYPE: DNA
<213> ORGANISM: Homo sapiens

<400> SEQUENCE: 88
caggtgttgt cgggcctcgc                                                   20

<210> SEQ ID NO 89
<211> LENGTH: 20
<212> TYPE: DNA
<213> ORGANISM: Homo sapiens

<400> SEQUENCE: 89
tactcaatgc gtacattggt                                                   20

<210> SEQ ID NO 90
<211> LENGTH: 20
<212> TYPE: DNA
<213> ORGANISM: Homo sapiens

<400> SEQUENCE: 90
aaggctgacc acatccggaa                                                   20

<210> SEQ ID NO 91
<211> LENGTH: 20
<212> TYPE: DNA
<213> ORGANISM: Homo sapiens

<400> SEQUENCE: 91
tacattggtg gggccacgag                                                   20
```

```
<210> SEQ ID NO 92
<211> LENGTH: 20
<212> TYPE: DNA
<213> ORGANISM: Homo sapiens

<400> SEQUENCE: 92
ctgtcagtga aaaccactcg                                                    20

<210> SEQ ID NO 93
<211> LENGTH: 20
<212> TYPE: DNA
<213> ORGANISM: Homo sapiens

<400> SEQUENCE: 93
ggtcatcgat gggagcaacg                                                    20

<210> SEQ ID NO 94
<211> LENGTH: 20
<212> TYPE: DNA
<213> ORGANISM: Homo sapiens

<400> SEQUENCE: 94
caccaccccg cgggactaga                                                    20

<210> SEQ ID NO 95
<211> LENGTH: 20
<212> TYPE: DNA
<213> ORGANISM: Homo sapiens

<400> SEQUENCE: 95
ggtctggcgc tcccgctcgg                                                    20

<210> SEQ ID NO 96
<211> LENGTH: 20
<212> TYPE: DNA
<213> ORGANISM: Homo sapiens

<400> SEQUENCE: 96
ccaccacccc gcgggactag                                                    20

<210> SEQ ID NO 97
<211> LENGTH: 20
<212> TYPE: DNA
<213> ORGANISM: Homo sapiens

<400> SEQUENCE: 97
ttaggggtgc caccaccccg                                                    20

<210> SEQ ID NO 98
<211> LENGTH: 20
<212> TYPE: DNA
<213> ORGANISM: Homo sapiens

<400> SEQUENCE: 98
ttcacaccat cacgacgcgt                                                    20

<210> SEQ ID NO 99
<211> LENGTH: 20
<212> TYPE: DNA
<213> ORGANISM: Homo sapiens

<400> SEQUENCE: 99
acaccatcac gacgcgtggg                                                    20
```

<210> SEQ ID NO 100
<211> LENGTH: 20
<212> TYPE: DNA
<213> ORGANISM: Homo sapiens

<400> SEQUENCE: 100
ctacgagtct gacgggatcg                                          20

<210> SEQ ID NO 101
<211> LENGTH: 20
<212> TYPE: DNA
<213> ORGANISM: Homo sapiens

<400> SEQUENCE: 101
acgacgcgtg ggtggcaagc                                          20

<210> SEQ ID NO 102
<211> LENGTH: 111
<212> TYPE: PRT
<213> ORGANISM: Artificial Sequence
<220> FEATURE:
<223> OTHER INFORMATION: Synthetic

<400> SEQUENCE: 102

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Trp Thr Phe Gly Gly Gly Thr Lys Leu Glu Ile Lys
            100                 105                 110

<210> SEQ ID NO 103
<211> LENGTH: 117
<212> TYPE: PRT
<213> ORGANISM: Artificial Sequence
<220> FEATURE:
<223> OTHER INFORMATION: Synthetic

<400> SEQUENCE: 103

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Thr Trp Val Lys Gln Lys Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Lys Gly Lys Ala Thr Leu Thr Val Asp Thr Ser Ser Ser Thr Ala Phe
65                  70                  75                  80

Met Gln Leu Ser Ser Leu Thr Ser Glu Asp Thr Ala Val Tyr Phe Cys
                85                  90                  95

Ala Asn Tyr Gly Asn Tyr Trp Phe Ala Tyr Trp Gly Gln Gly Thr Gln
            100                 105                 110

Val Thr Val Ser Ala
        115

<210> SEQ ID NO 104
<211> LENGTH: 107
<212> TYPE: PRT
<213> ORGANISM: Artificial Sequence
<220> FEATURE:
<223> OTHER INFORMATION: Synthetic

<400> SEQUENCE: 104

Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Thr Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Ser Tyr Pro Ile
                85                  90                  95

Thr Phe Gly Gln Gly Thr Arg Leu Glu Ile Lys
            100                 105

<210> SEQ ID NO 105
<211> LENGTH: 112
<212> TYPE: PRT
<213> ORGANISM: Artificial Sequence
<220> FEATURE:
<223> OTHER INFORMATION: Synthetic

<400> SEQUENCE: 105

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Ala Tyr
            20                  25                  30

Tyr Trp Ser Trp Ile Arg Gln Pro Pro Gly Lys Gly Leu Glu Trp Ile
        35                  40                  45

Gly Asp Ile Asn His Gly Gly Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Ala
                85                  90                  95

Ser Leu Thr Ala Tyr Trp Gly Gln Gly Ser Leu Val Thr Val Ser Ser
            100                 105                 110

<210> SEQ ID NO 106
<211> LENGTH: 729
<212> TYPE: DNA
<213> ORGANISM: Artificial Sequence
<220> FEATURE:
<223> OTHER INFORMATION: Synthetic

<400> SEQUENCE: 106

```
cagatccagc tgcagcagag cggccccgag gtggtgaagc ccggcgccag cgtgaagatc      60
agctgcaagg ccagcggcta caccttcacc gactactaca tcacctgggt gaagcagaag     120
cccggccagg gcctggagtg gatcggctgg atctaccccg gcagcggcaa caccaagtac     180
aacgagaagt tcaagggcaa ggccaccctg accgtggaca ccagcagcag caccgccttc     240
atgcagctga gcagcctgac cagcgaggac accgccgtgt acttctgcgc caactacggc     300
aactactggt tcgcctactg gggccagggc acccaggtga ccgtgagcgc cggcggcggc     360
ggcagcggcg gcggcggcag cggcggcggc ggcagcgaca tcgtgctgac ccagagcccc     420
gccagcctgg ccgtgagcct gggccagaga gccaccatca gctgcaaggc cagccagagc     480
gtggacttcg acgcgacag ctacatgaac tggtaccagc agaagcccgg ccagccccc      540
aaggtgctga tctacgccgc cagcaacctg gagagcggca tccccgccag attcagcggc     600
agcggcagcg gcaccgactt caccctgaac atccaccccg tggaggagga ggacgccgcc     660
acctactact gccagcagag caacgaggac ccctggacct tcggcggcgg caccaagctg     720
gagatcaag                                                             729
```

<210> SEQ ID NO 107
<211> LENGTH: 120
<212> TYPE: DNA
<213> ORGANISM: Artificial Sequence
<220> FEATURE:
<223> OTHER INFORMATION: Synthetic

<400> SEQUENCE: 107

```
agcaagagaa gcagactgct gcacagcgac tacatgaaca tgacccccag aagacccggc      60
cccaccagaa agcactacca gccctacgcc cccccagag acttcgccgc ctacagaagc     120
```

<210> SEQ ID NO 108
<211> LENGTH: 1512
<212> TYPE: DNA
<213> ORGANISM: Artificial Sequence
<220> FEATURE:
<223> OTHER INFORMATION: Synthetic

<400> SEQUENCE: 108

```
atggcgcttc cggtgacagc actgctcctc cccttggcgc tgttgctcca cgcagcaagg      60
ccgcagatcc agctgcagca gagcggcccc gaggtggtga agcccggcgc cagcgtgaag     120
atcagctgca aggccagcgg ctacaccttc accgactact acatcacctg ggtgaagcag     180
aagcccggcc agggcctgga gtggatcggc tggatctacc ccggcagcgg caacaccaag     240
tacaacgaga agttcaaggg caaggccacc ctgaccgtgg acaccagcag cagcaccgcc     300
ttcatgcagc tgagcagcct gaccagcgag gacaccgccg tgtacttctg cgccaactac     360
ggcaactact ggttcgccta ctggggccag ggcacccagg tgaccgtgag cgccggcggc     420
ggcggcagcg gcggcggcgg cagcggcggc ggcggcagcg acatcgtgct gacccagagc     480
cccgccagcc tggccgtgag cctgggccag agagccacca tcagctgcaa ggccagccag     540
agcgtggact tcgacggcga cagctacatg aactggtacc agcagaagcc cggccagccc     600
cccaaggtgc tgatctacgc cgccagcaac ctggagagcg gcatccccgc cagattcagc     660
ggcagcggca gcggcaccga cttcaccctg aacatccacc ccgtggagga ggaggacgcc     720
gccacctact actgccagca gagcaacgag gacccctgga ccttcggcgg cggcaccaag     780
```

```
ctggagatca agagcgccgc cgccttcgtg cccgtgttcc tgcccgccaa gcccaccacc    840
acccccgccc ccagacccccc cacccccgcc cccaccatcg ccagccagcc cctgagcctg    900
agacccgagg cctgcagacc cgccgccggc ggcgccgtgc acaccagagg cctggacttc    960
gcctgcgaca tctacatctg gccccccctg ccggcacct cgggcgtgct gctgctgagc    1020
ctggtgatca ccctgtactg caaccacaga aacagaagca agagaagcag actgctgcac    1080
agcgactaca tgaacatgac ccccagaaga cccggcccca ccagaaagca ctaccagccc    1140 tacgccccccc ccagagactt cgccgcctac agaagcagag tgaagttcag cagaagcgcc    1200
gacgcccccg cctaccagca gggccagaac cagctgtaca cgagctgaa cctgggcaga    1260 agagaggagt acgacgtgct ggacaagaga agaggcagag accccgagat gggcggcaag    1320
cccagaagaa agaaccccca ggagggcctg tacaacgagc tgcagaagga caagatggcc    1380
gaggcctaca gcgagatcgg catgaagggc gagagaagaa gaggcaaggg ccacgacggc    1440
ctgtaccagg gcctgagcac cgccaccaag gacacctacg acgccctgca catgcaggcc    1500 ctgccccccca ga                                                         1512
```

<210> SEQ ID NO 109
<211> LENGTH: 483
<212> TYPE: PRT
<213> ORGANISM: Artificial Sequence
<220> FEATURE:
<223> OTHER INFORMATION: Synthetic

<400> SEQUENCE: 109

```
Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Thr Trp Val Lys Gln Lys Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Lys Gly Lys Ala Thr Leu Thr Val Asp Thr Ser Ser Ser Thr Ala Phe
65                  70                  75                  80

Met Gln Leu Ser Ser Leu Thr Ser Glu Asp Thr Ala Val Tyr Phe Cys
                85                  90                  95

Ala Asn Tyr Gly Asn Tyr Trp Phe Ala Tyr Trp Gly Gln Gly Thr Gln
            100                 105                 110

Val Thr Val Ser Ala Gly Gly Gly Gly Ser Gly Gly Gly Gly Ser Gly
        115                 120                 125

Gly Gly Gly Ser Asp Ile Val Leu Thr Gln Ser Pro Ala Ser Leu Ala
    130                 135                 140

Val Ser Leu Gly Gln Arg Ala Thr Ile Ser Cys Lys Ala Ser Gln Ser
145                 150                 155                 160

Val Asp Phe Asp Gly Asp Ser Tyr Met Asn Trp Tyr Gln Gln Lys Pro
                165                 170                 175

Gly Gln Pro Pro Lys Val Leu Ile Tyr Ala Ala Ser Asn Leu Glu Ser
            180                 185                 190

Gly Ile Pro Ala Arg Phe Ser Gly Ser Gly Ser Gly Thr Asp Phe Thr
        195                 200                 205

Leu Asn Ile His Pro Val Glu Glu Glu Asp Ala Ala Thr Tyr Tyr Cys
    210                 215                 220
```

Gln Gln Ser Asn Glu Asp Pro Trp Thr Phe Gly Gly Thr Lys Leu
225                 230                 235                 240

Glu Ile Lys Ser Ala Ala Phe Val Pro Val Phe Leu Pro Ala Lys
            245                 250                 255

Pro Thr Thr Thr Pro Ala Pro Arg Pro Pro Thr Pro Ala Pro Thr Ile
        260                 265                 270

Ala Ser Gln Pro Leu Ser Leu Arg Pro Glu Ala Cys Arg Pro Ala Ala
        275                 280                 285

Gly Gly Ala Val His Thr Arg Gly Leu Asp Phe Ala Cys Asp Ile Tyr
        290                 295                 300

Ile Trp Ala Pro Leu Ala Gly Thr Cys Gly Val Leu Leu Leu Ser Leu
305                 310                 315                 320

Val Ile Thr Leu Tyr Cys Asn His Arg Asn Arg Ser Lys Arg Ser Arg
                325                 330                 335

Leu Leu His Ser Asp Tyr Met Asn Met Thr Pro Arg Arg Pro Gly Pro
            340                 345                 350

Thr Arg Lys His Tyr Gln Pro Tyr Ala Pro Pro Arg Asp Phe Ala Ala
        355                 360                 365

Tyr Arg Ser Arg Val Lys Phe Ser Arg Ser Ala Asp Ala Pro Ala Tyr
370                 375                 380

Gln Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
                405                 410                 415

Gly Gly Lys Pro Arg Arg Lys Asn Pro Gln Glu Gly Leu Tyr Asn Glu
            420                 425                 430

Leu Gln Lys Asp Lys Met Ala Glu Ala Tyr Ser Glu Ile Gly Met Lys
        435                 440                 445

Gly Glu Arg Arg Arg Gly Lys Gly His Asp Gly Leu Tyr Gln Gly Leu
    450                 455                 460

Ser Thr Ala Thr Lys Asp Thr Tyr Asp Ala Leu His Met Gln Ala Leu
465                 470                 475                 480

Pro Pro Arg

<210> SEQ ID NO 110
<211> LENGTH: 11265
<212> TYPE: DNA
<213> ORGANISM: Artificial Sequence
<220> FEATURE:
<223> OTHER INFORMATION: Synthetic

<400> SEQUENCE: 110
agaatctgct cagactcctt cagtttacat attaggaaac tgaggcacag aaaggagcag      60
agacttgctc aagtccaccc aaagcagtag agcattgtgg ttaaatgcag gacttcagtc     120
agactgtctg ggtcaaatc ctggttccac ttggacatgg gtttccttac ataaatcact      180
tcacctctct gagcctcagt tttctcatat gcaaagtgag gataataata ataccttcct     240
tacatggtta ctgatatgag tattaaatgt gccagctcat gtgcctggcg tataggaggt     300
gctttataaa ccttagctgt taccactcat ggcattgcca aatgtgggac gggtctcctg     360
actctctggt gtgagattga tggaatccac actttccagt tccctttttct acctcctggg   420 tatcttctca tatggttgta agttccttgg aggaagggaa tgtggcttgc tctctccacc    480
acgctgagca tataagaggt gctgaatgag cgcttttatt cactcctctc atccccagcc    540

```
ctcaccagct gggagttgtt gtaggtgtca attttctgcc tctttccaac accctgtgag    600
gtgactgagc attgtcttcc ctcccaggca gctcacagtg taagcttgtg gacgatatcg    660
aattcgcacg acattgatta ttgactagtt attaatagta atcaattacg gggtcattag    720
ttcatagccc atatatggag ttccgcgtta cataacttac ggtaaatggc ccgcctggct    780
gaccgcccaa cgaccccgc ccattgacgt caataatgac gtatgttccc atagtaacgc    840
caatagggac tttccattga cgtcaatggg tggactattt acggtaaact gcccacttgg    900
cagtacatca agtgtatcat atgccaagta cgccccctat tgacgtcaat gacggtaaat    960
ggcccgcctg gcattatgcc cagtacatga ccttatggga ctttcctact tggcagtaca   1020
tctacgtatt agtcatcgct attaccatgg gtcgaggtga gccccacgtt ctgcttcact   1080
ctccccatct cccccccctc cccaccccca attttgtatt tatttatttt ttaattattt   1140
tgtgcagcga tgggggcggg ggggggggg gcgcgcgcca ggcggggcgg ggcggggcga   1200
ggggcggggc gggcgaggc ggagaggtgc ggcggcagcc aatcagagcg gcgcgctccg   1260
aaagtttcct tttatggcga ggcggcggcg gcggcggccc tataaaaagc gaagcgcgcg   1320
gcgggcggga gtcgctgcgt tgccttcgcc ccgtgccccg ctccgcgccg cctcgcgccg   1380
cccgccccgg ctctgactga ccgcgttact cccacaggtg agcgggcggg acggcccttc   1440
tcctccgggc tgtaattagc gcttggttta atgacggctc gtttcttttc tgtggctgcg   1500
tgaaagcctt aaagggctcc gggagggccc tttgtgcggg gggagcggc tcggggggtg   1560 cgtgcgtgtg tgtgtgcgtg gggagcgccg cgtgcggccc gcgctgcccg gcggctgtga   1620
gcgctgcggc gcggcgcgg ggctttgtgc gctccgcgtg tgcgcgaggg gagcgcggcc   1680
gggggcggtg ccccgcggtg cggggggct gcgaggggaa caaaggctgc gtgcggggtg   1740
tgtgcgtggg gggtgagca gggggtgtgg gcgcggcggt cgggctgtaa ccccccctg   1800 caccccctc cccgagttgc tgagcacggc ccggcttcgg gtgcggggct ccgtgcgggg   1860 cgtgcgcgg ggctcgccgt gccggcggg gggtggcggc aggtggggt gccgggcggg   1920 gcggggccgc ctcgggccgg ggagggctcg ggggagggc gcggcggccc cggagcgccg   1980
gcggctgtcg aggcgcggcg agccgcagcc attgcctttt atggtaatcg tgcgagaggg   2040
cgcagggact ccctttgtcc caaatctggc ggagccgaaa tctgggaggc gccgccgcac   2100 ccctctagc gggcgcgggc gaagcggtgc ggcgccggca ggaaggaaat gggcgggag   2160 ggccttcgtg cgtcgccgcg ccgccgtccc cttctccatc tccagcctcg ggctgccgc   2220 agggggacgg ctgccttcgg gggggacggg gcagggcggg gttcggcttc tggcgtgtga   2280
ccggcggctc tagagcctct gctaaccatg ttcatgcctt cttctttttc ctacaggggg   2340
gatccgttta tctgcagaat tcgcccttga cgtcgccacc atggcgcttc cggtgacagc   2400
actgctcctc cccttggcgc tgttgctcca cgcagcaagg ccgcagatcc agctgcagca   2460
gagcggcccc gaggtggtga agccggcgc cagcgtgaag atcagctgca aggccagcgg   2520
ctacaccttc accgactact acatcacctg ggtgaagcag aagcccggcc agggcctgga   2580
gtggatcggc tggatctacc ccggcagcgg caacaccaag tacaacgaga agttcaaggg   2640
caaggccacc ctgaccgtgg acaccagcag cagcaccgcc ttcatgcagc tgagcagcct   2700
gaccagcgag gacaccgccg tgtacttctg cgccaactac ggcaactact ggttcgccta   2760
ctggggccag ggcacccagg tgaccgtgag cgcggcggc ggcggcagcg gcggcggcgg   2820
cagcggcggc ggcggcagcg acatcgtgct gacccagagc cccgccagcc tggccgtgag   2880
cctgggccag agagccacca tcagctgcaa ggccagccag agcgtggact cgacggcga   2940
```

-continued

```
cagctacatg aactggtacc agcagaagcc cggccagccc cccaaggtgc tgatctacgc    3000
cgccagcaac ctggagagcg gcatccccgc cagattcagc ggcagcggca gcggcaccga    3060
cttcaccctg aacatccacc ccgtggagga ggaggacgcc gccacctact actgccagca    3120
gagcaacgag gaccccctgga ccttcggcgg cggcaccaag ctggagatca agagcgccgc    3180
cgccttcgtg cccgtgttcc tgcccgccaa gcccaccacc accccgccc ccagaccccc    3240
cacccccgcc cccaccatcg ccagccagcc cctgagcctg agacccgagg cctgcagacc    3300
cgccgccggc ggcgccgtgc acaccagagg cctggacttc gcctgcgaca tctacatctg    3360
ggcccccctg gccggcacct gcggcgtgct gctgctgagc ctggtgatca ccctgtactg    3420
caaccacaga aacagaagca agagaagcag actgctgcac agcgactaca tgaacatgac    3480
ccccagaaga cccggcccca ccagaaagca ctaccagccc tacgccccc ccagagactt    3540
cgccgcctac agaagcagag tgaagttcag cagaagcgcc gacgccccg cctaccagca    3600
gggccagaac cagctgtaca acgagctgaa cctgggcaga agagaggagt acgacgtgct    3660
ggacaagaga gaggcagag acccccgagat gggcggcaag cccagaagaa agaacccca    3720
ggagggcctg tacaacgagc tgcagaagga caagatggcc gaggcctaca gcgagatcgg    3780
catgaagggc gagagaagaa gaggcaaggg ccacgacggc ctgtaccagg cctgagcac    3840
cgccaccaag gacacctacg acgccctgca catgcaggcc ctgccccca gaggaagcgg    3900
agctactaac ttcagcctgc tgaagcaggc tggagacgtg gaggagaacc ctggacctat    3960
gtctcgctcc gttgccttag ctgtgctcgc gctactctct cttctggat tagaggctgt    4020
catggcgccc cgaaccctct tcctgggtgg aggcggttca ggcggaggtg gctctggcgg    4080
tggcggatcg atccagcgta ctccaaagat tcaggtttac tcacgtcatc cagcagagaa    4140
tggaaagtca aatttcctga attgctatgt gtctgggttt catccatccg acattgaagt    4200
tgacttactg aagaatggag agagaattga aaaagtggag cattcagact tgtctttcag    4260
caaggactgg tctttctatc tcttgtacta cactgaattc accccactg aaaaagatga    4320
gtatgcctgc cgtgtgaacc atgtgacttt gtcacagccc aagatagtta agtgggatcg    4380
agacatgggt ggtggtggtt ctggtggtgg tggttctggc ggcggcggct ccggtggtgg    4440
tggatccggc tcccactcct tgaagtattt ccacacttcc gtgtcccggc ccggccgcgg    4500
ggagccccgc ttcatctctg tgggctacgt ggacgacacc cagttcgtgc gcttcgacaa    4560
cgacgccgcg agtccgagga tggtgccgcg ggcgccgtgg atggagcagg aggggtcaga    4620
gtattgggac cgggagacac ggagcgccag ggacaccgca cagattttcc gagtgaatct    4680
gcggacgctg cgcggctact acaatcagag cgaggccggg tctcacaccc tgcagtggat    4740
gcatggctgc gagctgggc cgacgggcg cttcctccgc gggtatgaac agttcgccta    4800
cgacggcaag gattatctca ccctgaatga ggacctgcgc tcctggaccg cggtggacac    4860
ggcggctcag atctccgagc aaaagtcaaa tgatgcctct gaggcggagc accagagagc    4920
ctacctggaa gacacatgcg tggagtggct ccacaaatac ctggagaagg ggaaggagac    4980
gctgcttcac ctggagcccc caaagacaca cgtgactcac caccccatct ctgaccatga    5040
ggccacccta agtgctgggg cctgggctt ctaccctgcg agatcacac tgacctggca    5100
gcaggatggg gagggccata cccaggacac ggagctcgtg agaccaggc ctgcagggga    5160
tggaaccttc cagaagtggg cagctgtggt ggtgccttct ggagaggagc agagatacac    5220
gtgccatgtg cagcatgagg ggctacccga gcccgtcacc ctgagatgga agccggcttc    5280
```

```
ccagcccacc atccccatcg tgggcatcat tgctggcctg gttctccttg gatctgtggt    5340
ctctggagct gtggttgctg ctgtgatatg gaggaagaag agctcaggtg gaaaaggagg    5400
gagctactct aaggctgagt ggagcgacag tgcccagggg tctgagtctc acagcttgta    5460
atgatagccg ctgatcagcc tcgactgtgc cttctagttg ccagccatct gttgtttgcc    5520
cctcccccgt gccttccttg accctggaag gtgccactcc cactgtcctt tcctaataaa    5580
atgaggaaat tgcatcgcat tgtctgagta ggtgtcattc tattctgggg ggtggggtgg    5640
ggcaggacag caagggggag gattgggaag acaatagcag gcatgctggg gatgcggtgg    5700
gctctatggg tcgactgacc agatggacct ggctggagaa gaagagattg agctctactc    5760
aggtgggccc tcctccctct ggtctcttcc ggtatccccc acccctcagc ttgctgtaga    5820
gacggcaatc aggggaaatt ctggtccctg ccctcccgtc agcaccacgg acagctccca    5880
cgtctgtggg acgctctctg cagatgggga tgatctccca gccctgcccc gcctctccct    5940
cgttccccac cagccctctt tccagaaatt tccttcttca tccaagggac ttttcctccc    6000
agaacccgac acagacacca tcaactgcga ccagttcagc aggctgttgt gtgacatgga    6060
aggtgatgaa gagaccaggg aggcttatgc caatatcggt gaggaagcac ctgagcccag    6120
aaaaggacaa tcaagggcaa gagttctttg ctgccacttg tcaatatcac ccattcatca    6180
tgagccacgt cagtcccctc ccacagaaat cattgcaagg gggatgcgga gcaatggctg    6240
gaggaacgga gactccaggg aagagagggg agatggaggc cagtggggga aataggcccc    6300
ttcactaatg accaccaaga aaacaaaatc tcatgtttac atcctccacc tccatttcta    6360
tacgcatttc tgcttcttgc tcttctgtcc atcctttcta caaagcccat accatacacc    6420
cctttcccct ttcctcccag ctccttagcc aagctactct agtatttgta ataactagca    6480
tttactggat actcatagta tgctcattgc tgtccggtaa ccacgtgcgg accgggctcc    6540
ggtgcccgtc agtgggcaga gcgcacatcg cccacagtcc ccgagaagtt ggggggaggg    6600
gtcggcaatt gaaccggtgc ctagagaagg tggcgcgggg taaactggga aagtgatgtc    6660
gtgtactggc tccgcctttt tcccgagggt gggggagaac cgtatataag tgcagtagtc    6720
gccgtgaacg ttcttttttcg caacgggttt gccgccagaa cacaggtaag tgccgtgtgt    6780
ggttcccgcg ggcctggcct ctttacgggt tatggcccct gcgtgccttg aattacttcc    6840
actggctgca gtacgtgatt cttgatcccg agcttcgggt tggaagtggg tgggagagtt    6900
cgaggccttg cgcttaagga gccccttcgc ctcgtgcttg agttgaggcc tggcctgggc    6960
gctggggccg ccgcgtgcga atctggtggc accttgcgc ctgtctcgct gctttcgata    7020
agtctctagc catttaaaat ttttgatgac ctgctgcgac gctttttttc tggcaagata    7080
gtcttgtaaa tgcgggccaa gatctgcaca ctggtatttc ggttttttggg gccgcgggcg    7140 gcgacggggc ccgtgcgtcc cagcgcacat gttcggcgag gcgggcctg cgagcgcggc    7200 caccgagaat cggacggggg tagtctcaag ctggccggcc tgctctggtg cctggcctcg    7260
cgccgccgtg tatcgcccg ccctgggcgg caaggctggc ccggtcggca ccagttgcgt    7320
gagcggaaag atggccgctt cccggccctg ctgcagggag ctcaaaatgg aggacgcggc    7380
gctcgggaga gcggcgggt gagtcaccca cacaaaggaa aagggccttt ccgtcctcag    7440
ccgtcgcttc atgtgactcc acggagtacc gggcgccgtc caggcacctc gattagttct    7500
cgagcttttg gagtacgtcg tctttaggtt ggggggaggg gttttatgcg atggagtttc    7560
cccacactga gtgggtggag actgaagtta ggccagcttg gcacttgatg taattctcct    7620
tggaatttgc ccttttttgag tttggatctt ggttcattct caagcctcag acagtggttc    7680
```

```
aaagttttt  tcttccattt  caggtgtcgt  gacttgacgt  cgccaccatg  aggatatttg   7740
ctgtctttat  attcatgacc  tactggcatt  tgctgaacgc  atttactgtc  acggttccca   7800
aggacctata  tgtggtagag  tatggtagca  atatgacaat  tgaatgcaaa  ttcccagtag   7860
aaaaacaatt  agacctggct  gcactaattg  tctattggga  aatggaggat  aagaacatta   7920
ttcaatttgt  gcatggagag  gaagacctga  aggttcagca  tagtagctac  agacagaggg   7980
cccggctgtt  gaaggaccag  ctctccctgg  gaaatgctgc  acttcagatc  acagatgtga   8040
aattgcagga  tgcaggggtg  taccgctgca  tgatcagcta  tggtggtgcc  gactacaagc   8100
gaattactgt  gaaagtcaat  gccccataca  acaaaatcaa  ccaaagaatt  ttggttgtgg   8160
atccagtcac  ctctgaacat  gaactgacat  gtcaggctga  gggctacccc  aaggccgaag   8220
tcatctggac  aagcagtgac  catcaagtcc  tgagtggtaa  gaccaccacc  accaattcca   8280
agagagagga  gaaactttc   aatgtgacca  gcacactgag  aatcaacaca  caactaatg    8340 agattttcta  ctgcactttt  aggagattag  atcctgagga  aaaccataca  gctgaattgg   8400
tcatcccaga  actacctctg  gcacatcctc  caaatgaaag  gactcacttg  gtaattctgg   8460
gagccatctt  attatgcctt  ggtgtagcac  tgacattcat  cttccgttta  agaaaaggga   8520
gaatgatgga  tgtgaaaaaa  tgtggcatcc  aagatacaaa  ctcaaagaag  caaagtgata   8580
cacatttgga  ggagacgtaa  ccgctgatca  gcctcgaaac  ttgtttattg  cagcttataa   8640
tggttacaaa  taaagcaata  gcatcacaaa  tttcacaaat  aaagcatttt  tttcactgca   8700
ttctagttgt  ggtttgtcca  aactcatcaa  tgtatcttag  gcgcctgatg  cggtattttc   8760
tccttacgca  tctgtgcggt  atttcacacc  gcatacagta  ctgtcaaagc  aaccatagta   8820
cgcgccctgt  agcggcgcat  taagcgcggc  gggtgtggtg  gttacgcgca  gcgtgaccgc   8880
tacacttgcc  agcgccctag  cgcccgctcc  tttcgctttc  ttcccttcct  ttctcgccac   8940
gttcgccggc  tttccccgtc  aagctctaaa  tcggggctc   cctttagggt  tccgatttag   9000
tgctttacgg  cacctcgacc  ccaaaaaact  tgatttgggt  gatggttcac  gtagtgggcc   9060
atcgccctga  tagacggttt  ttcgcccttt  gacgttggag  tccacgttct  ttaatagtgg   9120
actcttgttc  caaactggaa  caacactcaa  ccctatctcg  ggctattctt  ttgatttata   9180
agggattttg  ccgatttcgg  cctattggtt  aaaaaatgag  ctgatttaac  aaaaatttaa   9240
cgcgaatttt  aacaaaatat  taacgtttac  aattttatgg  tgcactctca  gtacaatctg   9300
ctctgatgcc  gcatagttaa  gccagccccg  acacccgcca  acacccgctg  acgcgccctg   9360
acgggcttgt  ctgctcccgg  catccgctta  cagacaagct  gtgaccgtct  ccgggagctg   9420
catgtgtcag  aggttttcac  cgtcatcacc  gaaacgcgcg  agacgaaagg  gcctcgtgat   9480
acgcctattt  ttataggtta  atgtcatgaa  caataaaact  gtctgcttac  ataaacagta   9540
atacaagggg  tgttatgagc  catattcaac  gggaaacgtc  gaggccgcga  ttaaattcca   9600
acatggatgc  tgatttatat  gggtataaat  gggctcgcga  taatgtcggg  caatcaggtg   9660
cgacaatcta  tcgcttgtat  gggaagcccg  atgcgccaga  gttgtttctg  aaacatggca   9720
aaggtagcgt  tgccaatgat  gttacagatg  agatggtcag  actaaactgg  ctgacggaat   9780
ttatgcctct  tccgaccatc  aagcatttta  tccgtactcc  tgatgatgca  tggttactca   9840
ccactgcgat  ccccggaaaa  acagcattcc  aggtattaga  agaatatcct  gattcaggtg   9900
aaaatattgt  tgatgcgctg  gcagtgttcc  tgcgccggtt  gcattcgatt  cctgtttgta   9960
attgtccttt  taacagcgat  cgcgtatttc  gtctcgctca  ggcgcaatca  cgaatgaata  10020
```

| | |
|---|---|
| acggtttggt tgatgcgagt gattttgatg acgagcgtaa tggctggcct gttgaacaag | 10080 |
| tctggaaaga aatgcataaa cttttgccat tctcaccgga ttcagtcgtc actcatggtg | 10140 |
| atttctcact tgataacctt attttgacg aggggaaatt aataggttgt attgatgttg | 10200 |
| gacgagtcgg aatcgcagac cgataccagg atcttgccat cctatggaac tgcctcggtg | 10260 |
| agttttctcc ttcattacag aaacggcttt ttcaaaaata tggtattgat aatcctgata | 10320 |
| tgaataaatt gcagtttcat ttgatgctcg atgagttttt ctaatctcat gaccaaaatc | 10380 |
| ccttaacgtg agttttcgtt ccactgagcg tcagaccccg tagaaaagat caaaggatct | 10440 |
| tcttgagatc ctttttttct gcgcgtaatc tgctgcttgc aaacaaaaaa accaccgcta | 10500 |
| ccagcggtgg tttgtttgcc ggatcaagag ctaccaactc ttttccgaa ggtaactggc | 10560 |
| ttcagcagag cgcagatacc aaatactgtc cttctagtgt agccgtagtt aggccaccac | 10620 |
| ttcaagaact ctgtagcacc gcctacatac ctcgctctgc taatcctgtt accagtggct | 10680 |
| gctgccagtg gcgataagtc gtgtcttacc gggttggact caagacgata gttaccggat | 10740 |
| aaggcgcagc ggtcgggctg aacggggggt tcgtgcacac agcccagctt ggagcgaacg | 10800 |
| acctacaccg aactgagata cctacagcgt gagctatgag aaagcgccac gcttcccgaa | 10860 |
| gggagaaagg cggacaggta tccggtaagc ggcagggtcg aacaggaga cgcacgagg | 10920 |
| gagcttccag ggggaaacgc ctggtatctt tatagtcctg tcgggtttcg ccacctctga | 10980 |
| cttgagcgtc gatttttgtg atgctcgtca ggggggcgga gcctatggaa aaacgccagc | 11040 |
| aacgcggcct ttttacggtt cctggccttt tgctggcctt ttgctcacat gtgcggccgc | 11100 |
| acgcgtcata tttatggggt atatgtgaat atttattaca tgcatagaag gtataatgat | 11160 |
| catgtcagga tatttgaggt atccacattt gggattgttt aaagattaaa tgaaatagtg | 11220 |
| ttaaaagtat ttaatatgcc cttcaacaaa tgatgaggaa atctt | 11265 |

<210> SEQ ID NO 111
<211> LENGTH: 702
<212> TYPE: DNA
<213> ORGANISM: Artificial Sequence
<220> FEATURE:
<223> OTHER INFORMATION: Synthetic

<400> SEQUENCE: 111

| | |
|---|---|
| caggtgcagc tgcagcagtg gggcgccggc ctgctgaagc ccagcgagac cctgagcctg | 60 |
| acctgcgccg tgtacggcgg cagcttcagc gcctactact ggagctggat cagacagccc | 120 |
| cccggcaagg gcctggagtg gatcggcgac atcaaccacg cggcggcac caactacaac | 180 |
| cccagcctga gagcagagt gaccatcagc gtggacacca gcaagaacca gttcagcctg | 240 |
| aagctgaaca gcgtgaccgc cgccgacacc gccgtgtact actgcgccag cctgaccgcc | 300 |
| tactggggcc agggcagcct ggtgaccgtg agcagcggcg gcggcggcag cggcggcggc | 360 |
| ggcagcggcg gcggcggcag cgacatccag atgacccaga gccccaccag cctgagcgcc | 420 |
| agcgtgggcg acagagtgac catcacctgc agagccagcc agggcatcag cagctggctg | 480 |
| acctggtacc agcagaagcc cgagaaggcc cccaagagcc tgatctacgc cgccagcagc | 540 |
| ctgcagagcg gcgtgcccag cagattcagc ggcagcggca gcggcaccga cttcaccctg | 600 |
| accatcagca gcctgcagcc cgaggacttc gccacctact actgccagca gtacgacagc | 660 |
| taccccatca ccttcggcca gggcaccaga ctggagatca ag | 702 |

<210> SEQ ID NO 112
<211> LENGTH: 1491

<212> TYPE: DNA
<213> ORGANISM: Artificial Sequence
<220> FEATURE:
<223> OTHER INFORMATION: Synthetic

<400> SEQUENCE: 112

```
atggcgcttc cggtgacagc actgctcctc cccttggcgc tgttgctcca cgcagcaagg      60
ccgcaggtgc agctgcagca gtggggcgcc ggcctgctga agcccagcga gaccctgagc     120
ctgacctgcg ccgtgtacgg cggcagcttc agcgcctact actggagctg gatcagacag     180
ccccccggca agggcctgga gtggatcggc gacatcaacc acggcggcgg caccaactac     240
aaccccagcc tgaagagcag agtgaccatc agcgtggaca ccagcaagaa ccagttcagc     300
ctgaagctga acagcgtgac cgccgccgac accgccgtgt actactgcgc cagcctgacc     360
gcctactggg gccagggcag cctggtgacc gtgagcagcg cggcggcggc agcggcggc      420
ggcggcagcg cggcggcgg cagcgacatc agatgaccc agagccccac cagcctgagc      480
gccagcgtgg gcgacagagt gaccatcacc tgcagagcca gcagggcat cagcagctgg      540
ctgacctggt accagcagaa gcccgagaag gcccccaaga gcctgatcta cgccgccagc     600
agcctgcaga gcggcgtgcc cagcagattc agcggcagcg gcagcggcac cgacttcacc     660
ctgaccatca gcagcctgca gcccgaggac ttcgccacct actactgcca gcagtacgac     720
agctacccca tcaccttcgg ccagggcacc agactggaga tcaagagcgc cgccgccttc     780
gtgcccgtgt cctgcccgc caagcccacc accacccccg ccccagacc cccaccccc       840
gcccccacca cgccagcca gccctgagc ctgagaccg aggcctgcag acccgccgcc        900
ggcggcgccg tgcacaccag aggcctggac ttcgcctgcg acatctacat ctgggccccc     960
ctggccggca cctgcggcgt gctgctgctg agcctggtga tcaccctgta ctgcaaccac    1020
agaaacagaa agagaggcag aaagaagctg ctgtacatct tcaagcagcc cttcatgaga    1080
cccgtgcaga ccacccagga ggaggacggc tgcagctgca gattccccga ggaggaggag    1140
ggcggctgcg agctgagagt gaagttcagc agaagcgccg acgcccccgc ctaccagcag    1200
ggccagaacc agctgtacaa cgagctgaac ctgggcagaa gaggagta cgacgtgctg    1260
gacaagagaa gaggcagaga ccccgagatg ggcggcaagc cagagaaa gaacccccag      1320
gagggcctgt acaacgagct gcagaaggac aagatggccg aggcctacag cgagatcggc    1380
atgaagggcg agagaagaag aggcaagggc cacgacggcc tgtaccaggg cctgagcacc    1440
gccaccaagg acacctacga cgccctgcac atgcaggccc tgccccccag a              1491
```

<210> SEQ ID NO 113
<211> LENGTH: 476
<212> TYPE: PRT
<213> ORGANISM: Artificial Sequence
<220> FEATURE:
<223> OTHER INFORMATION: Synthetic

<400> SEQUENCE: 113

```
Gln Val Gln Leu Gln Gln Trp Gly Ala Gly Leu Leu Lys Pro Ser Glu
  1               5                  10                  15

Thr Leu Ser Leu Thr Cys Ala Val Tyr Gly Gly Ser Phe Ser Ala Tyr
             20                  25                  30

Tyr Trp Ser Trp Ile Arg Gln Pro Pro Gly Lys Gly Leu Glu Trp Ile
         35                  40                  45

Gly Asp Ile Asn His Gly Gly Gly Thr Asn Tyr Asn Pro Ser Leu Lys
     50                  55                  60
```

```
Ser Arg Val Thr Ile Ser Val Asp Thr Ser Lys Asn Gln Phe Ser Leu
 65                  70                  75                  80

Lys Leu Asn Ser Val Thr Ala Ala Asp Thr Ala Val Tyr Tyr Cys Ala
                 85                  90                  95

Ser Leu Thr Ala Tyr Trp Gly Gln Gly Ser Leu Val Thr Val Ser Ser
            100                 105                 110

Gly Gly Gly Gly Ser Gly Gly Gly Ser Gly Gly Gly Gly Ser Asp
        115                 120                 125

Ile Gln Met Thr Gln Ser Pro Thr Ser Leu Ser Ala Ser Val Gly Asp
        130                 135                 140

Arg Val Thr Ile Thr Cys Arg Ala Ser Gln Gly Ile Ser Ser Trp Leu
145                 150                 155                 160

Thr Trp Tyr Gln Gln Lys Pro Glu Lys Ala Pro Lys Ser Leu Ile Tyr
                165                 170                 175

Ala Ala Ser Ser Leu Gln Ser Gly Val Pro Ser Arg Phe Ser Gly Ser
            180                 185                 190

Gly Ser Gly Thr Asp Phe Thr Leu Thr Ile Ser Ser Leu Gln Pro Glu
        195                 200                 205

Asp Phe Ala Thr Tyr Tyr Cys Gln Gln Tyr Asp Ser Tyr Pro Ile Thr
        210                 215                 220

Phe Gly Gln Gly Thr Arg Leu Glu Ile Lys Ser Ala Ala Ala Phe Val
225                 230                 235                 240

Pro Val Phe Leu Pro Ala Lys Pro Thr Thr Thr Pro Ala Pro Arg Pro
                245                 250                 255

Pro Thr Pro Ala Pro Thr Ile Ala Ser Gln Pro Leu Ser Leu Arg Pro
            260                 265                 270

Glu Ala Cys Arg Pro Ala Ala Gly Gly Ala Val His Thr Arg Gly Leu
        275                 280                 285

Asp Phe Ala Cys Asp Ile Tyr Ile Trp Ala Pro Leu Ala Gly Thr Cys
        290                 295                 300

Gly Val Leu Leu Leu Ser Leu Val Ile Thr Leu Tyr Cys Asn His Arg
305                 310                 315                 320

Asn Arg Lys Arg Gly Arg Lys Lys Leu Leu Tyr Ile Phe Lys Gln Pro
                325                 330                 335

Phe Met Arg Pro Val Gln Thr Thr Gln Glu Glu Asp Gly Cys Ser Cys
            340                 345                 350

Arg Phe Pro Glu Glu Glu Glu Gly Gly Cys Glu Leu Arg Val Lys Phe
        355                 360                 365

Ser Arg Ser Ala Asp Ala Pro Ala Tyr Gln Gln Gly Gln Asn Gln Leu
        370                 375                 380

Tyr Asn Glu Leu Asn Leu Gly Arg Arg Glu Glu Tyr Asp Val Leu Asp
385                 390                 395                 400

Lys Arg Arg Gly Arg Asp Pro Glu Met Gly Gly Lys Pro Arg Arg Lys
                405                 410                 415

Asn Pro Gln Glu Gly Leu Tyr Asn Glu Leu Gln Lys Asp Lys Met Ala
            420                 425                 430

Glu Ala Tyr Ser Glu Ile Gly Met Lys Gly Glu Arg Arg Arg Gly Lys
        435                 440                 445

Gly His Asp Gly Leu Tyr Gln Gly Leu Ser Thr Ala Thr Lys Asp Thr
        450                 455                 460

Tyr Asp Ala Leu His Met Gln Ala Leu Pro Pro Arg
465                 470                 475
```

<210> SEQ ID NO 114
<211> LENGTH: 11235
<212> TYPE: DNA
<213> ORGANISM: Artificial Sequence
<220> FEATURE:
<223> OTHER INFORMATION: Synthetic

<400> SEQUENCE: 114

```
atgtcaggat atttgaggta tccacatttg ggattgttta agattaaat gaaatagtgt      60 taaaagtatt taatatgccc ttcaacaaat gatgaggaaa tcttagaatc tgctcagact    120
ccttcagttt acatattagg aaactgaggc acagaaagga gcagagactt gctcaagtcc    180
acccaaagca gtagagcatt gtggttaaat gcaggacttc agtcagactg tctgggttca    240
aatcctggtt ccacttggac atgggtttcc ttacataaat cacttcacct ctctgagcct    300
cagttttctc atatgcaaag tgaggataat aataatacct tccttacatg gttactgata    360
tgagtattaa atgtgccagc tcatgtgcct ggcgtatagg aggtgcttta taaaccttag    420
ctgttaccac tcatggcatt gccaaatgtg ggacgggtct cctgactctc tggtgtgaga    480
ttgatggaat ccacactttc cagttccctt ttctacctcc tgggtatctt ctcatatggt    540
tgtaagttcc ttggaggaag ggaatgtggc ttgctctctc caccacgctg agcatataag    600
aggtgctgaa tgagcgcttt tattcactcc tctcatcccc agccctcacc agctgggagt    660
tgttgtaggt gtcaattttc tgcctctttc caacaccctg tgaggtgact gagcattgtc    720
ttccctccca ggcagctcac agtgtaagct tgtggacgat atcgaattcg cacgacattg    780
attattgact agttattaat agtaatcaat tacggggtca ttagttcata gcccatatat    840
ggagttccgc gttacataac ttacggtaaa tggcccgcct ggctgaccgc ccaacgaccc    900
ccgcccattg acgtcaataa tgacgtatgt tcccatagta acgccaatag ggactttcca    960
ttgacgtcaa tgggtggact atttacggta aactgcccac ttggcagtac atcaagtgta   1020
tcatatgcca gtacgcccc ctattgacgt caatgacggt aaatggcccg cctggcatta   1080
tgcccagtac atgaccttat gggactttcc tacttggcag tacatctacg tattagtcat   1140
cgctattacc atgggtcgag gtgagcccca cgttctgctt cactctcccc atctccccc   1200 cctccccacc cccaattttg tatttattta ttttttaatt attttgtgca gcgatggggg   1260
cggggggggg ggggcgcgc gccaggcggg gcggggcggg gcgaggggcg gggcgggggcg   1320 aggcggagag gtgcggcggc agccaatcag agcggcgcgc tccgaaagtt tccttttatg   1380
gcgaggcggc ggcggcggcg gccctataaa aagcgaagcg cgcggcgggc gggagtcgct   1440
gcgttgcctt cgccccgtgc cccgctccgc gccgcctcgc gccgcccgcc ccggctctga   1500
ctgaccgcgt tactcccaca ggtgagcggg cgggacggcc cttctcctcc gggctgtaat   1560
tagcgcttgg tttaatgacg gctcgtttct tttctgtggc tgcgtgaaag ccttaaaggg   1620
ctccgggagg gccctttgtg cggggggag cggctcgggg ggtgcgtgcg tgtgtgtgtg   1680
cgtggggagc gccgcgtgcg gcccgcgctg cccggcggct gtgagcgctg cgggcgcggc   1740
gcggggcttt gtgcgctccg cgtgtgcgcg aggggagcgc ggccggggc ggtgccccgc   1800 ggtgcggggg ggctgcgagg ggaacaaagg ctgcgtgcgg ggtgtgtgcg tgggggggtg   1860
agcagggggt gtgggcgcgg cggtcgggct gtaacccccc cctgcaccc cctccccgag   1920 ttgctgagca cggcccggct tcgggtgcgg ggctccgtgc gggggcgtggc gcggggctcg   1980 ccgtgccggg cgggggtgg cggcaggtgg gggtgccggg cggggcgggg ccgcctcggg   2040
ccggggaggg ctcgggggag gggcgcggcg gccccggagc gccggcggct gtcgaggcgc   2100
```

```
ggcgagccgc agccattgcc ttttatggta atcgtgcgag agggcgcagg gacttccttt    2160
gtcccaaatc tggcggagcc gaaatctggg aggcgccgcc gcacccctc tagcgggcgc     2220
gggcgaagcg gtgcggcgcc ggcaggaagg aaatgggcgg ggagggcctt cgtgcgtcgc    2280
cgcgccgccg tccccttctc catctccagc ctcggggctg ccgcaggggg acggctgcct    2340
tcggggggga cggggcaggg cggggttcgg cttctggcgt gtgaccggcg gctctagagc    2400
ctctgctaac catgttcatg ccttcttctt tttcctacag gggggatccg tttatctgca    2460
gaattcgccc ttgacgtcgc caccatggcg cttccggtga cagcactgct cctcccttg     2520
gcgctgttgc tccacgcagc aaggccgcag gtgcagctgc agcagtgggg cgccggcctg    2580
ctgaagccca gcgagaccct gagcctgacc tgcgccgtgt acggcggcag cttcagcgcc    2640
tactactgga gctggatcag acagccccc ggcaagggcc tggagtggat cggcgacatc     2700
aaccacggcg gcggcaccaa ctacaacccc agcctgaaga gcagagtgac catcagcgtg    2760
gacaccagca agaaccagtt cagcctgaag ctgaacagcg tgaccgccgc cgacaccgcc    2820
gtgtactact gcgccagcct gaccgcctac tggggccagg gcagcctggt gaccgtgagc    2880
agcggcggcg gcggcagcgg cggcggcggc agcggcggcg gcggcagcga catccagatg    2940
acccagagcc ccaccagcct gagcgccagc gtgggcgaca gagtgaccat cacctgcaga    3000
gccagccagg gcatcagcag ctggctgacc tggtaccagc agaagcccga gaaggccccc    3060
aagagcctga tctacgccgc cagcagcctg cagagcggcg tgcccagcag attcagcggc    3120
agcggcagcg gcaccgactt caccctgacc atcagcagcc tgcagcccga ggacttcgcc    3180
acctactact gccagcagta cgacagctac cccatcacct tcggccaggg caccagactg    3240
gagatcaaga gcgccgccgc cttcgtgccc gtgttcctgc ccgccaagcc caccaccacc    3300
cccgccccca ccccccac cccgccccc accatcgcca gccagcccct gagcctgaga     3360
cccgaggcct gcagacccgc cgccggcggc gccgtgcaca ccagaggcct ggacttcgcc    3420
tgcgacatct acatctgggc cccctgcc ggcacctgcg gcgtgctgct gctgagcctg       3480
gtgatcaccc tgtactgcaa ccacagaaac agaaagagag cagaaagaa gctgctgtac    3540
atcttcaagc agcccttcat gagacccgtg cagaccaccc aggaggagga cggctgcagc    3600
tgcagattcc ccgaggagga ggagggcggc tgcgagctga gagtgaagtt cagcagaagc    3660
gccgacgccc ccgcctacca gcagggccag aaccagctgt acaacgagct gaacctgggc    3720
agaagagagg agtacgacgt gctggacaag agaagaggca gagaccccga gatgggcggc    3780
aagcccagaa gaaagaaccc caggagggc ctgtacaacg agctgcagaa ggacaagatg    3840
gccgaggcct acagcgagat cggcatgaag ggcgagagaa agagaggcaa gggccacgac    3900
ggcctgtacc agggcctgag caccgccacc aaggacacct acgacgccct gcacatgcag    3960
gccctgcccc ccagaggaag cggattcagc ctgctgaagc aggctggaga cgtggaggag    4020
aaccctggac ctatgtctcg ctccgttgcc ttagctgtgc tcgcgctact ctctctttct    4080
ggattagagg ctgtcatggc gccccgaacc ctcttcctgg tggaggcgg ttcaggcgga     4140
ggtggctctg gcggtggcgg atcgatccag cgtactccaa agattcaggt ttactcacgt    4200
catccagcag agaatggaaa gtcaaatttc ctgaattgct atgtgtctgg gtttcatcca    4260
tccgacattg aagttgactt actgaagaat ggagagagaa ttgaaaaagt ggagcattca    4320
gacttgtctt tcagcaagga ctggtctttt tatctcttgt actacactga attcaccccc    4380
actgaaaaag atgagtatgc ctgccgtgtg aaccatgtga ctttgtcaca gcccaagata    4440
gttaagtggg atcgagacat gggtggtggt ggttctggtg gtggtggttc tggcggcggc    4500
```

```
ggctccggtg gtggtggatc cggctcccac tccttgaagt atttccacac ttccgtgtcc    4560
cggcccggcc gcggggagcc ccgcttcatc tctgtgggct acgtggacga cacccagttc    4620
gtgcgcttcg acaacgacgc cgcgagtccg aggatggtgc cgcgggcgcc gtggatggag    4680
caggaggggt cagagtattg ggaccgggag acacggagcg ccaggacac cgcacagatt     4740
ttccgagtga atctgcggac gctgcgcggc tactacaatc agagcgaggc cgggtctcac    4800
accctgcagt ggatgcatgg ctgcgagctg ggcccgacg gcgcttcct ccgcgggtat      4860
gaacagttcg cctacgacgg caaggattat ctcaccctga atgaggacct gcgctcctgg    4920
accgcggtgg acacggcggc tcagatctcc gagcaaaagt caaatgatgc ctctgaggcg    4980
gagcaccaga gagcctacct ggaagacaca tgcgtggagt ggctccacaa atacctggag    5040
aaggggaagg agacgctgct tcacctggag cccccaaaga cacacgtgac tcaccacccc    5100
atctctgacc atgaggccac cctgaggtgc tgggccctgg gcttctaccc tgcggagatc    5160
acactgacct ggcagcagga tggggaggc catacccagg acacggagct cgtggagacc    5220
aggcctgcag gggatggaac cttccagaag tgggcagctg tggtggtgcc ttctggagag    5280
gagcagagat acacgtgcca tgtgcagcat gaggggctac ccgagcccgt caccctgaga    5340
tggaagccgg cttcccagcc caccatcccc atcgtgggca tcattgctgg cctggttctc    5400
cttggatctg tggtctctgg agctgtggtt gctgctgtga tatggaggaa gaagagctca    5460
ggtggaaaag gagggagcta ctctaaggct gagtggagcg acagtgccca ggggtctgag    5520
tctcacagct tgtaatgata gccgctgatc agcctcgact gtgccttcta gttgccagcc    5580
atctgttgtt tgcccctccc ccgtgccttc cttgaccctg gaaggtgcca ctcccactgt    5640
cctttcctaa taaaatgagg aaattgcatc gcattgtctg agtaggtgtc attctattct    5700
ggggggtggg gtggggcagg acagcaaggg ggaggattgg gaagacaata gcaggcatgc    5760
tggggatgcg gtgggctcta tgggtcgact gaccagatgg acctggctgg agaagaagag    5820
attgagctct actcaggtgg gccctcctcc ctctggtctc ttccggtatc ccccacccct    5880
cagcttgctg tagagacggc aatcagggga aattctggtc cctgccctcc cgtcagcacc    5940
acggacagct cccacgtctg tgggacgctc tctgcagatg gggatgatct cccagccctg    6000
ccccgcctct ccctcgttcc ccaccagccc tctttccaga aatttccttc ttcatccaag    6060
ggacttttcc tcccagaacc cgacacagac accatcaact cgaccagtt cagcaggctg     6120
ttgtgtgaca tggaaggtga tgaagagacc agggaggctt atgccaatat cggtgaggaa    6180
gcacctgagc ccagaaaagg acaatcaagg caagagttc tttgctgcca cttgtcaata     6240
tcacccattc atcatgagcc acgtcagtcc cctcccacag aaatcattgc aaggggatg     6300
cggagcaatg gctggaggaa cggagactcc agggaagaga ggggagatgg aggccagtgg   6360
gggaaatagg cccctttcact aatgaccacc aagaaaacaa aatctcatgt ttacatcctc   6420
cacctccatt tctatacgca tttctgcttc ttgctcttct gtccatcctt tctacaaagc   6480
ccataccata caccccttc cctttcctc ccagctcctt agccaagcta ctctagtatt      6540
tgtaataact agcatttact ggatactcat agtatgctca ttgctgtccg gtaaccacgt    6600
gcggaccggg ctccggtgcc cgtcagtggg cagagcgcac atcgcccaca gtccccgaga    6660
agttgggggg agggtcggc aattgaaccg gtgcctagag aaggtggcgc ggggtaaact     6720
gggaaagtga tgtcgtgtac tggctccgcc ttttttcccga gggtgggga gaaccgtata    6780
taagtgcagt agtcgccgtg aacgttcttt ttcgcaacgg gtttgccgcc agaacacagg    6840
```

```
taagtgccgt gtgtggttcc cgcgggcctg gcctctttac gggttatggc ccttgcgtgc    6900
cttgaattac ttccactggc tgcagtacgt gattcttgat cccgagcttc gggttggaag    6960
tgggtgggag agttcgaggc cttgcgctta aggagcccct tcgcctcgtg cttgagttga    7020
ggcctggcct gggcgctggg gccgccgcgt gcgaatctgg tggcaccttc gcgcctgtct    7080
cgctgctttc gataagtctc tagccattta aaattttga tgacctgctg cgacgctttt    7140
tttctggcaa gatagtcttg taaatgcggg ccaagatctg cacactggta tttcggtttt    7200
tggggccgcg ggcggcgacg gggcccgtgc gtcccagcgc acatgttcgg cgaggcgggg    7260
cctgcgagcg cggccaccga gaatcggacg ggggtagtct caagctggcc ggcctgctct    7320
ggtgcctggc ctcgcgccgc cgtgtatcgc cccgccctgg gcggcaaggc tggcccggtc    7380
ggcaccagtt gcgtgagcgg aaagatggcc gcttcccggc cctgctgcag ggagctcaaa    7440
atggaggacg cggcgctcgg gagagcgggc gggtgagtca cccacacaaa ggaaaagggc    7500
cttttccgtcc tcagccgtcg cttcatgtga ctccacggag taccgggcgc cgtccaggca    7560
cctcgattag ttctcgagct tttggagtac gtcgtcttta ggttgggggg aggggtttta    7620
tgcgatggag tttccccaca ctgagtgggt ggagactgaa gttaggccag cttggcactt    7680
gatgtaattc tccttggaat ttgccccttttt tgagtttgga tcttggttca ttctcaagcc    7740
tcagacagtg gttcaaagtt tttttcttcc atttcaggtg tcgtgacttg acgtcgccac    7800
catgaggata tttgctgtct ttatattcat gacctactgg catttgctga acgcatttac    7860
tgtcacggtt cccaaggacc tatatgtggt agagtatggt agcaatatga caattgaatg    7920
caaattccca gtagaaaaac aattagacct ggctgcacta attgtctatt gggaaatgga    7980
ggataagaac attattcaat ttgtgcatgg agaggaagac ctgaaggttc agcatagtag    8040
ctacagacag agggcccggc tgttgaagga ccagctctcc ctgggaaatg ctgcacttca    8100
gatcacagat gtgaaattgc aggatgcagg ggtgtaccgc tgcatgatca gctatggtgg    8160
tgccgactac aagcgaatta ctgtgaaagt caatgcccca taacacaaaa tcaaccaaag    8220
aattttggtt gtggatccag tcacctctga acatgaactg acatgtcagg ctgagggcta    8280
ccccaaggcc gaagtcatct ggacaagcag tgaccatcaa gtcctgagtg gtaagaccac    8340
caccaccaat tccaagagag aggagaaact tttcaatgtg accagcacac tgagaatcaa    8400
cacaacaact aatgagattt tctactgcac ttttaggaga ttagatcctg aggaaaacca    8460
tacagctgaa ttggtcatcc cagaactacc tctggcacat cctccaaatg aaaggactca    8520
cttggtaatt ctgggagcca tcttattatg ccttggtgta gcactgacat tcatcttccg    8580
tttaagaaaa gggagaatga tggatgtgaa aaaatgtggc atccaagata caaactcaaa    8640
gaagcaaagt gatacacatt tggaggagac gtaaccgctg atcagcctcg aaacttgttt    8700
attgcagctt ataatggtta caaataaagc aatagcatca caaatttcac aaataaagca    8760
ttttttttcac tgcattctag ttgtggtttg tccaaactca tcaatgtatc ttaggcgcct    8820
gatgcggtat tttctcctta cgcatctgtg cggtatttca caccgcatac agtactgtca    8880
aagcaaccat agtacgcgcc ctgtagcggc gcattaagcg cggcgggtgt ggtggttacg    8940
cgcagcgtga ccgctacact tgccagcgcc ctagcgcccg ctcctttcgc tttcttccct    9000
tcctttctcg ccacgttcgc cggctttccc cgtcaagctc taaatcgggg ctcccttta    9060
gggttccgat ttagtgcttt acggcacctc gaccccaaaa aacttgattt gggtgatggt    9120
tcacgtagtg ggccatcgcc ctgatagacg gttttcgcc ctttgacgtt ggagtccacg    9180
ttctttaata gtggactctt gttccaaact ggaacaacac tcaaccctat ctcgggctat    9240
```

```
tcttttgatt tataagggat tttgccgatt tcggcctatt ggttaaaaaa tgagctgatt      9300
taacaaaaat ttaacgcgaa ttttaacaaa atattaacgt ttacaatttt atggtgcact      9360
ctcagtacaa tctgctctga tgccgcatag ttaagccagc cccgacaccc gccaacaccc      9420
gctgacgcgc cctgacgggc ttgtctgctc ccggcatccg cttacagaca agctgtgacc      9480
gtctccggga gctgcatgtg tcagaggttt tcaccgtcat caccgaaacg cgcgagacga      9540
aagggcctcg tgatacgcct attttatag gttaatgtca tgaacaataa aactgtctgc      9600
ttacataaac agtaatacaa ggggtgttat gagccatatt caacgggaaa cgtcgaggcc      9660
gcgattaaat tccaacatgg atgctgattt atatgggtat aaatgggctc gcgataatgt      9720
cgggcaatca ggtgcgacaa tctatcgctt gtatgggaag cccgatgcgc cagagttgtt      9780
tctgaaacat ggcaaaggta gcgttgccaa tgatgttaca gatgagatgg tcagactaaa      9840
ctggctgacg gaattatgc ctcttccgac catcaagcat tttatccgta ctcctgatga      9900
tgcatggtta ctcaccactg cgatcccgg aaaaacagca ttccaggtat tagaagaata      9960
tcctgattca ggtgaaaata ttgttgatgc gctggcagtg ttcctgcgcc ggttgcattc      10020
gattcctgtt tgtaattgtc cttttaacag cgatcgcgta tttcgtctcg ctcaggcgca      10080
atcacgaatg aataacggtt tggttgatgc gagtgatttt gatgacgagc gtaatggctg      10140
gcctgttgaa caagtctgga agaaatgca taaactttg ccattctcac cggattcagt      10200
cgtcactcat ggtgatttct cacttgataa ccttattttt gacgagggga attaatagg      10260 ttgtattgat gttggacgag tcggaatcgc agaccgatac caggatcttg ccatcctatg      10320
gaactgcctc ggtgagtttt ctccttcatt acagaaacgg ctttttcaaa aatatggtat      10380
tgataatcct gatatgaata aattgcagtt tcatttgatg ctcgatgagt ttttctaatc      10440
tcatgaccaa atcccttaa cgtgagtttt cgttccactg agcgtcagac cccgtagaaa      10500
agatcaaagg atcttcttga tccttttttt ttctgcgcgt aatctgctgc ttgcaaacaa      10560
aaaaaccacc gctaccagcg gtggtttgtt tgccggatca agagctacca actcttttc      10620 cgaaggtaac tggcttcagc agagcgcaga taccaaatac tgtccttcta gtgtagccgt      10680
agttaggcca ccacttcaag aactctgtag caccgcctac atacctcgct ctgctaatcc      10740
tgttaccagt ggctgctgcc agtggcgata agtcgtgtct taccgggttg gactcaagac      10800
gatagttacc ggataaggcg cagcggtcgg gctgaacggg gggttcgtgc acacagccca      10860
gcttggagcg aacgacctac accgaactga gatacctaca gcgtgagcta tgagaaagcg      10920
ccacgcttcc cgaagggaga aaggcggaca ggtatccgt aagcggcagg gtcggaacag      10980
gagagcgcac gagggagctt ccaggggaa acgcctggta tctttatagt cctgtcgggt      11040
ttcgccacct ctgacttgag cgtcgatttt tgtgatgctc gtcaggggg cggagcctat      11100 ggaaaaacgc cagcaacgcg gcctttttac ggttcctggc cttttgctgg ccttttgctc      11160
acatgtgcgg ccgcacgcgt catatttatg gggtatatgt gaatatttat tacatgcata      11220
gaaggtataa tgatc                                                      11235

<210> SEQ ID NO 115
<211> LENGTH: 7176
<212> TYPE: DNA
<213> ORGANISM: Artificial Sequence
<220> FEATURE:
<223> OTHER INFORMATION: Synthetic
```

<400> SEQUENCE: 115

```
atgtcaggat atttgaggta tccacatttg ggattgttta aagattaaat gaaatagtgt    60
taaaagtatt taatatgccc ttcaacaaat gatgaggaaa tcttagaatc tgctcagact   120
ccttcagttt acatattagg aaactgaggc acagaaagga gcagagactt gctcaagtcc   180
acccaaagca gtagagcatt gtggttaaat gcaggacttc agtcagactg tctgggttca   240
aatcctggtt ccacttggac atgggtttcc ttacataaat cacttcacct ctctgagcct   300
cagttttctc atatgcaaag tgaggataat aataatacct tccttacatg gttactgata   360
tgagtattaa atgtgccagc tcatgtgcct ggcgtatagg aggtgcttta taaaccttag   420
ctgttaccac tcatggcatt gccaaatgtg ggacgggtct cctgactctc tggtgtgaga   480
ttgatggaat ccacactttc cagttccctt ttctacctcc tgggtatctt ctcatatggt   540
tgtaagttcc ttggaggaag ggaatgtggc ttgctctctc caccacgctg agcatataag   600
aggtgctgaa tgagcgcttt tattcactcc tctcatcccc agccctcacc agctgggagt   660
tgttgtaggt gtcaattttc tgcctctttc caacaccctg tgaggtgact gagcattgtc   720
ttccctccca ggcagctcac agtgtaagct tgtggacgat atcgaattcg cacgacattg   780
attattgact agttattaat agtaatcaat tacggggtca ttagttcata gcccatatat   840
ggagttccgc gttacataac ttacggtaaa tggcccgcct ggctgaccgc caacgaccc    900
ccgcccattg acgtcaataa tgacgtatgt tcccatagta acgccaatag ggactttcca   960
ttgacgtcaa tgggtggact atttacggta aactgcccac ttggcagtac atcaagtgta  1020
tcatatgcca gtacgcccc ctattgacgt caatgacggt aaatggcccg cctggcatta   1080
tgcccagtac atgaccttat gggactttcc tacttggcag tacatctacg tattagtcat   1140
cgctattacc atgggtcgag gtgagcccca cgttctgctt cactctcccc atctccccc    1200
cctccccacc cccaattttg tatttattta tttttaatt attttgtgca gcgatggggg    1260
cggggggggg gggggcgcgc gccaggcggg gcggggcggg gcgaggggcg gggcggggcg   1320
aggcggagag gtgcggcggc agccaatcag agcggcgcgc tccgaaagtt cctttttatg   1380
gcgaggcggc ggcggcggcg gccctataaa aagcgaagcg cgcggcgggc gggagtcgct   1440
gcgttgcctt cgccccgtgc cccgctccgc gccgcctcgc gccgcccgcc ccggctctga   1500
ctgaccgcgt tactcccaca ggtgagcggg cgggacggcc cttctcctcc gggctgtaat   1560
tagcgcttgg tttaatgacg gctcgttct tttctgtggc tgcgtgaaag ccttaaaggg    1620
ctccggggag gcccttttgtg cgggggggag cggctcgggg ggtgcgtgcg tgtgtgtgtg   1680
cgtggggagc gccgcgtgcg gcccgcgctg cccggcggct gtgagcgctg cgggcgcggc   1740
gcggggcttt gtgcgctccg cgtgtgcgcg aggggagcgc ggccggggc ggtgccccgc    1800
ggtgcggggg ggctgcgagg ggaacaaagg ctgcgtgcgg ggtgtgtgcg tggggggtg    1860
agcagggggt gtgggcgcgg cggtcgggct gtaaccccc cctgcacccc cctccccgag    1920
ttgctgagca cggcccggct tcgggtgcgg ggctccgtgc ggggcgtggc gcggggctcg   1980
ccgtgccggg cggggggtgg cggcaggtgg gggtgccggg cggggcgggg ccgcctcggg   2040
ccggggaggg ctcgggggag gggcgcgcg gcccccgagc gccggcggct gtcgaggcgc    2100
ggcgagccgc agccattgcc ttttatggta atcgtgcgag agggcgcagg gacttccttt   2160
gtcccaaatc tggcggagcc gaaatctggg aggcgccgcc gcaccccctc tagcgggcgc   2220
gggcgaagcg gtgcggcgcc ggcaggaagg aaatgggcgg ggagggcctt cgtgcgtcgc   2280
```

```
cgcgccgccg tccccttctc catctccagc ctcggggctg ccgcagggggg acggctgcct    2340 tcggggggga cggggcaggg cggggttcgg cttctggcgt gtgaccggcg gctctagagc    2400
ctctgctaac catgttcatg ccttcttctt tttcctacag gggggatccg tttatctgca    2460
gaattcgccc ttgacgtcgc caccatggcg cttccggtga cagcactgct cctcccttg     2520 gcgctgttgc tccacgcagc aaggccgcag gtgcagctgc agcagtgggg cgccggcctg    2580
ctgaagccca gcgagaccct gagcctgacc tgcgccgtgt acggcggcag cttcagcgcc    2640
tactactgga gctggatcag acagcccccc ggcaagggcc tggagtggat cggcgacatc    2700
aaccacggcg gcggcaccaa ctacaacccc agcctgaaga gcagagtgac catcagcgtg    2760
gacaccagca agaaccagtt cagcctgaag ctgaacagcg tgaccgccgc cgacaccgcc    2820
gtgtactact gcgccagcct gaccgcctac tggggccagg gcagcctggt gaccgtgagc    2880
agcggcggcg gcggcagcgg cggcggcggc agcggcggcg gcggcagcga catccagatg    2940
acccagagcc ccaccagcct gagcgccagc gtgggcgaca gagtgaccat cacctgcaga    3000
gccagccagg gcatcagcag ctggctgacc tggtaccagc agaagcccga aaggccccc     3060 aagagcctga tctacgccgc cagcagcctg cagagcggcg tgcccagcag attcagcggc    3120
agcggcagcg gcaccgactt cacccctgacc atcagcagcc tgcagcccga ggacttcgcc    3180
acctactact gccagcagta cgacagctac cccatcacct tcggccaggg caccagactg    3240
gagatcaaga gcgccgccgc cttcgtgccc gtgttcctgc ccgccaagcc caccaccacc    3300
cccgccccca cccccccccac cccgccccc accatcgcca gccagcccct gagcctgaga    3360
cccgaggcct gcagacccgc cgccggcggc gccgtgcaca ccagaggcct ggacttcgcc    3420
tgcgacatct acatctgggc ccccctggcc ggcacctgcg gcgtgctgct gctgagcctg    3480
gtgatcaccc tgtactgcaa ccacagaaac agaaagagag gcagaaagaa gctgctgtac    3540
atcttcaagc agcccttcat gagacccgtg cagaccaccc aggaggagga cggctgcagc    3600
tgcagattcc ccgaggagga ggagggcggc tgcgagctga gagtgaagtt cagcagaagc    3660
gccgacgccc ccgcctacca gcagggccag aaccagctgt acaacgagct gaacctgggc    3720
agaagagagg agtacgacgt gctggacaag agaagaggca gagaccccga gatgggcggc    3780
aagcccagaa gaaagaaccc ccaggagggc ctgtacaacg agctgcagaa ggacaagatg    3840
gccgaggcct acagcgagat cggcatgaag ggcgagagaa gaagaggcaa gggccacgac    3900
ggcctgtacc agggcctgag caccgccacc aaggacacct acgacgccct gcacatgcag    3960
gccctgcccc ccagaggaag cggattcagc ctgctgaagc aggctggaga cgtggaggag    4020
aaccctggac ctatgtctcg ctccgttgcc ttagctgtgc tcgcgctact ctctctttct    4080
ggattagagg ctgtcatggc gccccgaacc ctcttcctgg gtggaggcgg ttcaggcgga    4140
ggtggctctg gcggtggcgg atcgatccag cgtactccaa agattcaggt ttactcacgt    4200
catccagcag agaatggaaa gtcaaatttc ctgaattgct atgtgtctgg gtttcatcca    4260
tccgacattg aagttgactt actgaagaat ggagagagaa ttgaaaaagt ggagcattca    4320
gacttgtctt tcagcaagga ctggtctttc tatctcttgt actacactga attcacccccc    4380 actgaaaaag atgagtatgc ctgccgtgtg aaccatgtga ctttgtcaca gcccaagata    4440
gttaagtggg atcgagacat gggtggtggt ggttctggtg gtggtggttc tggcggcggc    4500
ggctccggtg gtggtggatc cggctcccac tccttgaagt atttccacac ttccgtgtcc    4560
cggcccggcc gcggggagcc ccgcttcatc tctgtgggct acgtggacga cacccagttc    4620
gtgcgcttcg acaacgacgc cgcgagtccg aggatggtgc cgcgggcgcc gtggatggag    4680
```

-continued

```
caggaggggt cagagtattg ggaccgggag acacggagcg ccaggacac cgcacagatt    4740 ttccgagtga atctgcggac gctgcgcggc tactacaatc agagcgaggc cgggtctcac    4800
accctgcagt ggatgcatgg ctgcgagctg gggcccgacg gcgcttcct ccgcgggtat    4860 gaacagttcg cctacgacgg caaggattat ctcaccctga atgaggacct gcgctcctgg    4920
accgcggtgg acacggcggc tcagatctcc gagcaaaagt caaatgatgc ctctgaggcg    4980
gagcaccaga gagcctacct ggaagacaca tgcgtggagt ggctccacaa atacctggag    5040
aaggggaagg agacgctgct tcacctggag cccccaaaga cacacgtgac tcaccacccc    5100
atctctgacc atgaggccac cctgaggtgc tgggccctgg gcttctaccc tgcggagatc    5160
acactgacct ggcagcagga tggggagggc catacccagg acacggagct cgtggagacc    5220
aggcctgcag gggatggaac cttccagaag tgggcagctg tggtggtgcc ttctggagag    5280
gagcagagat acacgtgcca tgtgcagcat gaggggctac ccgagcccgt caccctgaga    5340
tggaagccgg cttcccagcc caccatcccc atcgtgggca tcattgctgg cctggttctc    5400
cttggatctg tggtctctgg agctgtggtt gctgctgtga tatggaggaa gaagagctca    5460
ggtgaaaaag gagggagcta ctctaaggct gagtggagcg acagtgccca ggggtctgag    5520
tctcacagct tgtaatgata ccgctgatc agcctcgact gtgccttcta gttgccagcc    5580
atctgttgtt tgcccctccc ccgtgccttc cttgaccctg gaaggtgcca ctcccactgt    5640
cctttcctaa taaaatgagg aaattgcatc gcattgtctg agtaggtgtc attctattct    5700
ggggggtggg gtggggcagg acagcaaggg ggaggattgg gaagacaata gcaggcatgc    5760
tggggatgcg gtgggctcta tgggtcgact gaccagatgg acctggctgg agaagaagag    5820
attgagctct actcaggtgg gccctcctcc ctctggtctc ttccggtatc ccccaccct    5880 cagcttgctg tagagacggc aatcagggga aattctggtc cctgccctcc cgtcagcacc    5940
acggacagct cccacgtctg tgggacgctc tctgcagatg gggatgatct cccagccctg    6000
ccccgcctct ccctcgttcc ccaccagccc tctttccaga aatttccttc ttcatccaag    6060
ggacttttcc tcccagaacc cgacacagac accatcaact gcgaccagtt cagcaggctg    6120
ttgtgtgaca tggaaggtga tgaagagacc agggaggctt atgccaatat cggtgaggaa    6180
gcacctgagc ccagaaaagg acaatcaagg gcaagagttc tttgctgcca cttgtcaata    6240
tcacccattc atcatgagcc acgtcagtcc cctcccacag aaatcattgc aaggggggatg    6300 cggagcaatg gctggaggaa cggagactcc agggaagaga ggggagatgg aggccagtgg    6360
gggaaatagg cccttcact aatgaccacc aagaaaacaa atctcatgt ttacatcctc    6420 cacctccatt tctatacgca tttctgcttc ttgctcttct gtccatcctt tctacaaagc    6480
gacatccaga tgacccagag ccccaccagc ctgagcgcca gcgtgggcga cagagtgacc    6540
atcacctgca gagccagcca gggcatcagc agctggctga cctggtacca gcagaagccc    6600
gagaaggccc ccaagagcct gatctacgcc gccagcagcc tgcagagcgg cgtgcccagc    6660
agattcagcg gcagcggcag cggcaccgac ttcaccctga ccatcagcag cctgcagccc    6720
gaggacttcg ccacctacta ctgccagcag tacgacagct accccatcac cttcggccag    6780 ggcaccgac tggagatcaa gggcggcggc ggcagcggcg gcggcggcag cggcggcggc    6840
ggcagccagg tgcagctgca gcagtgggc gccggcctgc tgaagcccag cgagaccctg    6900
agcctgacct gcgccgtgta cggcggcagc ttcagcgcct actactggag ctggatcaga    6960
cagccccccg gcaagggcct ggagtggatc ggcgacatca ccacggcgg cggcaccaac    7020
```

| tacaacccca gcctgaagag cagagtgacc atcagcgtgg acaccagcaa gaaccagttc | 7080 |
| agcctgaagc tgaacagcgt gaccgccgcc gacaccgccg tgtactactg cgccagcctg | 7140 |
| accgcctact ggggccaggg cagcctggtg accgtg | 7176 |

<210> SEQ ID NO 116
<211> LENGTH: 1485
<212> TYPE: DNA
<213> ORGANISM: Artificial Sequence
<220> FEATURE:
<223> OTHER INFORMATION: Synthetic

<400> SEQUENCE: 116

| atggcgcttc cggtgacagc actgctcctc cccttggcgc tgttgctcca cgcagcaagg | 60 |
| ccggacatcc agatgaccca gagccccacc agcctgagcg ccagcgtggg cgacagagtg | 120 |
| accatcacct gcagagccag ccagggcatc agcagctggc tgacctggta ccagcagaag | 180 |
| cccgagaagg ccccaagag cctgatctac gccgccagca gcctgcagag cggcgtgccc | 240 |
| agcagattca gcgcagcgg cagcggcacc gacttcaccc tgaccatcag cagcctgcag | 300 |
| cccgaggact cgccaccta ctactgccag cagtacgaca gctaccccat caccttcggc | 360 |
| cagggcacca gactggagat caagggcggc ggcggcagcg gcggcggcgg cagcggcggc | 420 |
| ggcggcagcc aggtgcagct gcagcagtgg ggcgccggcc tgctgaagcc cagcgagacc | 480 |
| ctgagcctga cctgcgccgt gtacggcggc agcttcagcg cctactactg gagctggatc | 540 |
| agacagcccc ccggcaaggg cctggagtgg atcggcgaca tcaaccacgg cggcggcacc | 600 |
| aactacaacc cagcctgaa gagcagagtg accatcagcg tggacaccag caagaaccag | 660 |
| ttcagcctga gctgaacag cgtgaccgcc gccgacaccg ccgtgtacta ctgcgccagc | 720 |
| ctgaccgcct actggggcca gggcagcctg gtgaccgtga gcgccgccgc cttcgtgccc | 780 |
| gtgttcctgc cgccaagcc caccaccacc cccgccccca accccccac cccgccccc | 840 |
| accatcgcca gccagcccct gagcctgaga cccgaggcct gcagaccgc cgccggcggc | 900 |
| gccgtgcaca ccagaggcct ggacttcgcc tgcgacatct acatctgggc ccccctggcc | 960 |
| ggcacctgcg cgtgctgct gctgagcctg gtgatcaccc tgtactgcaa ccacagaaac | 1020 |
| agaaagagag cagaaagaa gctgctgtac atcttcaagc agcccttcat gagacccgtg | 1080 |
| cagaccaccc aggaggagga cggctgcagc tgcagattcc ccgaggagga ggagggcggc | 1140 |
| tgcgagctga gagtgaagtt cagcagaagc gccgacgccc ccgcctacca gcagggccag | 1200 |
| aaccagctgt acaacgagct gaacctgggc agaagagagg agtacgacgt gctggacaag | 1260 |
| agaagaggca gagaccccga gatgggcggc aagcccagaa gaagaacccc caggagggc | 1320 |
| ctgtacaacg agctgcagaa ggacaagatg gccgaggcct acagcgagat cggcatgaag | 1380 |
| ggcgagagaa gaagaggcaa gggccacgac ggcctgtacc agggcctgag caccgccacc | 1440 |
| aaggacacct acgacgccct gcacatgcag gccctgcccc ccaga | 1485 |

<210> SEQ ID NO 117
<211> LENGTH: 474
<212> TYPE: PRT
<213> ORGANISM: Artificial Sequence
<220> FEATURE:
<223> OTHER INFORMATION: Synthetic

<400> SEQUENCE: 117

Asp Ile Gln Met Thr Gln Ser Pro Thr Ser Leu Ser Ala Ser Val Gly
1               5                   10                  15

```
Asp Arg Val Thr Ile Thr Cys Arg Ala Ser Gln Gly Ile Ser Ser Trp
             20                  25                  30

Leu Thr Trp Tyr Gln Gln Lys Pro Glu Lys Ala Pro Lys Ser Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asp Ser Tyr Pro Ile
                 85                  90                  95

Thr Phe Gly Gln Gly Thr Arg Leu Glu Ile Lys Gly Gly Gly Gly Ser
            100                 105                 110

Gly Gly Gly Gly Ser Gly Gly Gly Ser Gln Val Gln Leu Gln Gln
        115                 120                 125

Trp Gly Ala Gly Leu Leu Lys Pro Ser Glu Thr Leu Ser Leu Thr Cys
130                 135                 140

Ala Val Tyr Gly Gly Ser Phe Ser Ala Tyr Tyr Trp Ser Trp Ile Arg
145                 150                 155                 160

Gln Pro Pro Gly Lys Gly Leu Glu Trp Ile Gly Asp Ile Asn His Gly
                165                 170                 175

Gly Gly Thr Asn Tyr Asn Pro Ser Leu Lys Ser Arg Val Thr Ile Ser
            180                 185                 190

Val Asp Thr Ser Lys Asn Gln Phe Ser Leu Lys Leu Asn Ser Val Thr
        195                 200                 205

Ala Ala Asp Thr Ala Val Tyr Tyr Cys Ala Ser Leu Thr Ala Tyr Trp
210                 215                 220

Gly Gln Gly Ser Leu Val Thr Val Ser Ala Ala Phe Val Pro Val
225                 230                 235                 240

Phe Leu Pro Ala Lys Pro Thr Thr Thr Pro Ala Pro Arg Pro Pro Thr
                245                 250                 255

Pro Ala Pro Thr Ile Ala Ser Gln Pro Leu Ser Leu Arg Pro Glu Ala
            260                 265                 270

Cys Arg Pro Ala Ala Gly Gly Ala Val His Thr Arg Gly Leu Asp Phe
        275                 280                 285

Ala Cys Asp Ile Tyr Ile Trp Ala Pro Leu Ala Gly Thr Cys Gly Val
290                 295                 300

Leu Leu Leu Ser Leu Val Ile Thr Leu Tyr Cys Asn His Arg Asn Arg
305                 310                 315                 320

Lys Arg Gly Arg Lys Lys Leu Leu Tyr Ile Phe Lys Gln Pro Phe Met
                325                 330                 335

Arg Pro Val Gln Thr Thr Gln Glu Glu Asp Gly Cys Ser Cys Arg Phe
            340                 345                 350

Pro Glu Glu Glu Glu Gly Gly Cys Glu Leu Arg Val Lys Phe Ser Arg
        355                 360                 365

Ser Ala Asp Ala Pro Ala Tyr Gln Gln Gly Gln Asn Gln Leu Tyr Asn
370                 375                 380

Glu Leu Asn Leu Gly Arg Arg Glu Glu Tyr Asp Val Leu Asp Lys Arg
385                 390                 395                 400

Arg Gly Arg Asp Pro Glu Met Gly Gly Lys Pro Arg Arg Lys Asn Pro
                405                 410                 415

Gln Glu Gly Leu Tyr Asn Glu Leu Gln Lys Asp Lys Met Ala Glu Ala
            420                 425                 430
```

Tyr Ser Glu Ile Gly Met Lys Gly Glu Arg Arg Gly Lys Gly His
        435                 440                 445

Asp Gly Leu Tyr Gln Gly Leu Ser Thr Ala Thr Lys Asp Thr Tyr Asp
    450                 455                 460

Ala Leu His Met Gln Ala Leu Pro Pro Arg
465                 470

<210> SEQ ID NO 118
<211> LENGTH: 11238
<212> TYPE: DNA
<213> ORGANISM: Artificial Sequence
<220> FEATURE:
<223> OTHER INFORMATION: Synthetic

<400> SEQUENCE: 118

```
tgcatagaag gtataatgat catgtcagga tatttgaggt atccacattt gggattgttt      60
aaagattaaa tgaaatagtg ttaaaagtat ttaatatgcc cttcaacaaa tgatgaggaa     120
atcttagaat ctgctcagac tccttcagtt tacatattag gaaactgagg cacagaaagg     180
agcagagact tgctcaagtc cacccaaagc agtagagcat tgtggttaaa tgcaggactt     240
cagtcagact gtctgggttc aaatcctggt tccacttgga catgggtttc cttacataaa     300
tcacttcacc tctctgagcc tcagttttct catatgcaaa gtgaggataa taataatacc     360
ttccttacat ggttactgat atgagtatta aatgtgccag ctcatgtgcc tggcgtatag     420
gaggtgcttt ataaacctta gctgttacca ctcatggcat tgccaaatgt gggacgggtc     480
tcctgactct ctggtgtgag attgatgaa tccacacttt ccagttccct tttctacctc     540
ctgggtatct tctcatatgg ttgtaagttc cttggaggaa gggaatgtgg cttgctctct     600
ccaccacgct gagcatataa gaggtgctga atgagcgctt ttattcactc ctctcatccc     660
cagccctcac cagctgggag ttgttgtagg tgtcaatttt ctgcctcttt ccaacaccct     720
gtgaggtgac tgagcattgt cttccctccc aggcagctca cagtgtaagc ttgtggacga     780
tatcgaattc gcacgacatt gattattgac tagttattaa tagtaatcaa ttacggggtc     840
attagttcat agcccatata tggagttccg cgttacataa cttacggtaa atggcccgcc     900
tggctgaccg cccaacgacc cccgcccatt gacgtcaata atgacgtatg ttcccatagt     960
aacgccaata gggactttcc attgacgtca atgggtggac tatttacggt aaactgccca    1020
cttggcagta catcaagtgt atcatatgcc aagtacgccc cctattgacg tcaatgacgg    1080
taaatggccc gcctggcatt atgcccagta catgacctta tgggactttc ctacttggca    1140
gtacatctac gtattagtca tcgctattac catgggtcga ggtgagcccc acgttctgct    1200
tcactctccc catctccccc ccctccccac cccaattttg tatttatttt atttttttaat    1260
tattttgtgc agcgatgggg gcggggggg ggggggcgcg cgccaggcgg ggcggggcgg    1320
ggcgagggg ggggcgggc gaggcggaga ggtgcggcgg cagccaatca gagcggcgcg    1380
ctccgaaagt ttcctttat ggcgaggcgg cggcggcggc ggccctataa aaagcgaagc    1440
gcgcggcggg cggagtcgc tgcgttgcct tcgccccgtg ccccgctccg cgccgcctcg    1500
cgccgcccgc cccggctctg actgaccgcg ttactcccac aggtgagcgg gcgggacggc    1560
ccttctcctc cgggctgtaa ttagcgcttg gtttaatgac ggctcgtttc ttttctgtgg    1620
ctgcgtgaaa gccttaaagg gctccgggag ggccctttgt gcgggggga gcggctcggg    1680
gggtgcgtgc gtgtgtgtgt gcgtgggag cgccgcgtgc ggcccgcgct gcccggcggc    1740
tgtgagcgct gcgggcgcgg cgcggggctt tgtgcgctcc gcgtgtgcgc gaggggagcg    1800
```

```
cggccggggg cggtgcccg cggtgcgggg gggctgcgag gggaacaaag gctgcgtgcg    1860
gggtgtgtgc gtgggggggt gagcagggggg tgtgggcgcg gcggtcgggc tgtaacccc    1920 ccctgcaccc ccctccccga gttgctgagc acggcccggc ttcgggtgcg gggctccgtg    1980
cggggcgtgg cgcggggctc gccgtgccgg gcgggggggtg gcggcaggtg ggggtgccgg   2040
gcggggcggg gccgcctcgg gccggggagg gctcggggga ggggcgcggc ggccccggag    2100
cgccggcggc tgtcgaggcg cggcgagccg cagccattgc cttttatggt aatcgtgcga    2160
gagggcgcag ggacttcctt tgtcccaaat ctggcggagc cgaaatctgg gaggcgccgc    2220
cgcaccccct ctagcgggcg cgggcgaagc ggtgcgcgc cggcaggaag gaaatgggcg     2280
gggagggcct tcgtgcgtcg ccgcgccgcc gtccccttct ccatctccag cctcggggct    2340
gccgcagggg gacggctgcc ttcggggggg acggggcagg gcggggttcg gcttctggcg    2400
tgtgaccggc ggctctagag cctctgctaa ccatgttcat gccttcttct ttttcctaca    2460 gggggggatcc gtttatctgc agaattcgcc cttgacgtcg ccaccatggc gcttccggtg    2520
acagcactgc tcctccccctt ggcgctgttg ctccacgcag caaggccgga catccagatg    2580
acccagagcc ccaccagcct gagcgccagc gtgggcgaca gagtgaccat cacctgcaga    2640
gccagccagg gcatcagcag ctggctgacc tggtaccagc agaagcccga gaaggccccc    2700
aagagcctga tctacgccgc cagcagcctg cagagcggcg tgcccagcag attcagcggc    2760
agcggcagcg gcaccgactt caccctgacc atcagcagcc tgcagcccga ggacttcgcc    2820
acctactact gccagcagta cgacagctac cccatcacct tcggccaggg caccagactg    2880
gagatcaagg gcggcggcgg cagcggcggc ggcggcagcg gcggcggcgg cagccaggtg    2940
cagctgcagc agtggggcgc cggcctgctg aagcccagcg agaccctgag cctgacctgc    3000
gccgtgtacg gcggcagctt cagcgcctac tactggagct ggatcagaca gccccccggc    3060
aagggcctgg agtggatcgg cgacatcaac cacggcggcg gcaccaacta caaccccagc    3120
ctgaagagca gagtgaccat cagcgtggac accagcaaga accagttcag cctgaagctg    3180
aacagcgtga ccgccgccga caccgccgtg tactactgcg ccagcctgac cgcctactgg    3240
ggccagggca gcctggtgac cgtgagcgcc gccgccttcg tgcccgtgtt cctgcccgcc    3300
aagcccacca ccacccccgc ccccagaccc ccaccccccg ccccccaccat cgccagccag    3360 cccctgagcc tgagacccga ggcctgcaga cccgccgccg gcggcgccgt gcacaccaga    3420
ggcctggact cgcctgcga catctacatc tgggccccc tggccggcac ctgcggcgtg     3480
ctgctgctga gcctggtgat cacccctgtac tgcaaccaca gaaacagaaa gagaggcaga   3540
aagaagctgc tgtacatctt caagcagccc ttcatgagac ccgtgcagac cacccaggag    3600
gaggacggct gcagctgcag attccccgag gaggaggagg cgggctgcga gctgagagtg    3660
aagttcagca gaagcgccga cgcccccgcc taccagcagg gccagaacca gctgtacaac    3720
gagctgaacc tgggcagaag agaggagtac gacgtgctgg acaagagaag aggcagagac    3780
cccgagatgg gcggcaagcc cagaagaaag aaccccccagg agggcctgta caacgagctg    3840
cagaaggaca gatggccgga ggcctacagc gagatcggca tgaagggcga gagaagaaga    3900
ggcaagggcc acgacggcct gtaccagggc ctgagcaccg ccaccaagga cacctacgac    3960
gccctgcaca tgcaggccct gcccccccaga ggaagcggag ctactaactt cagcctgctg    4020
aagcaggctg gagacgtgga ggagaaccct ggacctatgt ctcgctccgt tgccttagct    4080
gtgctcgcgc tactctctct ttctggatta gaggctgtca tggcgcccg aaccctcttc    4140
```

```
ctgggtggag gcggttcagg cggaggtggc tctggcggtg gcggatcgat ccagcgtact    4200
ccaaagattc aggtttactc acgtcatcca gcagagaatg gaaagtcaaa tttcctgaat    4260
tgctatgtgt ctgggtttca tccatccgac attgaagttg acttactgaa gaatggagag    4320
agaattgaaa agtgtagca ttcagacttg tctttcagca aggactggtc tttctatctc     4380
ttgtactaca ctgaattcac ccccactgaa aaagatgagt atgcctgccg tgtgaaccat    4440
gtgactttgt cacagcccaa gatagttaag tgggatcgag acatgggtgg tggtggttct    4500
ggtggtggtg gttctggcgg cggcggctcc ggtggtggtg gatccggctc ccactccttg    4560
aagtatttcc acacttccgt gtcccggccc ggccgcgggg agccccgctt catctctgtg    4620
ggctacgtgg acgacaccca gttcgtgcgc ttcgacaacg acgccgcgag tccgaggatg    4680
gtgccgcggg cgccgtggat ggagcaggag gggtcagagt attgggaccg ggagacacgg    4740
agcgccaggg acaccgcaca gattttccga gtgaatctgc ggacgctgcg cggctactac    4800
aatcagagcg aggccgggtc tcacaccctg cagtggatgc atggctgcga gctggggccc    4860
gacgggcgct tcctccgcgg gtatgaacag ttcgcctacg acggcaagga ttatctcacc    4920
ctgaatgagg acctgcgctc ctggaccgcg gtggacacgg cggctcagat ctccgagcaa    4980
aagtcaaatg atgcctctga ggcggagcac cagagagcct acctggaaga cacatgcgtg    5040
gagtggctcc acaaataccT ggagaagggg aaggagacgc tgcttcacct ggagccccca    5100
aagacacacg tgactcacca ccccatctct gaccatgagg ccaccctgag gtgctgggcc    5160
ctgggcttct accctgcgga tcacactg acctggcagc aggatgggga gggccatacc    5220
caggacacgg agctcgtgga gaccaggcct gcagggatg aaccttcca gaagtgggca    5280
gctgtggtgg tgccttctgg agaggagcag agatacacgt gccatgtgca gcatgagggg    5340
ctacccgagc ccgtcaccct gagatggaag ccggcttccc agcccaccat ccccatcgtg    5400
ggcatcattg ctggcctggt tctccttgga tctgtggtct ctggagctgt ggttgctgct    5460
gtgatatgga ggaagaagag ctcaggtgga aaaggaggga gctactctaa ggctgagtgg    5520
agcgacagtg cccaggggtc tgagtctcac agcttgtaat gatagccgct gatcagcctc    5580
gactgtgcct tctagttgcc agccatctgt tgtttgcccc tccccgtgc cttccttgac     5640
cctggaaggt gccactccca ctgtccttc ctaataaaat gaggaaattg catcgcattg     5700
tctgagtagg tgtcattcta ttctgggggg tggggtgggg caggacagca agggggagga    5760
ttgggaagac aatagcaggc atgctgggga tgcggtgggc tctatgggtc gactgaccag    5820
atggacctgg ctggagaaga agagattgag ctctactcag gtgggccctc ctccctctgg    5880
tctcttccgg tatcccccac ccctcagctt gctgtagaga cggcaatcag gggaaattct    5940
ggtccctgcc ctcccgtcag caccacggac agctcccacg tctgtgggac gctctctgca    6000
gatggggatg atctcccagc cctgccccgc ctctccctcg ttccccacca gccctctttc    6060
cagaaatttc cttcttcatc caagggactt ttcctcccag aacccgacac agacaccatc    6120
aactgcgacc agttcagcag gctgttgtgt gacatggaag gtgatgaaga gaccagggag    6180
gcttatgcca atatcggtga ggaagcacct gagcccagaa aaggacaatc aagggcaaga    6240
gttctttgct gccacttgtc aatatcaccc attcatcatg agccacgtca gtcccctccc    6300
acagaaatca ttgcaagggg gatgcggagc aatggctgga ggaacggaga ctccagggaa    6360
gagaggggag atggaggcca gtgggggaaa taggcccctt cactaatgac caccaagaaa    6420
acaaaatctc atgtttacat cctccacctc catttctata cgcatttctg cttcttgctc    6480
ttctgtccat cctttctaca aagcccatac catacacccc tttcccttt cctcccagct    6540
```

```
ccttagccaa gctactctag tatttgtaat aactagcatt tactggatac tcatagtatg    6600
ctcattgctg tccggtaacc acgtgcggac cgggctccgg tgcccgtcag tgggcagagc    6660
gcacatcgcc cacagtcccc gagaagttgg ggggagggt cggcaattga accggtgcct    6720
agagaaggtg gcgcgggta aactgggaaa gtgatgtcgt gtactggctc cgccttttc     6780
ccgagggtgg gggagaaccg tatataagtg cagtagtcgc cgtgaacgtt cttttcgca    6840
acgggtttgc cgccagaaca caggtaagtg ccgtgtgtgg ttcccgcggg cctgcctct    6900
ttacgggtta tggcccttgc gtgccttgaa ttacttccac tggctgcagt acgtgattct    6960
tgatcccgag cttcggggttg gaagtgggtg ggagagttcg aggccttgcg cttaaggagc   7020
cccttcgcct cgtgcttgag ttgaggcctg gcctgggcgc tggggccgcc gcgtgcgaat    7080
ctggtggcac cttcgcgcct gtctcgctgc tttcgataag tctctagcca tttaaaattt    7140
ttgatgacct gctgcgacgc ttttttctg gcaagatagt cttgtaaatg cgggccaaga    7200
tctgcacact ggtatttcgg tttttggggc cgcgggcggc gacggggccc gtgcgtccca    7260
gcgcacatgt tcggcgaggc ggggcctgcg agcgcggcca ccgagaatcg gacgggggta    7320
gtctcaagct ggccggcctg ctctggtgcc tggcctcgcg ccgccgtgta tcgccccgcc    7380
ctgggcggca aggctggccc ggtcggcacc agttgcgtga gcggaaagat ggccgcttcc    7440
cggccctgct gcagggagct caaaatggag gacgcggcgc tcgggagagc gggcgggtga    7500
gtcacccaca caaaggaaaa gggcctttcc gtcctcagcc gtcgcttcat gtgactccac    7560
ggagtaccgg gcgccgtcca ggcacctcga ttagttctcg agcttttgga gtacgtcgtc    7620
tttaggttgg ggggagggt tttatgcgat ggagtttccc cacactgagt gggtggagac    7680
tgaagttagg ccagcttggc acttgatgta attctccttg gaatttgccc tttttgagtt    7740
tggatcttgg ttcattctca agcctcagac agtggttcaa agttttttc ttccatttca    7800
ggtgtcgtga cttgacgtcg ccaccatgag gatatttgct gtctttatat tcatgaccta    7860
ctggcatttg ctgaacgcat ttactgtcac ggttcccaag gacctatatg tggtagagta    7920
tggtagcaat atgacaattg aatgcaaatt cccagtagaa aaacaattag acctggctgc    7980
actaattgtc tattgggaaa tggaggataa gaacattatt caatttgtgc atggagagga    8040
agacctgaag gttcagcata gtagctacag acagagggcc cggctgttga aggaccagct    8100
ctccctggga aatgctgcac ttcagatcac agatgtgaaa ttgcaggatg caggggtgta    8160
ccgctgcatg atcagctatg gtggtgccga ctacaagcga attactgtga aagtcaatgc    8220
cccatacaac aaaatcaacc aaagaatttt ggttgtggat ccagtcacct ctgaacatga    8280
actgacatgt caggctgagg ctacccccaa ggccgaagtc atctggacaa gcagtgacca    8340
tcaagtcctg agtggtaaga ccaccaccac caattccaag agagaggaga aacttttcaa    8400
tgtgaccagc acactgagaa tcaacacaac aactaatgag atttctact gcactttag    8460
gagattagat cctgaggaaa accatacagc tgaattggtc atcccagaac tacctctggc    8520
acatcctcca aatgaaagga ctcacttggt aattctggga gccatcttat tatgccttgg    8580
tgtagcactg acattcatct tccgtttaag aaaagggaga atgatggatg tgaaaaaatg    8640
tggcatccaa gatacaaact caaagaagca agtgatacca catttggagg agacgtaacc    8700
gctgatcagc ctcgaaactt gtttattgca gcttataatg gttacaaata aagcaatagc    8760
atcacaaatt tcacaaataa agcattttt tcactgcatt ctagttgtgg tttgtccaaa    8820
ctcatcaatg tatcttaggc gcctgatgcg gtatttctc cttacgcatc tgtgcggtat    8880
```

```
ttcacaccgc atacagtact gtcaaagcaa ccatagtacg cgccctgtag cggcgcatta   8940
agcgcggcgg gtgtggtggt tacgcgcagc gtgaccgcta cacttgccag cgccctagcg   9000
cccgctcctt tcgctttctt cccttccttt ctcgccacgt tcgccggctt tccccgtcaa   9060
gctctaaatc gggggctccc tttagggttc cgatttagtg ctttacggca cctcgacccc   9120
aaaaaacttg atttgggtga tggttcacgt agtgggccat cgccctgata gacggttttt   9180
cgcccttttga cgttggagtc cacgttcttt aatagtggac tcttgttcca aactggaaca   9240
acactcaacc ctatctcggg ctattctttt gatttataag ggattttgcc gatttcggcc   9300
tattggttaa aaaatgagct gatttaacaa aaatttaacg cgaattttaa caaaatatta   9360
acgtttacaa ttttatggtg cactctcagt acaatctgct ctgatgccgc atagttaagc   9420
cagccccgac acccgccaac acccgctgac gcgccctgac gggcttgtct gctcccggca   9480
tccgcttaca gacaagctgt gaccgtctcc gggagctgca tgtgtcagag gttttcaccg   9540
tcatcaccga aacgcgcgag acgaaagggc ctcgtgatac gcctattttt ataggttaat   9600
gtcatgaaca ataaaactgt ctgcttacat aaacagtaat acaaggggtg ttatgagcca   9660
tattcaacgg gaaacgtcga ggccgcgatt aaattccaac atggatgctg atttatatgg   9720
gtataaatgg gctcgcgata atgtcgggca atcaggtgcg acaatctatc gcttgtatgg   9780
gaagcccgat gcgccagagt tgtttctgaa acatggcaaa ggtagcgttg ccaatgatgt   9840
tacagatgag atggtcagac taaactggct gacggaattt atgcctcttc cgaccatcaa   9900
gcattttatc cgtactcctg atgatgcatg gttactcacc actgcgatcc ccggaaaaac   9960
agcattccag gtattagaag aatatcctga ttcaggtgaa aatattgttg atgcgctggc  10020
agtgttcctg cgccggttgc attcgattcc tgtttgtaat tgtccttttta acagcgatcg  10080
cgtatttcgt ctcgctcagg cgcaatcacg aatgaataac ggtttggttg atgcgagtga  10140
ttttgatgac gagcgtaatg gctggcctgt tgaacaagtc tggaaagaaa tgcataaact  10200
tttgccattc tcaccggatt cagtcgtcac tcatggtgat ttctcacttg ataaccttat  10260
ttttgacgag gggaaattaa taggttgtat tgatgttgga cgagtcggaa tcgcagaccg  10320
ataccaggat cttgccatcc tatggaactg cctcggtgag ttttctcctt cattacagaa  10380
acggcttttt caaaaatatg gtattgataa tcctgatatg aataaattgc agtttcattt  10440
gatgctcgat gagtttttct aatctcatga ccaaaatccc ttaacgtgag ttttcgttcc  10500
actgagcgtc agacccccgta gaaaagatca aaggatcttc ttgagatcct ttttttctgc  10560
gcgtaatctg ctgcttgcaa acaaaaaaac caccgctacc agcggtggtt tgtttgccgg  10620
atcaagagct accaactctt tttccgaagg taactggctt cagcagagcg cagataccaa  10680
atactgtcct tctagtgtag ccgtagttag gccaccactt caagaactct gtagcaccgc  10740
ctacatacct cgctctgcta atcctgttac cagtggctgc tgccagtggc gataagtcgt  10800
gtcttaccgg gttggactca agacgatagt taccggataa ggcgcagcgg tcgggctgaa  10860
cggggggttc gtgcacacag cccagcttgg agcgaacgac ctacaccgaa ctgagatacc  10920
tacagcgtga gctatgagaa agcgccacgc ttcccgaagg gagaaaggcg gacaggtatc  10980
cggtaagcgg cagggtcgga acaggagagc gcacgaggga gcttccaggg ggaaacgcct  11040
ggtatcttta tagtcctgtc gggtttcgcc acctctgact tgagcgtcga ttttttgtgat  11100
gctcgtcagg ggggcggagc ctatggaaaa acgccagcaa cgcggccttt ttacggttcc  11160
tggccttttg ctggccttttt gctcacatgt gcggccgcac gcgtcatatt tatggggtat  11220
atgtgaatat ttattaca                                                 11238
```

<210> SEQ ID NO 119
<211> LENGTH: 3015
<212> TYPE: DNA
<213> ORGANISM: Artificial Sequence
<220> FEATURE:
<223> OTHER INFORMATION: Synthetic

<400> SEQUENCE: 119

```
cagatccagc tgcagcagag cggccccgag gtggtgaagc ccggcgccag cgtgaagatc      60
agctgcaagg ccagcggcta caccttcacc gactactaca tcacctgggt gaagcagaag     120
cccggccagg gcctggagtg gatcggctgg atctacccccg gcagcggcaa caccaagtac     180
aacgagaagt tcaagggcaa ggccaccctg accgtggaca ccagcagcag caccgccttc     240
atgcagctga gcagcctgac cagcgaggac accgccgtgt acttctgcgc caactacggc     300
aactactggt tcgcctactg gggccagggc acccaggtga ccgtgagcgc cggcggcggc     360
ggcagcggcg gcggcggcag cggcggcggc ggcagcgaca tcgtgctgac ccagagcccc     420
gccagcctgg ccgtgagcct gggccagaga gccaccatca gctgcaaggc cagccagagc     480
gtggacttcg acgccgacag ctacatgaac tggtaccagc agaagcccgg ccagcccccc     540
aaggtgctga tctacgccgc cagcaacctg gagagcggca tccccgccag attcagcggc     600
agcggcagcg gcaccgactt caccctgaac atccaccccg tggaggagga ggacgccgcc     660
acctactact gccagcagag caacgaggac ccctggacct tcggcggcgg caccaagctg     720
gagatcaaga gcgccgccgc cttcgtgccc gtgttcctgc ccgccaagcc caccaccacc     780
cccgccccca cccccccccac ccccgccccc accatcgcca gccagcccct gagcctgaga     840
cccgaggcct gcagacccgc cgccggcggc gccgtgcaca ccagaggcct ggacttcgcc     900
tgcgacatct acatctgggc ccccctggcc ggcacctgcg gcgtgctgct gctgagcctg     960
gtgatcaccc tgtactgcaa ccacagaaac agaagcaaga aagcagact gctgcacagc    1020
gactacatga acatgacccc cagaagaccc ggccccacca gaaagcacta ccagccctac    1080
gccccccccca gagacttcgc cgcctacaga agcagagtga agttcagcag aagcgccgac    1140
gcccccgcct accagcaggg ccagaaccag ctgtacaacg agctgaacct gggcagaaga    1200
gaggagtacg acgtgctgga caagagaaga ggcagagacc ccgagatggg cggcaagccc    1260
agaagaaaga acccccagga gggcctgtac aacgagctgc agaaggacaa gatggccgag    1320
gcctacagcg agatcggcat gaagggcgag agaagaagag caagggcca cgacggcctg    1380
taccagggcc tgagcaccgc caccaaggac acctacgacg ccctgcacat gcaggccctg    1440
cccccccagag gaagcggagc tactaacttc agcctgctga gcaggctgg agacgtggag    1500
gagaaccctg gacctatgtc tcgctccgtt gccttagctg tgctcgcgct actctctctt    1560
tctggattag aggctgtcat ggcgccccga acctcttcc tgggtggagg cggttcaggc    1620
ggaggtggct ctggcggtgg cggatcgatc cagcgtactc aaagattca ggtttactca    1680
cgtcatccag cagagaatgg aaagtcaaat ttcctgaatt gctatgtgtc tgggtttcat    1740
ccatccgaca ttgaagttga cttactgaag aatggagaga gaattgaaaa agtggagcat    1800
tcagacttgt ctttcagcaa ggactggtct ttctatctct tgtactacac tgaattcacc    1860
cccactgaaa aagatgagta tgcctgccgt gtgaaccatg tgactttgtc acagcccaag    1920
atagttaagt gggatcgaga catggtggt ggtggttctg gtggtggtgg ttctggcggc    1980
ggcggctccg gtggtggtgg atccggctcc cactccttga agtatttcca cacttccgtg    2040
```

```
tcccggcccg gccgcgggga gccccgcttc atctctgtgg gctacgtgga cgacacccag    2100
ttcgtgcgct tcgacaacga cgccgcgagt ccgaggatgg tgccgcgggc gccgtggatg    2160
gagcaggagg ggtcagagta ttgggaccgg gagacacgga gcgccaggga caccgcacag    2220
attttccgag tgaatctgcg gacgctgcgc ggctactaca atcagagcga ggccgggtct    2280
cacaccctgc agtggatgca tggctgcgag ctggggcccg acgggcgctt cctccgcggg    2340
tatgaacagt tcgcctacga cggcaaggat tatctcaccc tgaatgagga cctgcgctcc    2400
tggaccgcgg tggacacggc ggctcagatc tccgagcaaa agtcaaatga tgcctctgag    2460
gcggagcacc agagagccta cctggaagac acatgcgtgg agtggctcca caaatacctg    2520
gagaagggga aggagacgct gcttcacctg gagcccccaa agacacacgt gactcaccac    2580
cccatctctg accatgaggc caccctgagg tgctgggccc tgggcttcta ccctgcggag    2640
atcacactga cctggcagca ggatggggag ggccataccc aggacacgga gctcgtggag    2700
accaggcctg cagggatggg aaccttccag aagtgggcag ctgtggtggt gccttctgga    2760
gaggagcaga gatacacgtg ccatgtgcag catgaggggc tacccgagcc cgtcaccctg    2820
agatggaagc cggcttccca gcccaccatc cccatcgtgg gcatcattgc tggcctggtt    2880
ctccttggat ctgtggtctc tggagctgtg gttgctgctg tgatatggag gaagaagagc    2940
tcaggtggaa aaggagggag ctactctaag gctgagtgga gcgacagtgc ccaggggtct    3000
gagtctcaca gcttg                                                    3015
```

<210> SEQ ID NO 120
<211> LENGTH: 2985
<212> TYPE: DNA
<213> ORGANISM: Artificial Sequence
<220> FEATURE:
<223> OTHER INFORMATION: Synthetic

<400> SEQUENCE: 120

```
caggtgcagc tgcagcagtg gggcgccggc ctgctgaagc ccagcgagac cctgagcctg      60
acctgcgccg tgtacggcgg cagcttcagc gcctactact ggagctggat cagacagccc     120
cccggcaagg gcctggagtg gatcggcgac atcaaccacg cggcggcac caactacaac      180 cccagcctga gagcagagt gaccatcagc gtggacacca gcaagaacca gttcagcctg     240
aagctgaaca gcgtgaccgc cgccgacacc gccgtgtact actgcgccag cctgaccgcc     300
tactggggcc agggcagcct ggtgaccgtg agcagcggcg gcggcggcag cggcggcggc     360
ggcagcggcg gcggcggcag cgacatccag atgacccaga gccccaccag cctgagcgcc     420
agcgtgggcg acagagtgac catcacctgc agagccagcc agggcatcag cagctggctg     480
acctggtacc agcagaagcc cgagaaggcc cccaagagcc tgatctacgc cgccagcagc     540
ctgcagagcg gcgtgcccag cagattcagc ggcagcggca gcggcaccga cttcacccctg    600 accatcagca gcctgcagcc cgaggacttc gccacctact actgccagca gtacgacagc     660 tacccccatca ccttcggcca gggcaccaga ctggagatca gagcgccgc cgccttcgtg     720 cccgtgttcc tgcccgccaa gcccaccacc accccgccc cagacccccc cacccccgcc     780
cccaccatcg ccagccagcc cctgagcctg agacccgagg cctgcagacc cgccgccggc     840
ggcgccgtgc acaccagagg cctggacttc gcctgcgaca tctacatctg ggcccccctg     900
gccggcacct gcggcgtgct gctgctgagc ctggtgatca ccctgtactg caaccacaga     960
aacagaaaga gaggcagaaa gaagctgctg tacatcttca gcagcccctt catgagaccc    1020
gtgcagacca cccaggagga ggacggctgc agctgcagat tccccgagga ggaggagggc    1080
```

```
ggctgcgagc tgagagtgaa gttcagcaga agcgccgacg cccccgccta ccagcagggc    1140
cagaaccagc tgtacaacga gctgaacctg ggcagaagag aggagtacga cgtgctggac    1200
aagagaagag gcagagaccc cgagatgggc ggcaagccca agaagaagaa cccccaggag    1260
ggcctgtaca acgagctgca gaaggacaag atggccgagg cctacagcga gatcggcatg    1320
aagggcgaga agaagaagag caagggccac gacggcctgt accagggcct gagcaccgcc    1380
accaaggaca cctacgacgc cctgcacatg caggccctgc cccccagagg aagcggattc    1440
agcctgctga gcaggctgga gacgtggaga gaaccctg gacctatgtc tcgctccgtt    1500
gccttagctg tgctcgcgct actctctctt tctggattag aggctgtcat ggcgccccga    1560
accctcttcc tgggtggagg cggttcaggc ggaggtggct ctggcggtgg cggatcgatc    1620
cagcgtactc caaagattca ggtttactca cgtcatccag cagagaatgg aaagtcaaat    1680
ttcctgaatt gctatgtgtc tgggtttcat ccatccgaca ttgaagttga cttactgaag    1740
aatggagaga gaattgaaaa agtggagcat tcagacttgt cttttcagcaa ggactggtct    1800 ttctatctct tgtactacac tgaattcacc cccactgaaa aagatgagta tgcctgccgt    1860
gtgaaccatg tgactttgtc acagcccaag atagttaagt gggatcgaga catggtggt    1920 ggtggttctg gtggtggtgg ttctggcggc ggcggctccg gtggtggtgg atccggctcc    1980
cactccttga gtatttcca cacttccgtg tcccggcccg gccgcgggga gccccgcttc    2040
atctctgtgg gctacgtgga cgacacccag ttcgtgcgct cgacaacga cgccgcgagt    2100 ccgaggatgg tgccgcgggc gccgtggatg gagcaggagg ggtcagagta ttgggaccgg    2160
gagacacgga gcgccaggga caccgcacag attttccgag tgaatctgcg gacgctgcgc    2220
ggctactaca atcagagcga ggccgggtct cacaccctgc agtggatgca tggctgcgag    2280
ctggggcccg acgggcgctt cctccgcggg tatgaacagt tcgcctacga cggcaaggat    2340
tatctcaccc tgaatgagga cctgcgctcc tggaccgcgg tggacacggc ggctcagatc    2400
tccgagcaaa agtcaaatga tgcctctgag gcggagcacc agagagccta cctggaagac    2460
acatgcgtgg agtggctcca caaatacctg gagaagggga aggagacgct gcttcacctg    2520
gagcccccaa agacacacgt gactcaccac cccatctctg accatgaggc caccctgagg    2580
tgctgggccc tgggcttcta ccctgcggag atcacactga cctggcagca ggatggggag    2640
ggccataccc aggacacgga gctcgtggag accaggcctg caggggatgg aaccttccag    2700
aagtgggcag ctgtggtggt gccttctgga gaggagcaga gatacacgtg ccatgtgcag    2760
catgaggggc tacccgagcc cgtcaccctg agatggaagc cggcttccca gcccaccatc    2820
cccatcgtgg gcatcattgc tggcctggtt ctccttggat ctgtggtctc tggagctgtg    2880
gttgctgctg tgatatggag gaagaagagc tcaggtggaa aaggaggggag ctactctaag    2940 gctgagtgga gcgacagtgc ccaggggtct gagtctcaca gcttg                    2985
```

<210> SEQ ID NO 121
<211> LENGTH: 2988
<212> TYPE: DNA
<213> ORGANISM: Artificial Sequence
<220> FEATURE:
<223> OTHER INFORMATION: Synthetic

<400> SEQUENCE: 121

```
gacatccaga tgacccagag ccccaccagc ctgagcgcca gcgtgggcga cagagtgacc      60
atcacctgca gagccagcca gggcatcagc agctggctga cctggtacca gcagaagccc     120
```

-continued

| | |
|---|---|
| gagaaggccc ccaagagcct gatctacgcc gccagcagcc tgcagagcgg cgtgcccagc | 180 |
| agattcagcg gcagcggcag cggcaccgac ttcaccctga ccatcagcag cctgcagccc | 240 |
| gaggacttcg ccacctacta ctgccagcag tacgacagct accccatcac cttcggccag | 300 |
| ggcaccagac tggagatcaa gggcggcggc ggcagcggcg gcggcggcag cggcggcggc | 360 |
| ggcagccagg tgcagctgca gcagtggggc gccggcctgc tgaagcccag cgagaccctg | 420 |
| agcctgacct gcgccgtgta cggcggcagc ttcagcgcct actactggag ctggatcaga | 480 |
| cagccccccg gcaagggcct ggagtggatc ggcgacatca ccacggcgg cggcaccaac | 540 |
| tacaacccca gcctgaagag cagagtgacc atcagcgtgg acaccagcaa gaaccagttc | 600 |
| agcctgaagc tgaacagcgt gaccgccgcc gacaccgccg tgtactactg cgccagcctg | 660 |
| accgcctact ggggccaggg cagcctggtg accgtgagcg ccgccgcctt cgtgcccgtg | 720 |
| ttcctgcccg ccaagcccac caccaccccc gcccccagac cccccacccc cgcccccacc | 780 |
| atcgccagcc agcccctgag cctgagaccc gaggcctgca gacccgccgc cggcggcgcc | 840 |
| gtgcacacca gaggcctgga cttcgcctgc gacatctaca tctgggcccc cctggccggc | 900 |
| acctgcggcg tgctgctgct gagcctggtg atcaccctgt actgcaacca cagaaacaga | 960 |
| aagagaggca gaaagaagct gctgtacatc ttcaagcagc ccttcatgag acccgtgcag | 1020 |
| accacccagg aggaggacgg ctgcagctgc agattccccg aggaggagga gggcggctgc | 1080 |
| gagctgagag tgaagttcag cagaagcgcc gacgcccccg cctaccagca gggccagaac | 1140 |
| cagctgtaca acgagctgaa cctgggcaga gagaggagt acgacgtgct ggacaagaga | 1200 |
| agaggcagag accccgagat gggcggcaag cccagaagaa agaaccccca ggagggcctg | 1260 |
| tacaacgagc tgcagaagga caagatggcc gaggcctaca gcgagatcgg catgaagggc | 1320 |
| gagagaagaa gaggcaaggg ccacgacggc ctgtaccagg gcctgagcac cgccaccaag | 1380 |
| gacacctacg acgccctgca catgcaggcc ctgcccccca ggaagcgg agctactaac | 1440 |
| ttcagcctgc tgaagcaggc tggagacgtg aggagaacc ctggacctat gtctcgctcc | 1500 |
| gttgccttag ctgtgctcgc gctactctct ctttctggat tagaggctgt catggcgccc | 1560 |
| cgaaccctct tcctgggtgg aggcggttca ggcggaggtg gctctggcgg tggcggatcg | 1620 |
| atccagcgta ctccaaagat tcaggtttac tcacgtcatc cagcagagaa tggaaagtca | 1680 |
| aatttcctga attgctatgt gtctgggttt catccatccg acattgaagt tgacttactg | 1740 |
| aagaatggag agagaattga aaaagtggag cattcagact tgtctttcag caaggactgg | 1800 |
| tctttctatc tcttgtacta cactgaattc accccccactg aaaaagatga gtatgcctgc | 1860 |
| cgtgtgaacc atgtgacttt gtcacagccc aagatagtta agtgggatcg agacatgggt | 1920 |
| ggtggtggtt ctggtggtgg tggttctggc ggcggcggct ccgtgtggtg tggatccggc | 1980 |
| tcccactcct tgaagtattt ccacacttcc gtgtccggc ccggccgcgg ggagccccgc | 2040 |
| ttcatctctg tgggctacgt ggacgacacc cagttcgtgc gcttcgacaa cgacgccgcg | 2100 |
| agtccgagga tggtgccgcg ggcgccgtgg atggagcagg aggggtcaga gtattgggac | 2160 |
| cgggagacac ggagcgccag ggacaccgca cagattttcc gagtgaatct gcggacgctg | 2220 |
| cgcggctact acaatcagag cgaggccggg tctcacaccc tgcagtggat gcatggctgc | 2280 |
| gagctggggc ccgacgggcg cttcctccgc gggtatgaac agttcgccta cgacggcaag | 2340 |
| gattatctca ccctgaatga ggaccgcgc tcctggaccg cggtggacac ggcggctcag | 2400 |
| atctccgagc aaaagtcaaa tgatgcctct gaggcggagc accagagagc ctacctggaa | 2460 |
| gacacatgcg tggagtggct ccacaaatac ctggagaagg ggaaggagac gctgcttcac | 2520 |

```
ctggagcccc caaagacaca cgtgactcac cacccatct ctgaccatga ggccaccctg    2580
aggtgctggg ccctgggctt ctaccctgcg gagatcacac tgacctggca gcaggatggg    2640
gagggccata cccaggacac ggagctcgtg gagaccaggc ctgcagggga tggaaccttc    2700
cagaagtggg cagctgtggt ggtgccttct ggagaggagc agagatacac gtgccatgtg    2760
cagcatgagg ggctacccga gcccgtcacc ctgagatgga agccggcttc ccagcccacc    2820
atccccatcg tgggcatcat tgctggcctg gttctccttg gatctgtggt ctctggagct    2880
gtggttgctg ctgtgatatg gaggaagaag agctcaggtg gaaaggagg gagctactct    2940 aaggctgagt ggagcgacag tgcccagggg tctgagtctc acagcttg                2988
```

<210> SEQ ID NO 122
<211> LENGTH: 88
<212> TYPE: PRT
<213> ORGANISM: Artificial Sequence
<220> FEATURE:
<223> OTHER INFORMATION: Synthetic

<400> SEQUENCE: 122

Ser Ala Ala Ala Phe Val Pro Val Phe Leu Pro Ala Lys Pro Thr Thr
1               5                   10                  15

Thr Pro Ala Pro Arg Pro Pro Thr Pro Ala Pro Thr Ile Ala Ser Gln
            20                  25                  30

Pro Leu Ser Leu Arg Pro Glu Ala Cys Arg Pro Ala Ala Gly Gly Ala
        35                  40                  45

Val His Thr Arg Gly Leu Asp Phe Ala Cys Asp Ile Tyr Ile Trp Ala
    50                  55                  60

Pro Leu Ala Gly Thr Cys Gly Val Leu Leu Leu Ser Leu Val Ile Thr
65                  70                  75                  80

Leu Tyr Cys Asn His Arg Asn Arg
                85

<210> SEQ ID NO 123
<211> LENGTH: 40
<212> TYPE: PRT
<213> ORGANISM: Homo sapiens

<400> SEQUENCE: 123

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser
        35                  40

<210> SEQ ID NO 124
<211> LENGTH: 42
<212> TYPE: PRT
<213> ORGANISM: Homo sapiens

<400> SEQUENCE: 124

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 125
<211> LENGTH: 112
<212> TYPE: PRT
<213> ORGANISM: Homo sapiens

<400> SEQUENCE: 125

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 126
<211> LENGTH: 264
<212> TYPE: DNA
<213> ORGANISM: Artificial Sequence
<220> FEATURE:
<223> OTHER INFORMATION: Synthetic

<400> SEQUENCE: 126

```
agcgccgccg ccttcgtgcc cgtgttcctg cccgccaagc ccaccaccac ccccgccccc    60
agaccccca ccccgccccc accatcgccc agccagcccc tgagcctgag acccgaggcc   120
tgcagaccccg ccgccggcgg cgccgtgcac accagaggcc tggacttcgc ctgcgacatc   180
tacatctggg ccccccggc cggcacctgc ggcgtgctgc tgctgagcct ggtgatcacc   240
ctgtactgca accacagaaa caga                                          264
```

<210> SEQ ID NO 127
<211> LENGTH: 126
<212> TYPE: DNA
<213> ORGANISM: Artificial Sequence
<220> FEATURE:
<223> OTHER INFORMATION: Synthetic

<400> SEQUENCE: 127

```
aagagaggca gaaagaagct gctgtacatc ttcaagcagc ccttcatgag acccgtgcag    60
accacccagg aggaggacgg ctgcagctgc agattccccg aggaggagga gggcggctgc   120
gagctg                                                             126
```

<210> SEQ ID NO 128
<211> LENGTH: 336
<212> TYPE: DNA
<213> ORGANISM: Artificial Sequence
<220> FEATURE:
<223> OTHER INFORMATION: Synthetic

<400> SEQUENCE: 128

```
agagtgaagt tcagcagaag cgccgacgcc ccgcctacc agcagggcca gaaccagctg    60
tacaacgagc tgaacctggg cagaagagag gagtacgacg tgctggacaa gagaagaggc   120
```

| | |
|---|---|
| agagaccccg agatgggcgg caagcccaga agaaagaacc cccaggaggg cctgtacaac | 180 |
| gagctgcaga aggacaagat ggccgaggcc tacagcgaga tcggcatgaa gggcgagaga | 240 |
| agaagaggca agggccacga cggcctgtac cagggcctga gcaccgccac caaggacacc | 300 |
| tacgacgccc tgcacatgca ggccctgccc cccaga | 336 |

<210> SEQ ID NO 129
<211> LENGTH: 1128
<212> TYPE: DNA
<213> ORGANISM: Homo sapiens

<400> SEQUENCE: 129

| | |
|---|---|
| atggaaactc tttctaatgc aagtggtact tttgccatac gccttttaaa gatactgtgt | 60 |
| caagataacc cttcgcacaa cgtgttctgt tctcctgtga gcatctcctc tgccctggcc | 120 |
| atggttctcc tagggcaaa gggaaacacc gcaacccaga tggcccaggc actgtcttta | 180 |
| aacacagagg aagacattca tcgggctttc cagtcgcttc tcactgaagt gaacaaggct | 240 |
| ggcacacagt acctgctgag aacggccaac aggctctttg agagaaaac ttgtcagttc | 300 |
| ctctcaacgt ttaaggaatc ctgtcttcaa ttctaccatg ctgagctgaa ggagcttttcc | 360 |
| tttatcagag ctgcagaaga gtccaggaaa cacatcaaca cctgggtctc aaaaaagacc | 420 |
| gaaggtaaaa ttgaagagtt gttgccgggt agctcaattg atgcagaaac caggctggtt | 480 |
| cttgtcaatg ccatctactt caaaggaaag tggaatgaac cgtttgacga acatacaca | 540 |
| agggaaatgc cctttaaaat aaaccaggag gagcaaaggc cagtgcagat gatgtatcag | 600 |
| gaggccacgt ttaagctcgc ccacgtgggc gaggtgcgcg cgcagctgct ggagctgccc | 660 |
| tacgccagga aggagctgag cctgctggtg ctgctgcctg acgacggcgt ggagctcagc | 720 |
| acggtggaaa aaagtctcac tttgagaaa ctcacagcct ggaccaagcc agactgtatg | 780 |
| aagagtactg aggttgaagt tctccttcca aaatttaaac tacaagagga ttatgacatg | 840 |
| gaatctgtgc ttcggcattt gggaattgtt gatgccttcc aacagggcaa ggctgacttg | 900 |
| tcggcaatgt cagcggagag agacctgtgt ctgtccaagt tcgtgcacaa gagttttgtg | 960 |
| gaggtgaatg aagaaggcac cgaggcagcg gcagcgtcga gctgctttgt agttgcagag | 1020 |
| tgctgcatgg aatctggccc caggttctgt gctgaccacc cttccttttt cttcatcagg | 1080 |
| cacaacagag ccaacagcat tctgttctgt ggcaggttct catcgcca | 1128 |

<210> SEQ ID NO 130
<211> LENGTH: 8963
<212> TYPE: DNA
<213> ORGANISM: Artificial Sequence
<220> FEATURE:
<223> OTHER INFORMATION: Synthetic

<400> SEQUENCE: 130

| | |
|---|---|
| cctgcaggca gctgcgcgct cgctcgctca ctgaggccgc ccgggcgtcg ggcgaccttt | 60 |
| ggtcgcccgg cctcagtgag cgagcgagcg cgcagagagg gagtggccaa ctccatcact | 120 |
| aggggttcct gcggccgcac gcgtgttcta gggtggaaac taagagaatg atgtacctag | 180 |
| agggcgctgg aagctctaaa gccctagcag ttactgcttt tactattagt ggtcgttttt | 240 |
| ttctcccccc cgcccccga caaatcaaca gaacaaagaa aattacctaa acagcaagga | 300 |
| catagggagg aacttcttgg cacagaactt tccaaacact ttttcctgaa gggatacaag | 360 |
| aagcaagaaa ggtactcttt cactaggacc ttctctgagc tgtcctcagg atgcttttgg | 420 |
| gactattttt cttacccaga gaatggagaa accctgcagg gaattcccaa gctgtagtta | 480 |

-continued

```
taaacagaag ttctccttct gctaggtagc attcaaagat cttaatcttc tgggtttccg   540
ttttctcgaa tgaaaaatgc aggtccgagc agttaactgg ctggggcacc attagcaagt   600
cacttagcat ctctggggcc agtctgcaaa gcgaggggc agccttaatg tgcctccagc    660
ctgaagtcct agaatgagcg cccggtgtcc caagctgggg cgcgcacccc agatcggagg   720
gcgccgatgt acagacagca aactcaccca gtctagtgca tgccttctta aacatcacga   780
gactctaaga aaggaaact gaaacggga aagtccctct ctctaacctg gcactgcgtc     840
gctggcttgg agacaggtga cggtccctgc gggccttgtc ctgattggct gggcacgcgt   900
ttaatataag tggaggcgtc gcgctggcgg gcattcctga agctaagctt gtggacgata   960
tcgaattcgc acgacattga ttattgacta gttattaata gtaatcaatt acggggtcat  1020
tagttcatag cccatatatg gagttccgcg ttacataact tacggtaaat ggcccgcctg  1080
gctgaccgcc caacgacccc cgcccattga cgtcaataat gacgtatgtt cccatagtaa  1140
cgccaatagg gactttccat tgacgtcaat gggtggacta tttacggtaa actgcccact  1200
tggcagtaca tcaagtgtat catatgccaa gtacgccccc tattgacgtc aatgacggta  1260
aatggcccgc ctggcattat gcccagtaca tgaccttatg gactttcct acttggcagt   1320
acatctacgt attagtcatc gctattacca tgggtcgagg tgagccccac gttctgcttc  1380
actctcccca tctccccccc ctccccaccc ccaattttgt atttatttat tttttaatta  1440
ttttgtgcag cgatggggc ggggggggg ggggcgcgcg ccaggcgggg cggggcgggg    1500
cgaggggcgg ggcggggcga ggcggagagg tgcggcggca gccaatcaga gcggcgcgct  1560
ccgaaagttt cctttatgg cgaggcggcg gcggcggcgg ccctataaaa agcgaagcgc   1620
gcggcgggcg ggagtcgctg cgttgccttc gcccgtgcc ccgctccgcg ccgcctcgcg   1680
ccgcccgccc cggctctgac tgaccgcgtt actcccacag gtgagcgggc gggacggccc  1740
ttctcctccg ggctgtaatt agcgcttggt ttaatgacgg ctcgtttctt ttctgtggct  1800
gcgtgaaagc cttaaagggc tccggagggg ccctttgtgc gggggggagc ggctcggggg  1860
gtgcgtgcgt gtgtgtgtgc gtggggagcg ccgcgtgcgg cccgcgctgc ccggcggctg  1920
tgagcgctgc gggcgcggcg cggggctttg tcgctccgc gtgtgcgcga ggggagcgcg  1980
gccggggcg gtgccccgcg gtgcgggggg gctgcgaggg gaacaaaggc tgcgtgcggg   2040
gtgtgtgcgt ggggggtga gcaggggtg tgggcgcggc ggtcgggctg taacccccc     2100
ctgcaccccc ctccccgagt tgctgagcac ggcccggctt cgggtgcggg gctccgtgcg  2160
gggcgtggcg cggggctcgc cgtgccggc gggggtggc ggcaggtggg ggtgccgggc    2220
ggggcggggc cgcctcgggc cggggagggc tcggggagg ggcgcggcgg ccccggagcg   2280
ccggcggctg tcgagcgcg gcgagccgca gccattgcct tttatggtaa tcgtgcgaga   2340
gggcgcaggg acttcctttg tcccaaatct ggcggagccg aaatctggga ggcgccgccg  2400
cacccctct agcgggcgcg ggcgaagcgg tgcggcgccg gcaggaagga atgggcggg    2460
gagggccttc gtgcgtcgcc gcgccgccgt ccccttctcc atctccagcc tcgggctgc   2520
cgcagggga cggctgcctt cggggggac ggggcagggc ggggttcggc ttctggcgtg    2580
tgaccggcgg ctctagagcc tctgctaacc atgttcatgc cttcttcttt ttcctacagg  2640
ggggatccgt ttatctgcag aattcgccct tgacgtcgcc accatggaaa ctctttctaa  2700
tgcaagtggt acttttgcca tacgcctttt aaagatactg tgtcaagata acccttcgca  2760
caacgtgttc tgttctcctg tgagcatctc ctctgccctg gccatggttc tcctagggc   2820
```

```
aaagggaaac accgcaaccc agatggccca ggcactgtct ttaaacacag aggaagacat   2880
tcatcgggct ttccagtcgc ttctcactga agtgaacaag gctggcacac agtacctgct   2940
gagaacggcc aacaggctct tggagagaaa aacttgtcag ttcctctcaa cgtttaagga   3000
atcctgtctt caattctacc atgctgagct gaaggagctt tcctttatca gagctgcaga   3060
agagtccagg aaacacatca acacctgggt ctcaaaaaag accgaaggta aaattgaaga   3120
gttgttgccg ggtagctcaa ttgatgcaga aaccaggctg gttcttgtca atgccatcta   3180
cttcaaagga aagtggaatg aaccgtttga cgaaacatac acaagggaaa tgcccttta   3240 aataaaccag gaggagcaaa ggccagtgca gatgatgtat caggaggcca cgtttaagct   3300
cgcccacgtg ggcgaggtgc gcgcgcagct gctggagctg ccctacgcca ggaaggagct   3360
gagcctgctg gtgctgctgc ctgacgacg cgtggagctc agcacggtgg aaaaaagtct   3420
cacttttgag aaactcacag cctggaccaa gccagactgt atgaagagta ctgaggttga   3480
agttctcctt ccaaaattta aactacaaga ggattatgac atggaatctg tgcttcggca   3540
tttgggaatt gttgatgcct tccaacaggg caaggctgac ttgtcggcaa tgtcagcgga   3600
gagagacctg tgtctgtcca agttcgtgca caagagtttt gtggaggtga atgaagaagg   3660
caccgaggca gcggcagcgt cgagctgctt tgtagttgca gagtgctgca tggaatctgg   3720
ccccaggttc tgtgctgacc acccttcct tttcttcatc aggcacaaca gagccaacag   3780
cattctgttc tgtggcaggt tctcatcgcc aggaagcgga gctactaact tcagcctgct   3840
gaagcaggct ggagacgtgg aggagaaccc tggacctatg tctcgctccg ttgccttagc   3900
tgtgctcgcg ctactctctc tttctggatt agaggctgtc atggcgcccc gaaccctctt   3960
cctgggtgga ggcggttcag gcggaggtgg ctctggcggt ggcggatcga tccagcgtac   4020
tccaaagatt caggtttact cacgtcatcc agcagagaat ggaaagtcaa atttcctgaa   4080
ttgctatgtg tctgggtttc atccatccga cattgaagtt gacttactga gaatggaga   4140 gagaattgaa aaagtggagc attcagactt gtctttcagc aaggactggt ctttctatct   4200
cttgtactac actgaattca cccccactga aaaagatgag tatgcctgcc gtgtgaacca   4260
tgtgactttg tcacagccca agatagttaa gtgggatcga gacatgggtg gtggtggttc   4320
tggtggtggt ggttctggcg gcggcggctc cggtggtggt ggatccggct cccactcctt   4380
gaagtatttc cacacttccg tgtcccggcc cggccgcggg gagccccgct tcatctctgt   4440
gggctacgtg gacgacaccc agttcgtgcg cttcgacaac gacgccgcga gtccgaggat   4500
ggtgccgcgg gcgccgtgga tggagcagga ggggtcagag tattgggacc gggagacacg   4560
gagcgccagg gacaccgcac agattttccg agtgaatctg cggacgctgc gcggctacta   4620
caatcagagc gaggccgggt ctcacaccct gcagtggatg catggctgcg agctggggcc   4680
cgacgggcgc ttcctccgcg ggtatgaaca gttcgcctac gacggcaagg attatctcac   4740
cctgaatgag gacctgcgct cctggaccgc ggtggacacg cggctcaga tctccgagca   4800 aaagtcaaat gatgcctctg aggcggagca ccagagagcc tacctggaag acacatgcgt   4860
ggagtggctc cacaaatacc tggagaaggg gaaggagacg ctgcttcacc tggagccccc   4920
aaagacacac gtgactcacc accccatctc tgaccatgag gccaccctga ggtgctgggc   4980
cctgggcttc taccctgcgg agatcacact gacctggcag caggatgggg agggccatac   5040
ccaggacacg gagctcgtgg agaccaggcc tgcaggggat ggaaccttcc agaagtgggc   5100
agctgtggtg gtgccttctg agaggagca gagatacacg tgccatgtgc agcatgaggg   5160
gctacccgag cccgtcaccc tgagatggaa gccggcttcc cagcccacca tccccatcgt   5220
```

```
gggcatcatt gctggcctgg ttctccttgg atctgtggtc tctggagctg tggttgctgc   5280
tgtgatatgg aggaagaaga gctcaggtgg aaaaggaggg agctactcta aggctgagtg   5340
gagcgacagt gcccaggggt ctgagtctca cagcttgtaa tgatagccgc tgatcagcct   5400
cgactgtgcc ttctagttgc cagccatctg ttgtttgccc ctcccccgtg ccttccttga   5460
ccctggaagg tgccactccc actgtccttt cctaataaaa tgaggaaatt gcatcgcatt   5520
gtctgagtag gtgtcattct attctggggg gtggggtggg gcaggacagc aaggggagg    5580 attgggaaga caatagcagg catgctgggg atgcggtggg ctctatgggt cgacccagcg   5640
tgagtctctc ctaccctccc gctctggtcc ttcctctccc gctctgcacc ctctgtggcc   5700
ctcgctgtgc tctctcgctc cgtgacttcc cttctccaag ttctccttgg tggcccgccg   5760
tggggctagt ccaggctgg atctcgggga agcggcgggg tggcctggga gtggggaagg    5820
gggtgcgcac ccgggacgcg cgctacttgc ccctttcggc ggggagcagg ggagaccttt   5880
ggcctacggc gacgggaggg tcgggacaaa gtttagggcg tcgataagcg tcagagcgcc   5940
gaggttgggg gagggtttct cttccgctct ttcgcggggc ctctggctcc cccagcgcag   6000
ctggagtggg ggacgggtag gctcgtccca aaggcgcggc gctgaggttt gtgaacgcgt   6060
ggaggggcgc ttggggtctg ggggaggcgt cgcccgggta agcctgtctg ctgcggctct   6120
gcttccctta gactggagag ctgtggactt cgtctaggcg cccgctaagt tcgcatgtcc   6180
tagcacctct gggtctatgt ggggccacac cgtggggagg aaacagcacg cgacgtttgt   6240
agaatgcttg gctgtgatac aaagcggttt cgaataatta acttatttgt tcccatcaca   6300
tgtcactttt aaaaaattat aagaactacc cgttattgac atctttctgt gtgccaagga   6360
ctttatgtgc tttgcgtcat ttaatttga aaacagttat cttccgccat agataactac    6420
tatggttatc ttctggtaac cacgtgcgga ccgaggctgc agcgtcgtcc tccctaggaa   6480
cccctagtga tggagttggc cactccctct ctgcgcgctc gctcgctcac tgaggccggg   6540
cgaccaaagg tcgcccgacg cccgggcttt gcccgggcgg cctcagtgag cgagcgagcg   6600
cgcagctgcc tgcaggggcg cctgatgcgg tattttctcc ttacgcatct gtgcggtatt   6660
tcacaccgca tacgtcaaag caaccatagt acgcgccctg tagcggcgca ttaagcgcgg   6720
cgggtgtggt ggttacgcgc agcgtgaccg ctacacttgc cagcgcccta gcgcccgctc   6780
ctttcgcttt cttcccttcc tttctcgcca cgttcgccgg ctttccccgt caagctctaa   6840
atcgggggct ccctttaggg ttccgattta gtgctttacg gcacctcgac cccaaaaaac   6900
ttgatttggg tgatggttca cgtagtgggc catcgccctg atagacggtt tttcgccctt   6960
tgacgttgga gtccacgttc tttaatagtg gactcttgtt ccaaactgga acaacactca   7020
accctatctc gggctattct tttgatttat aagggatttt gccgatttcg gcctattggt   7080 taaaaatga gctgatttaa caaaaattta acgcgaattt taacaaaata ttaacgttta    7140
caattttatg gtgcactctc agtacaatct gctctgatgc cgcatagtta agccagcccc   7200
gacacccgcc aacacccgct gacgcgccct gacgggcttg tctgctcccg gcatccgctt   7260
acagacaagc tgtgaccgtc tccgggagct gcatgtgtca gaggttttca ccgtcatcac   7320 cgaaacgcg gagacgaaag ggcctcgtga tacgcctatt tttataggtt aatgtcatga    7380
acaataaaac tgtctgctta cataaacagt aatacaaggg gtgttatgag ccatattcaa   7440
cgggaaacgt cgaggccgcg attaaattcc aacatggatg ctgatttata tgggtataaa   7500
tgggctcgcg ataatgtcgg gcaatcaggt gcgacaatct atcgcttgta tgggaagccc   7560
```

| | | |
|---|---|---|
| gatgcgccag agttgtttct gaaacatggc aaaggtagcg ttgccaatga tgttacagat | 7620 |
| gagatggtca gactaaactg gctgacggaa tttatgcctc ttccgaccat caagcatttt | 7680 |
| atccgtactc ctgatgatgc atggttactc accactgcga tccccggaaa aacagcattc | 7740 |
| caggtattag aagaatatcc tgattcaggt gaaaatattg ttgatgcgct ggcagtgttc | 7800 |
| ctgcgccggt tgcattcgat tcctgtttgt aattgtcctt ttaacagcga tcgcgtattt | 7860 |
| cgtctcgctc aggcgcaatc acgaatgaat aacggtttgg ttgatgcgag tgattttgat | 7920 |
| gacgagcgta atggctggcc tgttgaacaa gtctggaaag aaatgcataa acttttgcca | 7980 |
| ttctcaccgg attcagtcgt cactcatggt gatttctcac ttgataacct tatttttgac | 8040 |
| gagggaaat taataggttg tattgatgtt ggacgagtcg gaatcgcaga ccgataccag | 8100 |
| gatcttgcca tcctatggaa ctgcctcggt gagttttctc cttcattaca gaaacggctt | 8160 |
| tttcaaaaat atggtattga taatcctgat atgaataaat tgcagtttca tttgatgctc | 8220 |
| gatgagtttt tctaatctca tgaccaaaat cccttaacgt gagttttcgt tccactgagc | 8280 |
| gtcagacccc gtagaaaaga tcaaaggatc ttcttgagat ccttttttc tgcgcgtaat | 8340 |
| ctgctgcttg caaacaaaaa aaccaccgct accagcggtg gtttgtttgc cggatcaaga | 8400 |
| gctaccaact cttttccga aggtaactgg cttcagcaga gcgcagatac caaatactgt | 8460 |
| ccttctagtg tagccgtagt taggccacca cttcaagaac tctgtagcac cgcctacata | 8520 |
| cctcgctctg ctaatcctgt taccagtggc tgctgccagt ggcgataagt cgtgtcttac | 8580 |
| cgggttggac tcaagacgat agttaccgga taaggcgcag cggtcgggct gaacggggg | 8640 |
| ttcgtgcaca cagcccagct tggagcgaac gacctacacc gaactgagat acctacagcg | 8700 |
| tgagctatga gaaagcgcca cgcttcccga agggagaaag gcggacaggt atccggtaag | 8760 |
| cggcagggtc ggaacaggag agcgcacgag ggagcttcca gggggaaacg cctggtatct | 8820 |
| ttatagtcct gtcgggtttc gccacctctg acttgagcgt cgattttgt gatgctcgtc | 8880 |
| agggggggcgg agcctatgga aaaacgccag caacgcggcc tttttacggt tcctggcctt | 8940 |
| ttgctggcct tttgctcaca tgt | 8963 |

<210> SEQ ID NO 131
<211> LENGTH: 2944
<212> TYPE: DNA
<213> ORGANISM: Artificial Sequence
<220> FEATURE:
<223> OTHER INFORMATION: Synthetic

<400> SEQUENCE: 131

| | | |
|---|---|---|
| atggaaactc tttctaatgc aagtggtact tttgccatac gccttttaaa gatactgtgt | 60 |
| caagataacc cttcgcacaa cgtgttctgt tctcctgtga gcatctcctc tgccctggcc | 120 |
| atggttctcc tagggggcaaa gggaaacacc gcaacccaga tggcccaggc actgtcttta | 180 |
| aacacagagg aagacattca tcgggctttc cagtcgcttc tcactgaagt gaacaaggct | 240 |
| ggcacacagt acctgctgag aacggccaac aggctctttg gagagaaaac ttgtcagttc | 300 |
| ctctcaacgt ttaaggaatc ctgtcttcaa ttctaccatg ctgagctgaa ggagcttttcc | 360 |
| tttatcagag ctgcagaaga gtccaggaaa cacatcaaca cctgggtctc aaaaaagacc | 420 |
| gaaggtaaaa ttgaagagtt gttgccgggt agctcaattg atgcagaaac caggctggtt | 480 |
| cttgtcaatg ccatctactt caaaggaaag tggaatgaac cgtttgacga acatacaca | 540 |
| aggggaaatgc cctttaaaat aaaccaggag gagcaaggc cagtgcagat gatgtatcag | 600 |
| gaggccacgt ttaagctcgc ccacgtgggc gaggtgcgcg cgcagctgct ggagctgccc | 660 |

| | |
|---|---|
| tacgccagga aggagctgag cctgctggtg ctgctgcctg acgacggcgt ggagctcagc | 720 |
| acggtggaaa aaagtctcac tttttgagaaa ctcacagcct ggaccaagcc agactgtatg | 780 |
| aagagtactg aggttgaagt tctccttcca aaatttaaac tacaagagga ttatgacatg | 840 |
| gaatctgtgc ttcggcattt gggaattgtt gatgccttcc aacagggcaa ggctgacttg | 900 |
| tcggcaatgt cagcggagag agacctgtgt ctgtccaagt tcgtgcacaa gagttttgtg | 960 |
| gaggtgaatg aagaaggcac cgaggcagcg gcagcgtcga gctgctttgt agttgcagag | 1020 |
| tgctgcatgg aatctggccc caggttctgt gctgaccacc ctttcctttt cttcatcagg | 1080 |
| cacaacagag ccaacagcat tctgttctgt ggcaggttct catcgccagg aagcggagct | 1140 |
| actaacttca gcctgctgaa gcaggctgga gacgtggagg agaaccctgg acctatgtct | 1200 |
| cgctccgttg ccttagctgt gctcgcgcta ctctctcttt ctggattaga ggctgtcatg | 1260 |
| gcgccccgaa ccctcttcct gggtggaggc ggttcaggcg gaggtggctc tggcggtggc | 1320 |
| ggatcgatcc agcgtactcc aaagattcag gtttactcac gtcatccagc agagaatgga | 1380 |
| aagtcaaatt tcctgaattg ctatgtgtct gggtttcatc catccgacat tgaagttgac | 1440 |
| ttactgaaga atggagagag aattgaaaaa gtggagcatt cagacttgtc tttcagcaag | 1500 |
| gactggtctt tctatctctt gtactacact gaattcaccc ccactgaaaa agatgagtat | 1560 |
| gcctgccgtg tgaaccatgt gactttgtca cagcccaaga tagttaagtg ggatcgagac | 1620 |
| atgggtggtg gtggttctgg tggtggtggt tctggcggcg gcggctccgg tggtggtgga | 1680 |
| tccggctccc actccttgaa gtatttccac acttccgtgt cccggcccgg ccgcggggag | 1740 |
| ccccgcttca tctctgtggg ctacgtggac gacacccagt tcgtgcgctt cgacaacgac | 1800 |
| gccgcgagtc cgaggatggt gccgcgggcg ccgtggatgg agcaggaggg gtcagagtat | 1860 |
| tgggaccggg agacacggag cgccaggac accgcacaga ttttccgagt gaatctgcgg | 1920 |
| acgctgcgcg gctactacaa tcagagcgag gccgggtctc acaccctgca gtggatgcat | 1980 |
| ggctgcgagc tggggcccga cgggcgcttc ctccgcgggt atgaacagtt cgcctacgac | 2040 |
| ggcaaggatt atctcaccct gaatgaggac ctgcgctcct ggaccgcggt ggacacggcg | 2100 |
| gctcagatct ccgagcaaaa gtcaaatgat gcctctgagg cggagcacca gagagcctac | 2160 |
| ctggaagaca catgcgtgga gtggctccac aaatacctgg agaagggga ggagacgctg | 2220 |
| cttcacctgg agcccccaaa gacacacgtg actcaccacc ccatctctga ccatgaggcc | 2280 |
| accctgaggt gctgggccct gggcttctac cctgcggaga tcacactgac ctggcagcag | 2340 |
| gatggggagg ccataccca ggacacggag ctcgtggaga ccaggcctgc aggggatgga | 2400 |
| accttccaga gtgggcagc tgtggtggtg ccttctggag aggagcagag atacacgtgc | 2460 |
| catgtgcagc atgagggct acccgagccc gtcaccctga gatggaagcc ggcttcccag | 2520 |
| cccaccatcc ccatcgtggg catcattgct ggcctggttc ccttggatc tgtggtctct | 2580 |
| ggagctgtgg ttgctgctgt gatatggagg aagaagagct caggtggaaa ggagggagc | 2640 |
| tactctaagg ctgagtggag cgacagtgcc cagggggtctg agtctcacag cttgtaatga | 2700 |
| tagccgctga tcagcctcga ctgtgccttc tagttgccag ccatctgttg tttgcccctc | 2760 |
| ccccgtgcct tccttgaccc tggaaggtgc cactcccact gtcctttcct aataaaatga | 2820 |
| ggaaattgca tcgcattgtc gagtaggtgt cattctattc tggggggtgg ggtggggcag | 2880 |
| gacagcaagg gggaggattg ggaagacaat agcaggcatg ctggggatgc ggtgggctct | 2940 |
| atgg | 2944 |

<210> SEQ ID NO 132
<211> LENGTH: 57
<212> TYPE: DNA
<213> ORGANISM: Artificial Sequence
<220> FEATURE:
<223> OTHER INFORMATION: Synthetic

<400> SEQUENCE: 132
cccttaacgt gagttttcgt tccactgagc gtcagacccc gtagaaaaga tcaaagg      57

<210> SEQ ID NO 133
<211> LENGTH: 54
<212> TYPE: DNA
<213> ORGANISM: Artificial Sequence
<220> FEATURE:
<223> OTHER INFORMATION: Synthetic

<400> SEQUENCE: 133
gtccaacccg gtaagacacg acttatcgcc actggcagca gccactggta acag         54

<210> SEQ ID NO 134
<211> LENGTH: 53
<212> TYPE: DNA
<213> ORGANISM: Artificial Sequence
<220> FEATURE:
<223> OTHER INFORMATION: Synthetic

<400> SEQUENCE: 134
cacttgccag cgccctagcg cccgctcctt tcgctttctt cccttccttt ctc          53

<210> SEQ ID NO 135
<211> LENGTH: 33
<212> TYPE: DNA
<213> ORGANISM: Artificial Sequence
<220> FEATURE:
<223> OTHER INFORMATION: Synthetic

<400> SEQUENCE: 135
gggcgcgtca gcgggtgttg gcgggtgtcg ggg                                33

<210> SEQ ID NO 136
<211> LENGTH: 8702
<212> TYPE: DNA
<213> ORGANISM: Artificial Sequence
<220> FEATURE:
<223> OTHER INFORMATION: Synthetic

<400> SEQUENCE: 136
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120 agggggttcct gcggccgcac gcgtgttcta gggtggaaac taagagaatg atgtacctag    180
agggcgctgg aagctctaaa gccctagcag ttactgcttt tactattagt ggtcgttttt    240
ttctcccccc cgcccccccga caaatcaaca gaacaaagaa aattacctaa acagcaagga    300
catagggagg aacttcttgg cacagaactt tccaaacact ttttcctgaa gggatacaag    360
aagcaagaaa ggtactcttt cactaggacc ttctctgagc tgtcctcagg atgcttttgg    420
gactattttt cttacccaga gaatggagaa accctgcagg gaattcccaa gctgtagtta    480
taaacagaag ttctccttct gctaggtagc attcaaagat cttaatcttc tgggtttccg    540
ttttctcgaa tgaaaatgc aggtccgagc agttaactgg ctggggcacc attagcaagt     600
cacttagcat ctctggggcc agtctgcaaa gcgaggggc agccttaatg tgcctccagc    660

```
ctgaagtcct agaatgagcg cccggtgtcc aagctgggg cgcgcacccc agatcggagg      720
gcgccgatgt acagacagca aactcaccca gtctagtgca tgccttctta aacatcacga      780
gactctaaga aaaggaaact gaaaacggga aagtccctct ctctaacctg gcactgcgtc      840
gctggcttgg agacaggtga cggtccctgc gggccttgtc ctgattggct gggcacgcgt      900
ttaatataag tggaggcgtc gcgctggcgg gcattcctga agctaagctt gtggacgata      960
tcgaattcgc acgacattga ttattgacta gttattaata gtaatcaatt acggggtcat     1020
tagttcatag cccatatatg gagttccgcg ttacataact tacggtaaat ggcccgcctg     1080
gctgaccgcc caacgacccc cgcccattga cgtcaataat gacgtatgtt cccatagtaa     1140
cgccaatagg gactttccat tgacgtcaat gggtggacta tttacggtaa actgcccact     1200
tggcagtaca tcaagtgtat catatgccaa gtacgccccc tattgacgtc aatgacggta     1260
aatggcccgc ctggcattat gcccagtaca tgaccttatg gactttcct acttggcagt      1320 acatctacgt attagtcatc gctattacca tgggtcgagg tgagccccac gttctgcttc     1380
actctcccca tctccccccc ctccccaccc ccaattttgt atttatttat tttttaatta     1440
ttttgtgcag cgatggggc gggggggggg ggggcgcgcg ccaggcgggg cgggcgggg      1500 cgagggcgg ggcggggcga ggcggagagg tgcggcggca gccaatcaga gcggcgcgct     1560
ccgaaagttt cctttatgg cgaggcgcg gcggcggcgg ccctataaaa agcgaagcgc      1620
gcggcgggcg ggagtcgctg cgttgccttc gccccgtgcc ccgctccgcg ccgcctcgcg     1680
ccgcccgccc cggctctgac tgaccgcgtt actcccacag gtgagcgggc gggacggccc     1740
ttctcctccg ggctgtaatt agcgcttggt ttaatgacgg ctcgtttctt ttctgtggct     1800
gcgtgaaagc cttaaagggc tccgggaggg ccctttgtgc gggggggagc ggctcggggg     1860
gtgcgtgcgt gtgtgtgtgc gtggggagcg ccgcgtgcgg ccgcgctgc ccggcggctg      1920 tgagcgctgc gggcgcggcg cggggctttg tgcgctccgc gtgtgcgcga ggggagcgcg     1980 gccggggcg gtgccccgcg gtgcgggggg gctgcgaggg gaacaaaggc tgcgtgcggg      2040
gtgtgtgcgt ggggggtga gcaggggtg tgggcgcggc ggtcgggctg taacccccc        2100 ctgcaccccc ctccccgagt tgctgagcac ggcccggctt cgggtgcggg gctccgtgcg     2160
gggcgtggcg cggggctcgc cgtgccgggc gggggtggc ggcaggtggg ggtgccgggc      2220
ggggcggggc cgcctcgggc cggggagggc tcggggaggg ggcgcggcgg ccccggagcg     2280
ccggcggctg tcgaggcgcg gcgagccgca gccattgcct tttatggtaa tcgtgcgaga     2340
gggcgcaggg acttcctttg tcccaaatct ggcggagccg aaatctggga ggcgccgccg     2400 cacccctct agcgggcgcg ggcgaagcgg tgcggcgccg gcaggaagga atgggcggg      2460 gagggccttc gtgcgtcgcc gcgccgccgt ccccttctcc atctccagcc tcggggctgc     2520
cgcaggggga cggctgcctt cggggggac ggggcaggggc ggggttcggc ttctggcgtg     2580
tgaccggcgg ctctagagcc tctgctaacc atgttcatgc cttcttcttt ttcctacagg     2640
ggggatccgt ttatctgcag aattcgccct tgacgtcgcc accatggaaa ctctttctaa     2700
tgcaagtggt acttttgcca tacgcctttt aaagatactg tgtcaagata acccttcgca     2760
caacgtgttc tgttctcctg tgagcatctc ctctgccctg ccatggttc tctaggggc      2820 aaagggaaac accgcaaccc agatggccca ggcactgtct ttaaacacag aggaagacat     2880
tcatcgggct ttccagtcgc ttctcactga agtgaacaag gctggcacac agtacctgct     2940
gagaacggcc aacaggctct ttggagagaa aacttgtcag ttcctctcaa cgtttaagga     3000
```

```
atcctgtctt caattctacc atgctgagct gaaggagctt tcctttatca gagctgcaga    3060
agagtccagg aaacacatca acacctgggt ctcaaaaaag accgaaggta aaattgaaga    3120
gttgttgccg ggtagctcaa ttgatgcaga aaccaggctg gttcttgtca atgccatcta    3180
cttcaaagga aagtggaatg aaccgtttga cgaaacatac acaagggaaa tgcccttaa    3240
aataaaccag gaggagcaaa ggccagtgca gatgatgtat caggaggcca cgtttaagct    3300
cgcccacgtg ggcgaggtgc gcgcgcagct gctggagctg ccctacgcca ggaaggagct    3360
gagcctgctg gtgctgctgc ctgacgacgg cgtggagctc agcacggtgg aaaaaagtct    3420
cacttttgag aaactcacag cctggaccaa gccagactgt atgaagagta ctgaggttga    3480
agttctcctt ccaaaattta aactacaaga ggattatgac atggaatctg tgcttcggca    3540
tttgggaatt gttgatgcct tccaacaggg caaggctgac ttgtcggcaa tgtcagcgga    3600
gagagacctg tgtctgtcca agttcgtgca caagagtttt gtggaggtga atgaagaagg    3660
caccgaggca gcggcagcgt cgagctgctt tgtagttgca gagtgctgca tggaatctgg    3720
ccccaggttc tgtgctgacc acctttcct tttcttcatc aggcacaaca gagccaacag    3780
cattctgttc tgtggcaggt tctcatcgcc aggaagcgga gctactaact tcagcctgct    3840
gaagcaggct ggagacgtgg aggagaaccc tggacctatg actgaccct ggatcctgtt    3900
cctggtggcc gccgccacca gggtgcacag cggcattcat gtcttcattt gggctgtt    3960
cagtgcaggc cttcctaaaa cagaagccaa ctgggtgaat gtaataagtg atttgaaaaa    4020
aattgaagat cttattcaat ctatgcatat tgatgctact ttatacgg aaagtgatgt    4080
tcaccccagt tgcaaagtaa cagcaatgaa gtgctttctc ttggagttac aagttatttc    4140
acttgagtcc ggagatgcaa gtattcatga tacagtagaa aatctgatca tcctagcaaa    4200
caacagtttg tcttctaatg ggaatgtaac agaatctgga tgcaaagaat gtgaggaact    4260
ggaggaaaaa aatattaaag aattttgca gagttttgta catattgtcc aaatgttcat    4320
caacacttct agcggcggcg gcagcggcgg cggcggcagc ggcggcggcg gcagcggcgg    4380
cggcggcagc ggcggcggca gcctgcagat cacgtgccct ccccccatgt ccgtggaaca    4440
cgcagacatc tgggtcaaga gctacagctt gtactccagg gagcggtaca tttgtaactc    4500
tggtttcaag cgtaaagccg gcacgtccag cctgacggag tgcgtgttga caaggccac    4560
gaatgtcgcc cactggacaa cccccagtct caaatgcatt agagaccctg ccctggttca    4620
ccaaaggcca gcgccaccct ccacagtaac gacggcaggg gtgaccccac agccagagag    4680
cctctcccct tctggaaaag agcccgcagc ttcatctccc agctcaaaca acacagcggc    4740
cacaacagca gctattgtcc cgggctccca gctgatgcct tcaaaatcac cttccacagg    4800
aaccacagag ataagcagtc atgagtcctc ccacggcacc ccctctcaga caacagccaa    4860
gaactgggaa ctcacagcat ccgcctccca ccagccgcca ggtgtgtatc cacagggcca    4920
cagcgacacc actgtggcta tctccacgtc cactgtcctg ctgtgtgggc tgagcgctgt    4980
gtctctcctg gcatgctacc tcaagtcaag gcaaactccc ccgctggcca gcgttgaaat    5040
ggaagccatg gaggctctgc cggtgacttg ggggaccagc agcagagatg aagacttgga    5100
aaactgctct caccacctat gataaccgct gatcagcctc gactgtgcct tctagttgcc    5160
agccatctgt tgtttgcccc tccccgtgc cttccttgac cctggaaggt gccactccca    5220
ctgtcctttc ctaataaaat gaggaaattg catcgcattg tctgagtagg tgtcattcta    5280
ttctgggggg tggggtgggg caggacagca agggggagga ttgggaagac aatagcaggc    5340
atgctgggga tgcggtgggc tctatgggtc gacccagcgt gagtctctcc taccctcccg    5400
```

```
ctctggtcct tcctctcccg ctctgcaccc tctgtggccc tcgctgtgct ctctcgctcc    5460
gtgacttccc ttctccaagt tctccttggt ggcccgccgt ggggctagtc cagggctgga    5520
tctcggggaa gcggcggggt ggcctggag tggggaaggg ggtgcgcacc cgggacgcgc     5580
gctacttgcc cctttcggcg gggagcaggg gagacctttg gcctacggcg acggagggt     5640 cgggacaaag tttagggcgt cgataagcgt cagagcgccg aggttggggg agggtttctc    5700
ttccgctctt tcgcggggcc tctggctccc ccagcgcagc tggagtgggg gacgggtagg    5760
ctcgtcccaa aggcgcggcg ctgaggtttg tgaacgcgtg gaggggcgct tggggtctgg    5820
gggaggcgtc gcccgggtaa gcctgtctgc tgcggctctg cttcccttag actggagagc    5880
tgtggacttc gtctaggcgc ccgctaagtt cgcatgtcct agcacctctg ggtctatgtg    5940
gggccacacc gtggggagga aacagcacgc gacgtttgta aatgcttgg ctgtgataca     6000 aagcggtttc gaataattaa cttatttgtt cccatcacat gtcacttta aaaaattata    6060 agaactaccc gttattgaca tctttctgtg tgccaaggac tttatgtgct ttgcgtcatt    6120
taattttgaa acagttatc ttccgccata gataactact atggttatct tctggtaacc    6180
acgtgcggac cgaggctgca gcgtcgtcct ccctaggaac ccctagtgat ggagttggcc    6240
actccctctc tgcgcgctcg ctcgctcact gaggccgggc gaccaaaggt cgcccgacgc    6300
ccgggctttg cccgggcggc ctcagtgagc gagcgagcgc gcagctgcct gcaggggcgc    6360
ctgatgcggt attttctcct tacgcatctg tgcggtattt cacaccgcat acgtcaaagc    6420
aaccatagta cgcgccctgt agcggcgcat taagcgcggc gggtgtggtg gttacgcgca    6480
gcgtgaccgc tacacttgcc agcgccctag cgcccgctcc tttcgctttc ttcccttcct    6540
ttctcgccac gttcgccggc tttccccgtc aagctctaaa tcgggggctc cctttagggt    6600
tccgatttag tgctttacgg cacctcgacc ccaaaaaact tgatttgggt gatggttcac    6660
gtagtgggcc atcgccctga tagacggttt ttcgcccttt gacgttggag tccacgttct    6720
ttaatagtgg actcttgttc caaactggaa caacactcaa ccctatctcg gctattctt    6780 ttgatttata agggattttg ccgatttcgg cctattggtt aaaaaatgag ctgatttaac    6840
aaaaatttaa cgcgaatttt aacaaaatat taacgtttac aatttatgg tgcactctca    6900 gtacaatctg ctctgatgcc gcatagttaa gccagccccg acaccgcca acacccgctg     6960 acgcgcccta cgggcttgt ctgctcccgg catccgctta cagacaagct gtgaccgtct     7020
ccgggagctg catgtgtcag aggttttcac cgtcatcacc gaaacgcgcg agacgaaagg    7080
gcctcgtgat acgcctattt ttataggtta atgtcatgaa caataaaact gtctgcttac    7140
ataaacagta atacaagggg tgttatgagc catattcaac gggaaacgtc gaggccgcga    7200
ttaaattcca acatggatgc tgatttatat gggtataaat gggctcgcga taatgtcggg    7260
caatcaggtg cgacaatcta tcgcttgtat gggaagcccg atgcgccaga gttgtttctg    7320
aaacatggca aaggtagcgt tgccaatgat gttacagatg agatggtcag actaaactgg    7380
ctgacggaat ttatgcctct tccgaccatc aagcatttta tccgtactcc tgatgatgca    7440
tggttactca ccactgcgat ccccggaaaa acagcattcc aggtattaga agaatatcct    7500
gattcaggtg aaaatattgt tgatgcgctg gcagtgttcc tgcgccggtt gcattcgatt    7560
cctgtttgta attgtccttt taacagcgat cgcgtatttc gtctcgctca ggcgcaatca    7620
cgaatgaata acggtttggt tgatgcgagt gattttgatg acgagcgtaa tggctggcct    7680
gttgaacaag tctggaaaga aatgcataaa cttttgccat tctcaccgga ttcagtcgtc    7740
```

```
actcatggtg atttctcact tgataacctt attttttgacg aggggaaatt aataggttgt   7800
attgatgttg gacgagtcgg aatcgcagac cgataccagg atcttgccat cctatggaac   7860
tgcctcggtg agttttctcc ttcattacag aaacggcttt ttcaaaaata tggtattgat   7920
aatcctgata tgaataaatt gcagtttcat ttgatgctcg atgagttttt ctaatctcat   7980
gaccaaaatc ccttaacgtg agttttcgtt ccactgagcg tcagaccccg tagaaaagat   8040
caaaggatct tcttgagatc ctttttttct gcgcgtaatc tgctgcttgc aaacaaaaaa   8100
accaccgcta ccagcggtgg tttgtttgcc ggatcaagag ctaccaactc tttttccgaa   8160
ggtaactggc ttcagcagag cgcagatacc aaatactgtc cttctagtgt agccgtagtt   8220
aggccaccac ttcaagaact ctgtagcacc gcctacatac ctcgctctgc taatcctgtt   8280
accagtggct gctgccagtg gcgataagtc gtgtcttacc gggttggact caagacgata   8340
gttaccggat aaggcgcagc ggtcgggctg aacggggggt tcgtgcacac agcccagctt   8400
ggagcgaacg acctacaccg aactgagata cctacagcgt gagctatgag aaagcgccac   8460
gcttcccgaa gggagaaagg cggacaggta tccggtaagc ggcagggtcg aacaggaga   8520
gcgcacgagg gagcttccag ggggaaacgc ctggtatctt tatagtcctg tcgggtttcg   8580
ccacctctga cttgagcgtc gatttttgtg atgctcgtca gggggggcgga gcctatggaa   8640
aaacgccagc aacgcggcct ttttacggtt cctggccttt tgctggcctt ttgctcacat   8700
gt                                                                  8702

<210> SEQ ID NO 137
<211> LENGTH: 2684
<212> TYPE: DNA
<213> ORGANISM: Artificial Sequence
<220> FEATURE:
<223> OTHER INFORMATION: Synthetic

<400> SEQUENCE: 137
atggaaactc tttctaatgc aagtggtact tttgccatac gccttttaaa gatactgtgt     60
caagataacc cttcgcacaa cgtgttctgt tctcctgtga gcatctcctc tgccctggcc    120
atggttctcc taggggcaaa gggaaacacc gcaacccaga tggcccaggc actgtcttta    180
aacacagagg aagacattca tcgggctttc cagtcgcttc tcactgaagt gaacaaggct    240
ggcacacagt acctgctgag aacgccaac aggctctttg agagaaaac ttgtcagttc    300
ctctcaacgt ttaaggaatc ctgtcttcaa ttctaccatg ctgagctgaa ggagctttcc    360
tttatcagag ctgcagaaga gtccaggaaa cacatcaaca cctgggtctc aaaaaagacc    420
gaaggtaaaa ttgaagagtt gttgccgggt agctcaattg atgcagaaac caggctggtt    480
cttgtcaatg ccatctactt caaaggaaag tggaatgaac cgtttgacga acatacaca    540
agggaaatgc cctttaaaat aaaccaggag gagcaaggc cagtgcagat gatgtatcag    600
gaggccacgt ttaagctcgc ccacgtgggc gaggtgcgcg cgcagctgct ggagctgccc    660
tacgccagga aggagctgag cctgctggtg ctgctgcctg acgacggcgt ggagctcagc    720
acggtggaaa aaagtctcac ttttgagaaa ctcacagcct ggaccaagcc agactgtatg    780
aagagtactg aggttgaagt tctccttcca aaatttaaac tacaagagga ttatgacatg    840
gaatctgtgc ttcggcattt gggaattgtt gatgccttcc aacagggcaa ggctgacttg    900
tcggcaatgt cagcggagag agacctgtgt ctgtccaagt tcgtgcacaa gagttttgtg    960
gaggtgaatg aagaaggcac cgaggcagcg gcagcgtcga gctgctttgt agttgcagag   1020
tgctgcatgg aatctggccc caggttctgt gctgaccacc cttttccttt cttcatcagg   1080
```

```
cacaacagag ccaacagcat tctgttctgt ggcaggttct catcgccagg aagcggagct   1140
actaacttca gcctgctgaa gcaggctgga gacgtggagg agaaccctgg acctatggac   1200
tggacctgga tcctgttcct ggtggccgcc gccaccaggg tgcacagcgg cattcatgtc   1260
ttcattttgg gctgtttcag tgcagggctt cctaaaacag aagccaactg ggtgaatgta   1320
ataagtgatt tgaaaaaaat tgaagatctt attcaatcta tgcatattga tgctacttta   1380
tatacggaaa gtgatgttca ccccagttgc aaagtaacag caatgaagtg ctttctcttg   1440
gagttacaag ttatttcact tgagtccgga gatgcaagta ttcatgatac agtagaaaat   1500
ctgatcatcc tagcaaacaa cagtttgtct tctaatggga atgtaacaga atctggatgc   1560
aaagaatgtg aggaactgga ggaaaaaaat attaaagaat ttttgcagag ttttgtacat   1620
attgtccaaa tgttcatcaa cacttctagc ggcggcggca gcggcggcgg cggcagcggc   1680
ggcggcggca gcggcggcgg cggcagcggc ggcggcagcc tgcagatcac gtgccctccc   1740
cccatgtccg tggaacacgc agacatctgg gtcaagagct acagcttgta ctccagggag   1800
cggtacattt gtaactctgg tttcaagcgt aaagccggca cgtccagcct gacggagtgc   1860
gtgttgaaca aggccacgaa tgtcgcccac tggacaaccc ccagtctcaa atgcattaga   1920
gaccctgccc tggttcacca aaggccagcg ccaccctcca cagtaacgac ggcaggggtg   1980
accccacagc cagagagcct ctcccttct ggaaaagagc ccgcagcttc atctcccagc   2040
tcaaacaaca cagcggccac aacagcagct attgtcccgg gctcccagct gatgccttca   2100
aaatcacctt ccacaggaac cacagagata agcagtcatg agtcctccca cggcacccc   2160 tctcagacaa cagccaagaa ctgggaactc acagcatccg cctcccacca gccgccaggt   2220
gtgtatccac agggccacag cgacaccact gtggctatct ccacgtccac tgtcctgctg   2280
tgtgggctga gcgctgtgtc tctcctggca tgctacctca agtcaaggca aactccccg   2340 ctggccagcg ttgaaatgga agccatggag gctctgccgg tgacttgggg gaccagcagc   2400
agagatgaag acttggaaaa ctgctctcac cacctatgat aaccgctgat cagcctcgac   2460
tgtgccttct agttgccagc catctgttgt ttgcccctcc ccgtgccttt ccttgaccct   2520
ggaaggtgcc actcccactg tcctttccta ataaaatgag gaaattgcat cgcattgtct   2580
gagtaggtgt cattctattc tggggggtgg ggtggggcag gacagcaagg gggaggattg   2640
ggaagacaat agcaggcatg ctggggatgc ggtgggctct atgg   2684
```

<210> SEQ ID NO 138
<211> LENGTH: 4395
<212> TYPE: DNA
<213> ORGANISM: Artificial Sequence
<220> FEATURE:
<223> OTHER INFORMATION: Synthetic

<400> SEQUENCE: 138

```
gacattgatt attgactagt tattaatagt aatcaattac ggggtcatta gttcatagcc     60
catatatgga gttccgcgtt acataactta cggtaaatgg cccgcctggc tgaccgccca    120 acgaccccg cccattgacg tcaataatga cgtatgttcc catagtaacg ccaatagga    180 ctttccattg acgtcaatgg gtggactatt tacggtaaac tgcccacttg gcagtacatc    240
aagtgtatca tatgccaagt acgccccta ttgacgtcaa tgacggtaaa tggcccgcct    300
ggcattatgc ccagtacatg acctatggg actttcctac ttggcagtac atctacgtat    360
tagtcatcgc tattaccatg gtcgaggtg agccccacgt tctgcttcac tctccccatc    420
```

| | |
|---|---|
| tcccccccct ccccacccccc aatttttgtat ttatttattt tttaattatt ttgtgcagcg | 480 |
| atggggggcgg gggggggggg ggcgcgcgcc aggcggggcg gggcggggcg aggggcgggg | 540 |
| cggggcgagg cggagaggtg cggcggcagc caatcagagc ggcgcgctcc gaaagtttcc | 600 |
| ttttatggcg aggcggcggc ggcggcggcc ctataaaaag cgaagcgcgc ggcgggcggg | 660 |
| agtcgctgcg ttgccttcgc cccgtgcccc gctccgcgcc gcctcgcgcc gcccgccccg | 720 |
| gctctgactg accgcgttac tcccacaggt gagcgggcgg gacggcccct tcctccgggg | 780 |
| ctgtaattag cgcttggttt aatgacggct cgtttctttt ctgtggctgc gtgaaagcct | 840 |
| taaagggctc cggggagggcc ctttgtgcgg ggggagcgg ctcggggggt gcgtgcgtgt | 900 |
| gtgtgtgcgt ggggagcgcc gcgtgcggcc cgcgctgccc ggcggctgtg agcgctgcgg | 960 |
| gcgcggcgcg gggctttgtg cgctccgcgt gtgcgcgagg ggagcgcggc cggggcggt | 1020 |
| gccccgcggt gcgggggggc tgcgagggga acaaaggctg cgtgcggggt gtgtgcgtgg | 1080 |
| gggggtgagc aggggggtgtg ggcgcggcgg tcgggctgta accccccct gcacccccct | 1140 |
| ccccgagttg ctgagcacgg cccggcttcg ggtgcggggc tccgtgcggg gcgtggcgcg | 1200 |
| gggctcgccg tgccgggcgg ggggtggcgg caggtggggg tgccgggcgg ggcggggccg | 1260 |
| cctcgggccg ggagggctc gggggagggg gcgggcggcc ccggagcgcc ggcggctgtc | 1320 |
| gaggcgcggc gagccgcagc cattgccttt tatggtaatc gtgcgagagg gcgcagggac | 1380 |
| ttcctttgtc ccaaatctgg cggagccgaa atcgggaggg cgccgccgca ccccctctag | 1440 |
| cgggcgcggg cgaagcggtg cggcgccggc aggaaggaaa tgggcgggga gggccttcgt | 1500 |
| gcgtcgccgc gccgccgtcc ccttctccat ctccagcctc ggggctgccg caggggacg | 1560 |
| gctgccttcg gggggacgg ggcagggcgg ggttcggctt ctggcgtgtg accggcggct | 1620 |
| ctagagcctc tgctaaccat gttcatgcct tcttcttttt cctacagggg ggatccgttt | 1680 |
| atctgcagaa ttcgcccttg acgtcgccac catggaaact cttttctaatg caagtggtac | 1740 |
| ttttgccata cgccttttaa agatactgtg tcaagataac ccttcgcaca acgtgttctg | 1800 |
| ttctcctgtg agcatctcct ctgccctggc catggttctc ctaggggcaa agggaaacac | 1860 |
| cgcaacccag atggcccagg cactgtcttt aaacacagag gaagacattc atcgggcttt | 1920 |
| ccagtcgctt ctcactgaag tgaacaaggc tggcacacag tacctgctga aacggccaa | 1980 |
| caggctcttt ggagagaaaa cttgtcagtt cctctcaacg tttaaggaat cctgtcttca | 2040 |
| attctaccat gctgagctga aggagctttc ctttatcaga gctgcagaag agtccaggaa | 2100 |
| acacatcaac acctgggtct caaaaaagac cgaaggtaaa attgaagagt tgttgccggg | 2160 |
| tagctcaatt gatgcagaaa ccaggctggt tcttgtcaat gccatctact tcaaaggaaa | 2220 |
| gtggaatgaa ccgtttgacg aaacatacac aaggggaaatg cccttaaaa taaaccagga | 2280 |
| ggagcaaagg ccagtgcaga tgatgtatca ggaggccacg tttaagctcg cccacgtggg | 2340 |
| cgaggtgcgc gcgcagctgc tggagctgcc ctacgccagg aaggagctga gcctgctggt | 2400 |
| gctgctgcct gacgacggcg tggagctcag cacggtggaa aaaagtctca cttttgagaa | 2460 |
| actcacagcc tggaccaagc cagactgtat gaagagtact gaggttgaag ttctccttcc | 2520 |
| aaaatttaaa ctacaagagg attatgacat ggaatctgtg cttcggcatt tgggaattgt | 2580 |
| tgatgccttc caacagggca aggctgactt gtcggcaatg tcagcggaga gagacctgtg | 2640 |
| tctgtccaag ttcgtgcaca agagttttgt ggaggtgaat gaagaaggca ccgaggcagc | 2700 |
| ggcagcgtcg agctgctttg tagttgcaga gtgctgcatg gaatctggcc ccaggttctg | 2760 |
| tgctgaccac ccttttccttt tcttcatcag gcacaacaga gccaacagca ttctgttctg | 2820 |

```
tggcaggttc tcatcgccag gaagcggagc tactaacttc agcctgctga agcaggctgg    2880
agacgtggag gagaaccctg gacctatgga ctggacctgg atcctgttcc tggtggccgc    2940
cgccaccagg gtgcacagcg gcattcatgt cttcattttg gctgtttca gtgcagggct    3000 tcctaaaaca gaagccaact gggtgaatgt aataagtgat ttgaaaaaaa ttgaagatct    3060
tattcaatct atgcatattg atgctacttt atatacggaa agtgatgttc accccagttg    3120
caaagtaaca gcaatgaagt gctttctctt ggagttacaa gttatttcac ttgagtccgg    3180
agatgcaagt attcatgata cagtagaaaa tctgatcatc ctagcaaaca acagtttgtc    3240
ttctaatggg aatgtaacag aatctggatg caaagaatgt gaggaactgg aggaaaaaaa    3300
tattaaagaa tttttgcaga gttttgtaca tattgtccaa atgttcatca acacttctag    3360
cggcggcggc agcggcggcg gcggcagcgg cggcggcggc agcggcggcg gcggcagcgg    3420
cggcggcagc ctgcagatca cgtgccctcc ccccatgtcc gtggaacacg cagacatctg    3480
ggtcaagagc tacagcttgt actccaggga gcggtacatt tgtaactctg gtttcaagcg    3540
taaagccggc acgtccagcc tgacggagtg cgtgttgaac aaggccacga atgtcgccca    3600
ctggacaacc cccagtctca aatgcattag agaccctgcc ctggttcacc aaaggccagc    3660
gccaccctcc acagtaacga cggcaggggt gaccccacag ccagagagcc tctccccttc    3720
tggaaaagag cccgcagctt catctcccag ctcaaacaac acagcggcca acagcagc    3780 tattgtcccg ggctcccagc tgatgccttc aaaatcacct tccacaggaa ccacagagat    3840
aagcagtcat gagtcctccc acggcacccc ctctcagaca acagccaaga actgggaact    3900
cacagcatcc gcctcccacc agccgccagg tgtgtatcca cagggccaca gcgacaccac    3960
tgtggctatc tccacgtcca ctgtcctgct gtgtgggctg agcgctgtgt ctctcctggc    4020
atgctacctc aagtcaaggc aaactccccc gctggccagc gttgaaatgg aagccatgga    4080
ggctctgccg gtgacttggg ggaccagcag cagagatgaa gacttggaaa actgctctca    4140
ccacctatga taaccgctga tcagcctcga ctgtgccttc tagttgccag ccatctgttg    4200
tttgcccctc ccccgtgcct tccttgaccc tggaaggtgc cactcccact gtcctttcct    4260
aataaaatga ggaaattgca tcgcattgtc tgagtaggtg tcattctatt ctgggggtg    4320 gggtggggca ggacagcaag ggggaggatt gggaagacaa tagcaggcat gctggggatg    4380
cggtgggctc tatgg                                                     4395
```

<210> SEQ ID NO 139
<211> LENGTH: 4789
<212> TYPE: DNA
<213> ORGANISM: Artificial Sequence
<220> FEATURE:
<223> OTHER INFORMATION: Synthetic

<400> SEQUENCE: 139

```
gacattgatt attgactagt tattaatagt aatcaattac ggggtcatta gttcatagcc     60
catatatgga gttccgcgtt acataactta cggtaaatgg cccgcctggc tgaccgccca    120
acgacccccg cccattgacg tcaataatga cgtatgttcc catagtaacg ccaatagggg    180
ctttccattg acgtcaatgg gtggactatt tacggtaaac tgcccacttg gcagtacatc    240
aagtgtatca tatgccaagt acgcccccta ttgacgtcaa tgacggtaaa tggcccgcct    300
ggcattatgc ccagtacatg acctatggga ctttcctac ttggcagtac atctacgtat    360
tagtcatcgc tattaccatg gtcgaggtg agccccacgt tctgcttcac tctccccatc    420
```

```
tccccccccct ccccaccccc aattttgtat ttatttattt tttaattatt ttgtgcagcg      480 atggggcgg gggggggggg ggcgcgcgcc aggcggggcg gggcggggcg aggggcgggg       540
cggggcgagg cggagaggtg cggcggcagc caatcagagc ggcgcgctcc gaaagtttcc      600
ttttatggcg aggcggcggc ggcggcggcc ctataaaaag cgaagcgcgc ggcgggcggg      660
agtcgctgcg ttgccttcgc cccgtgcccc gctccgcgcc gcctcgcgcc gcccgccccg      720
gctctgactg accgcgttac tcccacaggt gagcgggcgg gacggcccct tcctccgggg      780
ctgtaattag cgcttggttt aatgacggct cgtttctttt ctgtggctgc gtgaaagcct      840
taaagggctc cggggagggcc ctttgtgcgg ggggagcgg ctcggggggt gcgtgcgtgt      900
gtgtgtgcgt ggggagcgcc gcgtgcggcc cgcgctgccc ggcggctgtg agcgctgcgg      960
gcgcggcgcg gggctttgtg cgctccgcgt gtgcgcgagg ggagcgcggc cgggggcggt      1020
gccccgcggt gcggggggc tgcgagggga acaaaggctg cgtgcggggt gtgtgcgtgg      1080
gggggtgagc aggggtgtg ggcgcggcgg tcgggctgta accccccct gcacccccct      1140 ccccgagttg ctgagcacgg cccggcttcg ggtgcgggc tccgtgcggg gcgtggcgcg      1200
gggctcgccg tgccgggcgg ggggtggcgg caggtggggg tgccgggcgg ggcggggccg      1260 cctcggggccg ggagggctc gggggagggg cgcggcggcc ccggagcgcc ggcggctgtc      1320
gaggcgcggc gagccgcagc cattgccttt tatggtaatc gtgcgagagg gcgcagggac      1380
ttcctttgtc ccaaatctgg cggagccgaa atcgggagg cgccgccgca ccccctctag      1440
cgggcgcggg cgaagcggtg cggcgccggc aggaaggaaa tgggcgggga gggccttcgt      1500
gcgtcgccgc gccgccgtcc ccttctccat ctccagcctc ggggctgccg caggggacg      1560 gctgccttcg gggggacgg ggcagggcgg ggttcggctt ctggcgtgtg accggcggct      1620
ctagagcctc tgctaaccat gttcatgcct tcttctttt cctacagggg ggatccgttt      1680
atctgcagaa ttcgcccttg acgtcgccac catggcgctt ccggtgacag cactgctcct      1740 cccttggcg ctgttgctcc acgcagcaag gccgcagatc cagctgcagc agagcggccc      1800
cgaggtggtg aagcccggcg ccagcgtgaa gatcagctgc aaggccagcg gctacacctt      1860
caccgactac tacatcacct gggtgaagca gaagcccggc cagggcctgg agtggatcgg      1920
ctggatctac cccggcagcg gcaacaccaa gtacaacgag aagttcaagg gcaaggccac      1980
cctgaccgtg gacaccagca gcagcaccgc cttcatgcag ctgagcagcc tgaccagcga      2040
ggacaccgcc gtgtacttct cgccaactac cggcaactac tggttcgcct actggggcca      2100
gggcacccag gtgaccgtga gccggcggcg cggcggcagc ggcggcggcg gcagcggcgg      2160
cggcggcagc gacatcgtgc tgacccagag ccccgccagc ctggccgtga gcctgggcca      2220
gagagccacc atcagctgca aggccagcca gagcgtggac ttcgacggcg acagctacat      2280
gaactggtac cagcagaagc ccggccagcc ccccaaggtg ctgatctacg ccgccagcaa      2340
cctggagagc ggcatccccg ccagattcag cggcagcggc agcggcaccg acttcacccct      2400 gaacatccac cccgtggagg aggaggacgc cgccacctac tactgccagc agagcaacga      2460
ggacccctgg accttcggcg gcggcaccaa gctggagatc aagagcgccg ccgccttcgt      2520
gcccgtgttc ctgccccgcca agcccaccac caccccccgcc cccagacccc ccacccccgc      2580
ccccaccatc gccagccagc ccctgagcct gagacccgag gcctgcagac cgccgccgg      2640 cggcgccgtg cacaccagag gcctggactt cgcctgcgac atctacatct gggcccccct      2700
ggccggcacc tgcggcgtgc tgctgctgag cctggtgatc accctgtact gcaaccacag      2760
aaacagaagc aagagaagca gactgctgca cagcgactac atgaacatga cccccagaag      2820
```

| | |
|---|---|
| acccggcccc accagaaagc actaccagcc ctacgccccc cccagagact cgccgccta | 2880 |
| cagaagcaga gtgaagttca gcagaagcgc cgacgccccc gcctaccagc agggccagaa | 2940 |
| ccagctgtac aacgagctga acctgggcag aagagaggag tacgacgtgc tggacaagag | 3000 |
| aagaggcaga gaccccgaga tgggcggcaa gcccagaaga aagaaccccc aggagggcct | 3060 |
| gtacaacgag ctgcagaagg acaagatggc cgaggcctac agcgagatcg gcatgaaggg | 3120 |
| cgagagaaga agaggcaagg gccacgacgg cctgtaccag ggcctgagca ccgccaccaa | 3180 |
| ggacacctac gacgccctgc acatgcaggc cctgccccc agaggaagcg gagctactaa | 3240 |
| cttcagcctg ctgaagcagg ctggagacgt ggaggagaac cctggaccta tgtctcgctc | 3300 |
| cgttgcctta gctgtgctcg cgctactctc tctttctgga ttagaggctg tcatggcgcc | 3360 |
| ccgaaccctc ttcctgggtg gaggcggttc aggcggaggt ggctctggcg gtggcggatc | 3420 |
| gatccagcgt actccaaaga ttcaggttta ctcacgtcat ccagcagaga atggaaagtc | 3480 |
| aaatttcctg aattgctatg tgtctgggtt tcatccatcc gacattgaag ttgacttact | 3540 |
| gaagaatgga gagagaattg aaaaagtgga gcattcagac ttgtctttca gcaaggactg | 3600 |
| gtctttctat ctcttgtact acactgaatt caccccccact gaaaaagatg agtatgcctg | 3660 |
| ccgtgtgaac catgtgactt tgtcacagcc caagatagtt aagtgggatc gagacatggg | 3720 |
| tggtggtggt tctggtggtg gtggttctgg cggcggcggc tccggtggtg gtggatccgg | 3780 |
| ctccccactcc ttgaagtatt tccacacttc cgtgtcccgg cccggccgcg gggagccccg | 3840 |
| cttcatctct gtgggctacg tggacgacac ccagttcgtg cgcttcgaca cgacgcgc | 3900 |
| gagtccgagg atggtgccgc gggcgccgtg gatggagcag gaggggtcag agtattggga | 3960 |
| ccggagaca cggagcgcca gggacaccgc acagattttc cgagtgaatc tgcggacgct | 4020 |
| gcgcggctac tacaatcaga gcgaggccgg gtctcacacc ctgcagtgga tgcatggctg | 4080 |
| cgagctgggg cccgacgggc gcttcctccg cgggtatgaa cagttcgcct acgacggcaa | 4140 |
| ggattatctc accctgaatg aggacctgcg ctcctggacc gcggtggaca cggcggctca | 4200 |
| gatctccgag caaaagtcaa atgatgcctc tgaggcggag caccagagag cctacctgga | 4260 |
| agacacatgc gtggagtggc tccacaaata cctggagaag gggaaggaga cgctgcttca | 4320 |
| cctggagccc ccaaagacac acgtgactca ccaccccatc tctgaccatg aggccaccct | 4380 |
| gaggtgctgg gccctgggct tctaccctgc ggagatcaca ctgacctggc agcaggatgg | 4440 |
| ggagggccat acccaggaca cggagctcgt ggagaccagg cctgcagggg atggaacctt | 4500 |
| ccagaagtgg gcagctgtgg tggtgccttc tggagaggag cagagataca cgtgccatgt | 4560 |
| gcagcatgag gggctacccg agcccgtcac cctgagatgg aagccggctt cccagcccac | 4620 |
| catccccatc gtgggcatca ttgctggcct ggttctcctt ggatctgtgg tctctggagc | 4680 |
| tgtggttgct gctgtgatat ggaggaagaa gagctcaggt ggaaaaggag ggagctactc | 4740 |
| taaggctgag tggagcgaca gtgcccaggg gtctgagtct cacagcttg | 4789 |

<210> SEQ ID NO 140
<211> LENGTH: 4759
<212> TYPE: DNA
<213> ORGANISM: Artificial Sequence
<220> FEATURE:
<223> OTHER INFORMATION: Synthetic

<400> SEQUENCE: 140

```
gacattgatt attgactagt tattaatagt aatcaattac ggggtcatta gttcatagcc      60
catatatgga gttccgcgtt acataactta cggtaaatgg cccgcctggc tgaccgccca     120
acgaccccg cccattgacg tcaataatga cgtatgttcc catagtaacg ccaatagga     180
ctttccattg acgtcaatgg gtggactatt tacggtaaac tgcccacttg gcagtacatc     240
aagtgtatca tatgccaagt acgccccta ttgacgtcaa tgacggtaaa tggcccgcct     300
ggcattatgc ccagtacatg accttatggg actttcctac ttggcagtac atctacgtat     360
tagtcatcgc tattaccatg gtcgaggtg agccccacgt tctgcttcac tctccccatc     420
tccccccct ccccacccc aattttgtat ttatttattt tttaattatt ttgtgcagcg     480
atggggcgg ggggggggg ggcgcgcgcc aggcggggcg gggcggggcg aggggcgggg     540
cggggcgagg cggagaggtg cggcggcagc caatcagagc ggcgcgctcc gaaagtttcc     600
ttttatggcg aggcggcggc ggcggcgcc ctataaaaag cgaagcgcgc ggcgggcggg     660
agtcgctgcg ttgccttcgc cccgtgcccc gctccgcgcc gcctcgcgcc gcccgccccg     720
gctctgactg accgcgttac tcccacaggt gagcgggcgg gacggccctt ctcctccggg     780
ctgtaattag cgcttggttt aatgacggct cgtttctttt ctgtggctgc gtgaaagcct     840
taaagggctc cgggagggcc ctttgtgcgg ggggagcgg ctcggggggt gcgtgcgtgt     900
gtgtgtgcgt ggggagcgcc gcgtgcggcc cgcgctgccc ggcggctgtg agcgctgcgg     960
gcgcggcgcg gggctttgtg cgctccgcgt gtgcgcgagg ggagcgcggc cggggcggt    1020
gccccgcggt gcggggggc tgcgagggga acaaaggctg cgtgcggggt gtgtgcgtgg    1080
gggggtgagc aggggggtgtg ggcgcggcgg tcgggctgta accccccct gcaccccct    1140
ccccgagttg ctgagcacgg cccggcttcg ggtgcggggc tccgtgcggg gcgtggcgcg    1200
gggctcgccg tgccgggcgg ggggtggcgg caggtggggg tgccgggcgg ggcggggccg    1260
cctcgggccg gggagggctc gggggagggg cgcggcggcc ccggagcgcc ggcggctgtc    1320
gaggcgcggc gagccgcagc cattgccttt tatggtaatc gtgcgagagg gcgcagggac    1380
ttcctttgtc ccaaatctgg cggagccgaa atctgggagg cgccgccgca cccctctag    1440
cgggcgcggg cgaagcggtg cggcgccggc aggaaggaaa tgggcgggga gggccttcgt    1500
gcgtcgccgc gccgccgtcc ccttctccat ctccagcctc ggggctgccg caggggacg    1560
gctgccttcg gggggacgg ggcagggcgg ggttcggctt ctggcgtgtg accggcggct    1620
ctagagcctc tgctaaccat gttcatgcct tcttcttttt cctacagggg ggatccgttt    1680
atctgcagaa ttcgcccttg acgtcgccac catggcgctt ccggtgacag cactgctcct    1740
ccccttggcg ctgttgctcc acgcagcaag gccgcaggtg cagctgcagc agtggggcgc    1800
cggcctgctg aagcccagcg agaccctgag cctgacctgc gccgtgtacg gcggcagctt    1860
cagcgcctac tactgagct ggatcagaca gcccccgc aagggcctgg agtggatcgg    1920
cgacatcaac cacggcggcg gcaccaacta caacccagc ctgaagagca gagtgaccat    1980
cagcgtggac accagcaaga accagttcag cctgaagctg aacagcgtga ccgccgccga    2040
caccgccgtg tactactgcg ccagcctgac cgcctactgg ggccagggca gcctggtgac    2100
cgtgagcagc ggcggcgggc gcagcggcg cggcggcagc ggcggcggcg gcagcgacat    2160
ccagatgacc cagagcccca ccagcctgag cgccagcgtg ggcgacagag tgaccatcac    2220
ctgcagagcc agccagggca tcagcagctg gctgacctgg taccagcaga agcccgagaa    2280
```

```
ggcccccaag agcctgatct acgccgccag cagcctgcag agcggcgtgc ccagcagatt   2340
cagcggcagc ggcagcggca ccgacttcac cctgaccatc agcagcctgc agcccgagga   2400
cttcgccacc tactactgcc agcagtacga cagctacccc atcaccttcg gccagggcac   2460
cagactggag atcaagagcg ccgccgcctt cgtgcccgtg ttcctgcccg ccaagcccac   2520
caccacccc gccccagac cccccacccc cgccccacc atcgccagcc agcccctgag   2580
cctgagaccc gaggcctgca gacccgccgc cggcggcgcc gtgcacacca gaggcctgga   2640
cttcgcctgc gacatctaca tctgggcccc cctggccggc acctgcggcg tgctgctgct   2700
gagcctggtg atcaccctgt actgcaacca cagaaacaga aagagaggca gaaagaagct   2760
gctgtacatc ttcaagcagc ccttcatgag acccgtgcag accacccagg aggaggacgg   2820
ctgcagctgc agattccccg aggaggagga gggcggctgc gagctgagag tgaagttcag   2880
cagaagcgcc gacgccccg cctaccagca gggccagaac cagctgtaca cgagctgaa   2940
cctgggcaga agagaggagt acgacgtgct ggacaagaga gaggcagag accccgagat   3000
gggcggcaag cccagaagaa agaaccccca ggagggcctg tacaacgagc tgcagaagga   3060
caagatggcc gaggcctaca gcgagatcgg catgaagggc gagagaagaa gaggcaaggg   3120
ccacgacggc ctgtaccagg gcctgagcac cgccaccaag gacacctacg acgccctgca   3180
catgcaggcc ctgcccccca gaggaagcgg attcagcctg ctgaagcagg ctggagacgt   3240
ggaggagaac cctggaccta tgtctcgctc cgttgcctta gctgtgctcg cgctactctc   3300
tctttctgga ttagaggctg tcatggcgcc ccgaaccctc ttcctgggtg aggcggttc   3360
aggcggaggt ggctctggcg gtggcggatc gatccagcgt actccaaaga ttcaggttta   3420
ctcacgtcat ccagcagaga atggaaagtc aaatttcctg aattgctatg tgtctgggtt   3480
tcatccatcc gacattgaag ttgacttact gaagaatgga gagagaattg aaaaagtgga   3540
gcattcagac ttgtctttca gcaaggactg gtctttctat ctcttgtact acactgaatt   3600
caccccact gaaaaagatg agtatgcctg ccgtgtgaac catgtgactt tgtcacagcc   3660
caagatagtt aagtgggatc gagacatggg tggtggtggt tctggtggtg gtggttctgg   3720
cggcggcggc tccggtggtg gtggatccgg ctcccactcc ttgaagtatt ccacacttc   3780
cgtgtcccgg cccggccgcg gggagccccg cttcatctct gtgggctacg tggacgacac   3840
ccagttcgtg cgcttcgaca cgacgcgcc gagtccgagg atggtgccgc gggcgccgtg   3900
gatggagcag gaggggtcag agtattggga ccgggagaca cggagcgcca gggacaccgc   3960
acagattttc cgagtgaatc tgcggacgct gcgcggctac tacaatcaga gcaggccgg   4020
gtctcacacc ctgcagtgga tgcatggctg cgagctgggg cccgacgggc gcttcctccg   4080
cgggtatgaa cagttcgcct acgacggcaa ggattatctc accctgaatg aggacctgcg   4140
ctcctggacc gcggtggaca cggcggctca gatctccgag caaaagtcaa atgatgcctc   4200
tgaggcggag caccagagag cctacctgga agacacatgc gtggagtggc tccacaaata   4260
cctggagaag gggaaggaga cgctgcttca cctggagccc ccaaagacac acgtgactca   4320
ccaccccatc tctgaccatg aggccaccct gaggtgctgg gccctgggct ctaccctgc   4380
ggagatcaca ctgacctggc agcaggatgg ggagggccat acccaggaca cggagctcgt   4440
ggagaccagg cctgcagggg atggaacctt ccagaagtgg gcagctgtgg tggtgccttc   4500
tggagaggag cagagataca cgtgccatgt gcagcatgag gggctacccg agcccgtcac   4560
cctgagatgg aagccggctt cccagcccac catccccatc gtgggcatca ttgctggcct   4620
ggttctcctt ggatctgtgg tctctggagc tgtggttgct gctgtgatat ggaggaagaa   4680
```

```
gagctcaggt ggaaaaggag ggagctactc taaggctgag tggagcgaca gtgcccaggg    4740
gtctgagtct cacagcttg                                                 4759

<210> SEQ ID NO 141
<211> LENGTH: 4762
<212> TYPE: DNA
<213> ORGANISM: Artificial Sequence
<220> FEATURE:
<223> OTHER INFORMATION: Synthetic

<400> SEQUENCE: 141
gacattgatt attgactagt tattaatagt aatcaattac ggggtcatta gttcatagcc      60
catatatgga gttccgcgtt acataactta cggtaaatgg cccgcctggc tgaccgccca     120 acgaccccg cccattgacg tcaataatga cgtatgttcc catagtaacg ccaatagggga     180 ctttccattg acgtcaatgg gtggactatt tacggtaaac tgcccacttg gcagtacatc     240
aagtgtatca tatgccaagt acgcccccta ttgacgtcaa tgacggtaaa tggcccgcct     300
ggcattatgc ccagtacatg accttatggg actttcctac ttggcagtac atctacgtat     360
tagtcatcgc tattaccatg gtcgaggtg agccccacgt tctgcttcac tctccccatc      420 tccccccct ccccaccccc aattttgtat ttatttattt tttaattatt ttgtgcagcg      480 atggggggcgg ggggggggg ggcgcgcgcc aggcggggcg gggcggggcg aggggcgggg     540
cggggcgagg cggagaggtg cggcggcagc caatcagagc ggcgcgctcc gaaagtttcc     600
ttttatggcg aggcggcggc ggcggcggcc ctataaaaag cgaagcgcgc ggcgggcggg     660
agtcgctgcg ttgccttcgc cccgtgcccc gctccgcgcc gcctcgcgcc gcccgccccg     720
gctctgactg accgcgttac tcccacaggt gagcgggcgg gacggccctt ctcctccggg     780
ctgtaattag cgcttggttt aatgacggct cgtttctttt ctgtggctgc gtgaaagcct     840
taaagggctc cggagggcc ctttgtgcgg ggggagcgg ctcggggggt gcgtgcgtgt      900
gtgtgtgcgt ggggagcgcc gcgtgcggcc cgcgctgccc ggcggctgtg agcgctgcgg    960
gcgcggcgcg gggctttgtg cgctccgcgt gtgcgcgagg ggagcgcggc cggggcggt     1020 gccccgcggt gcggggggc tgcgagggga acaaaggctg cgtgcgggt gtgtgcgtgg      1080 gggggtgagc aggggtgtg ggcgcggcgg tcgggctgta accccccct gcaccccct      1140 ccccgagttg ctgagcacgg cccggcttcg ggtgcgggc tccgtgcggg gcgtggcgcg    1200
gggctcgccg tgccgggcgg gggtggcgg caggtgggggg tgccgggcgg ggcggggccg    1260
cctcgggccg gggagggctc gggggagggg cgcggcggcc ccggagcgcc ggcggctgtc    1320
gaggcgcggc gagccgcagc cattgccttt tatggtaatc gtgcgagagg gcgcagggac    1380
ttcctttgtc ccaaatctgg cggagccgaa atctgggagg cgccgccgca ccccctctag   1440
cgggcgcggg cgaagcggtg cggcgccggc aggaaggaaa tgggcgggga gggccttcgt    1500
gcgtcgccgc gccgccgtcc ccttctccat ctccagcctc ggggctgccg caggggggacg    1560 gctgccttcg ggggggacgg ggcagggcgg ggttcggctt ctggcgtgtg accggcggct    1620
ctagagcctc tgctaaccat gttcatgcct tcttcttttt cctacagggg ggatccgttt    1680
atctgcagaa ttcgcccttg acgtcgccac catggcgctt ccggtgacag cactgctcct    1740 cccttggcg ctgttgctcc acgcagcaag gccggacatc cagatgaccc agagccccac    1800
cagcctgagc gccagcgtgg gcgacagagt gaccatcacc tgcagagcca gccagggcat    1860
cagcagctgg ctgacctggt accagcagaa gcccgagaag gccccaagga gcctgatcta    1920
```

```
cgccgccagc agcctgcaga gcggcgtgcc cagcagattc agcggcagcg gcagcggcac    1980
cgacttcacc ctgaccatca gcagcctgca gcccgaggac ttcgccacct actactgcca    2040
gcagtacgac agctaccccca tcaccttcgg ccagggcacc agactggaga tcaagggcgg    2100
cggcggcagc ggcggcggcg gcagcggcgg cggcggcagc caggtgcagc tgcagcagtg    2160
gggcgccggc ctgctgaagc ccagcgagac cctgagcctg acctgcgccg tgtacggcgg    2220
cagcttcagc gcctactact ggagctggat cagacagccc cccggcaagg gcctggagtg    2280
gatcggcgac atcaaccacg gcggcggcac caactacaac cccagcctga gagcagagt    2340
gaccatcagc gtggacacca gcaagaacca gttcagcctg aagctgaaca gcgtgaccgc    2400
cgccgacacc gccgtgtact actgcgccag cctgaccgcc tactgggcc agggcagcct    2460
ggtgaccgtg agcgccgccg ccttcgtgcc cgtgttcctg cccgccaagc ccaccaccac    2520
ccccgccccc agaccccca cccccgcccc caccatcgcc agccagcccc tgagcctgag    2580
acccgaggcc tgcagacccg ccgcggcg cgccgtgcac accagaggcc tggacttcgc    2640
ctgcgacatc tacatctggg ccccctggc cggcacctgc ggcgtgctgc tgctgagcct    2700
ggtgatcacc ctgtactgca accacagaaa cagaaagaga ggcagaaaga agctgctgta    2760
catcttcaag cagcccttca tgagacccgt gcagaccacc caggaggagg acggctgcag    2820
ctgcagattc cccgaggagg aggagggcgg ctgcgagctg agagtgaagt tcagcagaag    2880
cgccgacgcc cccgcctacc agcagggcca gaaccagctg tacaacgagc tgaacctggg    2940
cagaagagag gagtacgacg tgctggacaa gagaagaggc agagacccccg agatgggcgg    3000
caagcccaga gaaagaacc cccaggaggg cctgtacaac gagctgcaga aggacaagat    3060
ggccgaggcc tacagcgaga tcggcatgaa gggcgagaga agaagaggca agggccacga    3120
cggcctgtac cagggcctga gcaccgccac caaggacacc tacgacgccc tgcacatgca    3180
ggccctgccc cccagaggaa gcggagctac taacttcagc ctgctgaagc aggctggaga    3240
cgtggaggag aaccctggac ctatgtctcg ctccgttgcc ttagctgtgc tcgcgctact    3300
ctctctttct ggattagagg ctgtcatggc gccccgaacc ctcttcctgg gtggaggcgg    3360
ttcaggcgga ggtggctctg gcggtggcgg atcgatccag cgtactccaa agattcaggt    3420
ttactcacgt catccagcag agaatggaaa gtcaaatttc ctgaattgct atgtgtctgg    3480
gtttcatcca tccgacattg aagttgactt actgaagaat ggagagagaa ttgaaaaagt    3540
ggagcattca gacttgtctt tcagcaagga ctggtctttc tatctcttgt actacactga    3600
attcacccc actgaaaaag atgagtatgc ctgccgtgtg aaccatgtga ctttgtcaca    3660
gcccaagata gttaagtggg atcgagacat gggtggtggt ggttctggtg gtggtggttc    3720
tggcggcggc ggctccggtg gtggtggatc cggctccac tccttgaagt atttccacac    3780
ttccgtgtcc cggcccggcc gcgggagcc ccgcttcatc tctgtgggct acgtggacga    3840
cacccagttc gtgcgcttcg acaacgacgc cgcgagtccg aggatggtgc cgcgggcgcc    3900
gtggatggag caggaggggt cagagtattg ggaccgggag acacgagcg ccaggacac    3960
cgcacagatt ttccgagtga atctgcggac gctgcgcggc tactacaatc agagcgaggc    4020
cgggtctcac accctgcagt ggatgcatgg ctgcgagctg gggcccgacg gcgcttcct    4080
ccgcgggtat gaacagttcg cctacgacgg caaggattat ctcaccctga atgaggacct    4140
gcgctcctgg accgcggtgg acacggcgg tcagatctcc gagcaaaagt caaatgatgc    4200
ctctctgaggcg gagcaccaga gagcctacct ggaagacaca tgcgtggagt ggctccacaa    4260
atacctggag aaggggaagg agacgctgct tcacctggag cccccaaaga cacacgtgac    4320
```

```
tcaccacccc atctctgacc atgaggccac cctgaggtgc tgggccctgg gcttctaccc    4380
tgcggagatc acactgacct ggcagcagga tggggagggc catacccagg acacggagct    4440
cgtggagacc aggcctgcag gggatggaac cttccagaag tgggcagctg tggtggtgcc    4500
ttctggagag gagcagagat acacgtgcca tgtgcagcat gaggggctac ccgagcccgt    4560
caccctgaga tggaagccgg cttcccagcc caccatcccc atcgtgggca tcattgctgg    4620
cctggttctc cttggatctg tggtctctgg agctgtggtt gctgctgtga tatgtgaggaa    4680 gaagagctca ggtggaaaag gagggagcta ctctaaggct gagtggagcg acagtgccca    4740
ggggtctgag tctcacagct tg                                             4762
```

<210> SEQ ID NO 142
<211> LENGTH: 500
<212> TYPE: PRT
<213> ORGANISM: Artificial Sequence
<220> FEATURE:
<223> OTHER INFORMATION: Synthetic

<400> SEQUENCE: 142

```
Met Ser Arg Ser Val Ala Leu Ala Val Leu Ala Leu Leu Ser Leu Ser
1               5                   10                  15

Gly Leu Glu Ala Val Met Ala Pro Arg Thr Leu Phe Leu Gly Gly Gly
                20                  25                  30

Gly Ser Gly Gly Gly Gly Ser Gly Gly Gly Ser Ile Gln Arg Thr
            35                  40                  45

Pro Lys Ile Gln Val Tyr Ser Arg His Pro Ala Glu Asn Gly Lys Ser
        50                  55                  60

Asn Phe Leu Asn Cys Tyr Val Ser Gly Phe His Pro Ser Asp Ile Glu
65                  70                  75                  80

Val Asp Leu Leu Lys Asn Gly Glu Arg Ile Glu Lys Val Glu His Ser
                85                  90                  95

Asp Leu Ser Phe Ser Lys Asp Trp Ser Phe Tyr Leu Leu Tyr Tyr Thr
            100                 105                 110

Glu Phe Thr Pro Thr Glu Lys Asp Glu Tyr Ala Cys Arg Val Asn His
        115                 120                 125

Val Thr Leu Ser Gln Pro Lys Ile Val Lys Trp Asp Arg Asp Met Gly
130                 135                 140

Gly Gly Gly Ser Gly Gly Gly Gly Ser Gly Gly Gly Gly Ser Gly Gly
145                 150                 155                 160

Gly Gly Ser Gly Ser His Ser Leu Lys Tyr Phe His Thr Ser Val Ser
                165                 170                 175

Arg Pro Gly Arg Gly Glu Pro Arg Phe Ile Ser Val Gly Tyr Val Asp
            180                 185                 190

Asp Thr Gln Phe Val Arg Phe Asp Asn Asp Ala Ala Ser Pro Arg Met
        195                 200                 205

Val Pro Arg Ala Pro Trp Met Glu Gln Glu Gly Ser Glu Tyr Trp Asp
210                 215                 220

Arg Glu Thr Arg Ser Ala Arg Asp Thr Ala Gln Ile Phe Arg Val Asn
225                 230                 235                 240

Leu Arg Thr Leu Arg Gly Tyr Tyr Asn Gln Ser Glu Ala Gly Ser His
                245                 250                 255

Thr Leu Gln Trp Met His Gly Cys Glu Leu Gly Pro Asp Gly Arg Phe
            260                 265                 270
```

-continued

```
Leu Arg Gly Tyr Glu Gln Phe Ala Tyr Asp Gly Lys Asp Tyr Leu Thr
            275                 280                 285
Leu Asn Glu Asp Leu Arg Ser Trp Thr Ala Val Asp Thr Ala Ala Gln
        290                 295                 300
Ile Ser Glu Gln Lys Ser Asn Asp Ala Ser Glu Ala Glu His Gln Arg
305                 310                 315                 320
Ala Tyr Leu Glu Asp Thr Cys Val Glu Trp Leu His Lys Tyr Leu Glu
                325                 330                 335
Lys Gly Lys Glu Thr Leu Leu His Leu Glu Pro Pro Lys Thr His Val
            340                 345                 350
Thr His His Pro Ile Ser Asp His Glu Ala Thr Leu Arg Cys Trp Ala
        355                 360                 365
Leu Gly Phe Tyr Pro Ala Glu Ile Thr Leu Thr Trp Gln Gln Asp Gly
    370                 375                 380
Glu Gly His Thr Gln Asp Thr Glu Leu Val Glu Thr Arg Pro Ala Gly
385                 390                 395                 400
Asp Gly Thr Phe Gln Lys Trp Ala Ala Val Val Pro Ser Gly Glu
                405                 410                 415
Glu Gln Arg Tyr Thr Cys His Val Gln His Glu Gly Leu Pro Glu Pro
            420                 425                 430
Val Thr Leu Arg Trp Lys Pro Ala Ser Gln Pro Thr Ile Pro Ile Val
        435                 440                 445
Gly Ile Ile Ala Gly Leu Val Leu Leu Gly Ser Val Val Ser Gly Ala
    450                 455                 460
Val Val Ala Ala Val Ile Trp Arg Lys Lys Ser Ser Gly Gly Lys Gly
465                 470                 475                 480
Gly Ser Tyr Ser Lys Ala Glu Trp Ser Asp Ser Ala Gln Gly Ser Glu
                485                 490                 495
Ser His Ser Leu
            500

<210> SEQ ID NO 143
<211> LENGTH: 417
<212> TYPE: PRT
<213> ORGANISM: Artificial Sequence
<220> FEATURE:
<223> OTHER INFORMATION: Synthetic

<400> SEQUENCE: 143

Met Asp Trp Thr Trp Ile Leu Phe Leu Val Ala Ala Ala Thr Arg Val
1               5                   10                  15
His Ser Gly Ile His Val Phe Ile Leu Gly Cys Phe Ser Ala Gly Leu
            20                  25                  30
Pro Lys Thr Glu Ala Asn Trp Val Asn Val Ile Ser Asp Leu Lys Lys
        35                  40                  45
Ile Glu Asp Leu Ile Gln Ser Met His Ile Asp Ala Thr Leu Tyr Thr
    50                  55                  60
Glu Ser Asp Val His Pro Ser Cys Lys Val Thr Ala Met Lys Cys Phe
65                  70                  75                  80
Leu Leu Glu Leu Gln Val Ile Ser Leu Glu Ser Gly Asp Ala Ser Ile
                85                  90                  95
His Asp Thr Val Glu Asn Leu Ile Ile Leu Ala Asn Asn Ser Leu Ser
            100                 105                 110
Ser Asn Gly Asn Val Thr Glu Ser Gly Cys Lys Glu Cys Glu Glu Leu
        115                 120                 125
```

Glu Lys Asn Ile Lys Glu Phe Leu Gln Ser Phe Val His Ile Val
130                 135                 140

Gln Met Phe Ile Asn Thr Ser Ser Gly Gly Ser Gly Gly Gly
145                 150                 155                 160

Ser Gly Gly Gly Ser Gly Gly Gly Ser Gly Gly Gly Ser Leu
                165                 170                 175

Gln Ile Thr Cys Pro Pro Pro Met Ser Val Glu His Ala Asp Ile Trp
                180                 185                 190

Val Lys Ser Tyr Ser Leu Tyr Ser Arg Glu Arg Tyr Ile Cys Asn Ser
                195                 200                 205

Gly Phe Lys Arg Lys Ala Gly Thr Ser Ser Leu Thr Glu Cys Val Leu
                210                 215                 220

Asn Lys Ala Thr Asn Val Ala His Trp Thr Thr Pro Ser Leu Lys Cys
225                 230                 235                 240

Ile Arg Asp Pro Ala Leu Val His Gln Arg Pro Ala Pro Pro Ser Thr
                245                 250                 255

Val Thr Thr Ala Gly Val Thr Pro Gln Pro Glu Ser Leu Ser Pro Ser
                260                 265                 270

Gly Lys Glu Pro Ala Ala Ser Ser Pro Ser Ser Asn Asn Thr Ala Ala
                275                 280                 285

Thr Thr Ala Ala Ile Val Pro Gly Ser Gln Leu Met Pro Ser Lys Ser
290                 295                 300

Pro Ser Thr Gly Thr Thr Glu Ile Ser Ser His Glu Ser Ser His Gly
305                 310                 315                 320

Thr Pro Ser Gln Thr Thr Ala Lys Asn Trp Glu Leu Thr Ala Ser Ala
                325                 330                 335

Ser His Gln Pro Pro Gly Val Tyr Pro Gln Gly His Ser Asp Thr Thr
                340                 345                 350

Val Ala Ile Ser Thr Ser Thr Val Leu Leu Cys Gly Leu Ser Ala Val
                355                 360                 365

Ser Leu Leu Ala Cys Tyr Leu Lys Ser Arg Gln Thr Pro Pro Leu Ala
370                 375                 380

Ser Val Glu Met Glu Ala Met Glu Ala Leu Pro Val Thr Trp Gly Thr
385                 390                 395                 400

Ser Ser Arg Asp Glu Asp Leu Glu Asn Cys Ser His His Leu Gly Ser
                405                 410                 415

Gly

<210> SEQ ID NO 144
<211> LENGTH: 376
<212> TYPE: PRT
<213> ORGANISM: Homo sapiens

<400> SEQUENCE: 144

Met Glu Thr Leu Ser Asn Ala Ser Gly Thr Phe Ala Ile Arg Leu Leu
1               5                   10                  15

Lys Ile Leu Cys Gln Asp Asn Pro Ser His Asn Val Phe Cys Ser Pro
                20                  25                  30

Val Ser Ile Ser Ser Ala Leu Ala Met Val Leu Leu Gly Ala Lys Gly
            35                  40                  45

Asn Thr Ala Thr Gln Met Ala Gln Ala Leu Ser Leu Asn Thr Glu Glu
        50                  55                  60

Asp Ile His Arg Ala Phe Gln Ser Leu Leu Thr Glu Val Asn Lys Ala
65                  70                  75                  80

Gly Thr Gln Tyr Leu Leu Arg Thr Ala Asn Arg Leu Phe Gly Glu Lys
            85                  90                  95

Thr Cys Gln Phe Leu Ser Thr Phe Lys Glu Ser Cys Leu Gln Phe Tyr
            100                 105                 110

His Ala Glu Leu Lys Glu Leu Ser Phe Ile Arg Ala Ala Glu Glu Ser
            115                 120                 125

Arg Lys His Ile Asn Thr Trp Val Ser Lys Thr Glu Gly Lys Ile
130                 135                 140

Glu Glu Leu Leu Pro Gly Ser Ser Ile Asp Ala Glu Thr Arg Leu Val
145                 150                 155                 160

Leu Val Asn Ala Ile Tyr Phe Lys Gly Lys Trp Asn Glu Pro Phe Asp
                165                 170                 175

Glu Thr Tyr Thr Arg Glu Met Pro Phe Lys Ile Asn Gln Glu Glu Gln
            180                 185                 190

Arg Pro Val Gln Met Met Tyr Gln Glu Ala Thr Phe Lys Leu Ala His
            195                 200                 205

Val Gly Glu Val Arg Ala Gln Leu Leu Glu Leu Pro Tyr Ala Arg Lys
            210                 215                 220

Glu Leu Ser Leu Val Leu Leu Pro Asp Asp Gly Val Glu Leu Ser
225                 230                 235                 240

Thr Val Glu Lys Ser Leu Thr Phe Glu Lys Leu Thr Ala Trp Thr Lys
            245                 250                 255

Pro Asp Cys Met Lys Ser Thr Glu Val Glu Val Leu Leu Pro Lys Phe
            260                 265                 270

Lys Leu Gln Glu Asp Tyr Asp Met Glu Ser Val Leu Arg His Leu Gly
            275                 280                 285

Ile Val Asp Ala Phe Gln Gln Gly Lys Ala Asp Leu Ser Ala Met Ser
            290                 295                 300

Ala Glu Arg Asp Leu Cys Leu Ser Lys Phe Val His Lys Ser Phe Val
305                 310                 315                 320

Glu Val Asn Glu Glu Gly Thr Glu Ala Ala Ala Ser Ser Cys Phe
            325                 330                 335

Val Val Ala Glu Cys Cys Met Glu Ser Gly Pro Arg Phe Cys Ala Asp
            340                 345                 350

His Pro Phe Leu Phe Phe Ile Arg His Asn Arg Ala Asn Ser Ile Leu
            355                 360                 365

Phe Cys Gly Arg Phe Ser Ser Pro
            370                 375

<210> SEQ ID NO 145
<211> LENGTH: 1203
<212> TYPE: DNA
<213> ORGANISM: Artificial Sequence
<220> FEATURE:
<223> OTHER INFORMATION: Synthetic

<400> SEQUENCE: 145
ggctccggtg cccgtgtgcg gaccgggctc cggtgcccgt cagtgggcag agcgcacatc      60
gcccacagtc cccgagaagt tgggggagg ggtcggcaat tgaaccggtg cctagagaag      120
gtggcgcggg gtaaactggg aaagtgatgt cgtgtactgg ctccgccttt ttcccgaggg      180
tgggggagaa ccgtatataa gtgcagtagt cgccgtgaac gttcttttc gcaacgggtt      240 tgccgccaga acacaggtaa gtgccgtgtg tggttcccgc gggcctggcc tctttacggg      300
ttatggccct tgcgtgcctt gaattacttc cactggctgc agtacgtgat tcttgatccc      360

```
gagcttcggg ttggaagtgg gtgggagagt tcgaggcctt gcgcttaagg agccccttcg      420
cctcgtgctt gagttgaggc ctggcctggg cgctggggcc gccgcgtgcg aatctggtgg      480
caccttcgcg cctgtctcgc tgctttcgat aagtctctag ccatttaaaa ttttgatga       540 cctgctgcga cgcttttttt ctggcaagat agtcttgtaa atgcgggcca agatctgcac      600
actggtattt cggttttgg ggccgcgggc ggcgacgggg cccgtgcgtc ccagcgcaca       660
tgttcggcga ggcggggcct gcgagcgcgg ccaccgagaa tcggacgggg gtagtctcaa      720
gctggccggc ctgctctggt gcctggcctc gcgccgccgt gtatcgcccc gccctgggcg      780
gcaaggctgg cccggtcggc accagttgcg tgagcggaaa gatggccgct cccggccct      840 gctgcaggga gctcaaaatg gaggacgcgg cgctcgggag agcgggcggg tgagtcaccc      900
acacaaagga aagggccttt tccgtcctca gccgtcgctt catgtgactc cacggagtac      960
cgggcgccgt ccaggcacct cgattagttc tcgagctttt ggagtacgtc gtctttaggt      1020 tgggggagg ggttttatgc gatggagttt ccccacactg agtgggtgga gactgaagtt      1080
aggccagctt ggcacttgat gtaattctcc ttggaatttg cccttttga gtttggatct       1140 tggttcattc tcaagcctca gacagtggtt caaagttttt ttcttccatt tcaggtgtcg      1200
tga                                                                    1203

<210> SEQ ID NO 146
<211> LENGTH: 873
<212> TYPE: DNA
<213> ORGANISM: Homo sapiens

<400> SEQUENCE: 146
atgaggatat ttgctgtctt tatattcatg acctactggc atttgctgaa cgcatttact        60
gtcacggttc ccaaggacct atatgtggta gagtatggta gcaatatgac aattgaatgc       120
aaattcccag tagaaaaaca attagacctg gctgcactaa ttgtctattg ggaaatggag       180
gataagaaca ttattcaatt tgtgcatgga gaggaagacc tgaaggttca gcatagtagc       240
tacagacaga gggcccggct gttgaaggac cagctctccc tgggaaatgc tgcacttcag       300
atcacagatg tgaaattgca ggatgcaggg gtgtaccgct gcatgatcag ctatggtggt       360
gccgactaca gcgaattac tgtgaaagtc aatgccccat acaacaaaat caaccaaaga       420
attttggttg tggatccagt cacctctgaa catgaactga catgtcaggc tgagggctac       480
cccaaggccg aagtcatctg gacaagcagt gaccatcaag tcctgagtgg taagaccacc       540
accaccaatt ccaagagaga ggagaaactt ttcaatgtga ccagcacact gagaatcaac       600
acaacaacta atgagatttt ctactgcact tttaggagat tagatcctga ggaaaaccat       660
acagctgaat tggtcatccc agaactacct ctggcacatc ctccaaatga aaggactcac       720
ttggtaattc tgggagccat cttattatgc cttggtgtag cactgacatt catcttccgt       780
ttaagaaaag ggagaatgat ggatgtgaaa aaatgtggca tccaagatac aaactcaaag       840
aagcaaagtg atacacattt ggaggagacg taa                                    873

<210> SEQ ID NO 147
<211> LENGTH: 122
<212> TYPE: DNA
<213> ORGANISM: Artificial Sequence
<220> FEATURE:
<223> OTHER INFORMATION: Synthetic
```

<400> SEQUENCE: 147

| aacttgttta | ttgcagctta | taatggttac | aaataaagca | atagcatcac | aaatttcaca | 60 |
| aataaagcat | tttttttcact | gcattctagt | tgtggtttgt | ccaaactcat | caatgtatct | 120 |
| ta | | | | | | 122 |

<210> SEQ ID NO 148
<211> LENGTH: 10645
<212> TYPE: DNA
<213> ORGANISM: Artificial Sequence
<220> FEATURE:
<223> OTHER INFORMATION: Synthetic

<400> SEQUENCE: 148

| agtaatcaat | tacggggtca | ttagttcata | gcccatatat | ggagttccgc | gttacataac | 60 |
| ttacggtaaa | tggcccgcct | ggctgaccgc | ccaacgaccc | ccgcccattg | acgtcaataa | 120 |
| tgacgtatgt | tcccatagta | acgccaatag | ggactttcca | ttgacgtcaa | tgggtggact | 180 |
| atttacggta | aactgcccac | ttggcagtac | atcaagtgta | tcatatgcca | agtacgcccc | 240 |
| ctattgacgt | caatgacggt | aaatggcccg | cctggcatta | tgcccagtac | atgaccttat | 300 |
| gggactttcc | tacttggcag | tacatctacg | tattagtcat | cgctattacc | atgggtcgag | 360 |
| gtgagcccca | cgttctgctt | cactctcccc | atctcccccc | cctccccacc | cccaattttg | 420 |
| tatttattta | ttttttaatt | attttgtgca | gcgatggggg | cggggggggg | ggggcgcgc | 480 |
| gccaggcggg | gcggggcggg | gcgaggggcg | gggcggggcg | aggcggagag | gtgcggcggc | 540 |
| agccaatcag | agcggcgcgc | tccgaaagtt | tccttttatg | gcgaggcggc | ggcggcggcg | 600 |
| gccctataaa | aagcgaagcg | cgcggcgggc | gggagtcgct | gcgttgcctt | cgccccgtgc | 660 |
| cccgctccgc | gccgcctcgc | gccgcccgcc | ccggctctga | ctgaccgcgt | tactcccaca | 720 |
| ggtgagcggg | cgggacggcc | cttctcctcc | gggctgtaat | tagcgcttgg | tttaatgacg | 780 |
| gctcgttttct | tttctgtggc | tgcgtgaaag | ccttaaaggg | ctccgggagg | gccctttgtg | 840 |
| cggggggggag | cggctcgggg | ggtgcgtgcg | tgtgtgtgtg | cgtggggagc | gccgcgtgcg | 900 |
| gcccgcgctg | cccggcggct | gtgagcgctg | cgggcgcggc | gcggggctttt | gtgcgctccg | 960 |
| cgtgtgcgcg | aggggagcgc | ggccgggggc | ggtgccccgc | ggtgcggggg | ggctgcgagg | 1020 |
| ggaacaaagg | ctgcgtgcgg | ggtgtgtgcg | tggggggggtg | agcaggggggt | gtgggcgcgg | 1080 |
| cggtcgggct | gtaaccccc | cctgcacccc | cctccccgag | ttgctgagca | cggcccggct | 1140 |
| tcgggtgcgg | ggctccgtgc | ggggcgtggc | gcggggctcg | ccgtgccggg | cggggggtgg | 1200 |
| cggcaggtgg | gggtgccggg | cggggcgggg | ccgcctcggg | ccggggaggg | ctcggggggag | 1260 |
| gggcgcggcg | gccccggagc | gccggcggct | gtcgaggcgc | ggcgagccgc | agccattgcc | 1320 |
| ttttatggta | atcgtgcgag | agggcgcagg | gacttccttt | gtcccaaatc | tggcggagcc | 1380 |
| gaaatctggg | aggcgccgcc | gcaccccctc | tagcgggcgc | gggcgaagcg | gtgcggcgcc | 1440 |
| ggcaggaagg | aaatgggcgg | ggagggcctt | cgtgcgtcgc | cgcgccgccg | tcccttctc | 1500 |
| catctccagc | ctcggggctg | ccgcagggggg | acggctgcct | tcgggggggga | cggggcaggg | 1560 |
| cggggttcgg | cttctggcgt | gtgaccgcg | gctctagagc | ctctgctaac | catgttcatg | 1620 |
| ccttcttctt | tttcctacag | ggggatccg | tttatctgca | gaattcgccc | ttgacgtcgc | 1680 |
| caccatggaa | actctttcta | atgcaagtgg | tactttgcc | atacgccttt | taaagatact | 1740 |
| gtgtcaagat | aaccccttcgc | acaacgtgtt | ctgttctcct | gtgagcatct | cctctgccct | 1800 |

```
ggccatggtt ctcctagggg caaagggaaa caccgcaacc cagatggccc aggcactgtc    1860
tttaaacaca gaggaagaca ttcatcgggc tttccagtcg cttctcactg aagtgaacaa    1920
ggctggcaca cagtacctgc tgagaacggc caacaggctc tttggagaga aaacttgtca    1980
gttcctctca acgtttaagg aatcctgtct tcaattctac catgctgagc tgaaggagct    2040
ttcctttatc agagctgcag aagagtccag gaaacacatc aacacctggg tctcaaaaaa    2100
gaccgaaggt aaaattgaag agttgttgcc gggtagctca attgatgcag aaaccaggct    2160
ggttcttgtc aatgccatct acttcaaagg aaagtggaat gaaccgtttg acgaaacata    2220
cacaagggaa atgccccttta aaataaacca ggaggagcaa aggccagtgc agatgatgta    2280
tcaggaggcc acgtttaagc tcgcccacgt gggcgaggtg cgcgcgcagc tgctggagct    2340
gccctacgcc aggaaggagc tgagcctgct ggtgctgctg cctgacgacg cgtggagct    2400 cagcacggtg gaaaaaagtc tcacttttga gaaactcaca gcctggacca gccagactg    2460 tatgaagagt actgaggttg aagttctcct tccaaaattt aaactacaag aggattatga    2520
catggaatct gtgcttcggc atttgggaat tgttgatgcc ttccaacagg caaggctga    2580 cttgtcggca atgtcagcgg agagagacct gtgtctgtcc aagttcgtgc acaagagttt    2640
tgtggaggtg aatgaagaag caccgaggc agcggcagcg tcgagctgct ttgtagttgc    2700
agagtgctgc atggaatctg gccccaggtt ctgtgctgac cacccttttcc ttttcttcat    2760 caggcacaac agagccaaca gcattctgtt ctgtggcagg ttctcatcgc caggaagcgg    2820
agctactaac ttcagcctgc tgaagcaggc tggagacgtg gaggagaacc ctggacctat    2880
ggactggacc tggatcctgt tcctggtggc cgccgccacc agggtgcaca gcggcattca    2940
tgtcttcatt ttgggctgtt tcagtgcagg gcttcctaaa acagaagcca actgggtgaa    3000
tgtaataagt gatttgaaaa aaattgaaga tcttattcaa tctatgcata ttgatgctac    3060
tttatatacg gaaagtgatg ttcaccccag ttgcaaagta acagcaatga agtgctttct    3120
cttggagtta caagttattt cacttgagtc cggagatgca agtattcatg atacagtaga    3180
aaatctgatc atcctagcaa acaacagttt gtcttctaat gggaatgtaa cagaatctgg    3240
atgcaaagaa tgtgaggaac tggaggaaaa aaatattaaa gaattttgc agagttttgt    3300 acatattgtc caaatgttca tcaacacttc tagcggcggc ggcagcggcg gcggcggcag    3360
cggcggcggc ggcagcggcg gcggcggcag cggcggcggc agcctgcaga tcacgtgccc    3420 tcccccatg tccgtggaac acgcagacat ctgggtcaag agctacagct tgtactccag    3480
ggagcggtac atttgtaact ctggtttcaa gcgtaaagcc ggcacgtcca gcctgacgga    3540
gtgcgtgttg aacaaggcca cgaatgtcgc ccactggaca acccccagtc tcaaatgcat    3600
tagagaccct gccctggttc accaaaggcc agcgccaccc tccacagtaa cgacggcagg    3660
ggtgacccca cagccagaga gcctctcccc ttctggaaaa gagcccgcag cttcatctcc    3720
cagctcaaac aacacagcgg ccacaacagc agctattgtc ccgggctccc agctgatgcc    3780
ttcaaaatca ccttccacag gaaccacaga gataagcagt catgagtcct cccacggcac    3840
cccctctcag acaacagcca agaactggga actcacagca tccgcctccc accagccgcc    3900
aggtgtgtat ccacagggcc acagcgcac cactgtggct atctccacgt ccactgtcct    3960
gctgtgtggg ctgagcgctg tgtctctcct ggcatgctac ctcaagtcaa ggcaaactcc    4020
cccgctggcc agcgttgaaa tggaagccat ggaggctctg ccggtgactt ggggaccag    4080 cagcagagat gaagacttgg aaaactgctc tcaccaccta tgataaccgc tgatcagcct    4140
cgactgtgcc ttctagttgc cagccatctg ttgtttgccc ctcccccgtg ccttccttga    4200
```

```
ccctggaagg tgccactccc actgtccttt cctaataaaa tgaggaaatt gcatcgcatt   4260
gtctgagtag gtgtcattct attctggggg gtggggtggg gcaggacagc aaggggagg    4320
attgggaaga caatagcagg catgctgggg atgcggtggg ctctatgggt cgacccagcg   4380
tgagtctctc ctaccctccc gctctggtcc ttcctctccc gctctgcacc ctctgtggcc   4440
ctcgctgtgc tctctcgctc cgtgacttcc cttctccaag ttctccttgg tggcccgccg   4500
tggggctagt ccagggctgg atctcgggga agcggcgggg tggcctggga gtggggaagg   4560
gggtgcgcac ccgggacgcg cgctacttgc ccctttcggc ggggagcagg ggagaccttt   4620
ggcctacggc gacgggaggg tcgggacaaa gtttagggcg tcgataagcg tcagagcgcc   4680
gaggttgggg gagggtttct cttccgctct ttcgcggggc ctctggctcc cccagcgcag   4740
ctggagtggg ggacgggtag gctcgtccca aaggcgcggc gctgaggttt gtgaacgcgt   4800
ggaggggcgc ttggggtctg ggggaggcgt cgcccgggta agcctgtctg ctgcggctct   4860
gcttcccttA gactggagag ctgtggactt cgtctaggcg cccgctaagt tcgcatgtcc   4920
tagcacctct gggtctatgt ggggccacac cgtgggggagg aaacagcacg cgacgtttgt   4980
agaatgcttg gctgtgatac aaagcggttt cgaataatta acttatttgt tcccatcaca   5040
tgtcactttt aaaaaattat aagaactacc cgttattgac atctttctgt gtgccaagga   5100
ctttatgtgc tttgcgtcat ttaattttga aaacagttat cttccgccat agataactac   5160
tatggttatc ttctggtaac cacgtgcgga ccgggctccg gtgcccgtgt gcggaccggg   5220
ctccggtgcc cgtcagtggg cagagcgcac atcgcccaca gtccccgaga agttgggggg   5280
aggggtcggc aattgaaccg gtgcctagag aaggtggcgc ggggtaaact gggaaagtga   5340
tgtcgtgtac tggctccgcc ttttcccga gggtggggga gaaccgtata taagtgcagt   5400
agtcgccgtg aacgttcttt ttcgcaacgg gtttgccgcc agaacacagg taagtgccgt   5460
gtgtggttcc cgcgggcctg gcctctttac gggttatggc ccttgcgtgc cttgaattac   5520
ttccactggc tgcagtacgt gattcttgat cccgagcttc gggttggaag tgggtgggag   5580
agttcgaggc cttgcgctta aggagcccct tcgcctcgtg cttgagttga ggcctggcct   5640
gggcgctggg gccgccgcgt gcgaatctgg tgccaccttc gcgcctgtct cgctgctttc   5700
gataagtctc tagccatttA aaatttttga tgacctgctg cgacgctttt tttctggcaa   5760
gatagtcttg taaatgcggg ccaagatctg cacactggta tttcggtttt tggggccgcg   5820
ggcggcgacg gggcccgtgc gtcccagcgc acatgttcgg cgaggcgggg cctgcgagcg   5880
cggccaccga gaatcggacg ggggtagtct caagctggcc ggcctgctct ggtgcctggc   5940
ctcgcgccgc cgtgtatcgc cccgccctgg gcggcaaggc tggcccggtc ggcaccagtt   6000
gcgtgagcgg aaagatggcc gcttcccggc cctgctgcag ggagctcaaa atggaggacg   6060
cggcgctcgg gagagcgggc gggtgagtca cccacacaaa ggaaaagggc ctttccgtcc   6120
tcagccgtcg cttcatgtga ctccacggag taccggcgc cgtccaggca cctcgattag   6180
ttctcgagct tttggagtac gtcgtctttA ggttgggggg aggggtttta tgcgatggag   6240
tttccccaca ctgagtgggt ggagactgaa gttaggccag cttggcactt gatgtaattc   6300
tccttggaat ttgccctttt tgagtttgga tcttggttca ttctcaagcc tcagacagtg   6360
gttcaaagtt ttttcttcc atttcaggtg tcgtgacttg acgtcgccac catgaggata   6420
tttgctgtct ttatattcat gacctactgg catttgctga acgcatttac tgtcacggtt   6480
cccaaggacc tatatgtggt agagtatggt agcaatatga caattgaatg caaattccca   6540
```

```
gtagaaaaac aattagacct ggctgcacta attgtctatt gggaaatgga ggataagaac    6600
attattcaat ttgtgcatgg agaggaagac ctgaaggttc agcatagtag ctacagacag    6660
agggcccggc tgttgaagga ccagctctcc ctgggaaatg ctgcacttca gatcacagat    6720
gtgaaattgc aggatgcagg ggtgtaccgc tgcatgatca gctatggtgg tgccgactac    6780
aagcgaatta ctgtgaaagt caatgcccca tacaacaaaa tcaaccaaag aattttggtt    6840
gtggatccag tcacctctga acatgaactg acatgtcagg ctgagggcta ccccaaggcc    6900
gaagtcatct ggacaagcag tgaccatcaa gtcctgagtg gtaagaccac caccaccaat    6960
tccaagagag aggagaaact tttcaatgtg accagcacac tgagaatcaa cacaacaact    7020
aatgagattt tctactgcac ttttaggaga ttagatcctg aggaaaacca tacagctgaa    7080
ttggtcatcc cagaactacc tctggcacat cctccaaatg aaaggactca cttggtaatt    7140
ctgggagcca tcttattatg ccttggtgta gcactgacat tcatcttccg tttaagaaaa    7200
gggagaatga tggatgtgaa aaaatgtggc atccaagata caaactcaaa gaagcaaagt    7260
gatacacatt tggaggagac gtaaccgctg atcagcctcg aaacttgttt attgcagctt    7320
ataatggtta caaataaagc aatagcatca caaatttcac aaataaagca ttttttttcac    7380 tgcattctag ttgtggtttg tccaaactca tcaatgtatc ttaggcgcct gatgcggtat    7440
tttctcctta cgcatctgtg cggtatttca caccgcatac agtactgtca aagcaaccat    7500
agtacgcgcc ctgtagcggc gcattaagcg cggcgggtgt ggtggttacg cgcagcgtga    7560
ccgctacact tgccagcgcc ctagcgcccg ctcctttcgc tttcttccct tcctttctcg    7620
ccacgttcgc cggctttccc cgtcaagctc taaatcgggg gctcccttta gggttccgat    7680
ttagtgcttt acggcacctc gaccccaaaa aacttgattt gggtgatggt tcacgtagtg    7740
ggccatcgcc ctgatagacg gttttttcgcc ctttgacgtt ggagtccacg ttctttaata    7800
gtggactctt gttccaaact ggaacaacac tcaaccctat ctcgggctat tcttttgatt    7860
tataagggat tttgccgatt tcggcctatt ggttaaaaaa tgagctgatt taacaaaaat    7920
ttaacgcgaa ttttaacaaa atattaacgt ttacaatttt atggtgcact ctcagtacaa    7980
tctgctctga tgccgcatag ttaagccagc cccgacaccc gccaacaccc gctgacgcgc    8040
cctgacgggc ttgtctgctc ccggcatccg cttacagaca agctgtgacc gtctccggga    8100
gctgcatgtg tcagaggttt tcaccgtcat caccgaaacg cgcgagacga aagggcctcg    8160
tgatacgcct atttttatag gttaatgtca tgaacaataa aactgtctgc ttacataaac    8220
agtaatacaa ggggtgttat gagccatatt caacgggaaa cgtcgaggcc gcgattaaat    8280
tccaacatgg atgctgattt atatgggtat aaatgggctc gcgataatgt cggcaatca    8340 ggtgcgacaa tctatcgctt gtatgggaag cccgatgcgc cagagttgtt tctgaaacat    8400
ggcaaaggta gcgttgccaa tgatgttaca gatgagatgg tcagactaaa ctggctgacg    8460
gaatttatgc ctcttccgac catcaagcat tttatccgta ctcctgatga tgcatggtta    8520
ctcaccactg cgatccccgg aaaaacagca ttccaggtat tagaagaata tcctgattca    8580
ggtgaaaata ttgttgatgc gctggcagtg ttcctgcgcc ggttgcattc gattcctgtt    8640
tgtaattgtc ctttttaacag cgatcgcgta tttcgtctcg ctcaggcgca atcacgaatg    8700
aataacggtt tggttgatgc gagtgatttt gatgacgagc gtaatggctg gcctgttgaa    8760
caagtctgga agaaaatgca taaacttttg ccattctcac cggattcagt cgtcactcat    8820
ggtgatttct cacttgataa ccttattttt gacgagggga aattaatagg ttgtattgat    8880
gttggacgag tcggaatcgc agaccgatac caggatcttg ccatcctatg gaactgcctc    8940
```

```
ggtgagtttt ctccttcatt acagaaacgg cttttcaaa aatatggtat tgataatcct    9000
gatatgaata aattgcagtt tcatttgatg ctcgatgagt ttttctaatc tcatgaccaa    9060
aatcccttaa cgtgagtttt cgttccactg agcgtcagac cccgtagaaa agatcaaagg    9120
atcttcttga gatccttttt ttctgcgcgt aatctgctgc ttgcaaacaa aaaaaccacc    9180
gctaccagcg gtggtttgtt tgccggatca agagctacca actcttttc cgaaggtaac    9240 tggcttcagc agagcgcaga taccaaatac tgtccttcta gtgtagccgt agttaggcca    9300
ccacttcaag aactctgtag caccgcctac atacctcgct ctgctaatcc tgttaccagt    9360
ggctgctgcc agtggcgata gtcgtgtct taccgggttg gactcaagac gatagttacc    9420
ggataaggcg cagcggtcgg gctgaacggg gggttcgtgc acacagccca gcttggagcg    9480
aacgacctac accgaactga gatacctaca gcgtgagcta tgagaaagcg ccacgcttcc    9540
cgaagggaga aaggcggaca ggtatccggt aagcggcagg gtcggaacag gagagcgcac    9600
gagggagctt ccagggggaa acgcctggta tctttatagt cctgtcgggt ttcgccacct    9660
ctgacttgag cgtcgatttt tgtgatgctc gtcaggggg cggagcctat ggaaaaacgc    9720
cagcaacgcg gcctttttac ggttcctggc cttttgctgg ccttttgctc acatgtgcgg    9780
ccgcacgcgt gttctagggt ggaaactaag agaatgatgt acctagaggg cgctggaagc    9840
tctaaagccc tagcagttac tgcttttact attagtggtc gttttttct ccccccgcc     9900 cccgacaaa tcaacagaac aaagaaaatt acctaaacag caaggacata gggaggaact    9960
tcttggcaca gaacttcca aacactttt cctgaaggga tacaagaagc aagaaaggta    10020
ctctttcact aggaccttct ctgagctgtc ctcaggatgc ttttgggact atttttctta    10080
cccagagaat ggagaaaccc tgcagggaat tcccaagctg tagttataaa cagaagttct    10140
ccttctgcta ggtagcattc aaagatctta atcttctggg tttccgtttt ctcgaatgaa    10200
aaatgcaggt ccgagcagtt aactggctgg ggcaccatta gcaagtcact tagcatctct    10260
ggggccagtc tgcaaagcga gggggcagcc ttaatgtgcc tccagcctga agtcctagaa    10320
tgagcgcccg gtgtcccaag ctggggcgcg cacccagat cggagggcgc cgatgtacag    10380
acagcaaact cacccagtct agtgcatgcc ttcttaaaca tcacgagact ctaagaaaag    10440
gaaactgaaa acgggaaagt ccctctctct aacctggcac tgcgtcgctg gcttggagac    10500
aggtgacggt ccctgcgggc cttgtcctga ttggctgggc acgcgtttaa tataagtgga    10560
ggcgtcgcgc tggcgggcat tcctgaagct aagcttgtgg acgatatcga attcgcacga    10620
cattgattat tgactagtta ttaat                                          10645

<210> SEQ ID NO 149
<211> LENGTH: 1178
<212> TYPE: DNA
<213> ORGANISM: Artificial Sequence
<220> FEATURE:
<223> OTHER INFORMATION: Synthetic

<400> SEQUENCE: 149
ggctccggtg cccgtcagtg ggcagagcgc acatcgccca cagtcccga gaagttgggg      60 ggaggggtcg gcaattgaac cggtgcctag agaaggtggc gcggggtaaa ctgggaaagt     120
gatgtcgtgt actggctccg ccttttcc gagggtgggg gagaaccgta tataagtgca      180
gtagtcgccg tgaacgttct ttttcgcaac gggtttgccg ccagaacaca ggtaagtgcc     240
gtgtgtggtt cccgcgggcc tggcctcttt acgggttatg gcccttgcgt gccttgaatt     300
```

```
-continued acttccactg gctgcagtac gtgattcttg atcccgagct tcgggttgga agtgggtggg      360
agagttcgag gccttgcgct taaggagccc cttcgcctcg tgcttgagtt gaggcctggc      420
ctgggcgctg gggccgccgc gtgcgaatct ggtggcacct tcgcgcctgt ctcgctgctt      480
tcgataagtc tctagccatt taaaatttt gatgacctgc tgcgacgctt ttttctggc      540 aagatagtct tgtaaatgcg ggccaagatc tgcacactgg tatttcggtt tttggggccg      600
cgggcggcga cggggcccgt gcgtcccagc gcacatgttc ggcgaggcgg ggcctgcgag      660
cgcggccacc gagaatcgga cgggggtagt ctcaagctgg ccggcctgct ctggtgcctg      720
gcctcgcgcc gccgtgtatc gccccgccct gggcggcaag gctggcccgg tcggcaccag      780
ttgcgtgagc ggaaagatgg ccgcttcccg gccctgctgc agggagctca aaatggagga      840
cgcggcgctc gggagagcgg gcgggtgagt cacccacaca aaggaaaagg gcctttccgt      900
cctcagccgt cgcttcatgt gactccacgg agtaccgggc gccgtccagg cacctcgatt      960
agttctcgag cttttggagt acgtcgtctt taggttgggg ggaggggttt tatgcgatgg     1020
agtttcccca cactgagtgg gtggagactg aagttaggcc agcttggcac ttgatgtaat     1080
tctccttgga atttgccctt tttgagtttg gatcttggtt cattctcaag cctcagacag     1140
tggttcaaag ttttttctt ccatttcagg tgtcgtga                              1178
```